US011021695B2

(12) United States Patent
Hom et al.

(10) Patent No.: US 11,021,695 B2
(45) Date of Patent: *Jun. 1, 2021

(54) METHODS AND COMPOSITIONS RELATED TO THIOESTERASE ENZYMES

(71) Applicant: GENOMATICA, INC., San Diego, CA (US)

(72) Inventors: Louis Hom, South San Francisco, CA (US); Na Trinh, Burlingame, CA (US); Murtaza Alibhai, Austin, TX (US); Zhihao Hu, South San Francisco, CA (US); Eli Groban, South San Francisco, CA (US); Vikranth Arlagadda, South San Francisco, CA (US); Elizabeth Clarke, South San Francisco, CA (US)

(73) Assignee: Genomatica, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/958,229

(22) Filed: Apr. 20, 2018

(65) Prior Publication Data

US 2019/0093089 A1 Mar. 28, 2019

Related U.S. Application Data

(60) Continuation of application No. 15/439,053, filed on Feb. 22, 2017, now Pat. No. 9,951,322, which is a continuation of application No. 14/826,657, filed on Aug. 14, 2015, now Pat. No. 9,587,231, which is a division of application No. 12/645,497, filed on Dec. 23, 2009, now Pat. No. 9,175,234.

(60) Provisional application No. 61/140,600, filed on Dec. 23, 2008.

(51) Int. Cl.
| | |
|---|---|
| *C12N 9/16* | (2006.01) |
| *C12N 15/00* | (2006.01) |
| *C12N 9/18* | (2006.01) |
| *C12N 15/63* | (2006.01) |
| *C10L 1/02* | (2006.01) |
| *C07H 21/04* | (2006.01) |
| *C12P 21/06* | (2006.01) |

(52) U.S. Cl.
CPC ............... *C12N 9/16* (2013.01); *C12N 9/18* (2013.01); *C12N 15/00* (2013.01); *C12N 15/63* (2013.01); *C07H 21/04* (2013.01); *C10L 1/02* (2013.01); *C12P 21/06* (2013.01)

(58) Field of Classification Search
CPC ...................................................... C12N 9/16
See application file for complete search history.

(56) References Cited

U.S. PATENT DOCUMENTS

| | | |
|---|---|---|
| 3,172,892 A | 3/1965 | Le Suer |
| 3,438,757 A | 4/1969 | Honnen et al. |
| 3,980,569 A | 9/1976 | Pindar et al. |
| 5,000,000 A | 3/1991 | Ingram et al. |
| 5,028,539 A | 7/1991 | Ingram et al. |
| 5,424,202 A | 6/1995 | Ingram et al. |
| 5,455,167 A | 10/1995 | Voelker et al. |
| 5,482,846 A | 1/1996 | Ingram et al. |
| 5,602,030 A | 2/1997 | Ingrahm et al. |
| 5,898,023 A | 4/1999 | Francisco et al. |
| 5,955,329 A * | 9/1999 | Yuan ............... C12N 15/8247 435/19 |
| 6,165,235 A | 12/2000 | Kolp et al. |
| 6,261,814 B1 | 7/2001 | Rosazza et al. |
| 6,982,155 B1 | 1/2006 | Fukuda et al. |
| 7,041,814 B1 | 5/2006 | Weinstock et al. |
| 7,056,714 B2 | 6/2006 | Rosazza et al. |
| 7,118,896 B2 | 10/2006 | Kalscheuer et al. |
| 7,211,418 B2 | 5/2007 | Metz et al. |
| 7,273,966 B2 | 9/2007 | Voelker et al. |
| 7,425,433 B2 | 9/2008 | Rosazza et al. |
| 7,608,700 B2 | 10/2009 | Klaenhammer et al. |

(Continued)

FOREIGN PATENT DOCUMENTS

| | | |
|---|---|---|
| BR | 10 2004 052 | 4/2016 |
| DE | 10 2004 052 115 | 4/2006 |

(Continued)

OTHER PUBLICATIONS

Studer. Residue mutations and their impact on protein structure and function: detecting beneficial and pathogenic changes. Residue mutations and their impact on protein structure and function: detecting beneficial and pathogenic changes. Biochem. J. (2013) 449, 581-594.*

Abbadi et al., "Knockout of the regulatory site of 3-ketoacyl-ACP synthase III enhances short-and medium-chain acyl-ACP synthesis", Plant Journal, Dec. 25, 2001, vol. 24, Issue 1, pp. 1-9.

(Continued)

*Primary Examiner* — Yong D Pak
(74) *Attorney, Agent, or Firm* — Harness Dickey & Pierce P.L.C.

(57) ABSTRACT

The present invention relates to novel mutant thioesterase enzymes and naturally-occurring equivalents thereof, compositions made from such enzymes and uses of thioesterase enzymes. In particular, the present invention provides mutant thioesterase enzymes that have altered properties, for example, altered substrate specificity, altered activity, altered selectivity, and/or altered proportional yields in the product mixtures. The present invention also provides polynucleotides encoding such mutant thioesterase enzymes, and vectors and host cells comprising such polynucleotides. The invention further provides for novel uses of thioesterases in the production of various fatty acid derivatives, which are useful as, or as components of, industrial chemicals and fuels.

3 Claims, 226 Drawing Sheets

Specification includes a Sequence Listing.

(56) References Cited

U.S. PATENT DOCUMENTS

| | | |
|---|---|---|
| 2003/0040474 A1 | 2/2003 | Kapeller-Libermann et al. |
| 2003/0097686 A1 | 5/2003 | Knauf et al. |
| 2003/0129601 A1 | 7/2003 | Cole |
| 2004/0180400 A1 | 9/2004 | Rosazza et al. |
| 2005/0130126 A1 | 6/2005 | Durmaz et al. |
| 2005/0250135 A1 | 11/2005 | Klaenhammer et al. |
| 2006/0014977 A1 | 1/2006 | Miller et al. |
| 2006/0195947 A1 | 8/2006 | Davis et al. |
| 2006/0206963 A1 | 9/2006 | Voelker et al. |
| 2007/0251141 A1 | 11/2007 | Bist et al. |
| 2007/0261138 A1 | 11/2007 | Graham et al. |
| 2008/0070287 A1 | 3/2008 | Soe et al. |
| 2008/0161595 A1 | 7/2008 | Huang et al. |
| 2008/0295388 A1 | 12/2008 | Bazzani et al. |
| 2009/0038211 A1 | 2/2009 | Sarin et al. |
| 2009/0047721 A1 | 2/2009 | Trimbur et al. |
| 2009/0075333 A1 | 3/2009 | Campbell et al. |
| 2009/0084025 A1 | 4/2009 | Bhatia et al. |
| 2009/0180987 A1 | 7/2009 | Stritzker et al. |
| 2010/0071259 A1 | 3/2010 | Hu et al. |
| 2010/0105963 A1 | 4/2010 | Hu |
| 2010/0154293 A1 | 6/2010 | Hom et al. |
| 2010/0242345 A1 | 9/2010 | Keasling et al. |
| 2010/0249470 A1 | 9/2010 | Schirmer et al. |
| 2010/0251601 A1 | 10/2010 | Hu et al. |
| 2010/0257777 A1 | 10/2010 | Sanchez-Riera et al. |
| 2010/0257778 A1 | 10/2010 | Gaertner et al. |
| 2010/0274033 A1 | 10/2010 | Sanchez-Riera et al. |
| 2011/0072714 A1 | 3/2011 | Gaertner |
| 2011/0146142 A1 | 6/2011 | Lee et al. |
| 2011/0162259 A1 | 7/2011 | Gaertner |

FOREIGN PATENT DOCUMENTS

| | | |
|---|---|---|
| WO | WO-92/11373 | 7/1992 |
| WO | WO-97/12047 | 4/1997 |
| WO | WO-00/09721 | 2/2000 |
| WO | WO-2007/136762 A2 | 11/2007 |
| WO | WO-2008/119082 A2 | 10/2008 |
| WO | WO-2009/002480 | 12/2008 |
| WO | WO-2009/042950 A1 | 4/2009 |
| WO | WO-2009/140695 A2 | 11/2009 |
| WO | WO-2010/022090 A1 | 2/2010 |
| WO | WO-2010/042664 A1 | 4/2010 |
| WO | WO-2010/062480 A2 | 6/2010 |
| WO | WO-2010/075483 A2 | 7/2010 |
| WO | WO-2010/118409 A1 | 10/2010 |
| WO | WO-2010/118410 A1 | 10/2010 |
| WO | WO-2010/126891 A1 | 11/2010 |
| WO | WO-2011/038132 A1 | 3/2011 |
| WO | WO-2011/038134 A1 | 3/2011 |

OTHER PUBLICATIONS

Abdel-Hamid et al., "Coordinate Expression of the Acetyl Coenzyme A Carboxylase Genes, accB and accC, Is Necessary for Normal Regulation of Biotin Synthesis in *Escherichia coli*", J. Bacteriol., Jan. 15, 2007, vol. 189, Issue 2, pp. 369-376.

Abdel-Hamid et al., "Pyruvate oxidase contributes to the aerobic growth efficiency of *Escherichia coli*", Microbiol. Jul. 2001, vol. 147, Issue 6, pp. 1483-1498.

Alper et al., "Engineering for biofuels: exploiting innate microbial capacity or importing biosynthetic potential?", NRM, Oct. 2009, vol. 7, pp. 715-723.

Alvarez et al., "Triacylglycerols in prokaryotic microorganisms", Appl.Microbiol.Biotechnol., Dec. 2002, vol. 60, Issue 4, pp. 367-376.

Antoni et al., "Biofuels from microbes," Appl. Microbial. Biotechnol., Nov. 2007, vol. 77, pp. 23-35.

Atsumi et al., "Metabolic engineering for advanced biofuels production from *Escherichia coli*", Current Opin.Biotech, Sep. 2008, vol. 19, pp. 414-419.

Atsumi et al., "Metabolic engineering of *Escherichia coli* for 1-butanol production", Metabolic Engineering, Nov. 2008, vol. 10, pp. 305-311.

Atsumi et al., "Non-fermentative pathways for synthesis of branched-chain higher alcohols as biofuels," Nature, Jan. 3, 2008, vol. 451, pp. 86-89.

Barnes, Jr. et al., "Studies on the Mechanism of Fatty Acid Synthesis. XIX. Preparation and General Properties of Palmityl Thioesterase", J. Biol. Chem., Jun. 10, 1968, vol. 243, Issue 11, pp. 2955-2962.

Beekwilder et al., "Functional Characterization of Enzymes Forming Volatile Esters from Strawberry and Banana", Plant Physiology, Aug. 2004, vol. 135, pp. 1865-1878.

Beinert, H., "Recent developments in the field of iron-sulfur proteins", FASEB J. May 1990, vol. 4 pages, 2483-2491.

Bergler et al., "Protein EnvM is the NADH-dependent Enoyl-ACP Reductase (FabI) of *Escherichia coli*," J. Biol. Chem., Feb. 25, 1994, vol. 269, Issue 8, pp. 5943-5946.

Bergler et al., "The enoyl-[acyl-carrier-protein] reductase (FabI) of *Escherichia coli*, which catalyzes a key regulatory step in fatty acid biosynthesis, accepts NADH and NADPH as cofactors and is inhibited by palmitoyl-CoA", Eur. J. Biochem. Dec. 15, 1996, vol. 242, pp. 689-694.

Berrios-Rivera et al., "The Effect of Increasing NADH Availability on the Redistribution of Metabolic Fluxes in *Escherichia coli* Chemostat Cultures", Metabolic Engineering, Jul. 2002, vol. 4, pp. 230-237.

Birge et al., "Acyl Carrier Protein. XVI.Intermediate Reactions of Unsaturated Fatty Acid Synthesis in *Escerichia coli* and Studies of fab B Mutants", J.Biol.Chem. Aug. 25, 1972, vol. 247, Issue 16, pp. 4921-4929.

Black et al., "Cloning, Sequencing, and Expression of the fadD Gene of *Escherichia coli* Encoding Acyl Coenzyme A Synthetase", J. Biol. Chem., vol. 267, Dec. 15, 1992, No. 35, pp. 25513-25520.

Black et al., "Long-Chain Acyl-CoA—Dependent Regulation of Gene Expression in Bacteria, Yeast and Mammals", J. Nutrition, Feb. 2000, pp. 305S-309S.

Black et al., "Mutational Analysis of a Fatty Acyl-Coenzyme A Synthetase Signature Motif Identifies Seven Amino Acid Residues That Modulate Fatty Acid Substrate Specificity", J. Biol. Chem. Feb. 21, 1997, vol. 272, Issue 8, pp. 4896-4903.

Black, P., "Primary Sequence of the *Escherichia coli* fadL Gene Encoding an Outer Membrane Protein Required for Long-Chain Fatty Acid Transport", J. Bacteriology, Jan. 1991, vol. 173, Issue pp. 435-442.

Blanchard et al., "Overexpression and Kinetic Characterization of the Carboxyltransferase Component of Acetyl-CoA Carboxylase", J.Biol.Chem. Jul. 24, 1998, vol. 273, Issue 30, pp. 19140-19145.

Bonamore et al., "The desaturase from Bacillus subtilis, a promising tool for the selective olefination of phospholipids", J.Biotechnology, Jan. 2, 2006, vol. 121, pp. 49-53.

Bond-Watts et al., "Enzyme mechanism as a kinetic control element for designing synthetic biofuel pathways", Nature Chem Bio, Feb. 2011, vol. 537 pp. 1-6 (Suppl. S1-S28).

Bonner et al., "Purification and Properties of Fatty Acyl Thioesterase I from *Escherichia coli*", J.Biol.Chem. May 25, 1972, vol. 247, Issue 10, pp. 3123-3133.

Boonstra et al., "The udhA Gene of *Escherichia coli* Encodes a Soluble Pyridine Nucleotide Transhydrogenase", J. Bacteriol. Feb. 1, 1999, vol. 181 Issue 3, pp. 1030-1034.

Boulanger et al., "Purification and Structural and Functional Characterization of FhuA, a Transporter of the *Escherichia coli* Outer Membrane", Biochemistry, Nov. 12, 1996, vol. 35, Issue 45, pp. 14216-14224.

Branden et al. Prediction, Engineering, and Design of Protein Structures, Introduction to Protein Structure, Garland Publishing Inc., New York, pp. 247, 1991.

Bredwell et al., "Reactor Design Issues for Synthesis-Gas Fermentations", Biotechnol. Oct. 1, 1999, Prog. vol. 15, pp. 834-844.

Broun et al., "A bifunctional oleate 12-hydroxylase: Desaturase from Lesquerella fend/err", Plant Journal, Nov. 13, 1998, vol. 13, Issue 2, pp. 201-210.

(56) References Cited

OTHER PUBLICATIONS

Bunch et al., "The ldhA gene encoding the fermentative lactate dehydrogenase of *Escherichia coli*", Microbiol. Feb. 1997, vol. 143, Issue 1, pp. 187-195.

Cahoon et al., "A Determinant of Substrate Specificity Predicted from the Acyl-Acyl Carrier Protein Desaturase of Developing Cat's Claw Seed", Plant Physiol, Jun. 1998, vol. 117, pp. 593-598.

Cahoon et al., "Modification of the Fatty Acid Composition of *Escherichia coli* by Coexpression of a Plant Acyl-Acyl Carrier Protein Desaturase and Ferredoxin", J.Bacteriol. Feb. 1996, vol. 178, Issue pp. 936-939.

Cahoon et al., "Redesign of soluble fatty acid desaturases from plants for altered substrate specificity and double bond position", Proc. Natl. Acad. Sci. May 13, 1997, vol. 94, pp. 4872-4877.

Campbell et al., "A New *Escherichia coli* metabolic competency: growth on fatty acids by a novel anaerobic .beta.-oxidation pathway", Mol. Microbiol., Feb. 2003, vol. 47, Issue 3, pp. 793-805.

Campbell et al., "*Escherichia coli* FadR Positively Regulates Transcription of the fabB Fatty Acid Biosynthetic Gene", J.Bacteriol. Oct. 2001, vol. 183, Issue 20, pp. 5982-5990.

Campbell et al., "The Enigmatic *Escherichia coli* neu Gene is yafH", J. Bacteriol., Jul. 2002, vol. 184, Issue 13, pp. 3759-3764.

Cann et al., "Production of 2-methyl-1-butanol in engineered *Escherichia coli*", Appl Microbiol Biotechnol. Nov. 2008, vol. 81, pp. 89-98.

Canoira et al., "Biodiesel from Jojoba oil-wax: Transesterification with methanol and properties as a fuel", Biomass and Bioenergy, Jan. 2006, vol. 30, pp. 76-81.

Canonaco et al., "Metabolic flux response to phosphoglucose isomerase knock-out in *Escherichia coli* and impact of overexpression of the soluble transhydrogenase UdhA", FEMS Microbiology Letters, Nov. 2001, vol. 204, pp. 247-252.

Caviglia et al., "Rat Long Chain Acyl-CoA Synthetase 5, but Not 1, 2, 3, or 4, Complements *Escherichia coli* fadD," J. Biol. Chem, Jan. 7, 2004, vol. 279, No. 12, pp. 11163-11169.

Chan et al., "Current understanding of fatty acid biosynthesis and the acyl carrier protein," Biochem. J. Aug. 15, 2010, vol. 430, Issue 1, pp. 1-19.

Chang et al., "Genetic and Biochemical Analyses of *Escherichia coli* Strains Having a Mutation in the Structural Gene (poxB) for Pyruvate Oxidase," J. Bacteriol. May 1983, vol. 154, Issue 2, pp. 756-762.

Chassagnole et al., "Dynamic Modeling of the Central Carbon Metabolism of *Escherichia coli*", Biotech & Engineering Jul. 5, 2002, vol. 79, Issue 1, pp. 54-73.

Chen et al., "Biosynthesis of Ansatrienin (mycotrienin) and naphthomycin, Identification and Analysis of Two Separate Biosynthetic Gene Clusters in Streptomyces Collinus Tu 1892," Apr. 1999, Eur. J. Biochem. vol. 261, pp. 98-107.

Chen, "Permeability issues in whole-cell bioprocesses and cellular membrane engineering", Appl Microbiol Biotechnol. Mar. 2007, vol. 74, pp. 730-738.

Cheng et al., "Mammalian Wax Biosynthesis, II. Expression Cloning of a Wax Synthase cDNAs Encoding a Member of the Acyltransferase Enzyme Family*," J. Biol. Chem., Sep. 3, 2004, vol. 279, Issue 36, pp. 37798-37807.

Cho et al. "Defective Export of a Periplasmic Enzyme Disrupts Regulation of Fatty Acid Synthesis," J. Biol. Chem. Mar. 3, 1995, vol. 270, No. 9, pp. 4216-4219.

Cho et al., "*Escherichia coli* thioesterase I, molecular cloning and sequencing of the structural gene and identification s a periplasmic enzyme", J.Biol. Chem., May 5, 1993, vol. 268, No. 13, pp. 9238-9245.

Cho et al., "Transcriptional regulation of the fad regulon genes of *Escherichia coli* by ArcA", Microbiology, Aug. 1, 2006, vol. 152, pp. 2207-2219.

Choi et al., ".beta.-Ketoacyl-acyl Carrier Protein Synthase III (FabH) Is a Determining Factor in Branched-Chain Fatty Acid Biosynthesis" J. of Bacteriology, Feb. 2000, vol. 182, Issue 2, pp. 365-370.

Coleman et al., "Enzymes of triacylglycerol synthesis and their regulation" Progress in Lipid Research, Mar. 2004, vol. 43, pp. 134-176.

Collister et al., "Modification of the petroleum system concept: Origins of alkanes and isoprenoids in crude oils" AAPG Bulletin, May 2004, vol. 88, Issue 5, pp. 587-611.

Conway et al., "Cloning and Sequencing of the Alcohol Dehydrogenase II Gene from Zymomonas mobilis" J. Bacteriol. Jun. 1987, vol. 169, Issue 6, pp. 2591-2597.

Cropp et al., "Identification of a Cyclohexylcarbonyl CoA Biosynthetic Gene Cluster and Application in the Production of Doramectin," Nature Biotechnology, Sep. 2000, vol. 18, pp. 980-983.

Da Silva et al., "Comparison of the Genomes of Two Xanthomonas Pathogens with Differing Host Specificities", Nature, May 23, 2002, vol. 417, pp. 459-463.

Database EMBL (Online), Jul. 1996, "Synechococcus, PCC7942 Ribosomal Protein 51 of 30S Ribosome (rpsl), ORF271, ORF231, ORF341, Carboxyltransferase alpha subunit (accA), ORF245, ORF227, and GTP cyclohydrolase I (folE) genes, complete cds, and ORF205 gene, partial cds.," XP002564232, 2 pages.

Datsenko et al., "One-step Inactivation of Chromosomal Genes in *Escherichia coli* K-12 using PCR Products," Proc. Natl. Acad. Sci USA, Jun. 6, 2000, vol. 97, pp. 6640-6645.

Davis et al., "Inhibition of *Escherichia coli* Acetyl Coenzyme a Carboxylase by Acyl-Acyl Carrier Protein" J.Bacteriol. Mar. 2001, vol. 183, Issue 4, pp. 1499-1503.

Davis et al., "Overproduction of Acetyl-CoA Carboxylase Activity Increases the Rate of Fatty Acid Biosynthesis in *Escherichia coli*" J.Biol.Chem. Sep. 15, 2000, vol. 275, Issue 37, pp. 28593-28598.

Davis, J.B., "Microbial Incorporation of Fatty Acids Derived From n-Alkanes Into Glycerides and Waxes" Applied Microbiology, May 1964, vol. 12, pp. 210-214.

De Lay et al., "In Vivo Functional Analyses of the Type II Acyl Carrier Proteins of Fatty Acid Biosynthesis", J. Biol. Chem. Jul. 13, 2007, vol. 282, pp. 20319-20328.

De Mendoza et al., "Thermal Regulation of Membrane Fluidity in *Escherichia coli*. Effects of Overproduction of P-Ketoacylacyl Carrier Protein Synthase 1," J. Biol. Chem. Feb. 25, 1983, vol. 258, Issue 4, pp. 2098-2101.

Dehesh et al., "KAS IV: A 3-ketoacyl-ACP synthase from *Cuphea* sp. Is a medium chain specific condensing enzyme", The Plant Journal, Aug. 1998, vol. 15, Issue 3, pp. 383-390.

Dehesh et al., "Production of high levels of 8:0 and 10:0 fatty acids in transgenic canola by overexpression of Ch FatB2, a thioesterase cDNA from Cuphea hookeriana" The Plant Journal, Feb. 1996, vol. 9, Issue 2, pp. 167-172.

Dellomonaco et al., "The path to next generation biofuels: successes and challenges in the era of synthetic biology," Microbial Cell Factories. Jan. 20, 2010, vol. 3, pp. 1-15.

Demirbas, A., "Relationships derived from physical properties of vegetable oil and biodiesel fuels", Jul. 2008, Fuel vol. 87, pp. 1743-1748.

Denoya, et al., "A Second Branded-Chain a-Keto Acid Dehydrogenase Gene Cluster (bkdFGH) from Streptomyces Avermitilis: Its Relationship to Avermectin Biosynthesis and the Construction of a bkdF Mutant Suitable for the Production of Novel Antiparasitic Avermectins," Journal of Bacteriology, Jun. 1995, vol. 177, No. 12, pp. 3504-3511, 8 pages.

DeVeaux et al., "Genetic and Biochemical Characterization of a Mutation (fatA) That Allows trans Unsaturated Fatty Acids to Replace the Essential cis Unsaturated Fatty Acids of *Escherichia coli*" J.Bacteriology, Mar. 1989, vol. 171, Issue 3, pp. 1562-1568.

Doan et al., "Functional expression of five Arabidopsis fatty acyl-CoA reductase genes in *Escherichia coli*", J. Plant Physiology, May 15, 2009, vol. 166, pp. 787-796.

Domergue et al., "Acyl Carriers Used as Substrates by the Desaturases and Elongases Involved in Very Long-chain Polyunsaturated Fatty Acids Biosynthesis Reconstituted in Yeast" J.Biol.Chem, Sep. 12, 2003, vol. 278, Issue 37, pp. 35115-35126.

Domka et al., "YliH (BssR) and YceP (BssS) Regulate *Escherichia coli* K-12 Biofilm Bormation by Influencing Cell Signaling" Appl. And Environ. Microbiol. Apr. 2006, vol. 72, Issue 4, pp. 2449-2459.

(56) References Cited

OTHER PUBLICATIONS

Dormann et al., "Specificities of the Acyl-Acyl Carrier Protein (ACP) Thioesterase and Glycerol-3-Phosphate Acyltransferase for Octadecenoyl-ACP Isomers (Identification of a Petroselinoyl-ACP Thioesterase in Umbelliferae)," Plant Physiol. Mar. 1994, vol. 104, pp. 839-844.
Doss, R.P., "Composition and Enzymatic Activity of the Extracellular Matrix Secreted by Germlings of Botrytis cinerea," Appl. And Environ. Microbiol., Feb. 1999, vol. 65, Issue 2, pp. 404-408.
Duan et al., "De novo Biosynthesis of Biodiesel by *Escherichia coli* in Optimized Fed-Batch Cultivation", PLoS ONE, May 2011, vol. 6, Issue 5, pp. 1-7.
Durre, P., "Fermentative Butanol Production: Bulk Chemical and Biofuel" Ann. N. Y. Acad. Sci. Mar. 2008, vol. 1125, pp. 353-362.
Dworkin et al., "The PspA Protein of *Escherichia coli* is a Negative Regulator of sigma54-Dependent Transcription," J. Bacteriol. Jan. 2000, vol. 182, Issue 2, pp. 311-319.
Edwards et al., "The *Escherichia coli* MG1655 in silico metabolic genotype: Its definition, characteristics, and capabilities", PNAS, May 9, 2000, vol. 97, Issue 10, pp. 5528-5533.
Elbahloul et al., "Pilot-Scale Production of Fatty Acid Ethyl Esters by an Engineered *Escherichia coli* Strain Harboring the p(Microdiesel) Plasmid", Appl. and Environ. Microbiol. Jun. 23, 2010, vol. 76, Issue 13, pp. 4560-4565.
Examination Report issued on Australian Application 2016225853, dated Sep. 15, 2017, 3 pages.
Examiner's Report issued on Australian Appl. 2009329970, dated Mar. 17, 2016, 3 pages.
Extended European Search Report on EP 19161705.9 dated Oct. 4, 2019, 10 pages.
Farewell et al., "Role of the *Escherichia coli* FadR Regulator in Stasis Survival and Growth Phase-Dependent Expression of the uspA, fad, and fab Genes", J. Bacteriol. Nov. 1996, vol. 178, Issue pp. 6443-6450.
Fehler et al., "Biosynthesis of Hydrocarbons in Anabaena variabilis. Incorporation of [methyl- 14C]-and [methy/-2H2] Methionine into 7- and 8-Methylheptadecanes*", Biochemistry, Jan. 1970, vol. 9, No. 2, pp. 418-422.
Feng et al., "A New Member of the *Escherichia coli* fad Regulon: Transcriptional Regulation of fadM (ybaW)", J. Bacteriol. Oct. 2009, vol. 191, Issue 20, pp. 6320-6328.
Feng et al., "*Escherichia coli* Unsaturated Fatty Acid Synthesis: Complex Transcription of the fabA Gene and in Vivo Identification of the Essential Reaction Catalyzed by FabB", J.Biol. Chem. Oct. 2009, vol. 284, Issue 43, pp. 29526-29535.
Feng et al., "Overlapping Repressor Binding Sites Result in Additive Regulation of *Escherichia coli* FadH by FadR and ArcA", J. of Bacteriology, Sep. 2010, vol. 192, Issue 17, pp. 4289-4299.
Fischer et al., "Selection and optimization of microbial hosts for biofuels production", Metabolic Engineering, Jul. 3, 2008, vol. 10, pp. 295-304.
Flaman et al., "Site-directed Mutagenesis of Acyl Carrier Protein (ACP) Reveals Amino Acid Residues Involved in ACP Structure and Acyl-ACP Synthetase Activity," J.Biol.Chem. Sep. 21, 2001, vol. 276, Issue 38, pp. 35934-35939.
Fleischman et al., "Putative long-chain fatty-acid—CoA ligase [*Mycobactcterium smegmatis* str. MC2 155]", GenBank71854.1, 2006, 3 pages.
Fouts, D. et al., "Acyl-CoA thioesterase I", UniProtKB Accession No. B5Y0L7_KLEP3, Nov. 25, 2008.
Fozo et al., "The fabM Gene Product of *Streptococcus* mutans Is Responsible for the Synthesis of Monounsaturated Fatty Acids and Is Necessary for Survival at Low pH", J. Bacteriol. Jun. 17, 2004, vol. 186, Issue 13, pp. 4152-4158.
Fujita et al., "Regulation of fatty acid metabolism in bacteria", Mol. Microbiology, Nov. 2007, vol. 66, Issue 4, pp. 829-839.
Ghisla et al., "Acyl-CoA dehydrogenases—A mechanistic overview," Eur. J. Biochem. Feb. 2004, vol. 271, pp. 494-508.

Han et al., "A Novel Alternate Anaplerotic Pathway to the Glyoxylate Cycle in Streptomycetes," J. Bacteriol. Aug. 1997, vol. 179, Issue 16, pp. 5157-5164.
Hantke, K., "Ferrous iron transport mutants in *Escherichia coli* K12," FEMS Microbiology Letters, Sep. 1987, vol. 44, pp. 53-57.
Hawkins, D.J.; Kridl, J.C., "Characterization of acyl-ACP thioesterases of mangosteen (*Garcinia mangostana*) seed and high levels of Stearate production in transgenic canola", Plant Journal, Mar. 1998, vol. 13, Issue 6, pp. 743-752.
He et al., "*Nocardia* sp. Carboxylic Acid Reductase: Cloning, Expression, and Characterization of a New Aldehyde Oxidoreductase Family," Applied and Environmental Microbiology, Mar. 2004, vol. 70 Issue 3, pp. 1874-1881.
Heath et al., "Inhibition of .beta.-Ketoacyl-Acyl Carrier Protein Synthase III (FabH) by Acyl-Acyl Carrier Protein in *Escherichia coli*", J.Biol. Chem. May 3, 1996, vol. 271, Issue 18, pp. 10996-11000.
Heath et al., "Lipid Biosynthesis as a Target for Antibacterial Agents," Prog. Lipid Res. Nov. 2001, vol. 40, Issue 6, pp. 467-497.
Heath et al., "Regulation of Fatty Acid Elongation and Initiation by Acyl-Acyl Carrier Protein in *Escherichia coli*", J.Biol.Chem. Jan. 26, 1996, vol. 271, Issue 4, pp. 1833-1836.
Heath et al., "Regulation of Malonyl-CoA Metabolism by Acyl-Acyl Carrier Protein and .beta.-Ketoacyl-Acyl Carrier Protein Synthases in *Escherichia coli*", J.Biol.Chem. Jun. 30, 1995, vol. 270, Issue 26, pp. 15531-15538.
Heath et al., "Roles of the FabA and FabZ .beta.-Hydroxyacyl-Acyl Carrier Protein Dehydratases in *Escherichia coli* Fatty Acid Biosynthesis", J.Biol.Chem. Nov. 1, 1996, vol. 271, Issue 44, pp. 27795-27801.
Henry et al., "*Escherichia coli* Transcription Factor That Both Activates Fatty Acid Synthesis and Represses Fatty Acid Degradation", J. Mol. Biol. Dec. 20, 1991, vol. 222, pp. 843-849.
Hunt et al., "Characterization of an Acyl-CoA Thioesterase That Functions as a Major Regulator of Peroxisomal Lipid Metabolism" J.Biol.Chem. Jan. 11, 2002, vol. 277, Issue 2, pp. 1128-1138.
Imahara et al., "Thermodynamic study on cloud point of biodiesel with its fatty acid composition", Fuel Sep. 2006, vol. 85, pp. 1666-1670.
International Preliminary Report on Patentability issued on PCT/US2009/069356, dated Jun. 29, 2011, 9 pages.
International Search Report and Written Opinion on PCT/US2008/058788, dated Jan. 27, 2009, 21 pages.
International Search Report and Written Opinion on PCT/US2009/004734, dated Nov. 17, 2009, 9 pages.
International Search Report and Written Opinion on PCT/US2009/054213, dated Oct. 6, 2009, 8 pages.
International Search Report and Written Opinion on PCT/US2009/069356, dated Oct. 18, 2010, 16 pages.
International Search Report and Written Opinion on PCT/US2009/59903, dated Jun. 2, 2010, 18 pages.
International Search Report and Written Opinion on PCT/US2009/59904, dated Apr. 5, 2010, 11 pages.
Ishige et al., "Long-Chain Aldehyde Dehydrogenase That Participates in n-Alkane Utilization and Wax Ester Synthesis in *Acinetobacter* sp. Strain M-1", Appl. Environ. Microbiol. Aug. 2000, vol. 66, Issue 8, pp. 3481-3486.
Ishige et al., "Wax Ester Production from n-Alkanes by *Acinetobacter* sp. Strain M-1: Ultrastructure of Cellular Inclusions and Role of Acyl Coenzyme A Reductase", Appl. Environ. Microbiol. Apr. 2002, vol. 68, Issue 3, pp. 1192-1195.
Jayakumar et al., "Cloning and expression of the multifunctional human fatty acid synthase and its subdomains in *Escherichia coli*", PNAS, Dec. 1996, vol. 93, pp. 14509-14514.
Johnson et al., "Genetic Analysis of the Role of *Saccharomyces cerevisiae* Acyl-CoA Synthetase Genes in Regulating Protein N-Myristoylation," Jul. 8, 1994, J. Biol. Chem. vol. 269, pp. 18037-18046.
Jones et al., "Palmitoyl-Acyl Carrier Protein (ACP) Thioesterase and the Evolutionary-Origin of Plant Acyl-ACP Thioesterases", Plant Cell, Mar. 1995, vol. 7, pp. 359-371.
Joshi et al., "Flow properties of biodiesel fuel blends at low temperatures", Jun. 2007, Fuel, vol. 86, pp. 143-151.

(56) References Cited

OTHER PUBLICATIONS

Kalscheuer et al., "A novel bifunctional wax ester synthase/acyl-CoA:diacylglycerol acyltransferase mediates wax ester and triacylglycerol biosynthesis in Acinetobacter calcoacetius ADP1" Journal of Biological Chemistry, Mar. 7, 2003, vol. 278, No. 10, pp. 8075-8082.

Kalscheuer et al., "Analysis of Storage Lipid Accumulation in Alcanivorax borkumensis:Evidence for Alternative Triacylglycerol Biosynthesis Routes in Bacteria," J. Bacteriol. Feb. 2007, vol. 189, Issue 3, pp. 918-928.

Kalscheuer et al., "Microdiesel: *Escherichia coli* engineered for fuel production," Microbiology, vol. 152, Jan. 1, 2006, pp. 2529-2536.

Kalscheuer et al., "Neutral Lipid Biosynthesis in Engineered *Escherichia coli*: Jojoba Oil-like Wax Esters and Fatty Acid Butyl Esters," Applied and Environmental Microbiology, Feb. 1, 2006, vol. 72, No. 2, pp. 1373-1379.

Kalscheuer et al., "Synthesis of Novel Lipids in *Saccharomyces Cerevisiae* by Heterologous Expression of an Unspecific Bacterial Acyltransferase" Appl. Environ. Microbiol. Dec. 2004, vol. 70, Issue 12, pp. 7119-7125.

Kameda et al., "Further purification, characterization and salt activation of acyl-CoA synthetase from *Escherichia coli*", Biochimica et Biophysica Acta, May 29, 1985, vol. 840, pp. 29-36.

Keasling et al., "Metabolic engineering delivers next-generation biofuels", Nature Biotechology, Mar. 2008, vol. 26, Issue 3, pp. 298-299.

Knoll et al., "Biochemical Studies of Three *Saccharomyces cerevisiae* Acyl-CoA Synthetases, Faalp, Faa2p, and Faa3p," J. Biol. Chem. Jun. 10, 1994, vol. 269, Issue 23, pp. 16348-16356.

Knothe et al., "Kinematic viscosity of biodiesel components (fatty acid alkyl esters) and related compounds at low temperatures," Nov. 2007, Fuel vol. 86, pp. 2560-2567.

Knothe et al., "Kinematic viscosity of biodiesel fuel components and related compounds. Influence of compound structure and comparison to petrodiesel fuel components", Jun. 2005, Fuel vol. 84, pp. 1059-1065.

Knothe, "'Designer' Biodiesel: Optimizing Fatty Ester Composition to Improve Fuel Properties," Energy & Fuels, Feb. 19, 2008, vol. 22, pp. 1358-1364.

Knothe., "Dependence of biodiesel fuel properties on the structure of fatty acid alkyl esters," Fuel Processing Technology, vol. 86, Jun. 2005, pp. 1059-1070.

Koch et al., "Effect of Antifoam Agents on the Medium and Microbial Cell Properties and Process Performance in Small and Large Reactors," Process Biochem. Accepted Jun. 23, 1994, vol. 30, Issue 5, pp. 435-446.

Kolkman et al., "Directed evolution of proteins by exon shuffling," Nat Biotechnol. May 2001, vol. 19, pp. 423-427.

Kumari et al., "Regulation of Acetyl Coenzyme A Synthetase in *Escherichia coli*", J. Bacteriol. Aug. 2000, vol. 182, Issue 15, pp. 4173-4179.

Lai et al., "Isolation and Characterization of 13-Ketoacyl-Acyl Carrier Protein Reductase (fabG) Mutants of *Escherichia coli* and *Salmonella enterica* Serovar Typhimurium," J.Bacteriology Mar. 2, 2004, vol. 186, Issue 6, pp. 1869-1878.

Lang et al., "Preparation and characterization of bio-diesels from various bio-oils", Bioresource Tech. Oct. 2001, vol. 80, pp. 53-62.

Lee et al., "Enhanced preference for .pi.-bond containing substrates is correlated to Pro110 in the substrate-binding tunnel of *Escherichia coli* thioesterase I/protease I/lysophospholipase L.sub.1" Biochim. Et Biophys. Acta, Aug. 2007, vol. 1774, pp. 959-967.

Lee et al., "Functional role of catalytic triad and oxyanion hole-forming residues on enzyme activity of *Escherichia coli* thioesterase I/proteas I/ phospholipase L1" Journal of Biochem, Jul. 1, 2006, vol. 397, pp. 69-76.

Lee et al., "Metabolic engineering of microorganisms for biofuels production: from bugs to synthetic biology to fuels", Current Opinion in Biotechnology, Nov. 2008, vol. 19, pp. 556-563.

Lee, et al., "Functional fole of catalytic tria and oxyanion hole-forming residues on enzyme activity of *Escherichia coli* thioesterase l/protease l/phospholipase L1," Biochem. J., 2006, vol. 397, pp. 69-76.

Lennen et al., "A Process for Microbial Hydrocarbon Synthesis: Overproduction of Fatty Acids in *Escherichia coli* and Catalytic Conversion to Alkane", Biotech. Bioengineering vol. 106, Jun. 1, 2010, Issue 2, pp. 193-202.

Leonard et al., "A Cuphea .beta.-ketoacyl-ACP synthase shifts the synthesis of fatty acids towards shorter chains in *Arabidopsis* seeds expressing Cuphea FatB thioesterases", Plant Journal, Mar. 1998, vol. 13, Issue 5, pp. 621-628.

Li et al., "Alteration of the Fatty Acid Profile of Streptomyces Coelicolor by Replacement of the Initiation Enzyme 3-Ketoacyl Acyl Carrier Protein Synthase III (FabH)", J. Bacteriol. Jun. 2005, vol. 187, Issue 11, pp. 3795-3799.

Li et al., "Conversion of Fatty Aldehydes to Alka(e)nes and Formate by a Cyanobacterial Aldehyde Decarbonylase: Cryptic Redox by an Unusual Dimetal Oxygenase", J. Am. Chem. Soc. Apr. 27, 2011, vol. 133, pp. 6158-6161.

Li et al., "Growth Rate Regulation of Escherichia coli Acetyl Coenzyme A Carboxylase, Which Catalyzes the First Committed Step of Lipid Biosynthesis", J. Bacteriol. Jan. 1993, vol. 175, Issue 2, pp. 332-340.

Li et al., "Purification, Characterization, and Properties of an Aryl Aldehyde Oxidoreductase from *Nocardia* sp. Strain NRRL 5646," Journal of Bacteriology, Jun. 1997, vol. 179, No. 11, pp. 3482-3487, 6 pages.

Li et al., "The Gene Encoding the Biotin Carboxylase Subunit of *Escherichia coli* Acetyl-CoA carboxylase", J.Biol.Chem. Jan. 15, 1992, vol. 267, Issue 2, pp. 855-863.

Cann et al., "Production of 2-methyl-1-butanol in engineered *Escherichia coli*," Appl. Microbiol Biotechnol. Nov. 2008, vol. 81, Issue 2, pp. 89-98.

Link et al., "Methods for Generating Precise Deletions and Insertions in the Genome of Wild-Type Escherichia coli: Application to Open Reading Frame Characterization," J. Bacteriol. Oct. 1997, vol. 179, Issue 20, pp. 6228-6237.

Liu, et al., "Production and secretion of fatty acids in genetically engineered cyanobacteria," Mar. 29, 2010, PNAS Early Edition, pp. 1-6.

Lo et al., "Substrate Specificities of *Excherichia coli* Thioesterase l/Protease l/Lysophospholipase L1 are Governed by Its Switch Loop Movement," Biochemistry, Feb. 1, 2005, vol. 44, No. 6, pp. 1971-1979.

Lu et al., "Overproduction of free fatty acids in *E. coli*: Implications for biodiesel production," Metabolic Engineering, Nov. 2008, vol. 10, pp. 333-339.

Maniatis et al., "Regulation of Inducible and Tissue-Specific Gene Expression," Science, Jun. 5, 1987, vol. 236, pp. 1237-1245.

Marr et al., "Effect of Temperature on the Composition of Fatty Acids in *Escherichia coli*", J.Bacteriol. Jul. 19, 1962, vol. 84, pp. 1260-1267.

Matsumoto et al., "Yeast whole-cell biocatalyst contructed by intracellular overproduction of Rhizopus oryzae lipase is applicable to biodiesel fuel production," Appl Microbiol Biotechnol, Nov. 2001, vol. 57, Issue 4, pp. 515-520.

Mayer et al., "Identification of amino acid residues involved in substrate specificity of plant acyl-ACP thioesterases using a bioinformatics-guided approach" BMC Plant Biology, Jan. 3, 2007, vol. 7, pp. 1-11.

Metz et al., "Purification of a Jojoba Embryo Fatty Acyl-Coenzyme A Reductase and Expression of Its eDNA in High Erucic Acid Rapeseed", Plant Physiol. Mar. 2000, vol. 122, pp. 635-644.

Miller et al., "A Highly Catalytic and Selective Conversion of Carboxylic Acids to 1-Alkenes of One Less Carbon Atom," J. Org. Chem. Jan. 1, 1993, vol. 58, Issue 1, pp. 18-20.

Mohan et al., "An *Escherichia coli* Gene (FabZ) Encoding (3R)-Hydroxymyristoyl Acyl Carrier Protein Dehydrase. Relation to fubA and Suppression of Mutations in Lipid A Biosynthesis", J.Biol.Chem. vol. 269, Issue 52, pp. 32896-32903.

(56) References Cited

OTHER PUBLICATIONS

Morgan-Kiss et al, "The *Escherichia coli* fadK (ydiD) Gene Encodes an Anerobically Regulated Short Chain Acyl-CoA Synthetase," J. Biol. Chem., Sep. 3, 2004, vol. 279, Issue 36, pp. 37324-37333.
Morgan-Kiss et al., "The Lactococcus lactis FabF Fatty Acid Synthetic Enzyme can Functionally Replace both the FabB and FabF Proteins of *Escherichia coli* and the FabH Protein of Lactococcus lactis," Arch. Microbiol. Jun. 4, 2008, vol. 190, pp. 427-437.
Murli et al., "A Role for the umuDC Gene Products of *Escherichia coli* in Increasing Resistance to DNA Damage in Stationary Phase by Inhibiting the Transition to Exponential Growth," J. Bacteriol. Feb. 2000, vol. 182, Issue 4, pp. 1127-1135.
Muthusamy et al., "Biosurfactants: Properties, commercial production and application," Current Science, Mar. 25, 2008, vol. 94, No. 6, pp. 736-747.
Naggert et al., "Cloning and sequencing of the medium-chain S-acyl fatty acid synthetase thioester hydrolase cDNA from rat mammary gland," Biochem. J. Apr. 15, 1987, vol. 243, pp. 597-601.
Nomura et al., "Expression of 3-Ketoacyl-Acyl Carrier Protein Reductase (fabG) Genes Enhances Production of Polyhydroxyalkanoate Copolymer from Glucose in Recombinant *Escherichia coli* JM109," Appl. Environ. Microbiology, Aug. 5, 2005, vol. 71, Issue 8, pp. 4297-4306.
Notice of Allowance on U.S. Appl. No. 14/826,657 dated Nov. 8, 2016, 7 pages.
Notice of Allowance on U.S. Appl. No. 14/826,657, dated Nov. 23, 2015, 9 pages.
Notice of Allowance on U.S. Appl. No. 14/826,657, dated Feb. 26, 2016, 7 pages.
Notice of Allowance on U.S. Appl. No. 15/439,053, dated Dec. 21, 2017, 8 pages.
Nunn et al., "Transport of long-chain fatty acids by *Escherichia coli*: Mapping and characterization of mutants in the fadL gene" PNAS, Jul. 1978, vol. 75, Issue 7, pp. 3377-3381.
Office Action issued on Canadian Application 2747516, dated Mar. 15, 2016, 7 pages.
Office Action issued on CN Application 201510993452.9, dated on Sep. 13, 2018, 22 pages with translation.
Office Action Issued on EP Application 09803969.6, dated Dec. 8, 2017, 4 pages.
Office Action issued on ID Application W00201102255, dated Jan. 17, 2019, 3 pages with translation.
Office Action issued on U.S. Appl. No. 12/645,497, dated Feb. 29, 2012, 6 pages.
Office Action issued on U.S. Appl. No. 14/826,657, dated Jun. 10, 2016, 7 pages.
Office Action issues on U.S. Appl. No. 12/645,497, dated Oct. 7, 2013, 17 pages.
Office Action on BR Application, dated Jan. 23, 2019, 15 pages, translation of the relevant parts of written opinion.
Office Action on CA Application 2747516, dated Mar. 27, 2017, 4 pages.
Office Action on EP Application 09803969.6, dated Sep. 24, 2015, 7 pages
Office Action on EP Application 19161705.9, dated Apr. 4, 2019, 1 page.
Office Action on IN Application 5606/DELNP/2011, dated Sep. 20, 2017, 10 pages with translation.
Office Action on U.S. Appl. No. 12/645,497, dated Apr. 24, 2015, 7 pages.
Office Action on U.S. Appl. No. 12/645,497, dated Jan. 12, 2015, 19 pages.
Office Action on U.S. Appl. No. 12/645,497, dated Sep. 15, 2011, 14 pages.
Office Action on U.S. Appl. No. 15/439,053, dated Aug. 11, 2017, 7 pages.
Peng et al., "Effect of fadR gene knockout on the metabolism of *Escherichia coli* based on analyses of protein expressions, enzyme activities and intracellular metabolite concentrations" Enzyme and Microbial Tech. Feb. 2006, vol. 38, pp. 512-520.
Perez et al., "*Escherichia coli* YqhD Exhibits Aldehyde Reductase Activity and Protects from the Harmful Effect of Lipid Peroxidation-derived Aldehydes" J. Biol. Chem. Mar. 21, 2008, vol. 283, Issue 12, pp. 7346-7353.
Pillai et al., "Functional characterization of .beta.-ketoacyl-ACP reductase (FabG) from Plasmodium falciparum" Biochem. and Biophysical Research, Mar. 18, 2003, Comm. 303, pp. 387-392.
Qiu et al., "Crystal structure and substrate specificity of the .beta.-ketoacyl-acyl carrier protein synthase III (FabH) from *Staphylococcus aureus*," Aug. 2005, Protein Science, vol. 14, pp. 2087-2094.
Rawlings et al., "Biosynthesis of fatty acids and related metabolites", Natural Product Reports, Jul. 15, 1998, pp. 275-308.
Rawlings et al., "The Gene Encoding *Escherichia coli* Acyl Carrier Protein Lies within a Cluster of Fatty Acid Biosynthetic Genes", J.Biol.Chem. Mar. 25, 1992, vol. 26, Issue 9, pp. 5751-5754.
Ray et al., "Activation of long chain fatty acids with acyl carrier protein: Demonstration of a new enzyme, acyl-acyl carrier protein synthetase, in *Escherichia coli*" PNAS, Dec. 1976, vol. 73, Issue 12, pp. 4374-4378.
Rehm et al., "Heterologous expression of the acyl-acyl carrier protein thioesterase gene from the plant Umbellularia californica mediates polyhydroxyalkanoate biosynthesis in recombinant *Escherichia coli*", Appl. Microbiol. And Biotech. Feb. 9, 2001, vol. 55, pp. 205-209.
Reid et al., "Sucrose utilisation in bacteria: genetic organisation and regulation," Appl Microbial Biotechnol. May 2005, vol. 67, pp. 312-321.
Reiser et al., "Isolation of Mutants of Acinetobacter calcoaceticus Deficient in Wax Ester Synthesis of Complementation of One Mutation with a Gene Encoding a Fatty Acyl Coenzyme A Reductase," J. Bacteriol. May 1997, vol. 179, Issue 9, pp. 2969-2975.
Ren et al., "FabG, an NADPH-Dependent 3-Ketoacyl Reductase of *Pseudomonas aeruginosa*, Provides Precursors for Medium-Chain-Length Poly-3-Hydroxyalkanoate Biosynthesis in *Escherichia coli*", J. Bacteriol. vol. 182, Issue 10, May 2010, pp. 2978-2981.
Rock et al., "Acyl-Acyl Carrier Protein Synthetase from *Escherichia coli*", Meth.Enzymol. Jul. 12, 1981, vol. 71, pp. 163-168.
Romero et al., "Metabolic Engineering of Bacillus Subtilis for Ethanol Production: Lactate Dehydrogenase Plays a Key Role in Fermentative Metabolism", Applied & Environmental Microbiology, Aug. 10, 2007, vol. 73, Issue 16, pp. 5190-5198.
Rudd, K.E.,"Multifunctional acyl-CoA thioesterase I an protease I and lysophospholipase L1 [*Escherichia coli* str. K-12 substr. MG1655]", GenBank Database, May 17, 2008, Accession No. NP_415027, 1-14.
Rude et al., "New microbial fuels: a biotech perspective", Current Opinion in Microbiology, Jun. 2009, vol. 12, pp. 274-281.
Rude et al., "Terminal Olefin (1-Alkene) Biosynthesis by a Novel P450 Fatty Acid Decarboxylase from *Jeotgalicoccus* Species", Appl. Environ. Microbiol., vol. 77, No. 5, Mar. 2011, pp. 1718-1727.
Sabirova et al., "Mutation in a "tesB-Like" Hydroxyacyl-Coenzyme A-Specific Thioesterase Gene Causes Hyperproduction of Extracellular Polyhydroxyalkanoates by Alcanivorax borkumensis SK2," J. Bacteriol. Dec. 2006, vol. 188, Issue 23, pp. 8452-8459.
Saito et al., "Crystal structure of enoyl-acyl carrier protein reductase (FabK) from *Streptococcus neumonia* reveals the binding mode of an inhibitor", Protein Science, Jan. 2, 2008, Issue 17, pp. 691-699.
Salas et al., "Characterization of substrate specificity of plant FatA and FatB acyl-ACP thioesterases," Archives of Biochem. and Biophysics, Aug. 2002, vol. 403, pp. 25-34.
Sanchez et al., "Effect of Overexpression of a Soluble Pyridine Nucleotide Transhydrogenase (UdhA) on the Production of Poly(3-hydroxybutyrate) in *Escherichia coli*", Mar.-Apr. 2006, Biotechnol. Prog. vol. 22, pp. 420-425.
Schirmer et al., "Microbial Biosynthesis of Alkanes", Science, vol. 329, Jul. 30, 2010, pp. 559-562.
Schujman et al., "A malonyl-CoA-dependent switch in the bacterial response to a dysfunction of lipid metabolism," Molecular Microbiology, Jun. 2008, vol. 68 Issue 4, pp. 987-996.
Schweizer et al., "Microbial Type I Fatty Acid Synthases (FAS): Major Players in a Network of Cellular FAS Systems", Microbiol. Mol.Biol.Rev. Sep. 2004, vol. 68, Issue 3, pp. 501-517.

(56) References Cited

OTHER PUBLICATIONS

Shahid et al., "A review of biodiesel as vehicular fuel", Renew. Sustain.Ener.Reviews, Dec. 2008, vol. 12, pp. 2484-2494.
Shimada et al., "Enzymatic alcoholysis for biodiesel fuel production and application of the reaction to oil processing",(Review), J. Mol. Ctal. B: Enzym. Jun. 7, 2002, vol. 17, pp. 133-142.
Shockey et al., "*Arabidopsis* Contains Nine Long-Chain Acyl-Coenzyme A Synthetase Genes that Participate in Fatty Acid and Glycerolipid Metabolism," Plant Physiology, Aug. 2002, vol. 129, pp. 1710-1722.
Spencer et al., "Thioesterases I and II of *Escherichia coli*," J. Biol. Chem. Sep. 10, 1978, vol. 253, Issue 17, pp. 5922-5926.
Stoveken et al., "The Wax Ester Synthase/Acyl Coenzyme A:Diacylglycerol Acyltransferase from *Acinetobacter* sp. Strain ADP1: Characterization of a Novel Type of Acyltransferase", J. Bacteriology, Feb. 2005, vol. 187, Issue 4, pp. 1369-1376.
Subrahmanyam et al., "Overproduction of a Functional Fatty Acid Biosynthetic Enzyme Blocks Fatty Acid Synthesis in *Escherichia coli*," J. Bacteriol. Sep. 1998, vol. 180, Issue 17, pp. 4596-4602.
Sukovich et al., "Widespread Head-to-Head Hydrocarbon Biosynthesis in Bacteria and Role of OleA", Appl. Environ. Microbiology, Jun. 4, 2010, vol. 76, Issue 12, pp. 3850-3862.
Sulzenbacher et al., "Crystal Structure of *E. coli* Alcohol Dehydrogenase YqhD: Evidence of a Covalently Modified NADP Coenzyme," J. Mol. Biol. Sep. 10, 2004, vol. 342, pp. 489-502.
Ta et al., "Cloning, Sequencing, and Overexpression oaf [2Fe—2S] Ferredoxin Gene from *Escherichia coli*", J. Biol. Chem. Jun. 5, 1992, vol. 267, Issue 16, pp. 11120-11125.
Teerawanichpan et al., "Fatty Acyl-CoA Reductase and Wax Synthase from Euglena gracilis in the Biosynthesis of Medium-Chain Wax Esters", Mar. 2010, Lipids 45, Issue 3, pp. 263-273.
Thomason et al., "Identification of the *Escherichia coli* K-12 ybhE Gene as pgl, Encoding 6-Phosphogluconolactonase" J.Bacteriol. Dec. 2004, vol. 186, Issue 24, pp. 8248-8253.
Thorpe et al., "Structure and mechanism of action of the Acyl-CoA dehydrogenases," FASEB J. Jun. 1995, vol. 9, pp. 718-725.
Tong et al., "Acetyl-Coenzyme A Carboxylases: Versatile Targets for Drug Discovery," J. Cellular Biochem. Dec. 15, vol. 2006, Issue 99, pp. 1476-1488.
Toomey et al., "Studies on the Mechanism of Fatty Acid Synthesis XVI. Preparation and General Properties of Acyl-Malonyl Acyl Carrier Proteincondensing Enzyme From *Escherichia coli*," J. Biol. Chem. Mar. 10, 1966, vol. 241, Issue 5, pp. 1159-1165.
Trinh et al., "Design, construction and performance of the most efficient biomass producing *E. coli* bacterium" Metabolic Engineering, Nov. 2006, vol. 8, Issue 6, pp. 628-638.
Tsay et al., "Isolation and Characterization of the .beta.-Ketoacyl-acyl Carrier Protein Synthase I11 Gene (fabH) from *Escherichia coli* K-12", J.Biol.Chem. Apr. 5, 1992, vol. 267, Issue 10, pp. 6807-6814.
UniProt accession No. Q325A2 "Subname: Full=Acyl-CoA thioesterase I" (2005), 1 page.
Uthoff et al., "Thio Wax Ester Biosynthesis Utilizing the Unspecific Bifunctional Wax Ester Synthase/Acyl Coenzyme A: Diacylglycerol Acyltransferase of *Acinetobacter* sp. Strain ADP1," Appl. Environ. Microbial. Feb. 3, 2005, vol. 71, Issue 2, pp. 790-796.

Vadali et al., "Cofactor engineering of intracellular CoA/acetyl-CoA and its effect on metabolic flux redistribution in *Escherichia coli*," Metabolic Engineering, Apr. 2004, vol. 6, pp. 133-139.
Van Der Meer et al., "Compound-Specific Isotopic Fractionation Patterns Suggest Different Carbon Metabolisms among Chloroflexus-Like Bacteria in Hot-Spring Microbial Mats," Appl. Environ. Microbiology, Oct. 6, 2003, vol. 69, Issue 10, pp. 6000-6006.
Venturi, "Regulation of quorum sensing in Pseudomonas," FEMS Microbiol. Rev., Mar. 2006, vol. 30, pp. 274-291.
Voelker et al., "Alteration of the Specificity and Regulation of Fatty Acid Synthesis of *Escherichia coli* by Expression of a Plant Medium-Chain Acyl-Acyl Carrier Protein Thioesterase," J. Bacteriol. Dec. 1994, vol. 176, Issue 23, pp. 7320-7327.
Waltermann et al., "Key enzymes for biosynthesis of neutral lipid storage compounds in prokaryotes: Properties, function and occurrence of wax ester synthases/acyl-CoA: diacylglycerol acyltransferases," Biochemie, Mar. 2007, vol. 89, Issue 2, pp. 1-13.
International Search Report and Written Opinion for PCT/US2007/011923, dated Feb. 22, 2008, 18 pages.
Yang et al. "Efficient Method for the Synthesis of Chiral Pyrrolidine Derivatives via Ring-Closing Enyne Metathesis Reaction", Organic Letters, Mar. 1, 2007, vol. 9, No. 5, pp. 769-771.
Yang Fan et al., "Genome dynamics and diversity of *Shigella* species, the etiologic agents of bacillary dysentery," Nucleic Acids Research, Oxford University Press, Jan. 1, 2005, vol. 33, No. 19, pp. 6445-6458.
Zhang et al., "Inhibiting Bacterial Fatty Acid Synthesis", J.Biol. Chem. Jun. 2006, vol. 281, Issue 26, pp. 17541-17544.
Zhang et al., "Structural Basis for Catalytic and Inhibitory Mechanisms of .beta.-Hydroxyacyl-acyl Carrier Protein Dehydratase (FabZ)", J.Biol.Chem. Feb. 29, 2008, vol. 283, Issue 9, pp. 5370-5379.
Zhang et al., "The FabR (YijC) Transcription Factor Regulates Unsaturated Fatty Acid Biosynthesis in *Escherichia coli*\*," J. Biol. Chem. May 3, 2002, vol. 277, Issue 18, pp. 15558-15565.
Zhang et al, "Transcriptional Analysis of Essential Genes of the *Escherichia coli* Fatty Acid Biosynthesis Gene Cluster by Functinoal Replacement with the Analougous *Salmonella typhimurium* Gene Cluster, "J. Bacteriol., Jul. 1998, vol. 180, pp. 3295-3303.
Zhang Hanxing et al., "Molecular effect of FadD on the regulation and metabolism of fatty acid in *Escherichia coli*.", FEMS Microbiology Letters, Jun. 2006, vol. 259, No. 2, pp. 249-253.
Zheng et al., "Evaluation of Different Biomass Materials as Feedstock for Fermentable Sugar Production", Appl. Biochem. Biotech. Apr. 2007, vol. 137 pp. 423-436.
Zhu et al., "Functions of the Clostridium acetobutylicium FabF and FabZ proteins in unsaturated fatty acid biosynthesis", BMC Microbiology Jun. 4, 2009, vol. 9, pp. 119-218.
Zimhony et al., "Characterization of *Mycobacterium smegmatis* Expressing the Mycobacterium tuberculosis Fatty Acid Synthase I (fas1) Gene", J.Bacteriol. Jul. 2004, vol. 186, Issue 13, pp. 4051-4055.
Substantive Examination Report Stage II in ID Patent Application No. P00201902582 dated Jul. 29, 2020 (3 pages).
Substantive Examination Report Stage I on ID P00201902582 dated Mar. 27, 2020 (with English translation) (3 pages).

\* cited by examiner

FIG. 1

Accession Numbers are from NCBI, GenBank, Release 159.0 as of March 2008
EC Numbers are from KEGG, Release 42.0 as of April 2007 (plus daily updates up to March 2008)

| CATEGORY | GENE | NAME | ACCESSION | EC NUMBER | MODIFICATION | USE | ORGANISM |
|---|---|---|---|---|---|---|---|
| 1. Fatty Acid Production Increase / Product Production Increase | | | | | | | |
| increase acyl-CoA | | | | | | | |
| reduce catabolism of derivatives and intermediates | | | | | | | |
| reduce feedback inhibition | | | | | | | |
| attenuate other pathways that consume fatty acids | | | | | | | |
| | accA | Acetyl-CoA carboxylase, subunit A (carboxyltransferase alpha) | AAC73296, NP_414727 | 6.4.1.2 | Over-express | increase Malonyl-CoA production | Escherichia coli, Lactococci |
| | accB | Acetyl-CoA carboxylase, subunit B (BCCP: biotin carboxyl carrier protein) | NP_417721 | 6.4.1.2 | Over-express | increase Malonyl-CoA production | Escherichia coli, Lactococci |
| | accC | Acetyl-CoA carboxylase, subunit C (biotin carboxylase) | NP_417722 | 6.4.1.2, 6.3.4.14 | Over-express | increase Malonyl-CoA production | Escherichia coli, Lactococci |
| | accD | Acetyl-CoA carboxylase, subunit D (carboxyltransferase | NP_416819 | 6.4.1.2 | Over-express | increase Malonyl-CoA production | Escherichia coli, Lactococci |

FIG. 1 Cont.

| | | | | | |
|---|---|---|---|---|---|
| aceE | pyruvate dehydrogenase, subunit E1 (beta) | NP_414656, AAC73226 | 1.2.4.1 | Over-express | increase Acetyl-CoA production | Escherichia coli |
| aceF | pyruvate dehydrogenase, subunit E2 | NP_414657 AAC75356, NP_416799 | 2.3.1.12 | Over-express | increase Acetyl-CoA production | Escherichia coli |
| ackA | acetate kinase | BAB81430 | 2.7.2.1 | Delete or reduce | increase Acetyl-CoA production | Escherichia coli |
| ackB | acetate kinase AckB | AAC74178 | 2.7.2.1 | Delete or reduce | increase Acetyl-CoA production | Escherichia coli |
| acpP | acyl carrier protein | AP_002424 | NONE | Over-express | increase Acetyl-CoA production | Escherichia coli |
| fadD | acyl-CoA synthase | CAA47743 | 2.3.1.86, 6.2.1.3 | Over-express | increase Fatty acid production | Escherichia coli W3110 |
| adhE | alcohol dehydrogenase | BAA11024 | 1.1.1.1, 1.2.1.10 | Delete or reduce | increase Acetyl-CoA production | Escherichia coli W3111 |
| cer1 | Aldehyde decarbonylase | NP_415474 | 4.1.99.5 | Over-express | increase Acetyl-CoA production | Arabidopsis thaliana |
| fabA | beta-hydroxydecanoyl thioester dehydrase | AAC74176 | 4.2.1.60 | express | fatty acyl-CoA production | E. coli K12 |
| fabD | [acyl-carrier-protein] S-malonyltransferase | AAC74179 | 2.3.1.39 | Over-express | increase Acetyl-CoA production | E. coli K12 |
| fabF | 3-oxoacyl-[acyl-carrier-protein] synthase II | AAC74177 | 2.3.1.179 | Delete or OverExpress | increase Acetyl-CoA production | E. coli K12 |
| fabG | 3-oxoacyl-[acyl-carrier protein] reductase | | 1.1.1.100 | Over-express | increase Acetyl-CoA production | E. coli K12 |

FIG. 1 Cont.

| | | | | | |
|---|---|---|---|---|---|
| fabH | 3-oxoacyl-[acyl-carrier-protein] synthase III | AAC74175 | 2.3.1.180 | Over-express | increase Acetyl-CoA production | E. coli K12, lactococci |
| fabI | enoyl-[acyl-carrier-protein] reductase, NADH-dependent | NP_415804 | 1.3.1.9 | express | fatty acyl-CoA production | E. coli K12, lactococci |
| fabR | Transcriptional Repressor | NP_418398 | NONE | Delete or reduce | modulate unsaturated fatty acid production | E. coli K12 |
| fabZ | (3R)-hydroxymyristol acyl carrier protein dehydratase | NP_414722 | 4.2.1.- | | | E. coli K12 |
| fadE | acyl-CoA dehydrogenase | AAC73325 | 1.3.99.3, 1.3.99.- | Delete or reduce | increase Acetyl-CoA production | |
| acr1 | Fatty Acyl-CoA reductase | YP_047869, AAC45217 | 1.2.1.42 | Over-express | for fatty alcohol production | Acinetobacter sp., i.e. calcoaceticus |
| GST, gshB | Glutathione synthase | P04425 | 6.3.2.3 | Delete or reduce | increase Acyl-CoA | E. coli K12 |
| gpsA | biosynthetic sn-glycerol 3-phosphate dehydrogenase | AAC76632, NP_418065 | EC: 1.1.1.94 | Delete or reduce | increase Acetyl-CoA production | E. coli K12 |
| ldhA | lactate dehydrogenase | AAC74462, NP_415898 | EC: 1.1.1.27, 1.1.1.28 | Delete or reduce | increase Acetyl-CoA production | E. coli K12 |
| Lipase | Triglyceride Lipase | CAA89087, CAA98876 | 3.1.1.3 | express | increase Fatty acid production | Saccharomyces cerevisiae |
| | Malonyl-CoA decarboxylase | AAA26500 | 4.1.1.9, 4.1.1.41 | Over-express | | Saccharopolyspora erythraea |

FIG. 1 Cont.

| | | | | | |
|---|---|---|---|---|---|
| panD | aspartate 1-decarboxylase | BAB96708 | 4.1.1.11 | Over-express | increase Acyl-CoA | Escherichia coli W3110 |
| panK a.k.a. coaA | pantothenate kinase | AAC76952 | 2.7.1.33 | Over-express | increase Acetyl-CoA production | E. coli |
| panK a.k.a. coaA, R106K | pantothenate kinase | AAC76952 | 2.7.1.33 | Express, Over-express, R106K mutation | increase Acetyl-CoA production | E. coli |
| pdh | Pyruvate dehydrogenase | BAB34380, AAC73226, NP_415392 | 1.2.4.1 | Over-express | increase Acetyl-CoA production | |
| pflB | formate acetyltransferase (pyruvate formate lyase) | AAC73989, P09373 | EC: 2.3.1.54 | Delete or reduce | increase Acetyl-CoA production | |
| plsB | acyltransferase | AAC77011 | 2.3.1.15 | D311E mutation | reduce limits on Acyl-CoA pool | E. coli K12 |
| poxB | pyruvate oxidase | AAC73958, NP_415392 | 1.2.2.2 | Delete or reduce | increase Acetyl-CoA production | |
| pta | phosphotransacetylase | AAC75357, NP_416800 | 2.3.1.8 | Delete or reduce | increase Acetyl-CoA production | |
| udhA | pyridine nucleotide transhydrogenase | CAA46822 | 1.6.1.1 | Over-express | conversion NADH to NADPH or vice versa | |
| | fused 3-hydroxybutyryl-CoA epimerase/delta(3)-cis-delta(2)-trans-enoyl-CoA isomerase/enoyl-CoA hydratase and 3-hydroxyacyl-CoA | | 4.2.1.17, 5.1.2.3, 5.3.3.8, 1.1.1.35 | | | |
| fadB | | AP_003956 | | Delete or reduce | Block fatty acid degradation | E. coli |

FIG. 1 Cont.

| | | | | | | |
|---|---|---|---|---|---|---|
| | | dehydrogenase | | | | |
| | fadJ | 3-hydroxyacyl-CoA dehydrogenase; K01692 enoyl-CoA hydratase; K01782 3-hydroxybutyryl-CoA epimerase | AAC75401 | 1.1.1.35, 4.2.1.17, 5.1.2.3 | Delete or reduce | Block fatty acid degradation | E. coli |
| | fadA | 3-ketoacyl-CoA thiolase | BAE77458 | 2.3.1.16 | Delete or reduce | Block fatty acid degradation | E. coli |
| | fadI | beta-ketoacyl-CoA thiolase | AAC75402 | 2.3.1.16 | Delete or reduce | Block fatty acid degradation | E. coli |
| | YdiO | acyl-coA dehydrogenase | YP_852786 | 1.3.99.- | Delete or reduce | Block fatty acid degradation | E. coli |

2. Structure Control

2A. Chain Length Control

| | | | | | | | |
|---|---|---|---|---|---|---|---|
| 2 | tesA | thioesterase | P0ADA1 | 3.1.2.-; 3.1.1.5 | Delete and/or express | C18 Chain Length | |
| | tesA without leader sequence | thioesterase | AAC73596, NP_415027 | 3.1.2.-; 3.1.1.5 | express or overexpress | C18:1 | E.coli |
| | tesA without leader sequence:L109P | thioesterase | P0ADA1 | 3.1.2.-; 3.1.1.5 | Express and/or overexpress mutation L109P | <C18 Chain Length | E. coli |

FIG. 1 Cont.

| | | | | | |
|---|---|---|---|---|---|
| fatB1 (umbellularia) | thioesterase | Q41635 | 3.1.2.14 | express or overexpress | C12:0 | Umbellularia californica |
| fatB2 (umbellularia)DELETE umbelluria) | thioesterase | AAC49269 | 3.1.2.14 | express or overexpress | C8:0 - C10:0 | Cuphea hookeriana |
| fatB3 | thioesterase | AAC72881 | 3.1.2.14 | express or overexpress | C14:0 - C16:0 | Cuphea hookeriana |
| fatB (cinnamonum) | thioesterase | Q39473 | 3.1.2.14 | express or overexpress | C14:0 | Cinnamomum camphora |
| fatB[M141T]* | thioesterase | CAA85388 | 3.1.2.14 | express or overexpress | C16:1 | Arabidopsis thaliana |
| fatA1 (Helianthus) | thioesterase | AAL79361 | 3.1.2.14 | express or overexpress | C18:1 | Helianthus annuus |
| atfata (ARABIDOPSIS FATA ACYL-ACP THIOESTERASE) | thioesterase | NP_189147, NP_193041 | 3.1.2.14 | express or overexpress | C18:1 | Arabidopsis thaliana |
| fatA | thioesterase | CAC39106 | 3.1.2.14 | express or overexpress | C18:1 | Brassica juncea |
| fatA (cuphea) | thioesterase | AAC72883 | 3.1.2.14 | express or overexpress | C18:1 | Cuphea hookeriana |
| 2B. Branching Control | | | | | | |
| attenuate FabH | | | | | | |

FIG. 1 Cont.

| | | | | | |
|---|---|---|---|---|---|
| express FabH from S. glaucescens or S. coelicolor and knock out endogenouse FabH | | | | | |
| express FabH from B. subtilis and knock out endogenouse FabH | | | | increase branched chain fatty acid derivatives | |
| bdk - E3 - dihydroplipoyl dehyrodgenase subunit | decarboxylase subunits of branched-chain α-keto acid dehydrogenase complex | | EC 1.2.4.4 | | |
| bkd - E1 - alpha/beta subunit | | | EC 1.2.4.4 | | |
| bkd - E2 - dihydrolipoyl transacylase subunit | | | EC 1.2.4.4 | | |
| bkdA1 | branched-chain α-keto acid dehydrogenase a-subunit (E1a) | NP_628006 | EC 1.2.4.4 | express or Over-Express | make branched-chain acyl-CoA precursors | Streptomyces coelicolor |
| bkdB1 | branched-chain α-keto acid dehydrogenase a- | NP_628005 | EC 1.2.4.4 | express or Over-Express | make branched-chain acyl-CoA | Streptomyces coelicolor |

FIG. 1 Cont.

| | | | | | precursors | |
|---|---|---|---|---|---|---|
| | subunit (E1b) | | | | | |
| bkdC1 | dihydrolipoyl transacetylase (E2) | NP_628004 | EC 2.3.1.168 | express or Over-Express | make branched-chain acyl-CoA precursors | Streptomyces coelicolor |
| bkdA2 | branched-chain a-ketoacid dehydrogenase a-subunit (E1a) | NP_733618 | EC 1.2.4.4 | express or Over-Express | make branched-chain acyl-CoA precursors | Streptomyces coelicolor |
| bkdB2 | branched-chain a-ketoacid dehydrogenase b-subunit (E1b) | NP_628019 | EC 1.2.4.4 | express or Over-Express | make branched-chain acyl-CoA precursors | Streptomyces coelicolor |
| bkdC2 | dihydrolipoyl transacetylase (E2) | NP_628018 | EC 2.3.1.168 | express or Over-Express | make branched-chain acyl-CoA precursors | Streptomyces coelicolor |
| bkdA | branched-chain a-ketoacid dehydrogenase a-subunit (E1a) | BAC72074 | EC 1.2.4.4 | express or Over-Express | make branched-chain acyl-CoA precursors | Streptomyces avermitilis |
| bkdB | branched-chain a-ketoacid dehydrogenase b-subunit (E1b) | BAC72075 | EC 1.2.4.4 | express or Over-Express | make branched-chain acyl-CoA precursors | Streptomyces avermitilis |
| bkdC | dihydrolipoyl transacetylase (E2) | BAC72076 | EC 2.3.1.168 | express or Over-Express | make branched-chain acyl-CoA precursors | Streptomyces avermitilis |
| bkdF | branched-chain a-ketoacid dehydrogenase a- | BAC72088 | EC 1.2.4.4 | express or Over-Express | make branched-chain acyl-CoA precursors | Streptomyces avermitilis |

FIG. 1 Cont.

| | | | | | |
|---|---|---|---|---|---|
| bkdG | branched-chain a-ketoacid dehydrogenase b-subunit (E1b) | BAC72089 | EC 1.2.4.4 | express or Over-Express | make branched-chain acyl-CoA precursors | *Streptomyces avermitilis* |
| bkdH | dihydrolipoyl transacetylase (E2) | BAC72090 | EC 2.3.1.168 | express or Over-Express | make branched-chain acyl-CoA precursors | *Streptomyces avermitilis* |
| bkdAA | branched-chain a-ketoacid dehydrogenase a-subunit (E1a) | NP_390285 | EC 1.2.4.4 | express or Over-Express | make branched-chain acyl-CoA precursors | *Bacillus subtilis* |
| bkdAB | branched-chain a-ketoacid dehydrogenase b-subunit (E1b) | NP_390284 | EC 1.2.4.4 | express or Over-Express | make branched-chain acyl-CoA precursors | *Bacillus subtilis* |
| bkdB | dihydrolipoyl transacetylase (E2) | NP_390283 | EC 2.3.1.168 | express or Over-Express | make branched-chain acyl-CoA precursors | *Bacillus subtilis* |
| bkdA1 | branched-chain a-ketoacid dehydrogenase a-subunit (E1a) | AAA65614 | EC 1.2.4.4 | express or Over-Express | make branched-chain acyl-CoA precursors | *Pseudomonas putida* |
| bkdA2 | branched-chain a-ketoacid dehydrogenase b-subunit (E1b) | AAA65615 | EC 1.2.4.4 | express or Over-Express | make branched-chain acyl-CoA precursors | *Pseudomonas putida* |
| bkdC | dihydrolipoyl transacetylase (E2) | AAA65617 | EC 2.3.1.168 | express or Over-Express | make branched-chain acyl-CoA precursors | *Pseudomonas putida* |

FIG. 1 Cont.

| | | | | | precursors | |
|---|---|---|---|---|---|---|
| lpd | dihydrolipoamide dehydrogenase (E3) | NP_414658 | 1.8.1.4 | express or Over-Express | make branched-chain acyl-CoA precursors | Escherichia coli |
| IlvE | branched-chain amino acid aminotransferase | YP_026247 | 2.6.1.42 | express or Over-Express | make branched a-ketoacids | Escherichia coli |
| IlvE | branched-chain amino acid aminotransferase | AAF34406 | 2.6.1.42 | express or Over-Express | make branched a-ketoacids | Lactococcus lactis |
| IlvE | branched-chain amino acid aminotransferase | NP_745648 | 2.6.1.42 | express or Over-Express | make branched a-ketoacids | Pseudomonas putida |
| IlvE | branched-chain amino acid aminotransferase | NP_629657 | 2.6.1.42 | express or Over-Express | make branched a-ketoacids | Streptomyces coelicolor |
| ccr | crotonyl-CoA reductase | NP_630556 | 1.6.5.5, 1.1.1 | express or Over-Express | Converting crotonyl-CoA to butyryl-CoA | Streptomyces coelicolor |
| ccr | crotonyl-CoA reductase | AAD53915 | 1.6.5.5, 1.1.1 | express or Over-Express | Converting crotonyl-CoA to butyryl-CoA | Streptomyces cinnamonensis |
| IcmA, isobutyryl-CoA mutase | isobutyryl-CoA mutase, subunit A | NP_629554 | 5.4.99.2 | express or Over-Express | converting butyryl-CoA to isobutyryl-CoA | Streptomyces coelicolor |
| IcmA, isobutyryl-CoA mutase | isobutyryl-CoA mutase, subunit A | AAC08713 | 5.4.99.2 | express or Over-Express | converting butyryl-CoA to isobutyryl-CoA | Streptomyces cinnamonensis |
| IcmB, isobutyryl-CoA mutase | isobutyryl-CoA mutase, subunit B | NP_630904 | 5.4.99.2 | express or Over-Express | converting butyryl-CoA to isobutyryl-CoA | Streptomyces coelicolor |

FIG. 1 Cont.

| | | | | | |
|---|---|---|---|---|---|
| IcmB, isobutyryl-CoA mutase | isobutyryl-CoA mutase, subunit B | CAB59633 | 5.4.99.2 | express or Over-Express | converting butyryl-CoA to isobutyryl-CoA | *Streptomyces cinnamonensis* |
| FabH, ACPs and fabF genes with specificity for branched chain acyl-CoAs | | | | | | |
| IlvE | branched-chain amino acid aminotransferase | CAC12788 | EC 2.6.1.42 | over express | branched chain amino acid amino transferase | Staphylococcus carnosus |
| FabH1 | beta-ketoacyl-ACP synthase III | NP_626634 | 2.3.1.180 | express or Over-Express | initiation of branched-chain fatty acid biosynthesis | *Streptomyces coelicolor* |
| ACP | acyl-carrier protein | NP_626635 | NONE | express or Over-Express | initiation and elongation of branched-chain fatty acid biosynthesis | *Streptomyces coelicolor* |
| FabF | beta-ketoacyl-ACP synthase II | NP_626636 | 2.3.1.179 | express or Over-Express | elongation of branched-chain fatty acid biosynthesis | *Streptomyces coelicolor* |
| FabH3 | beta-ketoacyl-ACP synthase III | NP_823466 | 2.3.1.180 | express or Over-Express | initiation of branched-chain fatty acid biosynthesis | *Streptomyces avermitilis* |

FIG. 1 Cont.

| | | | | | |
|---|---|---|---|---|---|
| FabC3 (ACP) | acyl-carrier protein | NP_823467 | NONE | express or Over-Express | initiation and elongation of branched-chain fatty acid biosynthesis | *Streptomyces avermitilis* |
| FabF | beta-ketoacyl-ACP synthase II | NP_823468 | 2.3.1.179 | express or Over-Express | elongation of branched-chain fatty acid biosynthesis | *Streptomyces avermitilis* |
| FabH_A | beta-ketoacyl-ACP synthase III | NP_389015 | 2.3.1.180 | express or Over-Express | initiation of branched-chain fatty acid biosynthesis | *Bacillus subtillis* |
| FabH_B | beta-ketoacyl-ACP synthase III | NP_388898 | 2.3.1.180 | express or Over-Express | initiation of branched-chain fatty acid biosynthesis | *Bacillus subtillis* |
| ACP | acyl-carrier protein | NP_389474 | NONE | express or Over-Express | initiation and elongation of branched-chain fatty acid biosynthesis | *Bacillus subtillis* |
| FabF | beta-ketoacyl-ACP synthase II | NP_389016 | 2.3.1.179 | express or Over-Express | elongation of branched-chain fatty acid biosynthesis | *Bacillus subtillis* |
| SmalDRAFT_0818 | beta-ketoacyl-ACP synthase III | ZP_01643059 | 2.3.1.180 | express or Over-Express | initiation of branched-chain fatty acid biosynthesis | *Stenotrophomonas maltophilia* |

FIG. 1 Cont.

| | | | | | |
|---|---|---|---|---|---|
| SmalDRAFT_08 21 | acyl-carrier protein | ZP_01643063 | NONE | express or Over-Express | initiation and elongation of branched-chain fatty acid biosynthesis | Stenotrophomonas maltophilia |
| SmalDRAFT_08 22 | beta-ketoacyl-ACP synthase II | ZP_01643064 | 2.3.1.179 | express or Over-Express | elongation of branched-chain fatty acid biosynthesis | Stenotrophomonas maltophilia |
| FabH | beta-ketoacyl-ACP synthase III | YP_123672 | 2.3.1.180 | express or Over-Express | initiation of branched-chain fatty acid biosynthesis | Legionella pneumophila |
| ACP | acyl-carrier protein | YP_123675 | NONE | express or Over-Express | initiation and elongation of branched-chain fatty acid biosynthesis | Legionella pneumophila |
| FabF | beta-ketoacyl-ACP synthase II | YP_123676 | 2.3.1.179 | express or Over-Express | elongation of branched-chain fatty acid biosynthesis | Legionella pneumophila |
| FabH | beta-ketoacyl-ACP synthase III | NP_415609 | 2.3.1.180 | delete or reduce | initiation of branched-chain fatty acid biosynthesis | Escherichia coli |
| FabF | beta-ketoacyl-ACP synthase II | NP_415613 | 2.3.1.179 | delete or reduce | elongation of branched-chain fatty acid biosynthesis | Escherichia coli |

FIG. 1 Cont.

*To Produce Cyclic Fatty Acids*

| | | | | | |
|---|---|---|---|---|---|
| AnsJ | dehydratase (putative) | not available | not available | express or Over-Express | cyclohexylcarbonyl-CoA boiosynthesis | *Streptomyces collinus* |
| AnsK | CoA ligase (putative) | not available | not available | express or Over-Express | cyclohexylcarbonyl-CoA boiosynthesis | *Streptomyces collinus* |
| AnsL | dehydrogenase (putative) | not available | not available | express or Over-Express | cyclohexylcarbonyl-CoA boiosynthesis | *Streptomyces collinus* |
| ChcA | enoyl-CoA reductase | U72144 | EC 1.3.1.34 | express or Over-Express | cyclohexylcarbonyl-CoA boiosynthesis | *Streptomyces collinus* |
| AnsM | oxidorecutase (putative) | not available | not available | express or Over-Express | cyclohexylcarbonyl-CoA boiosynthesis | *Streptomyces collinus* |
| PlmJ | dehydratase (putative) | AAQ84158 | not available | express or Over-Express | cyclohexylcarbonyl-CoA boiosynthesis | *Streptomyces sp. HK803* |
| PlmK | CoA ligase (putative) | AAQ84158 | not available | express or Over-Express | cyclohexylcarbonyl-CoA boiosynthesis | *Streptomyces sp. HK803* |
| PlmL | dehydrogenase (putative) | AAQ84159 | not available | express or Over-Express | cyclohexylcarbonyl-CoA boiosynthesis | *Streptomyces sp. HK803* |
| ChcA | enoyl-CoA reductase | AAQ84160 | EC 1.3.1.34 | express or Over-Express | cyclohexylcarbonyl-CoA boiosynthesis | *Streptomyces sp. HK803* |
| PlmM | oxidorecutase (putative) | AAQ84161 | not available | express or Over-Express | cyclohexylcarbonyl-CoA boiosynthesis | *Streptomyces sp. HK803* |

FIG. 1 Cont.

| | | | | | |
|---|---|---|---|---|---|
| | ChcB | enoyl-CoA isomerase | AF268489 | not available | express or Over-Express | cyclohexylcarbonyl-CoA boiosynthesis | Streptomyces collinus |
| | ChcB/CaiD | enoyl-CoA isomerase | NP_629292 | 4.2.1.- | express or Over-Express | cyclohexylcarbonyl-CoA boiosynthesis | Streptomyces coelicolor |
| | ChcB/CaiD | enoyl-CoA isomerase | NP_824296 | 4.2.1.- | express or Over-Express | cyclohexylcarbonyl-CoA boiosynthesis | Streptomyces avermitilis |
| 2C. Saturation Level Control | | | | | | | |
| | Sfa | Suppressor of FabA | AAN79592, AAC44390 | NONE | Over-express | increase monounsaturated fatty acids | E.coli |
| also see FabA in sec. 1 | | | | | express | produce unsaturated fatty acids | |
| | GnsA | suppressors of the secG null mutation | ABD18647.1 | NONE | Over-express | increase unsaturated fatty acid esters | E.coli |
| | GnsB | suppressors of the secG null mutation | AAC74076.1 | NONE | Over-express | increase unsaturated fatty acid esters | E.coli |

FIG. 1 Cont.

| | also see section 2A - items with :0 are unsaturated (no double bonds) and with :1 are saturated (1 double bond) | | | | | |
|---|---|---|---|---|---|---|
| | fabB | 3-oxoacyl-[acyl-carrier-protein] synthase I | BAA16180 | EC:2.3.1.41 | overexpress | modulate unsaturated fatty acid production | Escherichia coli |
| | fabK | trans-2-enoyl-ACP reductase II | AAF98273 | 1.3.1.9 | express | modulate unsaturated fatty acid production | Streptococcus pneumoniae |
| | fabL | enoyl-(acyl carrier protein) reductase | AAU39821 | 1.3.1.9 | express | modulate unsaturated fatty acid production | Bacillus licheniformis DSM 13 |
| | fabM | trans-2, cis-3-decenoyl-ACP isomerase | DAA05501 | 4.2.1.17 | Over-express | modulate unsaturated fatty acid production | Streptococcus mutans |
| Fatty Aldehyde Output | | | | | | | |
| | thioesterase | see chain length control section | | | express | produce | |
| Export | | | | | | | |

FIG. 1 Cont.

| Wax ester exporter (FATP family, Fatty Acid (long chain) Transport Protein) | | | | | |
|---|---|---|---|---|---|
| | ABC transport protein | putative alkane transporter | NP_524723 | NONE | express | export wax | Drosophila melanogaster |
| | | | AAN73268 | NONE | express | export products | Rhodococcus erythropolis |
| | CER5 | wax transporter | At1g51500, AY734542, At3g21090, At1g51460 | NONE | express | | Arabidopsis thaliana |
| | AtMRP5 | Arabidopsis thaliana multidrug resistance-associated | NP_171908 | NONE | express | export products | Arabidopsis thaliana |
| | AmiS2 | ABC transporter AmiS2 | JC5491 | NONE | express | export products | Rhodococcus sp. |
| | AtPGP1 | ARABIDOPSIS THALIANA P GLYCOPROTEIN1 | NP_181228 | NONE | express | export products | Arabidopsis thaliana |
| | AcrA | putative multidrug-efflux transport protein acrA | CAF23274 | NONE | express | export products | Candidatus Protochlamydia amoebophila UWE25 |
| | AcrB | probable multidrug-efflux transport protein, acrB | CAF23275 | NONE | express | export products | Candidatus Protochlamydia amoebophila UWE25 |
| | TolC | Outer membrane protein [Cell envelope | ABD59001 | NONE | express | export products | Francisella t

FIG. 1 Cont.

| | | | | | | novicida |
|---|---|---|---|---|---|---|
| | AcrE | transmembrane protein affects septum formation and cell membrane permeability | YP_312213 | NONE | express | Shigella sonnei Ss046 |
| | AcrF | Acriflavine resistance protein F | P24181 | NONE | express | Escherichia coli |
| | tll1618 | multidrug efflux transporter | NP_682408.1 | NONE | express | Thermosynechococcus elongatus BP-1] |
| | tll1619 | multidrug efflux transporter | NP_682409.1 | NONE | express | Thermosynechococcus elongatus BP-1] |
| | tll0139 | multidrug efflux transporter | NP_680930.1 | NONE | export products | Thermosynechococcus elongatus BP-1] |
| 5. Fermentation | | | | | | |
| | replication checkpoint genes | | | | | increase output efficiency |
| | umuD | DNA polymerase V, subunit | YP_310132 | 3.4.21.- | Over-express | Shigella sonnei Ss046 |
| | umuC | DNA polymerase V, subunit | ABC42261 | 2.7.7.7 | Over-express | Escherichia coli |

FIG. 1 Cont.

| NADH:NADPH transhydrogenase (alpha and beta subunits) (pntA, pntB) | P07001; P0AB70 | 1.6.1.2 | express | increase output efficiency | Shigella flexneri |
|---|---|---|---|---|---|

Concentrations of free fatty acids (FFA) and fatty acid ethyl esters (FAEE) produced from three individual colonies of C41 (DE3, ΔfadEΔfabR)/ pETDuet-1-tesA + pCDFDuet-1-fadD +pHZ1.97_atfA2 t

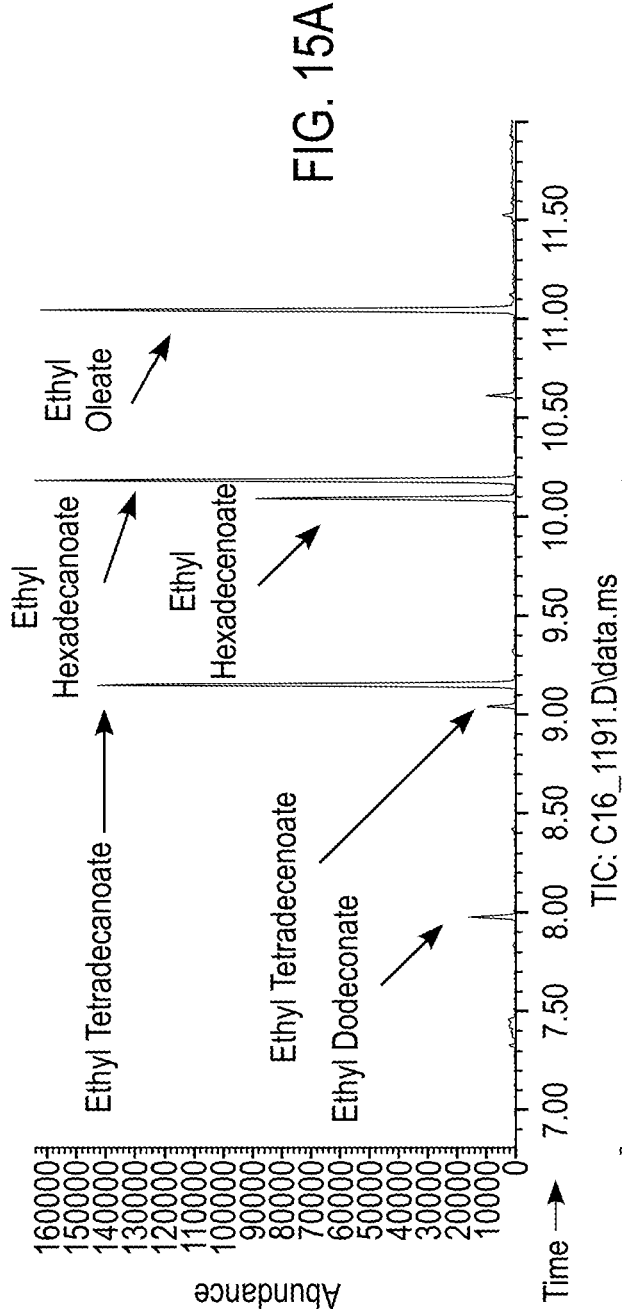
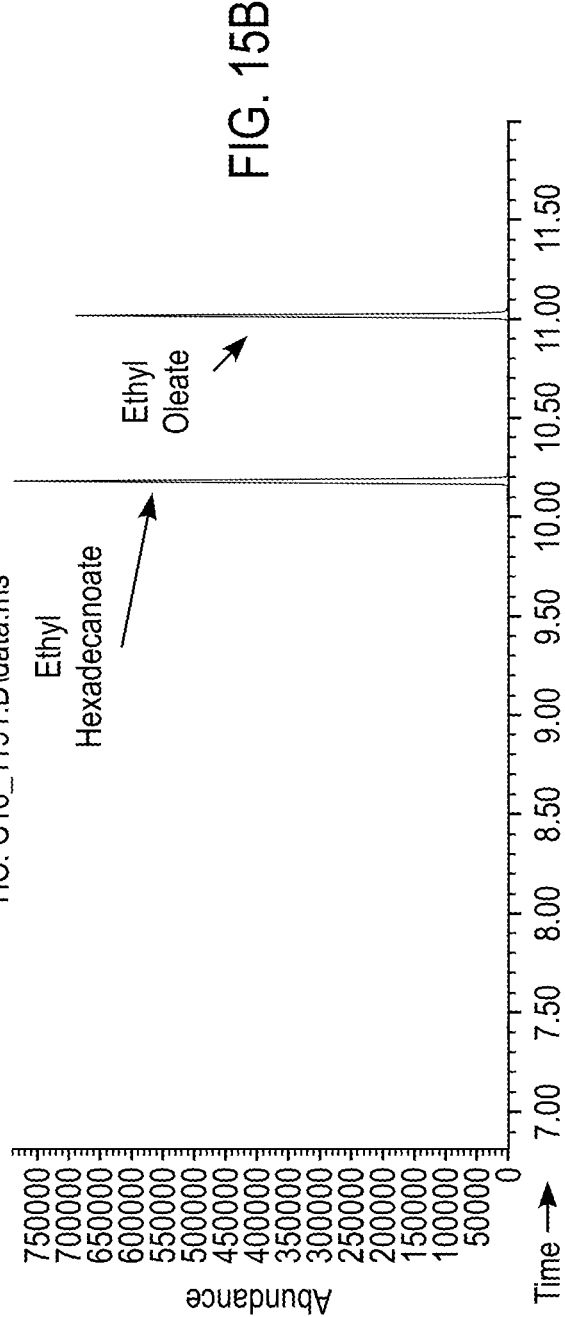
FIG. 15A
FIG. 15B

FIG. 17

SEQ ID NO:1 - DNA SEQUENCE OF EXPRESSION VECTOR POP-80

```
CACTATACCA ATTGAGATGG GCTAGTCAAT GATAATTACT AGTCCTTTTC CTTTGAGTTG
TGGGTATCTG TAAATTCTGC TAGACCTTTG CTGGAAAACT TGTAAATTCT GCTAGACCCT
CTGTAAATTC CGCTAGACCT TTGTGTGTTT TTTTTGTTTA TATTCAAGTG GTTATAATTT
ATAGAATAAA GAAAGAATAA AAAAAGATAA AAAGAATAGA TCCCAGCCCT GTGTATAACT
CACTACTTTA GTCAGTTCCG CAGTATTACA AAAGGATGTC GCAAACGCTG TTTGCTCCTC
TACAAAACAG ACCTTAAAAC CCTAAAGGCG TCGGCATCCG CTTACAGACA AGCTGTGACC
GTCTCCGGGA GCTGCATGTG TCAGAGGTTT TCACCGTCAT CACCGAAACG CGCGAGGCAG
CAGATCAATT CGCGCGCGAA GGCGAAGCGG CATGCATTTA CGTTGACACC ATCGAATGGT
GCAAAACCTT TCGCGGTATG GCATGATAGC GCCCGGAAGA GAGTCAATTC AGGGTGGTGA
ATGTGAAACC AGTAACGTTA TACGATGTCG CAGAGTATGC CGGTGTCTCT TATCAGACCG
TTTCCCGCGT GGTGAACCAG GCCAGCCACG TTTCTGCGAA AACGCGGGAA AAAGTGGAAG
CGGCGATGGC GGAGCTGAAT TACATTCCCA ACCGCGTGGC ACAACAACTG GCGGGCAAAC
AGTCGTTGCT GATTGGCGTT GCCACCTCCA GTCTGGCCCT GCACGCGCCG TCGCAAATTG
TCGCGGCGAT TAAATCTCGC GCCGATCAAC TGGGTGCCAG CGTGGTGGTG TCGATGGTAG
AACGAAGCGG CGTCGAAGCC TGTAAAGCGG CGGTGCACAA TCTTCTCGCG CAACGCGTCA
GTGGGCTGAT CATTAACTAT CCGCTGGATG ACCAGGATGC CATTGCTGTG GAAGCTGCCT
GCACTAATGT TCCGGCGTTA TTTCTTGATG TCTCTGACCA GACACCCATC AACAGTATTA
TTTTCTCCCA TGAAGACGGT ACGCGACTGG GCGTGGAGCA TCTGGTCGCA TTGGGTCACC
AGCAAATCGC GCTGTTAGCG GGCCCATTAA GTTCTGTCTC GGCGCGTCTG CGTCTGGCTG
GCTGGCATAA ATATCTCACT CGCAATCAAA TTCAGCCGAT AGCGGAACGG GAAGGCGACT
GGAGTGCCAT GTCCGGTTTT CAACAAACCA TGCAAATGCT GAATGAGGGC ATCGTTCCCA
CTGCGATGCT GGTTGCCAAC GATCAGATGG CGCTGGGCGC AATGCCGCGC ATTACCGAGT
CCGGGCTGCG CGTTGGTGCG GATATCTCGG TAGTGGGATA CGACGATACC GAAGACAGCT
CATGTTATAT CCCGCCGTTA ACCACCATCA AACAGGATTT TCGCCTGCTG GGGCAAACCA
GCGTGGACCG CTTGCTGCAA CTCTCTCAGG GCCAGGCGGT GAAGGCCAAT CAGCTGTTGC
```

FIG. 17 Cont.

```
CCGTCTCACT GGTGAAAAGA AAAACCACCC TGGCGCCCAA TACGCAAACC GCCTCTCCCC
GCGCGTTGGC CGATTCATTA ATGCAGCTGG CACGACAGGT TTCCCGACTG GAAAGCGGGC
AGTGAGCGCA ACGCAATTAA TGTAAGTTAG CGCGAATTGA TCTGGTTTGA CAGCTTATCA
TCGACTGCAC GGTGCACCAA TGCTTCTGGC GTCAGGCAGC CATCGGAAGC TGTGGTATGG
CTGTGCAGGT CGTAAATCAC TGCATAATTC GTGTCGCTCA AGGCGCACTC CCGTTCTGGA
TAATGTTTTT TGCGCCGACA TCATAACGGT TCTGGCAAAT ATTCTGAAAT GAGCTGTTGA
CAATTAATCA TCCGGCTCGT ATAATGTGTG GAATTGTGAG CGGATAACAA TTTCACACAG
GAAACAGCGC CGCTGAGAAA AAGCGAAGCG GCACTGCTCT TTAACAATTT ATCAGACAAT
CTGTGTGGGC ACTCGACCGG AATTATCGAT TAACTTTATT ATTAAAAATT AAAGAGGTAT
ATATTAATGT ATCGATTAAA TAAGGAGGAA TAAACCATGG ATCCGAGCTC GAGATCTGCA
GCTGGTACCA TATGGGAATT CGAAGCTTGG GCCCGAACAA AAACTCATCT CAGAAGAGGA
TCTGAATAGC GCCGTCGACC ATCATCATCA TCATCATTGA GTTTAAACGG TCTCCAGCTT
GGCTGTTTTG GCGGATGAGA GAAGATTTTC AGCCTGATAC AGATTAAATC AGAACGCAGA
AGCGGTCTGA TAAAACAGAA TTTGCCTGGC GGCAGTAGCG CGGTGGTCCC ACCTGACCCC
ATGCCGAACT CAGAAGTGAA ACGCCGTAGC GCCGATGGTA GTGTGGGGTC TCCCCATGCG
AGAGTAGGGA ACTGCCAGGC ATCAAATAAA ACGAAAGGCT CAGTCGAAAG ACTGGGCCTT
TCGTTTTATC TGTTGTTTGT CGGTGAACGC TCTCCTGACG CCTGATGCGG TATTTTCTCC
TTACGCATCT GTGCGGTATT TCACACCGCA TATGGTGCAC TCTCAGTACA ATCTGCTCTG
ATGCCGCATA GTTAAGCCAG CCCCGACACC CGCCAACACC CGCTGACGAG CTTAGTAAAG
CCCTCGCTAG ATTTTAATGC GGATGTTGCG ATTACTTCGC CAACTATTGC GATAACAAGA
AAAAGCCAGC CTTTCATGAT ATATCTCCCA ATTTGTGTAG GGCTTATTAT GCACGCTTAA
AAATAATAAA AGCAGACTTG ACCTGATAGT TTGGCTGTGA GCAATTATGT GCTTAGTGCA
TCTAACGCTT GAGTTAAGCC GCGCCGCGAA GCGGCGTCGG CTTGAACGAA TTGTTAGACA
TTATTTGCCG ACTACCTTGG TGATCTCGCC TTTCACGTAG TGGACAAATT CTTCCAACTG
ATCTGCGCGC GAGGCCAAGC GATCTTCTTC TTGTCCAAGA TAAGCCTGTC TAGCTTCAAG
TATGACGGGC TGATACTGGG CCGGCAGGCG CTCCATTGCC CAGTCGGCAG CGACATCCTT
CGGCGCGATT TTGCCGGTTA CTGCGCTGTA CCAAATGCGG GACAACGTAA GCACTACATT
```

FIG. 17 Cont.

```
TCGCTCATCG CCAGCCCAGT CGGGCGGCGA GTTCCATAGC GTTAAGGTTT CATTTAGCGC
CTCAAATAGA TCCTGTTCAG GAACCGGATC AAAGAGTTCC TCCGCCCGCTG GACCTACCAA
GGCAACGCTA TGTTCTCTTG CTTTTGTCAG CAAGATAGCC AGATCAATGT CGATCGTGGC
TGGCTCGAAG ATACCTGCAA GAATGTCATT GCGCTGCCAT TCTCCAAATT GCAGTTCGCG
CTTAGCTGGA TAACGCCACG GAATGATGTC GTCGTGCACA ACAATGGTGA CTTCTACAGC
GCGGAGAATC TGCTCTCTC CAGGGGAAGC CGAAGTTTCC AAAAGGTCGT TGATCAAAGC
TCGCCGCGTT GTTTCATCAA GCCTTACGGT CACCGTAACC AGCAAATCAA TATCACTGTG
TGGCTTCAGG CCGCCATCCA CTGCGGAGCC GTACAAATGT ACGGCCAGCA ACGTCGGTTC
GAGATGGCGC TCGATGACGC CAACTACCTC TGATAGTTGA GTCGATACTT CGGCGATCAC
CGCTTCCCTC ATGATGTTTA ACTTTGTTTT AGGGCGACTG CCCTGCTGCG TAACATCGTT
GCTGCTCCAT AACATCAAAC ATCGACCCAC GGCGTAACGC GCTTGCTGCT TGGATGCCCG
AGGCATAGAC TGTACCCCAA AAAAACAGTC ATAACAAGCC ATGAAAACCG CCACTGCGCC
GTTACCACCG CTGCGTTCGG TCAAGGTTCT GGACCAGTTG CGTGAGCGCA TACGCTACTT
GCATTACAGC TTACGAACCG AACAGGCTTA TGTCCACTGG GTTCGTGCCT TCATCCGTTT
CCACGGTGTG CGTCACCCGG CAACCTTGGG CAGCAGCGAA GTCGAGGCAT TTCTGTCCTG
GCTGGCGAAC GAGCGCAAGG TTTCGGTCTC CACGCCATCGT CAGGCATTGG CGGCCTTGCT
GTTCTTCTAC GGCAAGGTGC TGTGCACGGA TCTGCCCCTG CTTCAGGAGA TCGGAAGACC
TCGGCCCGTCG CGGCCTTGC CGGTGGTGCT GACCCCGGAT GAAGTGGTTC GCATCCTCGG
TTTTCTGGAA GGCGAGCATC GTTTGTTCGC CCAGCTTCTG TATGGAACGG GCATGCGGAT
CAGTGAGGGT TTGCAACTGC GGGTCAAGGA TCTGGATTTC GATCACGGCA CGATCATCGT
GCGGGAGGGC AAGGGCTCCA AGGATCGGGC CTTGATGTTA CCCGAGAGCT TGGCACCCAG
CCTGCGCGAG CAGGGGAATT AATTCCCACG GGTTTTGCTG CCCGCAAACG GGCTGTTCTG
GTGTTGCTAG TTTGTTATCA GAATCGCAGA TCCGGCTTCA GCCGGTTTGC CGGCTGAAAG
```

FIG. 17 Cont.

```
CGCTATTTCT TCCAGAATTG CCATGATTTT TTCCCCACGG GAGGCGTCAC TGGCTCCCGT
GTTGTCGGCA GCTTTGATTC GATAAGCAGC ATCGCCTGTT TCAGGCTGTC TATGTGTGAC
TGTTGAGCTG TAACAAGTTG TCTCAGGTGT TCAATTTCAT GTTCTAGTTG CTTTGTTTTA
CTGGTTTCAC CTGTTCTATT AGGTGTTACA TGCTGTTCAT CTGTTACATT GTCGATCTGT
TCATGTGAA CAGCTTTGAA TGCACCAAAA ACTCGTAAAA GCTCTGATGT ATCTATCTTT
TTTACACCGT TTTCATCTGT GCATATGGAC AGTTTCCCT TTGATATGTA ACGGTGAACA
GTTGTTCTAC TTTTGTTTGT TAGTCTTGAT GCTTCACTGA TAGATACAAG AGCCATAAGA
ACCTCAGATC CTTCCGTATT TAGCCAGTAT GTTCTCTAGT GTGGTTCGTT GTTTTTGCGT
GAGCCATGAG AACGAACCAT TGAGATCATA CTTACTTTGC ATGTCACTCA AAAATTTGC
CTCAAAACTG GTGAGCTGAA TTTTTGCAGT TAAAGCATCG TGTAGTGTTT TTCTTAGTCC
GTTATGTAGG TAGGAATCTG ATGTAATGGT TGTTGGTATT TTGTCACCAT TCATTTTTAT
CTGGTTGTTC TCAAGTTCGG TTACGAGATC CATTTGTCTA TCTAGTTCAA CTTGGAAAAT
CAACGTATCA GTCGGGCGGC CTCGCTTATC AACCACCAAT TTCATATTGC TGTAAGTGTT
TAAATCTTTA CTTATTGGTT TCAAAACCCA TTGGTTAAGC CTTTTAAACT CATGGTAGTT
ATTTTCAAGC ATTAACATGA ACTTAAATTC ATCAAGGCTA ATCTCTATAT TTGCCTTGTG
AGTTTTCTTT TGTGTTAGTT CTTTTAATAA CCACTCATAA ATCCCTCATAG AGTATTTGTT
TTCAAAAGAC TTAACATGTT CCAGATTATA TTTTATGAAT TTTTTAACT GGAAAAGATA
AGGCAATATC TCTTCACTAA AAACTAATTC TAATTTTTCG CTTGAGAACT TGGCATAGTT
TGTCCACTGG AAAATCTCAA AGCCTTTAAC CAAAGGATTC CTGATTTCCA CAGTTCTCGT
CATCAGCTCT CTGGTTGCTT TAGCTAATAC ACCATAAGCA TTTTCCCTAC TGATGTTCAT
CATCTGAGCG TATTGGTTAT AAGTGAACGA TACCGTCCGT TCTTTCCTTG TAGGGTTTTC
AATCGTGGGG TTGAGTAGTG CCACACAGCA TAAAATTAGC TTGGTTTCAT GCTCCGTTAA
GTCATAGCGA CTAATCGCTA GTTCATTTGC TTTGAAAACA ACTAATTCAG ACATACATCT
CAATTGGTCT AGGTGATTTT AAT
```

FIG. 18

SEQ ID NO:2- DNA sequence of *E.coli* codon-optimized gene *fadD35* from *Mycobacterium tuberculosis* HR7Rv

```
CCATGGCAGC AGCGGAAGTG GTTGATCCAA ATCGTCTGAG CTATGATCGT GGCCCGAGCG CGCCGAGCCT
GTTGGAGAGC ACCATCGGTG CAAACCTGGC CGCTACGGCG GCCCGTTACG GCCACCCGGA GGCCCTGGTG
GACATGGTCG CACCGCCGTCG CTTCAATTAT AGCGAGCTGC TGACGGATGT TCACCGTTTG GCTACGGGCC
TGGTGCCTGC TGGTATTGGC CCAGGCGACC GTGTGGGTAT TTGGGCGCCG AATCGTTGGG AGTGGGTTCT
GGTCCAGTAT GCAACGGCGG AGATTGGTGC GATCCTGGTT ACGATTAACC CGGCTTATCG CGTGCGTGAG
GTTGAATACG CGCTGCGTCA ATCTGGCGTC GCGATGGTCA TTGCGGTTGC GTCCTTCAAG GACGCTGATT
ACGCTGCGAT GCTGGCGGAG GTTGCCCGC CCTGGCTGAC GTGATCCTGT TGGAAAGCGA CCGCCTGATC
CCGTTGGGAC GCACTGGCAG GTGCCCGAGC GGATCTGCCG GCGCGTACCG AGACCGCTGC CCGCCTGAGC
GGTTCCGATC CGGTTAACAT CCTTATTTGG TTGGTGAGCT GTTGGGTTAT ACGGCGCAGG ATCGTATTTG
ACCGCAATAT CCGTTCTACC ACTGCTTTGG TATGGTCATG GGCAACTTGG CGGCGACCTC CCACGGTGCG
CATCCCGGTG TTCCGGCGCC AGGTTTCGAC CCAGCGGCTA TTGCAGAACT GGGTCTGCCG GGTGCAAGAT GAACGCTGTA
CGTCTCTGTA CGGCGTTCCG ACCATGTTTA CGGCAGG CGCAGCCGTGT CCGGTTGAAG TCATGCGTAA AGTGATCAGC
GGGTTCTTTG CGTACCGGCA TCATGGCAGG CAGCATTTGC TACGGTATGA CCGAGACCGAG CCCGGTGAGC ACCCAAACCC
CGTATGCACA TGCCGGGTGT CGTCGTGTGG GCACCCGTTG GCACCCGTCC CCGCACCTGG AAATTAAAGT
GTGCGGACGA TAGCGTGAC CGCGGTTCC GCGCGGTGTT GTTGGCGAAT TTTGCACGCG TGGCTACTCT
TGTTGACCCA GCGACCGGCG GTTATTGGAA TGACCCGCAG AAAACGGCAG AGGTGATCGA CGCTGATGGT TGGATGCATA
GTCATGGCGG GTTATTGGAA TGACCCGCAG AAAACGGCAG GTTACGTTCG TATTGCAGGC CGCATTAAAG ACCTGGTGGT
CCGGTGACCT GGCGGAAATG GACCCGCGTGA AATTGAGGAG CTGCTGCATA CCCATCCGGA CATCGTTGAT
TCGTGGCGGT GAGAACATTA GCCCGCGTGA AATTGAGGAG CTGCTGCATA CCCATCCGGA CATCGTTGAT
GGTCACGTGA TCGGTGTTCC GGATGCGAAA TATGGCGAAG AGCTGATGGC AGTTGTGAAG CTGCGTAATG
ATGCGCCGGA GTTGACGATT GAACGCCTGC GTGAGTATTG CATGGGTCGC ATCGCACGCT TTAAAATCCC
GCGCTACTTG TGGATCGTTG ACGAGTTCCC GATGACCGTG ACCGGCAAGG TCCGTAAGGT CGAGATGCGT
CAGCAGGCAT TGGAATATCT GCGTGGGTCAA CAGTAAGAAT TC
```

FIG. 19

SEQ ID NO:3-DNA sequence of E.coli codon-optimized gene fadD1 from Pseudomonas aeruginosa PAO1

```
TCATGATCGA GAATTTTTGG AAGGACAAGT ATCCGGCAGG TATTGCAGCA GAAATTAATC CGGATCAGTA
TCCGAATATT CTGAGCGTCC TGAAGGAGAG CTGCCAACGT TTTGCCGACCA AGCCGGGCGTT TACGAACTTG
GGTAAGACCT TGACCTATGG TGAGCTGTAC AAACTGTCTG GCGACTTCGC AGCGTACCTG CAACAACATA
CCGATCTGAA ACCGGGTGAT CGTATTGCCG TTCAGCTGCC GAACGTTCTG CAGTGTCCGA TCGTTGTCTT
CGGCGCAATG CGTGCGGGTC TGATCGTGGT GAACACGAAC CCGTTGTATA CGGCGCGTGA GTTGGAACAC
CAGTTTAATG ATAGCGGCGC AAAAGCGGTG CAGGTGATTG CTAATATGGC CCACCTGGTT GAAGGTGTTT
TGCCGAAGAC CGGTGTTAAA CAGGTGATTG TCACCGAGGT GGGCGACATT CCTGCCACGC TGAAGCGTTT
CATTGTCAAT TTCGTCGTCA AACACATTAA GAAGATGGTC CCGGCCTATT CCCTGCCGCA GGCCACGTCG
TTGACCGATG CACTGGCCCG TGGTGCAGGC AAGAGCTTCC AAGAAGCGGC ACCGCAGGCA GACGACGTCG
CGGTGCTGCA GTACACCGGC GGTACCACGG GCGTGCGATG GGGTCGCGAAC CTGACCCATC GTAACCTGGT
CGCTAACATG TTGCAGTGTA AAGCGCTGAT GGGTGCGAAC CTGAACGAGG GTTGCGAAAT CTTGATTGCC
CCGTGCCGC TGTATCACAT TTATGCGTTT ACCTTCCACT GTATGGCTAT GATGCTGACG GGTAATCATA
ACATTCTGAT CACCAATCCG CGCGACCTGC CGAGCATGCT GAAGGACCTG GGTCAGTGGA AGTTCACGGG
TTTCGTGGGT CTGAATACGC TGTTCGTCGC GCTGTGCAAT AATGAGACCT TCCGTAAGCT GGACTTTAGC
GCACTGAAGC TGACCCTGAG CGGCGGCATG GCGCTGCAGC TGGCCACGGC GGAACGTTGG AAAGAGGTCA
CGGGCTGCGC TATTTGCGAG GGTTATGGTA TGACCGAAAC GGCCCCGGTG GTTTCCGTCA ACCCGTTTCA
GAACATTCAA GTTGGCACCA TCGGTATTCC GGTGCCAAGC ACCTTGTGTA AGGTTATTGG CGATGACGGT
CAAGAAGTTC CGCTGGGCGA GCGCGGTGAA GCGCGGTCCGA AGGGTCCGCA GGTTATGAAG GGCTACTGGC
AGCGCCAGGA GGCAACGGAC GAGATTCTGG ACGCTGATGG TTGGTTGAAA ACCGGCGATA TTGCAATTAT
TCAAGAAGAC GGCTATATGC GCATTGTCGA TCGTGTCGAA GACATGATTT TGGTTAGCGG TTTCAACGTT
TACCCGAATG AATTGGAAGA TGTTTTGGCG ACCTTGCCGG GTGTGCTGCA ATGCGCAGCG ATCGGTATCC
CGGATGAAAA GAGCGGCGAG TCTATCAAGG TTTTCGTTGT TGTGAAGCCG GGTGCGACCC TGACCAAAGA
GCAGGTCATG CAGCATATGC ACGATAACCT GACCGGCTAC AAACGCCCGA AAGCAGTGGA GTTCCGTGAT
AGCCTGCCAA CGACCAATGT TGGCAAGATT TTGCGTCGTG AGCTGCGCGA TGAAGAGCTG AAAAAGGCAG
GCCAGAAGTA AGAATTC
```

FIG. 20

SEQ ID NO:4-the BsyhfLBspHIF primer based on the DNA sequence deposited at NCBI with the accession code NC_000964.

CATCATGAATCTTGTTTC

FIG. 21

SEQ ID NO:5-the BsyhfIEcoR primer based on the DNA sequence deposited at NCBI with the accession code NC_000964.

CGGAATTCTTATTGGGGCAAAATATC

FIG. 22

SEQ ID NO:6-DNA sequence of the *Bacillus subtilis yhfL* gene.

```
TCATGAATCT TGTTTCAAAA TTGGAAGAAA CAGCCATCTGA GAAGCCCGAC AGCATGCGAT GCAGGTTTAA
AGATCACATG ATGACGTATC AAGAGCTGAA TGAATATATT CAGCGGATTTG CGGACGGCCT TCAGGAAGCC
GGTATGGAGA AAGGGGACCA TTTAGCTTTG CTGCTTGGCA ATTCGCCTGA GTTGTACACG TTTTATCATC GCGTTTTTTG
GCGCTTTAAA AGCTGGGATC GTAGTTGTTC CCATCAATCC GTTGTACACG CCGACAGAAA TTGGTTATAT
GCTGACAAAT GGCGATGTAA AGGCAATCGT GGGCGTTAGC CAGCTTTTGC CGCTTTATGA GAGCATGCAT
GAATCGCTGC CAAAGGTTGA GCTCGTCATT TTATGCCAGA CGGGGGAGGC CGAGCCGGAA GCTGCGGACC
CAGAGGTCAG GATGAAAATG ACAACGTTTG CAAAAATATT GCGGCCGACA TCTGCCGCTA AACAAAACCA
AGAACCTGTA CCTGATGATA CCGCGGTTAT TTTATATACG TCAGGAACGA CTGGAAAACC GAAAGGCGCG
ATGCTGACAC ATCAGAATTT GTACAGCAAT GCCAACGATG TCGCAGGCTA TTTGGGAATG GATGAGAGGG
ACAATGTGGT CTGCGCTCTT CCCATGTGTC ACGTGTTTTG TTTAACCGTC TGTATGAAAG CACCGCTGAT
GAGCGCGCA ACTGTATTGA ATTCAGTCCG GCATCTGTTT TTAAGCTTGT TAAGCAGCAG
CAGGCGACCA TTTTTGCCGG TGTGCCTACA ATGTATAACT ACTTGTTTCA GCATGAAAAC GGAAAGAAAG
ATGATTTTTC TTCGATCCGG CTGTGCATTT CGGGAGGCGC GTCCATGCCA GTCGCGTTGC TGACGGCGTT
TGAAGAAAAA TTCGGTGTTA CCATTTTGGA AGGCTACGGG CTCTCCGAAG CATCACCCGT CACGTGCTTT
AACCCGTTTG ACAGGGGCAG AAAGCCGGGC TCCATCGGGA CAAGTATCTT ACATGTCGAA AACAAGGTCG
TAGATCCGCT CGGACGCGAG CTGCCCCGCTC ACCAGGTCGG CGAATTGATC GTGAAAGGCC CCAATGTGAT
GAAGGGCTAT TATAAAAATGC CGATGGAAAC AGAGCATGCA TTAAAAGACG GGTGGCTTTA TACGGGGGAC
TTGGCAAGAC GGGATGAGGA CGGCTATTTT TACATTGTTG ACCGGAAAAA AGACATGATC ATTGTAGGAG
GATACAATGT GTATCCGCCG GAGGTGGAGG AGTGCTGTA CAGCCATCCG GACGTCAAGG AGGCGGTTGT
CATCGGCGTG CCGGACCCCC AAAGCGGGGA AGCGGGTAAA AGCGGTAAAG TGCCGAAACG CTCTGGGTA
ACAGAGGAGG ACATCATGCA GCACTGCGAA AAGCATCTGG CAAAATACAA GCGGCCTGCC GCCATTACGT
TTCTTGACGA TATTCCGAAA AATGCCGACGG GGAAAATGCT CAGACGGGCA CTGAGAGATA TTTTGCCCCA
ATAAGAATTC
```

FIG. 23

SEQ ID NO:7-the Scfaa3pPciF primer designed based on the DNA sequence deposited at NCBI with the accession code NC_001141.

CGACATGTCCGAACAACAC

FIG. 24

SEQ ID NO:8 - the Scfaa3pPCII primer designed based on the DNA sequence deposited at NCBI with the accession code NC_001141.

GCAAGCTTCTAAGAATTTTCTTTG

FIG. 25

SEQ ID NO:9 - DNA sequence of the faa3p structural gene from Saccharomyces cerevisiae.

```
TCATGAGTCT GGATCGTCCC TGGCTGCAGA GCTATCCGAA AGGCGTTCCC GCCGAAATCG ACGTCAACGA
ATTCCATTCG GTCGCCTCGG TCTTCGACGC TTCCGTCGCG AAATTCCGCG ACCGTCCCGC CTACTCCAGC
TTCGGCAAGG TCCTCACCTA TGGTGAGACG GACGCGCTGG TCACCCAGTT CGCCGCCTAC CTGCTGGGTG
AGCTCAAGCT CAAGAAGGGT GACCGCGTCG CCCTGATGAT GCCCAACTGC CTGCAGTACC CGGTGGCCAC
CTTCGGGGTG CTGCGCGCCG GCCTGACCGT GGTCAACGTC AACCCGCTGT ACACCCGGCG CGAACTCAAG
CACCAGCTGG TTGATGCCGG CGTCAGCGCC CTGGTGGTGG TCGACAACTT CGGCGACACC GTCGAACAGG
TCATCGCCGA TACACCGGTC AAGCACGTGG TCACCACCGG CCTGGGCGAC CTGCTCGGCG CCAAGGGCGC
GATCGTCAAC TTCGTGCTGA AGTACATCAA GAAGATGGTG CCCAACTACC ACATCAAGGG CGCCGTCCGC
TTCAAGCAGG CGCTCAAGCT GGGCAGCCGC CACGCGCTTC CGCCGGTCGA GATCGACCAC GACGACATTG
CCTTCCTGCA GTACACCGGC GGGACCACCG GCGTGCCAA GGGTGCGATG CTGACCAACC GCAACCTGAT
CGCCAACATG CAGCAGGCGT CAGCGTGGCT GTCCACCTCC GGCATCGAGC CGGGCAAGGA AGTGATCATC
ACTGCCCTGC CGCTGTACCA CATCTTCGCA TTGACCGCGA ACGGGCCTGGT CTTTATGAAG TTCGGTGGCT
GCAACCACCT GATCACCAAC CCAACGCGACA TGAAGGGCTT CGTCAAGGCA CTCAAGGGCA CCCGCTTCAC
TGCCATCACC GGCGTCAAACA CGCTGTTCAA CGGCCTGCTC AACACCCCGG GCTTCGACGA GATCGACTTC
TCTTCGGTCA AGTTCACCCT GGGCGGCGGC ATGGCGGTGC AACGTGCCGT GGCCGAACGC TGGAAGAAGG
TCACCGGGCGT GACCCTGGTC GAAGCCCTATG GCCTGACCGA GACCTCGCCC GCGGCCTGCA TCAATCCGCT
CACCCTGCCC GAGTACAACG TGCCATCGG CCTGCCAATC CCGTCTACCG ATGCCTGCAT CAAGGACGAC
AACGGCAACA TCCTGGCGCT GGGCGAAGTG GGCGAGCTGT GCATCAAGGG CCCGCAGGTA ATGAAGGGCT
ACTGGCAGCG TCCGGAAGAA ACCAGGGCCG CCATCGATGC CGTCGACCGC GGACGGCTGG CTGCACACCG GCCGACATGGC
GAAGATGGAC GAACAGGGCT TCTTCTACAT CGTCGACCGC AAGAAGGACA TGATCCTGGT GTCCGGCTTC
AACGTGTACC CGAATGAGGT CGAAGACGTC ATCGGGATGA TGCCGGGCGT GCTGAAGTC GCCGCCGTCG
GTGTCCCCGA CGAAAAGTCC GGCGAAGTGG TCAAGGTCGT GATCGTGAAG AAGGACCCGA ACCTGACCGC
GGAAATGGTC AAGGAACATG CGCGGGCAAA CCTGACCGGT TACAAGCACC CCAGAATCGT AGAATTCCGA
AAGGAGCTGC CGAAGACCAA CGTCGGCAAG ATCCTCCGTC GCGAGCTGCG TGATACGCCC GCCCCGTAAG
AATTC
```

FIG. 26

SEQ ID NO:10 - the Smprk59BspF primer based on the DNA sequence deposited at NCBI with the accession code NZ_AAVZ01000044.

AGTCATGAGTCTGGATCG

FIG. 27

SEQ ID NO:11 - the Smprk59HindR primer based on the DNA sequence deposited at NCBI with the accession code NZ_AAVZ01000044.

GGAAGCTTACGGGGCGGGGCG

FIG. 28

SEQ ID NO:12 - the primer PrkBsp

GCGAACGGCCTGGTCTTTATGAAGTTCGGTGG

FIG. 29

SEQ ID NO:13 - DNA sequence of the gene encoding the protein ZP_01644857 from *Stenotrophomonas maltophilia* R551-3.

```
TCATGAGTCT GGATCGTCCC TGGCTGCAGA GCTATCCGAA AGGCGTTCCC GCCGAAATCG ACGTCAACGA
ATTCCATTCG GTCGCCTCGG TCTTCGACGC TTCCGTCGCG GACGCGCTGG AAATTCCCGC ACCGTCCCGC CTACTCCAGC
TTCGGCAAGG TCCTCACCTA TGGTGAGACG GACGCGCTGG TCACCCAGTT CGCCGCCTAC CTGCTGGGTG
AGCTCAAGCT CAAGAAGGGT GACCGCGTCG CCCTGATGAT GCCCAACTGC CTGCAGTACC CGGTGGCCAC
CTTCGGCGTG CTGCGCGCCG GCCTGACCGT GGTCAACGTC AACCCGCGCG TCGGCGCCGT CGAACTCAAG
CACCAGCTGG TTGATGCCGG CGTCAGCGCC CTGGTGGTGG TCGACAACTT CGGCGACACC GTCGAACAGG
TCATCGCCGA TACACCGGTC AAGCACGTGG TCACCACCGG CCTGGGCGAC CTGCTCCGGG CCAAGGGCGC
GATCGTCAAC TTCGTGCTGA AGTACATCAA GAAGATGGTG CCCAACTACC ACATCAAGGG CGCCGTCCGC
TTCAAGCAGG CGCTCAAGCT GGGCAGCCGC CACGCGCTTC CGCCGGTCGA GATCGACCAC GACGACATTG
CCTTCCTGCA GTACACCGGC GGGACCACCG GCGTGGCCAA GGGTGCGATG CTGACCAACC GCAACCTGAT
CGCCAACATG CAGCAGGCGT CAGCGTGGCT GTCCACCTCC GGCATCGAGC CGGGCAAGGA AGTGATCATC
ACTGCCCTGC CGCTGTACCA CATCTTCGCA TTGACCGCGA ACGGCCTGGT CTTTATGAAG TTCGGTGGCT
GCAACCACCT GATCACCAAC CCAACGCGACA TGAAGGGCTT CGTAAAGGAG CTCAAGGGCA CCCGCTTCAC
TGCCATCACC GGCGTCAACA CGCTGTTCAA CGGCCCTGCTC AACACCCCGG GCTTCGACGA GATCGACTTC
TCTTCGGTCA AGTTCACCCT GGGCGCGGGC ATGGCGGGTC AACGTGCCGT GGCCGAACGC TGGAAGAAGG
TCACCGGCGT GACCCTGGTC GAAGCCTATG GCCTGACCGA GACCTCGCCC GCGCCTGCA TCAATCCGCT
CACCCTGCCC GAGTACAACG GTGCCATCGG CCTGCCGATC CCGTCTACCG ATGCCTGCAT CAAGGACGAC
AACGGCAACA TCCTGGCGCT GGGCGAAGTG GGCGCAAGGG GCATCAAGGG CCCGCAGGTA ATGAAGGGCT
ACTGGGCAGC TCCGGAAGAA ACCGCCACCG CCATCGATGC GGACGGCTGG CTGCACACCG GCGACATGGC
GAAGATGGAC GAACAGGGCT TCTTCTACAT CGTCGACCGC AAGAAGGACA TGATCCTGGT GTCCGGCTTC
AACGTGTACC CGAATGAGGT CGAAGACGTC ATCGCGATGA TGCCGGGCGT GCTGAAGTC GCCGGCCGTCG
GTGTCCCGGA CGAAAAGTCC GGCGAAGTGG TCAAGGTCGT GATCGTGAAG AAGGACCCGA ACCTGACCGC
GGAAATGGTC AAGGAACATG CGCGGGCAAA CCTGACCGGT TACAAGCACC CCAGAATCGT AGAATTCCGA
AAGGAGCTGC CGAAGACCAA CGTCGGCAAG ATCCTCCGTC GCGAGCTGCG TGATACGCCC GCCCCGTAAG
AATTC
```

FIG. 30

SEQ ID NO:14 - Protein sequence of ZP_01644857 from *Stenotrophomonas maltophilia* ATCC 17679.

```
MSLDRPWLQS YPKGVPAEID VNEFHSVASV FDASVAKFRD RPAYSSFGKV ITYGETDTLV
NQFAAYLLGE LKLKKGDRVA LMMPNCLQYP VATFGVLRAG LTVVNVNPLY TARELKHQLV
DAGVSALVVV DNFGDTVEQV IADTPVKHVI TTGLGDLLGA KGAIVNFVLK YVKKMVPNYH
IKGAVRFKQA LKLGSRHTLP AVEIDHDDIA FLQYTGGTTG VAKGAMLTNR NLIANMQQAS
AWLSTSGIEP GKEVIITALP LYHIFALTAN GLVFMKFGGC NHLITNPRDM KGFVKELKGT
RFTAITGVNT LFNGLLNTPG FDEIDFSSVK FTLGGGMAVQ RAVAERWKKT TGVTLVEAYG
LTETSPAACI NPLTLPEYNG SIGLPIPSTD ACIKDDNGNI LPLGEVGELC IKGPQVMKGY
WQRPEETATA IDADGWLHTG DMARMDEQGF FYIVDRKKDM ILVSGFNVYP NEVEDVIAMM
PGVLEVAAVG VPDEKSGEVV KVVIVKKDPN LTAEMVKEHA RANLTGYKHP RIVEFRKELP
KTNVGKILRR ELRDTPAP
```

FIG. 32

AAR91681.1

Nucleotide sequence (SEQ ID NO:15)

>gi|40796034:488-4012 Nocardia sp. NRRL 5646 ATP/NADPH-dependent carboxylic acid reductase (car) gene, complete cds ATGGCAGTGGATTCACCGGATGAGCGGCTACAGCGCCGCATTGCACAGTTGTTTGCAGAAGATG
AGCAGGTCAAGGCCGCACGTCCGCTCGAAGCGGTGAGCGCGGCGGTGAGCGCGCCCGGTATGCG
GCTGGCGCAGATCGCCGCCACTGTTATGGCGGGTTACGCCGACCGCCCGGCCGCCGGGCAGCGT
GCGTTCGAACTGAACACCGACGACGCGACGGGCCGCACCTCGCTGCGGTTACTTCCCCGATTCG
AGACCATCACCTATCGCGAACTGTGGCAGCGAGTCGGCGAGGTTGCCGCGGCCTGGCATCATGA
TCCCGAGAACCCCTTGCGCGCAGGTGATTTCGTCGCCCTGCTCGGCTTCACCAGCATCGACTAC
GCCACCCTCGACCTGGCCGATATCCACCTCGGCGCGGTTACCGTGCCGTTGCAGGCCAGCGCGG
CGGTGTCCCAGCTGATCGCTATCCTCACCGAGACTTCGCCGCGGCTGCTCGCCTCGACCCCGGA
GCACCTCGATGCGGCGGTCGAGTGCCTACTCGCGGGCACCACACCGGAACGACTGGTGGTCTTC
GACTACCACCCCGAGGACGACGACCAGCGTGCGGCCTTCGAATCCGCCCGCCGCCGCCTTGCCG
ACGCGGGCAGCTTGGTGATCGTCGAAACGCTCGATGCCGTGCGTGCCCGGGGCCGCGACTTACC
GGCCGCGCCACTGTTCGTTCCCGACACCGACGACGACCCGCTGGCCCTGCTGATCTACACCTCC
GGCAGCACCGGAACGCCGAAGGGCGCGATGTACACCAATCGGTTGGCCGCCACGATGTGGCAGG
GGAACTCGATGCTGCAGGGGAACTCGCAACGGGTCGGGATCAATCTCAACTACATGCCGATGAG
CCACATCGCCGGTCGCATATCGCTGTTCGGCGTGCTCGCTCGCGGTGGCACCGCATACTTCGCG
GCCAAGAGCGACATGTCGACACTGTTCGAAGACATCGGCTTGGTACGTCCCACCGAGATCTTCT
TCGTCCCGCGCGTGTGCGACATGGTCTTCCAGCGCTATCAGAGCGAGCTGGACCGGCGCTCGGT
GGCGGGCGCCGACCTGGACACGCTCGATCGGGAAGTGAAAGCCGACCTCCGGCAGAACTACCTC
GGTGGGCGCTTCCTGGTGGCGGTCGTCGGCAGCGCGCCGCTGGCCGCGGAGATGAAGACGTTCA
TGGAGTCCGTCCTCGATCTGCCACTGCACGACGGGTACGGGTCGACCGAGGCGGGCGCAAGCGT
GCTGCTCGACAACCAGATCCAGCGGCCGCCGGTGCTCGATTACAAGCTCGTCGACGTGCCCGAA
CTGGGTTACTTCCGCACCGACCGGCCGCATCCGCGCGGTGAGCTGTTGTTGAAGGCGGAGACCA
CGATTCCGGGCTACTACAAGCGGCCCGAGGTCACCGCGGAGATCTTCGACGAGGACGGCTTCTA
CAAGACCGGCGATATCGTGGCCGAGCTCGAGCACGATCGGCTGGTCTATGTCGACCGTCGCAAC
AATGTGCTCAAACTGTCGCAGGGCGAGTTCGTGACCGTCGCCCATCTCGAGGCCGTGTTCGCCA
GCAGCCCGCTGATCCGGCAGATCTTCATCTACGGCAGCAGCGAACGTTCCTATCTGCTCGCGGT
GATCGTCCCCACCGACGACGCGCTGCGCGGCCGCGACACCGCCACCTTGAAATCGGCACTGGCC
GAATCGATTCAGCGCATCGCCAAGGACGCGAACCTGCAGCCCTACGAGATTCCGCGCGATTTCC
TGATCGAGACCGAGCCGTTCACCATCGCCAACGGACTGCTCTCCGGCATCGCGAAGCTGCTGCG
CCCCAATCTGAAGGAACGCTACGGCGCTCAGCTGGAGCAGATGTACACCGATCTCGCGACAGGC
CAGGCCGATGAGCTGCTCGCCCTGCGCCGCGAAGCCGCCGACCTGCCGGTGCTCGAAACCGTCA
GCCGGGCAGCGAAAGCGATGCTCGGCGTCGCCTCCGCCGATATGCGTCCCGACGCGCACTTCAC
CGACCTGGGCGGCGATTCCCTTTCCGCGCTGTCGTTCTCGAACCTGCTGCACGAGATCTTCGGG
GTCGAGGTGCCGGTGGGTGTCGTCGTCAGCCCGGCGAACGAGCTGCGCGATCTGGCGAATTACA
TTGAGGCGGAACGCAACTCGGGCGCGAAGCGTCCCACCTTCACCTCGGTGCACGGCGGCGGTTC

FIG. 32 (continued)

```
CGAGATCCGCGCCGCCGATCTGACCCTCGACAAGTTCATCGATGCCCGCACCCTGGCCGCCGCC
GACAGCATTCCGCACGCGCCGGTGCCAGCGCAGACGGTGCTGCTGACCGGCGCGAACGGCTACC
TCGGCCGGTTCCTGTGCCTGGAATGGCTGGAGCGGCTGGACAAGACGGGTGGCACGCTGATCTG
CGTCGTGCGCGGTAGTGACGCGGCCGCGGCCCGTAAACGGCTGGACTCGGCGTTCGACAGCGGC
GATCCGGCCTGCTCGAGCACTACCAGCAACTGGCCGCACGGACCCTGGAAGTCCTCGCCGGTG
ATATCGGCGACCCGAATCTCGGTCTGGACGACGCGACTTGGCAGCGGTTGGCCGAAACCGTCGA
CCTGATCGTCCATCCCGCCGCGTTGGTCAACCACGTCCTTCCTACACCCAGCTGTTCGGCCCC
AATGTCGTCGGCACCGCCGAAATCGTCCGGTTGGCGATCACGGCGCGGCGCAAGCCGGTCACCT
ACCTGTCGACCGTCGGAGTGGCCGACCAGGTCGACCCGGCGGAGTATCAGGAGGACAGCGACGT
CGGCGAGATGAGCGCGGTGGCGCGTCGTGCGCGAGAGTTACGCCAACGGCTACGGCAACAGCAAG
TGGGCGGGGGAGGTCCTGCTGCGCGAAGCACACGATCTGTGTGGCTTGCCGGTCGCGGTGTTCC
GTTCGGACATGATCCTGGCGCACAGCCGGTACGCGGGTCAGCTCAACGTCCAGGACGTGTTCAC
CCGGCTGATCCTCAGCCTGGTCGCCACCGGCATCGCGCCGTACTCGTTCTACCGAACCGACGCG
GACGGCAACCGGCAGCGGGCCCACTATGACGGCTTGCCGGCCGGACTTCACGGCGGCCGGCGATCA
CCGCGCTCGGCATCCAAGCCACCGAAGGCTTCCGGACCTACGACGTGCTCAATCCGTACGACGA
TGGCATCTCCCTCGATGAATTCGTCGACTGGCTCGTCGAATCCGGCCACCCGATCCAGCGCATC
ACCGACTACAGCGACTGGTTCCACCGTTCGAGACGGCGATCCGCGCGCTGCCGGAAAAGCAAC
GCCAGGCCTCGGTGCTGCCGTTCCTGGACGCCTACCGCAACCCCTGCCCGGCGGTCCGCGGCGC
GATACTCCCGGCCAAGGAGTTCCAAGCGGCGGTGCAAACAGCCAAAATCGGTCCGGAACAGGAC
ATCCCGCATTTGTCCGCGCCACTGATCGATAAGTACGTCAGCGATCTGGAACTGCTTCAGCTGC
TCTGA
```

Amino acid sequence (SEQ ID NO:16)

```
>gi|40796035|gb|AAR91681.1| ATP/NADPH-dependent carboxylic acid
reductase [Nocardia sp. NRRL 5646]
```

```
MAVDSPDEPLQRRIAQLFAEDEQVKAARPLEAVSAAVSAPGMRLAQIAATVMAGYADRPAAGQR
AFELNTDDATGRTSLRLLPRFETITYRELWQRVGEVAAAWHDPENPLRAGDFVALLGFTSIDY
ATLDLADIHLGAVTVPLQASAAVSQLIAILTETSPRLLASTPEHLDAAVECLLAGTTPERLVVF
DYHPEDDRQSAAFESAARRLADAGSLVIVETLDAVRARGRDLPAAPLFVPDTDDDPLALLIYTS
GSTGTPKGAMYTNRLAATMWQGNSMLQGNSQRVGINLNYMPMSHIAGRISLFGVLARGGTAYFA
AKSDMSTLFEDIGLVRPTEIFFVPRVCDMVFQRYQSELDRSVAGADLDTLDREVKADLRQNYL
GGRFLVAVVGSAPLAAEMKTFMESVLDLPLHDGYGSTEAGASVLLDNQIQRPPVLDYKLVDVPE
LGYFRTDRPHPRGELLLKAETTIPGYYKRPEVTAEIFDEDGFYKTGDIVAELEHDRLVYVDRRN
NVLKLSQGEFVTVAHLEAVFASSPLIRQIFIYGSSERSYLLAVIVPTDDALRGRDTATLKSALA
ESIQRIARDANLQPYEIPRDFLIETEPPTIANGLLSGIAKLLRPNLKERYGAQLEQMYTDLATG
QADELLALRREAADLPVLETVSRAAKAMLGVASADMRPDAHFTDLGGDSLSALSFSNLLSEIFG
VEVPVGVVSPANELRDLANYIEAEPNSGAKRPTPTSVHGGGSEIRAADLTLDKFIDARTLAAA
DSIPHAPVPAQTVLLTGANGYLGRFLCLEWLERLDKTGGTLICVVRGSDAAAARKRLDSAFDSG
DPGLLEHYQQLAARTLEVLAGDIGDPNLGLDDATWQRLAETVDLIVHPAALVNHVLPYTQLFGP
NVVGTAEIVRLAITARRKPVTYLSTVGVAQVDFAEYQEDSDVREMSAVEVVRESYANGYGNSK
WAGEVLLREAHDLCGLPVAVFRSDMILAHSRYAGQLNVQDVFTRLILSLVATGIAPYSFYRTDA
DGNRQRAHYDGLPADFTAAAITALGIQATEGFRTYDVLNFYDGISLDRFVDWLVESGHPIQRI
TDYSDWFBRFETAIRALPEKQRQASVLPLIDAYRNPCPAVRGAILPAKEFQAAVQTAKIGPEQD
IPHLSAPLIDKYVSDLELLQLL
```

FIG. 33

Motif 1

-G-Y-X-X-S/A/T-K-W/L (SEQ ID NO:17); and

-G-X-X-G-X-L-G (SEQ ID NO:18); and

-L/V/I-G-G-D-S-X-X-A (SEQ ID NO:19); and

-[LIVMFY]-{E}-{VES}-[STG]-[STAG]-G-[ST]-[STEIA]-[SG]-X-[PASLIVM]-[KR] (SEQ ID NO:20), wherein {X} stands for any amino acid except X and [$X_1X_2$] stands for $X_1$ or $X_2$ Motif 2

RTVLL$X_1$GA$X_2$G$X_3$LGR$X_4$L$X_5$L$X_6$WL (SEQ ID NO:21)

wherein $X_1$ is S or T;

$X_2$ is T or N;

$X_3$ is F or W;

$X_4$ is F or Y;

$X_5$ is A or T; and $X_6$ is E or Q

Motif 3

LXXGXXGXLGXXLXLWLXR (SEQ ID NO:22)

Motif 4

WAXEVLLR (SEQ ID NO:23), where X can be any amino acid; or

LXXGXXGXLGXXLX$X_1$X$X_2$L$X_3$R (SEQ ID NO:24), wherein $X_1$ is Leu or Ile;

$X_2$ is Trp or Leu; and $X_3$ varies between 13 amino acids or 14 amino acids

Motif 5

-G-Y-X-X-S/A/T-K-W/L (SEQ ID NO:17); and

-L/V/I-G-G-D-S-X-X-A (SEQ ID NO:19); and

FIG. 33 (continued)

-[LIVMFY]-{E}-{VES}-[STG]-[STAG]-G-[ST]-[STEIA]-[SG]-X-[PASLIVM]-[KR] (SEQ ID NO:20), wherein {X} stands for any amino acid except X and [$X_1X_2$] stands for $X_1$ or $X_2$; and RTVLL$X_1$GA$X_2$G$X_3$LGR$X_4$L$X_5$L$X_6$WL (SEQ ID NO:21), wherein $X_1$ is S or T;

$X_2$ is T or N;

$X_3$ is F or W;

$X_4$ is F or Y;

$X_5$ is A or T; and $X_6$ is E or Q

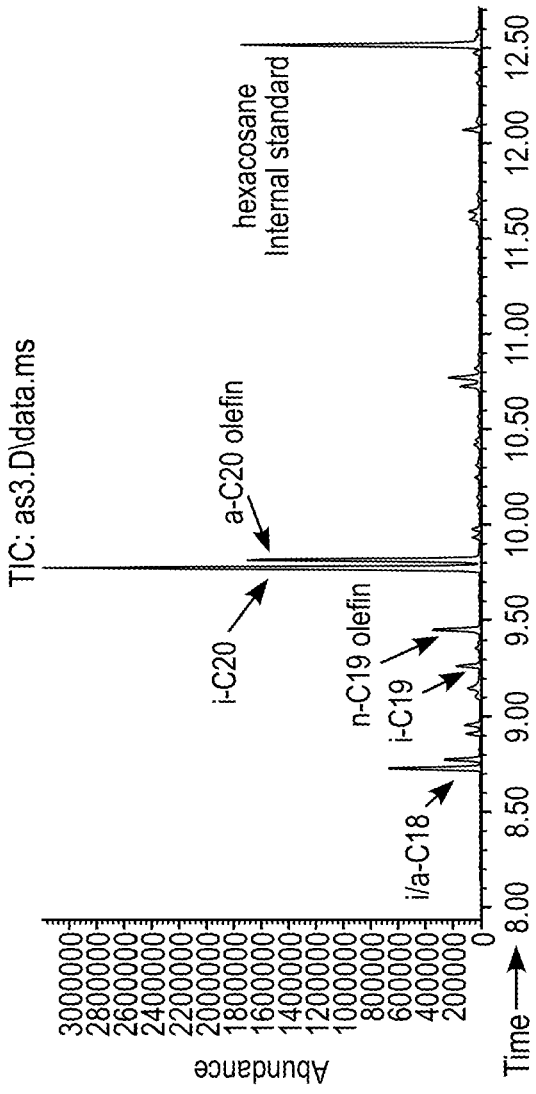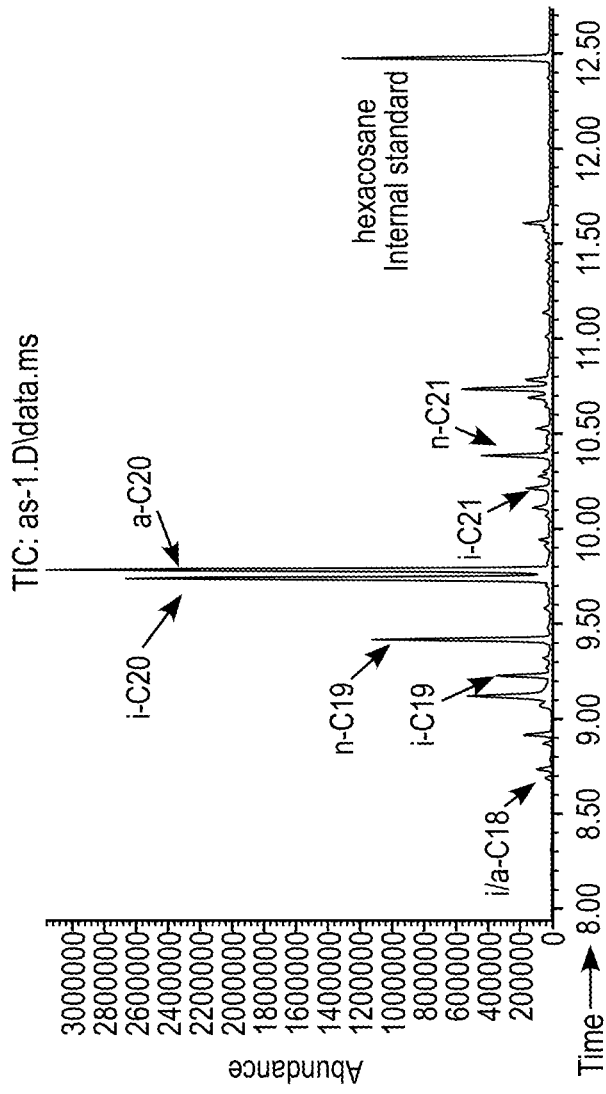
FIG. 34A
FIG. 34B

FIG. 41A

SEQ ID NO:25

```
ATGGCAACAC TTAAGAGGGA TAAGGGCTTA GATAATACTT TGAAAGTATT AAAGCAAGGT   60
TATCTTTACA CAACAAATCA GAGAAATCGT CTAAACACAT CAGTTTTCCA AACTAAAGCA  120
CTCGGTGGTA AACCATTCGT AGTTGTGACT GGTAAGGAAG GCGCTGAAAT GTTCTACAAC  180
AATGATGTTG TTCAACGTGA AGGCATGTTA CCAAAACGTA TCGTTAATAC GCTTTTTGGT  240
AAAGGTGCAA TCCATACGGT AGATGGTAAA AACACGTAG ACAGAAAAGC ATTGTTCATG  300
AGCTTGATGA CTGAAGGTAA CTTGAATTAT GTACGAGAAT TAACGCGTAC ATTATGGCAT  360
GCGAACACAC AACGTATGGA AAGTATGGAT GAGGTAAATA TTTACCGTGA ATCTATCGTA  420
CTACTTACAA AAGTAGGAAC ACGTTGGGCA GGCGTTCAAG CACCACCTGA AGATATCGAA  480
AGAATCGCAA CAGACATGGA CATCATGATC GATTCATTTA GAGCACTTGG TGGTGCCTTT  540
AAAGGTTACA AGGCATCAAA AGAAGCACGT CGTCGTGTTG AAGATTGGTT AGAAGAACAA  600
ATTATTGAGA CTCGTAAAGG GAATATTCAT CCACCAGAAG GTACAGCACT TTACGAATTT  660
GCACATTGGG AAGACTACTT AGGTAACCCA ATGGACTCAA GAACTTGTGC GATTGACTTA  720
ATGAACACAT TCCGCCCATT AATCGCAATC AACAGATTCG TTTCATTCGG TTTACACGCG  780
ATGAACGAAA ACCCAATCAC ACGTGAAAAA ATTAAATCAG AACCTGACTA TGCATATAAA  840
TTCGCTCAAG AAGTTCGTCG TTACTATCCA TTCGTTCCAT TCCTTCCAGG TAAAGCGAAA  900
GTAGACATCG ACTTCCAAGG CGTTACAATT CCTGCAGGTG TAGGTCTTGC ATTAGATGTT  960
TATGGTACAA CGCATGATGA ATCACTTTGG GACGATCCAA ATGAATTCCG CCCAGAAAGA 1020
TTCGAAACTT GGGACGGATC ACCATTTGAC CTTATTCCAC AAGGTGGTGG AGATTACTGG 1080
ACAAATCACC GTTGTGCAGG TGAATGGATC ACAGTAATCA TCATGGAAGA AACAATGAAA 1140
TACTTTGCAG AAAAAATAAC TTATGATGTT CCAGAACAAG ATTTAGAAGT GGACTTAAAC 1200
AGTATCCCAG GATACGTTAA GAGTGGCTTT GTAATCAAAA ATGTTCGCGA AGTTGTAGAC 1260
AGAACATAA  1270
```

FIG. 41B

*Jeotgalicoccus sp.* ATCC8456 orf880 (SEQ ID NO:26)

```
MATLKRDKGL DNTLKVLKQG YLYTTNQRNR LNTSVFQTKA LGGKPFVVVT GKEGAEMFYN   60
NDVVQREGML PKRIVNTLFG KGAIHTVDGK KHVDRKALFM SLMTEGNLNY VRELTRTLWH  120
ANTQRMESMD EVNIYRESIV LLTKVGTRWA GVQAPPEDIE RIATDMDIMI DSFRALGGAF  180
KGYKASKEAR RRVEDWLEEQ IIETRKGNIH PPEGTALYEF AHWEDYLGNP MDSRTCAIDL  240
MNTFRPLIAI NRFVSFGLHA MNENPITREK IKSEPDYAYK FAQEVRRYYP FVPFLPGKAK  300
VDIDFQGVTI PAGVGLALDV YGTTHDESLW DDPNEFRPER FETWDGSPFD LIPQGGGDYW  360
TNHRCAGEWI TVIIMEETMK YFAEKITYDV PEQDLEVDLN SIPGYVKSGF VIKNVREVVD  420
RT         430
```

FIG. 41C

*Jeotgalicoccus* sp. ATCC8456 16s rRNA (partial sequence) (SEQ ID NO:27)

```
GGTTACCTTG TTACGACTTC ACCCCAATTA TCAATCCCAC CTTTGACGGC TACCTCCATT     60
AAGGTTAGTC CACCGGCTTC AGGTGTTAYC GACTTCGTG GTGTGACGGG CGGTGTGTAC     120
AAGACCCGGG AACGTATTCA CCGTAGCATG CTGATCTACG ATTACTAGCG ATTCCAGCTT    180
CATGGAGTCG AGTTGCAGAC TCCAATCCGA ACTGAGAACA GTTTTATGGG ATTCGCTTGG    240
CCTCGCGGCT TCGCTGCCCT TTGTAACCTG CCCATTGTAG CACGTGTGTA GCCCAAATCA    300
TAAGGGGCAT GATGATTTGA CGTCATCCCC ACCTTCCTCC GGTTTGTCAC CGGCAGTCAA    360
TCTAGAGTGC CCAACTGAAT GATGGCAACT AAATTTAAGG GTTGCGCTCG TTGCGGGACT    420
TAACCCAACA TCTCACGACA CGAGCTGACG ACAACCATGC ACCACCTGTC TCTCTGCCCA    480
AAAGGGAAAC CATATCTCTR TGGCGATCAG AGGATGTCAA GATTTGGTAA GGTTCTTCGC    540
GTTGCTTCGA ATTAAACCAC ATGCTCCACC GCTTGTGCGG GTCCCCGTCA ATTCCTTTGA    600
GTTTCAACCT TGCGGTCGTA CTCCCCAGGC GGAGTGCTTA ATGCGTTAGC TGCAGCACTG    660
AGGGGCGGAA ACCCCCCAAC ACTTAGCACT CATCGTTTAC GGCGTGGACT ACCAGGGTAT    720
CTAATCCTGT TTGATCCCCA CGCTTTCGCA CCTCAGCGTC AGTTACAGAC CAGAGAGCCG    780
CCTTCGCCCA CTGGTGTTCC TCCATATCTC TGCGCATTTC ACCGCTACAC ATGGAATTCC    840
ACTCTCCTCT TCTGCACTCA AGTAAAACAG TTTCCAATGA CCCTCCCCGG TTGAGCCGGG    900
GGCTTTCACA TCAGACTTAT TCTACCGCCT ACGCGCGCTT TACGCCCAAT AATTCCGGAT    960
AACGCTTGCC ACCTACGTAT TACCGCGGCT GCTGGCACGT AGTTAGCCGT GGCTTTCTGG    1020
TTAAGTACCG TCATCTCTAG GCCAGTTACT ACCTAAAGTG TTCTTCCTTA CAACAGAGT     1080
TTTACGAGCC GAAACCCTTC TTCACTCACG CGGCGTTGCT CCGTCAGACT TGCGTYCATT    1140
GCGGAAGATT CCCTACTGCT GCCTCCCGTA GGAGTCTGGG CCGTGTCTCA GTCCCAGTGT    1200
GGCCGATCAC CCTCTCAGGT CGGCTATGCA TCGTTGCCTT GGTGAGCCAC TACCTCACCA    1260
ACTAGCTAAT GCACCGCAGG CCCATCCTTT AGTGACAGAT AAATCCGCCT TCATTAAGA     1320
TTACTTGTGT AATCCAACTT ATCCGGTATT AGCTACCGTT TCCGGTAGTT ATCCCAGTCT    1380
AAAGGGTAGG TTGCCCACGT GTTACTCACC CGTCCGCCGC TCGATTGTAA GGAGCAAGCT    1440
CCTTACGCTC GCGCTCGACT TGCATGTATT AGGCACGCCG CCAGCGTTCA TCCTGAGCCA    1500
GGATCAA                                                              1510
```

FIG. 44

G-D-S-L-X(5)-M (SEQ ID NO:28), wherein:

the Ser residue at position 3 is a catalytic residue;
the Asp residue at position 2 may be substituted with Asn
or Thr; the Leu residue at position 4 may be substituted
with Cys or Gln; the Met residue at position 10 may be
substituted with Cys, Asp, Leu, Asn, Thr, or Val;

and

V-X(2)-G-X-N-D-X-L (SEQ ID NO:29), wherein:

the Asn residue at position 7 is in the oxyanion hole;
the Val residue at position 1 may be substituted with Leu;
the Asn residue at position 6 may be substituted with Val,
Leu, Cys, Ala, Gly, His, Ile, Thr, or Trp;
the Asp residue at position 7 may be substituted with Glu;
the Leu residue at position 9 may be substituted with Ile,
Trp, Phe, Thr, Met, Ala, Glu, Asn, or Val;

and

D-X(2)-H-P-X(7)-I (SEQ ID NO:30), wherein:

the Asp and His residues at positions 1 and 4,
respectively, are the catalytic residues;
the Pro residue at position 5 may be substituted with Gly,
Ala, Phe, Leu, Ser, or Val;
the Ile residue at position 13 may be substituted with Leu
or Val.

FIG. 45A

| POSITION | MUTATION | 1PNP_MOD_Z_C10 | 1PNP_MOD_Z_C12 | 1PNP_MOD_Z_C14 |
|---|---|---|---|---|
| 1 | A1S | 6.394 | 11.580 | 20.629 |
| 7 | L7M | 6.757 | 10.090 | 5.929 |
| 7 | L7V | 8.265 | 9.279 | 2.303 |
| 9 | D9N | 15.267 | 13.647 | 15.639 |
| 12 | S12A | 4.555 | 3.215 | 1.903 |
| 13 | A13D | 3.735 | 0.903 | -0.729 |
| 13 | A13V | 1.335 | 2.360 | 4.034 |
| 14 | G14S | 8.257 | 2.097 | 0.756 |
| 14 | G14T | -1.567 | 0.967 | 4.298 |
| 14 | G14V | 11.223 | 18.158 | 34.850 |
| 15 | Y15E | -4.756 | 2.142 | 10.078 |
| 15 | Y15V | -7.702 | -0.520 | 8.702 |
| 16 | R16G | 14.325 | 9.226 | 9.948 |
| 16 | R16L | 4.133 | 3.273 | 2.956 |
| 16 | R16M | 3.672 | 2.753 | 2.318 |
| 16 | R16N | 4.646 | 3.498 | 3.499 |
| 16 | R16P | 18.984 | 9.296 | 9.170 |
| 16 | R16T | 3.488 | 3.178 | 1.476 |
| 17 | M17C | 6.067 | 4.794 | 3.792 |
| 17 | M17D | 1.338 | 2.867 | 3.168 |
| 17 | M17L | 3.438 | 2.420 | 2.893 |
| 17 | M17N | -0.090 | 3.106 | 4.076 |
| 17 | M17T | 4.221 | 3.513 | 3.074 |
| 17 | M17V | 6.474 | 2.281 | 2.390 |
| 20 | S20A | 4.359 | 3.370 | 3.415 |
| 20 | S20C | 4.227 | 3.784 | 2.849 |
| 20 | S20D | 5.378 | 4.972 | 4.722 |
| 20 | S20G | 8.105 | 7.279 | 7.378 |
| 20 | S20L | 5.108 | 4.383 | 4.563 |
| 20 | S20T | 4.956 | 4.936 | 4.330 |
| 20 | S20W | 3.016 | 3.156 | 3.283 |
| 21 | A21G | 2.006 | 2.215 | 3.213 |
| 21 | A21P | 2.704 | 3.717 | 1.674 |
| 22 | A22N | 5.224 | 3.894 | 6.827 |
| 24 | P24V | 6.943 | 3.729 | 2.463 |
| 25 | A25D | 2.272 | 3.185 | 2.194 |
| 25 | A25E | 4.782 | 4.521 | 6.391 |
| 25 | A25L | 4.174 | 4.394 | 2.472 |
| 25 | A25N | 3.676 | 3.556 | 5.959 |
| 25 | A25Q | 4.144 | 4.118 | 6.491 |
| 25 | A25V | 6.800 | 7.356 | 12.294 |
| 26 | L26Q | 2.404 | 2.435 | 4.533 |

| FIG. 45A Cont. | | | | |
|---|---|---|---|---|
| 26 | L26V | 1.964 | 2.454 | 4.533 |
| 28 | N28K | 1.848 | 2.279 | 4.313 |
| 28 | N28R | 5.484 | 4.999 | 2.939 |
| 35 | T35L | 1.142 | 4.391 | 1.387 |
| 35 | T35Y | 1.199 | 3.823 | 1.851 |
| 36 | S36H | 1.023 | 1.356 | 3.701 |
| 38 | V38F | 2.942 | 3.043 | 4.848 |
| 39 | N39A | 10.899 | 5.838 | 2.829 |
| 39 | N39Q | -4.841 | 0.211 | 4.206 |
| 40 | A40G | 1.657 | 1.721 | 4.380 |
| 40 | A40V | 1.830 | 5.274 | 6.003 |
| 42 | I42A | 3.954 | 6.892 | 4.294 |
| 42 | I42C | 2.384 | 3.148 | 1.925 |
| 42 | I42D | -2.516 | 4.972 | 8.169 |
| 42 | I42E | 3.313 | 4.990 | 3.795 |
| 42 | I42G | 0.206 | 6.193 | 8.664 |
| 42 | I42L | 4.257 | 5.214 | 3.866 |
| 42 | I42M | 2.715 | 3.983 | 3.127 |
| 42 | I42S | 3.726 | 7.405 | 6.433 |
| 42 | I42T | 3.416 | 3.318 | 3.326 |
| 42 | I42W | 5.408 | 5.595 | 4.665 |
| 42 | I42Y | 3.969 | 4.791 | 3.842 |
| 43 | S43A | 3.516 | 6.311 | 3.717 |
| 43 | S43D | 5.985 | 8.842 | 6.907 |
| 43 | S43E | 3.582 | 4.171 | 3.005 |
| 43 | S43F | -11.125 | -0.402 | 12.329 |
| 43 | S43L | 16.778 | 17.685 | 15.484 |
| 43 | S43M | 2.612 | 5.188 | 4.064 |
| 43 | S43N | 9.913 | 6.791 | 3.931 |
| 43 | S43W | -7.274 | 1.086 | 11.516 |
| 44 | G44F | -5.359 | 0.298 | 13.270 |
| 44 | G44M | -12.661 | -2.567 | 4.780 |
| 44 | G44Y | 2.451 | 1.502 | 8.818 |
| 45 | D45A | -0.294 | 7.110 | 12.755 |
| 45 | D45C | -6.455 | 1.912 | 7.439 |
| 45 | D45E | -1.230 | 3.649 | 3.532 |
| 45 | D45F | -4.849 | 0.586 | 4.376 |
| 45 | D45G | -6.106 | 2.534 | 16.202 |
| 45 | D45Q | -7.477 | 0.879 | 9.370 |
| 45 | D45S | -7.344 | -0.597 | 7.240 |
| 45 | D45T | -6.113 | 1.664 | 6.578 |
| 45 | D45W | -1.352 | 3.401 | 5.645 |
| 46 | T46A | -1.206 | 4.649 | 8.853 |

| FIG. 45A Cont. | | | | |
|---|---|---|---|---|
| 46 | T46C | -0.158 | 6.112 | 9.179 |
| 46 | T46D | -2.233 | 4.810 | 18.146 |
| 46 | T46G | -2.206 | 8.812 | 24.221 |
| 46 | T46L | 3.091 | -9.678 | -9.140 |
| 46 | T46N | 1.300 | 6.292 | 5.688 |
| 46 | T46S | 1.575 | 7.837 | 12.557 |
| 46 | T46V | 3.620 | -0.054 | -3.090 |
| 46 | T46W | -8.251 | 0.760 | 13.198 |
| 47 | S47A | 3.529 | -7.577 | -12.577 |
| 47 | S47M | 9.633 | -2.784 | -5.012 |
| 48 | Q48F | -1.201 | 1.752 | 6.042 |
| 48 | Q48M | -0.580 | 1.282 | 4.104 |
| 48 | Q48T | 4.000 | 2.879 | 1.431 |
| 48 | Q48V | 3.521 | 5.933 | 11.056 |
| 48 | Q48W | 3.544 | 4.791 | 8.102 |
| 48 | Q48Y | 2.699 | 4.581 | 9.029 |
| 49 | Q49A | 3.075 | 7.455 | 13.528 |
| 49 | Q49C | 4.129 | 7.572 | 12.456 |
| 49 | Q49D | 3.858 | 7.266 | 15.064 |
| 49 | Q49E | 0.055 | 4.704 | 13.375 |
| 49 | Q49G | 4.621 | 9.500 | 17.760 |
| 49 | Q49H | 3.926 | 6.799 | 9.786 |
| 49 | Q49I | 1.460 | 6.572 | 13.667 |
| 49 | Q49K | -1.162 | 2.210 | 3.123 |
| 49 | Q49L | 3.327 | 6.028 | 9.720 |
| 49 | Q49M | 3.427 | 5.613 | 8.580 |
| 49 | Q49R | -1.520 | 1.685 | 3.754 |
| 49 | Q49S | 5.086 | 9.440 | 18.283 |
| 49 | Q49V | 2.715 | 7.616 | 14.223 |
| 49 | Q49W | 0.828 | 5.899 | 14.478 |
| 49 | Q49Y | 2.372 | 5.654 | 9.781 |
| 50 | G50A | 5.543 | 9.039 | 18.106 |
| 50 | G50C | -3.097 | 4.373 | 16.692 |
| 50 | G50F | -10.720 | -3.587 | 9.503 |
| 50 | G50L | -8.672 | 0.760 | 16.872 |
| 50 | G50M | -4.800 | 3.932 | 21.633 |
| 50 | G50N | -13.424 | -7.278 | 4.358 |
| 50 | G50Q | 3.493 | 12.040 | 35.531 |
| 50 | G50S | 1.734 | 6.818 | 17.432 |
| 50 | G50T | -5.130 | 0.190 | 10.072 |
| 51 | L51A | 3.336 | 3.415 | 3.086 |
| 51 | L51C | 1.954 | 2.391 | 3.215 |
| 52 | A52H | 1.944 | 2.621 | 4.263 |

| FIG. 45A Cont. | | | | |
|---|---|---|---|---|
| 52 | A52L | 1.102 | 2.133 | 4.436 |
| 52 | A52M | 3.578 | 4.394 | 6.355 |
| 52 | A52R | 1.914 | 2.434 | 3.812 |
| 52 | A52W | 1.736 | 3.672 | 9.699 |
| 52 | A52Y | 0.370 | 1.666 | 3.212 |
| 53 | R53A | 1.209 | 7.046 | 13.260 |
| 53 | R53E | -9.522 | -4.303 | 4.973 |
| 53 | R53I | -1.622 | 4.962 | 16.230 |
| 53 | R53K | -1.692 | 1.524 | 6.340 |
| 53 | R53L | -4.533 | 1.906 | 12.539 |
| 53 | R53N | -2.528 | 2.000 | 7.059 |
| 53 | R53S | -2.788 | 1.701 | 6.482 |
| 53 | R53V | -0.921 | 5.737 | 17.575 |
| 56 | A56R | 2.198 | 2.171 | 3.566 |
| 56 | A56W | 2.282 | 2.445 | 5.129 |
| 56 | A56Y | 1.802 | 2.064 | 4.384 |
| 58 | L58I | 2.722 | 2.920 | 3.325 |
| 66 | V66I | 1.736 | 2.860 | 4.030 |
| 68 | V68L | 3.914 | 4.070 | 3.982 |
| 69 | E69G | -2.706 | 0.579 | 3.911 |
| 69 | E69Q | -3.745 | -0.973 | 8.478 |
| 69 | E69S | -1.111 | 1.609 | 7.270 |
| 70 | L70T | -1.234 | 11.389 | 20.877 |
| 70 | L70V | 0.646 | 4.270 | 5.541 |
| 72 | G72A | 14.643 | 5.142 | 18.492 |
| 73 | N73A | -2.509 | 0.071 | 7.473 |
| 73 | N73C | 0.690 | 2.962 | 14.842 |
| 73 | N73G | -12.646 | -5.398 | 13.811 |
| 73 | N73L | 2.964 | 10.775 | 46.587 |
| 73 | N73V | -3.024 | 1.071 | 16.512 |
| 74 | D74E | -7.071 | 0.624 | 11.720 |
| 75 | G75A | 2.975 | -2.755 | 13.425 |
| 75 | G75K | -1.950 | -6.794 | 6.570 |
| 75 | G75M | 1.306 | -8.006 | 3.391 |
| 76 | L76A | -3.537 | -8.281 | 7.135 |
| 76 | L76E | -5.399 | -9.182 | 3.000 |
| 76 | L76F | 1.580 | 1.298 | 24.980 |
| 76 | L76I | 3.841 | 5.135 | 28.435 |
| 76 | L76M | 5.727 | 3.927 | 11.869 |
| 76 | L76N | -2.468 | -6.507 | 6.317 |
| 76 | L76T | -0.255 | -4.430 | 12.575 |
| 76 | L76V | -4.196 | -4.995 | 3.901 |
| 76 | L76W | 13.746 | 6.221 | 34.187 |

| FIG. 45A Cont. | | | | |
|---|---|---|---|---|
| 77 | R77A | -3.079 | -0.533 | 9.859 |
| 77 | R77C | 0.461 | 5.456 | 21.068 |
| 77 | R77D | -2.838 | 2.127 | 12.211 |
| 77 | R77E | -4.589 | 2.902 | 16.241 |
| 77 | R77F | -1.292 | 2.850 | 22.678 |
| 77 | R77G | 7.203 | 11.587 | 27.111 |
| 77 | R77H | -5.359 | -2.852 | 8.936 |
| 77 | R77K | 1.376 | 3.625 | 6.073 |
| 77 | R77L | 10.539 | 10.057 | 17.946 |
| 77 | R77N | -0.025 | 2.762 | 10.326 |
| 77 | R77Q | 6.394 | 4.821 | 3.779 |
| 77 | R77S | 0.104 | 4.522 | 13.675 |
| 77 | R77V | -1.637 | 5.296 | 30.686 |
| 77 | R77W | 0.720 | 4.567 | 29.256 |
| 78 | G78A | 3.983 | -0.533 | -3.270 |
| 79 | F79A | 3.124 | -3.257 | -6.141 |
| 79 | F79D | 4.524 | -4.371 | -11.941 |
| 79 | F79E | 3.348 | -5.838 | -13.264 |
| 79 | F79G | 5.101 | -2.922 | -5.652 |
| 79 | F79M | -0.425 | 1.923 | 10.143 |
| 79 | F79V | 0.611 | 2.531 | 3.984 |
| 79 | F79W | 4.875 | -2.198 | -5.513 |
| 79 | F79Y | 3.484 | 1.699 | 1.233 |
| 80 | Q80G | -0.466 | 4.758 | 20.284 |
| 80 | Q80L | 0.197 | 1.684 | 5.931 |
| 80 | Q80M | 2.809 | 4.351 | 10.080 |
| 80 | Q80S | 0.014 | 3.640 | 12.533 |
| 80 | Q80W | 0.534 | 2.981 | 8.956 |
| 80 | Q80Y | 1.256 | 3.247 | 11.036 |
| 81 | P81A | -0.430 | 3.378 | 5.476 |
| 81 | P81E | 1.832 | 4.174 | 7.861 |
| 81 | P81K | 1.207 | 3.924 | 8.595 |
| 81 | P81L | 0.378 | 4.145 | 3.931 |
| 81 | P81M | -2.990 | 3.056 | 5.618 |
| 81 | P81W | 0.666 | 5.866 | 15.345 |
| 81 | P81Y | 3.189 | 5.997 | 9.827 |
| 82 | Q82F | 0.609 | 3.479 | 7.065 |
| 82 | Q82I | 1.002 | 2.176 | 5.633 |
| 82 | Q82N | -1.675 | 1.981 | 3.202 |
| 82 | Q82P | -1.744 | 2.992 | 8.294 |
| 82 | Q82T | 3.210 | 1.693 | 1.736 |
| 82 | Q82V | 2.235 | 3.292 | 3.811 |
| 82 | Q82W | 1.434 | 5.370 | 12.954 |

| FIG. 45A Cont. | | | | |
|---|---|---|---|---|
| 82 | Q82Y | 1.101 | 4.214 | 9.354 |
| 83 | Q83A | 6.362 | 7.643 | 5.270 |
| 84 | T84S | 0.270 | 2.141 | 3.881 |
| 86 | Q86A | 11.786 | 12.454 | 13.768 |
| 86 | Q86T | 10.110 | 11.117 | 15.340 |
| 87 | T87A | -0.037 | 2.065 | 5.832 |
| 87 | T87C | -0.229 | 2.934 | 9.499 |
| 87 | T87E | 1.415 | 3.575 | 5.069 |
| 87 | T87F | -1.975 | 0.230 | 12.052 |
| 87 | T87G | -0.739 | 2.096 | 6.515 |
| 87 | T87H | -0.673 | 2.639 | 9.426 |
| 87 | T87L | -0.419 | 3.398 | 14.653 |
| 87 | T87M | -0.551 | 1.374 | 4.720 |
| 87 | T87V | 1.404 | 2.950 | 5.025 |
| 87 | T87W | -0.755 | 2.064 | 10.109 |
| 91 | I91L | 2.206 | 2.297 | 3.351 |
| 91 | I91V | 6.585 | 5.278 | 4.212 |
| 92 | L92V | 3.616 | 3.994 | 4.208 |
| 93 | Q93A | 5.091 | 4.992 | 4.817 |
| 93 | Q93E | 3.105 | 2.687 | 2.646 |
| 93 | Q93G | 3.130 | 3.245 | 3.007 |
| 93 | Q93H | 3.975 | 3.697 | 4.434 |
| 93 | Q93I | 3.468 | 3.105 | 3.551 |
| 93 | Q93Y | 3.010 | 3.046 | 3.534 |
| 94 | D94G | 3.178 | 1.754 | 1.189 |
| 94 | D94K | 3.315 | 1.934 | 1.442 |
| 94 | D94V | 3.440 | 2.590 | 2.720 |
| 95 | V95L | 4.707 | 7.185 | 10.389 |
| 95 | V95M | 1.595 | 2.323 | 3.021 |
| 95 | V95T | 3.638 | 4.230 | 4.113 |
| 96 | K96A | 2.873 | 3.606 | 3.557 |
| 96 | K96L | 2.738 | 3.675 | 3.829 |
| 96 | K96Y | 3.791 | 4.548 | 4.760 |
| 97 | A97K | 2.718 | 3.068 | 2.788 |
| 97 | A97W | 2.510 | 2.579 | 3.691 |
| 98 | A98K | 2.626 | 2.900 | 3.829 |
| 98 | A98L | 2.724 | 3.677 | 5.565 |
| 98 | A98W | 3.024 | 3.845 | 5.805 |
| 99 | N99C | 2.700 | 3.443 | 2.569 |
| 99 | N99G | 4.074 | 4.878 | 3.934 |
| 99 | N99L | 4.330 | 4.878 | 4.479 |
| 99 | N99M | 2.867 | 3.104 | 2.038 |
| 99 | N99P | 3.020 | 3.900 | 3.152 |

| FIG. 45A Cont. | | | | |
|---|---|---|---|---|
| 99 | N99Q | 3.088 | 3.415 | 3.069 |
| 99 | N99R | 4.286 | 5.058 | 4.131 |
| 99 | N99W | 2.850 | 3.827 | 1.514 |
| 99 | N99Y | 5.543 | 4.922 | 4.730 |
| 100 | A100G | 4.451 | 4.465 | 4.153 |
| 100 | A100H | 0.957 | 3.338 | 5.958 |
| 100 | A100I | 1.009 | 3.065 | 4.565 |
| 100 | A100K | 1.952 | 6.498 | 9.431 |
| 100 | A100R | -0.695 | 1.432 | 3.879 |
| 100 | A100T | 0.930 | 2.475 | 4.441 |
| 100 | A100V | 3.365 | 7.715 | 11.388 |
| 101 | E101A | 3.144 | 2.270 | 1.757 |
| 101 | E101G | 5.108 | 4.874 | 5.154 |
| 101 | E101L | 7.257 | 7.646 | 8.984 |
| 101 | E101M | 3.983 | 4.000 | 3.570 |
| 101 | E101S | 4.213 | 4.112 | 4.699 |
| 101 | E101T | 5.114 | 4.805 | 6.246 |
| 101 | E101V | 4.472 | 5.342 | 5.700 |
| 102 | P102S | 4.145 | 5.235 | 6.224 |
| 105 | M105C | 3.337 | 3.633 | 7.462 |
| 105 | M105I | 3.337 | 2.850 | 5.146 |
| 105 | M105L | 0.486 | 0.666 | 4.783 |
| 105 | M105V | 5.143 | 5.027 | 11.562 |
| 106 | Q106A | 3.307 | 5.346 | 4.692 |
| 106 | Q106C | 1.652 | 3.004 | 3.267 |
| 106 | Q106D | -0.831 | -5.674 | 4.967 |
| 106 | Q106G | 0.911 | 3.061 | 6.930 |
| 106 | Q106H | 3.551 | 2.788 | 11.614 |
| 106 | Q106K | 0.523 | 4.879 | 6.237 |
| 106 | Q106M | 1.581 | 1.185 | 6.878 |
| 106 | Q106R | 1.323 | 4.645 | 8.251 |
| 106 | Q106S | 2.178 | 5.220 | 10.217 |
| 106 | Q106T | 2.225 | 3.935 | 5.199 |
| 106 | Q106V | -0.434 | 0.829 | 6.395 |
| 106 | Q106W | 7.654 | 0.324 | 16.161 |
| 106 | Q106Y | 1.290 | 2.930 | 4.395 |
| 107 | I107C | 1.869 | 7.490 | 8.798 |
| 107 | I107L | 1.267 | 8.935 | 13.483 |
| 107 | I107M | 1.316 | 4.696 | 6.909 |
| 107 | I107Q | -1.349 | 2.297 | 5.374 |
| 107 | I107V | 1.727 | 5.387 | 5.546 |
| 108 | R108A | 2.439 | -2.014 | 5.537 |
| 108 | R108D | 6.314 | -0.089 | 10.152 |

| FIG. 45A Cont. | | | | |
|---|---|---|---|---|
| 108 | R108F | 5.682 | 3.958 | 4.773 |
| 108 | R108I | 3.876 | -2.651 | 5.136 |
| 108 | R108L | 0.689 | -6.243 | 5.281 |
| 108 | R108S | 3.181 | -0.031 | 7.566 |
| 108 | R108V | 0.722 | -3.072 | 6.040 |
| 108 | R108W | 18.196 | 12.645 | 5.488 |
| 108 | R108Y | 3.304 | -0.165 | 7.301 |
| 109 | L109M | 0.743 | 4.940 | 8.682 |
| 109 | L109V | 1.441 | -1.769 | 4.328 |
| 110 | P110E | 3.550 | 0.955 | 3.314 |
| 110 | P110F | 5.785 | -6.804 | -1.807 |
| 110 | P110N | 4.801 | -5.215 | 3.764 |
| 110 | P110W | 3.459 | -6.699 | -1.484 |
| 111 | A111C | 12.672 | 4.560 | 6.257 |
| 111 | A111L | 5.262 | 1.291 | 4.013 |
| 111 | A111Q | 4.678 | 3.109 | 3.253 |
| 111 | A111R | 3.287 | 1.936 | 3.705 |
| 111 | A111V | 4.883 | 2.693 | 8.461 |
| 111 | A111W | 9.964 | 8.699 | 12.177 |
| 112 | N112A | 4.144 | 4.774 | 15.787 |
| 112 | N112F | 3.115 | 2.537 | 7.389 |
| 112 | N112G | 3.637 | 4.620 | 10.565 |
| 112 | N112I | 0.819 | 0.171 | 11.828 |
| 112 | N112L | -3.870 | -3.621 | 4.766 |
| 112 | N112P | 1.980 | 2.011 | 11.645 |
| 112 | N112V | 2.140 | 1.583 | 13.793 |
| 112 | N112W | 3.839 | 4.910 | 19.845 |
| 112 | N112Y | -0.190 | 1.507 | 11.835 |
| 113 | Y113A | 3.598 | 4.764 | 9.665 |
| 113 | Y113D | 0.785 | 2.906 | 4.157 |
| 113 | Y113G | 3.788 | 3.762 | 4.740 |
| 113 | Y113I | 5.657 | 5.345 | 7.568 |
| 113 | Y113M | 3.602 | 2.503 | 5.842 |
| 114 | G114F | 0.911 | 1.324 | 4.351 |
| 114 | G114K | 4.656 | 4.586 | 4.314 |
| 114 | G114L | 3.867 | 5.743 | 12.412 |
| 114 | G114M | 2.565 | 5.242 | 13.172 |
| 114 | G114W | 0.253 | 0.903 | 3.468 |
| 114 | G114Y | 1.840 | 4.894 | 14.604 |
| 115 | R115A | 4.529 | 3.272 | 8.124 |
| 115 | R115C | 4.177 | 3.552 | 6.305 |
| 115 | R115E | 4.847 | 3.429 | 8.136 |
| 115 | R115G | 4.070 | 5.954 | 16.468 |

| FIG. 45A Cont. | | | | |
|---|---|---:|---:|---:|
| 115 | R115I | 2.218 | 2.090 | 4.740 |
| 115 | R115N | 3.044 | 4.272 | 7.232 |
| 115 | R115Q | 2.297 | 2.565 | 3.644 |
| 115 | R115S | 3.737 | 4.546 | 7.056 |
| 115 | R115W | 3.879 | 2.470 | 7.235 |
| 115 | R115Y | 3.224 | 3.648 | 9.522 |
| 116 | R116C | 2.854 | 2.857 | 3.579 |
| 116 | R116D | 3.327 | 2.880 | 2.274 |
| 116 | R116H | 2.748 | 3.277 | 4.951 |
| 116 | R116T | 2.464 | 2.657 | 3.147 |
| 116 | R116V | 2.951 | 2.874 | 4.116 |
| 116 | R116W | 3.104 | 5.198 | 14.499 |
| 117 | Y117C | 6.675 | 6.817 | 4.454 |
| 117 | Y117H | 2.743 | 4.861 | 4.621 |
| 117 | Y117I | 5.647 | 5.993 | 4.154 |
| 117 | Y117L | 4.993 | 7.391 | 6.723 |
| 117 | Y117M | 2.081 | 5.075 | 5.217 |
| 117 | Y117N | 3.349 | 4.700 | 3.926 |
| 117 | Y117S | 5.030 | 5.742 | 4.660 |
| 117 | Y117T | 5.542 | 5.207 | 1.889 |
| 117 | Y117V | 6.015 | 5.039 | 1.300 |
| 117 | Y117W | -2.334 | 0.471 | 7.263 |
| 118 | N118H | 0.512 | 1.428 | 6.319 |
| 118 | N118L | 1.598 | 0.958 | 8.703 |
| 118 | N118M | 2.010 | 2.961 | 6.341 |
| 118 | N118P | -0.832 | -1.966 | 5.482 |
| 118 | N118W | 3.397 | 1.114 | 4.463 |
| 119 | E119C | 6.373 | 5.141 | 7.221 |
| 119 | E119D | 2.931 | 2.142 | 4.557 |
| 119 | E119F | 5.693 | 5.823 | 10.266 |
| 119 | E119K | 7.496 | 8.591 | 15.835 |
| 119 | E119M | 4.702 | 3.479 | 5.351 |
| 119 | E119P | 0.089 | -3.003 | 9.754 |
| 119 | E119R | 8.707 | 9.759 | 17.979 |
| 119 | E119T | 2.287 | 2.383 | 3.146 |
| 119 | E119W | 9.580 | 10.352 | 19.702 |
| 119 | E119Y | 9.350 | 9.436 | 15.291 |
| 120 | A120D | 4.191 | 3.321 | 3.841 |
| 120 | A120G | 4.420 | 5.180 | 8.547 |
| 120 | A120I | 0.912 | 3.418 | 7.663 |
| 120 | A120L | 1.580 | 1.987 | 3.530 |
| 120 | A120T | 1.659 | 3.057 | 4.009 |
| 120 | A120W | 3.462 | 6.175 | 16.518 |

| FIG. 45A Cont. | | | | |
|---|---|---|---|---|
| 121 | F121A | -3.589 | -10.094 | 5.171 |
| 121 | F121C | -0.082 | -2.789 | 9.095 |
| 121 | F121L | -5.058 | -5.323 | 11.514 |
| 121 | F121M | 5.655 | 0.053 | 7.119 |
| 121 | F121V | 0.041 | 0.880 | 3.163 |
| 121 | F121Y | 5.012 | 2.070 | 12.144 |
| 122 | S122A | 2.242 | 1.706 | 6.562 |
| 122 | S122C | -0.273 | -0.816 | 4.001 |
| 122 | S122D | 1.254 | -0.098 | 3.277 |
| 122 | S122E | 1.103 | -4.994 | 7.905 |
| 122 | S122F | 7.194 | 10.424 | 21.883 |
| 122 | S122G | 0.956 | 0.171 | 7.614 |
| 122 | S122I | 4.496 | 10.648 | 14.247 |
| 122 | S122L | 3.754 | 7.072 | 21.707 |
| 122 | S122M | 3.706 | 5.077 | 4.995 |
| 122 | S122P | -1.009 | -2.338 | 10.147 |
| 122 | S122V | 3.999 | 8.868 | 16.170 |
| 122 | S122W | 4.006 | 6.033 | 19.886 |
| 122 | S122Y | 5.510 | 9.236 | 22.214 |
| 123 | A123C | 2.585 | 4.047 | 3.338 |
| 123 | A123E | 2.551 | 2.618 | 3.222 |
| 123 | A123F | 2.687 | 3.711 | 5.874 |
| 123 | A123H | 3.250 | 6.451 | 5.071 |
| 123 | A123L | 3.577 | 6.736 | 6.773 |
| 123 | A123R | 1.525 | 4.273 | 2.798 |
| 123 | A123T | 2.814 | 4.735 | 7.298 |
| 123 | A123V | 3.161 | 6.871 | 7.478 |
| 123 | A123W | 2.648 | 6.055 | 7.330 |
| 123 | A123Y | 2.962 | 4.380 | 8.914 |
| 124 | I124A | -0.562 | 1.899 | 3.815 |
| 124 | I124C | 0.236 | 1.648 | 3.855 |
| 124 | I124L | 1.512 | 3.595 | 4.736 |
| 125 | Y125F | 4.483 | 4.223 | 8.143 |
| 125 | Y125W | 5.467 | 0.988 | 2.558 |
| 126 | P126H | 2.813 | 4.522 | 3.032 |
| 126 | P126Y | 3.280 | 4.782 | 4.765 |
| 132 | F132E | 3.891 | 2.969 | 1.705 |
| 133 | D133K | 4.876 | 4.529 | 5.272 |
| 133 | D133Y | 3.220 | 2.963 | 3.695 |
| 134 | V134S | 3.028 | 2.367 | 3.015 |
| 136 | L136M | 2.870 | 2.522 | 6.068 |
| 139 | F139W | 3.157 | 0.616 | -0.147 |
| 140 | F140C | 5.288 | -1.783 | -1.192 |

| FIG. 45A Cont. | | | | |
|---|---|---:|---:|---:|
| 140 | F140M | 9.127 | 7.726 | 9.142 |
| 141 | M141A | 19.387 | 7.458 | 8.597 |
| 141 | M141C | 24.744 | 13.096 | 16.316 |
| 141 | M141D | 3.833 | -9.983 | -11.956 |
| 141 | M141F | 7.928 | -0.323 | -1.087 |
| 141 | M141G | 8.556 | 0.266 | -1.457 |
| 141 | M141L | 26.699 | 7.856 | 12.106 |
| 141 | M141P | 28.456 | 11.233 | 15.930 |
| 141 | M141T | 16.276 | -2.612 | -3.803 |
| 141 | M141V | 5.450 | 2.714 | 2.404 |
| 141 | M141W | 22.542 | -6.189 | -11.732 |
| 141 | M141Y | 7.007 | -2.350 | -2.470 |
| 142 | E142C | 8.448 | 3.735 | 9.778 |
| 142 | E142L | -3.282 | -4.875 | 3.795 |
| 142 | E142M | -2.761 | -2.385 | 3.791 |
| 142 | E142N | 1.555 | 1.436 | 4.438 |
| 142 | E142P | 3.497 | -5.193 | 5.681 |
| 142 | E142Q | 0.112 | -5.551 | 3.055 |
| 142 | E142W | 5.517 | -0.083 | 1.084 |
| 143 | E143P | 1.430 | 1.276 | 3.559 |
| 145 | Y145A | 7.436 | 2.636 | 1.728 |
| 145 | Y145C | 3.459 | -0.037 | -1.380 |
| 145 | Y145D | 14.809 | 2.255 | 0.802 |
| 145 | Y145E | 17.603 | 3.655 | 1.660 |
| 145 | Y145G | 6.679 | 1.119 | 0.709 |
| 145 | Y145L | 19.163 | 2.153 | 0.684 |
| 145 | Y145M | 20.306 | 2.929 | 2.071 |
| 145 | Y145N | 5.399 | 1.985 | 1.132 |
| 145 | Y145Q | 10.267 | 1.374 | 1.497 |
| 145 | Y145T | 12.043 | 1.401 | 0.033 |
| 145 | Y145W | 3.067 | 0.831 | 1.859 |
| 146 | L146A | 3.575 | 1.649 | 1.428 |
| 146 | L146C | 4.149 | 1.316 | 1.323 |
| 146 | L146D | 4.297 | 1.036 | 0.012 |
| 146 | L146E | 3.500 | 1.346 | 0.616 |
| 146 | L146G | 6.333 | 1.300 | 2.477 |
| 146 | L146H | 4.022 | 0.923 | 0.846 |
| 146 | L146S | 4.476 | 1.765 | 2.197 |
| 146 | L146W | 6.590 | 1.383 | 1.912 |
| 147 | K147P | 12.887 | 0.241 | 0.155 |
| 149 | Q149L | 1.904 | 3.314 | 1.490 |
| 151 | M151C | 5.917 | -0.371 | 2.395 |
| 151 | M151I | 8.570 | -1.585 | 3.131 |

| FIG. 45A Cont. | | | | |
|---|---|---|---|---|
| 151 | M151T | 4.843 | -0.831 | 2.369 |
| 151 | M151V | 12.233 | -0.991 | 3.783 |
| 152 | Q152L | 8.055 | 2.425 | 1.226 |
| 153 | D153I | -0.251 | -1.341 | 5.536 |
| 153 | D153K | 0.496 | 4.381 | 24.183 |
| 153 | D153M | -0.031 | -0.252 | 6.594 |
| 153 | D153W | 0.825 | 1.942 | 5.668 |
| 155 | G155F | 0.748 | 4.224 | 17.841 |
| 155 | G155H | 0.577 | 0.713 | 4.600 |
| 155 | G155W | 1.260 | 3.722 | 25.886 |
| 155 | G155Y | 1.028 | 4.734 | 24.337 |
| 156 | I156C | 0.643 | 4.084 | 14.550 |
| 156 | I156F | -1.220 | 5.882 | 21.266 |
| 156 | I156M | 1.352 | 3.366 | 5.773 |
| 156 | I156V | 1.058 | 8.647 | 28.646 |
| 158 | P158A | 28.337 | 25.604 | 23.049 |
| 158 | P158F | 4.767 | -13.452 | -15.087 |
| 158 | P158G | 15.067 | 18.931 | 18.163 |
| 158 | P158S | 1.396 | 2.691 | 3.567 |
| 159 | N159C | 3.930 | 2.253 | 1.220 |
| 159 | N159G | 5.704 | 6.742 | 8.472 |
| 159 | N159I | 6.698 | 0.339 | -1.825 |
| 159 | N159K | 3.480 | 1.811 | 0.050 |
| 159 | N159T | 9.890 | 5.559 | 4.096 |
| 159 | N159V | 7.525 | 3.005 | 0.453 |
| 160 | R160A | 9.519 | 6.024 | 3.348 |
| 160 | R160C | 3.506 | 2.581 | 1.641 |
| 160 | R160D | 8.278 | 4.382 | 2.706 |
| 160 | R160E | 5.409 | 3.130 | 1.951 |
| 160 | R160G | 7.865 | 5.128 | 4.129 |
| 160 | R160H | 5.935 | 4.122 | 4.113 |
| 160 | R160N | 6.060 | 4.902 | 3.730 |
| 160 | R160Q | 5.514 | 3.157 | 0.989 |
| 160 | R160S | 7.526 | 4.396 | 1.913 |
| 160 | R160W | 4.083 | 3.664 | 4.125 |
| 161 | D161G | 3.772 | 2.804 | 4.563 |
| 161 | D161I | 4.057 | 3.561 | 5.100 |
| 161 | D161K | 4.293 | 3.763 | 5.362 |
| 161 | D161L | 4.309 | 5.132 | 5.641 |
| 161 | D161M | 4.022 | 4.129 | 4.522 |
| 161 | D161N | 1.985 | 3.184 | 4.521 |
| 161 | D161Q | 3.578 | 3.372 | 4.481 |
| 161 | D161R | 3.649 | 2.933 | 4.841 |

| FIG. 45A Cont. | | | | |
|---|---|---|---|---|
| 161 | D161S | 2.066 | 2.033 | 3.739 |
| 161 | D161V | 2.584 | 2.273 | 4.309 |
| 161 | D161W | 6.250 | 5.868 | 8.648 |
| 162 | A162G | 1.092 | 2.969 | 4.532 |
| 163 | Q163G | 9.939 | 14.921 | 22.736 |
| 163 | Q163L | 5.669 | 7.675 | 11.903 |
| 163 | Q163M | 6.592 | 6.612 | 10.149 |
| 163 | Q163S | 11.573 | 17.725 | 20.165 |
| 164 | P164A | 3.492 | 2.729 | 3.086 |
| 164 | P164C | 7.690 | 10.246 | 19.449 |
| 164 | P164D | 3.378 | 2.709 | 1.181 |
| 164 | P164K | 2.978 | 2.832 | 3.739 |
| 164 | P164L | 2.884 | 2.488 | 3.158 |
| 164 | P164M | 4.425 | 4.031 | 3.981 |
| 164 | P164N | 3.045 | 2.408 | 3.364 |
| 164 | P164R | 3.349 | 2.698 | 4.469 |
| 164 | P164T | 2.855 | 1.824 | 3.006 |
| 164 | P164V | 3.112 | 2.173 | 2.366 |
| 164 | P164W | 3.153 | 2.758 | 3.762 |
| 165 | F165G | 2.593 | 0.257 | 3.167 |
| 165 | F165H | 4.419 | 2.655 | 6.687 |
| 165 | F165K | 4.942 | -2.230 | -3.292 |
| 165 | F165M | 7.251 | 0.917 | -0.403 |
| 165 | F165R | 4.877 | -2.313 | -1.664 |
| 165 | F165S | 4.960 | 1.864 | 3.145 |
| 165 | F165T | 5.339 | -2.331 | -3.829 |
| 165 | F165W | 0.010 | 0.235 | 4.654 |
| 165 | F165Y | 3.225 | 2.345 | 3.191 |
| 166 | I166L | 18.318 | 14.606 | 16.175 |
| 166 | I166V | 4.327 | 4.575 | 6.647 |
| 167 | A167C | 4.510 | 3.914 | 1.380 |
| 167 | A167T | 11.776 | 8.525 | 9.337 |
| 168 | D168A | 2.457 | 2.548 | 4.035 |
| 168 | D168G | 3.636 | 4.073 | 4.581 |
| 168 | D168H | 2.674 | 3.053 | 3.474 |
| 168 | D168R | 3.855 | 3.280 | 6.154 |
| 168 | D168T | 2.600 | 2.800 | 3.557 |
| 169 | W169A | 2.642 | 5.199 | 5.873 |
| 169 | W169E | 4.386 | 6.114 | 6.052 |
| 169 | W169K | 4.477 | 3.840 | 13.096 |
| 169 | W169Q | 5.338 | 6.843 | 7.989 |
| 169 | W169R | 1.304 | 1.991 | 5.210 |
| 169 | W169S | 2.189 | 3.655 | 4.112 |

| FIG. 45A Cont. | | | | |
|---|---|---|---|---|
| 169 | W169T | 1.785 | 2.162 | 6.470 |
| 169 | W169V | 1.067 | 0.726 | 3.672 |
| 170 | M170F | 4.885 | 3.909 | 3.829 |
| 170 | M170V | 3.485 | 3.100 | 4.452 |
| 172 | K172M | 4.747 | 3.595 | 2.023 |
| 173 | Q173N | 4.134 | 3.905 | 5.313 |
| 173 | Q173W | 1.146 | 1.915 | 3.827 |
| 175 | Q175I | 3.342 | 3.221 | 3.491 |
| 175 | Q175Y | 2.746 | 2.780 | 3.254 |
| 176 | P176H | 4.015 | 4.074 | 5.270 |
| 176 | P176K | 3.495 | 3.084 | 3.649 |
| 176 | P176L | 2.672 | 3.069 | 3.829 |
| 176 | P176N | 3.029 | 3.025 | 2.671 |
| 176 | P176R | 2.964 | 2.174 | 3.241 |
| 176 | P176W | 3.269 | 3.097 | 3.591 |
| 176 | P176Y | 2.764 | 2.738 | 3.305 |
| 178 | V178T | 3.190 | 2.694 | 4.114 |
| 178 | V178W | 3.680 | 2.786 | 3.353 |
| 179 | N179G | 3.629 | 2.391 | 1.826 |
| 179 | N179H | 4.365 | 3.812 | 4.765 |
| 179 | N179R | 4.654 | 3.519 | 5.557 |
| 179 | N179T | 3.572 | 2.829 | 5.611 |
| 179 | N179V | 4.917 | 2.799 | 6.588 |
| 179 | N179Y | 4.669 | 3.002 | 3.265 |
| 180 | H180A | 2.979 | 3.267 | 2.634 |
| 180 | H180G | 3.183 | 3.983 | 3.849 |
| 180 | H180R | 4.458 | 2.264 | 4.203 |
| 180 | H180S | 1.578 | 1.692 | 4.349 |
| 180 | H180V | 3.685 | 2.490 | 2.811 |
| 180 | H180W | 3.961 | 2.513 | 6.242 |
| 181 | D181A | 3.031 | 2.584 | 3.438 |
| 181 | D181H | 5.520 | 3.286 | 7.065 |
| 181 | D181I | 3.956 | 3.717 | 5.388 |
| 181 | D181L | 5.749 | 4.543 | 9.373 |
| 181 | D181P | 3.013 | 2.523 | 2.960 |
| 181 | D181Q | 2.775 | 2.594 | 3.340 |
| 181 | D181R | 4.136 | 3.057 | 5.542 |
| 181 | D181S | 2.912 | 2.871 | 3.726 |
| 181 | D181W | 3.880 | 3.401 | 4.580 |
| 182 | S182A | 3.017 | 2.728 | 3.484 |
| 182 | S182G | 3.546 | 2.190 | 6.319 |
| 182 | S182I | 2.625 | 2.695 | 3.706 |
| 182 | S182K | 8.925 | 8.192 | 7.944 |

FIG. 45A Cont.

| 182 | S182L | 5.685 | 4.213 | 6.957 |
|---|---|---|---|---|
| 182 | S182P | 5.587 | 4.401 | 8.903 |
| 182 | S182Q | 2.495 | 0.896 | 4.219 |
| 182 | S182R | 4.486 | 3.007 | 6.811 |
| 182 | S182T | 2.619 | 1.235 | 5.003 |

FIG. 45B

| POSITION | MUTATION | 1MOD_Z_SUBSSPEC_C 10 | 1MOD_Z_SUBSSPEC_C 12 | 1MOD_Z_SUBSSPEC_C 14 |
|---|---|---|---|---|
| 1 | A1L | 48.514 | -37.653 | -2.752 |
| 1 | A1Q | -2.486 | 6.325 | -9.186 |
| 1 | A1S | -23.759 | 5.850 | 28.101 |
| 1 | A1V | -2.350 | 7.164 | -11.124 |
| 2 | D2E | -0.668 | 3.150 | -5.543 |
| 2 | D2K | -0.305 | 5.631 | -11.357 |
| 2 | D2P | -6.441 | 5.960 | -1.667 |
| 2 | D2W | -3.805 | 7.712 | -9.961 |
| 3 | T3K | 5.877 | -2.945 | -3.760 |
| 3 | T3R | -2.123 | 5.157 | -7.326 |
| 3 | T3W | -2.285 | 3.375 | -4.461 |
| 4 | L4A | 3.568 | 3.162 | -14.912 |
| 4 | L4S | 0.968 | -2.325 | 3.295 |
| 4 | L4Y | -15.139 | 4.369 | 17.118 |
| 5 | L5F | -3.514 | 8.841 | -8.569 |
| 5 | L5G | -11.850 | 9.755 | -0.504 |
| 5 | L5H | -5.668 | -18.894 | 49.806 |
| 5 | L5S | -6.262 | 6.972 | -0.005 |
| 5 | L5Y | -19.759 | 10.741 | 10.891 |
| 6 | I6T | -3.743 | 7.482 | -5.797 |
| 6 | I6V | -9.941 | 6.836 | 2.442 |
| 7 | L7A | -5.015 | 11.193 | -9.807 |
| 7 | L7C | -9.123 | 4.609 | 5.775 |
| 7 | L7M | -1.148 | 3.062 | -3.124 |
| 7 | L7N | -23.486 | 17.456 | 3.062 |
| 7 | L7S | -21.759 | 9.573 | 16.783 |
| 7 | L7T | -17.077 | 11.361 | 5.000 |
| 7 | L7V | 3.865 | 1.108 | -9.460 |
| 7 | L7Y | -24.305 | 10.558 | 19.031 |
| 8 | G8S | -13.718 | 2.133 | 11.525 |
| 9 | D9N | 5.692 | -7.515 | 5.187 |
| 9 | D9T | -40.636 | -2.082 | 46.771 |
| 11 | L11C | -35.128 | -5.595 | 46.137 |
| 11 | L11I | -13.652 | -0.536 | 15.468 |

| FIG. 45B Cont. | | | | |
|---|---|---|---|---|
| 11 | L11M | -32.833 | 6.911 | 24.870 |
| 11 | L11Q | -41.620 | -0.115 | 44.870 |
| 11 | L11V | -19.849 | -6.977 | 31.806 |
| 12 | S12A | 6.708 | -2.948 | -2.736 |
| 12 | S12I | -26.505 | 14.101 | 7.264 |
| 12 | S12L | -21.879 | 0.349 | 26.470 |
| 12 | S12M | -17.035 | 0.167 | 20.715 |
| 12 | S12T | -7.390 | 2.766 | 3.778 |
| 12 | S12V | -25.521 | 15.319 | 4.377 |
| 13 | A13C | -9.325 | 4.944 | 2.581 |
| 13 | A13D | 32.086 | -15.227 | -22.702 |
| 13 | A13G | -28.452 | 26.850 | -2.137 |
| 13 | A13H | -12.806 | 8.058 | 5.847 |
| 13 | A13I | -14.177 | 3.234 | 10.398 |
| 13 | A13L | -30.387 | 5.884 | 35.766 |
| 13 | A13N | -3.062 | 3.141 | -1.433 |
| 13 | A13T | -12.269 | 3.614 | 12.379 |
| 13 | A13V | -4.275 | -0.630 | 5.539 |
| 13 | A13W | -26.301 | 23.469 | 0.282 |
| 14 | G14A | 15.742 | -13.198 | -1.573 |
| 14 | G14E | 5.397 | 0.611 | -6.750 |
| 14 | G14F | -44.312 | 6.850 | 55.040 |
| 14 | G14I | -37.226 | 8.878 | 26.630 |
| 14 | G14K | -24.419 | 35.111 | -22.056 |
| 14 | G14M | -16.669 | 15.904 | -6.011 |
| 14 | G14P | 15.233 | -7.375 | -5.306 |
| 14 | G14Q | 25.688 | -15.179 | -13.185 |
| 14 | G14R | 6.925 | -14.406 | 13.589 |
| 14 | G14S | 22.348 | -11.496 | -6.715 |
| 14 | G14T | -12.570 | 1.759 | 10.891 |
| 14 | G14V | -18.570 | -5.806 | 28.673 |
| 15 | Y15A | -75.656 | 19.556 | 80.927 |
| 15 | Y15C | -39.128 | 12.344 | 23.426 |
| 15 | Y15D | -74.258 | 43.275 | 39.073 |
| 15 | Y15E | -32.800 | 6.091 | 26.067 |
| 15 | Y15G | -47.292 | 12.391 | 32.158 |
| 15 | Y15I | -44.407 | 13.117 | 27.968 |
| 15 | Y15L | -73.290 | 30.039 | 59.718 |
| 15 | Y15M | -73.452 | 24.000 | 70.121 |
| 15 | Y15N | -43.062 | 23.117 | 11.489 |
| 15 | Y15Q | -72.323 | 25.932 | 65.202 |
| 15 | Y15R | -92.269 | 17.478 | 109.234 |
| 15 | Y15S | -75.065 | 25.546 | 69.960 |
| 15 | Y15V | -41.259 | 7.801 | 32.581 |

| FIG. 45B Cont. | | | | |
|---|---|---|---|---|
| 16 | R16D | -8.774 | 7.575 | 0.524 |
| 16 | R16E | -5.011 | 7.720 | -5.363 |
| 16 | R16G | 28.215 | -21.411 | -6.573 |
| 16 | R16H | -7.914 | 9.169 | -3.427 |
| 16 | R16I | -0.280 | 3.855 | -6.008 |
| 16 | R16L | 8.269 | -4.406 | -5.040 |
| 16 | R16M | 9.344 | -4.647 | -6.250 |
| 16 | R16N | 9.935 | -6.821 | -3.508 |
| 16 | R16P | 51.387 | -35.710 | -17.460 |
| 16 | R16Q | 4.075 | -0.155 | -5.847 |
| 16 | R16S | -5.871 | 4.193 | 1.815 |
| 16 | R16T | 3.495 | -0.583 | -2.877 |
| 16 | R16V | -6.086 | 8.203 | -4.556 |
| 16 | R16W | -23.129 | 7.092 | 22.863 |
| 17 | M17A | -3.645 | 3.664 | -2.657 |
| 17 | M17C | 6.282 | -3.557 | -1.398 |
| 17 | M17G | -9.032 | 5.122 | 3.684 |
| 17 | M17K | -13.259 | 7.042 | 6.617 |
| 17 | M17L | 4.052 | -3.628 | 1.102 |
| 17 | M17N | -11.390 | 4.171 | 5.996 |
| 17 | M17P | -20.005 | 6.222 | 21.479 |
| 17 | M17Q | -5.632 | 3.510 | 1.479 |
| 17 | M17R | -35.521 | 17.215 | 12.264 |
| 17 | M17S | -11.030 | 5.576 | 3.461 |
| 17 | M17T | 3.889 | -2.597 | -0.271 |
| 17 | M17V | 14.905 | -9.201 | -2.173 |
| 18 | S18M | 0.112 | 7.232 | -3.934 |
| 18 | S18N | 0.015 | 9.473 | -5.033 |
| 19 | A19L | -6.717 | 17.108 | -2.989 |
| 21 | A21I | -3.083 | 3.373 | 0.989 |
| 21 | A21L | -4.278 | 4.701 | 1.385 |
| 21 | A21Y | -5.124 | 4.452 | -2.411 |
| 22 | A22C | 6.943 | -2.433 | -3.957 |
| 22 | A22D | 14.773 | -5.646 | -7.477 |
| 22 | A22E | 11.129 | -2.711 | -8.694 |
| 22 | A22F | -12.514 | 11.321 | -6.786 |
| 22 | A22G | 4.332 | -4.220 | -1.670 |
| 22 | A22H | 8.390 | -2.695 | -5.240 |
| 22 | A22I | 8.287 | -2.334 | -5.832 |
| 22 | A22K | 9.295 | 0.125 | -12.082 |
| 22 | A22L | -19.620 | 23.539 | 5.209 |
| 22 | A22M | -11.636 | 6.813 | 1.109 |
| 22 | A22N | 4.307 | -7.830 | 0.264 |
| 22 | A22R | -6.132 | 11.008 | -0.286 |

| FIG. 45B Cont. | | | | |
|---|---|---|---|---|
| 22 | A22Y | -19.310 | 6.748 | 11.043 |
| 23 | W23Y | -1.403 | -0.711 | 3.214 |
| 24 | P24A | 6.161 | -3.805 | -3.538 |
| 24 | P24C | 9.579 | -3.072 | -6.030 |
| 24 | P24D | 9.398 | -5.564 | -0.832 |
| 24 | P24F | 15.315 | -4.793 | -9.878 |
| 24 | P24G | -7.553 | 4.764 | 0.056 |
| 24 | P24I | 13.817 | 1.190 | -19.977 |
| 24 | P24S | 3.455 | -1.630 | -1.128 |
| 24 | P24T | 10.354 | -2.892 | -7.378 |
| 24 | P24V | 13.455 | -6.072 | -4.944 |
| 24 | P24W | 5.419 | -0.007 | -6.885 |
| 25 | A25R | -5.375 | 3.096 | 0.902 |
| 26 | L26C | -6.311 | 2.183 | 3.029 |
| 26 | L26D | -6.712 | 6.234 | -2.083 |
| 26 | L26E | -2.278 | 3.954 | -0.044 |
| 26 | L26F | -16.378 | 7.429 | 5.473 |
| 26 | L26G | -6.244 | 5.883 | -2.051 |
| 26 | L26H | -8.302 | 6.568 | 4.000 |
| 26 | L26I | -1.937 | 3.000 | 0.176 |
| 26 | L26K | -4.717 | 3.498 | 2.396 |
| 26 | L26N | -8.819 | 6.422 | -0.305 |
| 26 | L26R | -3.717 | 3.166 | 1.670 |
| 26 | L26S | -8.217 | 4.080 | 2.235 |
| 26 | L26W | -9.254 | 6.984 | -0.717 |
| 26 | L26Y | -14.706 | 5.977 | 5.854 |
| 27 | L27A | -8.050 | 7.944 | -3.130 |
| 27 | L27C | -5.059 | 9.017 | -0.242 |
| 27 | L27F | -6.512 | 3.963 | 0.806 |
| 27 | L27M | -2.595 | 3.705 | 0.374 |
| 27 | L27W | -12.365 | 14.970 | -8.559 |
| 27 | L27Y | -6.815 | 7.772 | 2.044 |
| 28 | N28A | 4.358 | -1.564 | -2.019 |
| 28 | N28P | -5.254 | 2.668 | 3.319 |
| 28 | N28W | -1.947 | 3.038 | -1.930 |
| 29 | D29P | -5.799 | 5.545 | -1.589 |
| 29 | D29V | -2.063 | 0.188 | 3.333 |
| 30 | K30P | -4.941 | 4.702 | 0.439 |
| 31 | W31E | -2.309 | 3.466 | -2.047 |
| 31 | W31N | -3.410 | 3.069 | -0.543 |
| 32 | Q32V | 3.151 | -1.954 | -2.135 |
| 32 | Q32Y | 3.842 | -2.646 | -2.135 |
| 33 | S33F | -1.224 | -0.570 | 3.187 |
| 36 | S36H | -0.796 | -1.048 | 3.275 |

| FIG. 45B Cont. | | | | |
|---|---|---|---|---|
| 37 | V37F | -1.234 | 7.783 | -4.023 |
| 37 | V37H | -23.808 | 0.319 | 18.465 |
| 37 | V37Q | 1.461 | -7.507 | 3.723 |
| 37 | V37S | -11.174 | 17.420 | -2.521 |
| 37 | V37W | -4.480 | 4.142 | 0.643 |
| 38 | V38D | -13.150 | 21.406 | -3.554 |
| 38 | V38E | 8.287 | -3.522 | -4.164 |
| 38 | V38G | -3.210 | 14.667 | -6.981 |
| 38 | V38K | 3.078 | -1.348 | -1.535 |
| 38 | V38P | -15.665 | 31.043 | -7.826 |
| 38 | V38R | 4.395 | -4.029 | -0.831 |
| 39 | N39A | 7.740 | -5.051 | -4.795 |
| 39 | N39C | -3.868 | 4.812 | -0.080 |
| 39 | N39E | -9.497 | 23.942 | -8.061 |
| 39 | N39F | -11.076 | -1.921 | 23.099 |
| 39 | N39G | -1.114 | 11.188 | -6.371 |
| 39 | N39M | -4.250 | -0.603 | 8.626 |
| 39 | N39Q | -34.766 | 16.333 | 16.681 |
| 39 | N39T | 8.287 | -1.565 | -5.526 |
| 39 | N39V | -2.894 | -1.279 | 3.632 |
| 39 | N39W | -18.000 | 10.536 | 7.291 |
| 39 | N39Y | -29.138 | -9.609 | 29.122 |
| 40 | A40D | 6.311 | 7.420 | -9.751 |
| 40 | A40G | -2.671 | -4.754 | 5.178 |
| 40 | A40H | 3.201 | 0.142 | -2.847 |
| 40 | A40L | -9.253 | 6.102 | 2.391 |
| 40 | A40M | -2.431 | 4.957 | -1.300 |
| 40 | A40P | -30.635 | 15.391 | 14.052 |
| 40 | A40T | -7.222 | 0.826 | 5.131 |
| 40 | A40V | -7.301 | 1.738 | 4.670 |
| 40 | A40Y | -2.431 | 11.696 | -5.667 |
| 41 | S41C | -8.846 | 6.593 | 1.365 |
| 41 | S41P | -22.604 | 2.786 | 16.815 |
| 41 | S41T | -28.989 | 16.352 | 9.998 |
| 42 | I42D | -12.486 | 0.852 | 6.716 |
| 42 | I42G | -10.282 | -0.119 | 5.994 |
| 42 | I42K | -4.953 | 4.980 | -0.273 |
| 42 | I42P | -19.197 | 10.716 | 5.013 |
| 42 | I42S | -6.509 | 2.387 | 3.429 |
| 43 | S43A | -4.055 | 3.085 | 0.698 |
| 43 | S43C | 3.201 | -0.232 | -2.530 |
| 43 | S43F | -33.923 | 5.379 | 24.151 |
| 43 | S43G | -22.314 | 13.085 | 7.221 |
| 43 | S43H | -24.346 | 9.594 | 12.120 |

| FIG. 45B Cont. | | | | |
|---|---|---|---|---|
| 43 | S43L | -1.259 | -3.574 | 4.309 |
| 43 | S43P | 8.821 | -3.125 | -4.720 |
| 43 | S43R | -15.955 | 13.110 | 1.781 |
| 43 | S43T | -14.768 | 9.244 | 4.264 |
| 43 | S43V | -8.541 | 3.833 | 3.835 |
| 43 | S43W | -25.190 | 2.711 | 19.095 |
| 44 | G44A | -8.980 | 2.981 | 3.501 |
| 44 | G44C | -31.232 | 10.541 | 17.176 |
| 44 | G44E | -24.556 | 6.985 | 10.219 |
| 44 | G44F | -20.625 | -3.499 | 20.810 |
| 44 | G44H | -29.042 | 9.120 | 16.612 |
| 44 | G44K | -17.377 | 7.053 | 6.033 |
| 44 | G44L | -42.261 | 13.110 | 24.309 |
| 44 | G44M | -20.466 | 2.419 | 10.431 |
| 44 | G44N | -19.648 | 5.213 | 8.372 |
| 44 | G44Q | -36.536 | 13.110 | 19.388 |
| 44 | G44R | -11.367 | 5.775 | 3.290 |
| 44 | G44S | -24.088 | 4.446 | 11.374 |
| 44 | G44W | -12.402 | -7.257 | 11.249 |
| 44 | G44Y | -4.272 | -8.961 | 7.534 |
| 45 | D45A | -27.495 | 3.323 | 57.388 |
| 45 | D45C | -21.997 | 7.000 | 12.481 |
| 45 | D45E | -10.071 | 5.579 | 3.564 |
| 45 | D45F | -29.067 | 8.007 | 46.447 |
| 45 | D45G | -48.829 | 0.424 | 119.153 |
| 45 | D45H | -18.448 | 6.929 | 23.624 |
| 45 | D45I | -6.720 | 5.653 | 0.630 |
| 45 | D45K | -37.257 | 31.502 | -7.671 |
| 45 | D45L | -7.433 | 6.277 | 0.675 |
| 45 | D45M | -26.257 | 11.576 | 28.094 |
| 45 | D45P | -42.156 | 7.773 | 29.050 |
| 45 | D45Q | -24.346 | 4.756 | 16.521 |
| 45 | D45S | -21.074 | 3.733 | 14.648 |
| 45 | D45T | -20.414 | 6.825 | 11.284 |
| 45 | D45V | -10.335 | 5.180 | 4.151 |
| 45 | D45W | -11.232 | 3.359 | 6.567 |
| 46 | T46A | -14.214 | 2.511 | 9.862 |
| 46 | T46C | -13.923 | 3.284 | 8.937 |
| 46 | T46D | -36.257 | -4.446 | 103.506 |
| 46 | T46E | 18.609 | -6.192 | -10.318 |
| 46 | T46F | 20.410 | -4.483 | -36.259 |
| 46 | T46G | -45.971 | -1.509 | 118.329 |
| 46 | T46I | 19.981 | -1.435 | -44.847 |
| 46 | T46K | -11.876 | 7.822 | 4.565 |

| FIG. 45B Cont. | | | | |
|---|---|---|---|---|
| 46 | T46L | 34.731 | -19.608 | -11.966 |
| 46 | T46N | -9.385 | 4.506 | 3.971 |
| 46 | T46R | -13.114 | 10.684 | -1.435 |
| 46 | T46S | -14.108 | 1.040 | 11.126 |
| 46 | T46V | 19.600 | -4.892 | -32.965 |
| 46 | T46W | -28.066 | 2.012 | 22.210 |
| 47 | S47A | 57.886 | -16.416 | -91.082 |
| 47 | S47C | 21.248 | -11.254 | -7.971 |
| 47 | S47E | -45.162 | -9.539 | 141.859 |
| 47 | S47F | 8.082 | -4.845 | -2.530 |
| 47 | S47G | 18.557 | -9.209 | -7.564 |
| 47 | S47L | 29.665 | -15.743 | -11.131 |
| 47 | S47M | 27.607 | -15.693 | -9.415 |
| 47 | S47P | -38.971 | 24.810 | 17.741 |
| 47 | S47Q | -66.257 | 5.703 | 145.741 |
| 47 | S47T | 4.863 | -3.648 | -0.860 |
| 47 | S47V | 34.652 | -19.085 | -12.372 |
| 47 | S47W | -27.776 | -8.761 | 31.668 |
| 47 | S47Y | -49.305 | -2.513 | 129.741 |
| 48 | Q48C | -2.921 | -0.781 | 3.203 |
| 48 | Q48D | 19.124 | -1.546 | -42.376 |
| 48 | Q48E | 3.933 | 10.164 | -41.906 |
| 48 | Q48F | -9.042 | -0.332 | 8.034 |
| 48 | Q48G | 4.230 | -1.454 | -2.327 |
| 48 | Q48I | -3.554 | 0.017 | 3.023 |
| 48 | Q48M | -5.876 | -0.406 | 5.393 |
| 48 | Q48S | 6.886 | -0.320 | -16.024 |
| 48 | Q48T | 8.648 | -3.257 | -11.082 |
| 48 | Q48V | -9.114 | -5.450 | 39.624 |
| 48 | Q48W | -4.114 | -5.078 | 26.094 |
| 48 | Q48Y | -7.876 | -4.892 | 34.918 |
| 49 | Q49A | -32.553 | 5.896 | 34.139 |
| 49 | Q49C | -9.095 | -2.526 | 10.088 |
| 49 | Q49D | -28.813 | -4.625 | 39.485 |
| 49 | Q49E | -42.634 | 0.688 | 51.267 |
| 49 | Q49G | -35.398 | 1.833 | 41.366 |
| 49 | Q49H | -7.222 | -1.529 | 7.582 |
| 49 | Q49I | -40.276 | 7.667 | 41.762 |
| 49 | Q49K | -7.776 | 3.185 | 3.767 |
| 49 | Q49L | -20.195 | 3.604 | 21.267 |
| 49 | Q49M | -16.211 | 2.771 | 17.109 |
| 49 | Q49P | -28.383 | 16.576 | 9.275 |
| 49 | Q49R | -27.431 | 15.167 | 18.990 |
| 49 | Q49S | -32.959 | -2.542 | 42.554 |

| FIG. 45B Cont. | | | | |
|---|---|---|---|---|
| 49 | Q49V | -36.455 | 7.354 | 37.406 |
| 49 | Q49W | -43.122 | 3.188 | 49.485 |
| 49 | Q49Y | -25.236 | 6.000 | 25.030 |
| 50 | G50A | -28.650 | -7.750 | 42.158 |
| 50 | G50C | -69.057 | 7.250 | 77.208 |
| 50 | G50E | -125.886 | -16.708 | 169.188 |
| 50 | G50F | -100.114 | 6.833 | 115.426 |
| 50 | G50I | -119.951 | 14.646 | 132.158 |
| 50 | G50K | -114.098 | 34.333 | 106.317 |
| 50 | G50L | -104.341 | 10.167 | 117.406 |
| 50 | G50M | -86.537 | -1.708 | 107.109 |
| 50 | G50N | -110.114 | 7.354 | 127.109 |
| 50 | G50P | -20.185 | 5.821 | 24.955 |
| 50 | G50Q | -68.081 | -17.958 | 99.980 |
| 50 | G50R | -18.604 | 6.226 | 21.722 |
| 50 | G50S | -9.658 | 0.432 | 15.431 |
| 50 | G50T | -19.026 | 5.720 | 23.175 |
| 50 | G50W | -138.488 | -14.833 | 182.752 |
| 50 | G50Y | -132.797 | 3.188 | 158.693 |
| 51 | L51C | -3.366 | -0.563 | 4.634 |
| 51 | L51D | -21.821 | 14.750 | 12.554 |
| 51 | L51F | 6.797 | 0.479 | -8.733 |
| 51 | L51H | 3.463 | 1.000 | -5.267 |
| 51 | L51N | -2.959 | 5.583 | -1.703 |
| 51 | L51S | -2.472 | -2.438 | 5.327 |
| 51 | L51T | -6.134 | 5.568 | 1.972 |
| 51 | L51V | -13.528 | 10.271 | 6.812 |
| 51 | L51W | 2.813 | 3.188 | -6.356 |
| 51 | L51Y | 5.008 | 2.458 | -8.436 |
| 52 | A52C | -3.691 | 3.083 | 1.564 |
| 52 | A52D | 15.577 | -4.417 | -14.772 |
| 52 | A52H | -6.293 | -1.813 | 9.386 |
| 52 | A52I | -10.927 | 1.938 | 11.465 |
| 52 | A52L | -10.439 | -1.500 | 14.139 |
| 52 | A52M | -6.537 | -2.333 | 10.079 |
| 52 | A52P | -12.248 | 8.034 | 8.464 |
| 52 | A52R | -4.911 | -1.917 | 7.703 |
| 52 | A52V | -5.967 | 0.375 | 6.911 |
| 52 | A52W | -21.171 | -7.958 | 33.347 |
| 52 | A52Y | -2.715 | 0.889 | 3.175 |
| 53 | R53A | -23.023 | 11.009 | 15.186 |
| 53 | R53C | -17.173 | 8.372 | 16.158 |
| 53 | R53D | -61.107 | 5.393 | 62.316 |
| 53 | R53E | -53.598 | 10.416 | 49.405 |

| FIG. 45B Cont. | | | | |
|---|---|---|---|---|
| 53 | R53F | -22.670 | 7.561 | 26.509 |
| 53 | R53G | -27.889 | 13.292 | 18.392 |
| 53 | R53I | -33.215 | 7.447 | 29.700 |
| 53 | R53K | -9.026 | 3.101 | 10.419 |
| 53 | R53L | -39.575 | 9.411 | 34.848 |
| 53 | R53N | -25.092 | 10.598 | 17.844 |
| 53 | R53S | -25.284 | 11.146 | 17.591 |
| 53 | R53T | -16.014 | 9.740 | 12.198 |
| 53 | R53V | -32.257 | 6.580 | 29.489 |
| 53 | R53W | -51.375 | 11.146 | 46.241 |
| 53 | R53Y | -44.556 | 23.064 | 27.717 |
| 54 | L54A | -0.494 | 6.215 | -5.194 |
| 54 | L54C | -0.341 | 3.566 | -2.916 |
| 54 | L54E | -7.697 | 11.055 | -1.734 |
| 54 | L54F | -8.732 | 13.064 | -2.451 |
| 54 | L54G | -8.195 | 11.922 | -1.987 |
| 54 | L54M | -4.517 | 11.100 | -5.278 |
| 54 | L54N | -8.540 | 11.192 | -0.932 |
| 54 | L54S | -5.360 | 10.598 | -3.844 |
| 54 | L54T | 4.218 | 0.279 | -4.857 |
| 54 | L54W | -16.433 | 14.023 | 5.143 |
| 54 | L54Y | -36.088 | 21.192 | 20.165 |
| 55 | P55Y | -2.716 | 10.187 | -6.460 |
| 56 | A56P | 4.908 | -3.557 | -2.114 |
| 56 | A56W | -1.261 | -3.740 | 4.848 |
| 56 | A56Y | -1.682 | -2.826 | 4.468 |
| 57 | L57A | -0.292 | 3.416 | -7.234 |
| 57 | L57C | -1.542 | 3.810 | -5.863 |
| 57 | L57F | -10.431 | 4.348 | 8.411 |
| 57 | L57K | -3.069 | 5.351 | -6.669 |
| 57 | L57P | -2.068 | 4.419 | -3.115 |
| 57 | L57Q | -0.708 | 9.401 | -19.895 |
| 57 | L57R | -4.042 | 6.427 | -7.395 |
| 57 | L57Y | -4.690 | 3.953 | -0.702 |
| 58 | L58A | -8.023 | 7.108 | -1.992 |
| 58 | L58D | -10.755 | 16.068 | -17.476 |
| 58 | L58E | -11.079 | 10.011 | -3.202 |
| 58 | L58F | -5.616 | 1.373 | 6.718 |
| 58 | L58G | -16.773 | 13.129 | -0.298 |
| 58 | L58H | -11.727 | 9.652 | -1.266 |
| 58 | L58N | -9.227 | 9.545 | -5.460 |
| 58 | L58R | -4.523 | 5.466 | -0.559 |
| 58 | L58S | -9.782 | 9.509 | -4.411 |
| 58 | L58W | -8.903 | 8.434 | -3.444 |

| FIG. 45B Cont. | | | | |
|---|---|---|---|---|
| 58 | L58Y | -20.199 | 11.659 | 8.976 |
| 59 | K59R | 3.366 | -1.817 | -1.750 |
| 60 | Q60M | 4.708 | -2.892 | -1.669 |
| 60 | Q60P | -1.727 | 4.814 | -7.879 |
| 61 | H61D | -2.368 | 4.942 | -1.778 |
| 61 | H61G | -0.677 | 5.349 | -3.583 |
| 61 | H61P | -5.801 | 9.826 | -2.426 |
| 62 | Q62P | -1.522 | 6.163 | -3.537 |
| 62 | Q62W | 0.517 | 3.663 | -3.398 |
| 63 | P63I | -1.672 | 5.116 | -2.519 |
| 63 | P63L | -3.313 | 8.779 | -3.907 |
| 63 | P63N | -3.800 | 6.514 | -3.341 |
| 63 | P63S | -6.199 | 9.244 | -1.639 |
| 63 | P63T | -5.552 | 7.035 | -0.435 |
| 63 | P63V | -1.821 | 3.314 | -0.944 |
| 63 | P63W | -8.488 | 14.360 | -3.491 |
| 64 | R64D | 4.846 | -1.337 | -3.444 |
| 64 | R64E | 4.000 | -0.930 | -2.981 |
| 64 | R64F | -0.229 | 4.186 | -3.167 |
| 64 | R64P | -10.975 | 17.791 | -3.907 |
| 64 | R64Q | 4.000 | -3.779 | -0.713 |
| 64 | R64W | -5.652 | 13.895 | -5.759 |
| 64 | R64Y | -3.512 | 4.709 | -0.435 |
| 65 | W65A | -0.180 | 7.222 | -7.393 |
| 65 | W65E | -4.203 | 10.470 | -6.143 |
| 65 | W65G | -3.453 | 5.128 | -1.837 |
| 65 | W65K | -2.289 | 3.077 | -0.607 |
| 65 | W65M | -1.820 | 5.812 | -4.000 |
| 65 | W65N | 1.969 | 3.504 | -5.920 |
| 65 | W65V | 2.867 | 3.205 | -6.634 |
| 66 | V66I | -4.164 | 0.598 | 4.125 |
| 66 | V66M | -3.578 | 4.658 | -0.786 |
| 66 | V66S | -2.986 | 4.976 | -2.414 |
| 67 | L67A | -3.969 | 4.402 | -0.071 |
| 67 | L67T | -7.016 | 5.427 | 2.295 |
| 68 | V68A | -6.742 | 6.453 | 0.955 |
| 68 | V68M | -1.352 | 11.410 | -10.384 |
| 68 | V68S | -11.469 | 20.983 | -8.777 |
| 68 | V68T | -1.586 | 3.162 | -1.545 |
| 69 | E69A | -22.982 | 16.124 | 25.784 |
| 69 | E69C | -27.267 | 18.336 | 32.255 |
| 69 | E69D | -12.881 | 9.166 | 7.837 |
| 69 | E69F | -8.037 | -2.814 | 27.745 |
| 69 | E69G | -19.465 | 8.204 | 33.922 |

| FIG. 45B Cont. | | | | |
|---|---|---|---|---|
| 69 | E69H | -29.722 | 23.071 | 28.431 |
| 69 | E69K | -31.846 | 29.398 | 20.098 |
| 69 | E69L | -31.663 | 23.292 | 33.137 |
| 69 | E69M | -20.088 | 14.265 | 22.157 |
| 69 | E69N | -24.264 | 20.903 | 18.529 |
| 69 | E69P | -8.107 | 8.625 | 0.694 |
| 69 | E69Q | -12.685 | 0.500 | 20.368 |
| 69 | E69S | -7.881 | 1.378 | 11.070 |
| 69 | E69V | -17.560 | 12.274 | 19.902 |
| 69 | E69Y | -14.996 | 9.708 | 18.627 |
| 70 | L70A | -15.803 | 12.459 | 7.812 |
| 70 | L70C | -25.143 | 25.504 | 10.784 |
| 70 | L70E | -13.800 | 8.929 | 9.742 |
| 70 | L70F | -39.355 | 28.425 | 42.353 |
| 70 | L70H | -65.873 | 36.582 | 13.112 |
| 70 | L70I | -0.564 | 4.531 | -8.529 |
| 70 | L70K | -31.663 | 54.796 | -36.667 |
| 70 | L70Q | -38.916 | 26.168 | 46.176 |
| 70 | L70S | -29.832 | 28.027 | 17.745 |
| 70 | L70T | -40.915 | 15.063 | 16.072 |
| 70 | L70V | -13.714 | 9.442 | 15.784 |
| 70 | L70W | -49.136 | 2.894 | 125.098 |
| 71 | G71A | -8.513 | 16.566 | -13.824 |
| 72 | G72A | 22.432 | -24.937 | 8.474 |
| 72 | G72C | 21.780 | -32.504 | 13.627 |
| 72 | G72P | 10.352 | -30.115 | 39.118 |
| 72 | G72S | 21.377 | -40.558 | 32.549 |
| 73 | N73A | -29.185 | -1.819 | 32.298 |
| 73 | N73C | -24.471 | -13.119 | 36.623 |
| 73 | N73G | -60.831 | 4.272 | 42.783 |
| 73 | N73H | -74.207 | 3.435 | 75.507 |
| 73 | N73I | -69.846 | 2.305 | 71.833 |
| 73 | N73L | -51.872 | -22.497 | 73.274 |
| 73 | N73P | -49.890 | -4.079 | 56.019 |
| 73 | N73R | -58.084 | 25.638 | 40.205 |
| 73 | N73S | -58.040 | 4.960 | 57.181 |
| 73 | N73T | -73.034 | 8.354 | 48.013 |
| 73 | N73V | -26.508 | -2.816 | 23.507 |
| 73 | N73W | -74.912 | 0.723 | 78.484 |
| 74 | D74E | -41.254 | 9.715 | 21.961 |
| 74 | D74G | -38.954 | 4.667 | 89.632 |
| 75 | G75A | 9.297 | -24.747 | 18.474 |
| 75 | G75C | 23.923 | -64.804 | 47.614 |
| 75 | G75D | 15.818 | -49.619 | 42.702 |

| FIG. 45B Cont. | | | | |
|---|---|---|---|---|
| 75 | G75E | 27.467 | -60.889 | 32.263 |
| 75 | G75F | 40.940 | -80.201 | 30.596 |
| 75 | G75I | 56.288 | -47.816 | 6.007 |
| 75 | G75K | 7.136 | -23.671 | 19.033 |
| 75 | G75L | 40.186 | -37.753 | 8.046 |
| 75 | G75M | 28.831 | -33.386 | 12.322 |
| 75 | G75N | 12.028 | -49.143 | 51.298 |
| 75 | G75P | 11.221 | -46.762 | 49.456 |
| 75 | G75T | 31.818 | -72.476 | 40.684 |
| 75 | G75V | 63.116 | -96.709 | 2.526 |
| 75 | G75W | 38.449 | -79.196 | 35.158 |
| 75 | G75Y | 33.712 | -71.630 | 34.544 |
| 76 | L76A | 4.254 | -26.297 | 24.066 |
| 76 | L76C | -3.767 | -33.401 | 31.460 |
| 76 | L76D | 11.872 | -33.853 | 15.321 |
| 76 | L76E | 2.008 | -21.772 | 21.039 |
| 76 | L76F | -13.754 | -17.278 | 28.638 |
| 76 | L76G | 11.076 | -26.171 | 18.605 |
| 76 | L76I | -15.703 | -13.259 | 25.974 |
| 76 | L76K | 3.502 | -46.226 | 34.344 |
| 76 | L76M | 4.075 | -25.209 | 16.437 |
| 76 | L76N | 4.000 | -21.108 | 18.836 |
| 76 | L76P | 5.176 | -40.689 | 28.019 |
| 76 | L76Q | 4.075 | -42.610 | 30.763 |
| 76 | L76R | 9.978 | -45.153 | 26.623 |
| 76 | L76T | 2.008 | -23.259 | 22.618 |
| 76 | L76V | -14.075 | -40.576 | 48.251 |
| 76 | L76W | 8.661 | -28.449 | 22.816 |
| 77 | R77A | -22.007 | -7.714 | 67.702 |
| 77 | R77C | -25.130 | -8.190 | 76.386 |
| 77 | R77D | -28.288 | 3.503 | 64.895 |
| 77 | R77E | -36.975 | 6.013 | 22.454 |
| 77 | R77F | -28.674 | -18.032 | 101.561 |
| 77 | R77G | -16.254 | -3.544 | 16.303 |
| 77 | R77H | -28.393 | -9.884 | 87.351 |
| 77 | R77K | -8.288 | 3.291 | 15.246 |
| 77 | R77L | 0.864 | -7.152 | 6.763 |
| 77 | R77N | -15.340 | -2.899 | 43.140 |
| 77 | R77Q | 9.993 | -8.455 | -10.982 |
| 77 | R77S | -20.639 | 0.540 | 50.684 |
| 77 | R77V | -36.636 | -4.367 | 32.980 |
| 77 | R77W | -26.814 | -26.127 | 110.421 |
| 78 | G78A | 22.730 | -17.820 | -27.298 |
| 78 | G78C | 36.028 | -33.799 | -34.053 |

| FIG. 45B Cont. | | | | |
|---|---|---|---|---|
| 78 | G78D | -4.147 | 15.831 | -15.895 |
| 78 | G78E | 40.144 | -9.272 | -21.526 |
| 78 | G78F | 43.831 | -23.671 | -9.421 |
| 78 | G78M | 49.932 | -21.392 | -16.526 |
| 78 | G78N | 33.677 | -19.460 | -51.947 |
| 78 | G78P | -15.060 | -11.524 | 56.737 |
| 78 | G78Q | 20.695 | -8.878 | -37.123 |
| 78 | G78R | 77.008 | -35.000 | -23.401 |
| 78 | G78S | 36.034 | -12.184 | -15.309 |
| 78 | G78T | 40.625 | -28.984 | -53.526 |
| 78 | G78V | 47.305 | -21.994 | -13.829 |
| 78 | G78Y | 51.432 | -48.085 | -48.877 |
| 79 | F79A | 6.341 | -4.286 | -10.157 |
| 79 | F79D | 43.407 | -15.253 | -17.842 |
| 79 | F79E | 46.373 | -16.677 | -18.697 |
| 79 | F79G | 7.214 | -5.504 | -10.133 |
| 79 | F79H | 17.305 | -4.778 | -8.467 |
| 79 | F79M | -3.406 | -1.510 | 14.105 |
| 79 | F79N | 6.131 | -4.183 | -9.759 |
| 79 | F79P | -36.890 | 7.215 | 21.138 |
| 79 | F79Q | 5.265 | -2.800 | -10.157 |
| 79 | F79V | -1.942 | 0.926 | 3.988 |
| 79 | F79W | 6.393 | -4.327 | -10.227 |
| 80 | Q80A | -1.822 | 1.091 | 3.239 |
| 80 | Q80E | 22.898 | -6.456 | -11.033 |
| 80 | Q80G | -26.000 | -1.108 | 21.368 |
| 80 | Q80L | -7.949 | -0.316 | 6.500 |
| 80 | Q80M | -7.186 | -1.804 | 7.454 |
| 80 | Q80S | -17.483 | 0.475 | 13.079 |
| 80 | Q80W | -3.107 | -0.478 | 10.827 |
| 80 | Q80Y | -10.915 | -2.120 | 10.711 |
| 81 | P81A | -3.368 | 2.009 | 6.002 |
| 81 | P81E | -8.966 | 1.329 | 5.579 |
| 81 | P81K | -3.077 | 0.245 | 9.094 |
| 81 | P81M | -5.049 | 3.516 | 7.852 |
| 81 | P81N | 4.802 | -2.748 | -8.845 |
| 81 | P81T | 3.413 | -1.675 | -6.878 |
| 81 | P81W | -21.339 | 2.690 | 13.737 |
| 81 | P81Y | -3.032 | 0.678 | 7.993 |
| 82 | Q82F | -2.987 | 0.750 | 7.665 |
| 82 | Q82I | -5.831 | -0.538 | 5.086 |
| 82 | Q82N | -3.092 | 2.329 | 4.410 |
| 82 | Q82P | -4.556 | 1.380 | 11.155 |
| 82 | Q82R | 4.297 | -0.253 | -3.072 |

| FIG. 45B Cont. | | | | |
|---|---|---|---|---|
| 82 | Q82S | 4.932 | -1.994 | -1.757 |
| 82 | Q82W | -4.287 | 0.028 | 13.356 |
| 82 | Q82Y | -3.413 | 0.348 | 9.913 |
| 83 | Q83C | 31.076 | -11.709 | -11.954 |
| 83 | Q83F | 23.703 | -8.418 | -9.651 |
| 83 | Q83G | 40.229 | -16.044 | -14.553 |
| 83 | Q83K | 25.992 | -10.063 | -9.684 |
| 83 | Q83L | 43.110 | -17.532 | -15.243 |
| 83 | Q83M | 23.110 | -8.449 | -9.158 |
| 83 | Q83N | 23.873 | -9.367 | -8.796 |
| 83 | Q83R | 27.305 | -10.728 | -10.046 |
| 83 | Q83S | 26.288 | -9.684 | -10.375 |
| 83 | Q83T | 22.856 | -8.513 | -8.895 |
| 83 | Q83V | 16.338 | -5.835 | -9.834 |
| 83 | Q83W | 10.890 | -4.968 | -4.990 |
| 83 | Q83Y | 10.200 | -4.159 | -5.385 |
| 84 | T84A | 32.364 | -14.910 | -14.615 |
| 84 | T84E | -7.487 | 7.532 | -2.495 |
| 84 | T84F | 21.114 | -9.535 | -9.813 |
| 84 | T84L | 76.709 | -40.900 | -29.197 |
| 84 | T84M | 28.726 | -12.829 | -13.555 |
| 84 | T84N | 28.558 | -11.962 | -14.615 |
| 84 | T84Q | 12.308 | -3.090 | -9.272 |
| 84 | T84R | -3.233 | 5.841 | -4.782 |
| 84 | T84S | -6.479 | 0.379 | 6.694 |
| 84 | T84V | 29.006 | -13.841 | -12.432 |
| 84 | T84W | 1.580 | 3.529 | -6.840 |
| 84 | T84Y | 20.591 | -7.382 | -12.328 |
| 85 | E85A | 4.771 | -2.367 | -1.892 |
| 85 | E85C | 3.185 | 0.075 | -3.659 |
| 85 | E85D | -7.151 | 2.864 | 3.846 |
| 85 | E85L | 4.976 | -1.948 | -2.744 |
| 85 | E85Q | 6.729 | -2.829 | -3.430 |
| 85 | E85R | 4.043 | -1.081 | -2.952 |
| 85 | E85S | 3.241 | -0.171 | -3.368 |
| 85 | E85T | 7.812 | -2.121 | -5.655 |
| 85 | E85W | 3.222 | -0.416 | -2.994 |
| 85 | E85Y | 4.043 | -1.283 | -2.661 |
| 86 | Q86G | 4.938 | -2.540 | -1.850 |
| 86 | Q86K | 3.147 | -1.038 | -2.017 |
| 86 | Q86T | -1.930 | -1.657 | 3.976 |
| 86 | Q86V | -3.700 | 0.465 | 3.451 |
| 86 | Q86W | -4.017 | 0.682 | 3.493 |
| 87 | T87A | -11.920 | 1.314 | 20.762 |

| FIG. 45B Cont. | | | | |
|---|---|---|---|---|
| 87 | T87C | -18.065 | 0.661 | 33.629 |
| 87 | T87D | 16.335 | -7.543 | -18.399 |
| 87 | T87E | -5.938 | 0.017 | 6.590 |
| 87 | T87F | -21.738 | -10.278 | 59.434 |
| 87 | T87G | -16.102 | 3.355 | 25.238 |
| 87 | T87H | -19.447 | 1.110 | 35.448 |
| 87 | T87L | -23.665 | -4.033 | 52.510 |
| 87 | T87M | -8.718 | -0.373 | 10.270 |
| 87 | T87P | 23.571 | -12.808 | -23.364 |
| 87 | T87S | -4.575 | 0.824 | 7.406 |
| 87 | T87V | -6.865 | 0.988 | 11.531 |
| 87 | T87W | -18.829 | -2.482 | 40.483 |
| 88 | L88C | -6.393 | 7.763 | -0.986 |
| 89 | R89A | 3.607 | 0.988 | -8.608 |
| 89 | R89G | 12.153 | -4.849 | -15.112 |
| 89 | R89H | -0.829 | -1.094 | 3.420 |
| 89 | R89L | -1.338 | 3.029 | -2.594 |
| 89 | R89P | 0.298 | 8.131 | -14.483 |
| 89 | R89T | -6.247 | 2.090 | 8.385 |
| 89 | R89V | -4.875 | 1.491 | 3.285 |
| 89 | R89W | -3.156 | 0.212 | 5.727 |
| 90 | Q90E | 5.607 | -2.073 | -7.210 |
| 90 | Q90N | -2.684 | 3.355 | -0.566 |
| 90 | Q90P | -7.580 | 7.084 | -1.746 |
| 90 | Q90W | -5.338 | 7.559 | -2.664 |
| 90 | Q90Y | 3.062 | -3.420 | -0.007 |
| 91 | I91G | -2.783 | 8.825 | -7.128 |
| 91 | I91L | -1.200 | -3.476 | 5.349 |
| 91 | I91M | -3.783 | 18.667 | -17.404 |
| 91 | I91S | -7.700 | 13.825 | -7.495 |
| 91 | I91V | 11.800 | -7.603 | -4.193 |
| 91 | I91Y | -130.617 | 56.048 | 79.018 |
| 92 | L92A | -7.033 | 10.175 | -4.009 |
| 92 | L92C | -3.700 | 4.937 | -1.624 |
| 92 | L92G | -11.533 | 16.286 | -6.119 |
| 92 | L92H | -0.367 | 7.635 | -8.321 |
| 92 | L92N | -11.533 | 17.397 | -7.404 |
| 92 | L92S | -4.987 | 4.064 | -0.291 |
| 92 | L92T | -9.367 | 7.635 | 1.495 |
| 92 | L92Y | -29.117 | 37.714 | -11.532 |
| 93 | Q93E | 4.133 | -4.032 | 0.119 |
| 93 | Q93H | 2.300 | -5.460 | 3.789 |
| 93 | Q93I | 3.133 | -4.984 | 2.321 |
| 93 | Q93L | 3.050 | -3.317 | 0.486 |

| FIG. 45B Cont. | | | | |
|---|---|---|---|---|
| 93 | Q93P | -48.617 | 39.143 | 8.284 |
| 93 | Q93S | 3.717 | -4.190 | 0.761 |
| 93 | Q93W | 5.217 | -3.794 | -1.349 |
| 93 | Q93Y | 0.300 | -3.000 | 3.147 |
| 94 | D94E | 7.467 | -3.397 | -4.284 |
| 94 | D94F | 6.967 | -5.063 | -1.899 |
| 94 | D94G | 11.800 | -7.762 | -4.009 |
| 94 | D94H | 13.800 | -8.476 | -5.385 |
| 94 | D94K | 11.383 | -7.762 | -3.550 |
| 94 | D94N | 7.967 | -5.222 | -2.725 |
| 94 | D94P | -1.759 | 3.442 | -2.973 |
| 94 | D94Q | 8.300 | -5.063 | -3.275 |
| 94 | D94R | 8.883 | -7.365 | -1.165 |
| 94 | D94S | 11.883 | -7.603 | -4.284 |
| 94 | D94V | 6.800 | -6.571 | 0.119 |
| 95 | V95F | -14.444 | 19.641 | -2.010 |
| 95 | V95G | -3.341 | 4.897 | -0.833 |
| 95 | V95L | -2.454 | -0.446 | 5.163 |
| 95 | V95N | -5.730 | 8.519 | -1.552 |
| 95 | V95Q | -9.824 | 15.955 | -4.036 |
| 95 | V95W | -14.919 | 18.147 | 5.089 |
| 96 | K96P | -11.034 | 13.513 | 3.644 |
| 96 | K96V | 3.128 | -2.117 | -3.207 |
| 97 | A97P | -11.793 | 15.571 | -1.193 |
| 98 | A98L | -0.757 | -1.326 | 3.089 |
| 98 | A98P | -9.850 | 15.654 | -1.281 |
| 98 | A98V | -1.084 | 3.199 | -1.912 |
| 98 | A98W | -0.383 | -1.853 | 3.015 |
| 98 | A98Y | -1.766 | 3.167 | -1.029 |
| 99 | N99D | -4.549 | 11.436 | -6.029 |
| 99 | N99Y | 3.045 | -2.132 | -0.924 |
| 100 | A100D | -7.199 | 9.321 | -0.539 |
| 100 | A100E | -5.283 | 7.590 | -1.160 |
| 100 | A100H | -7.605 | 1.927 | 9.161 |
| 100 | A100I | -5.441 | 2.429 | 4.297 |
| 100 | A100K | -12.555 | 4.919 | 11.534 |
| 100 | A100L | -9.798 | 6.115 | 5.931 |
| 100 | A100M | -7.905 | 2.654 | 8.144 |
| 100 | A100Q | -8.669 | 7.686 | 2.958 |
| 100 | A100R | -7.803 | 3.071 | 6.618 |
| 100 | A100T | -4.549 | 0.827 | 4.788 |
| 100 | A100V | -11.755 | 3.637 | 12.720 |
| 100 | A100W | -23.755 | 20.774 | -0.839 |
| 100 | A100Y | -5.362 | 3.519 | 3.056 |

| FIG. 45B Cont. | | | | |
|---|---|---|---|---|
| 101 | E101A | 3.495 | -1.919 | -2.110 |
| 101 | E101D | 3.895 | -1.748 | -3.127 |
| 101 | E101L | 0.095 | -1.876 | 3.568 |
| 101 | E101P | -9.055 | 15.944 | -16.263 |
| 101 | E101T | 1.245 | -2.731 | 3.314 |
| 102 | P102E | -12.081 | 17.750 | -3.056 |
| 102 | P102F | -9.305 | 13.893 | -11.686 |
| 102 | P102H | -12.475 | 18.744 | -3.578 |
| 102 | P102L | -7.436 | 8.199 | 0.899 |
| 102 | P102Q | -4.706 | 10.474 | -4.820 |
| 102 | P102R | -10.454 | 15.699 | -2.990 |
| 102 | P102S | -2.255 | 0.132 | 3.568 |
| 102 | P102W | -2.711 | 4.769 | -1.487 |
| 102 | P102Y | -14.505 | 21.457 | -17.873 |
| 103 | L103E | 0.706 | 4.474 | -3.054 |
| 103 | L103G | 4.690 | 0.635 | -6.454 |
| 103 | L103K | -4.458 | 9.958 | -3.083 |
| 103 | L103N | 0.589 | 3.481 | -2.413 |
| 103 | L103Q | -1.164 | 3.581 | -1.378 |
| 103 | L103R | 0.799 | 3.605 | -2.617 |
| 104 | L104C | -6.164 | 8.519 | -1.159 |
| 104 | L104P | -4.154 | 6.608 | -1.276 |
| 104 | L104S | -8.906 | 10.603 | 0.278 |
| 104 | L104W | -3.547 | 10.801 | -4.133 |
| 105 | M105A | -0.717 | -2.474 | 3.415 |
| 105 | M105C | -0.822 | -5.327 | 6.454 |
| 105 | M105E | -6.570 | 3.647 | 4.461 |
| 105 | M105G | -11.635 | 7.558 | 6.781 |
| 105 | M105I | 1.934 | -5.712 | 3.415 |
| 105 | M105L | -2.711 | -4.494 | 7.958 |
| 105 | M105V | -0.244 | -9.269 | 9.788 |
| 106 | Q106D | 7.079 | -27.635 | 19.330 |
| 106 | Q106G | -7.042 | 0.250 | 8.513 |
| 106 | Q106H | -0.927 | -12.442 | 13.840 |
| 106 | Q106K | -11.084 | 7.910 | 5.735 |
| 106 | Q106L | 1.383 | -12.763 | 11.291 |
| 106 | Q106M | -1.346 | -8.115 | 9.951 |
| 106 | Q106R | -9.142 | 2.750 | 8.578 |
| 106 | Q106S | -8.407 | 0.218 | 10.245 |
| 106 | Q106T | -7.776 | -0.290 | 5.036 |
| 106 | Q106V | -7.173 | -2.763 | 11.748 |
| 106 | Q106W | 12.407 | -34.141 | 19.330 |
| 106 | Q106Y | -8.150 | -0.092 | 5.138 |
| 107 | I107C | -1.534 | 0.799 | 3.913 |

| FIG. 45B Cont. | | | | |
|---|---|---|---|---|
| 107 | I107E | -4.030 | 3.950 | 3.734 |
| 107 | I107G | -1.332 | -1.499 | 11.249 |
| 107 | I107K | -3.634 | 5.924 | -5.054 |
| 107 | I107L | -3.000 | 1.239 | 8.823 |
| 107 | I107M | -1.049 | 0.068 | 4.390 |
| 107 | I107Q | -3.567 | 2.070 | 8.366 |
| 107 | I107S | -29.598 | 3.928 | 0.798 |
| 107 | I107Y | 36.578 | -5.114 | -0.752 |
| 108 | R108A | 3.281 | -6.028 | 6.974 |
| 108 | R108C | 2.405 | -4.806 | 6.497 |
| 108 | R108D | 5.395 | -8.381 | 6.020 |
| 108 | R108E | 26.776 | -5.423 | 0.965 |
| 108 | R108F | 3.857 | -4.120 | -2.370 |
| 108 | R108G | 12.329 | -2.682 | 0.611 |
| 108 | R108H | 31.677 | -5.713 | 0.507 |
| 108 | R108I | 5.242 | -7.874 | 4.887 |
| 108 | R108L | 3.565 | -8.683 | 15.185 |
| 108 | R108M | 15.246 | -4.409 | 1.742 |
| 108 | R108R | 3.003 | -2.983 | -2.668 |
| 108 | R108S | 2.814 | -5.409 | 6.815 |
| 108 | R108V | 1.613 | -5.353 | 11.944 |
| 108 | R108W | 8.281 | -6.954 | -11.813 |
| 108 | R108Y | 3.048 | -5.582 | 6.417 |
| 109 | L109A | 7.292 | -7.405 | -5.849 |
| 109 | L109C | 1.708 | -3.847 | 6.159 |
| 109 | L109D | 6.047 | -5.175 | -8.314 |
| 109 | L109E | 7.922 | -7.238 | -9.229 |
| 109 | L109F | 38.618 | -8.122 | 1.663 |
| 109 | L109G | 3.920 | -4.806 | -0.203 |
| 109 | L109K | 5.579 | -7.378 | 1.626 |
| 109 | L109M | -1.997 | 0.453 | 7.213 |
| 109 | L109P | 7.333 | -7.249 | -6.584 |
| 109 | L109Q | -2.254 | -0.032 | 10.076 |
| 109 | L109R | 33.518 | -6.685 | 1.118 |
| 109 | L109S | 6.960 | -6.714 | -6.843 |
| 109 | L109T | 2.715 | -5.509 | 7.630 |
| 109 | L109V | 2.162 | -4.505 | 6.497 |
| 109 | L109Y | 5.570 | -8.370 | 5.205 |
| 110 | P110A | 2.679 | -6.318 | 10.672 |
| 110 | P110C | 41.790 | -7.316 | 0.470 |
| 110 | P110D | 35.246 | -6.316 | 0.528 |
| 110 | P110E | 25.303 | -5.151 | 0.936 |
| 110 | P110F | 11.249 | -12.603 | -4.795 |
| 110 | P110G | 22.385 | -5.018 | 1.243 |

| FIG. 45B Cont. | | | | |
|---|---|---|---|---|
| 110 | P110H | 3.511 | -7.456 | 11.050 |
| 110 | P110K | 50.147 | -8.246 | 0.084 |
| 110 | P110L | 47.994 | -6.901 | -0.814 |
| 110 | P110M | 39.297 | -6.690 | 0.271 |
| 110 | P110N | 7.949 | -10.958 | 3.913 |
| 110 | P110R | 7.863 | -11.231 | 5.245 |
| 110 | P110S | 29.892 | -6.653 | 1.617 |
| 110 | P110V | 3.893 | -6.814 | 7.074 |
| 110 | P110W | 8.879 | -10.612 | -1.435 |
| 111 | A111C | 18.210 | -13.170 | -4.264 |
| 111 | A111E | 4.235 | -0.045 | -5.452 |
| 111 | A111L | 10.134 | -9.844 | 1.347 |
| 111 | A111M | 6.125 | -1.287 | 0.262 |
| 111 | A111P | 9.977 | -2.263 | 0.578 |
| 111 | A111Q | 4.058 | -2.121 | -2.152 |
| 111 | A111V | 2.767 | -7.589 | 7.617 |
| 111 | A111Y | 10.686 | -0.775 | -0.868 |
| 112 | N112A | -7.410 | -4.888 | 16.891 |
| 112 | N112F | -4.527 | -2.871 | 3.255 |
| 112 | N112G | -6.119 | -0.915 | 9.300 |
| 112 | N112I | -4.954 | -11.138 | 22.931 |
| 112 | N112K | 8.311 | -7.746 | 0.620 |
| 112 | N112L | -7.258 | -10.647 | 25.175 |
| 112 | N112P | -5.663 | -6.719 | 17.320 |
| 112 | N112R | 4.992 | -0.296 | -0.461 |
| 112 | N112V | -5.309 | -10.022 | 21.743 |
| 112 | N112W | -10.220 | -6.585 | 23.063 |
| 112 | N112Y | -11.461 | -4.286 | 21.281 |
| 113 | Y113A | -6.094 | 0.223 | 7.617 |
| 113 | Y113C | 11.856 | -6.585 | -5.749 |
| 113 | Y113D | -7.587 | 4.576 | 3.129 |
| 113 | Y113M | 1.071 | -3.906 | 4.383 |
| 113 | Y113W | -17.785 | -0.784 | 3.317 |
| 114 | G114F | -14.414 | -1.098 | 3.101 |
| 114 | G114L | -8.575 | 0.558 | 10.356 |
| 114 | G114M | -11.511 | 1.004 | 13.525 |
| 114 | G114P | 8.958 | -0.057 | -1.263 |
| 114 | G114W | -18.493 | -0.453 | 3.122 |
| 114 | G114Y | -13.511 | 0.335 | 17.122 |
| 115 | R115A | 2.071 | -21.595 | 11.017 |
| 115 | R115C | 1.509 | -13.387 | 6.638 |
| 115 | R115E | 2.970 | -22.000 | 10.431 |
| 115 | R115G | -14.783 | -18.936 | 24.914 |
| 115 | R115I | -1.375 | -10.092 | 7.328 |

| FIG. 45B Cont. | | | | |
|---|---|---|---|---|
| 115 | R115N | -6.805 | -4.486 | 8.983 |
| 115 | R115P | -3.772 | -2.867 | 5.190 |
| 115 | R115Q | -1.375 | -3.792 | 3.534 |
| 115 | R115S | -4.258 | -5.757 | 7.362 |
| 115 | R115V | -0.588 | -4.659 | 3.328 |
| 115 | R115W | 3.745 | -3.737 | 2.823 |
| 115 | R115Y | -6.393 | -15.584 | 15.190 |
| 116 | R116D | 4.169 | -3.561 | -1.707 |
| 116 | R116E | 4.281 | -2.058 | -2.707 |
| 116 | R116H | -2.873 | -4.370 | 5.293 |
| 116 | R116V | 0.311 | -6.393 | 3.534 |
| 116 | R116W | -15.532 | -15.410 | 23.500 |
| 117 | Y117A | 8.618 | -0.333 | -0.960 |
| 117 | Y117C | 4.169 | 0.948 | -4.397 |
| 117 | Y117E | 13.547 | -1.374 | -0.748 |
| 117 | Y117H | -7.404 | 8.000 | 2.052 |
| 117 | Y117L | -6.393 | 7.538 | 1.397 |
| 117 | Y117M | -11.749 | 11.584 | 3.879 |
| 117 | Y117N | -3.397 | 5.341 | -0.052 |
| 117 | Y117Q | 9.722 | -0.448 | -1.022 |
| 117 | Y117R | 8.844 | 0.284 | -1.554 |
| 117 | Y117T | 6.940 | 2.220 | -7.707 |
| 117 | Y117V | 10.124 | 0.023 | -9.328 |
| 117 | Y117W | -24.071 | -3.272 | 24.121 |
| 118 | N118A | -0.663 | -9.399 | 6.224 |
| 118 | N118C | 5.667 | -25.526 | 9.983 |
| 118 | N118E | 0.086 | -15.410 | 9.121 |
| 118 | N118G | 8.101 | -17.838 | 3.190 |
| 118 | N118H | -9.764 | -9.977 | 14.983 |
| 118 | N118I | 14.918 | -47.665 | 14.707 |
| 118 | N118K | 8.213 | 1.699 | -8.569 |
| 118 | N118L | -5.157 | -26.509 | 20.569 |
| 118 | N118M | -6.955 | -6.335 | 10.190 |
| 118 | N118P | -4.371 | -30.902 | 22.466 |
| 118 | N118Q | 2.933 | -12.289 | 4.603 |
| 118 | N118S | 3.150 | -0.526 | 0.013 |
| 118 | N118T | 15.330 | -44.197 | 12.259 |
| 118 | N118V | 19.150 | -54.081 | 14.672 |
| 118 | N118W | 8.176 | -24.023 | 6.845 |
| 119 | E119C | 3.998 | -4.613 | 1.487 |
| 119 | E119D | 1.897 | -3.588 | 5.105 |
| 119 | E119F | 0.766 | -3.860 | 9.645 |
| 119 | E119G | 4.624 | -5.115 | 1.026 |
| 119 | E119K | -0.810 | -4.215 | 15.895 |

| FIG. 45B Cont. | | | | |
|---|---|---|---|---|
| 119 | E119M | 3.554 | -4.257 | 1.816 |
| 119 | E119P | 0.442 | -13.546 | 41.158 |
| 119 | E119R | -0.547 | -4.843 | 17.013 |
| 119 | E119W | -0.184 | -5.722 | 18.592 |
| 119 | E119Y | 1.695 | -5.052 | 10.368 |
| 120 | A120D | 3.291 | -2.918 | -1.605 |
| 120 | A120E | 3.377 | -0.130 | -0.382 |
| 120 | A120G | -0.386 | -2.228 | 8.263 |
| 120 | A120I | -5.537 | 0.743 | 15.697 |
| 120 | A120L | -0.527 | -0.931 | 4.645 |
| 120 | A120T | -1.982 | 0.847 | 3.789 |
| 120 | A120W | -6.143 | -2.981 | 29.382 |
| 121 | F121A | 5.352 | -25.847 | 63.855 |
| 121 | F121C | -0.022 | -12.312 | 38.789 |
| 121 | F121D | 20.543 | -30.262 | 28.263 |
| 121 | F121E | 15.756 | -25.052 | 27.474 |
| 121 | F121K | -9.116 | -2.226 | 3.346 |
| 121 | F121L | -11.497 | -11.203 | 72.671 |
| 121 | F121M | 9.614 | -13.839 | 12.211 |
| 121 | F121P | 9.109 | -26.203 | 52.737 |
| 121 | F121Q | 6.240 | -19.111 | 39.776 |
| 121 | F121R | 14.604 | -25.554 | 32.803 |
| 121 | F121S | 6.523 | -22.772 | 50.303 |
| 121 | F121Y | 3.392 | -11.036 | 23.658 |
| 122 | S122A | 0.160 | -4.467 | 13.526 |
| 122 | S122C | -1.214 | -3.985 | 16.487 |
| 122 | S122D | 10.119 | -5.248 | 3.251 |
| 122 | S122E | 7.149 | -19.592 | 38.329 |
| 122 | S122F | -4.952 | -3.504 | 27.145 |
| 122 | S122G | -1.154 | -6.182 | 23.197 |
| 122 | S122I | -7.962 | 4.069 | 13.066 |
| 122 | S122L | -8.042 | -4.320 | 39.776 |
| 122 | S122P | -3.558 | -10.115 | 43.395 |
| 122 | S122V | -7.739 | 1.015 | 21.947 |
| 122 | S122W | -5.941 | -5.659 | 37.145 |
| 122 | S122Y | -6.931 | -3.337 | 33.066 |
| 123 | A123F | -5.958 | -0.357 | 6.272 |
| 123 | A123T | -10.509 | 2.225 | 7.988 |
| 123 | A123V | -3.817 | -0.031 | 4.011 |
| 123 | A123W | -4.095 | -0.373 | 4.667 |
| 123 | A123Y | -10.030 | -2.335 | 12.426 |
| 124 | I124A | -5.925 | 1.023 | 5.095 |
| 124 | I124C | -3.568 | -0.943 | 4.728 |
| 124 | I124G | -36.078 | 27.280 | 6.272 |

| FIG. 45B Cont. | | | | |
|---|---|---|---|---|
| 124 | I124H | -2.221 | 4.313 | -2.310 |
| 124 | I124K | -8.107 | 6.450 | 1.537 |
| 124 | I124L | -2.997 | -0.473 | 3.629 |
| 124 | I124R | -3.539 | 4.043 | -0.631 |
| 124 | I124S | 1.707 | 4.203 | -6.213 |
| 124 | I124T | 38.234 | -15.577 | -21.006 |
| 124 | I124Y | -60.150 | 34.258 | 22.544 |
| 125 | Y125C | 11.946 | -28.984 | 19.408 |
| 125 | Y125F | -0.389 | -7.830 | 8.817 |
| 125 | Y125G | 6.710 | -11.556 | 5.385 |
| 125 | Y125I | -28.114 | -11.401 | 40.059 |
| 125 | Y125L | -1.665 | -11.584 | 14.148 |
| 125 | Y125P | 4.631 | -9.803 | 5.660 |
| 125 | Y125Q | -26.916 | -3.654 | 30.533 |
| 125 | Y125R | -68.533 | 19.368 | 46.805 |
| 125 | Y125S | 42.186 | -49.313 | 11.420 |
| 125 | Y125T | -12.485 | -12.995 | 26.331 |
| 125 | Y125V | 3.323 | -24.588 | 23.136 |
| 125 | Y125W | 10.092 | -9.533 | -0.310 |
| 126 | P126C | -60.210 | 44.423 | 11.657 |
| 126 | P126F | -4.940 | 5.962 | -1.538 |
| 126 | P126R | 7.874 | 2.280 | -10.237 |
| 126 | P126T | 8.473 | -5.247 | -2.722 |
| 126 | P126V | 4.701 | -1.346 | -3.195 |
| 127 | K127I | -0.569 | 3.214 | -2.840 |
| 127 | K127P | -1.202 | 5.012 | -5.867 |
| 127 | K127S | 3.994 | -1.002 | -5.753 |
| 128 | L128A | 0.269 | 7.225 | -8.047 |
| 128 | L128C | 9.371 | -0.192 | -9.053 |
| 128 | L128S | -0.030 | 9.643 | -10.296 |
| 128 | L128T | 7.275 | 5.082 | -12.663 |
| 128 | L128V | 4.118 | -0.884 | -6.171 |
| 129 | A129H | -4.820 | 3.819 | 0.651 |
| 129 | A129I | -4.439 | 7.465 | -3.852 |
| 129 | A129K | -11.287 | 9.423 | 1.065 |
| 129 | A129N | -6.557 | 8.819 | -2.959 |
| 129 | A129W | -5.944 | 12.347 | -8.947 |
| 129 | A129Y | -6.852 | 12.229 | -7.084 |
| 130 | K130E | 3.231 | -3.927 | 0.407 |
| 130 | K130I | 3.683 | -3.434 | 0.000 |
| 130 | K130P | -2.893 | 5.932 | -4.232 |
| 130 | K130V | 6.198 | -2.500 | -3.491 |
| 131 | E131A | -4.419 | 3.237 | 1.541 |
| 131 | E131C | -6.547 | 5.699 | 0.395 |

| FIG. 45B Cont. | | | | |
|---|---|---|---|---|
| 131 | E131F | -6.074 | 4.757 | 1.478 |
| 131 | E131G | -4.926 | 7.523 | -6.548 |
| 131 | E131I | -6.277 | 2.568 | 6.446 |
| 131 | E131K | -4.641 | 3.599 | 0.769 |
| 131 | E131L | -5.770 | 3.328 | 3.898 |
| 131 | E131N | -5.359 | 5.082 | -0.178 |
| 131 | E131V | -5.534 | 3.906 | 2.242 |
| 131 | E131W | -4.622 | 5.091 | -1.962 |
| 132 | F132D | 3.453 | 1.596 | -9.860 |
| 132 | F132E | 8.293 | -3.049 | -4.911 |
| 132 | F132N | 3.250 | 0.684 | -7.567 |
| 132 | F132T | 3.486 | 0.137 | -6.930 |
| 133 | D133R | 3.323 | -2.665 | -0.414 |
| 133 | D133S | 3.443 | -3.654 | 0.533 |
| 133 | D133T | 3.024 | -3.984 | 1.302 |
| 133 | D133V | 3.503 | -2.445 | -0.828 |
| 134 | V134D | -21.228 | 24.423 | -5.325 |
| 134 | V134E | -7.814 | 10.027 | -3.077 |
| 134 | V134I | 4.939 | -3.602 | -1.771 |
| 134 | V134K | -0.365 | 3.997 | -7.694 |
| 134 | V134M | 5.838 | 0.632 | -6.450 |
| 134 | V134N | -0.736 | 3.298 | -5.465 |
| 134 | V134Q | -1.277 | 4.635 | -7.312 |
| 134 | V134R | -1.750 | 5.243 | -7.694 |
| 134 | V134W | -26.198 | 33.489 | -10.178 |
| 134 | V134Y | -10.928 | 13.049 | -3.254 |
| 136 | L136A | -7.528 | 6.456 | 1.185 |
| 136 | L136C | -6.018 | -0.852 | 6.864 |
| 136 | L136D | -9.614 | 9.162 | 0.628 |
| 136 | L136E | -5.846 | 5.338 | 0.598 |
| 136 | L136F | -4.136 | 4.132 | 0.070 |
| 136 | L136G | -10.658 | 8.926 | 1.889 |
| 136 | L136H | -3.933 | 5.368 | -1.367 |
| 136 | L136K | -6.600 | 11.103 | -4.358 |
| 136 | L136M | -0.449 | -7.500 | 8.580 |
| 136 | L136N | -3.296 | 6.015 | -2.628 |
| 136 | L136P | -8.426 | 14.397 | -5.824 |
| 136 | L136Q | -18.174 | 11.731 | 5.266 |
| 136 | L136R | -4.948 | 7.574 | -2.540 |
| 136 | L136S | -21.766 | 11.236 | 9.408 |
| 136 | L136T | -7.788 | 5.309 | 2.592 |
| 137 | L137E | -4.281 | 11.397 | -7.026 |
| 137 | L137G | -3.962 | 4.221 | -0.164 |
| 137 | L137H | -8.165 | 11.221 | -2.921 |

| FIG. 45B Cont. | | | | |
|---|---|---|---|---|
| 137 | L137P | -9.383 | 3.103 | 6.405 |
| 137 | L137Q | -7.528 | 9.897 | -2.246 |
| 137 | L137S | -10.658 | 9.426 | 1.390 |
| 137 | L137Y | -5.528 | 3.985 | 1.625 |
| 138 | P138E | 3.719 | -6.985 | 3.208 |
| 138 | P138N | 14.328 | -10.809 | -3.713 |
| 138 | P138R | 9.255 | -12.868 | 3.472 |
| 138 | P138T | 6.646 | -10.279 | 3.531 |
| 138 | P138V | 8.443 | -8.750 | 0.217 |
| 139 | F139A | 13.261 | -9.939 | -12.583 |
| 139 | F139D | 22.456 | -13.350 | -28.446 |
| 139 | F139G | 11.100 | -11.047 | -4.964 |
| 139 | F139H | 21.136 | -18.248 | -15.173 |
| 139 | F139M | 4.233 | -10.551 | 11.048 |
| 139 | F139S | 14.845 | -11.207 | -13.923 |
| 139 | F139W | 4.315 | -0.967 | -0.962 |
| 140 | F140C | 13.261 | -12.504 | -7.315 |
| 140 | F140G | 22.180 | -21.615 | -10.857 |
| 140 | F140M | 6.586 | -6.484 | -3.060 |
| 140 | F140N | 14.509 | -12.504 | -10.440 |
| 140 | F140P | 14.521 | -14.254 | -6.929 |
| 140 | F140S | 13.285 | -17.402 | 2.565 |
| 141 | M141A | 18.951 | -17.373 | -11.512 |
| 141 | M141C | 17.618 | -16.863 | -9.250 |
| 141 | M141D | 31.280 | -26.367 | -23.714 |
| 141 | M141E | 34.413 | -29.516 | -25.054 |
| 141 | M141F | 9.687 | -2.686 | -1.501 |
| 141 | M141G | 16.238 | -13.277 | -13.179 |
| 141 | M141K | 35.697 | -31.601 | -23.982 |
| 141 | M141L | 24.101 | -23.350 | -12.077 |
| 141 | M141P | 21.952 | -21.397 | -10.738 |
| 141 | M141Q | 31.268 | -28.598 | -19.101 |
| 141 | M141R | 8.419 | -2.332 | -1.309 |
| 141 | M141T | 30.715 | -26.878 | -21.244 |
| 141 | M141V | 3.541 | -0.867 | -0.696 |
| 141 | M141W | 45.505 | -37.388 | -36.482 |
| 141 | M141Y | 13.755 | -4.050 | -1.834 |
| 142 | E142A | 5.325 | -15.609 | 18.667 |
| 142 | E142C | 8.747 | -11.688 | 2.179 |
| 142 | E142L | -5.095 | -5.857 | 24.560 |
| 142 | E142M | -6.139 | -1.163 | 17.595 |
| 142 | E142N | 0.451 | -2.854 | 4.708 |
| 142 | E142P | 11.340 | -20.566 | 13.905 |
| 142 | E142Q | 5.445 | -14.414 | 15.929 |

| FIG. 45B Cont. | | | | |
|---|---|---|---|---|
| 142 | E142S | 1.892 | -10.974 | 17.714 |
| 142 | E142W | 10.739 | -10.595 | -4.994 |
| 142 | E142Y | 4.725 | -12.563 | 13.935 |
| 143 | E143I | -0.176 | -1.331 | 3.466 |
| 143 | E143P | -1.049 | -0.495 | 4.376 |
| 144 | V144D | 4.483 | -1.002 | -1.005 |
| 144 | V144E | 4.422 | -0.983 | -0.994 |
| 144 | V144G | 4.613 | -1.149 | -0.882 |
| 144 | V144H | 4.672 | -4.731 | -4.312 |
| 144 | V144N | 4.180 | -0.926 | -0.946 |
| 144 | V144P | 3.802 | -3.760 | -3.706 |
| 144 | V144Q | 4.314 | -4.232 | -4.280 |
| 144 | V144R | 4.387 | -4.254 | -4.460 |
| 144 | V144S | 3.922 | -3.958 | -3.648 |
| 144 | V144W | 5.056 | -5.435 | -3.976 |
| 144 | V144Y | 3.251 | -3.786 | -1.919 |
| 145 | Y145D | 4.432 | -4.427 | -4.222 |
| 145 | Y145E | 4.063 | -3.921 | -4.165 |
| 145 | Y145I | 5.026 | -1.079 | -1.181 |
| 145 | Y145L | 5.654 | -5.844 | -4.960 |
| 145 | Y145M | 5.093 | -5.521 | -3.911 |
| 145 | Y145Q | 3.497 | -4.090 | -2.025 |
| 145 | Y145T | 4.445 | -4.363 | -4.402 |
| 145 | Y145W | 3.246 | -1.035 | -0.331 |
| 147 | K147G | 11.439 | -6.436 | -4.857 |
| 147 | K147P | 23.533 | -13.093 | -10.453 |
| 147 | K147R | -2.386 | 0.133 | 4.839 |
| 147 | K147W | 10.731 | -6.162 | -4.184 |
| 148 | P148D | 3.769 | -0.621 | -6.375 |
| 148 | P148E | 3.503 | -0.504 | -6.137 |
| 148 | P148W | -1.846 | -0.230 | 4.796 |
| 150 | W150C | 18.216 | -17.412 | -4.912 |
| 150 | W150D | 72.093 | -67.695 | -20.400 |
| 150 | W150E | 52.797 | -45.435 | -18.400 |
| 150 | W150G | 3.150 | -7.412 | 2.763 |
| 150 | W150L | 5.529 | -7.017 | -0.074 |
| 150 | W150Q | 30.683 | -27.638 | -9.656 |
| 150 | W150T | 20.639 | -27.638 | 0.949 |
| 151 | M151A | 14.428 | -9.579 | -1.495 |
| 151 | M151C | 12.550 | -8.997 | 0.805 |
| 151 | M151E | 17.466 | -11.230 | -2.970 |
| 151 | M151F | 4.904 | -1.559 | -0.507 |
| 151 | M151G | 13.789 | -8.155 | -4.597 |
| 151 | M151I | 17.938 | -12.805 | 0.978 |

| FIG. 45B Cont. | | | | |
|---|---|---|---|---|
| 151 | M151Q | 8.538 | -7.121 | 3.711 |
| 151 | M151S | 14.949 | -9.319 | -3.490 |
| 151 | M151T | 11.075 | -8.442 | 2.302 |
| 151 | M151V | 21.832 | -14.853 | -1.126 |
| 151 | M151W | 30.917 | -18.538 | -9.499 |
| 152 | Q152A | -28.877 | 18.915 | 14.949 |
| 152 | Q152D | 9.714 | 7.277 | -16.260 |
| 152 | Q152E | -1.960 | 13.887 | -9.377 |
| 152 | Q152F | 27.379 | -12.045 | -19.005 |
| 152 | Q152H | -19.405 | 37.616 | -10.493 |
| 152 | Q152I | 34.251 | -17.356 | -21.935 |
| 152 | Q152K | -28.260 | 19.085 | 14.158 |
| 152 | Q152L | 35.176 | -28.994 | -13.284 |
| 152 | Q152R | -0.286 | 15.299 | -12.307 |
| 152 | Q152S | -3.458 | 0.667 | 3.042 |
| 152 | Q152T | 30.947 | -17.017 | -18.726 |
| 152 | Q152Y | -19.185 | 37.616 | -10.726 |
| 156 | I156C | -11.137 | -3.481 | 18.057 |
| 156 | I156F | -20.314 | -1.126 | 26.721 |
| 156 | I156L | 16.668 | -12.287 | -6.370 |
| 156 | I156Q | -4.765 | -5.965 | 13.019 |
| 156 | I156R | -11.137 | -7.481 | 22.790 |
| 156 | I156S | -11.564 | -7.932 | 23.859 |
| 158 | P158A | 9.534 | -9.674 | -0.454 |
| 158 | P158F | 127.486 | -65.116 | -30.085 |
| 158 | P158G | -1.503 | -1.061 | 3.172 |
| 158 | P158H | 37.125 | -18.739 | -24.309 |
| 158 | P158I | 54.844 | -27.076 | -14.134 |
| 158 | P158L | 97.675 | -53.754 | -18.385 |
| 158 | P158Q | 52.627 | -20.266 | -20.449 |
| 158 | P158S | -6.099 | 1.794 | 3.032 |
| 158 | P158T | 22.156 | -8.306 | -8.911 |
| 158 | P158V | 80.929 | -40.233 | -20.449 |
| 159 | N159C | 8.099 | -3.322 | -2.960 |
| 159 | N159E | 7.095 | 1.487 | -10.683 |
| 159 | N159G | -0.832 | -2.545 | 4.050 |
| 159 | N159I | 29.137 | -13.189 | -8.951 |
| 159 | N159K | 5.540 | -2.932 | -3.431 |
| 159 | N159L | 7.460 | -0.674 | -8.546 |
| 159 | N159M | 6.495 | 0.532 | -6.279 |
| 159 | N159Q | 0.814 | 3.100 | -4.653 |
| 159 | N159R | 6.307 | -3.887 | -0.652 |
| 159 | N159T | 17.061 | -8.306 | -4.538 |
| 159 | N159V | 20.222 | -8.173 | -7.413 |

| FIG. 45B Cont. | | | | |
|---|---|---|---|---|
| 160 | R160A | 10.296 | -7.094 | -4.500 |
| 160 | R160C | 3.487 | -1.140 | -5.209 |
| 160 | R160D | 11.400 | -6.335 | -10.830 |
| 160 | R160E | 7.313 | -3.793 | -7.627 |
| 160 | R160G | 8.009 | -4.380 | -7.758 |
| 160 | R160H | 5.313 | -3.486 | -3.902 |
| 160 | R160N | 4.655 | -3.674 | -1.485 |
| 160 | R160Q | 7.491 | -4.513 | -4.042 |
| 160 | R160S | 9.412 | -6.126 | -4.538 |
| 161 | D161E | 4.656 | -2.857 | -0.490 |
| 161 | D161K | 1.024 | -3.223 | 3.032 |
| 161 | D161N | -2.357 | -0.352 | 3.363 |
| 161 | D161R | 1.495 | -3.887 | 3.478 |
| 161 | D161S | -1.241 | -2.093 | 3.599 |
| 161 | D161V | -0.344 | -3.090 | 4.045 |
| 161 | D161W | -0.392 | -3.953 | 5.138 |
| 162 | A162G | -6.020 | 3.218 | 6.033 |
| 162 | A162I | 20.328 | -12.592 | -16.386 |
| 162 | A162L | 45.052 | -32.508 | -25.536 |
| 162 | A162T | 15.023 | -11.531 | -6.908 |
| 162 | A162V | 4.168 | -4.513 | 0.118 |
| 162 | A162Y | 38.646 | -24.547 | -29.719 |
| 163 | Q163A | -7.019 | 4.607 | 2.920 |
| 163 | Q163C | -3.679 | 5.155 | -4.156 |
| 163 | Q163G | -5.180 | 1.692 | 5.678 |
| 163 | Q163L | -2.460 | 0.436 | 3.452 |
| 163 | Q163S | -6.777 | 0.745 | 7.599 |
| 163 | Q163T | -9.289 | 9.808 | -3.757 |
| 164 | P164C | -3.585 | -0.626 | 7.638 |
| 165 | F165D | 8.103 | -4.668 | -4.721 |
| 165 | F165E | 4.989 | -3.493 | -1.631 |
| 165 | F165G | 3.488 | -4.056 | 2.156 |
| 165 | F165I | 23.345 | -17.771 | -8.202 |
| 165 | F165K | 13.525 | -8.775 | -5.850 |
| 165 | F165L | 4.126 | -0.465 | -6.349 |
| 165 | F165M | 11.424 | -6.874 | -6.050 |
| 165 | F165R | 12.962 | -9.467 | -3.425 |
| 165 | F165S | 5.364 | -4.121 | -1.033 |
| 165 | F165T | 14.576 | -9.225 | -6.781 |
| 165 | F165V | 11.668 | -6.858 | -6.515 |
| 165 | F165W | -2.723 | -3.448 | 7.447 |
| 166 | I166F | 37.399 | -30.900 | -10.263 |
| 166 | I166L | 9.198 | -11.481 | 2.065 |
| 166 | I166M | 5.235 | -6.223 | 0.805 |

| FIG. 45B Cont. | | | | |
|---|---|---|---|---|
| 167 | A167C | 5.857 | 2.000 | -4.993 |
| 167 | A167E | -3.668 | 5.326 | -1.714 |
| 167 | A167F | 2.286 | 18.325 | -15.878 |
| 167 | A167G | -1.869 | 3.648 | -1.981 |
| 167 | A167K | -7.595 | 12.598 | -5.673 |
| 167 | A167L | -4.976 | 21.915 | -14.585 |
| 167 | A167M | 3.192 | -2.803 | -0.721 |
| 167 | A167N | -16.524 | 26.701 | -11.796 |
| 167 | A167Q | -7.833 | 15.248 | -7.646 |
| 167 | A167R | 5.024 | 8.581 | -9.687 |
| 167 | A167T | 16.095 | -7.060 | -3.565 |
| 167 | A167V | 0.738 | 9.692 | -8.122 |
| 167 | A167Y | -1.107 | 6.487 | -6.294 |
| 168 | D168L | -16.048 | 9.521 | 1.605 |
| 168 | D168P | 22.857 | -55.287 | 36.798 |
| 168 | D168V | -7.000 | 3.795 | 0.993 |
| 168 | D168W | -4.738 | 4.393 | -0.776 |
| 169 | W169A | -6.365 | 0.702 | 5.848 |
| 169 | W169D | -7.402 | 6.347 | -1.283 |
| 169 | W169E | -3.004 | -0.617 | 4.143 |
| 169 | W169G | -7.527 | 3.923 | 2.395 |
| 169 | W169K | -1.442 | -9.900 | 13.477 |
| 169 | W169M | -5.079 | 1.163 | 3.740 |
| 169 | W169Q | -2.921 | -2.365 | 6.565 |
| 169 | W169R | -4.000 | -3.009 | 8.673 |
| 169 | W169S | -3.627 | -0.064 | 4.009 |
| 169 | W169T | -2.204 | -3.868 | 7.294 |
| 169 | W169V | -0.345 | -3.610 | 4.698 |
| 170 | M170A | -0.832 | -3.029 | 4.622 |
| 170 | M170F | 4.609 | -4.006 | -1.590 |
| 170 | M170G | -3.962 | 4.296 | -0.169 |
| 170 | M170H | 6.415 | -4.788 | 0.108 |
| 170 | M170L | 5.004 | -3.347 | -0.520 |
| 170 | M170N | -5.711 | 6.765 | -1.262 |
| 170 | M170Q | -13.710 | 16.776 | -9.668 |
| 170 | M170S | -5.041 | 5.346 | -0.005 |
| 170 | M170T | 3.297 | 2.198 | -10.060 |
| 170 | M170V | 1.052 | -4.130 | 5.350 |
| 170 | M170W | -12.257 | 9.383 | -0.475 |
| 170 | M170Y | 3.469 | -2.887 | 0.466 |
| 171 | A171E | 3.220 | -1.322 | -1.552 |
| 171 | A171F | 4.133 | -1.567 | -2.179 |
| 171 | A171I | 0.265 | -2.216 | 3.383 |
| 171 | A171V | 3.137 | -2.365 | 0.063 |

| FIG. 45B Cont. | | | | |
|---|---|---|---|---|
| 171 | A171W | 7.120 | -3.715 | -2.224 |
| 172 | K172A | 3.967 | -0.463 | -3.614 |
| 172 | K172M | 5.834 | -2.825 | -2.135 |
| 172 | K172P | -11.469 | 9.537 | -1.552 |
| 173 | Q173N | 0.469 | -3.667 | 5.623 |
| 173 | Q173W | -2.314 | -0.079 | 5.349 |
| 173 | Q173Y | -0.479 | -1.102 | 4.169 |
| 174 | L174A | -5.962 | 8.637 | -6.778 |
| 174 | L174F | -3.087 | 4.019 | -1.262 |
| 174 | L174G | 2.067 | 3.469 | -12.791 |
| 174 | L174Q | -11.267 | -17.425 | 66.163 |
| 174 | L174T | -5.267 | 5.927 | -2.007 |
| 174 | L174W | -6.644 | 5.130 | 3.383 |
| 176 | P176H | -0.434 | -2.463 | 5.240 |
| 176 | P176L | -1.717 | -0.549 | 4.202 |
| 177 | L177D | -0.977 | 4.112 | -7.366 |
| 177 | L177G | -1.006 | 3.497 | -5.928 |
| 177 | L177M | 3.081 | -1.028 | -4.556 |
| 177 | L177T | 3.197 | -2.899 | -0.438 |
| 178 | V178A | -1.717 | -0.673 | 4.421 |
| 178 | V178W | 3.793 | -4.685 | 1.197 |
| 179 | N179G | 3.130 | -0.720 | -1.281 |
| 179 | N179V | 3.340 | -3.342 | 1.391 |
| 179 | N179Y | 3.718 | -1.414 | -0.923 |
| 180 | H180E | 6.029 | -1.825 | -1.997 |
| 180 | H180R | 4.391 | -2.879 | 0.207 |
| 181 | D181A | 1.694 | -3.574 | 3.219 |
| 181 | D181H | 3.550 | -3.316 | 1.253 |
| 181 | D181Q | 0.644 | -2.494 | 3.219 |
| 181 | D181S | 0.003 | -2.185 | 3.874 |
| 181 | D181W | 1.606 | -4.160 | 4.421 |
| 182 | S182A | 1.111 | -2.895 | 3.055 |
| 182 | S182E | -0.551 | -1.630 | 3.929 |
| 182 | S182I | -0.638 | -2.031 | 4.803 |
| 182 | S182K | -2.644 | -1.270 | 3.607 |

FIG. 46A

| Mutations that Increase % Ester ||
|---|---|
| MUTATION | Z Score |
| A1R | 5.03 |
| D2H | 4.09 |
| D2R | 3.60 |
| L4G | 5.04 |
| L4M | 3.47 |
| L5Q | 3.20 |
| I6A | 4.33 |
| I6L | 5.83 |
| L7E | 6.00 |
| G8A | 3.98 |
| S12N | 4.13 |
| A13I | 4.23 |
| A13L | 7.83 |
| A13S | 8.38 |
| A13T | 11.78 |
| A13W | 3.67 |
| A13Y | 6.66 |
| G14K | 4.45 |
| G14R | 4.70 |
| G14S | 5.27 |
| G14T | 3.50 |
| A22D | 4.29 |
| A22E | 3.44 |
| A22H | 3.34 |
| A22Y | 9.47 |
| W23Y | 7.30 |
| P24C | 5.98 |
| P24G | 5.08 |
| P24T | 5.11 |
| A25P | 3.19 |
| L26C | 6.61 |
| L26D | 3.91 |
| L26E | 3.56 |
| L26G | 3.09 |
| L26N | 4.91 |
| N28A | 4.17 |
| N28M | 4.76 |
| D29V | 3.50 |
| S33G | 3.89 |

FIG. 46A Cont.

| | |
|---|---|
| S33M | 6.90 |
| K34A | 3.82 |
| K34H | 4.00 |
| K34M | 4.59 |
| T35G | 7.42 |
| T35M | 4.77 |
| S36A | 5.89 |
| V37A | 3.32 |
| V37G | 12.12 |
| V37H | 6.80 |
| V37S | 6.18 |
| V38D | 3.78 |
| V38G | 3.04 |
| V38P | 7.99 |
| N39E | 8.55 |
| N39Q | 10.27 |
| N39R | 8.30 |
| A40M | 8.09 |
| A40P | 4.48 |
| S41T | 3.18 |
| G44F | 15.32 |
| G44Y | 18.61 |
| D45P | 7.22 |
| D45Q | 6.10 |
| T46W | 5.89 |
| S47F | 11.65 |
| Q49I | 3.53 |
| G50A | 4.02 |
| G50K | 8.94 |
| G50M | 7.53 |
| G50S | 4.66 |
| R53S | 3.50 |
| L58D | 4.15 |
| L58M | 4.67 |
| L58R | 4.08 |
| W65L | 4.97 |
| L67G | 5.61 |
| V68G | 6.96 |
| V68M | 5.55 |
| V68N | 3.76 |
| E69P | 7.37 |
| E69Q | 4.96 |
| L70A | 3.26 |
| L70E | 5.28 |
| L70H | 6.20 |

FIG. 46A Cont.

| | |
|---|---|
| G71C | 5.41 |
| G72A | 8.49 |
| N73C | 43.13 |
| N73G | 20.82 |
| N73L | 99.80 |
| N73R | 55.92 |
| N73T | 21.73 |
| N73V | 23.14 |
| D74C | 3.40 |
| D74S | 6.08 |
| D74W | 3.06 |
| G75A | 5.56 |
| G75K | 9.24 |
| G75L | 4.21 |
| G75M | 5.22 |
| L76A | 8.09 |
| L76F | 6.06 |
| L76G | 9.97 |
| L76I | 12.96 |
| L76M | 8.95 |
| L76N | 7.26 |
| L76T | 8.29 |
| L76W | 3.88 |
| R77G | 3.68 |
| F79A | 4.32 |
| F79M | 3.53 |
| F79P | 5.17 |
| P81E | 3.67 |
| P81W | 9.66 |
| T84F | 3.46 |
| T84H | 6.48 |
| T84Y | 5.60 |
| Q86P | 5.77 |
| Q86W | 3.12 |
| T87M | 5.05 |
| T87S | 10.43 |
| T87W | 6.37 |
| L88C | 4.90 |
| L88F | 4.64 |
| L88G | 5.68 |
| L88H | 5.96 |
| L88Y | 6.92 |
| R89G | 3.31 |
| Q90P | 5.13 |
| Q90W | 4.08 |

FIG. 46A Cont.

| | |
|---|---|
| I91M | 3.07 |
| I91S | 3.57 |
| L92C | 3.80 |
| L92G | 3.16 |
| Q93F | 3.11 |
| Q93P | 4.58 |
| V95A | 4.03 |
| V95D | 12.50 |
| V95E | 5.71 |
| V95L | 4.40 |
| V95M | 5.04 |
| K96P | 4.05 |
| N99L | 3.35 |
| N99M | 4.20 |
| N99S | 4.70 |
| A100D | 3.22 |
| A100K | 4.15 |
| A100L | 7.81 |
| A100M | 4.13 |
| A100V | 3.06 |
| A100Y | 4.65 |
| L103A | 6.13 |
| L104A | 15.18 |
| L104C | 5.30 |
| L104P | 4.74 |
| L104Q | 9.63 |
| L104W | 10.14 |
| M105A | 5.23 |
| Q106A | 5.08 |
| Q106C | 3.89 |
| Q106T | 4.25 |
| Q106W | 3.32 |
| I107C | 3.47 |
| I107M | 3.01 |
| R108E | 4.03 |
| L109F | 6.41 |
| L109M | 3.71 |
| G114F | 3.10 |
| R115W | 3.53 |
| Y117P | 3.67 |
| E119D | 3.15 |
| E119P | 3.57 |
| A120P | 3.78 |
| F121A | 5.76 |
| F121C | 3.24 |

FIG. 46A Cont.

| | |
|---|---|
| F121W | 3.48 |
| K127P | 3.78 |
| L128F | 3.52 |
| A129L | 3.29 |
| A129Y | 3.90 |
| E131A | 3.45 |
| F132P | 4.96 |
| V134P | 5.07 |
| P135A | 5.45 |
| L136A | 6.42 |
| F139M | 4.10 |
| M141A | 5.51 |
| M141P | 5.32 |
| E142A | 3.32 |
| E143P | 3.02 |
| V144A | 3.51 |
| W150D | 7.23 |
| W150E | 3.06 |
| M151S | 3.79 |
| G155V | 5.25 |
| I156K | 5.55 |
| I156M | 3.06 |
| P158A | 5.79 |
| P158G | 10.16 |
| P158Q | 3.77 |
| P158S | 4.57 |
| N159E | 3.77 |
| N159I | 5.22 |
| R160H | 3.92 |
| R160I | 5.09 |
| R160K | 5.34 |
| D161G | 4.10 |
| A162T | 3.68 |
| A162Y | 8.66 |
| Q163A | 7.29 |
| Q163C | 7.72 |
| Q163E | 5.85 |
| Q163G | 11.71 |
| Q163I | 9.28 |
| Q163M | 4.29 |
| Q163S | 4.82 |
| Q163T | 3.00 |
| Q163V | 6.11 |
| P164C | 12.04 |
| F165D | 3.42 |

FIG. 46A Cont.

| | |
|---|---|
| F165S | 3.30 |
| I166A | 3.85 |
| I166L | 3.59 |
| W169M | 3.29 |
| M170E | 3.05 |
| M170G | 9.99 |
| M170N | 8.03 |
| M170S | 7.12 |
| Q173P | 3.78 |
| L174A | 3.78 |

FIG. 46B

| Mutations that Decrease % Ester ||
|---|---|
| MUTATION | Z Score |
| T3E | -3.75 |
| T3G | -3.15 |
| T3K | -4.44 |
| T3L | -5.16 |
| L5C | -3.52 |
| L5G | -7.94 |
| Y15A | -9.80 |
| Y15L | -7.41 |
| Y15Q | -9.62 |
| Y15R | -12.86 |
| Y15V | -5.13 |
| R16D | -5.44 |
| R16E | -7.34 |
| R16G | -5.66 |
| R16I | -5.18 |
| R16V | -4.68 |
| S18E | -3.37 |
| L27V | -4.40 |
| N28G | -3.88 |
| N28I | -4.84 |
| S33I | -3.77 |
| S33R | -4.67 |
| K34R | -6.85 |
| T35F | -3.95 |
| T35K | -4.93 |
| T35L | -5.21 |
| T35Q | -6.00 |
| T35V | -4.28 |
| S36F | -3.06 |
| S36I | -3.20 |
| S36L | -4.70 |
| S36W | -3.22 |
| V37L | -7.70 |
| V38E | -3.29 |
| V38F | -3.81 |
| V38K | -5.68 |
| V38L | -4.19 |
| A40D | -3.30 |
| A40G | -7.18 |
| I42T | -3.61 |

FIG. 46B Cont.

| Mutation | Value |
|---|---|
| T46L | -3.27 |
| L57A | -4.83 |
| L57F | -4.37 |
| L57G | -4.12 |
| L57H | -6.58 |
| L57K | -5.98 |
| L57N | -5.05 |
| L57P | -5.74 |
| L57R | -5.38 |
| L57S | -6.16 |
| L57T | -4.19 |
| L57V | -4.08 |
| L57W | -3.71 |
| L57Y | -5.01 |
| K59V | -4.45 |
| Q60E | -3.55 |
| Q60P | -3.08 |
| Q62G | -4.53 |
| W65V | -4.41 |
| V68L | -7.42 |
| R77L | -3.91 |
| G78M | -4.30 |
| V95F | -3.85 |
| V95N | -3.33 |
| K96C | -4.65 |
| K96L | -3.67 |
| K96N | -4.18 |
| K96Q | -5.36 |
| K96R | -7.65 |
| K96Y | -5.38 |
| A97E | -4.36 |
| A97F | -4.27 |
| A97R | -4.60 |
| A97W | -5.12 |
| A98E | -3.70 |
| N99A | -4.21 |
| N99D | -3.30 |
| A100S | -4.38 |
| P102I | -3.39 |
| L103Q | -3.11 |
| L103W | -3.89 |
| M105L | -3.83 |
| Q106G | -5.28 |
| Q106H | -5.37 |
| Q106K | -3.30 |

FIG. 46B Cont.

| | |
|---|---|
| Q106S | -4.63 |
| Q106V | -5.60 |
| F121P | -3.07 |
| A123E | -4.90 |
| Q152D | -4.56 |
| Q152E | -9.86 |
| Q152F | -11.08 |
| Q152H | -12.47 |
| Q152I | -8.55 |
| Q152K | -6.37 |
| Q152L | -7.44 |
| Q152S | -5.03 |
| Q152T | -7.31 |
| Q152Y | -14.60 |
| D153P | -4.17 |
| D153V | -4.45 |
| D154E | -3.11 |
| A167V | -3.05 |
| Q175L | -3.76 |
| P176D | -3.67 |
| V178K | -3.94 |
| N179H | -3.14 |
| N179W | -5.01 |
| H180E | -3.01 |
| H180L | -3.82 |
| H180P | -3.19 |
| H180R | -5.37 |
| D181C | -3.81 |
| D181E | -3.98 |
| S182K | -5.10 |
| S182L | -9.96 |
| S182N | -3.24 |
| S182R | -3.03 |
| S182T | -3.14 |
| S182V | -4.94 |

FIG. 46C

| Mutation | Total Fatty Acid Derivative Z-Score |
|---|---|
| D2L | 3.1 |
| D2P | 3.09 |
| D2R | 5.27 |
| L5G | 9.06 |
| L11I | 10.41 |
| S12N | 19.35 |
| S12T | 5.24 |
| A13N | 9.86 |
| G14C | 10.55 |
| G14P | 3.91 |
| G14S | 11.7 |
| G14T | 15.3 |
| G14V | 10.24 |
| Y15C | 15.73 |
| Y15I | 4.12 |
| Y15V | 14.38 |
| R16T | 10.83 |
| M17D | 5.66 |
| M17E | 13.02 |
| M17N | 12.87 |
| M17R | 8.13 |
| M17S | 17.91 |
| M17V | 14.03 |
| A19C | 8.28 |
| A21G | 3.99 |
| A22L | 8.35 |
| A22R | 9.85 |
| A22T | 11.82 |
| A25P | 4.3 |
| L26D | 6.02 |
| L26G | 5.13 |
| L26W | 3.97 |
| L27C | 18.8 |
| L27F | 4.85 |
| L27W | 4.46 |
| L27Y | 17.6 |
| N28I | 3.54 |
| N28P | 10.46 |

FIG. 46C Cont.

| | |
|---|---|
| D29P | 4.5 |
| K30P | 4.51 |
| W31D | 3.34 |
| W31G | 3.44 |
| W31N | 7.18 |
| W31P | 9.84 |
| W31R | 8.12 |
| W31S | 5.62 |
| W31T | 3.45 |
| V37Y | 3.31 |
| N39P | 4.07 |
| S41C | 6.16 |
| I42D | 3.81 |
| I42G | 5.49 |
| S43E | 5.31 |
| G44K | 4.38 |
| G44R | 5.74 |
| G44W | 4.52 |
| D45G | 2.99 |
| Q49E | 5.84 |
| G50A | 4.07 |
| G50K | 3.41 |
| G50M | 5.65 |
| G50Q | 3.87 |
| L51D | 7.74 |
| L51T | 3.23 |
| R53A | 14.19 |
| R53G | 19.1 |
| R53L | 3.99 |
| R53N | 19.72 |
| R53S | 10.86 |
| R53V | 8.46 |
| L54E | 10.38 |
| L54F | 7.61 |
| L54G | 16.55 |
| L54N | 18.34 |
| L54S | 6.45 |
| L54W | 7.15 |
| L58R | 4.52 |
| P63G | 3.98 |
| P63M | 3.85 |

FIG. 46C Cont.

| | |
|---|---|
| P63N | 4.85 |
| P63T | 3.32 |
| P63W | 3.16 |
| W65E | 3.44 |
| W65G | 3.87 |
| V66G | 3.15 |
| V66S | 5.47 |
| L67T | 2.95 |
| V68S | 3.59 |
| E69F | 4.13 |
| E69V | 6.21 |
| L70C | 12.11 |
| L70F | 6.04 |
| L70Q | 6.61 |
| L70S | 9.83 |
| L70T | 6.68 |
| L70V | 3.8 |
| G71A | 10.48 |
| N73G | 6.55 |
| N73L | 3.47 |
| D74A | 11.53 |
| D74C | 19.11 |
| G75A | 3.47 |
| G75C | 4.7 |
| G75F | 11.23 |
| G75R | 9.68 |
| G75W | 3.24 |
| L76I | 7.06 |
| R77A | 5.59 |
| R77C | 24.14 |
| R77D | 17.67 |
| R77F | 19.44 |
| R77G | 6.42 |
| R77H | 18.69 |
| R77K | 4.45 |
| R77L | 3.18 |
| R77N | 27.44 |
| R77Q | 5.4 |
| R77S | 26.28 |
| R77W | 14.62 |
| G78D | 30.26 |

FIG. 46C Cont.

| | |
|---|---|
| G78E | 7.28 |
| F79K | 3.58 |
| Q80G | 5.77 |
| T84H | 4.38 |
| T84N | 4.63 |
| T84Q | 3.61 |
| T87A | 4.56 |
| T87F | 10.68 |
| T87H | 3.02 |
| T87W | 4.76 |
| L88A | 3.11 |
| L88C | 5.35 |
| L88H | 5.98 |
| Q90N | 3.66 |
| Q90W | 10.88 |
| I91G | 40.44 |
| I91L | 7.89 |
| I91M | 8.25 |
| I91S | 50.1 |
| L92G | 48.24 |
| L92N | 56.72 |
| L92Q | 34.3 |
| L92S | 6.32 |
| L92T | 14.59 |
| L92Y | 35.1 |
| Q93P | 15.14 |
| D94P | 6.43 |
| V95F | 3.15 |
| V95N | 5.79 |
| V95Q | 9.2 |
| K96P | 7.91 |
| A97C | 3.52 |
| A97P | 11.7 |
| A98P | 5.42 |
| A98V | 5.62 |
| A100D | 12.11 |
| A100E | 8.23 |
| A100Q | 9.29 |
| A100Y | 3.33 |
| P102L | 5.39 |
| P102Q | 4.73 |

FIG. 46C Cont.

| | |
|---|---|
| P102R | 9.77 |
| L103E | 6.37 |
| L103K | 4.03 |
| L104A | 34.92 |
| L104Q | 14.84 |
| L104W | 14.88 |
| L104Y | 3.25 |
| M105C | 4.72 |
| M105E | 4.3 |
| M105F | 4.17 |
| M105L | 4.82 |
| Q106D | 4.12 |
| Q106G | 7.15 |
| Q106L | 4.33 |
| Q106V | 3.38 |
| Q106W | 3.87 |
| Q106Y | 6.66 |
| I107A | 38.63 |
| I107C | 19.37 |
| I107E | 7.18 |
| I107G | 11.8 |
| I107K | 29.78 |
| I107L | 38.5 |
| I107Q | 25.71 |
| I107S | 4.17 |
| I107T | 8.3 |
| R108G | 8.53 |
| L109F | 5.13 |
| L109V | 32.35 |
| L109Y | 13.22 |
| P110A | 20.08 |
| P110E | 3.92 |
| P110F | 4.31 |
| P110G | 4.8 |
| P110H | 22.31 |
| P110N | 24.19 |
| P110S | 3.14 |
| P110V | 11.63 |
| A111Y | 4.58 |
| N112F | 3.1 |
| N112P | 3.5 |

FIG. 46C Cont.

| | |
|---|---|
| Y113D | 7.02 |
| Y113E | 3.14 |
| Y113P | 6.39 |
| R115W | 13.16 |
| Y117A | 4.83 |
| Y117D | 6.71 |
| Y117E | 4.27 |
| Y117G | 7.9 |
| Y117P | 8.97 |
| Y117Q | 4.65 |
| N118F | 6.41 |
| E119P | 5.92 |
| A120P | 7.4 |
| F121C | 7.33 |
| F121L | 2.95 |
| F121M | 4.56 |
| F121N | 5.99 |
| F121Q | 7.56 |
| F121R | 5.7 |
| F121V | 5.95 |
| F121W | 8.69 |
| F121Y | 5.61 |
| S122D | 4.01 |
| S122F | 3.37 |
| S122L | 5.09 |
| S122P | 5.48 |
| S122W | 5.64 |
| S122Y | 7.13 |
| I124A | 3.2 |
| I124G | 4.26 |
| I124H | 3.91 |
| I124K | 4.95 |
| I124R | 5.09 |
| K127P | 4.82 |
| L128S | 5.28 |
| A129I | 7.03 |
| A129W | 5.66 |
| A129Y | 4.68 |
| K130P | 5.67 |
| L136A | 5.53 |
| L136D | 6.18 |

FIG. 46C Cont.

| | | |
|---|---|---|
| L136E | 14.63 | |
| L136G | 16.68 | |
| L136K | 4.2 | |
| L136N | 6.97 | |
| L136P | 5.97 | |
| L136Q | 3.19 | |
| L136S | 3.2 | |
| L136T | 9.17 | |
| L137A | 13.72 | |
| L137C | 4.56 | |
| L137H | 17.74 | |
| L137K | 4.68 | |
| L137Q | 16.1 | |
| L137S | 16.41 | |
| L137Y | 4.51 | |
| P138F | 8.47 | |
| F139L | 4 | |
| F139M | 9.77 | |
| F140C | 8.5 | |
| F140I | 5.75 | |
| F140L | 7.6 | |
| F140M | 11.44 | |
| F140V | 5.4 | |
| M141T | 3.63 | |
| E143P | 8.01 | |
| V144H | 3.57 | |
| Y145I | 6.61 | |
| L146G | 3 | |
| L146P | 10.14 | |
| W150G | 2.98 | |
| W150I | 6.42 | |
| W150V | 12.18 | |
| M151F | 6.24 | |
| M151L | 5.43 | |
| M151R | 8.2 | |
| M151S | 3.62 | |
| M151T | 5.19 | |
| M151W | 3.09 | |
| Q152N | 4.22 | |
| Q152V | 7.76 | |
| Q152Y | 4.88 | |

FIG. 46C Cont.

| | |
|---|---|
| D154C | 12.35 |
| D154E | 5.76 |
| G155I | 4.41 |
| I156C | 5.24 |
| I156K | 7.75 |
| I156T | 6.63 |
| I156V | 4.43 |
| P158G | 3.01 |
| P158T | 7.31 |
| A162T | 6.21 |
| Q163A | 5.37 |
| Q163C | 5.25 |
| Q163E | 5.17 |
| Q163I | 4.83 |
| Q163S | 5.27 |
| Q163T | 3.47 |
| Q163V | 3.25 |
| I166C | 3.39 |
| A167E | 8.68 |
| A167F | 8.37 |
| A167L | 5.18 |
| A167N | 6.56 |
| A167R | 4.61 |
| A167V | 3.39 |
| A167Y | 7.5 |
| W169K | 5.3 |
| M170N | 3.97 |
| M170S | 4.35 |
| Q173D | 3.48 |
| L174A | 7.12 |
| L174T | 11.05 |
| L174W | 3.59 |

FIG. 46D

| Mutation | % Short Chain Z-Score |
|---|---|
| A13V | 7.09 |
| R16A | 11.68 |
| M17T | 7.96 |
| A25S | 3.27 |
| D29M | 3.68 |
| W31L | 3.55 |
| T35Y | 4.06 |
| S36W | 3.53 |
| V38S | 3.40 |
| P55A | 3.39 |
| P55G | 4.06 |
| L57I | 4.09 |
| L58M | 3.45 |
| L58V | 4.08 |
| K59E | 3.50 |
| H61W | 3.16 |
| Q62M | 3.02 |
| P63V | 3.29 |
| R64M | 3.08 |
| W65L | 3.30 |
| V66C | 5.60 |
| L67C | 5.55 |
| L67M | 3.18 |
| G78F | 3.39 |
| G78M | 3.80 |
| G78R | 3.31 |
| G78T | 6.98 |
| G78V | 4.03 |
| F79K | 5.25 |
| F79Y | 3.92 |
| Q82A | 3.27 |
| Q82M | 3.26 |
| Q82R | 3.05 |
| Q83G | 3.70 |
| Q83K | 4.81 |
| T84M | 3.89 |
| T84V | 3.61 |
| E85A | 3.07 |

FIG. 46D Cont.

| | |
|---|---|
| E85C | 4.50 |
| E85G | 4.06 |
| E85Q | 4.15 |
| E85S | 3.63 |
| E85T | 3.30 |
| E85V | 3.44 |
| E85W | 3.96 |
| E85Y | 3.69 |
| Q86H | 3.43 |
| Q86Y | 3.32 |
| T87R | 3.52 |
| R89V | 3.51 |
| Q90L | 3.16 |
| Q93M | 3.31 |
| Q93N | 3.61 |
| Q93V | 3.18 |
| D94C | 3.53 |
| D94L | 3.52 |
| V95G | 3.30 |
| K96C | 3.24 |
| A97N | 4.73 |
| A97V | 4.59 |
| A98G | 3.67 |
| A98Y | 4.87 |
| M105I | 3.47 |
| Q106K | 3.18 |
| Q106R | 4.48 |
| R108W | 3.83 |
| A111E | 4.12 |
| A111N | 5.07 |
| A111S | 4.21 |
| A111W | 6.93 |
| A111Y | 4.86 |
| Y113A | 3.19 |
| Y113S | 3.04 |
| Y113V | 4.98 |
| G114K | 3.54 |
| G114Y | 3.66 |
| Y117R | 5.13 |
| E119M | 4.08 |
| E119Q | 3.49 |

FIG. 46D Cont.

| | |
|---|---|
| E119R | 3.28 |
| S122F | 3.57 |
| S122I | 5.40 |
| S122M | 6.27 |
| S122R | 5.14 |
| P126K | 3.97 |
| F132C | 4.67 |
| F132D | 4.72 |
| F132K | 3.54 |
| F132L | 4.13 |
| F132N | 4.95 |
| F132V | 4.28 |
| P135A | 3.60 |
| P135E | 4.28 |
| P135K | 3.75 |
| P135Q | 3.37 |
| L136H | 4.45 |
| F139L | 3.92 |
| E142W | 3.17 |
| V144Y | 3.35 |
| Y145A | 6.56 |
| Y145C | 8.23 |
| Y145D | 4.08 |
| Y145E | 7.49 |
| Y145G | 4.43 |
| Y145I | 5.79 |
| Y145L | 9.47 |
| Y145M | 4.49 |
| Y145N | 4.71 |
| Y145R | 7.80 |
| Y145S | 6.13 |
| Y145T | 5.12 |
| D153K | 3.32 |
| D153Q | 3.10 |
| D161K | 3.21 |
| A162I | 3.34 |
| F165K | 3.34 |
| D168W | 3.59 |
| Q173I | 4.32 |
| Q175M | 3.35 |
| P176Q | 4.15 |

FIG. 46D Cont.

| | |
|---|---|
| P176R | 4.03 |
| P176V | 31.09 |
| V178F | 6.09 |
| V178G | 4.08 |
| V178L | 4.38 |
| V178R | 6.56 |
| V178S | 4.09 |
| V178T | 7.82 |
| N179H | 3.08 |
| H180E | 3.85 |
| H180P | 3.13 |
| H180R | 4.08 |
| H180S | 4.02 |
| H180V | 3.27 |
| H180W | 3.32 |
| D181R | 3.24 |
| D181T | 3.06 |
| S182C | 3.07 |
| S182D | 6.28 |
| S182G | 3.84 |
| S182P | 5.05 |
| S182R | 3.11 |

FIG. 46E

| Mutation | % Short Chain Z-Score |
|---|---|
| A1C | -63.21 |
| A1F | -9.02 |
| A1L | -44.70 |
| A1Y | -8.32 |
| D2L | -5.90 |
| D2M | -4.92 |
| D2P | -19.11 |
| D2W | -20.50 |
| T3R | -26.69 |
| L4A | -6.44 |
| L4M | -4.38 |
| L4N | -42.37 |
| L4S | -40.54 |
| L4V | -5.67 |
| L4Y | -5.91 |
| L5E | -35.71 |
| L5F | -4.80 |
| L5G | -7.53 |
| L5K | -30.43 |
| L5N | -42.32 |
| L5S | -4.31 |
| L5W | -31.99 |
| I6T | -14.34 |
| L7A | -3.04 |
| L7E | -42.41 |
| L7K | -37.04 |
| L7M | -21.53 |
| L7W | -57.14 |
| G8K | -214.60 |
| D9N | -14.32 |
| D9T | -120.67 |
| L11A | -18.08 |
| L11C | -107.22 |
| L11I | -7.83 |
| L11M | -101.21 |
| L11Q | -91.91 |
| L11V | -116.56 |
| S12I | -93.25 |
| S12L | -12.25 |

FIG. 46E Cont.

| | |
|---|---|
| S12M | -4.54 |
| S12N | -18.74 |
| S12T | -3.35 |
| S12V | -78.58 |
| S12Y | -12.22 |
| A13C | -3.99 |
| G14C | -39.75 |
| G14E | -100.31 |
| G14I | -102.00 |
| G14M | -111.79 |
| G14N | -35.52 |
| G14P | -60.98 |
| G14S | -5.26 |
| G14T | -21.65 |
| G14V | -9.41 |
| Y15C | -18.57 |
| Y15E | -80.36 |
| Y15G | -77.73 |
| Y15I | -62.75 |
| Y15N | -102.87 |
| Y15V | -25.60 |
| R16T | -7.14 |
| M17D | -11.63 |
| M17E | -27.51 |
| M17G | -4.41 |
| M17L | -7.33 |
| M17N | -8.89 |
| M17P | -3.70 |
| M17R | -46.44 |
| M17S | -16.39 |
| M17V | -22.23 |
| S18M | -5.57 |
| S18N | -35.29 |
| S18T | -7.42 |
| A19E | -4.77 |
| A19L | -22.51 |
| A19V | -25.84 |
| A21P | -3.45 |
| A22D | -3.98 |
| A22E | -12.41 |
| A22F | -23.02 |

FIG. 46E Cont.

| | |
|---|---|
| A22H | -15.49 |
| A22I | -12.96 |
| A22K | -18.01 |
| A22L | -24.96 |
| A22P | -11.17 |
| A22R | -19.43 |
| A22S | -4.85 |
| A22T | -4.65 |
| A22Y | -10.55 |
| W23A | -24.50 |
| W23H | -87.01 |
| W23N | -13.53 |
| W23P | -19.15 |
| P24A | -6.88 |
| P24C | -8.82 |
| P24D | -16.32 |
| P24E | -17.09 |
| P24F | -26.45 |
| P24G | -17.75 |
| P24I | -4.37 |
| P24M | -22.41 |
| P24N | -13.92 |
| P24S | -12.83 |
| P24T | -9.58 |
| P24V | -4.54 |
| P24W | -30.72 |
| L26P | -21.59 |
| L27A | -19.17 |
| L27C | -8.14 |
| L27F | -4.31 |
| L27H | -61.92 |
| L27R | -58.76 |
| L27S | -62.16 |
| L27T | -45.28 |
| L27W | -8.60 |
| L27Y | -17.79 |
| K30P | -4.76 |
| W31D | -4.32 |
| W31P | -4.55 |
| W31R | -3.68 |
| S36F | -4.42 |

FIG. 46E Cont.

| | |
|---|---|
| S36L | -4.11 |
| V37G | -11.20 |
| V37H | -10.89 |
| V37N | -33.74 |
| V37Q | -10.59 |
| V37W | -30.09 |
| V37Y | -12.66 |
| V38P | -3.60 |
| N39E | -6.92 |
| N39G | -3.17 |
| N39K | -46.33 |
| N39M | -39.26 |
| N39P | -4.38 |
| N39Q | -3.40 |
| N39Y | -7.53 |
| I42D | -12.43 |
| I42G | -3.39 |
| I42P | -18.84 |
| G44A | -12.40 |
| G44E | -16.26 |
| G44K | -7.30 |
| G44M | -11.89 |
| G44N | -13.25 |
| G44R | -3.19 |
| G44S | -18.29 |
| G44W | -15.05 |
| G44Y | -10.81 |
| D45G | -5.89 |
| D45M | -4.57 |
| T46D | -7.57 |
| S47E | -3.25 |
| S47P | -21.28 |
| S47Q | -5.63 |
| S47R | -6.47 |
| S47Y | -8.31 |
| Q48Y | -3.34 |
| G50C | -8.06 |
| G50E | -31.84 |
| G50F | -19.16 |
| G50I | -19.41 |
| G50K | -16.73 |

FIG. 46E Cont.

| | |
|---|---|
| G50L | -19.75 |
| G50M | -14.11 |
| G50N | -20.46 |
| G50P | -53.52 |
| G50Q | -16.90 |
| G50R | -45.44 |
| G50S | -17.05 |
| G50T | -36.12 |
| G50W | -26.95 |
| G50Y | -26.67 |
| L51D | -10.49 |
| L51P | -44.08 |
| L51T | -4.49 |
| A52P | -40.24 |
| R53A | -6.83 |
| R53C | -48.10 |
| R53D | -16.24 |
| R53E | -15.22 |
| R53F | -60.20 |
| R53G | -6.40 |
| R53I | -15.55 |
| R53K | -3.63 |
| R53L | -14.72 |
| R53N | -4.40 |
| R53S | -6.28 |
| R53T | -38.15 |
| R53V | -13.28 |
| R53W | -15.21 |
| R53Y | -16.67 |
| L54C | -5.06 |
| L54E | -5.47 |
| L54G | -3.80 |
| L54N | -5.95 |
| L54Y | -17.42 |
| P55Y | -3.37 |
| L57P | -3.06 |
| H61A | -7.21 |
| H61D | -5.86 |
| H61E | -9.15 |
| P63D | -98.14 |
| P63E | -42.96 |

FIG. 46E Cont.

| | |
|---|---|
| P63G | -28.12 |
| P63K | -70.32 |
| P63M | -5.00 |
| P63N | -19.05 |
| P63Q | -34.79 |
| P63R | -64.59 |
| R64L | -4.58 |
| W65G | -12.80 |
| W65P | -8.14 |
| W65R | -3.23 |
| V66N | -5.41 |
| V66Q | -6.18 |
| V66S | -6.63 |
| V66W | -3.70 |
| V66Y | -6.28 |
| L67E | -8.21 |
| L67G | -6.01 |
| L67Q | -60.05 |
| L67R | -12.02 |
| L67S | -6.98 |
| L67W | -4.14 |
| V68E | -11.51 |
| V68G | -60.22 |
| V68N | -4.74 |
| V68P | -3.83 |
| V68Q | -5.95 |
| E69A | -28.03 |
| E69C | -27.17 |
| E69D | -61.95 |
| E69F | -24.68 |
| E69G | -28.66 |
| E69H | -28.86 |
| E69K | -32.28 |
| E69L | -25.27 |
| E69M | -27.85 |
| E69N | -27.47 |
| E69P | -25.46 |
| E69Q | -35.73 |
| E69S | -49.76 |
| E69V | -18.30 |
| E69W | -66.11 |

FIG. 46E Cont.

| | |
|---|---|
| E69Y | -37.18 |
| L70A | -42.86 |
| L70C | -3.55 |
| L70E | -42.71 |
| L70F | -19.50 |
| L70G | -94.13 |
| L70H | -25.17 |
| L70K | -29.95 |
| L70Q | -20.11 |
| L70S | -7.68 |
| L70T | -14.42 |
| L70W | -57.74 |
| G71C | -32.31 |
| G71S | -56.24 |
| G72A | -26.23 |
| G72M | -33.06 |
| G72P | -47.28 |
| N73A | -4.63 |
| N73G | -13.51 |
| N73H | -10.61 |
| N73I | -8.43 |
| N73L | -7.30 |
| N73P | -9.25 |
| N73R | -6.25 |
| N73S | -8.04 |
| N73T | -28.23 |
| N73W | -7.23 |
| D74A | -45.23 |
| D74C | -31.24 |
| D74F | -28.47 |
| D74G | -60.70 |
| D74Q | -24.51 |
| D74S | -38.03 |
| D74W | -49.27 |
| D74Y | -99.77 |
| G75A | -20.56 |
| G75C | -48.09 |
| G75D | -81.21 |
| G75E | -42.01 |
| G75F | -48.35 |
| G75I | -32.43 |

FIG. 46E Cont.

| | |
|---|---|
| G75K | -26.48 |
| G75L | -32.30 |
| G75M | -24.38 |
| G75N | -52.61 |
| G75P | -62.43 |
| G75R | -31.94 |
| G75T | -53.18 |
| G75V | -57.06 |
| G75W | -56.35 |
| G75Y | -57.62 |
| L76A | -22.79 |
| L76C | -7.92 |
| L76D | -12.58 |
| L76E | -30.25 |
| L76F | -19.25 |
| L76G | -26.23 |
| L76I | -6.81 |
| L76K | -4.47 |
| L76M | -4.68 |
| L76N | -31.55 |
| L76P | -8.17 |
| L76Q | -9.92 |
| L76R | -6.71 |
| L76T | -25.66 |
| L76V | -6.91 |
| L76W | -5.04 |
| R77A | -26.49 |
| R77C | -9.00 |
| R77D | -30.03 |
| R77E | -20.54 |
| R77F | -24.10 |
| R77G | -9.49 |
| R77H | -24.48 |
| R77N | -8.48 |
| R77S | -10.71 |
| R77V | -22.45 |
| R77W | -28.93 |
| G78A | -6.52 |
| G78C | -8.34 |
| G78D | -9.99 |
| G78E | -3.95 |

FIG. 46E Cont.

| | |
|---|---|
| G78N | -8.13 |
| G78P | -10.38 |
| G78Q | -18.48 |
| G78Y | -21.82 |
| F79P | -28.76 |
| F79Q | -6.47 |
| F79S | -4.11 |
| F79V | -3.46 |
| P81E | -3.29 |
| P81W | -3.14 |
| T84D | -88.05 |
| T84E | -41.00 |
| T84G | -26.25 |
| T84H | -10.81 |
| T84K | -63.88 |
| T84L | -23.82 |
| T84N | -7.78 |
| T84Q | -3.62 |
| T84R | -46.36 |
| T84W | -38.11 |
| T84Y | -24.81 |
| E85F | -13.79 |
| E85P | -53.55 |
| Q86A | -5.22 |
| T87F | -4.59 |
| L88A | -25.28 |
| L88E | -37.11 |
| L88G | -32.24 |
| L88H | -20.68 |
| L88Q | -42.32 |
| L88S | -46.95 |
| L88W | -30.65 |
| L88Y | -29.41 |
| R89P | -24.05 |
| Q90P | -31.92 |
| Q90W | -3.38 |
| I91E | -79.82 |
| I91L | -5.73 |
| I91M | -30.56 |
| I91N | -42.09 |
| I91Q | -38.31 |

FIG. 46E Cont.

| | |
|---|---|
| I91S | -4.95 |
| I91Y | -43.76 |
| L92C | -4.99 |
| L92E | -73.12 |
| L92G | -5.00 |
| L92H | -9.88 |
| L92N | -7.93 |
| L92Q | -19.11 |
| L92R | -84.60 |
| L92S | -8.48 |
| L92Y | -13.84 |
| Q93P | -32.68 |
| D94P | -7.30 |
| D94V | -3.57 |
| V95A | -3.75 |
| V95C | -5.62 |
| V95D | -29.29 |
| V95E | -30.46 |
| V95F | -20.99 |
| V95I | -8.56 |
| V95P | -59.35 |
| V95Q | -22.52 |
| V95W | -24.15 |
| V95Y | -33.39 |
| K96P | -8.92 |
| A97C | -7.38 |
| A97P | -15.17 |
| N99D | -33.21 |
| A100Q | -5.06 |
| A100Y | -4.26 |
| P102E | -46.58 |
| P102G | -3.79 |
| P102H | -45.32 |
| P102L | -3.44 |
| P102R | -10.05 |
| P102V | -8.26 |
| P102W | -22.77 |
| L103C | -3.18 |
| L103E | -24.55 |
| L103I | -3.75 |
| L103K | -5.44 |

FIG. 46E Cont.

| | |
|---|---|
| L103N | -11.31 |
| L103R | -4.04 |
| L103S | -4.81 |
| L103T | -11.37 |
| L103V | -6.38 |
| L104A | -11.07 |
| L104C | -3.49 |
| L104E | -28.11 |
| L104G | -31.37 |
| L104I | -7.05 |
| L104N | -32.01 |
| L104P | -3.12 |
| L104Q | -22.01 |
| L104S | -61.20 |
| L104W | -18.48 |
| L104Y | -23.89 |
| M105A | -28.83 |
| M105C | -10.71 |
| M105E | -8.53 |
| M105F | -3.85 |
| M105G | -18.71 |
| M105K | -34.14 |
| M105L | -5.29 |
| M105P | -102.51 |
| M105T | -11.34 |
| M105W | -50.61 |
| Q106D | -10.02 |
| Q106G | -9.34 |
| Q106H | -14.02 |
| Q106L | -20.17 |
| Q106W | -11.32 |
| I107A | -17.31 |
| I107E | -32.09 |
| I107F | -20.95 |
| I107G | -28.47 |
| I107K | -22.87 |
| I107L | -3.00 |
| I107Q | -18.95 |
| I107S | -23.44 |
| I107T | -7.98 |
| I107Y | -22.72 |

FIG. 46E Cont.

| | |
|---|---|
| R108A | -10.47 |
| R108C | -9.20 |
| R108D | -13.69 |
| R108E | -9.20 |
| R108F | -5.75 |
| R108G | -10.70 |
| R108H | -9.69 |
| R108I | -6.35 |
| R108L | -8.87 |
| R108M | -5.49 |
| R108S | -11.02 |
| R108V | -9.68 |
| R108Y | -9.49 |
| L109C | -41.59 |
| L109F | -28.41 |
| L109G | -42.09 |
| L109K | -69.64 |
| L109Q | -50.80 |
| L109R | -29.08 |
| L109T | -41.67 |
| L109V | -23.71 |
| L109Y | -43.56 |
| P110A | -33.63 |
| P110C | -25.47 |
| P110D | -24.31 |
| P110E | -17.72 |
| P110F | -43.41 |
| P110G | -23.80 |
| P110H | -34.80 |
| P110K | -30.19 |
| P110L | -23.19 |
| P110M | -23.20 |
| P110N | -33.38 |
| P110R | -51.79 |
| P110S | -22.47 |
| P110V | -33.71 |
| P110W | -39.36 |
| A111C | -9.89 |
| A111L | -3.57 |
| A111P | -4.23 |
| A111Q | -5.35 |

FIG. 46E Cont.

| | |
|---|---|
| A111R | -8.12 |
| A111V | -4.23 |
| N112I | -10.62 |
| N112L | -4.98 |
| N112P | -11.54 |
| N112Y | -5.03 |
| Y113D | -11.51 |
| Y113E | -3.61 |
| Y113Q | -3.02 |
| G114A | -9.61 |
| R115W | -10.95 |
| Y117D | -6.37 |
| Y117G | -4.14 |
| Y117P | -4.06 |
| N118F | -3.92 |
| E119C | -3.87 |
| E119L | -7.23 |
| A120P | -6.88 |
| F121A | -28.88 |
| F121C | -5.63 |
| F121D | -42.24 |
| F121E | -39.48 |
| F121G | -15.38 |
| F121K | -42.52 |
| F121L | -19.00 |
| F121N | -18.73 |
| F121P | -41.32 |
| F121Q | -11.85 |
| F121R | -13.32 |
| F121S | -29.43 |
| F121V | -9.75 |
| F121W | -3.56 |
| F121Y | -13.42 |
| S122D | -9.90 |
| S122E | -7.17 |
| S122L | -5.66 |
| S122P | -10.63 |
| I124D | -37.98 |
| I124E | -27.01 |
| I124G | -8.97 |
| I124H | -10.69 |

FIG. 46E Cont.

| | |
|---|---|
| I124K | -4.59 |
| I124R | -4.97 |
| I124W | -15.37 |
| I124Y | -23.96 |
| Y125C | -19.66 |
| Y125G | -21.01 |
| Y125H | -30.52 |
| Y125I | -17.04 |
| Y125L | -24.91 |
| Y125P | -21.87 |
| Y125Q | -23.99 |
| Y125R | -20.53 |
| Y125S | -21.85 |
| Y125T | -21.27 |
| Y125V | -21.89 |
| K127A | -6.42 |
| L128E | -27.59 |
| L128F | -22.69 |
| L128G | -29.74 |
| L128K | -21.82 |
| L128Q | -18.58 |
| L128R | -41.57 |
| L128S | -6.88 |
| L128W | -40.49 |
| A129D | -32.30 |
| A129F | -17.62 |
| A129L | -20.77 |
| A129W | -8.30 |
| A129Y | -11.75 |
| K130P | -8.51 |
| K130V | -4.75 |
| E131A | -12.26 |
| E131C | -7.90 |
| E131D | -3.75 |
| E131P | -60.42 |
| E131V | -3.20 |
| F132P | -67.58 |
| D133C | -5.33 |
| V134C | -3.68 |
| V134D | -5.51 |
| V134N | -14.94 |

FIG. 46E Cont.

| | |
|---|---|
| V134P | -64.09 |
| V134W | -9.68 |
| L136A | -4.43 |
| L136D | -25.03 |
| L136E | -9.24 |
| L136G | -11.96 |
| L136N | -12.24 |
| L136P | -12.86 |
| L136T | -5.66 |
| L137D | -77.81 |
| L137E | -44.88 |
| L137G | -64.00 |
| L137H | -9.52 |
| L137K | -21.51 |
| L137P | -59.72 |
| L137Q | -3.55 |
| L137R | -45.70 |
| L137S | -12.66 |
| P138G | -7.85 |
| P138N | -66.99 |
| P138V | -7.12 |
| F139A | -39.52 |
| F139C | -19.20 |
| F139D | -51.25 |
| F139E | -54.34 |
| F139G | -23.27 |
| F139H | -47.30 |
| F139M | -14.75 |
| F139N | -20.27 |
| F139S | -28.56 |
| F139T | -25.28 |
| F139V | -51.37 |
| F139W | -26.49 |
| F140A | -23.45 |
| F140C | -17.35 |
| F140G | -59.93 |
| F140I | -8.48 |
| F140L | -11.28 |
| F140M | -6.79 |
| F140N | -34.77 |
| F140P | -35.35 |

FIG. 46E Cont.

| | |
|---|---|
| F140S | -46.16 |
| F140T | -47.57 |
| F140V | -11.26 |
| F140W | -20.83 |
| M141C | -5.00 |
| M141D | -22.31 |
| M141E | -28.46 |
| M141F | -26.20 |
| M141G | -16.10 |
| M141K | -32.04 |
| M141L | -6.54 |
| M141P | -5.70 |
| M141Q | -22.98 |
| M141R | -33.51 |
| M141T | -10.69 |
| M141W | -48.57 |
| M141Y | -29.44 |
| E142A | -5.76 |
| E142C | -23.94 |
| E142G | -4.51 |
| E142I | -3.28 |
| E142L | -13.49 |
| E142M | -3.24 |
| E142P | -5.72 |
| E142Q | -6.34 |
| E142R | -6.85 |
| E142T | -4.28 |
| E142V | -4.47 |
| E143A | -7.08 |
| E143D | -5.09 |
| E143F | -5.68 |
| E143G | -3.69 |
| E143I | -4.21 |
| E143M | -8.02 |
| E143P | -6.28 |
| E143W | -4.76 |
| V144A | -3.67 |
| V144D | -17.15 |
| V144E | -13.28 |
| V144G | -18.12 |
| V144H | -15.74 |

FIG. 46E Cont.

| | |
|---|---|
| V144N | -19.72 |
| V144P | -9.89 |
| V144Q | -11.28 |
| V144R | -14.09 |
| V144S | -16.74 |
| Y145Q | -16.20 |
| Y145W | -24.17 |
| L146C | -5.36 |
| L146P | -7.13 |
| W150P | -8.88 |
| W150R | -3.07 |
| M151A | -22.29 |
| M151C | -13.48 |
| M151D | -53.94 |
| M151E | -36.34 |
| M151F | -6.85 |
| M151G | -28.78 |
| M151I | -12.66 |
| M151L | -7.96 |
| M151Q | -14.75 |
| M151R | -6.83 |
| M151S | -18.89 |
| M151T | -5.52 |
| M151V | -12.16 |
| M151W | -18.58 |
| Q152P | -4.80 |
| D153A | -7.19 |
| D153E | -3.25 |
| D153F | -4.87 |
| D154A | -23.82 |
| D154C | -3.67 |
| D154E | -22.22 |
| D154F | -58.92 |
| D154G | -25.00 |
| D154H | -31.59 |
| D154I | -64.36 |
| D154K | -29.79 |
| D154L | -60.21 |
| D154M | -25.21 |
| D154N | -28.72 |
| D154P | -58.38 |

FIG. 46E Cont.

| | |
|---|---|
| D154R | -28.30 |
| D154S | -39.88 |
| D154T | -59.86 |
| D154V | -59.21 |
| D154W | -60.95 |
| G155A | -3.44 |
| G155P | -27.12 |
| G155V | -5.61 |
| I156A | -11.30 |
| I156C | -7.69 |
| I156E | -30.46 |
| I156F | -12.66 |
| I156G | -54.46 |
| I156K | -19.45 |
| I156M | -11.92 |
| I156Q | -12.81 |
| I156R | -12.93 |
| I156S | -15.73 |
| I156T | -19.26 |
| I156Y | -20.27 |
| H157C | -5.78 |
| H157E | -22.88 |
| P158F | -13.72 |
| P158H | -12.61 |
| P158I | -21.00 |
| P158L | -11.13 |
| P158Q | -11.63 |
| P158V | -10.02 |
| P158W | -30.29 |
| N159P | -31.69 |
| N159W | -15.96 |
| A162K | -21.65 |
| A162L | -20.87 |
| A162N | -24.35 |
| A162R | -17.88 |
| A162Y | -21.36 |
| Q163A | -7.69 |
| Q163D | -52.48 |
| Q163E | -5.19 |
| Q163F | -30.51 |
| Q163I | -4.62 |

FIG. 46E Cont.

| | |
|---|---|
| Q163V | -10.61 |
| Q163W | -18.60 |
| Q163Y | -24.52 |
| F165L | -16.66 |
| I166A | -12.07 |
| I166F | -18.25 |
| I166M | -7.12 |
| I166S | -55.69 |
| I166Y | -14.41 |
| A167C | -4.32 |
| A167D | -22.48 |
| A167E | -3.95 |
| A167F | -13.29 |
| A167L | -6.74 |
| A167N | -10.52 |
| A167R | -8.46 |
| A167V | -5.29 |
| A167W | -81.07 |
| A167Y | -7.34 |
| D168M | -3.18 |
| D168R | -3.50 |
| M170E | -5.17 |
| M170F | -4.50 |
| M170G | -34.58 |
| M170N | -11.65 |
| M170S | -11.08 |
| M170T | -9.46 |
| A171S | -26.54 |
| Q173D | -10.77 |
| Q173P | -44.81 |
| L174A | -12.29 |
| L174G | -29.08 |
| L174S | -44.11 |
| L174T | -4.63 |
| L174W | -7.19 |
| L174Y | -47.03 |
| Q175F | -38.91 |
| P176L | -8.35 |
| P176Y | -4.38 |
| L177F | -4.63 |
| L177M | -4.34 |

FIG. 46E Cont.

| | |
|---|---|
| L177S | -3.75 |
| D181C | -6.46 |
| D181E | -6.68 |
| D181G | -3.39 |

FIG. 47

| Name | Sequence | |
|---|---|---|
| TesA_P_Domains_without_Signal_Peptide | | |
| EColi_1J00 | ---------------------------------------- | 0 |
| EColi_1JRL | ---------------------------------------- | 0 |
| EColi_O157_NP_286243 | ---------------------------------------- | 0 |
| Shigella_boydii_Sb227_YP_406934 | ---------------------------------------- | 0 |
| EColi_O157_ZP_02799578 | ---------------------------------------- | 0 |
| EColid_ZP_02902430 | ---------------------------------------- | 0 |
| EColi_ZP_03081449 | ---------------------------------------- | 0 |
| Shigella_dysenteriae_YP_402105 | ---------------------------------------- | 0 |
| Citrobacter_koseri_YP_001454190 | ---------------------------------------- | 0 |
| marine_metagenome_ECJ13936 | ---------------------------------------- | 0 |
| ABH77568_Sequence_7411_from_patent | ---------------------------------------- | 0 |
| Enterobacter_cancerogenus_ZP_03281441 | ---------------------------------------- | 0 |
| AAR53009_Sequence_12726_from_patent | GLSPSDRLSTPGPARRPRRGLTPARRSAATASAIRARTSGRSCFLPQLAIRQAQTAIAARRQQRIVSDEDQGGAVFAIKR | 80 |
| Enterobacter_YP_001175703 | ---------------------------------------- | 0 |
| Klebsiella_pneumoniae_YP_001334153 | ---------------------------------------- | 0 |
| Klebsiella_pneumoniae_YP_002240008 | ---------------------------------------- | 0 |
| Salmonella_enterica_NP_455101 | ---------------------------------------- | 0 |
| Salmonella_typhimurium_NP_459501 | ---------------------------------------- | 0 |
| Salmonella_enterica_YP_002225613 | ---------------------------------------- | 0 |
| Salmonella_enterica_YP_215534 | ---------------------------------------- | 0 |
| Salmonella_enterica_ZP_02344720 | ---------------------------------------- | 0 |
| Salmonella_enterica_ZP_02683026 | ---------------------------------------- | 0 |
| Salmonella_enterica_ZP_03163359 | ---------------------------------------- | 0 |
| Salmonella_enterica_ZP_03221362 | ---------------------------------------- | 0 |
| Salmonella_enterica_YP_001571431 | ---------------------------------------- | 0 |
| Klebsiella_ACC78298 | ---------------------------------------- | 0 |
| Enterobacter_sakazakii_YP_001438839 | ---------------------------------------- | 0 |
| Pectobacterium_atrosepticum_YP_049328 | ---------------------------------------- | 0 |
| Erwinia_tasmaniensis_YP_001908369 | ---------------------------------------- | 0 |
| Yersinia_pestis_ZP_02223456 | ---------------------------------------- | 0 |
| Yersinia_pestis_C092_NP_406570 | ---------------------------------------- | 0 |
| Yersinia_pestis_KIM_NP_668426 | ---------------------------------------- | 0 |
| Yersinia_pseudotuberculosis_YP_001140198 | ---------------------------------------- | 0 |
| Serratia_proteamaculans_YP_001477389 | ---------------------------------------- | 0 |
| Yersinia_pestis_Angola_YP_001605806 | ---------------------------------------- | 0 |

FIG. 47 (Cont.)

```
TesA_P_Domains_without_Signal_Peptide          ----------------------------------------------------------------
EColi_1J00                                     ----------------------------------------------------------------
EColi_1JRL                                     ----------------------------------------------------------------
EColi_O157_NP_286243                           ----------------------------------------------------------------
Shigella_boydii_Sb227_YP_406934                ----------------------------------------------------------------
EColi_O157_ZP_02799578                         ----------------------------------------------------------------
EColid_ZP_02902430                             ----------------------------------------------------------------
EColi_ZP_03081449                              ----------------------------------------------------------------
Shigella_dysenteriae_YP_402105                 ----------------------------------------------------------------
Citrobacter_koseri_YP_001454190                ----------------------------------------------------------------
marine_metagenome_ECJ13936                     ----------------------------------------------------------------
ABH77568_Sequence_7411_from_patent             ----------------------------------------------------------------
Enterobacter_cancerogenus_ZP_03281441          ----------------------------------------------------------------
AAR53009_Sequence_12726_from_patent            EQQIGNFVPGLAIEVAGGLIGEQNGRAPVKGPGQRHPLLFAAGELRRQVVQAFAKSQLLKQRAGIAPALAIAGAAQQRRQ
Enterobacter_YP_001175703                      ----------------------------------------------------------------
Klebsiella_pneumoniae_YP_001334153             ----------------------------------------------------------------
Klebsiella_pneumoniae_YP_002240008             ----------------------------------------------------------------
Salmonella_enterica_NP_455101                  ----------------------------------------------------------------
Salmonella_typhimurium_NP_459501               ----------------------------------------------------------------
Salmonella_enterica_YP_002225613               ----------------------------------------------------------------
Salmonella_enterica_YP_215534                  ----------------------------------------------------------------
Salmonella_enterica_ZP_02344720                ----------------------------------------------------------------
Salmonella_enterica_ZP_02683026                ----------------------------------------------------------------
Salmonella_enterica_ZP_03163359                ----------------------------------------------------------------
Salmonella_enterica_ZP_03221362                ----------------------------------------------------------------
Salmonella_enterica_YP_001571431               ----------------------------------------------------------------
Klebsiella_ACC78298                            ----------------------------------------------------------------
Enterobacter_sakazakii_YP_001438839            ----------------------------------------------------------------
Pectobacterium_atrosepticum_YP_049328          ----------------------------------------------------------------
Erwinia_tasmaniensis_YP_001908369              ----------------------------------------------------------------
Yersinia_pestis_ZP_02223456                    ----------------------------------------------------------------
Yersinia_pestis_C092_NP_406570                 ----------------------------------------------------------------
Yersinia_pestis_KIM_NP_668426                  ----------------------------------------------------------------
Yersinia_pseudotuberculosis_YP_001140198       ----------------------------------------------------------------
Serratia_proteamaculans_YP_001477389           ----------------------------------------------------------------
Yersinia_pestis_Angola_YP_001605806            ----------------------------------------------------------------
```

FIG. 47 (Cont.)

| Name | Sequence | Count |
|---|---|---|
| TesA_P_Domains_without_Signal_Peptide | | 0 |
| EColi_1J00 | | 0 |
| EColi_1JRL | | 0 |
| EColi_O157_NP_286243 | | 0 |
| Shigella_boydii_Sb227_YP_406934 | | 0 |
| EColi_O157_ZP_02799578 | | 0 |
| EColid_ZP_02902430 | | 0 |
| EColi_ZP_03081449 | | 0 |
| Shigella_dysenteriae_YP_402105 | | 0 |
| Citrobacter_koseri_YP_001454190 | | 0 |
| marine_metagenome_ECJ13936 | | 0 |
| ABH77568_Sequence_7411_from_patent | LKDKPDMPGSQRGAGLFIKRVEGLADQVHFPTAAIVQTGENGQQRGLTGTGFTNQGDGFGTFDNE | 65 |
| Enterobacter_cancerogenus_ZP_03281441 | | 0 |
| AAR53009_Sequence_12726_from_patent | LDVLQGVERRDQHKRLKNKTNVLRPQRRPRLFIHPVQRFAQHRYFPAAAIVEAGEDRQQGRFTGTRLADQGDGLPRFDNQ | 240 |
| Enterobacter_YP_001175703 | | 0 |
| Klebsiella_pneumoniae_YP_001334153 | | 0 |
| Klebsiella_pneumoniae_YP_002240008 | | 0 |
| Salmonella_enterica_NP_455101 | | 0 |
| Salmonella_typhimurium_NP_459501 | | 0 |
| Salmonella_enterica_YP_002225613 | | 0 |
| Salmonella_enterica_YP_215534 | | 0 |
| Salmonella_enterica_ZP_02344720 | | 0 |
| Salmonella_enterica_Zp_02683026 | | 0 |
| Salmonella_enterica_ZP_03163359 | | 0 |
| Salmonella_enterica_ZP_03221362 | | 0 |
| Salmonella_enterica_YP_001571431 | | 0 |
| Klebsiella_ACC78298 | MQRFAQHRYFPAAAIVQAGEDRQQGRFTGARLADQGDGLPRFDNQ | 45 |
| Enterobacter_sakazakii_Yp_001438839 | | 0 |
| Pectobacterium_atrosepticum_YP_049328 | | 0 |
| Erwinia_tasmaniensis_YP_001908369 | | 0 |
| Yersinia_pestis_ZP_02223456 | | 0 |
| Yersinia_pestis_C092_NP_406570 | | 0 |
| Yersinia_pestis_KIM_NP_668426 | | 0 |
| Yersinia_pseudotuberculosis_YP_00140198 | | 0 |
| Serratia_proteamaculans_YP_001477389 | | 0 |
| Yersinia_pestis_Angola_YP_001605806 | | 0 |

FIG. 47 (Cont.)

```
TesA_P_Domains_without_Signal_Peptide    --------------------------------------------ADTLLILGDSLSAGYRMSA    19
EColi_1J00                               --------------------------------------------ADTLLILGDSLSAGYRMSA    19
EColi_1JRL                               --------------------------------------------ADTLLILGDXLSAGYRMSA    19
EColi_0157_NP_286243                     ------------------MMNFNNVFR-----WHLPFLFLVLLTFRAAAADTLLILGDSLSAGYRMSA    45
EColi_0157_Sb227_YP_406934               ------------------MMNFNNVFR-----WHLPFLFLVLLTFRAAAADTLLILGNSLSAGYRMSA    45
Shigella_boydii_Sb227_YP_406934          ------------------MNFNNVFR------WHLPFLFLVLLTFRAAAADTLLILGDSLSAGYRMSA    44
EColi_0157_ZP_02799578                   ------------------MNFNNVFR------WHLPFLFLVLLTFRAAAADTLLILGDSLSAGYRMSA    44
EColid_ZP_02902430                       ------------------MNFNNVFR------WHLPFLFLVLLTFRAAAADTLLILGDSLSAGYRMSA    44
EColid_ZP_03081449                       ------------------MPFLFLVLLTFRAAAADTLLILGDSLSAGYRMSA    34
Shigella_dysenteriae_YP_402105           ------------------MMNFNNVFR-----WHLPFLFLVLLTFRAAAADTLLILGDSLSAGYRMSA    45
Citrobacter_koseri_YP_001454190          ------------------MPFLFLVLLTFRAAAADTLLILGDSLSAGYRMSA    34
marine_metagenome_ECJ13936               ------VLPLTDGLLKMMNFNNVFR-------WHLPIFLIFTCRAAAADTLLILGDSLSAGYRMSA    55
ABH77568_Sequence_7411_from_patent       FNSGEDGKLVFPLTDRLLKTMNFNNVFR----WHLPFLFLMLMTFRAAAADTLLILGDSLSAGYRWAA    129
Enterobacter_cancerogenus_ZP_03281441    ------------------MPFLFLILLTFRAMAADTLLILGDSLSAGYRWAA    34
AAR53009_Sequence_12726_from_patent      ------------------MHVPFLLLFLFTCRAMAADTLLILGDSLSAGYRWAA    304
Enterobacter_YP_001175703                ------------------LNSGKDGELMLPLTDGLLKMMNFKYVFR-----WHLPFLFLFLFTCRAMAADTLVLGDSLSAGYRWAA    45
Klebsiella_pneumoniae_YP_001334153       ------------------MPFLLLFLFLFTCRAMAADTLLILGDSLSAGYRWAA    34
Klebsiella_pneumoniaP_YP_002240008       ------------------MNFKYVFR------WVPFLLFLFLILLTFRAAAADTLLILGDSLSAGYRWAA    44
Salmonella_enterica_NP_455101            ------------------MNFNTVFR------WHLPFLFLILILLTFRAAAADTLLILGDSLSAGYRMTA    44
Salmonella_typhimurium_NP_459501         ------------------MNFNTVFR------WHLPFLFLILILLTFRAAAADTLLILGDSLSAGYRWAA    44
Salmonella_enterica_YP_002225613         ------------------MNFNTVFR------WHLPFLFLILILLTFRAAAADTLLILGDSLSAGYRWAA    44
Salmonella_enterica_YP_215534            ------MLTLTDGLPETMNFNTVFR-------WHLPFLFLILILLTFRAAAADTLLILGDSLSAGYRWAA    55
Salmonella_enterica_ZP_02344720          ------------------MNFNTVFR------WHLPFLFLILILLTFRAAAADTLLILGDSLSAGYRWAA    44
Salmonella_enterica_ZP_02683026          ------------------MNFNTVFR------WHLPFLFLILILLTFRAAAADTLLILGDSLSAGYRWAA    44
Salmonella_enterica_ZP_03163359          ------------------MNFNTVFR------WHLPFLFLILILLTFRAAAADTLLILGDSLSAGYRWAA    44
Salmonella_enterica_ZP_03221362          ------------------MNFNTVFR------WHLPFLFLILILLTFRAAAADTLLILGDSLSAGYRWAA    44
Salmonella_enterica_YP_001571431         ------------------MPFLFLFLFLFTFRVAAADTLLILGDSLSAGYRWAA    34
Klebsiella_ACC78298                      LNSGKDGELMLPLTDGLLKMMNFKWVFR----WHVPFLFLFLFTCLLALLSFRAAAADTLVLGDSLSAGYRWAA    109
Enterobacter_sakazakii_YP_001438839      ------MFPLTDGFIKMMNFKWVFR-------WHFPFLLLALLSFRAAAADTLVLGDSLSAGYRWAA    55
Pectobacterium_atrosepticum_YP_049328    MMNFKWFYVRSFAWRSTRWAGLRKHVFVLLLLGLCSVRAFAADTLLILGDSLSAGYQMPA    61
Erwinia_tasmaniensis_YP_001908369        ------------------MAFMTLRAAAADTLVLGDSLSAGYRWAA    29
Yersinia_pestis_ZP_02223456              ------------------MRAAATDTLLIIGDSLSAGYRLPI    24
Yersinia_pestis_C092_NP_406570           ------MMNFKWF--------RWHLPFLLLGLFSLRAAATDTLLILGDSLSAGYRLPI    46
Yersinia_pestis_KIM_NP_668426            ------MLTLTDVLIKMMNFKWF-RWHLPFLLLGLFSLRAAATDTLLILGDSLSAGYRLPI    56
Yersinia_pseudotuberculosis_YP_00140198  ------------------MNFKWF-RWHLPFLLLGLFSLRAAATDTLLILGDSLSAGYRLPI    45
Serratia_proteamaculans_YP_001477389     ------------------MGLFSLRAVAADTLLILGDSLSAGYRLPV    29
Yersinia_pestis_Angola_YP_001605806      ------MLIKMMNFKWF---RWHLPFLLLGLFSLRAAATDTLLILGDSLSAGYRLPI    50
                                                                                         10
```

FIG. 47 (Cont.)

```
                                              100       110       120       130       140       150       160       170
                                              +---------+---------+---------+---------+---------+---------+---------+
TesA_P_Domains_without_Signal_Peptide         AANAEPLLMQIRLPANYGRRYNEAFSAIYPKLAKEFDVPLLPFFMEEVYLKPQWMQDDGIHPNRDAQPFIADMMAKQLQP   176
EColi_1J00                                    AANAEPLLMQIRLPANYGRRYNEAFSAIYPKLAKEFDVPLLPFFMEEVYLKPQWMQDDGIHPNRDAQPFIADMMAKQLQP   176
EColi_1JRL                                    AANAEPLLMQIRPPANYGRRYNEAFSAIYPKLAKEFDVPLLPFFMEEVYLKPQWMQDDGIHPNRDAQPFIADMMAKQLQP   176
EColi_O157_NP_286243                          AANAEPLLMQIRLPANYGRRYNEAFSAIYPKLAKEFDVPLLPFFMEEVYLKPQWMQDDGIHPNRDAQPFIADMMAKQLQP   202
Shigella_boydii_Sb227_YP_406934               AANAEPLLMQIRLPANYGRRYNEAFSAIYPKLAKEFDVPLLPFLMEEVYLKPQWMQDDGIHPNRDAQPFIADMMAKQLQP   202
EColi_O157_ZP_02799578                        AANAEPLLMQIRLPANYGRRYNEAFSAIYPKLAKEFDVPLLPFLMEEVYLKPQWMQDDGIHPNRDAQPFIADMMAKQLQP   201
EColid_ZP_02902430                            AANAEPLLMQIRLPANYGRRYNEAFSAIYPKLAKEFDIPLLPFFMEEVYLKPQWMQDDGIHPNRDAQPFIADMMAKQLQP   201
EColi_ZP_03081449                             ADNAEPLLMQIRLPANYGRRYNEAFSAIYPKLAKEFDVPLLPFFMEEVYLKPQWMQDDGIHPNRDAQPFIADMMAKQLQP   191
Shigella_dysenteriae_YP_402105                AANAEPLLMQIRLPANYGRRYNETFSALYPKLAKEFDIPLLPFFMEEVYLKPQWMQDDGIHPNRDAQPFIADMMAKQLQP   202
Citrobacter_koseri_YP_001454190               AANAEPLLMQIRLPANYGRRYNETFSAIYPKLAKEFDIPLLPFFMEEVYLKPQWMQDDGIHPNRDAQPFIADMMAQQLTP   191
marine_metagenome_ECJ13936                    TANAEPLLMQIHLPANYGRRYNEAFSAIYPKLAKEFDIPLLPFFMEEVYLKPQWMQDDGIHPNRDAQPFIADMMAKQLSP   212
ABH77568_Sequence_7411_from_patent            AADAQPLLMQIHLPANYGRRYNEAFSAIYPKLAKEFDIPLLPFFMEEVYLKPQMMQDDGIHPNRDAQPFIADMMATRLAP   286
Enterobacter_cancerogenus_ZP_03281441         AANAQPLLMQIHLPANYGRRYNEAFGAIYPALAKEFAIPLLPFFMEEVYLKPQMMQDDGIHPNRDAQPFIADMMATRLAP   191
AAR53009_Sequence_12726_from_patent           AANAEPLLMQIHLPANYGRRYNESFSAIYPKLAKEFDIPLLPFFMEEVYLKPQMMQDDGIHPNRDAQPFIADMMAKRLAP   461
Enterobacter_YP_001175703                     AANAQPLLMQIHLPANYGRRYNESFSAIYPKLAKEFDIPLLPFFMEEVYLKPQMMQDDGIHPNRDAQPFIADMMATRLAP   202
Klebsiella_pneumoniae_YP_001334153            AANAEPLLMQIHLPANYGRRYNEAFGAIYPALAKEFAIPLLPFFMEEVYLKPQMMQDDGIHPNRDAQPFIADMMAKRLAP   191
Klebsiella_pneumoniae_YP_002240008            AADAQPLLMQIHLPANYGRRYNEAFGAIYPALAKEFAIPLLPFFMKEVYLKPQMMQDDGIHPNRDAQPFIADMMANRLAP   201
Salmonella_enterica_NP_455101                 AADAQPLLMQIHLPANYGRRYNESFSAIYPKLAKEFDIPLLPFFMEEVYLKPQMMQDDGIHPNRDAQPFIADMMAKQLTP   201
Salmonella_typhimutium_NP_459501              AADAQPLLMQIHLPANYGRRYNESFSAIYPKLAKEFDIPLLPFFMEEVYLKPQMMQDDGIHPNRDAQPFIADMMAKQLTP   201
Salmonella_enterica_YP_002225613              AADAQPLLMQIHLPANYGRRYNESFSAIYPKLAKEFDIPLLPFFMEEIYLKPQMMQDDGIHPNRDAQPFIADMMAKQLTP   212
Salmonella_enterica_YP_215534                 AADAQPLLMQIHLPANYGRRYNESFSAIYPKLAKEFDIPLLPFFMEEVYLKPQMMQDDGIHPNRDAQPFIADMMAKQLTP   201
Salmonella_enterica_ZP_02344720               AADAQPLLMQIHLPANYGRRYNESFSAIYPKLAKKFDIPLLPFFMEEVYLKPQMMQDDGIHPNRDAQPFIADMMAKQLTP   201
Salmonella_enterica_ZP_02683026               AADAQPLLMQIHLPANYGRRYNESFSAIYPKLAKEFDIPLLPFFMEEVYLKPQMMQDDGIHPNRDAQPFIADMMAKQLTP   201
Salmonella_enterica_ZP_03163359               AADAQPLLMQIHLPANYGRRYNESFSAIYLKLAKEFDIPLLPFFMEEVYLKPQMMQDDGIHPNHDAQPFIADMMAKQLTP   201
Salmonella_enterica_ZP_03221362               AADAQPLLMQIHLPANYGRRYNESFSAIYPKLAKEFDIPLLPFFMEEVYLKPQMMQDDGIHPNRDAQPFIADMMAKQLTP   201
Salmonella_enterica_YP_001571431              AANAQPLLMQIHLPANYGRRYNEAFGAIYPALAKEFAIPLLPFFMEEVYLKPQRMEEDGIHPNRDAQPNIAAWMENRLAP   191
Klebsiella_ACC78298                           TAGAEPLLMQIRIPANYGRRYNQAFEAIYPELAQSFSIPLLPFFMEEVYLKPQWMQDDGIHPNRDAQPFIADMMAQRLAP   266
Enterobacter_sakazakii_YP_001438839           QANAKPLLMQVRLPTNYGRRYTESFSNIYPKLAEQFALPLLPFFMEQVYLPEWIMEDGIHPTRDAQPFIAEMMAKQLEP   213
Pectobacterium_atrosepticum_YP_049328         AAKAQPLLMQVRLPANYGKRYTDSFAAIYPKLVPFFMEQVYLPEMQDDGIHPNPSAQPFIADLMAKQLAP           221
Erwinia_tasmaniensis_YP_001908369             AAKAQPLLMQIRIPPNYGRRYTDAFTAIYPQLAQQFDIPLLPFFMEQVAVKPEMMQDDGAQPFIADMMAQQLKP       186
Yersinia_pestis_ZP_02223456                   AAKAQPLLMQIRIPPNYGRRYTDAFTAIYPQLAQQFDIPLLPFFMEQVAVKPEMMQDDGLHPNGDAQPFIADMMAQQLKP   184
Yersinia_pestis_CO92_NP_406570                AAKAQPLLMQIRIPPNYGRRYTDAFTAIYPQLAQQFDIPLLPFFMEQVAVKPEMMQDDGLHPNGDAQPFIADMMAQQLKP   206
Yersinia_pestis_KIM_NP_668426                 AAKAQPLLMQIRIPPNYGRRYTDAFTAIYPQLAQQFDIPLLPFFMEQVVKAEMMQDDGLHPNKDAQPFIATWMAERLEP   216
Yersinia_pseudotuberculosis_YP_001140198      AAKAQPLLMQIRIPPNYGRRYTEAFSAIYPQLAKQFDIPLLPFYMEQVAVKPEMMQDDGLHPNGDAQPFIATWMAERLEP   205
Serratia_proteamaculans_YP_001477389          QAGAQPLLMQIRIPPNYGRRYTDAFTAIYPQLAQQFDIPLLPFFMEQVAVKPEMMQDDGLHPNGDAQPFIADMMAQQLKP   189
Yersinia_pestis_Angola_YP_001605806           AAKAQPLLMQIRIPPNYGRRYTDAFTAIYPQLAQQFDIPLLPFFMEQVAVKPEMMQDDGLHPNGDAQPFIADMMAQQLKP   210
```

FIG. 55

| Residue | Mutation | Sequence alignment near region of interest |
|---------|----------|-------------------------------------------|
| A1 | A1S | |

```
                                          1         10
E.coli_TesA_1U8U                          ADTLLILGDSLSA
gi|156977016|ref|YP_001447923.1           SEKLLVLGDSLSA
gi|209809090|ref|YP_002264628.1           SQTLLILGDSLSA
gi|59714227|ref|YP_207002.1               SQTLLILGDSLSA
gi|197337441|ref|YP_002158710.1           SQTLLILGDSLSA
gi|125620500|gb|EAZ48871.1                SKTLLVLGDSLSA
gi|15601538|ref|NP_233169.1               SKTLLVLGDSLSA
gi|121588086|ref|ZP_01677835.1            SKTLLVLGDSLSA
gi|153827484|ref|ZP_01980151.1            SKTLLVLGDSLSA
gi|163800656|ref|ZP_02194557.1            SEKLLVLGDSLSA
gi|91226151|ref|ZP_01261041.1             SEKLLVLGDSLSA
gi|28900726|ref|ZP_800381.1               SEKLLVLGDSLSA
gi|729449|sp|Q07792.1|ESTE_VIBMI          SEKLLVLGDSLSA
gi|90579358|ref|ZP_01235168.1             SQTLLVLGDSLSA
gi|89072709|ref|ZP_01159274.1             SQTLLVLGDSLSA
gi|78484894|ref|YP_390819.1               SQNLLVLGDSLSA
gi|94500900|ref|ZP_01307426.1             SDKILVLGDSLSA
gi|187478460|ref|YP_786484.1              SHTILVVGDSLSA
```

FIG. 55 Cont.

| | | | |
|---|---|---|---|
| L7 | | gi\|134094953\|ref\|YP_001100028.1 | SKTILVLGDSLSA |
| | | gi\|152980543\|ref\|YP_001353227.1 | SKTIVVLGDSLSA |
| | | gi\|86143029\|ref\|ZP_01061451.1 | SNSILFFGDSLTA |
| | L7V, L7M | E.coli_TesA_1U8U | ADTLLILGDSLSAGYRMS |
| | | gi\|54309970\|ref\|YP_130990.1 | GNTLLVVGDSLSAGYQMR |
| | | gi\|148548695\|ref\|YP_001268761.1 | AGTLLVVGDSISAGFGLD |
| | | gi\|90412817\|ref\|ZP_01220817.1 | GNTLLVVGDSLSAGYQMR |
| | | gi\|88859908\|ref\|ZP_01134547.1 | ---TILIVGDSLSAAYGLK |
| | | gi\|88703495\|ref\|ZP_01101211.1 | ---ILVVGDSISAAYGMS |
| | | gi\|192359766\|ref\|YP_001982095.1 | ---ILVVGDSLSAAYGID |
| | | gi\|163856534\|ref\|YP_001630831.1 | ---TLLVVGDSLSAEYGLA |
| | | gi\|187478460\|ref\|YP_786484.1 | SHTILVVGDSLSAEYGLK |
| | | gi\|33597579\|ref\|NP_885222.1 | --AVLVVGDSLSAEYGLR |
| | | gi\|33592804\|ref\|NP_880448.1 | --AVLVVGDSLSAEYGLR |
| | | gi\|121604790\|ref\|YP_982119.1 | --TVLIVGDSLSAEYGLK |
| | | gi\|91788891\|ref\|YP_549843.1 | ---TILIVGDSLSAEYGLK |
| | | gi\|124267005\|ref\|YP_001021009.1 | ---ILVVGDSLSAEYGLQ |
| | | gi\|171058584\|ref\|YP_001790933.1 | ---ILVVGDSLSAEYGLP |
| | | gi\|146220121\|gb\|ABQ11275.1 | AKTILVVGDSLSAEYGLA |
| | | gi\|121594614\|ref\|YP_986510.1 | APVILVVGDSLSAEYGLP |
| | | gi\|120611683\|ref\|YP_971361.1 | --VVLVVGDSLSAEYGIA |

FIG. 55 Cont.

| | | |
|---|---|---|
| | gi\|198263408\|gb\|EDY87686.1 | ---NLLIVGDSLSAAYGIA |
| | gi\|149377045\|ref\|ZP_01894796.1 | ----MIVGDSLSAAYGVQ |
| | gi\|92114738\|ref\|YP_574666.1 | ADTLLIVGDSLSAAHGIE |
| | gi\|153874618\|ref\|ZP_02002768.1 | --TLLIVGDSLSAAYGIA |
| | gi\|212241630\|ref\|NP_641185.1 | ---ILVVGDSLSAAHNIP |
| | gi\|78046442\|ref\|NP_362617.1 | ---VLVVGDSLSAAHNIP |
| | gi\|188992969\|ref\|YP_001904979.1 | AAPILVVGDSLSAAHNIP |
| | gi\|212230252\|ref\|NP_636169.1 | AAPILVVGDSLSAAHNIP |
| | gi\|166710711\|ref\|ZP_02241918.1 | ---ILVVGDSLSAAHNIP |
| | gi\|58583387\|ref\|YP_202403.1 | ---ILVVGDSLSAAHNIP |
| | gi\|152996229\|ref\|ZP_001341064.1 | ASTLLVMGDSLSAAYNLR |
| | gi\|71908327\|ref\|YP_285914.1 | AKTILIMGDSLSAGYGIR |
| | gi\|149928382\|ref\|ZP_01916622.1 | ---ILVMGDSLSAAYGLP |
| | gi\|126667344\|ref\|ZP_01738317.1 | ANTLLVMGDSLSAAYGVP |
| | | 1          10 |
| D9 | E.coli_TesA_1U8U | ADTLLILGDSLSAGYRMS |
| D9N | gi\|82542988\|ref\|YP_406934.1 | ADTLLILGNSLSAGYRMS |
| | gi\|193215472\|ref\|YP_001996671.1 | --TILFFGNSITAGMGLR |

FIG. 55 Cont.

| G14 | G14S | | 1 | 10 | 20 | |
|---|---|---|---|---|---|---|
| | | E.coli_TesA_1U8U | ADTLLILGDSLSAGYRMSASAAWP |
| | | gi\|149907876\|ref\|ZP_018896544.1 | ----ILLLGDSLSASYGMTQNEGWV |
| | | gi\|120598433\|ref\|YP_963007.1 | AAKVLILGDSLGASYGMSEQLGWV |
| | | gi\|124550111\|ref\|ZP_017707934.1 | AAKVLILGDSLGASYGMSEQLGWV |
| | | gi\|126174896\|ref\|ZP_001051045.1 | AAKVLILGDSLGASYGMAEQSGWV |
| | | gi\|160875896\|ref\|YP_001555212.1 | AAKVLILGDSLGASYGMAEQSGWV |
| | | gi\|153001225\|ref\|YP_001366906.1 | AAKVLILGDSLGASYGMAEQSGWV |
| | | gi\|149117668\|ref\|ZP_018443431 | AAKVLILGDSLGASYGMSEQLGWV |
| | | gi\|24374455\|ref\|NP_718498.1 | AAKVLILGDSLGASYGMSEQVGWV |
| | | gi\|179199985\|ref\|YP_869177.1 | AAKVLILGDSLGASYGMSEQIGWV |
| | | gi\|114047048\|ref\|YP_737598.1 | AAKVLILGDSLGASYGMSEQLGWV |
| | | gi\|139969820\|ref\|YP_733613.1 | AETILILGDSLSASYGMEENQGWI |
| | | gi\|119774622\|ref\|YP_927362.1 | ANPILILGDSLSASYGMEQDQGWV |
| | | gi\|60893017\|gb\|AAX37297.1 | ANPILILGDSLSASYGMEQDQGWV |
| | | gi\|127513331\|ref\|YP_001094528.1 | AAPILILGDSLSASYGMPENEGWV |
| | | gi\|212634759\|ref\|YP_002311284.1 | AAPILILGDSLSASYGMPEDQGWV |
| | | gi\|167624526\|ref\|YP_001674820.1 | AAPILILGDSLSASYGMPEDQGWV |
| | | gi\|157961485\|ref\|YP_001501519.1 | AAPILILGDSLSASYGMPEDQGWV |
| | | gi\|170727240\|ref\|YP_001761266.1 | AAPILILGDSLSASYGVDEDQGWV |
| | | gi\|157374835\|ref\|YP_001473435.1 | AAPILILGDSLSASYGVDEDKGWV |
| | | gi\|163749678\|ref\|ZP_02156924.1 | AAPLILILGDSLSASYGIDEDKGWV |

FIG. 55 Cont.

| R16 | R16G | | |
|---|---|---|---|
| | gi\|77163958\|ref\|YP_342483.1 | | ---ILILGDSLSASYGLSLEQGWV |
| | gi\|207088375\|gb\|EDZ65647.1 | | ---ILILGDSLSASYGLSLEQGWV |
| | | | 1      10      20 |
| | E.coli_TesA_1U8U | | ADTLLILGDSLSAGYRMSAS |
| | gi\|148548659\|ref\|YP_001268761.1 | | AGTLLVVGDSISAGFGLDSR |
| | gi\|114772942\|ref\|ZP_01450253.1 | | ---TVLILGDSLSAAYGLIQE |
| | gi\|109899221\|ref\|YP_662476.1 | | ---LLILGDSLSAGYGLTQA |
| | gi\|196157105\|ref\|YP_002126594.1 | | ---VLLILGDSLSAAYGLQQH |
| | gi\|71280033\|ref\|YP_269028.1 | | -DKILLIGDSLSAGYGLEQA |
| | gi\|88859908\|ref\|ZP_01134547.1 | | -TILIVGDSLSAAYGLKQS |
| | gi\|77360818\|ref\|YP_340393.1 | | -NTILILGDSLSAAYGLKQE |
| | gi\|194472458\|ref\|ZP_01614557.1 | | -NTILILGDSLSAAYGLQQE |
| | gi\|194369063\|ref\|ABF57909.2 | | -NTILILGDSLSAAYGLQQE |
| | gi\|149907876\|ref\|ZP_01896544.1 | | ---ILLLGDSLSASYGMTQN |
| | gi\|120598433\|ref\|YP_963007.1 | | AAKVLILGDSLGASYGMSEQ |
| | gi\|124550111\|ref\|ZP_01707934.1 | | AAKVLILGDSLGASYGMAEQ |
| | gi\|126174896\|ref\|YP_001051045.1 | | AAKVLILGDSLGASYGMAEQ |
| | gi\|160875896\|ref\|YP_001555212.1 | | AAKVLILGDSLGASYGMAEQ |
| | gi\|153001225\|ref\|YP_001366906.1 | | AAKVLILGDSLGASYGMAEQ |
| | gi\|149117668\|ref\|ZP_01844343.1 | | AAKVLILGDSLGASYGMAEQ |
| | gi\|243744555\|ref\|NP_718498.1 | | AAKVLILGDSLGASYGMSEQ |
| | gi\|179199985\|ref\|YP_869177.1 | | AAKVLILGDSLGASYGMSEQ |

FIG. 55 Cont.

| | |
|---|---|
| gi\|114047048\|ref\|YP_737598.1 | AAKVLILGDSLGASYGMSEQ |
| gi\|139969820\|ref\|YP_733613.1 | AAKVLILGDSLGASYGMSEQ |
| gi\|91793720\|ref\|YP_563371.1 | AATILVLGDSLSAGYGIDEH |
| gi\|114563734\|ref\|YP_751247.1 | AATILILGDSLSAGYGMPED |
| gi\|119774622\|ref\|YP_927362.1 | AETILILGDSLSASYGMEEN |
| gi\|60893017\|gb\|AAX37297.1 | ANPILILGDSLSASYGMEQD |
| gi\|127513331\|ref\|YP_001094528.1 | ANPILILGDSLSASYGMEQD |
| gi\|212634759\|ref\|YP_002311284.1 | AAPILILGDSLSASYGMPEN |
| gi\|167624526\|ref\|YP_001674820.1 | AAPILILGDSLSASYGMPED |
| gi\|157961485\|ref\|YP_001501519.1 | AAPILILGDSLSASYGMPED |
| gi\|170727240\|ref\|YP_001761266.1 | AAPILILGDSLSASYGVDED |
| gi\|157374835\|ref\|YP_001473435.1 | AAPILILGDSLSASYGVDED |
| gi\|163749678\|ref\|ZP_02156924.1 | AAPILILGDSLSASYGIDED |

FIG. 55 Cont.

| S20 | S20G | | |
|---|---|---|---|
| | E.coli_TesA_1U8U | GYRMSASAAWPALLND | |
| | gi\|74316704\|ref\|YP_314444.1 | GYGLAAGQGWVDRLRA | |
| | gi\|145589121\|ref\|YP_001155718.1 | EYGLSRGTGWVKLLET | |
| | gi\|30249426\|ref\|NP_841496.1 | GYGLPPGTGWVNLLER | |
| | gi\|34499190\|ref\|NP_903405.1 | GYGLAPGQGWAALLAR | |
| | gi\|119897957\|ref\|YP_933170.1 | GYGLKNGEAWPTLLQT | |
| | gi\|169182148\|ref\|ZP_02842667.1 | GYGLERGQEWPTLLQT | |
| | gi\|163856534\|ref\|YP_001630831.1 | EYGLARGTGWVPLLAR | |
| | gi\|187478460\|ref\|YP_786484.1 | EYGLKRGAGWVPLLAQ | |
| | gi\|335975791\|ref\|NP_885222.1 | EYGLRRGSGWVPMLAQ | |
| | gi\|33592804\|ref\|NP_880448.1 | EYGLRRGSGWVPLLAQ | |
| | gi\|118051335\|ref\|ZP_01519884.1 | EYGLTRGKGWVQLLQQ | |
| | gi\|121604790\|ref\|YP_982119.1 | EYGLRRGTGWVPLLEK | |
| | gi\|91788891\|ref\|YP_549843.1 | EYGLKRGTGWVPLLEK | |
| | gi\|124267005\|ref\|YP_001021009.1 | EYGLQRGSGWVALLEK | |
| | gi\|171058584\|ref\|YP_001790933.1 | EYGLPRGSGWVALLEA | |
| | gi\|146220121\|gb\|ABQ11275.1 | EYGLARGTGWVALLDQ | |
| | gi\|121594614\|ref\|YP_986510.1 | EYGLPRGTGWVALLDK | |
| | gi\|121610344\|ref\|YP_998151.1 | EYGLARGTGWVALLEQ | |
| | gi\|160899469\|ref\|YP_001565051.1 | EYGLARGTGWVALLQK | |
| | gi\|120611683\|ref\|YP_971361.1 | EYGIARGTGWVALLEK | |
| | gi\|153888470\|ref\|ZP_02009612.1 | EYGLARGTGWVALLDR | |
| | gi\|187928944\|ref\|YP_001899431.1 | GYGLAQGTGWVALLDR | |
| | gi\|175464361\|ref\|NP_519838.1 | GYGLAQGTGWVTLLGN | |

FIG. 55 Cont.

| | | |
|---|---|---|
| | gi\|207724196\|ref\|YP_002254594.1 | GYGLAQGTGWVALLGN |
| | gi\|83749049\|ref\|ZP_00946056.1 | GYGLAQGTGWVALLGN |
| | gi\|207743056\|ref\|YP_002259448.1 | GYGLAQGTGWVALLGN |
| | gi\|134094953\|ref\|YP_001100028.1 | EYGLARGEGWVNLLQK |
| | gi\|152980543\|ref\|YP_001353227.1 | EYGLARGEGWVSLLQK |
| | gi\|94310819\|ref\|YP_584029.1 | EYGIARGTGWVSLLQD |
| | gi\|73541078\|ref\|YP_295598.1 | EYGIARGSGWVSLLQQ |
| | gi\|113867511\|ref\|YP_726000.1 | EYGIARGAGWVTLLQD |
| | | 20            30 |
| A25 | | |
| A25V | E.coli_TesA_1U8U | ASAAWPALLNDKWQS |
| | gi\|543099970\|ref\|YP_130990.1 | AEQSWPVLLQPALKH |
| | gi\|90412817\|ref\|ZP_01220817.1 | AEQSWPVLLQPALKH |
| | gi\|182677824\|ref\|YP_001831970.1 | AQAAFPVVLEKALRN |
| | gi\|154245703\|ref\|YP_001416661.1 | ASAAFPVQLEAALKA |
| | gi\|115522331\|ref\|YP_779242.1 | ASGAFPVKLQKALKE |
| | gi\|211958502\|gb\|EEA93702.1 | PEDAFPVKLEKALQE |
| | gi\|83594979\|ref\|YP_428731.1 | PETAFPVQLEAALRA |
| | | 40 |
| N39 | | |
| N39A | E.coli_TesA_1U8U | SKTSVVNASISGDTS |
| | gi\|167645243\|ref\|YP_001682906.1 | VLAKVRAAGVSGDTS |
| | | 40            50 |
| I42 | | |
| I42S | E.coli_TesA_1U8U | |

FIG. 55 Cont.

| | | | |
|---|---|---|---|
| D45 | | gi\|149200040\|ref\|ZP_01877066.1 | SVVNASISGDTSQQGL<br>KVINAGSSGSTSAGGM<br>    40        50 |
| | D45Q,<br>D45S,<br>D45A | E.coli_TesA_1U8U<br>gi\|71280033\|ref\|YP_269028.1<br>gi\|88859908\|ref\|ZP_01134547.1<br>gi\|94500900\|ref\|ZP_01307426.1<br>gi\|90023084\|ref\|YP_528911.1<br>gi\|91762028\|ref\|ZP_01263993.1<br>gi\|71083551\|ref\|YP_266270.1<br>gi\|42521961\|ref\|NP_967341.1<br>gi\|149200040\|ref\|ZP_01877066.1 | NASISGDDTSQQGLAR<br>NTAISGQTTDNALLK<br>NVSVSGQTTGNALLT<br>NASISGQTTSEGLRQ<br>NASISGATTNAGLQR<br>DGSVSGSTSAGGLNR<br>DGSVSGSTSAGGLNR<br>NAGVSGSTTASGLSR<br>NAGSSGSTSAGGMSK |
| Q48 | | |     40        50 |
| | Q48W | E.coli_TesA_1U8U<br>gi\|82703094\|ref\|YP_412660.1 | NASISGDTSQQGLARLP<br>NNSISGETAWGGRNRIE |
| Q49 | | |     40        50 |
| | Q49A,<br>Q49G,<br>Q49D,<br>Q49S | E.coli_TesA_1U8U<br>gi\|148548659\|ref\|YP_001268761.1<br>gi\|114772924\|ref\|ZP_01450253.1<br>gi\|109899221\|ref\|YP_662476.1<br>gi\|196157105\|ref\|YP_002126594.1<br>gi\|77360818\|ref\|YP_340393.1 | ASISGDTSQGLARLPA<br>ASISGDTSAGGQARLPA<br>ASISGETTDGGLARLAR<br>AAISGETTDGALARLPR<br>AAVSGETTDGGLARFPR<br>ASISGETTGGALRRVDA |

FIG. 55 Cont.

| Accession | Sequence |
|---|---|
| gi\|119472458\|ref\|ZP_01614557.1 | ASISGETSGGALRRLDA |
| gi\|194369063\|gb\|ABF57909.2 | ASISGETSGGALRRLDA |
| gi\|149907876\|ref\|ZP_01896544.1 | ASISGETTAGGLSRLPG |
| gi\|120598433\|ref\|YP_963007.1 | GSVSGETTAGGLRRLPA |
| gi\|124550111\|ref\|ZP_01707934.1 | GSVSGETTAGGLRRLPA |
| gi\|126174896\|ref\|YP_001051045.1 | GSVSGETTAGGLRRLPA |
| gi\|160875896\|ref\|YP_001555212.1 | GSVSGETTAGGLRRLPA |
| gi\|153001225\|ref\|YP_001366906.1 | GSVSGETTAGGLRRLPA |
| gi\|149117668\|ref\|ZP_01844343.1 | GSVSGETTAGGLRRLPA |
| gi\|24374455\|ref\|NP_718498.1 | GSVSGETTAGGLRRLPA |
| gi\|117919985\|ref\|YP_869177.1 | GSVSGETTAGGLRRLPA |
| gi\|114047048\|ref\|YP_737598.1 | GSVSGETTAGGLRRLPA |
| gi\|139969820\|ref\|YP_733613.1 | GSVSGETTAGGLRRLPA |
| gi\|91793720\|ref\|YP_563371.1 | GSVSGETTAGALRRLPS |
| gi\|114563734\|ref\|YP_751247.1 | GSVSGETTAGGLRRLPS |
| gi\|119774622\|ref\|YP_927362.1 | AAVSGETSAGGLRRLPA |
| gi\|60893017\|gb\|AAX37297.1 | GSVSGETSAGGLRRLPG |
| gi\|127513331\|ref\|YP_001094528.1 | GSVSGETSAGGLRRLPA |
| gi\|425221961\|ref\|NP_967341.1 | AGLSGETTASGLSRMKW |
| gi\|88806192\|ref\|ZP_01121710.1 | AGLSGETTASGANRLDW |
| gi\|166220953\|ref\|YP_823109.1 | MGVSGDTTQDGLARLSM |
| gi\|162147014\|ref\|YP_001601475.1 | GGVSGDTSADALARLDW |
| gi\|90023084\|ref\|YP_528911.1 | ASISGATTNAGLQRMPA |
| gi\|85710420\|ref\|ZP_01041484.1 | AGVSGDTSAAGRDRLEF |
| gi\|94497924\|ref\|ZP_01304489.1 | AGVSGDTTAGRARLAF |
| gi\|103486193\|ref\|YP_615754.1 | AGVSGDTSAAGRQRLTY |

FIG. 55 Cont.

| G50 | G50A, G50T, G50L | | |
|---|---|---|---|
| | E.coli_TesA_1U8U | DTSQQGLARLPAL | |
| | gi\|109899221\|ref\|YP_662476.1 | ETTDGALARLPRL | |
| | gi\|71280033\|ref\|YP_269028.1 | QTTDNALLKIDAW | |
| | gi\|88859908\|ref\|ZP_01134547.1 | QTTGNALLTLNEH | |
| | gi\|77360818\|ref\|YP_340393.1 | ETTGGALRRVDAL | |
| | gi\|119472458\|ref\|ZP_01614557.1 | ETSGGALRRLDAL | |
| | gi\|194369063\|gb\|ABF57909.2 | ETSGGALRRLDAL | |
| | gi\|119475890\|ref\|ZP_01616242.1 | ETTDGALSRLPTL | |
| | gi\|207724196\|ref\|YP_002254594.1 | DTTAGARARLPAV | |
| | gi\|114321556\|ref\|YP_743239.1 | DTTRQALNRLAPL | |
| | gi\|77163958\|ref\|YP_342483.1 | ETTRGALARLDSL | |
| | gi\|207088375\|gb\|EDZ65647.1 | ETTRGALARLDSL | |
| | gi\|194364429\|ref\|YP_002027039.1 | ETTAGALTRLPGL | |
| | gi\|190572845\|ref\|YP_001970690.1 | ETTAGALTRLPAL | |
| | gi\|21241603\|ref\|NP_641185.1 | ETTSGALTRLPGL | |
| | gi\|78046442\|ref\|YP_362617.1 | ETTSGALTRLPGL | |
| | gi\|188992969\|ref\|YP_001904979.1 | ETTSGALTRLPGL | |
| | gi\|212230252\|ref\|NP_636169.1 | ETTSGALTRLPGL | |
| | gi\|166710711\|ref\|ZP_02241918.1 | ETTSGALTRLPGL | |
| | gi\|58583387\|ref\|YP_202403.1 | ETTSGALTRLPGL | |
| | gi\|188575357\|ref\|YP_001912286.1 | ETTSGALTRLPGL | |
| | gi\|15029382\|gb\|AAK81865.1\|AF395191_1 | ETTSGALARLPKL | |
| | gi\|500084257\|ref\|YP_045767.1 | ETTSGALARLPKL | |
| | gi\|169796818\|ref\|YP_001714611.1 | ETTSGALARLPKL | |

FIG. 55 Cont.

| | | | |
|---|---|---|---|
| | | gi\|126641035\|ref\|YP_001084019.1 | ETTSGALARLPKL |
| | | gi\|193076712\|gb\|ABO11417.2 | ETTSGALARLPKL |
| | | gi\|169633925\|ref\|YP_001707661.1 | ETTSGALARLPKL |
| | | gi\|184157266\|ref\|YP_001845605.1 | ETTSGALARLPKL |
| | | gi\|51243931\|ref\|YP_063815.1 | EVSAQTLARASDI |
| | | gi\|148651904\|ref\|YP_001278997.1 | ETSTGLVNRLDWV |
| | | gi\|71066667\|ref\|YP_265394.1 | ETSTGLVNRLDWV |
| | | gi\|93007258\|ref\|YP_581695.1 | ETSTGLVNRLDWV |
| E69 | E69Q | | 70 |
| | | E.coli_TesA_1U8U | PRWVLVELGGNDGLR |
| | | gi\|121998847\|ref\|YP_0010036341 | PEIVLLQLGGNDGLR |
| | | gi\|114321556\|ref\|YP_743239.1 | PEVLVVQLGGNDGLR |
| L70 | L70T | | 70 |
| | | E.coli_TesA_1U8U | RWVLVELGGNDGLRG |
| | | gi\|51243931\|ref\|YP_063815.1 | DIVILETGANDGLRG |
| | | gi\|39997510\|ref\|NP_953461.1 | DIVILVTGANDGLRG |
| | | gi\|148651904\|ref\|YP_001278997.1 | DITILTTGANDAMRG |
| G72 | G72A | | 70 |
| | | E.coli_TesA_1U8U | VLVELGGNDGLRGF |
| | | gi\|156977016\|ref\|YP_001447923.1 | VLIELGANDGLRGF |
| | | gi\|54309970\|ref\|YP_130990.1 | VIIELGANDGLRGF |
| | | gi\|37527678\|ref\|NP_931022.1 | VLIELGANDGLRGF |
| | | gi\|209809090\|ref\|YP_002264628.1 | VLIELGANDGLRGF |

FIG. 55 Cont.

| | | |
|---|---|---|
| G75 | gi\|59714227\|ref\|YP_207002.1 | VLIELGANDGLRGF |
| | gi\|197337441\|ref\|YP_002158710.1 | VLIELGANDGLRGF |
| | gi\|125620500\|gb\|EAZ48871.1 | VLIELGANDGLRGF |
| | gi\|15601538\|ref\|NP_233169.1 | VLIELGANDGLRGF |
| | gi\|121588086\|ref\|ZP_01677835.1 | VLIELGANDGLRGF |
| | gi\|153827484\|ref\|ZP_01980151.1 | VLIELGANDGLRGF |
| | gi\|163800656\|ref\|ZP_02194557.1 | VLIELGANDGLRGF |
| | gi\|91226151\|ref\|ZP_01261041.1 | VLIELGANDGLRGF |
| | gi\|28900726\|ref\|NP_800381.1 | VLIELGANDGLRGF |
| | gi\|729449\|sp\|Q07792\|ESTE_VIBMI | VIIELGANDGLRGF |
| | gi\|90412817\|ref\|ZP_01220817.1 | VLIELGANDGLRGF |
| | gi\|90579358\|ref\|ZP_01235168.1 | VLIELGANDGLRGF |
| | gi\|89072709\|ref\|ZP_01159274.1 | VLIELGANDGLRGF |
| | gi\|157369400\|ref\|YP_001477389.1 | VLIELGANDGLRGF |
| | gi\|165927624\|ref\|ZP_02223456.1 | VLIELGANDALRGF |
| | gi\|22125003\|ref\|NP_668426.1 | VLIELGANDALRGF |
| | gi\|162420602\|ref\|YP_001605806.1 | VLIELGANDALRGF |
| | gi\|153949498\|ref\|YP_001401981.1 | VLIELGANDALRGF |
| | gi\|16123257\|ref\|NP_406570.1 | VLIELGANDGLRGF |
| | gi\|77958377\|ref\|ZP_00822411.1 | VLIELGANDGLRGF |
| | | 70    80 |
| G75A | E.coli_TesA_1U8U | ELGGNDGLRGFQPQQT |
| | gi\|165927624\|ref\|ZP_02223456.1 | ELGANDALRGFPTQDI |
| | gi\|22125003\|ref\|NP_668426.1 | ELGANDALRGFPTQDI |
| | gi\|162420602\|ref\|YP_001605806.1 | ELGANDALRGFPTQDI |

FIG. 55 Cont.

| | | |
|---|---|---|
| | gi\|153949498\|ref\|YP_001401981.1 | ELGANDALRGFPTQDI |
| | gi\|16232257\|ref\|NP_406570.1 | ELGANDALRGFPTQDI |
| | gi\|74316704\|ref\|YP_314444.1 | ELGGNDALRGTPPAQI |
| | gi\|78484894\|ref\|YP_390819.1 | ELGANDALRGQSLQAT |
| | gi\|145589121\|ref\|YP_001155718.1 | ELGANDALRGLTIEQT |
| | gi\|152996229\|ref\|YP_001341064.1 | ELGANDALRGYPLDQT |
| | gi\|163856534\|ref\|YP_001630831.1 | ELGPNDALRGLSLKMT |
| | gi\|187478460\|ref\|YP_786484.1 | ELGSNDALRGLPLNMT |
| | gi\|33597579\|ref\|NP_885222.1 | ELGSNDALRGLALDMI |
| | gi\|33592804\|ref\|NP_880448.1 | ELGSNDALRGLALDMI |
| | gi\|118051335\|ref\|ZP_01519884.1 | ELGGNDALRGLALQST |
| | gi\|121604790\|ref\|YP_982119.1 | ELGGNDALRGLPLDMT |
| | gi\|91788891\|ref\|YP_549843.1 | ELGGNDALRGLPLAMT |
| | gi\|124267005\|ref\|YP_001021009.1 | ELGGNDALRGLPLAMT |
| | gi\|171058584\|ref\|YP_001170933.1 | ELGANDALRGLSLKAT |
| | gi\|146220121\|gb\|ABQ11275.1 | ELGGNDALRGLPLAST |
| | gi\|121594614\|ref\|YP_986510.1 | ELGGNDALRGLPLKSI |
| | gi\|121610344\|ref\|YP_998151.1 | ELGGNDALRGLPLQST |
| | gi\|160899469\|ref\|YP_001565051.1 | ELGGNDALRGLPLQGT |
| | gi\|120611683\|ref\|YP_971361.1 | ELGANDALRGVPLSTT |
| | gi\|186475782\|ref\|YP_001857252.1 | |
| | | 70               80 |
| L76 | E.coli_TesA_1U8U | ELGGNDGLRGFQPQQ |
| L76I, L76F, L76M | gi\|71066667\|ref\|YP_265394.1 | TIGANDAIRGIDVAT |
| | gi\|93007258\|ref\|YP_581695.1 | TIGANDAIRGIDVAT |

FIG. 55 Cont.

| | | | |
|---|---|---|---|
| | | gi\|71280033\|ref\|YP_269028.1 | ELGGNDGIRGFPVKL |
| | | gi\|78357184\|ref\|YP_388633.1 | ELGVNDTFMGLEYEE |
| | | gi\|46580334\|ref\|YP_011142.1 | ELGANDSFIGIEPDE |
| | | gi\|120602288\|ref\|YP_966688.1 | ELGANDSFIGIEPDE |
| | | gi\|148651904\|ref\|YP_001278997.1 | TTGANDAMRGIDVAT |
| | | gi\|51892159\|ref\|YP_074850.1 | ELGANDGMQARPVAE |
| | | gi\|116327860\|ref\|YP_797580.1 | ELGANDSMRGISPDQ |
| | | gi\|45657291\|ref\|YP_001377.1 | ELGANDSMRGISPDQ |
| | | gi\|24215621\|ref\|NP_712742.1 | ELGANDSMRGIFPDQ |
| R77 | R77L | | 70                80 |
| | | E.coli_TesA_1U8U | ELGGNDGLRGFQPQQT |
| | | gi\|197103612\|ref\|YP_002128989.1 | ALGGNDLLLGAEPREV |
| F79 | F79M | | 80 |
| | | E.coli_TesA_1U8U | GLRGFQPQQTEQT |
| | | gi\|90023084\|ref\|YP_528911.1 | GLQGMPVAGITRN |
| | | gi\|152988620\|ref\|YP_001347669.1 | GLRGMAPAQLQQN |
| | | gi\|116050859\|ref\|YP_790318.1 | GLRGMAPAQLQQN |
| | | gi\|107102405\|ref\|ZP_013663233.1 | GLRGMAPAQLQQN |
| | | gi\|155980552\|ref\|NP_251546.1 | GLRGMAPAQLQQN |
| | | gi\|49082664\|gb\|AAT50732.1 | GLRGMAPAQLQQN |
| | | gi\|77460235\|ref\|YP_349742.1 | GLRGMPPTQLQQN |
| Q80 | Q80S | | 80 |
| | | E.coli_TesA_1U8U | GLRGFQPQQTEQT |

FIG. 55 Cont.

| Accession | Sequence |
|---|---|
| gi\|180026282\|ref\|ZP_02997874.1 | GLQGLSVKQMENT |
| gi\|212706885\|ref\|ZP_03315013.1 | GLQGLSVEQLEIT |
| gi\|212711255\|ref\|ZP_03319383.1 | GLQGLSVEQLAIT |
| gi\|114772942\|ref\|ZP_01450253.1 | GLQGHSIKKLKNN |
| gi\|109899221\|ref\|YP_662476.1 | GLQGHSVSKMRDN |
| gi\|119774622\|ref\|YP_927362.1 | GLRGFSPTELKKN |
| gi\|60893017\|gb\|AAX37297.1 | GLRGFSPKQLKTN |
| gi\|127513331\|ref\|YP_001094528.1 | GLRGFSPKQLKNN |
| gi\|78484894\|ref\|YP_390819.1 | ALRGQSLQATQRN |
| gi\|94500900\|ref\|ZP_01307426.1 | GLRGLSISAMKSN |
| gi\|82703094\|ref\|YP_412660.1 | GLRGASIGSIRDN |
| gi\|30249426\|ref\|NP_841496.1 | GLQGRSITSIYEN |
| gi\|149928382\|ref\|ZP_01916622.1 | GLRGLSLDTMKDN |
| gi\|163856534\|ref\|YP_001630831.1 | ALRGLSLKMTEQN |
| gi\|153888470\|ref\|ZP_02009612.1 | ALRGLSLASSEGN |
| gi\|187928944\|ref\|ZP_001899431.1 | ALRGLSLASSEAN |
| gi\|175464361\|ref\|NP_519838.1 | ALRGLSLSASEAN |
| gi\|207724196\|ref\|YP_002254594.1 | ALRGLSLSASEAN |
| gi\|83749049\|ref\|ZP_00946056.1 | ALRGLSLSASEAN |
| gi\|207743056\|ref\|YP_002259448.1 | ALRGLSLAATQEN |
| gi\|134094953\|ref\|YP_001100028.1 | ALRGLSLIATQQN |
| gi\|152980543\|ref\|YP_001353227.1 | ALRGLSLQVTESN |
| gi\|735410781\|ref\|YP_295598.1 | GLRGLSLTEMRRN |
| gi\|771639581\|ref\|YP_342483.1 | |

80

| Q82 | Q82P, Q82F |
|---|---|

FIG. 55 Cont.

| | | | |
|---|---|---|---|
| Q83 | | E.coli_TesA_1U8U | GLRGFQPQQTEQTL |
| | | gi\|50120161\|ref\|YP_049328.1 | GLRGFPAPNIEQDL |
| | | gi\|89093794\|ref\|YP_011166740.1 | GLRGTPPFAIKRNL |
| | | gi\|198263408\|gb\|EDY87686.1 | GLRGFPPPITKNNL |
| | | | 80          90 |
| | Q83A | E.coli_TesA_1U8U | RGFQPQQTEQTLRQ |
| | | gi\|89093794\|ref\|ZP_01166740.1 | TGTPPFAIKRNLSR |
| | | gi\|78484894\|ref\|YP_390819.1 | RGQSLQATQRNLQT |
| | | gi\|94500900\|ref\|ZP_01307426.1 | RGLSISAMKSNLNS |
| | | gi\|146220121\|gb\|ABQ11275.1 | RGLSLKATEANLDQ |
| | | gi\|167562421\|ref\|ZP_02355337.1 | RGVPLTATESNLRE |
| | | gi\|167569605\|ref\|ZP_02362479.1 | RGVPLTATENNLRE |
| | | gi\|167893816\|ref\|ZP_02481218.1 | RGVPLAATEGNLRE |
| | | gi\|134277643\|ref\|ZP_01764358.1 | RGVPLAATEGNLRE |
| | | gi\|167738130\|ref\|ZP_02410904.1 | RGVPLAATEGNLRE |
| | | gi\|194505954\|ref\|YP_002035524.1 | RGVPLAATEGNLRE |
| | | gi\|76810223\|ref\|YP_333863.1 | RGVPLAATEGNLRE |
| | | gi\|161355201\|ref\|ZP_02101081.1 | RGVPLAATEGNLRE |
| | | gi\|167902268\|ref\|ZP_02489473.1 | RGVPLAATEGNLRE |
| | | gi\|194570836\|ref\|YP_002105836.1 | RGVPLAATEGNLRE |
| | | gi\|53719047\|ref\|YP_108033.1 | RGVPLAATEGNLRE |
| | | gi\|126453719\|ref\|YP_001066613.1 | RGVPLAATEGNLRE |
| | | gi\|126441228\|ref\|YP_001059345.1 | RGVPLAATEGNLRE |
| | | gi\|53723658\|ref\|YP_103103.1 | RGVPLAATEGNLRE |
| | | gi\|124384223\|ref\|YP_001029293.1 | RGVPLAATEGNLRE |

FIG. 55 Cont.

| | | | |
|---|---|---|---|
| Q86 | | gi\|67642011\|ref\|ZP_00440774.1 | RGVPLAATEGNLRE |
| | | gi\|167836274\|ref\|ZP_02463157.1 | RGVPLAATESNLRE |
| | | gi\|167581585\|ref\|ZP_02374459.1 | RGVPLAATESNLRE |
| | | gi\|83720994\|ref\|YP_442651.1 | RGVPLAATESNLRE |
| | | gi\|167619702\|ref\|ZP_02388333.1 | RGVPLAATESNLRE |
| | | | 80　　　　　90 |
| | Q86A, Q86T | E.coli_TesA_1U8U | FQPQQTEQTLRQI |
| | | gi\|59714227\|ref\|YP_207002.1 | FPPQKINANLEKI |
| | | gi\|197337441\|ref\|YP_002158710.1 | FPPQKINANLEEI |
| | | gi\|156934923\|ref\|YP_001438839.1 | FPPDTLSATLRKI |
| | | gi\|77360818\|ref\|YP_340393.1 | FPVSKLQANLTEL |
| | | gi\|119472458\|ref\|ZP_01614557.1 | FPVKKMQANLTSL |
| | | gi\|88703495\|ref\|ZP_01101211.1 | YPTSKLEANLSFM |
| | | gi\|90416813\|ref\|ZP_01224743.1 | QPLALMKANLQAM |
| | | gi\|171058584\|ref\|YP_001790933.1 | LPLAMTEANLLAM |
| | | gi\|146220121\|gb\|ABQ11275.1 | LSLKATEANLDQM |
| | | gi\|153888470\|ref\|ZP_02009612.1 | LSLASSEANMKAM |
| | | gi\|175464636\|ref\|NP_519838.1 | LSLSASEANLKAM |
| | | gi\|207724196\|ref\|YP_002254594.1 | LSLSASEANLKAM |
| | | gi\|83749049\|ref\|ZP_00946056.1 | LSLSASEANLKAM |
| | | gi\|207743056\|ref\|YP_002259448.1 | LSLSASEANLKAM |
| | | gi\|94310819\|ref\|YP_584029.1 | FPLQTTEANLRTI |
| | | gi\|113867511\|ref\|YP_726000.1 | LPLQTTEANLRNI |
| | | gi\|194289548\|ref\|YP_002005455.1 | LPLHTTEANLRNI |
| | | gi\|53804283\|ref\|YP_113859.1 | LPPAALKANLGAM |

FIG. 55 Cont.

| | | |
|---|---|---|
| | gi\|46580334\|ref\|YP_011142.1 | IEPDEVAANLDAI |
| | gi\|197103612\|ref\|YP_002128989.1 | AEPREVRANLDAI |
| | gi\|167645243\|ref\|YP_001682906.1 | IEPRVTKANLRAI |
| | gi\|84684212\|ref\|ZP_01012114.1 | IPLNSIEANLEQI |
| | gi\|206686219\|gb\|EDZ46701.1 | LEPQEARANLTRI |
| | gi\|206680133\|gb\|EDZ44620.1 | IDPVSSRANLESI |
| | gi\|114764037\|ref\|ZP_01443276.1 | LPPETSRANLEGI |
| | gi\|126725548\|ref\|ZP_01741390.1 | IDPQVSRANIRGI |
| | gi\|120602288\|ref\|YP_966688.1 | IEPDEVAANLDAI |
| | gi\|167624526\|ref\|YP_001674820.1 | FPPKQLKTNLTKI |
| | gi\|60893017\|gb\|AAX37297.1 | FSPKQLKTNLAEM |
| | gi\|186454892\|ref\|ZP_02965207.1 | IPVAATRTNLQTI |
| | gi\|194369063\|gb\|ABE57909.2 | FPVKKMQTNLTAL |
| T87 | T87H | |
| | | 90 |
| | E.coli_TesA_1U8U | QTEQTLRQILQD |
| | gi\|71280033\|ref\|YP_269028.1 | LLQKHLTELVTK |
| | gi\|88813651\|ref\|ZP_01128881.1 | EIRSHLGQIVRL |
| | gi\|42521961\|ref\|NP_967341.1 | DSEKHLAQSIEY |
| V95 | V95L | |
| | | 90       100 |
| | E.coli_TesA_1U8U | QILQDVKAANAEP |
| | gi\|78357184\|ref\|YP_388633.1 | AILQILTAQDVPV |
| | gi\|46580334\|ref\|YP_011142.1 | AILSLLAGHGIPA |
| | gi\|399975107\|ref\|NP_953461.1 | EMVRTLKERNVTV |
| | gi\|148651904\|ref\|YP_001278997.1 | TAIKRLQDGSVV |

FIG. 55 Cont.

| | |
|---|---|
| gi\|71066667\|ref\|YP_265394.1 | TAVKRLQDNDSVV |
| gi\|93007258\|ref\|YP_581695.1 | TAVKRLODNDSVV |
| gi\|51892159\|ref\|YP_074850.1 | GIIARLQEEGVAV |
| gi\|167645243\|ref\|YP_001682906.1 | AILQSLRSRRISA |
| gi\|197103612\|ref\|YP_002128989.1 | AIVRRLKARGVRV |
| gi\|162147014\|ref\|YP_001601475.1 | AILDRLRQAHVPV |
| gi\|182677824\|ref\|YP_001831970.1 | EILTRLRQRRIKA |
| gi\|154245703\|ref\|YP_001416661.1 | EIVQRLKGRGITV |
| gi\|170747446\|ref\|YP_001753706.1 | AIIERLKARGIPV |
| gi\|170743566\|ref\|YP_001722221.1 | AIVARLRGRGIPV |
| gi\|163700508\|ref\|ZP_02119362.1 | AIIARLKERGIPV |
| gi\|118592340\|ref\|ZP_01549732.1 | EIVRRLTDRGITV |
| gi\|90421721\|ref\|YP_530091.1 | QIVKKLKARNIAV |
| gi\|86747410\|ref\|YP_483906.1 | EIVKRLKARNIAV |
| gi\|39933272\|ref\|NP_945548.1 | EILKRLKARNLPV |
| gi\|192288623\|ref\|YP_001989228.1 | EILKRLKARNLPV |
| gi\|167367448\|ref\|ZP_023015901 | EILKRLKARNLPV |
| gi\|92116169\|ref\|YP_575898.1 | EILKRLKARDIAV |
| gi\|273755570\|ref\|NP_767099.1 | DIVQRLKARGIPV |
| gi\|146337546\|ref\|YP_001202594.1 | EIVKRLKARGIAV |
| gi\|148251997\|ref\|YP_001236582.1 | EIVQRLKARGIAV |
| gi\|90421109\|ref\|ZP_01229011.1 | QILAKLQARDQAA |
| gi\|114705373\|ref\|ZP_01438281.1 | KILEQLNERGQTV |
| gi\|13473671\|ref\|NP_105239.1 | EMLARLKQRKIAV |
| gi\|211958502\|gb\|EEA93702.1 | AMLARLSSRDIPV |
| gi\|163757370\|ref\|ZP_02164459.1 | AMITRLKERGIAV |

FIG. 55 Cont.

| | | QMIGRLKQRGIAV |
|---|---|---|
| A100 | A100V | 100 |
| | | E.coli_TesA_1U8U KAANAEPLLM |
| | | gi\|114772942\|ref\|ZP_01450253.1 QSANVQVAIQ |
| | | gi\|167624526\|ref\|YP_001674820.1 KAQQVTILLS |
| | | gi\|157374835\|ref\|YP_001473435.1 QAKDVEVLLS |
| | | gi\|78357184\|ref\|YP_388633.1 TAQDVPVLLM |
| | | gi\|51243931\|ref\|YP_063815.1 ADNDVVVVLA |
| | | gi\|39997510\|ref\|NP_953461.1 KERNVTVVLG |
| | | gi\|51892159\|ref\|YP_074850.1 QEEGVAVLLA |
| | | gi\|42521961\|ref\|NP_967341.1 QSQKVKVILG |
| | | gi\|198256435\|gb\|EDY80743.1 KYPEVKIVLA |
| | | gi\|186454892\|ref\|ZP_02965207.1 KKKDVKIIVA |
| | | gi\|116327860\|ref\|YP_797580.1 KKKNVKILLV |
| | | gi\|197103612\|ref\|YP_002128989.1 KARGVRVVLA |
| | | gi\|126739740\|ref\|ZP_01755431.1 RQEQVEVLLI |
| | | gi\|126725548\|ref\|ZP_01741390.1 AAKEVPVLLA |
| | | gi\|110678555\|ref\|YP_681562.1 AAQSVEVLLV |
| | | gi\|126730043\|ref\|ZP_01745855.1 EENDVEVLLI |
| | | gi\|85707175\|ref\|ZP_01038244.1 EAQGVEVLLV |
| | | gi\|149203588\|ref\|ZP_01880557.1 QANEVEVLLV |
| | | gi\|149915746\|ref\|ZP_01904271.1 RSRDVEVLLV |
| | | gi\|83950569\|ref\|ZP_00959302.1 EAREVPVLLV |
| | | gi\|84502882\|ref\|ZP_01000995.1 RAKGVEMLVI |

FIG. 55 Cont.

| | | | 100 110 | |
|---|---|---|---|---|
| | | gi\|198268949\|gb\|EDY93219.1 | | QDAGVDVLLV |
| | | gi\|198252001\|gb\|EDY76315.1 | | VDAGVEVLLV |
| | | gi\|84514338\|ref\|ZP_01001702.1 | | QQAGVAMLLV |
| | | gi\|126733689\|ref\|ZP_01749436.1 | | QDAGVEMLLV |
| | | gi\|162147014\|ref\|YP_001601475.1 | | RQAHVPVLLS |
| | | gi\|195970122\|ref\|NP_387325.1 | | KERGVAVLLA |
| | | gi\|163795307\|ref\|ZP_02189274.1 | | RSHRVPVLLA |
| M105 | M105C, M105V | E.coli_TesA_1U8U | | NAEPLLMQIRLPA |
| | | gi\|54309970\|ref\|YP_130990.1 | | DAKPMLVQIKVPP |
| | | gi\|90412817\|ref\|ZP_01220817.1 | | DAKPMLVQIKVPP |
| | | gi\|30249426\|ref\|NP_841496.1 | | NATPLLVGMQLPP |
| | | gi\|34499190\|ref\|NP_903405.1 | | KAKVLLVGMALPP |
| | | gi\|119897957\|ref\|YP_933170.1 | | GARVLLVGMRMPP |
| | | gi\|163856534\|ref\|YP_001630831.1 | | GARVLIVGMQIPP |
| | | gi\|187478460\|ref\|YP_786484.1 | | GAKVLIVGMQIPP |
| | | gi\|33597579\|ref\|NP_885222.1 | | GASVLVVGMQIPP |
| | | gi\|33592804\|ref\|NP_880448.1 | | GASVLVVGMQIPP |
| | | gi\|118051335\|ref\|ZP_01519884.1 | | GAQVLLVGMQVPP |
| | | gi\|121604790\|ref\|YP_982119.1 | | GAKVLLVGMQVPP |
| | | gi\|91788891\|ref\|YP_549843.1 | | GAKVLLVGMQVPP |
| | | gi\|171058584\|ref\|YP_001790933.1 | | GAAVMLVGMQVPP |
| | | gi\|146220121\|gb\|ABQ11275.1 | | GAKVLLVGQQVPP |

FIG. 55 Cont.

| | | | |
|---|---|---|---|
| | gi\|121594614\|ref\|YP_986510.1 | | GARVLLVGVQVPP |
| | gi\|160899469\|ref\|YP_001565051.1 | | GAKVLLVGMQVPP |
| | gi\|120611683\|ref\|YP_971361.1 | | GAKVLIVGMQVPP |
| | gi\|186475782\|ref\|YP_001857252.1 | | HAKVLLVGMYVPP |
| | gi\|209521452\|ref\|ZP_03270160.1 | | HAKVVLVGMYVPP |
| | gi\|170692416\|ref\|ZP_02883579.1 | | HAKVVLVGMYVPP |
| | gi\|187923902\|ref\|YP_001895544.1 | | HAKVVLVGMYVPP |
| | gi\|91783526\|ref\|YP_558732.1 | | RAQVLLVGMYVPP |
| | gi\|167562421\|ref\|ZP_02355337.1 | | NIPVLLCGMYAPP |
| | gi\|115522331\|ref\|YP_779242.1 | | NIAVFLCGMYAPP |
| | gi\|90421721\|ref\|YP_530091.1 | | DIAVLLCGMYAPP |
| | gi\|92116169\|ref\|YP_575898.1 | | GIPVMLCGMLAPP |
| | gi\|273755570\|ref\|NP_767099.1 | | GIAVMLCGMLAPP |
| | gi\|146337546\|ref\|YP_001202594.1 | | GIAVMLCGMLAPP |
| | gi\|148251997\|ref\|YP_001236582.1 | | GIAVMLCGMLAPP |
| | | | 100         110 |
| Q106 | Q106R, Q106S | E.coli_TesA_1U8U | AEPLLMQIRLPANY |
| | | gi\|149907876\|ref\|ZP_01896544.1 | IPVYVMSIRIPPNY |
| | | gi\|119503149\|ref\|ZP_01625233.1 | ASVLLSMEIPPNF |
| | | gi\|77163958\|ref\|YP_342483.1 | AQVLLVRMRLPPNY |
| | | gi\|207088375\|gb\|EDZ65647.1 | AQVLLVRMRLPPNY |
| | | gi\|124007358\|ref\|ZP_01692092.1 | IKILLVRMEAPPNL |
| | | | 110 |
| R108 | R108S, R108D, | | |

FIG. 55 Cont.

| R108Y | | |
|---|---|---|
| | E.coli_TesA_1U8U | LLMQIRLPANY |
| | gi\|77360818\|ref\|YP_340393.1 | ALMEIYIPPNY |
| | gi\|119472458\|ref\|ZP_01614557.1 | ALMEIYIPPNY |
| | gi\|194369063\|gb\|ABF57909.2 | ALMEIYIPPNY |
| | gi\|186475782\|ref\|YP_001857252.1 | LLVGMYVPPNY |
| | gi\|209521452\|ref\|ZP_03270160.1 | VLVGMYVPPNY |
| | gi\|170692416\|ref\|ZP_02883579.1 | VLVGMYVPPNY |
| | gi\|187923902\|ref\|YP_001895544.1 | VLVGMYVPPNY |
| | gi\|91783526\|ref\|YP_558732.1 | LLVGMYVPPNY |
| | gi\|167562421\|ref\|ZP_02355337.1 | LLVGMYVPPNY |
| | gi\|167569605\|ref\|ZP_02362479.1 | LLVGMYVPPNY |
| | gi\|167893816\|ref\|ZP_02481218.1 | LLVGMYVPSNY |
| | gi\|134277643\|ref\|ZP_01764358.1 | LLVGMYVPSNY |
| | gi\|167738130\|ref\|ZP_02410904.1 | LLVGMYVPSNY |
| | gi\|194505954\|ref\|YP_002035524.1 | LLVGMYVPSNY |
| | gi\|76810223\|ref\|YP_333863.1 | LLVGMYVPSNY |
| | gi\|161355201\|ref\|ZP_02101081.1 | LLVGMYVPSNY |
| | gi\|167902268\|ref\|ZP_02489473.1 | LLVGMYVPSNY |
| | gi\|194364429\|ref\|YP_002027039.1 | LLLGIDVPPNY |
| | gi\|190572845\|ref\|YP_001970690.1 | LLLGIDVPPNY |
| | gi\|212241603\|ref\|NP_641185.1 | LLLGIDVPPNY |
| | gi\|78046442\|ref\|YP_362617.1 | LLLGIDVPPNY |
| | gi\|188992969\|ref\|YP_001904979.1 | LLLGIDVPPNY |
| | gi\|212230252\|ref\|NP_636169.1 | LLLGIDVPPNY |
| | gi\|166710711\|ref\|ZP_02241918.1 | LLLGIDMPPNY |

FIG. 55 Cont.

| | | | |
|---|---|---|---|
| | gi\|58583387\|ref\|YP_202403.1 | | LLLGIDVPPNY |
| | gi\|198268949\|gb\|EDY93219.1 | | LLVGLDAPSNY |
| | gi\|198252001\|gb\|EDY76315.1 | | LLVGLDAPSNY |
| | gi\|185575357\|ref\|YP_001912286.1 | | LLLGIDVPPNY |
| | gi\|149203588\|ref\|ZP_01880557.1 | | LLVGLSAPGNY |
| | gi\|126733689\|ref\|ZP_01749436.1 | | LLVGLSVGANY |
| L109 | L109M | | 110 |
| | E.coli_TesA_1U8U | MQIRLPANYGRRY | |
| | gi\|119897957\|ref\|YP_933170.1 | VGMPMPPNYGTSY | |
| | gi\|169182148\|ref\|ZP_02842667.1 | IGMRMPPNYGPAY | |
| | gi\|56479332\|ref\|YP_160921.1 | IGMQMPPNYGPPY | |
| | gi\|166710711\|ref\|ZP_02241918.1 | LGIDMPPNYGPAY | |
| | gi\|146282380\|ref\|ZP_01172533.1 | LGMRMPPNLGQRY | |
| | gi\|150293082\|gb\|AAK81865.1\|AF395191_1 | LGMKMPPNYGTAY | |
| | gi\|39997510\|ref\|NP_953461.1 | GGMKMVANLGRDY | |
| | gi\|42521961\|ref\|NP_967341.1 | GGLYMPPNYGKDY | |
| | gi\|182411899\|ref\|YP_001816965.1 | AGMMMPPSMGPDY | |
| | gi\|198256435\|gb\|EDY80743.1 | AGMQMPPNLGEDY | |
| | gi\|186454892\|ref\|ZP_02965207.1 | AGMQMPPNMGEEY | |
| N112 | N112A | | 110 |
| | E.coli_TesA_1U8U | MQIRLPANYGRRYN | |
| | gi\|46580334\|ref\|YP_011142.1 | MGWQATMADTPDYA | |
| | gi\|120602288\|ref\|YP_966688.1 | MGWQATMADTPDYA | |

FIG. 55 Cont.

| | | | |
|---|---|---|---|
| Y113 | Y113I | E.coli_TesA_1U8U<br>gi\|167645243\|ref\|YP_001682906.1 | 110                 120<br>RLPANYGRRYNEAF<br>GAPPLIGATYAREF |
| R115 | R115N,<br>R115S,<br>R115E,<br>R115G,<br>R115A | E.coli_TesA_1U8U<br>gi\|89093794\|ref\|ZP_01166740.1<br>gi\|118051335\|ref\|ZP_01519884.1<br>gi\|146220121\|gb\|ABQ11275.1<br>gi\|121610344\|ref\|YP_998151.1<br>gi\|121594614\|ref\|YP_986510.1<br>gi\|194364429\|ref\|YP_002027039.1<br>gi\|92114738\|ref\|YP_574666.1<br>gi\|146307581\|ref\|YP_001188946.1<br>gi\|149276542\|ref\|ZP_01882686.1<br>gi\|167645243\|ref\|YP_001682906.1<br>gi\|114772942\|ref\|ZP_01450253.1<br>gi\|91788891\|ref\|YP_549843.1<br>gi\|53804283\|ref\|YP_113859.1<br>gi\|197103612\|ref\|YP_002128989.1<br>gi\|119774622\|ref\|YP_927362.1<br>gi\|119503149\|ref\|ZP_01625233.1<br>gi\|90023084\|ref\|YP_528911.1 | 110                 120<br>PANYGRRYNEAF<br>PSNYGAAYNKQF<br>PPNYGATYTEQF<br>PPNYGADYNQRF<br>PPNYGAAYADRF<br>PPNYGANYTRQF<br>PPNYGAGYRQRL<br>PPNYGAAYTDAF<br>PPNYGARYTSAF<br>PPNMGAEYATEF<br>PPLIGATYAREF<br>PTNYGARYNRMF<br>PPNYGGAYGAGF<br>PPNYGGRYAEAF<br>PPLLSGAWASAF<br>PTNYGGRYAKAF<br>PPNFGSRYTTLF<br>PPNFGSRYTQPF |

FIG. 55 Cont.

| | | | |
|---|---|---|---|
| | | gi\|121604790\|ref\|YP_982119.1 | PPNYGSAYAATF |
| | | gi\|160899469\|ref\|YP_001565051.1 | PPNYGSGYTRQF |
| | | gi\|120611683\|ref\|YP_971361.1 | PPNYGSDYTRRF |
| | | gi\|71066667\|ref\|YP_265394.1 | YDNLGSDYVKSF |
| | | gi\|93007258\|ref\|YP_581695.1 | YDNLGSDYVKSF |
| | | gi\|134094953\|ref\|YP_001100028.1 | PPNYGSDYTKQF |
| | | gi\|209904237\|ref\|ZP_03278741 | PPNYGNHFTERF |
| | | gi\|198256435\|gb\|EDY80743.1 | PPNLGEDYIKEF |
| | | gi\|114705373\|ref\|ZP_01438281.1 | PPNMGEDYAERF |
| | | gi\|186454892\|ref\|ZP_02965207.1 | PPNMGEEYNKAY |
| | | | 110        120 |
| Y117 | Y117L, Y117W | E.coli_TesA_1U8U | PANYGRRYNEAFSA |
| | | gi\|6993521\|ref\|ZP_00630194.1 | PDHDDP-LRRDWAG |
| | | gi\|197103612\|ref\|YP_002128989.1 | PPLLSGAWASAFDE |
| | | | 120 |
| E119 | E119R, E119K | E.coli_TesA_1U8U | GRRYNEAFSAIYP |
| | | gi\|88703495\|ref\|ZP_01101211.1 | GPRYTRSFRESFE |
| | | gi\|149928382\|ref\|ZP_01916622.1 | GPAYARRFGDTFP |
| | | gi\|171058584\|ref\|YP_001790933.1 | GQAYSRDFAGLFG |
| | | gi\|121594614\|ref\|YP_986510.1 | GANYTRQFAEVFE |
| | | gi\|160899469\|ref\|YP_001565051.1 | GSGYTRQFEQLFA |
| | | gi\|120611683\|ref\|YP_971361.1 | GSDYTRRFENVFP |
| | | gi\|152980543\|YP_001353227.1 | GTDYTRQFAELYP |

FIG. 55 Cont.

| | | | 120 | 130 |
|---|---|---|---|---|
| | | | | |
| | gi\|149377045\|ref\|ZP_01894796.1 | | | GQRYTRAFADIYP |
| | gi\|91775603\|ref\|YP_545359.1 | | | GPKYTREFIASYT |
| | gi\|146282380\|ref\|YP_001172533.1 | | | GQRYTRAFADAFD |
| | gi\|69935214\|ref\|ZP_00630194.1 | | | DP-LRRDWAGIWP |
| | gi\|114772942\|ref\|ZP_01450253.1 | | | GARYNRMFISAFS |
| | gi\|71280033\|ref\|YP_269028.1 | | | GQRYRKMFTDSYT |
| | gi\|77360818\|ref\|YP_340393.1 | | | GPRYSKMFTDSFT |
| | gi\|119472458\|ref\|ZP_01614557.1 | | | GPRYSKMFTDSFS |
| | gi\|194369063\|gb\|ABF57909.2 | | | GPRYSKMFTSSFT |
| | gi\|149907876\|ref\|ZP_01896544.1 | | | GPRYSKMFTDVFT |
| | gi\|91793720\|ref\|YP_563371.1 | | | GPRYSKAFNQVYH |
| | gi\|114563734\|ref\|YP_751247.1 | | | GPRYAKSFTQIYH |
| | gi\|119774622\|ref\|YP_927362.1 | | | GGRYAKAFADVYQ |
| | gi\|127513331\|ref\|YP_001094528.1 | | | GPRYAKQFTQVYQ |
| | gi\|170727240\|ref\|YP_001761266.1 | | | GPRYAKMFNQVYA |
| | gi\|119475890\|ref\|ZP_01616242.1 | | | GTRYTKMFYESYG |
| | gi\|89093794\|ref\|ZP_01166740.1 | | | GAAYNKQFSEIYP |
| | gi\|134094953\|ref\|YP_001100028.1 | | | GSDYTKQFSALFP |
| | gi\|66045308\|ref\|YP_235149.1 | | | GPRYTKAFEEVYS |
| | gi\|150293382\|gb\|AAK81865.1\|AF351191_1 | | | GTAYSKAFENNYK |
| F121 | F121L, F121Y | E.coli_TesA_1U8U | | RYNEAFSAIYPKLAK |
| | | gi\|78484894\|ref\|YP_390819.1 | | AYDQMLQQTFKQVAT |

FIG. 55 Cont.

| | | | | 120 | 130 |
|---|---|---|---|---|---|
| | | gi\|194364429\|ref\|YP_002027039.1 | | GYRQRLAAAYKALAT | |
| | | gi\|190572845\|ref\|YP_001970690.1 | | AYRQRLAAAYRALAT | |
| | | gi\|212241603\|ref\|NP_641185.1 | | AYRERLKATYADLSK | |
| | | gi\|78046442\|ref\|YP_362617.1 | | AYRERLKATYADLST | |
| | | gi\|188992969\|ref\|YP_001904979.1 | | AYRERLKATYADLSK | |
| | | gi\|21230252\|ref\|NP_636169.1 | | AYRERLKATYADLSK | |
| | | gi\|166710711\|ref\|ZP_022241918.1 | | AYRERLKATYADLAK | |
| | | gi\|58583387\|ref\|YP_202403.1 | | AYRERLKATYADLSK | |
| | | gi\|188575357\|ref\|YP_001912286.1 | | AYMQRYNRIYSQLEE | |
| | | gi\|512243931\|ref\|YP_063815.1 | | EYNKAYRETFPEVAK | |
| | | gi\|186454892\|ref\|ZP_02965207.1 | | | |
| S122 | | | | 120 | 130 |
| | S122F, | E.coli_TesA_1U8U | | YNEAFSAIYPKLAK | |
| | S122G, | gi\|209809090\|ref\|YP_002264628.1 | | YSQAFGSLYPKISE | |
| | S122V, | gi\|59714227\|ref\|YP_207002.1 | | YSQAFGSLYPKLSE | |
| | S122Y, | gi\|184461326\|gb\|ACC78298.1 | | YNEAFGAIYPALAK | |
| | S122E, | gi\|206576527\|ref\|YP_002240008.1 | | YNEAFGAIYPALAK | |
| | S122I | gi\|156977016\|ref\|YP_001447923.1 | | YSDMFYDIYPKLAE | |
| | | gi\|125620500\|gb\|EAZ48871.1 | | YSDAFYQIYPSLAE | |
| | | gi\|15601538\|ref\|NP_233169.1 | | YSDAFYQIYPSLAE | |
| | | gi\|121588086\|ref\|ZP_01677835.1 | | YSDAFYQIYPSLAE | |
| | | gi\|153827484\|ref\|ZP_019801511.1 | | YSDAFYQIYPSLAE | |
| | | gi\|156934923\|ref\|YP_001438839.1 | | YNQAFEAIYPELAW | |
| | | gi\|188026282\|ref\|ZP_02997874.1 | | YTSSFENVYPALAQ | |

FIG. 55 Cont.

| | | |
|---|---|---|
| | gi\|212706885\|ref\|ZP_03315013.1 | YTSSFEKVYPTLAE |
| | gi\|119897957\|ref\|YP_933170.1 | YTTRFEAAFADVAR |
| | gi\|91775603\|ref\|YP_545359.1 | YTREFIASYTELAK |
| | gi\|114772942\|ref\|ZP_01450253.1 | YNRMFISAFSDVAD |
| | gi\|149928382\|ref\|ZP_01916622.1 | YARRFGDTFPDVAR |
| | gi\|90023084\|ref\|YP_528911.1 | YTQPFEQYSSLAK |
| | gi\|152996229\|ref\|YP_001341064.1 | YTQMFFNLYKDIAS |
| | gi\|153888470\|ref\|ZP_02009612.1 | YSERFFAMFGKLAQ |
| | gi\|187928944\|ref\|YP_001899431.1 | YSERFFAMFGKLAQ |
| | gi\|113867511\|ref\|YP_726000.1 | YTEKFVSLYPKLAG |
| | gi\|194289548\|ref\|YP_002005455.1 | YTEKFVSLYPRLAG |
| | gi\|114321556\|ref\|YP_743239.1 | YNQRFEALFHELAE |
| | gi\|771639581\|ref\|YP_342483.1 | YTERFEQLFTDLKD |
| | gi\|207088375\|gb\|EDZ65647.1 | YTERFEQLFTDLKD |
| | gi\|53804283\|ref\|YP_113859.1 | YAEAFERVQELAE |
| | gi\|66045308\|ref\|YP_235149.1 | YTKAFEEVYSNLAE |

| | | 120  130 |
|---|---|---|
| A123 | A123T | |
| | E.coli_TesA_1U8U | YNEAFSAIYPKLAKE |
| | gi\|167624526\|ref\|YP_001674820.1 | YASQISTVYKELATE |
| | gi\|157961485\|ref\|YP_001501519.1 | YASQISTVYKELAEE |
| | gi\|163757370\|ref\|ZP_02164459.1 | YEAKFNTIYPDLAKK |

| | | 120  130 |
|---|---|---|
| Y125 | Y125F | |

FIG. 55 Cont.

| | |
|---|---|
| E.coli_TesA_1U8U | EAFSAIYPKLAKEF |
| gi\|114772942\|ref\|ZP_01450253.1 | RMFISAFSDVADEF |
| gi\|196157105\|ref\|YP_002126594.1 | QMFTQNFSKVADEQ |
| gi\|88859908\|ref\|ZP_01134547.1 | SLFTAVFSETTQKT |
| gi\|77360818\|ref\|YP_340393.1 | KMFTDSFTQVSKNT |
| gi\|119472458\|ref\|ZP_01614557.1 | KMFTDSFSQISEET |
| gi\|149907876\|ref\|ZP_01896544.1 | KMFTSSFTQISEDT |
| gi\|194369063\|gb\|ABF57909.2 | KMFTDVFTQVGSEK |
| gi\|88703495\|ref\|ZP_01101211.1 | RSFRESFERAATDT |
| gi\|78484894\|ref\|YP_390819.1 | QMLQQTFKQVATQN |
| gi\|94500900\|ref\|ZP_01307426.1 | QMFKQAFADVAEQQ |
| gi\|71908327\|ref\|YP_285914.1 | ADFHSSFTSIAQAK |
| gi\|119897957\|ref\|YP_933170.1 | TRFEAAFADVARER |
| gi\|169182148\|ref\|ZP_02842667.1 | QRFAEVFANVAAEK |
| gi\|56479332\|ref\|YP_160921.1 | QRFEQTFADVAREH |
| gi\|149928382\|ref\|ZP_01916622.1 | RRFGDTFPDVARKQ |
| gi\|163856534\|ref\|YP_001630831.1 | QRFAAVFPAVAKAE |
| gi\|187478460\|ref\|YP_786484.1 | ERFAKVFQNVAEKE |
| gi\|33597579\|ref\|NP_885222.1 | QRFAQVFPAVAEQE |
| gi\|33592804\|ref\|NP_880448.1 | QRFAQVFPAVAEQE |
| gi\|118051335\|ref\|ZP_01519884.1 | EQFAGMFKKVADTQ |
| gi\|121604790\|ref\|YP_982119.1 | ATFSGLFAKVAKEE |
| gi\|91788891\|ref\|YP_549843.1 | AGFAGLFPKVARAE |
| gi\|124267005\|ref\|YP_001021009.1 | EDFAALFGKVARAE |

FIG. 55 Cont.

| | | | |
|---|---|---|---|
| F140 | | gi\|171058584\|ref\|YP_001790933.1<br>gi\|121594614\|ref\|YP_986510.1<br>gi\|121610344\|ref\|YP_998151.1<br>gi\|160899469\|ref\|YP_001565051.1 | REFAGLFGKVAQRE<br>RQFAEVFENVAQER<br>DRFAALFTTVAQAR<br>RQFEQLFAKVAQEQ |
| | F140M | | 130           140 |
| | | E.coli_TesA_1U8U | LAKEFDVPLLPFFMEEVYL |
| | | gi\|94500900\|ref\|ZP_01307426.1 | VAEQQGVAFIPFFMLKPLMN |
| | | gi\|152996229\|ref\|YP_001341064.1 | IASKYNIAYLPFMLENVAL |
| | | gi\|88798847\|ref\|ZP_01114429.1 | LASTYNLPFLPFFMLEGVAE |
| | | gi\|149928382\|ref\|YP_001916622.1 | VARKQKVPLVPFFMLEGFAL |
| | | gi\|134094953\|ref\|YP_001100028.1 | LAQETKSSLVPFFMLQGVAE |
| | | gi\|152980543\|ref\|YP_001353227.1 | IAKETKSALVPFFMLKDVAD |
| | | gi\|198263408\|gb\|EDY87686.1 | LAQQHDVALVPFFMLEDIYQ |
| | | gi\|149200040\|ref\|ZP_01877066.1 | LAEKNKIELIPFFMLEEVAG |
| | | gi\|206686219\|gb\|EDZ46701.1 | LAAEFGAVLHPGMAAEAGG |
| | | gi\|94497924\|ref\|ZP_01304489.1 | LAHKYDAALYPFFMLDGVLG |
| M141 | M141P,<br>M141A,<br>M141L,<br>M141M,<br>M141G | |        140 |
| | | E.coli_TesA_1U8U | FDVPLLPFFMEEVYL-KP |
| | | gi\|156977016\|ref\|YP_001447923.1 | QQVALMPFFLEHVII-KP |
| | | gi\|54309970\|ref\|YP_130990.1 | LATPLLPFFLEQIIL-KQ |
| | | gi\|148548659\|ref\|YP_001268761.1 | KQVPLVPFFLEGVGG-VP |
| | | gi\|209809090\|ref\|YP_002264628.1 | HDIPLVPFFLEHVII-KP |
| | | gi\|59714227\|ref\|YP_207002.1 | HAIPLLPFFLEQVIV-KP |

FIG. 55 Cont.

| | | | |
|---|---|---|---|
| | | gi\|197337441\|ref\|YP_002158710.1 | HAIPLLPFFLEQVIV-KP |
| | | gi\|125620500\|gb\|EAZ48871.1 | FSIPLIPFFLEQVIL-KP |
| | | gi\|15601538\|ref\|NP_233169.1 | FSIPLIPFFLEQVIL-KP |
| | | gi\|121588086\|ref\|ZP_01677835.1 | FSIPLIPFFLEQVIL-KP |
| | | gi\|153827484\|ref\|ZP_01980151.1 | FSIPLIPFFLEQVIL-KP |
| | | gi\|163800656\|ref\|ZP_02194557.1 | QQVNLIPFFLEQVIV-KP |
| | | gi\|146279956\|ref\|YP_001170114.1 | YEADLEANFLDEPDA-RQ |
| | | gi\|91226151\|ref\|ZP_01261041.1 | QQVALMPFFLEHVVT-KP |
| | | gi\|28900726\|ref\|ZP_800381.1 | QQVQLMPFFLEHVIT-KP |
| | | gi\|119897957\|ref\|YP_933170.1 | RKVRLVPFLFDGFAD-KP |
| | | gi\|84684212\|ref\|ZP_01012114.1 | HDMIFMPYIFQGMMS-RT |
| | | gi\|206680133\|ref\|EDZ44620.1 | YDTLYVQDFFDGTVD-RP |
| | | gi\|145589121\|ref\|YP_001155718.1 | EHIQLLPFFENGLAT-NK |
| | | gi\|78357184\|ref\|YP_388633.1 | HRVMLHPFFPEGVAA-NP |
| | | gi\|85707175\|ref\|ZP_01038244.1 | YDTLFMPFFAGLGEG-DP |
| | | gi\|206686219\|ref\|EDZ46701.1 | FGAVLHPGMAAEAGG-DP |
| | | gi\|149203588\|ref\|ZP_01880557.1 | YGAFYAPFFAGLGGG-DP |
| | | gi\|126739740\|ref\|ZP_01755431.1 | YEAIFHPVVGEDPAA-AR |
| E142 | E142C | E.coli_TesA_1U8U | 130    140<br>KLAKEFDVPLLPFFMEEVYL |
| | | gi\|74316704\|ref\|YP_314444.1 | EVARSEKVTHVPCFVCEVGV |
| Y145 | Y145E,<br>Y145M,<br>Y145T, | E.coli_TesA_1U8U | 140    150<br>DVPLLPFFMEEVYL-KPQ |

FIG. 55 Cont.

| Y145D, Y145L, Y145A | | |
|---|---|---|
| | gi\|37527678\|ref\|NP_931022.1 | QIPLLPFYMEQVAI-KPE |
| | gi\|165927624\|ref\|ZP_02223456.1 | DIPLLPFFMEQVAV-KPE |
| | gi\|22125003\|ref\|NP_668426.1 | DIPLLPFFMEQVAV-KPE |
| | gi\|162420602\|ref\|YP_001605806.1 | DIPLLPFFMEQVAV-KPE |
| | gi\|153949498\|ref\|YP_001401981.1 | DIPLLPFFMEQVAV-KPE |
| | gi\|161232257\|ref\|NP_406570.1 | DIPLLPFFMEQVAV-KPE |
| | gi\|77958377\|ref\|ZP_00822411.1 | GIPLVPFFMEQVAV-KPE |
| | gi\|77979334\|ref\|ZP_00834753.1 | SIPLVPFFMEHVAV-KPE |
| | gi\|123443264\|ref\|YP_001007238.1 | NIPLVPFFMEAVAV-KPQ |
| | gi\|77974242\|ref\|ZP_00829783.1 | GIPLVPFFMEQVAV-KPE |
| | gi\|197286014\|ref\|ZP_02151886.1 | DIPLVPFFMEQVAV-KPE |
| | gi\|114772942\|ref\|ZP_01450253.1 | ALELIPFYMEQIAD-KPE |
| | gi\|109899221\|ref\|YP_662476.1 | DVPLVPFFLADIAL-NPE |
| | gi\|196157105\|ref\|YP_002126594.1 | DVTLLPFFLADIAL-NNE |
| | gi\|71280033\|ref\|YP_269028.1 | DIATIPFFLEEIAL-HQE |
| | gi\|163757370\|ref\|ZP_02164459.1 | GAHLMAYFMTDVAI-DSS |
| | gi\|84684212\|ref\|ZP_01012114.1 | DVVFYPFFLDGVTG-NPS |
| | gi\|126733689\|ref\|ZP_01749436.1 | DMIFMPYIFQGMMS-RTD |
| | gi\|84514338\|ref\|ZP_01001702.1 | DIALYADFMQEGM---S-E |
| | gi\|94500900\|ref\|ZP_01307426.1 | DVPLYHD-MFAGMRVTPA |
| | gi\|167562421\|ref\|ZP_02355337.1 | GVAFIPFMLKPLMN-KDK |
| | gi\|167569605\|ref\|ZP_02362479.1 | RVPLVPFLLAGIEN-KPD |
| | gi\|186475782\|ref\|YP_001857252.1 | RVPLVPFLLAGIEN-KPD |
| | gi\|77465602\|ref\|YP_355105.1 | RVPLVPFLLAGIED-KPD |
| | gi\|126464041\|ref\|YP_001045154.1 | GADLEPNFLDEPDA-RQR |
| | | GADLEPNFLDEPDA-RQR |

FIG. 55 Cont.

| | | | |
|---|---|---|---|
| M151 | M151V, M151I | gi\|146279956\|ref\|YP_001170114.1<br>gi\|94497924\|ref\|ZP_01304489.1 | EADLEANFLDEPDE-RQR<br>DAALYPFMLDGVLG-DRT |
| | | |         130        140        150 |
| | | E.coli_TesA_1U8U<br>gi\|50120161\|ref\|YP_049328.1<br>gi\|209809090\|ref\|YP_002264628.1<br>gi\|212706885\|ref\|ZP_03315013.1<br>gi\|212711255\|ref\|ZP_03319383.1<br>gi\|88859908\|ref\|ZP_01134547.1<br>gi\|90416813\|ref\|ZP_01224743.1<br>gi\|153874618\|ref\|ZP_02002768.1<br>gi\|37527678\|ref\|NP_931022.1<br>gi\|94500900\|ref\|ZP_01307426.1<br>gi\|196195006\|gb\|EDX89965.1<br>gi\|154245703\|ref\|YP_001416661.1 | AKEFDVPLLPFFMEEVYL-KPQWMQDDG<br>AEQFALPLLPFFMEQVYL-KPEWIMEDG<br>SEKHDIPLVPFFLEHVII-KPEWIMKDG<br>AEKNQIPLLPFFMESVIT-KPEWIQPDG<br>AEKNQLPLIPFFMESVIT-KPEWIQPDG<br>TQKTNTTLMPFFMLAVAG-NPELIQNDN<br>SEAEDVLLIPFQLEELSV-TEGMIQEDG<br>AAEYDIPLVPFFLDKVAL-NPALIQVDG<br>AEYNQIPLLPFYMEQVAI-KPEWVQQDG<br>AEQQGVAFIPFMLKPLMM-KDKYVQDDG<br>AQSTSAPWVPFFLDGVIE-QG-WVQDDG<br>AAAEGVLLYPFFLDGVAG-ERALVQPDG |
| Q152 | Q152L | |         130        140        150 |
| | | E.coli_TesA_1U8U<br>gi\|71280033\|ref\|YP_269028.1<br>gi\|169182148\|ref\|ZP_02842667.1<br>gi\|78357184\|ref\|YP_388633.1<br>gi\|46580334\|ref\|YP_011142.1<br>gi\|120602288\|ref\|YP_966688.1<br>gi\|119713520\|gb\|ABL97573.1 | KEFDVPLLPFFMEEVYL-KPQWMQDDGI<br>DQTGAHLMAYFMTDVAI-DSSLMLNDNL<br>AEKKVPLVPFLMDGFAD-RPELFLPDGI<br>ARHRVMLHPFFPEGVAA-NPALSLPDGI<br>AKHGTPLYADTLAGIWG-EDRMTLHDGL<br>AKHGTPLYADTLAGIWG-EDRMTLHDGL<br>EKHSLIFMPFLEEEVAL-QKALLPDYK |

FIG. 55 Cont.

| | | |
|---|---|---|
| | gi\|42521961\|ref\|NP_967341.1 | KKYKLTFIPFILDKVAG-NPKYNLADGI |
| | gi\|149200040\|ref\|ZP_01877066.1 | EKNKIELIPFMLEEVAG-HAKMNLPDGI |
| | gi\|126647348\|ref\|ZP_01719853.1 | EEKDVELIPFLLQDVGG-IKELNLPDGI |
| | gi\|193215472\|ref\|YP_001996671.1 | KENRAQLIPFLLEGVGG-QPNLNLPDGI |
| | gi\|182677824\|ref\|YP_001831970.1 | QQFDVPFYPFFLDGVAG-NPALELPDRV |
| | gi\|170747446\|ref\|YP_001753706.1 | ERYGLTLYPFFLDGIIG-DRAQHLDDMI |
| | gi\|170743566\|ref\|YP_001772221.1 | ERYGLVLYPFFLDGVAG-NRGLTLADGL |
| | gi\|163700508\|ref\|ZP_02119362.1 | ERHGLMLYPFFLDGVAT-DRSLTLPDGL |
| | gi\|118592340\|ref\|ZP_01549732.1 | KAHDALFYPFFLEGVAL-NPDLNLSDGM |
| | gi\|13473671\|ref\|NP_105239.1 | KKYDVALYPFFLDGVAG-QPGMQLEDGL |
| | gi\|211958502\|gb\|EEA93702.1 | EKHDALLYPFFLDGVAA-EPKLNLGDGM |
| | gi\|163757370\|ref\|ZP_02164459.1 | KKHDVVFYPFFLDGVTG-NPSLLLSDGM |
| | gi\|190893785\|ref\|YP_001980327.1 | EKHGVRLYDFFLDGVAL-DAGLKLDDGM |
| | gi\|167357739\|ref\|ZP_02292403.1 | EKHGLPLYAFFLDGVAL-EAGLKLDDGM |
| | gi\|116254256\|ref\|YP_770094.1 | EKHGLPLYAFFLDGVAL-EAGLKLEDGM |
| | gi\|150398267\|ref\|YP_001328734.1 | KEHDTVFYPFFLDGVVT-EAGLKLEDGM |
| | gi\|195970122\|ref\|NP_387325.2 | KEHNLVFYPFFLDGVVT-EVGLKLDDGM |
| | | 130   140   150 |
| D153 | D153K | |
| | E.coli_TesA_1U8U | AKEEFDVPLLPFFMEEVYL-KPQWMQDDGI |
| | gi\|209809090\|ref\|YP_002264628.1 | SEKHDIPLVPFFLEHVII-KPEWIMKDGL |
| | gi\|59714227\|ref\|YP_207002.1 | SEKHAIPLLPFFLEQVIV-KPEWMMKDGL |
| | gi\|197337441\|ref\|YP_002158710.1 | SEKHAIPLLPFFLEQVIV-KPEWMMKDGL |
| | gi\|90579358\|ref\|ZP_01235168.1 | SKDTNVPLLPFFLIDIIV-KPELMMKDGL |
| | gi\|89072709\|ref\|ZP_01159274.1 | SEDTNVPLLPFFLIDIIV-KPELMMKDGL |

FIG. 55 Cont.

| | | | |
|---|---|---|---|
| I156 | I156V | E.coli_TesA_1U8U<br>gi\|183220370\|ref\|YP_001838366.1<br>gi\|116327860\|ref\|YP_797580.1<br>gi\|45657291\|ref\|YP_001377.1<br>gi\|85707157\|ref\|ZP_01038244.1<br>gi\|24215621\|ref\|NP_712742.1 | AKEENVPLVPFILEKVAT-IRKLNQKDGI<br>AKEENLPLVPFFLNGVAG-VKKLNQKDGI<br>AKEENLILVPFFLDGVAG-IKNLNQKDGI<br>SEAYDTLFMPFFAGLGEG-DPSTLQKDGI<br>AKEENLILVPFFLDGVAG-IKNLNQKDGI |
| | | |        150          160 |
| | | E.coli_TesA_1U8U<br>gi\|121998847\|ref\|YP_001003634.1<br>gi\|15029382\|gb\|AAK81865.1\|AF395191_1<br>gi\|182677824\|ref\|YP_001831970.1 | KPQWMQDDGIHPNRDAQ<br>RDGMMQDDGVHPTAKAQ<br>NKSLMQKDLVHPNGKAQ<br>NPALELPDRVHPNQEGV |
| P158 | P158A | E.coli_TesA_1U8U<br>gi\|69935214\|ref\|ZP_00630194.1 |        150          160<br>KPQWMQDDGIHPNRDAQPFI<br>LPAMLQPDGLHASAKGVGLI |
| N159 | N159V,<br>N159T,<br>N159G | E.coli_TesA_1U8U<br>gi\|50120161\|ref\|YP_049328.1<br>gi\|209809090\|ref\|YP_002264628.1<br>gi\|90579358\|ref\|ZP_01235168.1<br>gi\|89072709\|ref\|ZP_01159274.1<br>gi\|180026282\|ref\|ZP_02997874.1<br>gi\|212706885\|ref\|ZP_03315013.1<br>gi\|212711255\|ref\|ZP_03319383.1 |        160<br>DDGIHPNRDAQPF<br>EDGIHPTRDAQPF<br>KDGLHPTPEAQPW<br>KDGLHPTAQAQPL<br>KDGLHPTAQAQPL<br>QDGIHPTVEAQPS<br>PDGIHPTAEAQPS<br>PDGIHPTEQAQPT |

FIG. 55 Cont.

| | | |
|---|---|---|
| | gi\|114772942\|ref\|ZP_01450253.1 | NDGIHPTAEAQPM |
| | gi\|88703495\|ref\|ZP_01101211.1 | QDGIHPTVEAQPM |
| | gi\|119503149\|ref\|ZP_01625233.1 | SDGIHPTAGAQSL |
| | gi\|90416813\|ref\|ZP_01224743.1 | EDGLHPTAMAQPI |
| | gi\|121998847\|ref\|YP_001003634.1 | DDGVHPTAKAQPE |
| | gi\|82703094\|ref\|YP_412660.1 | ADGIHPTARAQEK |
| | gi\|30249426\|ref\|NP_841496.1 | ADGIHPTIQAQEK |
| | gi\|87798847\|ref\|ZP_01114429.1 | ADGLHPTAAAQPI |
| | gi\|90023084\|ref\|YP_528911.1 | ADGLHPTAEAQPI |
| | gi\|56479332\|ref\|YP_160921.1 | SDGIHPTAEAQEL |
| | gi\|192359766\|ref\|YP_001982095.1 | RDGIHPTEEAQPL |
| | gi\|171058584\|ref\|YP_001790933.1 | PDRIHPTAWAHP- |
| | gi\|146220121\|gb\|ABQ11275.1 | PDRIHPTAAAHPT |
| | gi\|121594614\|ref\|YP_986510.1 | PDRIHPTAQAHPR |
| | gi\|160899469\|ref\|YP_001565051.1 | ADRIHPTAKAQPR |
| | gi\|186475782\|ref\|YP_001857252.1 | SDQIHPTQRAQPL |
| | gi\|134295954\|ref\|YP_001119689.1 | SDQMHPGEQAQRV |
| | gi\|83749049\|ref\|ZP_00946056.1 | EDRIHPVAAAQPT |
| | gi\|207724196\|ref\|YP_002254594.1 | EDRIHPVAAAQPT |
| | gi\|207743056\|ref\|YP_002259448.1 | EDRIHPVAAAQPT |
| R160 | | 160 |
| R160A, R160G, R160S, R160D | E.coli_TesA_1U8U | DDGIHPNRDAQPFI |
| | gi\|153949498\|ref\|YP_001401981.1 | DDGLHPNGDAQPFI |
| | gi\|22125003\|ref\|NP_668426.1 | DDGLHPNGDAQPFI |

FIG. 55 Cont.

| | | |
|---|---|---|
| | gi\|165927624\|ref\|ZP_022223456.1 | DDGLHPNGDAQPFI |
| | gi\|16123257\|ref\|NP_406570.1 | DDGLHPNGDAQPFI |
| | gi\|150398267\|ref\|YP_001328734.1 | EDGMHPNGEGIAVM |
| | gi\|211958502\|gb\|EEA93702.1 | GDGMHPTGEGVSII |
| | gi\|195970122\|ref\|NP_387325.1 | DDGMHPNGGGVGVM |
| | gi\|162420602\|ref\|YP_001605806.1 | DDGLHPNGDAQPFI |
| | gi\|77962143\|ref\|ZP_00825967.1 | DDGLHPNAEAQPFI |
| | gi\|90579358\|ref\|ZP_01235168.1 | KDGLHPTAQAQPLI |
| | gi\|77958377\|ref\|ZP_00822411.1 | DDGLHPNAEAQPFI |
| | gi\|77979334\|ref\|ZP_00834753.1 | DDGLHPNAAAQPFI |
| | gi\|77974242\|ref\|ZP_00829783.1 | DDGLHPNAEAQPFI |
| | gi\|212706885\|ref\|ZP_03315013.1 | PDGIHPTAEAQPSI |
| | gi\|123443264\|ref\|YP_001007238.1 | DDGLHPNAQAQPFI |
| | gi\|89072709\|ref\|ZP_01159274.1 | KDGLHPTAQAQPLI |
| | gi\|54309970\|ref\|YP_130990.1 | NDGLHPKSDAQPWI |
| | gi\|94310819\|ref\|YP_584029.1 | TDRIHPTSAAQPTL |
| | gi\|149915746\|ref\|ZP_01904271.1 | PDGIHPNSEGVERI |
| | gi\|183220370\|ref\|YP_001838366.1 | KDGIHPTDAGHKLV |
| Q163 | Q163S | 160 |
| | E.coli_TesA_1U8U | DDGIHPNRDAQPFI |
| | gi\|213023388\|ref\|ZP_03337835.1 | DDGIHPNATRSPFM |
| F165 | F165M | 160        170 |
| | E.coli_TesA_1U8U | NRDAQPFIADWMAK |

FIG. 55 Cont.

| | | | |
|---|---|---|---|
| | | gi\|114772942\|ref\|ZP_01450253.1 | TAEAQPMIAEFMLT |
| | | gi\|109899221\|ref\|YP_662476.1 | NAKAQPMIAKSMQA |
| | | gi\|88703495\|ref\|ZP_01101211.1 | TVEAQPMITDIVQP |
| I166 | I166L | | 160       170 |
| | | E.coli_TesA_1U8U | LIHPNRDAQPFIADWMAKQL |
| | | gi\|77360818\|ref\|YP_340393.1 | LHPNKTAQPILRDEMYNTI |
| | | gi\|195503149\|ref\|ZP_01625233.1 | IHPTAGAQSLLENVLPYA |
| | | gi\|89093794\|ref\|ZP_01166740.1 | IHPSAEGQPYLLNTVWPHL |
| | | gi\|145589121\|ref\|YP_001155718.1 | IHPNEKAQNIL-------- |
| | | gi\|87798847\|ref\|ZP_01114429.1 | LHPTAAAQPILLD------ |
| | | gi\|83647632\|ref\|YP_436067.1 | IHPNAKGQPQLVENVLPHL |
| | | gi\|163856534\|ref\|YP_001630831.1 | IHPNEQAQPLLLDNVWAAL |
| | | gi\|187478460\|ref\|YP_786484.1 | IHPNEMAQPALLNNVWPGL |
| | | gi\|33597579\|ref\|NP_885222.1 | IHPNEDAQPALLDNVWPVL |
| | | gi\|33592804\|ref\|NP_880448.1 | IHPNENAQPALLDNVWPLL |
| | | gi\|146220121\|gb\|ABQ11275.1 | IHPTAAAHPTLLDNVWVEL |
| | | gi\|186475782\|ref\|YP_001857252.1 | IHPTQRAQPLLLDNVWPAL |
| | | gi\|209521452\|ref\|ZP_03270160.1 | IHPTQQAQPVLLNNVWPAV |
| | | gi\|187923902\|ref\|YP_001895544.1 | IHPTQQAQPVLLNNVWPAV |
| | | gi\|91783526\|ref\|YP_558732.1 | IHPTQQAQPVLLNNVWPAV |
| | | gi\|167562421\|ref\|ZP_02355337.1 | IHPTQAAQRRLLDNVWPAV |
| | | gi\|167569605\|ref\|ZP_02362479.1 | IHPTQAAQRRLLDNVWPAL |
| | | gi\|167893816\|ref\|ZP_02481218.1 | IHPTQAAQRQLLDNVWPAL |
| | | gi\|134277643\|ref\|ZP_01764358.1 | IHPTQAAQRQLLDNVWPAL |

FIG. 55 Cont.

| | | | |
|---|---|---|---|
| | | gi\|167738130\|ref\|ZP_02410904.1 | IHPTQAAQRQLLDNVWPAL |
| | | gi\|194505954\|ref\|YP_002035524.1 | IHPTQAAQRQLLDNVWPAL |
| | | gi\|76810223\|ref\|YP_333863.1 | IHPTQAAQRQLLDNVWPAL |
| | | gi\|161355201\|ref\|ZP_02101081.1 | IHPTQAAQRQLLDNVWPAL |
| | | gi\|167902268\|ref\|ZP_02489473.1 | IHPTQAAQRQLLDNVWPAL |
| | | gi\|194570836\|ref\|YP_002105836.1 | IHPTQAAQRQLLDNVWPAL |
| | | gi\|53719047\|ref\|YP_108033.1 | IHPTQAAQRQLLDNVWPAL |
| | | gi\|126453719\|ref\|YP_001066613.1 | IHPTQAAQRQLLDNVWPAL |
| | | gi\|126441228\|ref\|YP_001059345.1 | IHPTQAAQRQLLDNVWPAL |
| | | gi\|53723658\|ref\|YP_103103.1 | IHPTQAAQRQLLDNVWPAL |
| | | gi\|124384223\|ref\|YP_001029293.1 | IHPTQAAQRQLLDNVWPAL |
| | | | 160                 170 |
| A167 | A167T | E.coli_TesA_1U8U | IHPNRDAQPFIADWM |
| | | gi\|114563734\|ref\|YP_751247.1 | IHPNEQAQDTITLIM |
| | | gi\|88703495\|ref\|ZP_01101211.1 | IHPTVEAQPMITDIV |

FIG. 56 dbj|AP007255.1
dbj|AP008229.1
dbj|AP008232.1
dbj|AP009384.1
dbj|BA000007.2
dbj|BA000032.2
dbj|BA000038.2
dbj|BAAW01000080.1
dbj|BAAW01003851.1
dbj|BAAW01008327.1
dbj|BAAW01012499.1
dbj|BAAW01015319.1
dbj|BAAX01023606.1
emb|AJ537556.1|UNK537556
emb|AL499619.1|LMFLCHR16
emb|AL499622.1|LMFLCHR32
emb|AL590842.1
emb|AL627267.1
emb|AL646052.1
emb|AL954747.1
emb|AM039952.1
emb|AM167904.1
emb|AM260479.1
emb|AM286415.1
emb|AM286690.1
emb|AM406670.1
emb|AM902716.1
emb|BX571871.1
emb|BX571965.1
emb|BX572593.1
emb|BX640416.1
emb|BX640432.1
emb|BX640446.1
emb|BX936398.1
emb|BX950851.1
emb|CAD61204.1
emb|CR378672.1
emb|CR543861.1
emb|CR954246.1
emb|CT573326.1
emb|CU207211.1
emb|CU234118.1
emb|X71116.1|VMP1662
gb|AAAA02045720.1
gb|AACV01025855.1
gb|AACV01026072.1
gb|AACV01029939.1
gb|AACY020000130.1
gb|AACY020014506.1
gb|AACY020022286.1
gb|AACY020022355.1
gb|AACY020039259.1
gb|AACY020045251.1
gb|AACY020046419.1
gb|AACY020047385.1
gb|AACY020055714.1
gb|AACY020063599.1
gb|AACY020074167.1
gb|AACY020074366.1
gb|AACY020093792.1
gb|AACY020108764.1
gb|AACY020111063.1
gb|AACY020111064.1
gb|AACY020134856.1
gb|AACY020145333.1
gb|AACY020145771.1
gb|AACY020184726.1
gb|AACY020237026.1
gb|AACY020242275.1
gb|AACY020259651.1
gb|AACY020262079.1
gb|AACY020281768.1
gb|AACY020291995.1
gb|AACY020301750.1
gb|AACY020307221.1
gb|AACY020329402.1
gb|AACY020351844.1
gb|AACY020355833.1
gb|AACY020365173.1
gb|AACY020368816.1
gb|AACY020373791.1
gb|AACY020376764.1
gb|AACY020385476.1
gb|AACY020397913.1
gb|AACY020399540.1
gb|AACY020412418.1
gb|AACY020413074.1
gb|AACY020413415.1
gb|AACY020421995.1
gb|AACY020440166.1
gb|AACY020442826.1
gb|AACY020448939.1
gb|AACY020462670.1
gb|AACY020484856.1
gb|AACY020500357.1
gb|AACY020501970.1
gb|AACY020503987.1
gb|AACY020508107.1
gb|AACY020520332.1
gb|AACY020525877.1
gb|AACY020527033.1
gb|AACY020528033.1
gb|AACY020529987.1
gb|AACY020536168.1
gb|AACY020538235.1
gb|AACY020539054.1
gb|AACY020548368.1
gb|AACY020551059.1
gb|AACY020557224.1
gb|AACY020559781.1
gb|AACY020561170.1
gb|AACY020561311.1
gb|AACY020577147.1
gb|AACY020597815.1
gb|AACY020603183.1
gb|AACY020608825.1
gb|AACY020629299.1
gb|AACY020714154.1
gb|AACY020727996.1
gb|AACY020759226.1
gb|AACY020784436.1
gb|AACY020834700.1
gb|AACY020839834.1
gb|AACY020868630.1

FIG. 56 Cont.

gb|AACY020917183.1
gb|AACY020958566.1
gb|AACY020990569.1
gb|AACY021019213.1
gb|AACY021020329.1
gb|AACY021023140.1
gb|AACY021026108.1
gb|AACY021059895.1
gb|AACY021060006.1
gb|AACY021070713.1
gb|AACY021076206.1
gb|AACY021115796.1
gb|AACY021166167.1
gb|AACY021245686.1
gb|AACY021260329.1
gb|AACY021268388.1
gb|AACY021275321.1
gb|AACY021288062.1
gb|AACY021314456.1
gb|AACY021334178.1
gb|AACY021344027.1
gb|AACY021383177.1
gb|AACY021451602.1
gb|AACY021583045.1
gb|AACY021586453.1
gb|AACY021608834.1
gb|AACY021641112.1
gb|AACY021691881.1
gb|AACY021705793.1
gb|AACY021712936.1
gb|AACY021721493.1
gb|AACY021739391.1
gb|AACY021784434.1
gb|AACY021819907.1
gb|AACY021848317.1
gb|AACY021853587.1
gb|AACY021891459.1
gb|AACY021899606.1
gb|AACY021919551.1
gb|AACY021938954.1 gb|AACY021947911.1
gb|AACY021963896.1
gb|AACY021984021.1
gb|AACY022040971.1
gb|AACY022045015.1
gb|AACY022065493.1
gb|AACY022078953.1
gb|AACY022105658.1
gb|AACY022129745.1
gb|AACY022140162.1
gb|AACY022151412.1
gb|AACY022158644.1
gb|AACY022178276.1
gb|AACY022209206.1
gb|AACY022212959.1
gb|AACY022218518.1
gb|AACY022219522.1
gb|AACY022231109.1
gb|AACY022242656.1
gb|AACY022277008.1
gb|AACY022282671.1
gb|AACY022329894.1
gb|AACY022348615.1
gb|AACY022377715.1
gb|AACY022380265.1
gb|AACY022465251.1
gb|AACY022510303.1
gb|AACY022575717.1
gb|AACY022607847.1
gb|AACY022636395.1
gb|AACY022672162.1
gb|AACY022685318.1
gb|AACY022706774.1
gb|AACY022710910.1
gb|AACY022761432.1
gb|AACY022779517.1
gb|AACY022786809.1
gb|AACY022792439.1
gb|AACY022794397.1
gb|AACY022850370.1
gb|AACY022879954.1
gb|AACY022895438.1
gb|AACY022931408.1 gb|AACY022939397.1
gb|AACY022975187.1
gb|AACY023000354.1
gb|AACY023011187.1
gb|AACY023028940.1
gb|AACY023036979.1
gb|AACY023064011.1
gb|AACY023073442.1
gb|AACY023081853.1
gb|AACY023088523.1
gb|AACY023101395.1
gb|AACY023108227.1
gb|AACY023127322.1
gb|AACY023150083.1
gb|AACY023151385.1
gb|AACY023214217.1
gb|AACY023220721.1
gb|AACY023225833.1
gb|AACY023293937.1
gb|AACY023309868.1
gb|AACY023317959.1
gb|AACY023341349.1
gb|AACY023344504.1
gb|AACY023397471.1
gb|AACY023419945.1
gb|AACY023423908.1
gb|AACY023459087.1
gb|AACY023466994.1
gb|AACY023470806.1
gb|AACY023471792.1
gb|AACY023472351.1
gb|AACY023474031.1
gb|AACY023483626.1
gb|AACY023512718.1
gb|AACY023518449.1
gb|AACY023573915.1
gb|AACY023574575.1
gb|AACY023575256.1
gb|AACY023580795.1
gb|AACY023597741.1
gb|AACY023600467.1
gb|AACY023629708.1
gb|AACY023630954.1

FIG. 56 Cont.

gb|AACY023638464.1
gb|AACY023647630.1
gb|AACY023649900.1
gb|AACY023659331.1
gb|AACY023667824.1
gb|AACY023676429.1
gb|AACY023685825.1
gb|AACY023793978.1
gb|AACY023794579.1
gb|AACY023802343.1
gb|AACY023803322.1
gb|AACY023804625.1
gb|AACY023810273.1
gb|AACY023812347.1
gb|AACY023824210.1
gb|AACY023824449.1
gb|AACY023825258.1
gb|AACY023825339.1
gb|AACY023828022.1
gb|AACY023831940.1
gb|AACY023837606.1
gb|AACY023837743.1
gb|AACY023841556.1
gb|AACY023874455.1
gb|AACY023876717.1
gb|AACY023882676.1
gb|AACY023908767.1
gb|AACY023929341.1
gb|AACY023947565.1
gb|AACY023964925.1
gb|AACY023970962.1
gb|AACY023972056.1
gb|AACY023974977.1
gb|AACY023980237.1
gb|AACY023984499.1
gb|AACY024025458.1
gb|AACY024034457.1
gb|AACY024063931.1
gb|AACY024085821.1
gb|AACY024096204.1
gb|AACY024096594.1 gb|AAFX01005675.1
gb|AAFX01011167.1
gb|AAFX01025782.1
gb|AAFX01038468.1
gb|AAFX01066401.1
gb|AAFX01106490.1
gb|AAFX01116872.1
gb|AAHY01746239.1
gb|AAK16084.1|AF288082_2
gb|AAK81865.1|AF395191_1
gb|AAMB02000002.1
gb|AAQ28697.1
gb|AAR43890.1
gb|AAR53009.1
gb|AASG02022698.1
gb|AASG02023246.1
gb|AASZ01000785.1
gb|AAT50732.1
gb|AATN01000167.1
gb|AATN01000814.1
gb|AATN01001106.1
gb|AATO01000008.1
gb|AATO01001850.1
gb|AATO01003739.1
gb|AATO01010104.1
gb|AAVS01000036.1
gb|AAVT01000002.1
gb|AAVV01000002.1
gb|AAX37297.1
gb|ABDH01009660.1
gb|ABDH01051283.1
gb|ABEF01005448.1
gb|ABEF01038687.1
gb|ABEF01040384.1
gb|ABEF01048738.1
gb|ABEF01052460.1
gb|ABF57909.2
gb|ABH77568.1
gb|ABO11417.2
gb|ABOK01442679.1
gb|ABOK01586584.1 gb|ABQ11275.1
gb|ABZ56880.1
gb|ACC78298.1
gb|AE003853.1
gb|AE004091.2
gb|AE005174.2
gb|AE005673.1
gb|AE005674.1
gb|AE008719.1
gb|AE009952.1
gb|AE011715.1
gb|AE012177.1
gb|AE013598.1
gb|AE014073.1
gb|AE014299.1
gb|AE014613.1
gb|AE015451.1
gb|AE016796.1
gb|AE016825.1
gb|AE016853.1
gb|AE017042.1
gb|AE017220.1
gb|AE017282.2
gb|AE017340.1
gb|AF288082.1|AF288082
gb|AF395190.2
gb|AY658457.1
gb|AY833091.1
gb|BZ549080.1
gb|CD439532.1
gb|CF322583.1
gb|CL669240.1
gb|CO742357.1
gb|CP000010.1
gb|CP000026.1
gb|CP000034.1
gb|CP000036.1
gb|CP000050.1
gb|CP000058.1
gb|CP000075.1
gb|CP000076.1
gb|CP000086.1
gb|CP000089.1

FIG. 56 Cont.

| | | |
|---|---|---|
| gb\|CP000090.1 | gb\|CP000503.1 | gb\|CP000908.1 |
| gb\|CP000094.1 | gb\|CP000507.1 | gb\|CZ545523.1 |
| gb\|CP000103.1 | gb\|CP000510.1 | gb\|DQ771288.1 |
| gb\|CP000109.2 | gb\|CP000512.1 | gb\|DQ775969.1 |
| gb\|CP000112.1 | gb\|CP000514.1 | gb\|DU774646.1 |
| gb\|CP000115.1 | gb\|CP000521.1 | gb\|DU780221.1 |
| gb\|CP000116.1 | gb\|CP000526.1 | gb\|DX074846.1 |
| gb\|CP000124.1 | gb\|CP000529.1 | gb\|EAZ48871.1 |
| gb\|CP000127.1 | gb\|CP000539.1 | gb\|EBB00196.1 |
| gb\|CP000151.1 | gb\|CP000544.1 | gb\|EBB00995.1 |
| gb\|CP000155.1 | gb\|CP000546.1 | gb\|EBB14613.1 |
| gb\|CP000250.1 | gb\|CP000548.1 | gb\|EBB44352.1 |
| gb\|CP000266.1 | gb\|CP000555.1 | gb\|EBB65340.1 |
| gb\|CP000267.1 | gb\|CP000563.1 | gb\|EBB86785.1 |
| gb\|CP000269.1 | gb\|CP000570.1 | gb\|EBC00015.1 |
| gb\|CP000282.1 | gb\|CP000572.1 | gb\|EBC61260.1 |
| gb\|CP000283.1 | gb\|CP000606.1 | gb\|EBC67157.1 |
| gb\|CP000284.1 | gb\|CP000614.1 | gb\|EBC78525.1 |
| gb\|CP000285.1 | gb\|CP000626.1 | gb\|EBC80168.1 |
| gb\|CP000301.1 | gb\|CP000644.1 | gb\|EBC89014.1 |
| gb\|CP000302.1 | gb\|CP000647.1 | gb\|EBD12471.1 |
| gb\|CP000304.1 | gb\|CP000653.1 | gb\|EBD44387.1 |
| gb\|CP000305.1 | gb\|CP000655.1 | gb\|EBD83454.1 |
| gb\|CP000308.1 | gb\|CP000668.1 | gb\|EBE34945.1 |
| gb\|CP000316.1 | gb\|CP000680.1 | gb\|EBE46909.1 |
| gb\|CP000319.1 | gb\|CP000681.1 | gb\|EBE51481.1 |
| gb\|CP000352.1 | gb\|CP000712.1 | gb\|EBF18406.1 |
| gb\|CP000380.1 | gb\|CP000720.1 | gb\|EBF25038.1 |
| gb\|CP000388.1 | gb\|CP000744.1 | gb\|EBF35305.1 |
| gb\|CP000438.1 | gb\|CP000749.1 | gb\|EBF42247.1 |
| gb\|CP000440.1 | gb\|CP000753.1 | gb\|EBF46989.1 |
| gb\|CP000444.1 | gb\|CP000783.1 | gb\|EBF47131.1 |
| gb\|CP000446.1 | gb\|CP000790.1 | gb\|EBF48585.1 |
| gb\|CP000447.1 | gb\|CP000821.1 | gb\|EBF48999.1 |
| gb\|CP000450.1 | gb\|CP000822.1 | gb\|EBF70249.1 |
| gb\|CP000453.1 | gb\|CP000826.1 | gb\|EBF74014.1 |
| gb\|CP000458.1 | gb\|CP000851.1 | gb\|EBF84055.1 |
| gb\|CP000462.1 | gb\|CP000868.1 | gb\|EBF86466.1 |
| gb\|CP000463.1 | gb\|CP000880.1 | gb\|EBF88229.1 |
| gb\|CP000469.1 | gb\|CP000884.1 | gb\|EBG02140.1 |
| gb\|CP000494.1 | gb\|CP000886.1 | gb\|EBG03131.1 |
| | gb\|CP000891.1 | gb\|EBH92870.1 |
| | gb\|CP000901.1 | gb\|EBI09735.1 |

FIG. 56 Cont.

gb|EBI25014.1
gb|EBI40029.1
gb|EBI56927.1
gb|EBI60584.1
gb|EBI75401.1
gb|EBJ53471.1
gb|EBJ62451.1
gb|EBJ63565.1
gb|EBJ64666.1
gb|EBK67121.1
gb|EBK79457.1
gb|EBL34868.1
gb|EBL54355.1
gb|EBL57875.1
gb|EBL69503.1
gb|EBL86174.1
gb|EBM55815.1
gb|EBM63919.1
gb|EBN11937.1
gb|EBO21799.1
gb|EBO27566.1
gb|EBO70247.1
gb|EBO84406.1
gb|EBP12605.1
gb|EBQ43581.1
gb|EBQ56471.1
gb|EBR96977.1
gb|EBS05704.1
gb|EBS21319.1
gb|EBS29947.1
gb|EBS52576.1
gb|EBS87208.1
gb|EBS97371.1
gb|EBT20408.1
gb|EBT33808.1
gb|EBT66016.1
gb|EBU12431.1
gb|EBU22544.1
gb|EBU77869.1
gb|EBV49315.1
gb|EBV56371.1 gb|EBV65046.1
gb|EBV84832.1
gb|EBW51301.1
gb|EBX02078.1
gb|EBX43817.1
gb|EBX78437.1
gb|EBY36073.1
gb|EBY78830.1
gb|EBY98532.1
gb|EBZ04862.1
gb|EBZ09819.1
gb|EBZ17831.1
gb|ECA00284.1
gb|ECA11464.1
gb|ECA76985.1
gb|ECB56272.1
gb|ECB74738.1
gb|ECB77773.1
gb|ECC13206.1
gb|ECC26498.1
gb|ECC37977.1
gb|ECC47879.1
gb|ECC73123.1
gb|ECC78215.1
gb|ECC91531.1
gb|ECD18906.1
gb|ECE14473.1
gb|ECE44114.1
gb|ECE87400.1
gb|ECF24361.1
gb|ECF30240.1
gb|ECF37835.1
gb|ECF93596.1
gb|ECF98523.1
gb|ECG10921.1
gb|ECG16969.1
gb|ECG23088.1
gb|ECG38755.1
gb|ECG70380.1
gb|ECH02658.1
gb|ECI03908.1
gb|ECI15831.1
gb|ECJ11841.1 gb|ECJ13936.1
gb|ECJ68205.1
gb|ECK39698.1
gb|ECK49422.1
gb|ECK84801.1
gb|ECL48993.1
gb|ECL92086.1
gb|ECM04375.1
gb|ECM61983.1
gb|ECM77528.1
gb|ECM90949.1
gb|ECM91670.1
gb|ECN07633.1
gb|ECN11725.1
gb|ECN27086.1
gb|ECN63461.1
gb|ECN88937.1
gb|ECO63169.1
gb|ECP23021.1
gb|ECP37860.1
gb|ECP43062.1
gb|ECP53348.1
gb|ECQ61864.1
gb|ECR76976.1
gb|ECS36544.1
gb|ECS77197.1
gb|ECS89566.1
gb|ECS93972.1
gb|ECT11214.1
gb|ECT28045.1
gb|ECU27475.1
gb|ECU27569.1
gb|ECU50903.1
gb|ECV05661.1
gb|ECV09153.1
gb|ECV17481.1
gb|ECV30343.1
gb|ECV59558.1
gb|ECV66424.1
gb|ECV92255.1
gb|ECW21397.1
gb|ECW27586.1
gb|ECW34552.1

FIG. 56 Cont.

gb|ECW51884.1
gb|ECW86476.1
gb|ECX03181.1
gb|ECX07607.1
gb|ECX51959.1
gb|ECY15974.1
gb|ECY51053.1
gb|ECY65264.1
gb|ECY72008.1
gb|ECZ13704.1
gb|ECZ32055.1
gb|ECZ32791.1
gb|ECZ63045.1
gb|ECZ95526.1
gb|EDA15220.1
gb|EDA34659.1
gb|EDA43162.1
gb|EDA65955.1
gb|EDA75330.1
gb|EDB33474.1
gb|EDB63930.1
gb|EDC11631.1
gb|EDC18259.1
gb|EDC79853.1
gb|EDC86032.1
gb|EDE13368.1
gb|EDF12274.1
gb|EDF13440.1
gb|EDG04054.1
gb|EDG10020.1
gb|EDG47637.1
gb|EDG96629.1
gb|EDH45122.1
gb|EDH65891.1
gb|EDH68511.1
gb|EDH71634.1
gb|EDH86342.1
gb|EDI26270.1
gb|EDI26458.1
gb|EDI44671.1
gb|EDI82121.1 gb|EDJ18110.1
gb|EDJ33361.1
gb|EDJ60226.1
gb|EDX89965.1
gb|EDY87686.1
gb|EDZ46701.1
gb|EDZ65647.1
gb|EJ085421.1
gb|EJ099644.1
gb|EJ137266.1
gb|EJ146674.1
gb|EJ191501.1
gb|EJ212903.1
gb|EJ225122.1
gb|EJ227792.1
gb|EJ245549.1
gb|EJ266991.1
gb|EJ278016.1
gb|EJ329588.1
gb|EJ334720.1
gb|EJ391923.1
gb|EJ426203.1
gb|EJ434827.1
gb|EJ471737.1
gb|EJ477947.1
gb|EJ484731.1
gb|EJ498664.1
gb|EJ500550.1
gb|EJ555922.1
gb|EJ564676.1
gb|EJ640224.1
gb|EJ645847.1
gb|EJ650695.1
gb|EJ662911.1
gb|EJ664069.1
gb|EJ665938.1
gb|EJ667820.1
gb|EJ669120.1
gb|EJ703050.1
gb|EJ721950.1
gb|EJ730460.1
gb|EJ770502.1
gb|EJ777637.1 gb|EJ785431.1
gb|EJ788765.1
gb|EJ815775.1
gb|EJ851744.1
gb|EJ873052.1
gb|EJ879757.1
gb|EJ902539.1
gb|EJ931567.1
gb|EJ937131.1
gb|EJ972947.1
gb|EJ990165.1
gb|EJ999222.1
gb|EK000110.1
gb|EK000629.1
gb|EK023293.1
gb|EK065797.1
gb|EK078447.1
gb|EK093951.1
gb|EK109020.1
gb|EK123650.1
gb|EK133187.1
gb|EK180280.1
gb|EK196880.1
gb|EK222554.1
gb|EK257255.1
gb|EK313225.1
gb|EK325827.1
gb|EK441511.1
gb|EK492959.1
gb|EK507776.1
gb|EK508176.1
gb|EK529306.1
gb|EK539522.1
gb|EK543851.1
gb|EK576280.1
gb|EK601818.1
gb|EK616119.1
gb|EK621481.1
gb|EK623494.1
gb|EK628542.1
gb|EK639369.1
gb|EK645136.1
gb|EK666683.1

FIG. 56 Cont.

gb|EK670222.1
gb|EK670523.1
gb|EK673679.1
gb|EK682200.1
gb|EK691103.1
gb|EK692669.1
gb|EK725644.1
gb|EK743461.1
gb|EK771460.1
gb|EK791447.1
gb|EK806766.1
gb|EK818832.1
gb|EK834533.1
gb|EK835979.1
gb|EK837640.1
gb|EK843333.1
gb|EK859387.1
gb|EK885080.1
gb|EK889609.1
gb|EK890943.1
gb|EK903712.1
gb|EK918170.1
gb|EK935500.1
gb|EK947561.1
gb|EK951364.1
gb|EK960146.1
gb|EK960826.1
gb|EK967818.1
gb|EK981215.1
gb|EK983743.1
gb|EK984099.1
gb|EK989854.1
gb|EK990735.1
gb|EK991845.1
gb|ER010920.1
gb|ER032330.1
gb|ER049290.1
gb|ER052609.1
gb|ER096625.1
gb|ER127282.1
gb|ER130376.1 gb|ER131376.1
gb|ER161971.1
gb|ER162312.1
gb|ER176379.1
gb|ER177550.1
gb|ER195612.1
gb|ER200449.1
gb|ER206437.1
gb|ER211547.1
gb|ER212475.1
gb|ER214473.1
gb|ER214855.1
gb|ER242449.1
gb|ER253849.1
gb|ER262881.1
gb|ER350440.1
gb|ER382137.1
gb|ER390228.1
gb|ER423386.1
gb|ER429221.1
gb|ER442323.1
gb|ER442792.1
gb|ER471256.1
gb|ER482389.1
gb|ER509480.1
gb|ER566372.1
gb|ER576118.1
gb|ER613314.1
gb|ER615495.1
gb|FH365651.1
pdb|1J00|A
pdb|1JRL|A
ref|NP_233169.1
ref|NP_251546.1
ref|NP_286243.1
ref|NP_406570.1
ref|NP_420568.1
ref|NP_455101.1
ref|NP_459501.1
ref|NP_519838.1
ref|NP_636169.1
ref|NP_641185.1
ref|NP_668426.1 ref|NP_712742.1
ref|NP_718498.1
ref|NP_744467.1
ref|NP_762242.1
ref|NP_792087.1
ref|NP_800381.1
ref|NP_841496.1
ref|NP_880448.1
ref|NP_885222.1
ref|NP_889542.1
ref|NP_903405.1
ref|NP_931022.1
ref|NP_936828.1
ref|NP_945548.1
ref|NW_001083568.1
ref|NZ_AAAU03000001.1
ref|NZ_AACX01000017.1
ref|NZ_AAGE02033712.1
ref|NZ_AAHN02000001.1
ref|NZ_AAHO01000021.1
ref|NZ_AAHR02000004.1
ref|NZ_AAHS03000025.1
ref|NZ_AAHV02000013.1
ref|NZ_AAHW02000002.1
ref|NZ_AAIQ02000012.1
ref|NZ_AAIR02000006.1
ref|NZ_AAKH02000182.1
ref|NZ_AAKI02000073.1
ref|NZ_AAKJ02000066.1
ref|NZ_AAKK02000006.1
ref|NZ_AAKL01000052.1
ref|NZ_AAKV01000034.1
ref|NZ_AAKW01000024.1
ref|NZ_AAKX01000089.1
ref|NZ_AAKY01000063.1
ref|NZ_AALC01000018.1
ref|NZ_AALD01000017.1
ref|NZ_AALE01000009.1
ref|NZ_AALF01000005.1
ref|NZ_AAMM02000007.1
ref|NZ_AAMR01000030.1
ref|NZ_AAMX01000013.1
ref|NZ_AAMY01000001.1

FIG. 56 Cont.

ref|NZ_AAND01000039.1
ref|NZ_AANX02000019.1
ref|NZ_AAOA01000001.1
ref|NZ_AAOE01000009.1
ref|NZ_AAOF01000028.1
ref|NZ_AAOH01000005.1
ref|NZ_AAOJ01000002.1
ref|NZ_AAOU01000004.1
ref|NZ_AAOW01000010.1
ref|NZ_AAPH01000018.1
ref|NZ_AAPI01000005.1
ref|NZ_AAPJ01000011.1
ref|NZ_AAPS01000016.1
ref|NZ_AAQN01000001.1
ref|NZ_AAQW01000001.1
ref|NZ_AATR01000024.1
ref|NZ_AATY01000043.1
ref|NZ_AAUB01000051.1
ref|NZ_AAUJ01000003.1
ref|NZ_AAUR01000070.1
ref|NZ_AAUS01000048.1
ref|NZ_AAUT01000048.1
ref|NZ_AAUU01000083.1
ref|NZ_AAVS01000036.1
ref|NZ_AAVT01000002.1
ref|NZ_AAVV01000002.1
ref|NZ_AAWD01000202.1
ref|NZ_AAWE01000074.1
ref|NZ_AAWF01000084.1
ref|NZ_AAWG01000076.1
ref|NZ_AAWP01000238.1
ref|NZ_AAWQ01000062.1
ref|NZ_AAWQ01000361.1
ref|NZ_AAWY01000065.1
ref|NZ_AAXY01000012.1
ref|NZ_AAYR01000001.1
ref|NZ_AAYS01000016.1
ref|NZ_AAYT01000001.1
ref|NZ_AAYU01000018.1
ref|NZ_AAYV01000012.1
ref|NZ_AAYX01000001.1 ref|NZ_AAZP01000003.1
ref|NZ_AAZW01000032.1
ref|NZ_ABAN01000007.3
ref|NZ_ABAO01000003.1
ref|NZ_ABAT01000020.1
ref|NZ_ABAU01000083.1
ref|NZ_ABBD01000590.1
ref|NZ_ABBE01000454.1
ref|NZ_ABBF01000179.1
ref|NZ_ABBG01000111.1
ref|NZ_ABBH01000617.1
ref|NZ_ABBI01000494.1
ref|NZ_ABBJ01000389.1
ref|NZ_ABBK01000366.1
ref|NZ_ABBL01000369.1
ref|NZ_ABBM01000232.1
ref|NZ_ABBN01000303.1
ref|NZ_ABBO01000334.1
ref|NZ_ABBP01000274.1
ref|NZ_ABBQ01000228.1
ref|NZ_ABBR01000205.1
ref|NZ_ABBZ01001487.1
ref|NZ_ABCD01000001.1
ref|NZ_ABCH01000016.1
ref|NZ_ABCP01000022.1
ref|NZ_ABCQ01000002.1
ref|NZ_ABCT01000025.1
ref|NZ_ABDZ01000018.1
ref|NZ_ABEI01000007.1
ref|NZ_ABEJ01000025.1
ref|NZ_ABEL01000001.1
ref|NZ_ABEW01000005.1
ref|NZ_ABEX01000002.1
ref|NZ_ABFF01000003.1
ref|NZ_ABFG01000003.1
ref|YP_001003634.1
ref|YP_001007238.1
ref|YP_001021009.1
ref|YP_001029293.1
ref|YP_001051045.1
ref|YP_001059345.1
ref|YP_001066613.1
ref|YP_001084019.1 ref|YP_001094528.1
ref|YP_001100028.1
ref|YP_001119689.1
ref|YP_001140725.1
ref|YP_001155718.1
ref|YP_001172533.1
ref|YP_001175703.1
ref|YP_001188046.1
ref|YP_001202594.1
ref|YP_001236582.1
ref|YP_001268761.1
ref|YP_001334153.1
ref|YP_001341064.1
ref|YP_001347669.1
ref|YP_001353227.1
ref|YP_001366906.1
ref|YP_001377.1
ref|YP_001401981.1
ref|YP_001438839.1
ref|YP_001447923.1
ref|YP_001454190.1
ref|YP_001473435.1
ref|YP_001477389.1
ref|YP_001501519.1
ref|YP_001526681.1
ref|YP_001555212.1
ref|YP_001565051.1
ref|YP_001571431.1
ref|YP_001579540.1
ref|YP_001605806.1
ref|YP_001630831.1
ref|YP_001641436.1
ref|YP_001668159.1
ref|YP_001674820.1
ref|YP_001707661.1
ref|YP_001714611.1
ref|YP_001748633.1
ref|YP_001761266.1
ref|YP_001765225.1
ref|YP_001790933.1
ref|YP_001808536.1
ref|YP_001831970.1
ref|YP_001845605.1

FIG. 56 Cont.

ref|YP_001857252.1
ref|YP_001899431.1
ref|YP_001904979.1
ref|YP_001908369.1
ref|YP_001912286.1
ref|YP_001927109.1
ref|YP_001946344.1
ref|YP_001970690.1
ref|YP_001982095.1
ref|YP_001989228.1
ref|YP_002005455.1
ref|YP_002027039.1
ref|YP_002035524.1
ref|YP_002093983.1
ref|YP_002098168.1
ref|YP_002105836.1
ref|YP_002126594.1
ref|YP_002151886.1
ref|YP_002158710.1
ref|YP_002210388.1
ref|YP_002225613.1
ref|YP_002231119.1
ref|YP_002240008.1
ref|YP_002254594.1
ref|YP_002259448.1
ref|YP_002264628.1
ref|YP_002299265.1
ref|YP_045767.1
ref|YP_049328.1
ref|YP_103103.1
ref|YP_108033.1
ref|YP_113859.1
ref|YP_130990.1
ref|YP_156150.1
ref|YP_202403.1
ref|YP_207002.1
ref|YP_215534.1
ref|YP_235149.1
ref|YP_261370.1
ref|YP_274258.1
ref|YP_285914.1 ref|YP_295598.1
ref|YP_314444.1
ref|YP_317035.1
ref|YP_333863.1
ref|YP_340393.1
ref|YP_342483.1
ref|YP_349742.1
ref|YP_362617.1
ref|YP_369458.1
ref|YP_386909.1
ref|YP_388633.1
ref|YP_390819.1
ref|YP_402105.1
ref|YP_406934.1
ref|YP_412660.1
ref|YP_423690.1
ref|YP_436067.1
ref|YP_442651.1
ref|YP_483906.1
ref|YP_523672.1
ref|YP_528911.1
ref|YP_530091.1
ref|YP_545359.1
ref|YP_549843.1
ref|YP_563371.1
ref|YP_567671.1
ref|YP_574666.1
ref|YP_584029.1
ref|YP_607529.1
ref|YP_625997.1
ref|YP_662476.1
ref|YP_693120.1
ref|YP_726000.1
ref|YP_733613.1
ref|YP_737598.1
ref|YP_743239.1
ref|YP_747911.1
ref|YP_751247.1
ref|YP_773797.1
ref|YP_779242.1
ref|YP_786484.1
ref|YP_790318.1
ref|YP_835563.1 ref|YP_857963.1
ref|YP_869177.1
ref|YP_927362.1
ref|YP_933170.1
ref|YP_944260.1
ref|YP_958323.1
ref|YP_963007.1
ref|YP_971361.1
ref|YP_982119.1
ref|YP_986510.1
ref|ZP_00415149.1
ref|ZP_00440774.1
ref|ZP_00822411.1
ref|ZP_00825967.1
ref|ZP_00829783.1
ref|ZP_00834753.1
ref|ZP_00946056.1
ref|ZP_00991723.1
ref|ZP_01043473.1
ref|ZP_01044690.1
ref|ZP_01066638.1
ref|ZP_01101211.1
ref|ZP_01114429.1
ref|ZP_01128881.1
ref|ZP_01134547.1
ref|ZP_01159274.1
ref|ZP_01166740.1
ref|ZP_01220817.1
ref|ZP_01224743.1
ref|ZP_01229011.1
ref|ZP_01235168.1
ref|ZP_01261041.1
ref|ZP_01366323.1
ref|ZP_01450253.1
ref|ZP_01519884.1
ref|ZP_01614557.1
ref|ZP_01616242.1
ref|ZP_01625233.1
ref|ZP_01677835.1
ref|ZP_01707934.1
ref|ZP_01738317.1
ref|ZP_01764358.1
ref|ZP_01814897.1

FIG. 56 Cont.
ref|ZP_01844343.1
ref|ZP_01867911.1
ref|ZP_01894796.1
ref|ZP_01896544.1
ref|ZP_01916622.1
ref|ZP_01980151.1
ref|ZP_01993202.1
ref|ZP_02002768.1
ref|ZP_02009612.1
ref|ZP_02055185.1
ref|ZP_02101081.1
ref|ZP_02156924.1
ref|ZP_02194557.1
ref|ZP_02223456.1
ref|ZP_02241918.1
ref|ZP_02301590.1
ref|ZP_02344720.2
ref|ZP_02355337.1
ref|ZP_02362479.1
ref|ZP_02374459.1
ref|ZP_02379324.1
ref|ZP_02388333.1
ref|ZP_02410904.1
ref|ZP_02463157.1
ref|ZP_02481218.1
ref|ZP_02489473.1
ref|ZP_02683026.2
ref|ZP_02799578.2
ref|ZP_02842667.1
ref|ZP_02883579.1
ref|ZP_02892970.1
ref|ZP_02902430.1
ref|ZP_02911087.1
ref|ZP_02946716.1
ref|ZP_02997848.1
ref|ZP_03026190.1
ref|ZP_03081449.1
ref|ZP_03163359.1
ref|ZP_03221362.1
ref|ZP_03278741.1
ref|ZP_03281441.1
sp|Q07792|ESTE_VIBMI

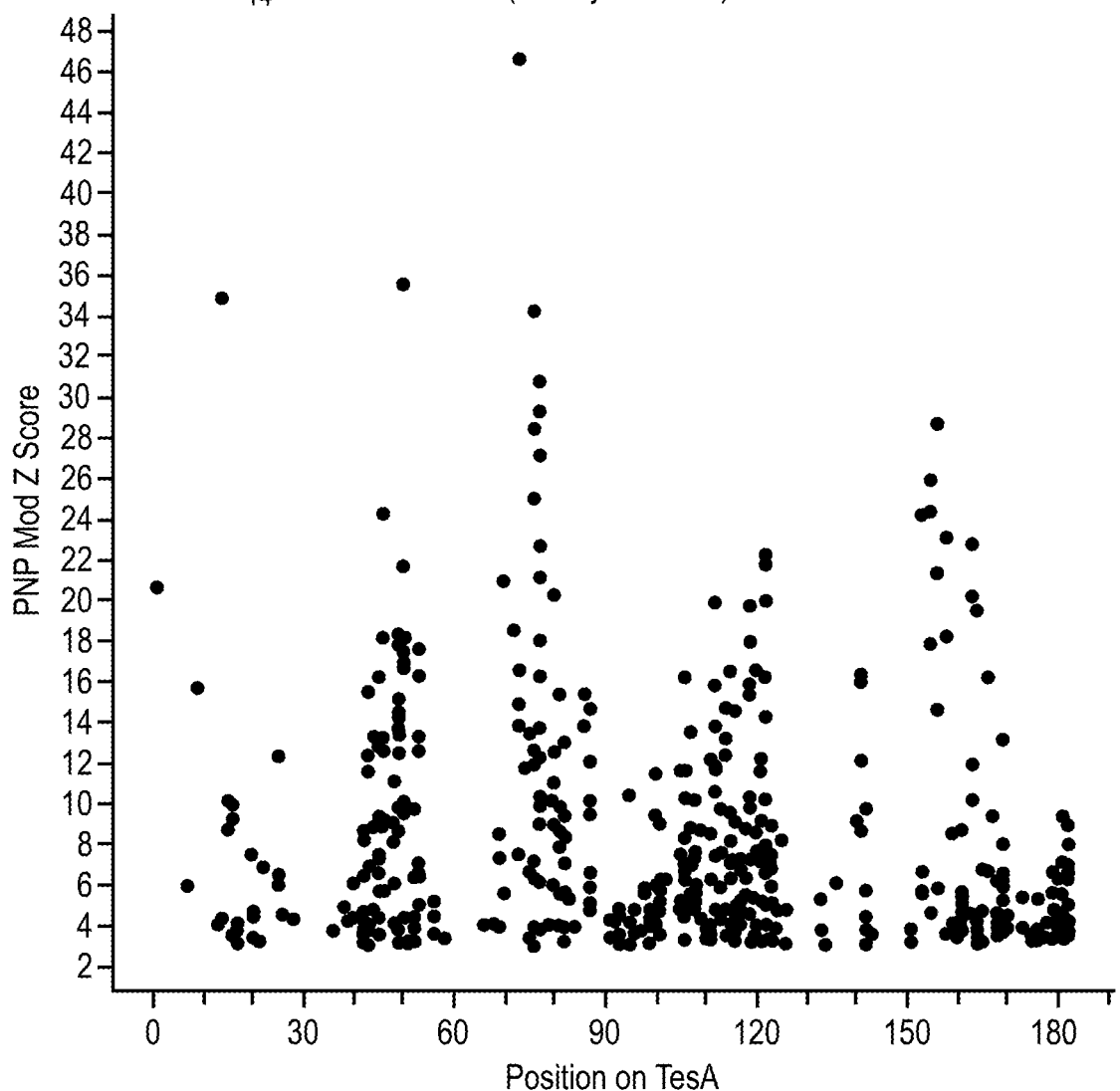

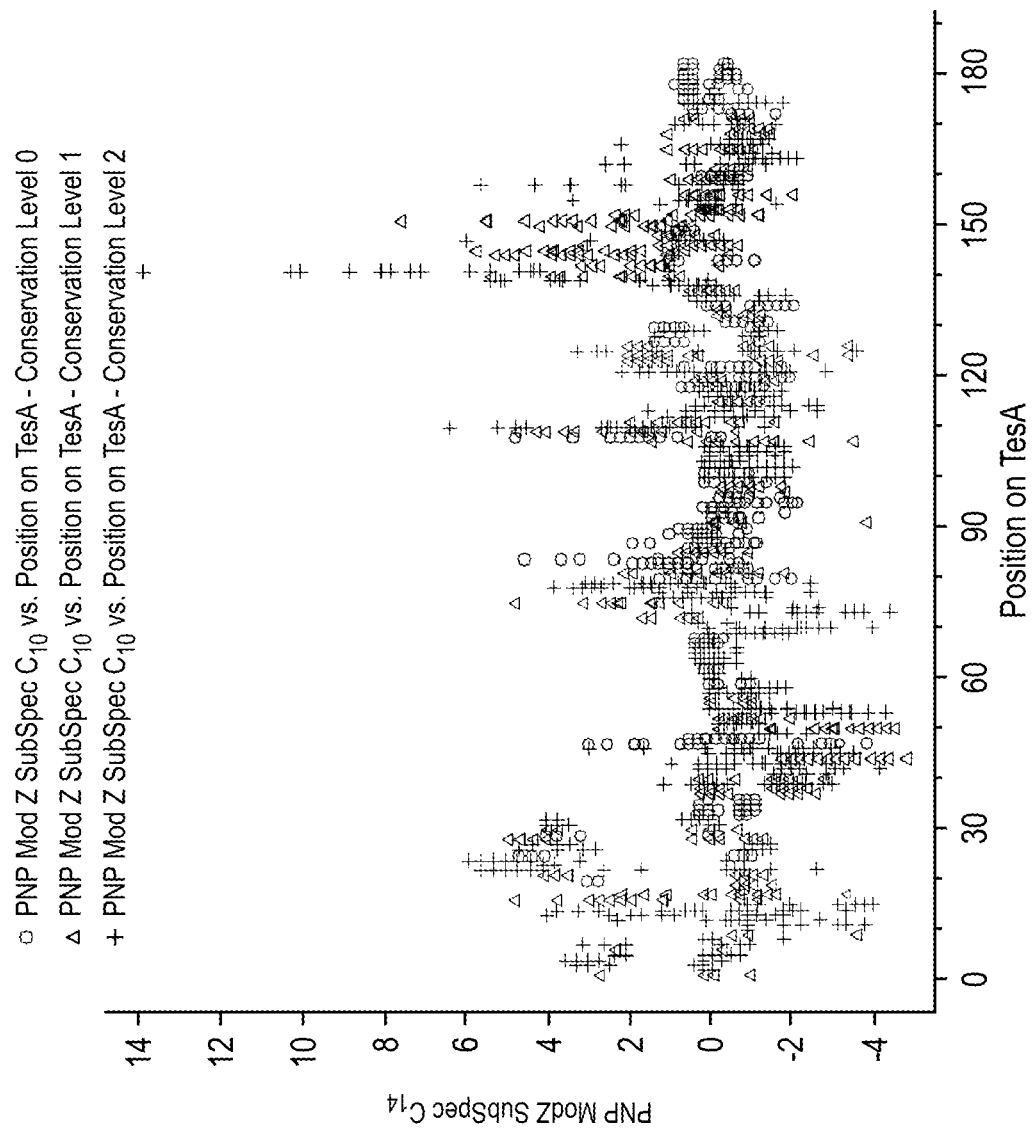
FIG. 57D  Z score vs. Substrate specificity for $C_{10}$ over $C_{12}$ and $C_{14}$ by position

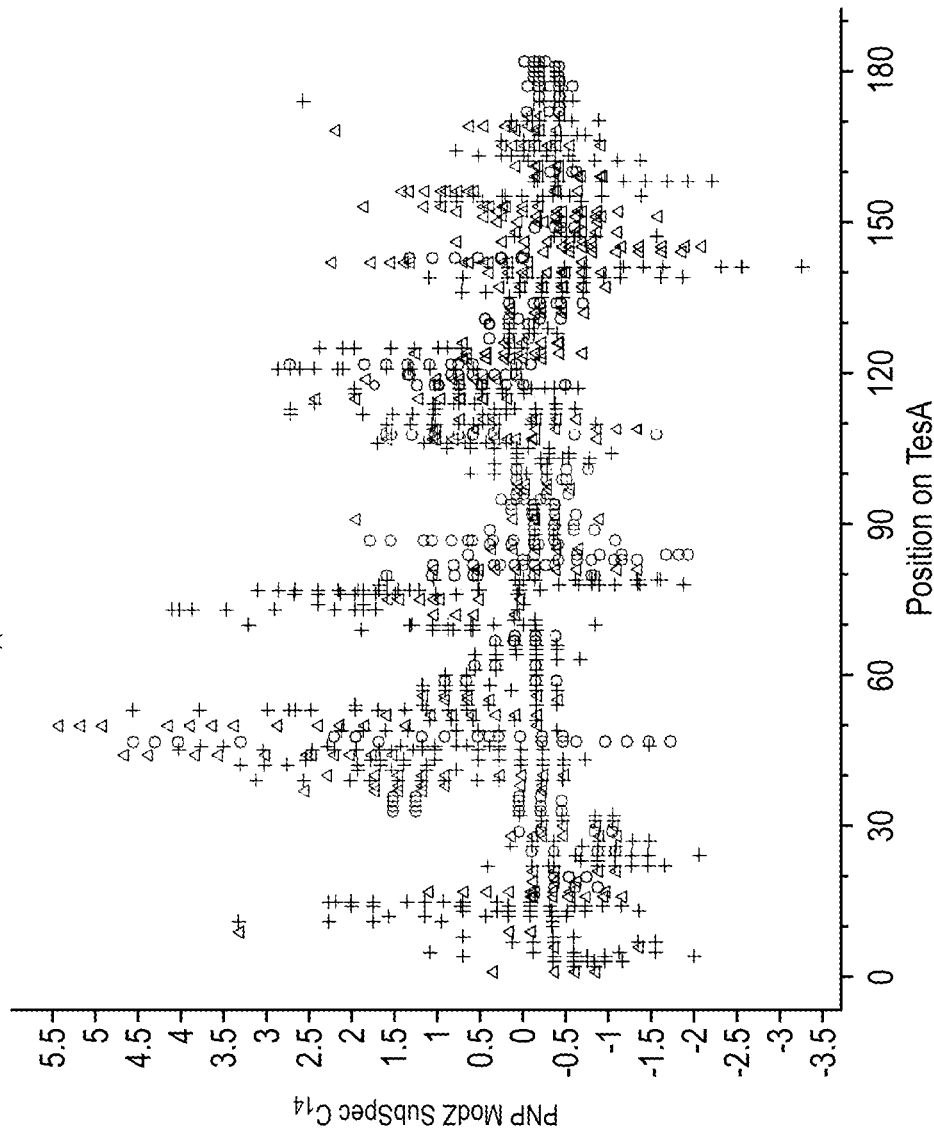
FIG. 57F   Z score vs. Substrate specificity for $C_{14}$ over $C_{10}$ and $C_{12}$ by position

FIG. 58

Met Ala Asp Thr Leu Leu Ile Leu Gly Asp Ser Leu Ser Ala Gly Tyr

Arg Met Ser Ala Ser Ala Ala Trp Pro Ala Leu Leu Asn Asp Lys Trp

Gln Ser Lys Thr Ser Val Val Asn Ala Ser Ile Ser Gly Asp Thr Ser

Gln Gln Gly Leu Ala Arg Leu Pro Ala Leu Leu Lys Gln His Gln Pro

Arg Trp Val Leu Val Glu Leu Gly Gly Asn Asp Gly Leu Arg Gly Phe

Gln Pro Gln Gln Thr Glu Gln Thr Leu Arg Gln Ile Leu Gln Asp Val

Lys Ala Ala Asn Ala Glu Pro Leu Leu Met Gln Ile Arg Leu Pro Ala

Asn Tyr Gly Arg Arg Tyr Asn Glu Ala Phe Ser Ala Ile Tyr Pro Lys

Leu Ala Lys Glu Phe Asp Val Pro Leu Leu Pro Phe Phe Met Glu Glu

Val Tyr Leu Lys Pro Gln Trp Met Gln Asp Gly Ile His Pro Asn

Arg Asp Ala Gln Pro Phe Ile Ala Asp Trp Met Ala Lys Gln Leu Gln

Pro Leu Val Asn His Asp Ser (SEQ ID NO:31)

FIG. 59

ATGGCGGACACGTTATTGATTCTGGGTGATAGCCTGAGCGCCGGGTATCGAATGTCTGCCAGCG
CGGCCTGGCCTGCCTTGTTGAATGATAAGTGGCAGAGTAAAACGTCGGTAGTTAATGCCAGCAT
CAGCGGCGACACCTCGCAACAAGGACTGGCGCGCCTTCCGGCTCTGCTGAAACAGCATCAGCCG
CGTTGGGTGCTGGTTGAACTGGGCGGCAATGACGGTTTGCGTGGTTTTCAGCCACAGCAAACCG
AGCAAACGCTGCGCCAGATTTTGCAGGATGTCAAAGCCGCCAACGCTGAACCATTGTTAATGCA
AATACGTCTGCCTGCAAACTATGGTCGCCGTTATAATGAAGCCTTTAGCGCCATTTACCCCAAA
CTCGCCAAAGAGTTTGATGTTCCGCTGCTGCCCTTTTTTATGGAAGAGGTCTACCTCAAGCCAC
AATGGATGCAGGATGACGGTATTCATCCCAACCGCGACGCCCAGCCGTTTATTGCCGACTGGAT
GGCGAAGCAGTTGCAGCCTTTAGTAAATCATGACTCATAA (SEQ ID NO:32)

SEQUENCE LISTING

```
<160> NUMBER OF SEQ ID NOS: 108

<210> SEQ ID NO 1
<211> LENGTH: 5903
<212> TYPE: DNA
<213> ORGANISM: Artificial Sequence
<220> FEATURE:
<223> OTHER INFORMATION: Description of Artificial Sequence: Synthetic
      polynucleotide expression vector pOP-80

<400> SEQUENCE: 1
cactatacca attgagatgg gctagtcaat gataattact agtcctttc ctttgagttg      60 tgggtatctg taaattctgc tagacctttg ctggaaaact tgtaaattct gctagaccct     120
ctgtaaattc cgctagacct ttgtgtgttt tttttgttta tattcaagtg gttataattt     180
atagaataaa gaaagaataa aaaaagataa aagaataga tcccagccct gtgtataact     240
cactacttta gtcagttccg cagtattaca aaaggatgtc gcaaacgctg tttgctcctc     300
tacaaaacag accttaaaac cctaaaggcg tcggcatccg cttacagaca agctgtgacc     360
gtctccggga gctgcatgtg tcagaggttt tcaccgtcat caccgaaacg cgcgaggcag     420
cagatcaatt cgcgcgcgaa ggcgaagcgg catgcattta cgttgacacc atcgaatggt     480
gcaaaacctt tcgcggtatg gcatgatagc gcccggaaga gagtcaattc agggtggtga     540
atgtgaaacc agtaacgtta tacgatgtcg cagagtatgc cggtgtctct tatcagaccg     600 tttccgcgt ggtgaaccag gccagccacg tttctgcgaa aacgcgggaa aaagtggaag     660
```

```
cggcgatggc ggagctgaat tacattccca accgcgtggc acaacaactg gcgggcaaac      720
agtcgttgct gattggcgtt gccacctcca gtctggccct gcacgcgccg tcgcaaattg      780
tcgcggcgat taaatctcgc gccgatcaac tgggtgccag cgtggtggtg tcgatggtag      840
aacgaagcgg cgtcgaagcc tgtaaagcgg cggtgcacaa tcttctcgcg caacgcgtca      900
gtgggctgat cattaactat ccgctggatg accaggatgc cattgctgtg aagctgcct       960 gcactaatgt tccggcgtta tttcttgatg tctctgacca gacacccatc aacagtatta     1020
ttttctccca tgaagacggt acgcgactgg gcgtggagca tctggtcgca ttgggtcacc     1080
agcaaatcgc gctgttagcg ggcccattaa gttctgtctc ggcgcgtctg cgtctggctg     1140
gctggcataa atatctcact cgcaatcaaa ttcagccgat agcggaacgg gaaggcgact     1200
ggagtgccat gtccggtttt caacaaacca tgcaaatgct gaatgagggc atcgttccca     1260
ctgcgatgct ggttgccaac gatcagatgg cgctgggcgc aatgcgcgcc attaccgagt     1320
ccgggctgcg cgttggtgcg gatatctcgg tagtgggata cgacgatacc gaagacagct     1380
catgttatat cccgccgtta accaccatca aacaggattt tcgcctgctg gggcaaacca     1440
gcgtggaccg cttgctgcaa ctctctcagg gccaggcggt gaagggcaat cagctgttgc     1500
ccgtctcact ggtgaaaaga aaaaccaccc tggcgcccaa tacgcaaacc gcctctcccc     1560
gcgcgttggc cgattcatta atgcagctgg cacgacaggt ttcccgactg gaaagcgggc     1620
agtgagcgca acgcaattaa tgtaagttag cgcgaattga tctggtttga cagcttatca     1680
tcgactgcac ggtgcaccaa tgcttctggc gtcaggcagc catcggaagc tgtggtatgg     1740
ctgtgcaggt cgtaaatcac tgcataattc gtgtcgctca aggcgcactc ccgttctgga     1800
taatgttttt tgcgccgaca tcataacggt tctggcaaat attctgaaat gagctgttga     1860
caattaatca tccggctcgt ataatgtgtg gaattgtgag cggataacaa tttcacacag     1920
gaaacagcgc cgctgagaaa aagcgaagcg gcactgctct ttaacaattt atcagacaat     1980
ctgtgtgggc actcgaccgg aattatcgat taactttatt attaaaaatt aaagaggtat     2040
atattaatgt atcgattaaa taaggaggaa taaaccatgg atccgagctc gagatctgca     2100
gctggtacca tatgggaatt cgaagcttgg gcccgaacaa aaactcatct cagaagagga     2160
tctgaatagc gccgtcgacc atcatcatca tcatcattga gtttaaacgg tctccagctt     2220
ggctgttttg gcggatgaga gaagattttc agcctgatac agattaaatc agaacgcaga     2280
agcggtctga taaaacagaa tttgcctggc ggcagtagcg cggtggtccc acctgacccc     2340
atgccgaact cagaagtgaa acgccgtagc gccgatggta gtgtggggtc tccccatgcg     2400
agagtaggga actgccaggc atcaaataaa acgaaaggct cagtcgaaag actgggcctt     2460
tcgttttatc tgttgtttgt cggtgaacgc tctcctgacg cctgatgcgg tattttctcc     2520
ttacgcatct gtgcggtatt tcacaccgca tatggtgcac tctcagtaca atctgctctg     2580
atgccgcata gttaagccag ccccgacacc cgccaacacc cgctgacgag cttagtaaag     2640
ccctcgctag attttaatgc ggatgttgcg attacttcgc caactattgc gataacaaga     2700
aaaagccagc ctttcatgat atatctccca atttgtgtag ggcttattat gcacgcttaa     2760
aaataataaa agcagacttg acctgatagt ttggctgtga caattatgt  gcttagtgca     2820 tctaacgctt gagttaagcc gcgccgcgaa gcggcgtcgg cttgaacgaa ttgttagaca     2880
ttatttgccg actaccttgg tgatctcgcc tttcacgtag tggacaaatt cttccaactg     2940 atctgcgcg  gaggccaagc gatcttcttc ttgtccaaga taagcctgtc tagcttcaag     3000
tatgacgggc tgatactggg ccggcaggcg ctccattgcc cagtcggcag cgacatcctt     3060
```

```
cggcgcgatt tgccggtta ctgcgctgta ccaaatgcgg gacaacgtaa gcactacatt      3120
tcgctcatcg ccagcccagt cgggcggcga gttccatagc gttaaggttt catttagcgc      3180
ctcaaataga tcctgttcag gaaccggatc aaagagttcc tccgccgctg gacctaccaa      3240
ggcaacgcta tgttctcttg cttttgtcag caagatagcc agatcaatgt cgatcgtggc      3300
tggctcgaag atacctgcaa gaatgtcatt gcgctgccat tctccaaatt gcagttcgcg      3360
cttagctgga taacgccacg gaatgatgtc gtcgtgcaca acaatggtga cttctacagc      3420
gcggagaatc tcgctctctc caggggaagc cgaagtttcc aaaaggtcgt tgatcaaagc      3480
tcgccgcgtt gtttcatcaa gccttacggt caccgtaacc agcaaatcaa tatcactgtg      3540
tggcttcagg ccgccatcca ctgcggagcc gtacaaatgt acggcagca acgtcggttc       3600 gagatggcgc tcgatgacgc caactacctc tgatagttga gtcgatactt cggcgatcac      3660
cgcttccctc atgatgttta actttgtttt agggcgactg ccctgctgcg taacatcgtt      3720
gctgctccat aacatcaaac atcgaccac ggcgtaacgc gcttgctgct tggatgcccg        3780
aggcatagac tgtaccccaa aaaacagtc ataacaagcc atgaaaaccg ccactgcgcc        3840
gttaccaccg ctgcgttcgg tcaaggttct ggaccagttg cgtgagcgca tacgctactt      3900
gcattacagc ttacgaaccg aacaggctta tgtccactgg gttcgtgcct tcatccgttt      3960
ccacggtgtg cgtcacccgg caaccttggg cagcagcgaa gtcgaggcat ttctgtcctg      4020
gctggcgaac gagcgcaagg tttcggtctc cacgcatcgt caggcattgg cggccttgct      4080
gttcttctac ggcaaggtgc tgtgcacgga tctgccctgg cttcaggaga tcggaagacc      4140
tcggccgtcg cggcgcttgc cggtggtgct gaccccggat gaagtggttc gcatcctcgg      4200
ttttctggaa ggcgagcatc gtttgttcgc ccagcttctg tatggaacgg gcatgcggat      4260
cagtgagggt ttgcaactgc gggtcaagga tctggatttc gatcacggca cgatcatcgt      4320 gcggagggc aagggctcca aggatcgggc cttgatgtta cccgagagct ggcaccccag       4380
cctgcgcgag caggggaatt aattcccacg ggttttgctg cccgcaaacg ggctgttctg      4440
gtgttgctag tttgttatca gaatcgcaga tccggcttca gccggtttgc cggctgaaag      4500
cgctatttct tccagaattg ccatgatttt ttccccacgg gaggcgtcac tggctcccgt      4560
gttgtcggca gctttgattc gataagcagc atcgcctgtt tcaggctgtc tatgtgtgac      4620
tgttgagctg taacaagttg tctcaggtgt tcaatttcat gttctagttg ctttgtttta      4680
ctggtttcac ctgttctatt aggtgttaca tgctgttcat ctgttacatt gtcgatctgt      4740
tcatggtgaa cagctttgaa tgcaccaaaa actcgtaaaa gctctgatgt atctatcttt      4800
tttacaccgt tttcatctgt gcatatggac agttttccct ttgatatgta acggtgaaca      4860
gttgttctac ttttgtttgt tagtcttgat gcttcactga tagatacaag agccataaga      4920
acctcagatc cttccgtatt tagccagtat gttctctagt gtggttcgtt gttttttgcgt     4980 gagccatgag aacgaaccat tgagatcata cttactttgc atgtcactca aaaatttgc       5040 ctcaaaactg gtgagctgaa tttttgcagt taaagcatcg tgtagtgttt tcttagtcc       5100 gttatgtagg taggaatctg atgtaatggt tgttggtatt tgtcaccat tcattttttat       5160 ctggttgttc tcaagttcgg ttacgagatc catttgtcta tctagttcaa cttggaaaat      5220
caacgtatca gtcgggcggc ctcgcttatc aaccaccaat ttcatattgc tgtaagtgtt      5280 taaatctttta cttattggtt tcaaaaccca ttggttaagc cttttaaact catggtagtt     5340
attttcaagc attaacatga acttaaattc atcaaggcta atctctatat ttgccttgtg      5400
```

| | |
|---|---:|
| agttttctttt tgtgttagtt cttttaataa ccactcataa atcctcatag agtatttgtt | 5460 |
| ttcaaaagac ttaacatgtt ccagattata ttttatgaat ttttttaact ggaaaagata | 5520 |
| aggcaatatc tcttcactaa aaactaattc taattttcg cttgagaact tggcatagtt | 5580 |
| tgtccactgg aaaatctcaa agcctttaac caaaggattc ctgatttcca cagttctcgt | 5640 |
| catcagctct ctggttgctt tagctaatac accataagca ttttccctac tgatgttcat | 5700 |
| catctgagcg tattggttat aagtgaacga taccgtccgt tctttccttg tagggttttc | 5760 |
| aatcgtgggg ttgagtagtg ccacacagca taaaattagc ttggtttcat gctccgttaa | 5820 |
| gtcatagcga ctaatcgcta gttcatttgc tttgaaaaca actaattcag acatacatct | 5880 |
| caattggtct aggtgatttt aat | 5903 |

```
<210> SEQ ID NO 2
<211> LENGTH: 1652
<212> TYPE: DNA
<213> ORGANISM: Mycobacterium tuberculosis

<400> SEQUENCE: 2
```

| | |
|---|---:|
| ccatggcagc agcggaagtg gttgatccaa atcgtctgag ctatgatcgt ggcccgagcg | 60 |
| cgccgagcct gttggagagc accatcggtg caaacctggc cgctacggcg gcccgttacg | 120 |
| gccaccgcga ggccctggtg gacatggtcg cacgccgtcg cttcaattat agcgagctgc | 180 |
| tgacggatgt tcaccgtttg gctacgggcc tggtgcgtgc tggtattggc ccaggcgacc | 240 |
| gtgtgggtat ttgggcgccg aatcgttggg agtgggttct ggtccagtat gcaacggcgg | 300 |
| agattggtgc gatcctggtt acgattaacc cggcttatcg cgtgcgtgag gttgaatacg | 360 |
| cgctgcgtca atctggcgtc gcgatggtca ttgcggttgc gtccttcaag gacgctgatt | 420 |
| acgctgcgat gctggcggag gttggtccgc gttgcccgga cctggctgac gtgatcctgt | 480 |
| tggaaagcga ccgttgggac gcactggcag gtgccgagcc ggatctgccg gcgctgcagc | 540 |
| agaccgctgc ccgcctggat ggttccgatc cggttaacat tcaatacacc agcggtacga | 600 |
| ccgcgtaccc gaaaggtgtt acgctgagcc accgcaatat cctgaataac ggttatttgg | 660 |
| ttggtgagct gttgggttat acggcgcagg atcgtatttg catcccggtg ccgttctacc | 720 |
| actgctttgg tatggtcatg ggcaacttgg cggcgacctc ccacggtgcg gcgatggtta | 780 |
| ttccggcgcc aggtttcgac ccagcggcta cgctgcgcgc ggtgcaagat gaacgctgta | 840 |
| cgtctctgta cggcgttccg accatgttta ttgcagaact gggtctgccg gatttcaccg | 900 |
| attacgagct gggttctttg cgtaccggca tcatggcagg cgcagcgtgt ccggttgaag | 960 |
| tcatgcgtaa agtgatcagc cgtatgcaca tgccgggtgt cagcatttgc tacggtatga | 1020 |
| ccgagacgag cccggtgagc acccaaaccc gtgcggacga tagcgtggac cgtcgtgtgg | 1080 |
| gcaccgttgg ccgcgtcggc ccgcacctgg aaattaaagt tgttgaccca gcgaccggcg | 1140 |
| aaaccgttcc cgcgcggtgtt gttggcgaat tttgcacgcg tggctactct gtcatggcgg | 1200 |
| gttattggaa tgacccgcag aaaacggcag aggtgatcga cgctgatggt tggatgcata | 1260 |
| ccggtgacct ggcggaaatg gacccgagcg gttacgttcg tattgcaggc cgcattaaag | 1320 |
| acctggtggt tcgtggcggt gagaacatta gcccgcgtga aattgaggag ctgctgcata | 1380 |
| cccatccgga catcgttgat ggtcacgtga tcggtgttcc ggatgcgaaa tatggcgaag | 1440 |
| agctgatggc agttgtgaag ctgcgtaatg atgcgccgga gttgacgatt gaacgcctgc | 1500 |
| gtgagtattg catgggtcgc atcgcacgct ttaaaatccc gcgctacttg tggatcgttg | 1560 |
| acgagttccc gatgaccgtg accggcaagg tccgtaaggt cgagatgcgt cagcaggcat | 1620 |

```
tggaatatct gcgtggtcaa cagtaagaat tc                                   1652
```

<210> SEQ ID NO 3
<211> LENGTH: 1697
<212> TYPE: DNA
<213> ORGANISM: Pseudomonas aeruginosa

<400> SEQUENCE: 3

```
tcatgatcga gaattttggg aaggacaagt atccggcagg tattgcagca gaaattaatc      60
cggatcagta tccgaatatt ctgagcgtcc tgaaggagag ctgccaacgt tttgcgacca     120
agccggcgtt tacgaacttg gtaagacct  tgacctatgg tgagctgtac aaactgtctg     180
gcgacttcgc agcgtacctg caacaacata ccgatctgaa accgggtgat cgtattgccg     240
ttcagctgcc gaacgttctg cagtacccga tcgttgtctt cggcgcaatg cgtgcgggtc     300
tgatcgtggt gaacacgaac ccgttgtata cggcgcgtga gttggaacac cagtttaatg     360
atagcggcgc aaaagcggtg gtttgtttgg ctaatatggc ccacctggtt gaaggtgttt     420
tgccgaagac cggtgttaaa caggtgattg tcaccgaggt gggcgacatt ctgccaccgc     480
tgaagcgttt cattgtcaat ttcgtcgtca aacacattaa gaagatggtc ccggcctatt     540
ccctgccgca ggccacgaag ttgaccgatg cactggcccg tggtgcaggc aagagcttcc     600
aagaagcggc accgcaggca gacgacgtcg cggtgctgca gtacaccggc ggtaccacgg     660
gcgtcgccaa gggtgcgatg ctgacccatc gtaacctggt cgctaacatg ttgcagtgta     720
aagcgctgat gggtgcgaac ctgaacgagg gttgcgaaat cttgattgcc ccgttgccgc     780
tgtatcacat ttatgcgttt accttccact gtatggctat gatgctgacg ggtaatcata     840
acattctgat caccaatccg cgcgacctgc cgagcatgct gaaggacctg ggtcagtgga     900
agttcacggg tttcgtgggt ctgaatacgc tgttcgtcgc gctgtgcaat aatgagacct     960
tccgtaagct ggactttagc gcactgaagc tgaccctgag cggcggcatg gcgctgcagc    1020
tggccacggc ggaacgttgg aaagaggtca cgggctgcgc tatttgcgag ggttatggta    1080
tgaccgaaac ggccccggtg gtttccgtca acccgtttca gaacattcaa gttggcacca    1140
tcggtattcc ggtgccaagc accttgtgta aggttattgg cgatgacggt caagaagttc    1200
cgctgggcga gcgcggtgag ttgtgcgtca agggtccgca ggttatgaag ggctactggc    1260
agcgccagga ggcaacggac gagattctgg acgctgatgg ttggttgaaa accggcgata    1320
ttgcaattat tcaagaagac ggctatatgc gcattgtcga tcgtaagaaa gacatgattt    1380
tggttagcgg tttcaacgtt tacccgaatg aattggaaga tgttttggcg accttgccgg    1440
gtgtgctgca atgcgcagcg atcggtatcc cggatgaaaa gagcggcgag tctatcaagg    1500
ttttcgttgt tgtgaagccg ggtgcgaccc tgaccaaaga gcaggtcatg cagcatatgc    1560
acgataacct gaccggctac aaacgcccga agcagtggaa gttccgtgat agcctgccaa    1620
cgaccaatgt tggcaagatt ttgcgtcgtg agctgcgcga tgaagagctg aaaaaggcag    1680
gccagaagta agaattc                                                   1697
```

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4

```
catcatgaat cttgtttc                                                  18
```

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 5

```
cggaattctt attggggcaa aatatc                                         26
```

<210> SEQ ID NO 6
<211> LENGTH: 1550
<212> TYPE: DNA
<213> ORGANISM: Bacillus subtilis

<400> SEQUENCE: 6

```
tcatgaatct tgtttcaaaa ttggaagaaa cagcatctga gaagcccgac agcatcgcat     60
gcaggtttaa agatcacatg atgacgtatc aagagctgaa tgaatatatt cagcgatttg    120
cggacggcct tcaggaagcc ggtatggaga aaggggacca tttagctttg ctgcttggca    180
attcgcctga ttttatcatc gcgttttttg gcgctttaaa agctgggatc gtagttgttc    240
ccatcaatcc gttgtacacg ccgacagaaa ttggttatat gctgacaaat ggcgatgtaa    300
aggcaatcgt gggcgttagc cagcttttgc cgctttatga gagcatgcat gaatcgctgc    360
caaaggttga gctcgtcatt ttatgccaga cgggggaggc cgagccggaa gctgcggacc    420
cagaggtcag gatgaaaatg acaacgtttg caaaaatatt gcggccgaca tctgccgcta    480
aacaaaacca agaacctgta cctgatgata ccgcggttat tttatatacg tcaggaacga    540
ctggaaaacc gaaaggcgcg atgctgacac atcagaattt gtacagcaat gccaacgatg    600
tcgcaggcta tttgggaatg gatgagaggg acaatgtggt ctgcgctctt cccatgtgtc    660
acgtgttttg tttaaccgtc tgtatgaatg caccgctgat gagcggcgca actgtattga    720
ttgagcctca attcagtccg gcatctgttt ttaagcttgt taagcagcag caggcgacca    780
ttttttgccgg tgtgcctaca atgtataact acttgtttca gcatgaaaac ggaaagaaag    840
atgatttttc ttcgatccgg ctgtgcattt cgggaggcgc gtccatgcca gtcgcgttgc    900
tgacggcgtt tgaagaaaaa ttcggtgtta ccattttgga aggctacggg ctctcggaag    960
catcacccgt cacgtgcttt aacccgtttg acagggcag aaagccgggc tccatcggga    1020
caagtatctt acatgtcgaa aacaaggtcg tagatccgct cggacgcgag ctgcccgctc    1080
accaggtcgg cgaattgatc gtgaaaggcc ccaatgtgat gaagggctat tataaaatgc    1140
cgatggaaac agagcatgca ttaaaagacg ggtggcttta tacggggggac ttggcaagac    1200
gggatgagga cggctatttt tacattgttg accggaaaaa agacatgatc attgtaggag    1260
gatacaatgt gtatccgcgg gaggtggagg aggtgctgta cagccatccg gacgtcaagg    1320
aggcggttgt catcggcgtg ccggaccccc aaagcgggga agcggtaaag ggatatgtgg    1380
tgccgaaacg ctctgggggta acagaggagg acatcatgca gcactgcgaa aagcatctgg    1440
caaaatacaa gcggcctgcc gccattacgt ttcttgacga tattccgaaa aatgcgacgg    1500
ggaaaatgct cagacgggca ctgagagata ttttgcccca ataagaattc                1550
```

<210> SEQ ID NO 7
<211> LENGTH: 19

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cgacatgtcc gaacaacac                                                19

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gcaagcttct aagaattttc tttg                                          24

<210> SEQ ID NO 9
<211> LENGTH: 1685
<212> TYPE: DNA
<213> ORGANISM: Saccharomyces cerevisiae

<400> SEQUENCE: 9
tcatgagtct ggatcgtccc tggctgcaga gctatccgaa aggcgttccc gccgaaatcg     60
acgtcaacga attccattcg gtcgcctcgg tcttcgacgc ttccgtcgcg aaattccgcg    120
accgtcccgc ctactccagc ttcggcaagg tcctcaccta tggtgagacg gacgcgctgg    180
tcacccagtt cgccgcctac ctgctgggtg agctcaagct caagaagggt gaccgcgtcg    240
ccctgatgat gcccaactgc ctgcagtacc cggtggccac cttcggcgtg ctgcgcgccg    300
gcctgaccgt ggtcaacgtc aacccgctgt acaccgcgcg cgaactcaag caccagctgg    360
ttgatgccgg cgtcagcgcc ctggtggtgg tcgacaactt cggcgacacc gtcgaacagg    420
tcatcgccga tacaccggtc aagcacgtgg tcaccaccgg cctgggcgac ctgctcggcg    480
ccaagggcgc gatcgtcaac ttcgtgctga agtacatcaa gaagatggtg cccaactacc    540
acatcaaggg cgccgtccgc ttcaagcagg cgctcaagct gggcagccgc cacgcgcttc    600
cgccggtcga gatcgaccac gacgacattg ccttcctgca gtacaccggc gggaccaccg    660
gcgtggccaa gggtgcgatg ctgaccaacc gcaacctgat cgccaacatg cagcaggcgt    720
cagcgtggct gtccacctcc ggcatcgagc cgggcaagga agtgatcatc actgccctgc    780
cgctgtacca catcttcgca ttgaccgcga acggcctggt ctttatgaag ttcggtggct    840
gcaaccacct gatcaccaac ccacgcgaca tgaagggctt cgtaaaggag ctcaagggca    900
cccgcttcac tgccatcacc ggcgtcaaca cgctgttcaa cggcctgctc aacacccgg    960 gcttcgacga gatcgacttc tcttcggtca agttcaccct gggcggcggc atggcggtgc   1020
aacgtgccgt ggccgaacgc tggaagaagg tcaccggcgt gacccctggtc gaagcctatg   1080 gcctgaccga gacctcgccc gcggcctgca tcaatccgct caccctgccc gagtacaacg   1140
gtgccatcgg cctgccgatc ccgtctaccg atgcctgcat caaggacgac aacggcaaca   1200
tcctggcgct gggcgaagtg ggcgagctgt gcatcaaggg cccgcaggta atgaagggct   1260
actggcagcg tccggaagaa accgccaccg ccatcgatgc ggacggctgg ctgcacaccg   1320
gcgacatggc gaagatggac gaacagggct tcttctacat cgtcgaccgc aagaaggaca   1380
tgatcctggt gtccggcttc aacgtgtacc cgaatgaggt cgaagacgtc atcgggatga   1440
```

```
tgccgggcgt gctggaagtc gccgccgtcg gtgtcccgga cgaaaagtcc ggcgaagtgg    1500
tcaaggtcgt gatcgtgaag aaggacccga acctgaccgc ggaaatggtc aaggaacatg    1560
cgcgggcaaa cctgaccggt tacaagcacc ccagaatcgt agaattccga aaggagctgc    1620
cgaagaccaa cgtcggcaag atcctccgtc gcgagctgcg tgatacgccc gccccgtaag    1680
aattc                                                                1685
```

```
<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
agtcatgagt ctggatcg                                                  18
```

```
<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ggaagcttac ggggcgggcg                                                20
```

```
<210> SEQ ID NO 12
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gcgaacggcc tggtctttat gaagttcggt gg                                  32
```

```
<210> SEQ ID NO 13
<211> LENGTH: 1685
<212> TYPE: DNA
<213> ORGANISM: Stenotrophomonas maltophilia

<400> SEQUENCE: 13
tcatgagtct ggatcgtccc tggctgcaga gctatccgaa aggcgttccc gccgaaatcg    60
acgtcaacga attccattcg gtcgcctcgg tcttcgacgc ttccgtcgcg aaattccgcg    120
accgtcccgc ctactccagc ttcggcaagg tcctcaccta tggtgagacg gacgcgctgg    180
tcacccagtt cgccgcctac ctgctgggtg agctcaagct caagaagggt gaccgcgtcg    240
ccctgatgat gccaactgc ctgcagtacc cggtggccac cttcggcgtg ctgcgcgccg    300
gcctgaccgt ggtcaacgtc aacccgctgt acaccgcgcg cgaactcaag caccagctgg    360
ttgatgccgg cgtcagcgcc ctggtggtgg tcgacaactt cggcgacacc gtcgaacagg    420
tcatcgccga taccggtc aagcacgtgg tcaccaccgg cctgggcgac ctgctcggcg    480
ccaagggcgc gatcgtcaac ttcgtgctga agtacatcaa gaagatggtg cccaactacc    540
acatcaaggg cgccgtccgc ttcaagcagg cgctcaagct gggcagccgc cacgcgcttc    600
cgccggtcga gatcgaccac gacgacattg ccttcctgca gtacaccggc gggaccaccg    660
```

```
gcgtggccaa gggtgcgatg ctgaccaacc gcaacctgat cgccaacatg cagcaggcgt    720
cagcgtggct gtccacctcc ggcatcgagc cgggcaagga agtgatcatc actgccctgc    780
cgctgtacca catcttcgca ttgaccgcga acggcctggt ctttatgaag ttcggtggct    840
gcaaccacct gatcaccaac ccacgcgaca tgaagggctt cgtaaaggag ctcaagggca    900
cccgcttcac tgccatcacc ggcgtcaaca cgctgttcaa cggcctgctc aacaccccgg    960
gcttcgacga gatcgacttc tcttcggtca agttcaccct gggcggcggc atggcggtgc   1020
aacgtgccgt ggccgaacgc tggaagaagg tcaccggcgt gaccctggtc gaagcctatg   1080
gcctgaccga gacctcgccc gcggcctgca tcaatccgct caccctgccc gagtacaacg   1140
gtgccatcgg cctgccgatc ccgtctaccg atgcctgcat caaggacgac aacggcaaca   1200
tcctggcgct gggcgaagtg ggcgagctgt gcatcaaggg cccgcaggta atgaagggct   1260
actggcagcg tccggaagaa accgccaccg ccatcgatgc ggacggctgg ctgcacaccg   1320
gcgacatggc gaagatggac gaacagggct tcttctacat cgtcgaccgc aagaaggaca   1380
tgatcctggt gtccggcttc aacgtgtacc cgaatgaggc gaagacgtc atcgcgatga   1440 tgccgggcgt gctggaagtc gccgccgtcg gtgtcccgga cgaaaagtcc ggcgaagtgg   1500
tcaaggtcgt gatcgtgaag aaggacccga acctgaccgc ggaaatggtc aaggaacatg   1560
cgcgggcaaa cctgaccggt tacaagcacc ccagaatcgt agaattccga aggagctgc   1620 cgaagaccaa cgtcggcaag atcctccgtc gcgagctgcg tgatacgccc gccccgtaag   1680
aattc                                                              1685
```

<210> SEQ ID NO 14
<211> LENGTH: 558
<212> TYPE: PRT
<213> ORGANISM: Stenotrophomonas maltophilia

<400> SEQUENCE: 14

```
Met Ser Leu Asp Arg Pro Trp Leu Gln Ser Tyr Pro Lys Gly Val Pro
1               5                   10                  15

Ala Glu Ile Asp Val Asn Glu Phe His Ser Val Ala Ser Val Phe Asp
            20                  25                  30

Ala Ser Val Ala Lys Phe Arg Asp Arg Pro Ala Tyr Ser Ser Phe Gly
        35                  40                  45

Lys Val Ile Thr Tyr Gly Glu Thr Asp Thr Leu Val Asn Gln Phe Ala
    50                  55                  60

Ala Tyr Leu Leu Gly Glu Leu Lys Leu Lys Lys Gly Asp Arg Val Ala
65                  70                  75                  80

Leu Met Met Pro Asn Cys Leu Gln Tyr Pro Val Ala Thr Phe Gly Val
                85                  90                  95

Leu Arg Ala Gly Leu Thr Val Val Asn Val Asn Pro Leu Tyr Thr Ala
            100                 105                 110

Arg Glu Leu Lys His Gln Leu Val Asp Ala Gly Val Ser Ala Leu Val
        115                 120                 125

Val Val Asp Asn Phe Gly Asp Thr Val Glu Gln Val Ile Ala Asp Thr
    130                 135                 140

Pro Val Lys His Val Ile Thr Thr Gly Leu Gly Asp Leu Leu Gly Ala
145                 150                 155                 160

Lys Gly Ala Ile Val Asn Phe Val Leu Lys Tyr Val Lys Lys Met Val
                165                 170                 175

Pro Asn Tyr His Ile Lys Gly Ala Val Arg Phe Lys Gln Ala Leu Lys
            180                 185                 190
```

Leu Gly Ser Arg His Thr Leu Pro Ala Val Glu Ile Asp His Asp Asp
        195                 200                 205

Ile Ala Phe Leu Gln Tyr Thr Gly Gly Thr Thr Gly Val Ala Lys Gly
    210                 215                 220

Ala Met Leu Thr Asn Arg Asn Leu Ile Ala Asn Met Gln Gln Ala Ser
225                 230                 235                 240

Ala Trp Leu Ser Thr Ser Gly Ile Glu Pro Gly Lys Glu Val Ile Ile
                245                 250                 255

Thr Ala Leu Pro Leu Tyr His Ile Phe Ala Leu Thr Ala Asn Gly Leu
        260                 265                 270

Val Phe Met Lys Phe Gly Gly Cys Asn His Leu Ile Thr Asn Pro Arg
            275                 280                 285

Asp Met Lys Gly Phe Val Lys Glu Leu Lys Gly Thr Arg Phe Thr Ala
        290                 295                 300

Ile Thr Gly Val Asn Thr Leu Phe Asn Gly Leu Leu Asn Thr Pro Gly
305                 310                 315                 320

Phe Asp Glu Ile Asp Phe Ser Ser Val Lys Phe Thr Leu Gly Gly Gly
                325                 330                 335

Met Ala Val Gln Arg Ala Val Ala Glu Arg Trp Lys Lys Thr Thr Gly
        340                 345                 350

Val Thr Leu Val Glu Ala Tyr Gly Leu Thr Glu Thr Ser Pro Ala Ala
            355                 360                 365

Cys Ile Asn Pro Leu Thr Leu Pro Glu Tyr Asn Gly Ser Ile Gly Leu
        370                 375                 380

Pro Ile Pro Ser Thr Asp Ala Cys Ile Lys Asp Asn Gly Asn Ile
385                 390                 395                 400

Leu Pro Leu Gly Glu Val Gly Glu Leu Cys Ile Lys Gly Pro Gln Val
                405                 410                 415

Met Lys Gly Tyr Trp Gln Arg Pro Glu Glu Thr Ala Thr Ala Ile Asp
        420                 425                 430

Ala Asp Gly Trp Leu His Thr Gly Asp Met Ala Arg Met Asp Glu Gln
            435                 440                 445

Gly Phe Phe Tyr Ile Val Asp Arg Lys Lys Asp Met Ile Leu Val Ser
        450                 455                 460

Gly Phe Asn Val Tyr Pro Asn Glu Val Glu Asp Val Ile Ala Met Met
465                 470                 475                 480

Pro Gly Val Leu Glu Val Ala Ala Val Gly Val Pro Asp Glu Lys Ser
                485                 490                 495

Gly Glu Val Val Lys Val Val Ile Val Lys Lys Asp Pro Asn Leu Thr
        500                 505                 510

Ala Glu Met Val Lys Glu His Ala Arg Ala Asn Leu Thr Gly Tyr Lys
            515                 520                 525

His Pro Arg Ile Val Glu Phe Arg Lys Glu Leu Pro Lys Thr Asn Val
        530                 535                 540

Gly Lys Ile Leu Arg Arg Glu Leu Arg Asp Thr Pro Ala Pro
545                 550                 555

<210> SEQ ID NO 15
<211> LENGTH: 3525
<212> TYPE: DNA
<213> ORGANISM: Nocardia iowensis

<400> SEQUENCE: 15
atggcagtgg attcaccgga tgagcggcta cagcgccgca ttgcacagtt gtttgcagaa    60

```
gatgagcagg tcaaggccgc acgtccgctc gaagcggtga gcgcggcggt gagcgcgccc    120
ggtatgcggc tggcgcagat cgccgccact gttatggcgg gttacgccga ccgcccggcc    180
gccgggcagc gtgcgttcga actgaacacc gacgacgcga cgggccgcac ctcgctgcgg    240
ttacttcccc gattcgagac catcacctat cgcgaactgt ggcagcgagt cggcgaggtt    300
gccgcggcct ggcatcatga tcccgagaac cccttgcgcg caggtgattt cgtcgccctg    360
ctcggcttca ccagcatcga ctacgccacc ctcgacctgg ccgatatcca cctcggcgcg    420
gttaccgtgc cgttgcaggc cagcgcggcg gtgtcccagc tgatcgctat cctcaccgag    480
acttcgccgc ggctgctcgc ctcgaccccg gagcacctcg atgcggcggt cgagtgccta    540
ctcgcgggca ccacaccgga acgactggtg gtcttcgact accaccccga ggacgacgac    600
cagcgtgcgg ccttcgaatc cgcccgccgc cgccttgccg acgcgggcag cttggtgatc    660
gtcgaaacgc tcgatgccgt gcgtgcccgg ggccgcgact taccggccgc gccactgttc    720
gttcccgaca ccgacgacga cccgctggcc ctgctgatct acacctccgg cagcaccgga    780
acgccgaagg gcgcgatgta caccaatcgg ttggccgcca cgatgtggca ggggaactcg    840
atgctgcagg gaactcgca acgggtcggg atcaatctca actacatgcc gatgagccac    900
atcgccggtc gcatatcgct gttcggcgtg ctcgctcgcg gtggcaccgc atacttcgcg    960
gccaagagcg acatgtcgac actgttcgaa gacatcggtc tggtacgtcc caccgagatc   1020
ttcttcgtcc cgcgcgtgtg cgacatggtc ttccagcgct atcagagcga gctggaccgg   1080
cgctcggtgg cgggcgccga cctggacacg ctcgatcggg aagtgaaagc cgacctccgg   1140
cagaactacc tcggtgggcg cttcctggtg gcggtcgtcg gcagcgcgcc gctggccgcg   1200
gagatgaaga cgttcatgga gtccgtcctc gatctgccac tgcacgacgg gtacgggtcg   1260
accgaggcgg gcgcaagcgt gctgctcgac aaccagatcc agcggccgcc ggtgctcgat   1320
tacaagctcg tcgacgtgcc cgaactgggt tacttccgca ccgaccggcc gcatccgcgc   1380
ggtgagctgt tgttgaaggc ggagaccacg attccgggct actacaagcg gcccgaggtc   1440
accgcggaga tcttcgacga ggacggcttc tacaagaccg gcgatatcgt ggccgagctc   1500
gagcacgatc ggctggtcta tgtcgaccgt cgcaacaatg tgctcaaact gtcgcagggc   1560
gagttcgtga ccgtcgccca tctcgaggcc gtgttcgcca gcagcccgct gatccggcag   1620
atcttcatct acggcagcag cgaacgttcc tatctgctcg cggtgatcgt ccccaccgac   1680
gacgcgctgc gcggccgcga caccgccacc ttgaaatcgg cactggccga atcgattcag   1740
cgcatcgcca aggacgcgaa cctgcagccc tacgagattc gcgcgatttt cctgatcgag   1800
accgagccgt tcaccatcgc caacggactg ctctccggca tcgcgaagct gctgcgcccc   1860
aatctgaagg aacgctacgg cgctcagctg gagcagatgt acaccgatct cgcgacaggc   1920
caggccgatg agctgctcgc cctgcgccgc gaagccgccg acctgccggt gctcgaaacc   1980
gtcagccggg cagcgaaagc gatgctcggc gtcgcctccg ccgatatgcg tcccgacgcg   2040
cacttcaccg acctgggcgg cgattcccct tccgcgctgt cgttctcgaa cctgctgcac   2100
gagatcttcg ggctcgaggt gccggtgggt gtcgtcgtca gcccggcgaa cgagctgcgc   2160
gatctggcga attacattga gcggaacgc aactcgggcg cgaagcgtcc caccttcacc   2220
tcggtgcacg gcggcggttc cgagatccgc gccgccgatc tgaccctcga caagttcatc   2280
gatgcccgca cctggccgc cgccgacagc attccgcacg cgccggtgcc agcgcagacg   2340
gtgctgctga ccggcgcgaa cggctacctc ggccggttcc tgtgcctgga atggctggag   2400
```

```
cggctggaca agacgggtgg cacgctgatc tgcgtcgtgc gcggtagtga cgcggccgcg    2460
gcccgtaaac ggctggactc ggcgttcgac agcggcgatc ccggcctgct cgagcactac    2520
cagcaactgg ccgcacggac cctggaagtc ctcgccggtg atatcggcga cccgaatctc    2580
ggtctggacg acgcgacttg gcagcggttg gccgaaaccg tcgacctgat cgtccatccc    2640
gccgcgttgg tcaaccacgt ccttccctac acccagctgt tcggcccaa tgtcgtcggc     2700
accgccgaaa tcgtccggtt ggcgatcacg gcgcggcgca agccggtcac ctacctgtcg    2760
accgtcggag tggccgacca ggtcgacccg gcggagtatc aggaggacag cgacgtccgc    2820
gagatgagcg cggtgcgcgt cgtgcgcgag agttacgcca acggctacgg caacagcaag    2880
tgggcggggg aggtcctgct cgcgcgaagca cacgatctgt gtggcttgcc ggtcgcggtg    2940
ttccgttcgg acatgatcct ggcgcacagc cggtacgcgg gtcagctcaa cgtccaggac    3000
gtgttcaccc ggctgatcct cagcctggtc gccaccggca tcgcgccgta ctcgttctac    3060
cgaaccgacg cggacggcaa ccggcagcgg gcccactatg acggcttgcc ggcggacttc    3120
acggcggcgg cgatcaccgc gctcggcatc caagccaccg aaggcttccg gacctacgac    3180
gtgctcaatc cgtacgacga tggcatctcc ctcgatgaat tcgtcgactg gctcgtcgaa    3240
tccggccacc cgatccagcg catcaccgac tacagcgact ggttccaccg tttcgagacg    3300
gcgatccgcg cgctgccgga aaagcaacgc caggcctcgg tgctgccgtt gctggacgcc    3360
taccgcaacc cctgcccggc ggtccgcggc gcgatactcc cggccaagga gttccaagcg    3420
gcggtgcaaa cagccaaaat cggtccggaa caggacatcc cgcatttgtc cgcgccactg    3480
atcgataagt acgtcagcga tctggaactg cttcagctgc tctga                   3525
```

<210> SEQ ID NO 16
<211> LENGTH: 1174
<212> TYPE: PRT
<213> ORGANISM: Nocardia iowensis

<400> SEQUENCE: 16

Met Ala Val Asp Ser Pro Asp Glu Arg Leu Gln Arg Arg Ile Ala Gln
1               5                   10                  15

Leu Phe Ala Glu Asp Glu Gln Val Lys Ala Ala Arg Pro Leu Glu Ala
            20                  25                  30

Val Ser Ala Ala Val Ser Ala Pro Gly Met Arg Leu Ala Gln Ile Ala
        35                  40                  45

Ala Thr Val Met Ala Gly Tyr Ala Asp Arg Pro Ala Ala Gly Gln Arg
    50                  55                  60

Ala Phe Glu Leu Asn Thr Asp Asp Ala Thr Gly Arg Thr Ser Leu Arg
65                  70                  75                  80

Leu Leu Pro Arg Phe Glu Thr Ile Thr Tyr Arg Glu Leu Trp Gln Arg
                85                  90                  95

Val Gly Glu Val Ala Ala Ala Trp His His Asp Pro Glu Asn Pro Leu
            100                 105                 110

Arg Ala Gly Asp Phe Val Ala Leu Leu Gly Phe Thr Ser Ile Asp Tyr
        115                 120                 125

Ala Thr Leu Asp Leu Ala Asp Ile His Leu Gly Ala Val Thr Val Pro
    130                 135                 140

Leu Gln Ala Ser Ala Ala Val Ser Gln Leu Ile Ala Ile Leu Thr Glu
145                 150                 155                 160

Thr Ser Pro Arg Leu Leu Ala Ser Thr Pro Glu His Leu Asp Ala Ala
                165                 170                 175

```
Val Glu Cys Leu Leu Ala Gly Thr Thr Pro Glu Arg Leu Val Val Phe
            180                 185                 190

Asp Tyr His Pro Glu Asp Asp Gln Arg Ala Ala Phe Glu Ser Ala
        195                 200                 205

Arg Arg Arg Leu Ala Asp Ala Gly Ser Leu Val Ile Val Glu Thr Leu
        210                 215                 220

Asp Ala Val Arg Ala Arg Gly Arg Asp Leu Pro Ala Ala Pro Leu Phe
225                 230                 235                 240

Val Pro Asp Thr Asp Asp Pro Leu Ala Leu Leu Ile Tyr Thr Ser
                245                 250                 255

Gly Ser Thr Gly Thr Pro Lys Gly Ala Met Tyr Thr Asn Arg Leu Ala
                260                 265                 270

Ala Thr Met Trp Gln Gly Asn Ser Met Leu Gln Gly Asn Ser Gln Arg
        275                 280                 285

Val Gly Ile Asn Leu Asn Tyr Met Pro Met Ser His Ile Ala Gly Arg
        290                 295                 300

Ile Ser Leu Phe Gly Val Leu Ala Arg Gly Gly Thr Ala Tyr Phe Ala
305                 310                 315                 320

Ala Lys Ser Asp Met Ser Thr Leu Phe Glu Asp Ile Gly Leu Val Arg
                325                 330                 335

Pro Thr Glu Ile Phe Phe Val Pro Arg Val Cys Asp Met Val Phe Gln
                340                 345                 350

Arg Tyr Gln Ser Glu Leu Asp Arg Arg Ser Val Ala Gly Ala Asp Leu
        355                 360                 365

Asp Thr Leu Asp Arg Glu Val Lys Ala Asp Leu Arg Gln Asn Tyr Leu
        370                 375                 380

Gly Gly Arg Phe Leu Val Ala Val Val Gly Ser Ala Pro Leu Ala Ala
385                 390                 395                 400

Glu Met Lys Thr Phe Met Glu Ser Val Leu Asp Leu Pro Leu His Asp
                405                 410                 415

Gly Tyr Gly Ser Thr Glu Ala Gly Ala Ser Val Leu Leu Asp Asn Gln
                420                 425                 430

Ile Gln Arg Pro Pro Val Leu Asp Tyr Lys Leu Val Asp Val Pro Glu
        435                 440                 445

Leu Gly Tyr Phe Arg Thr Asp Arg Pro His Pro Arg Gly Glu Leu Leu
        450                 455                 460

Leu Lys Ala Glu Thr Thr Ile Pro Gly Tyr Tyr Lys Arg Pro Glu Val
465                 470                 475                 480

Thr Ala Glu Ile Phe Asp Glu Asp Gly Phe Tyr Lys Thr Gly Asp Ile
                485                 490                 495

Val Ala Glu Leu Glu His Asp Arg Leu Val Tyr Val Asp Arg Arg Asn
                500                 505                 510

Asn Val Leu Lys Leu Ser Gln Gly Glu Phe Val Thr Val Ala His Leu
        515                 520                 525

Glu Ala Val Phe Ala Ser Ser Pro Leu Ile Arg Gln Ile Phe Ile Tyr
        530                 535                 540

Gly Ser Ser Glu Arg Ser Tyr Leu Leu Ala Val Ile Val Pro Thr Asp
545                 550                 555                 560

Asp Ala Leu Arg Gly Arg Asp Thr Ala Thr Leu Lys Ser Ala Leu Ala
                565                 570                 575

Glu Ser Ile Gln Arg Ile Ala Lys Asp Ala Asn Leu Gln Pro Tyr Glu
                580                 585                 590

Ile Pro Arg Asp Phe Leu Ile Glu Thr Glu Pro Phe Thr Ile Ala Asn
```

```
                    595                 600                 605
        Gly Leu Leu Ser Gly Ile Ala Lys Leu Leu Arg Pro Asn Leu Lys Glu
            610                 615                 620

Arg Tyr Gly Ala Gln Leu Glu Gln Met Tyr Thr Asp Leu Ala Thr Gly
        625                 630                 635                 640

Gln Ala Asp Glu Leu Leu Ala Leu Arg Arg Glu Ala Ala Asp Leu Pro
                        645                 650                 655

Val Leu Glu Thr Val Ser Arg Ala Ala Lys Ala Met Leu Gly Val Ala
                    660                 665                 670

Ser Ala Asp Met Arg Pro Asp Ala His Phe Thr Asp Leu Gly Gly Asp
                675                 680                 685

Ser Leu Ser Ala Leu Ser Phe Ser Asn Leu Leu His Glu Ile Phe Gly
            690                 695                 700

Val Glu Val Pro Val Gly Val Val Ser Pro Ala Asn Glu Leu Arg
        705                 710                 715                 720

Asp Leu Ala Asn Tyr Ile Glu Ala Glu Arg Asn Ser Gly Ala Lys Arg
                        725                 730                 735

Pro Thr Phe Thr Ser Val His Gly Gly Gly Ser Glu Ile Arg Ala Ala
                    740                 745                 750

Asp Leu Thr Leu Asp Lys Phe Ile Asp Ala Arg Thr Leu Ala Ala Ala
                755                 760                 765

Asp Ser Ile Pro His Ala Pro Val Pro Ala Gln Thr Val Leu Leu Thr
            770                 775                 780

Gly Ala Asn Gly Tyr Leu Gly Arg Phe Leu Cys Leu Glu Trp Leu Glu
        785                 790                 795                 800

Arg Leu Asp Lys Thr Gly Gly Thr Leu Ile Cys Val Val Arg Gly Ser
                        805                 810                 815

Asp Ala Ala Ala Arg Lys Arg Leu Asp Ser Ala Phe Asp Ser Gly
                    820                 825                 830

Asp Pro Gly Leu Leu Glu His Tyr Gln Gln Leu Ala Ala Arg Thr Leu
                835                 840                 845

Glu Val Leu Ala Gly Asp Ile Gly Asp Pro Asn Leu Gly Leu Asp Asp
            850                 855                 860

Ala Thr Trp Gln Arg Leu Ala Glu Thr Val Asp Leu Ile Val His Pro
        865                 870                 875                 880

Ala Ala Leu Val Asn His Val Leu Pro Tyr Thr Gln Leu Phe Gly Pro
                        885                 890                 895

Asn Val Val Gly Thr Ala Glu Ile Val Arg Leu Ala Ile Thr Ala Arg
                    900                 905                 910

Arg Lys Pro Val Thr Tyr Leu Ser Thr Val Gly Val Ala Asp Gln Val
                915                 920                 925

Asp Pro Ala Glu Tyr Gln Glu Asp Ser Asp Val Arg Glu Met Ser Ala
            930                 935                 940

Val Arg Val Val Arg Glu Ser Tyr Ala Asn Gly Tyr Gly Asn Ser Lys
        945                 950                 955                 960

Trp Ala Gly Glu Val Leu Leu Arg Glu Ala His Asp Leu Cys Gly Leu
                        965                 970                 975

Pro Val Ala Val Phe Arg Ser Asp Met Ile Leu Ala His Ser Arg Tyr
                    980                 985                 990

Ala Gly Gln Leu Asn Val Gln Asp  Val Phe Thr Arg Leu  Ile Leu Ser
                995                 1000                1005

Leu Val  Ala Thr Gly Ile Ala  Pro Tyr Ser Phe Tyr  Arg Thr Asp
                1010                1015                1020
```

```
Ala Asp Gly Asn Arg Gln Arg Ala His Tyr Asp Gly Leu Pro Ala
    1025                1030                1035

Asp Phe Thr Ala Ala Ala Ile Thr Ala Leu Gly Ile Gln Ala Thr
    1040                1045                1050

Glu Gly Phe Arg Thr Tyr Asp Val Leu Asn Pro Tyr Asp Asp Gly
    1055                1060                1065

Ile Ser Leu Asp Glu Phe Val Asp Trp Leu Val Glu Ser Gly His
    1070                1075                1080

Pro Ile Gln Arg Ile Thr Asp Tyr Ser Asp Trp Phe His Arg Phe
    1085                1090                1095

Glu Thr Ala Ile Arg Ala Leu Pro Glu Lys Gln Arg Gln Ala Ser
    1100                1105                1110

Val Leu Pro Leu Leu Asp Ala Tyr Arg Asn Pro Cys Pro Ala Val
    1115                1120                1125

Arg Gly Ala Ile Leu Pro Ala Lys Glu Phe Gln Ala Ala Val Gln
    1130                1135                1140

Thr Ala Lys Ile Gly Pro Glu Gln Asp Ile Pro His Leu Ser Ala
    1145                1150                1155

Pro Leu Ile Asp Lys Tyr Val Ser Asp Leu Glu Leu Leu Gln Leu
    1160                1165                1170

Leu
```

```
<210> SEQ ID NO 17
<211> LENGTH: 7
<212> TYPE: PRT
<213> ORGANISM: Unknown
<220> FEATURE:
<223> OTHER INFORMATION: Description of Unknown: Carboxylic acid
      reductase peptide motif
<220> FEATURE:
<221> NAME/KEY: MOD_RES
<222> LOCATION: (3)..(4)
<223> OTHER INFORMATION: Any naturally-occurring amino acid
<220> FEATURE:
<221> NAME/KEY: MOD_RES
<222> LOCATION: (5)..(5)
<223> OTHER INFORMATION: Ser, Ala or Thr
<220> FEATURE:
<221> NAME/KEY: MOD_RES
<222> LOCATION: (7)..(7)
<223> OTHER INFORMATION: Trp or Leu

<400> SEQUENCE: 17

Gly Tyr Xaa Xaa Xaa Lys Xaa
1               5

<210> SEQ ID NO 18
<211> LENGTH: 7
<212> TYPE: PRT
<213> ORGANISM: Unknown
<220> FEATURE:
<223> OTHER INFORMATION: Description of Unknown: Carboxylic acid
      reductase peptide motif
<220> FEATURE:
<221> NAME/KEY: MOD_RES
<222> LOCATION: (2)..(3)
<223> OTHER INFORMATION: Any naturally-occurring amino acid
<220> FEATURE:
<221> NAME/KEY: MOD_RES
<222> LOCATION: (5)..(5)
<223> OTHER INFORMATION: Any naturally-occurring amino acid

<400> SEQUENCE: 18

Gly Xaa Xaa Gly Xaa Leu Gly
```

1               5

<210> SEQ ID NO 19
<211> LENGTH: 8
<212> TYPE: PRT
<213> ORGANISM: Unknown
<220> FEATURE:
<223> OTHER INFORMATION: Description of Unknown: Carboxylic acid
      reductase peptide motif
<220> FEATURE:
<221> NAME/KEY: MOD_RES
<222> LOCATION: (1)..(1)
<223> OTHER INFORMATION: Leu, Val or Ile
<220> FEATURE:
<221> NAME/KEY: MOD_RES
<222> LOCATION: (6)..(7)
<223> OTHER INFORMATION: Any naturally-occurring amino acid

<400> SEQUENCE: 19

Xaa Gly Gly Asp Ser Xaa Xaa Ala
1               5

<210> SEQ ID NO 20
<211> LENGTH: 12
<212> TYPE: PRT
<213> ORGANISM: Unknown
<220> FEATURE:
<223> OTHER INFORMATION: Description of Unknown: Carboxylic acid
      reductase peptide motif
<220> FEATURE:
<221> NAME/KEY: MOD_RES
<222> LOCATION: (1)..(1)
<223> OTHER INFORMATION: Leu, Ile, Val, Met, Phe or Tyr
<220> FEATURE:
<221> NAME/KEY: MOD_RES
<222> LOCATION: (2)..(2)
<223> OTHER INFORMATION: Any naturally-occurring amino acid except Glu
<220> FEATURE:
<221> NAME/KEY: MOD_RES
<222> LOCATION: (3)..(3)
<223> OTHER INFORMATION: Any naturally-occurring amino acid except Val,
      Glu or Ser
<220> FEATURE:
<221> NAME/KEY: MOD_RES
<222> LOCATION: (4)..(4)
<223> OTHER INFORMATION: Ser, Thr or Gly
<220> FEATURE:
<221> NAME/KEY: MOD_RES
<222> LOCATION: (5)..(5)
<223> OTHER INFORMATION: Ser, Thr, Ala or Gly
<220> FEATURE:
<221> NAME/KEY: MOD_RES
<222> LOCATION: (7)..(7)
<223> OTHER INFORMATION: Ser or Thr
<220> FEATURE:
<221> NAME/KEY: MOD_RES
<222> LOCATION: (8)..(8)
<223> OTHER INFORMATION: Ser, Thr, Glu, Ile or Ala
<220> FEATURE:
<221> NAME/KEY: MOD_RES
<222> LOCATION: (9)..(9)
<223> OTHER INFORMATION: Ser or Gly
<220> FEATURE:
<221> NAME/KEY: MOD_RES
<222> LOCATION: (10)..(10)
<223> OTHER INFORMATION: Any naturally-occurring amino acid
<220> FEATURE:
<221> NAME/KEY: MOD_RES
<222> LOCATION: (11)..(11)
<223> OTHER INFORMATION: Pro, Ala, Ser, Leu, Ile, Val or Met
<220> FEATURE:
<221> NAME/KEY: MOD_RES
<222> LOCATION: (12)..(12)
<223> OTHER INFORMATION: Lys or Arg

<400> SEQUENCE: 20

```
Xaa Xaa Xaa Xaa Xaa Gly Xaa Xaa Xaa Xaa Xaa Xaa
1               5               10
```

<210> SEQ ID NO 21
<211> LENGTH: 21
<212> TYPE: PRT
<213> ORGANISM: Unknown
<220> FEATURE:
<223> OTHER INFORMATION: Description of Unknown: Carboxylic acid
      reductase peptide motif
<220> FEATURE:
<221> NAME/KEY: MOD_RES
<222> LOCATION: (6)..(6)
<223> OTHER INFORMATION: Ser or Thr
<220> FEATURE:
<221> NAME/KEY: MOD_RES
<222> LOCATION: (9)..(9)
<223> OTHER INFORMATION: Thr or Asn
<220> FEATURE:
<221> NAME/KEY: MOD_RES
<222> LOCATION: (11)..(11)
<223> OTHER INFORMATION: Phe or Trp
<220> FEATURE:
<221> NAME/KEY: MOD_RES
<222> LOCATION: (15)..(15)
<223> OTHER INFORMATION: Phe or Tyr
<220> FEATURE:
<221> NAME/KEY: MOD_RES
<222> LOCATION: (17)..(17)
<223> OTHER INFORMATION: Ala or Thr
<220> FEATURE:
<221> NAME/KEY: MOD_RES
<222> LOCATION: (19)..(19)
<223> OTHER INFORMATION: Glu or Gln

<400> SEQUENCE: 21

```
Arg Thr Val Leu Leu Xaa Gly Ala Xaa Gly Xaa Leu Gly Arg Xaa Leu
1               5                   10                  15

Xaa Leu Xaa Trp Leu
            20
```

<210> SEQ ID NO 22
<211> LENGTH: 20
<212> TYPE: PRT
<213> ORGANISM: Unknown
<220> FEATURE:
<223> OTHER INFORMATION: Description of Unknown: Carboxylic acid
      reductase peptide motif
<220> FEATURE:
<221> NAME/KEY: MOD_RES
<222> LOCATION: (2)..(3)
<223> OTHER INFORMATION: Any naturally-occurring amino acid
<220> FEATURE:
<221> NAME/KEY: MOD_RES
<222> LOCATION: (5)..(6)
<223> OTHER INFORMATION: Any naturally-occurring amino acid
<220> FEATURE:
<221> NAME/KEY: MOD_RES
<222> LOCATION: (8)..(8)
<223> OTHER INFORMATION: Any naturally-occurring amino acid
<220> FEATURE:
<221> NAME/KEY: MOD_RES
<222> LOCATION: (11)..(12)
<223> OTHER INFORMATION: Any naturally-occurring amino acid
<220> FEATURE:
<221> NAME/KEY: MOD_RES
<222> LOCATION: (14)..(14)
<223> OTHER INFORMATION: Any naturally-occurring amino acid
<220> FEATURE:
<221> NAME/KEY: MOD_RES
<222> LOCATION: (16)..(16)
<223> OTHER INFORMATION: Any naturally-occurring amino acid
<220> FEATURE:
<221> NAME/KEY: MOD_RES

```
<222> LOCATION: (19)..(19)
<223> OTHER INFORMATION: Any naturally-occurring amino acid

<400> SEQUENCE: 22

Leu Xaa Xaa Gly Xaa Xaa Gly Xaa Leu Gly Xaa Xaa Leu Xaa Leu Xaa
1               5                   10                  15

Trp Leu Xaa Arg
            20

<210> SEQ ID NO 23
<211> LENGTH: 8
<212> TYPE: PRT
<213> ORGANISM: Unknown
<220> FEATURE:
<223> OTHER INFORMATION: Description of Unknown: Carboxylic acid
      reductase peptide motif
<220> FEATURE:
<221> NAME/KEY: MOD_RES
<222> LOCATION: (3)..(3)
<223> OTHER INFORMATION: Any naturally-occurring amino acid

<400> SEQUENCE: 23

Trp Ala Xaa Glu Val Leu Leu Arg
1               5

<210> SEQ ID NO 24
<211> LENGTH: 35
<212> TYPE: PRT
<213> ORGANISM: Unknown
<220> FEATURE:
<223> OTHER INFORMATION: Description of Unknown: Carboxylic acid
      reductase peptide motif
<220> FEATURE:
<221> NAME/KEY: MOD_RES
<222> LOCATION: (2)..(3)
<223> OTHER INFORMATION: Any naturally-occurring amino acid
<220> FEATURE:
<221> NAME/KEY: MOD_RES
<222> LOCATION: (5)..(6)
<223> OTHER INFORMATION: Any naturally-occurring amino acid
<220> FEATURE:
<221> NAME/KEY: MOD_RES
<222> LOCATION: (8)..(8)
<223> OTHER INFORMATION: Any naturally-occurring amino acid
<220> FEATURE:
<221> NAME/KEY: MOD_RES
<222> LOCATION: (11)..(12)
<223> OTHER INFORMATION: Any naturally-occurring amino acid
<220> FEATURE:
<221> NAME/KEY: MOD_RES
<222> LOCATION: (14)..(14)
<223> OTHER INFORMATION: Any naturally-occurring amino acid
<220> FEATURE:
<221> NAME/KEY: MOD_RES
<222> LOCATION: (15)..(15)
<223> OTHER INFORMATION: Leu or Ile
<220> FEATURE:
<221> NAME/KEY: MOD_RES
<222> LOCATION: (16)..(16)
<223> OTHER INFORMATION: Any naturally-occurring amino acid
<220> FEATURE:
<221> NAME/KEY: MOD_RES
<222> LOCATION: (17)..(17)
<223> OTHER INFORMATION: Trp or Leu
<220> FEATURE:
<221> NAME/KEY: MOD_RES
<222> LOCATION: (19)..(32)
<223> OTHER INFORMATION: Any naturally-occurring amino acid
<220> FEATURE:
<221> NAME/KEY: MOD_RES
<222> LOCATION: (34)..(34)
<223> OTHER INFORMATION: Any naturally-occurring amino acid or absent

<400> SEQUENCE: 24
```

Leu Xaa Xaa Gly Xaa Xaa Gly Xaa Leu Gly Xaa Xaa Leu Xaa Xaa Xaa
1               5                   10                  15

Xaa Leu Xaa Xaa Xaa Xaa Xaa Xaa Xaa Xaa Xaa Xaa Xaa Xaa Xaa
            20                  25                  30

Leu Xaa Arg
        35

<210> SEQ ID NO 25
<211> LENGTH: 1269
<212> TYPE: DNA
<213> ORGANISM: Jeotgalicoccus sp.
<220> FEATURE:
<223> OTHER INFORMATION: ATCC8456

<400> SEQUENCE: 25

| | | |
|---|---|---|
| atggcaacac ttaagaggga taagggctta gataatactt tgaaagtatt aaagcaaggt | 60 |
| tatctttaca caacaaatca gagaaatcgt ctaaacacat cagttttcca aactaaagca | 120 |
| ctcggtggta aaccattcgt agttgtgact ggtaaggaag gcgctgaaat gttctacaac | 180 |
| aatgatgttg ttcaacgtga aggcatgtta ccaaaacgta tcgttaatac gcttttggt | 240 |
| aaaggtgcaa tccatacggt agatggtaaa aaacacgtag acagaaaagc attgttcatg | 300 |
| agcttgatga ctgaaggtaa cttgaattat gtacgagaat taacgcgtac attatggcat | 360 |
| gcgaacacac aacgtatgga agtatggat gaggtaaata tttaccgtga atctatcgta | 420 |
| ctacttacaa agtaggaac acgttgggca ggcgttcaag caccacctga agatatcgaa | 480 |
| agaatcgcaa cagacatgga catcatgatc gattcattta gagcacttgg tggtgccttt | 540 |
| aaaggttaca aggcatcaaa agaagcacgt cgtcgtgttg aagattggtt agaagaacaa | 600 |
| attattgaga ctcgtaaagg gaatattcat ccaccagaag gtacagcact ttacgaattt | 660 |
| gcacattggg aagactactt aggtaaccca atggactcaa gaacttgtgc gattgactta | 720 |
| atgaacacat tccgcccatt aatcgcaatc aacagattcg tttcattcgg tttacacgcg | 780 |
| atgaacgaaa acccaatcac acgtgaaaaa attaaatcag aacctgacta tgcatataaa | 840 |
| ttcgctcaag aagttcgtcg ttactatcca ttcgttccat tccttccagg taaagcgaaa | 900 |
| gtagacatcg acttccaagg cgttacaatt cctgcaggtg taggtcttgc attagatgtt | 960 |
| tatggtacaa cgcatgatga atcactttgg gacgatccaa atgaattccg cccagaaaga | 1020 |
| ttcgaaactt gggacggatc accatttgac cttattccac aaggtggtgg agattactgg | 1080 |
| acaaatcacc gttgtgcagg tgaatggatc acagtaatca tcatggaaga aacaatgaaa | 1140 |
| tactttgcag aaaaaataac ttatgatgtt ccagaacaag atttagaagt ggacttaaac | 1200 |
| agtatcccag gatacgttaa gagtggcttt gtaatcaaaa atgttcgcga agttgtagac | 1260 |
| agaacataa | 1269 |

<210> SEQ ID NO 26
<211> LENGTH: 422
<212> TYPE: PRT
<213> ORGANISM: Jeotgalicoccus sp.
<220> FEATURE:
<223> OTHER INFORMATION: ATCC8456

<400> SEQUENCE: 26

Met Ala Thr Leu Lys Arg Asp Lys Gly Leu Asp Asn Thr Leu Lys Val
1               5                   10                  15

Leu Lys Gln Gly Tyr Leu Tyr Thr Asn Gln Arg Asn Arg Leu Asn
            20                  25                  30

Thr Ser Val Phe Gln Thr Lys Ala Leu Gly Lys Pro Phe Val Val
        35                  40                  45

Val Thr Gly Lys Glu Gly Ala Glu Met Phe Tyr Asn Asn Asp Val Val
 50                  55                  60

Gln Arg Glu Gly Met Leu Pro Lys Arg Ile Val Asn Thr Leu Phe Gly
 65                  70                  75                  80

Lys Gly Ala Ile His Thr Val Asp Gly Lys His Val Asp Arg Lys
                    85                  90                  95

Ala Leu Phe Met Ser Leu Met Thr Glu Gly Asn Leu Asn Tyr Val Arg
                100                 105                 110

Glu Leu Thr Arg Thr Leu Trp His Ala Asn Thr Gln Arg Met Glu Ser
            115                 120                 125

Met Asp Glu Val Asn Ile Tyr Arg Glu Ser Ile Val Leu Leu Thr Lys
            130                 135                 140

Val Gly Thr Arg Trp Ala Gly Val Gln Ala Pro Glu Asp Ile Glu
145                 150                 155                 160

Arg Ile Ala Thr Asp Met Asp Ile Met Ile Asp Ser Phe Arg Ala Leu
                    165                 170                 175

Gly Gly Ala Phe Lys Gly Tyr Lys Ala Ser Lys Glu Ala Arg Arg
                180                 185                 190

Val Glu Asp Trp Leu Glu Glu Gln Ile Ile Glu Thr Arg Lys Gly Asn
            195                 200                 205

Ile His Pro Pro Glu Gly Thr Ala Leu Tyr Glu Phe Ala His Trp Glu
        210                 215                 220

Asp Tyr Leu Gly Asn Pro Met Asp Ser Arg Thr Cys Ala Ile Asp Leu
225                 230                 235                 240

Met Asn Thr Phe Arg Pro Leu Ile Ala Ile Asn Arg Phe Val Ser Phe
                    245                 250                 255

Gly Leu His Ala Met Asn Glu Asn Pro Ile Thr Arg Glu Lys Ile Lys
                260                 265                 270

Ser Glu Pro Asp Tyr Ala Tyr Lys Phe Ala Gln Glu Val Arg Arg Tyr
            275                 280                 285

Tyr Pro Phe Val Pro Phe Leu Pro Gly Lys Ala Lys Val Asp Ile Asp
        290                 295                 300

Phe Gln Gly Val Thr Ile Pro Ala Gly Val Gly Leu Ala Leu Asp Val
305                 310                 315                 320

Tyr Gly Thr Thr His Asp Glu Ser Leu Trp Asp Asp Pro Asn Glu Phe
                    325                 330                 335

Arg Pro Glu Arg Phe Glu Thr Trp Asp Gly Ser Pro Phe Asp Leu Ile
                340                 345                 350

Pro Gln Gly Gly Gly Asp Tyr Trp Thr Asn His Arg Cys Ala Gly Glu
            355                 360                 365

Trp Ile Thr Val Ile Ile Met Glu Glu Thr Met Lys Tyr Phe Ala Glu
        370                 375                 380

Lys Ile Thr Tyr Asp Val Pro Glu Gln Asp Leu Glu Val Asp Leu Asn
385                 390                 395                 400

Ser Ile Pro Gly Tyr Val Lys Ser Gly Phe Val Ile Lys Asn Val Arg
                    405                 410                 415

Glu Val Val Asp Arg Thr
                420

<210> SEQ ID NO 27
<211> LENGTH: 1507

```
<212> TYPE: DNA
<213> ORGANISM: Jeotgalicoccus sp.
<220> FEATURE:
<223> OTHER INFORMATION: ATCC8456

<400> SEQUENCE: 27
ggttaccttg ttacgacttc accccaatta tcaatcccac ctttgacggc tacctccatt      60
aaggttagtc caccggcttc aggtgttayc gactttcgtg gtgtgacggg cggtgtgtac     120
aagacccggg aacgtattca ccgtagcatg ctgatctacg attactagcg attccagctt     180
catggagtcg agttgcagac tccaatccga actgagaaca gttttatggg attcgcttgg     240
cctcgcggct tcgctgccct ttgtaacctg cccattgtag cacgtgtgta gcccaaatca     300
taagggcat gatgatttga cgtcatcccc accttcctcc ggtttgtcac cggcagtcaa      360
tctagagtgc ccaactgaat gatggcaact aaatttaagg gttgcgctcg ttgcgggact     420
taacccaaca tctcacgaca cgagctgacg acaaccatgc accacctgtc tctctgccca     480
aaagggaaac catatctctr tggcgatcag aggatgtcaa gatttggtaa ggttcttcgc     540
gttgcttcga attaaaccac atgctccacc gcttgtgcgg gtccccgtca attcctttga     600
gtttcaacct tgcggtcgta ctccccaggc ggagtgctta atgcgttagc tgcagcactg     660
aggggcggaa accccccaac acttagcact catcgtttac ggcgtggact accagggtat     720
ctaatcctgt ttgatcccca cgctttcgca cctcagcgtc agttacagac cagagagccg     780
ccttcgccca ctggtgttcc tccatatctc tgcgcatttc accgctacac atggaattcc     840
actctcctct tctgcactca agtaaaacag tttccaatga ccctcccgg ttgagccggg      900
ggctttcaca tcagacttat tctaccgcct acgcgcgctt tacgcccaat aattccggat     960
aacgcttgcc acctacgtat taccgcggct gctggcacgt agttagccgt ggctttctgg    1020
ttaagtaccg tcatctctag gccagttact acctaaagtg ttcttcctta acaacagagt    1080
tttacgagcc gaaacccttc ttcactcacg cggcgttgct ccgtcagact tgcgtycatt    1140
gcggaagatt ccctactgct gcctcccgta ggagtctggg ccgtgtctca gtcccagtgt    1200
ggccgatcac cctctcaggt cggctatgca tcgttgcctt ggtgagccac tacctcacca    1260
actagctaat gcaccgcagg cccatccttt agtgacagat aaatccgcct ttcattaaga    1320
ttacttgtgt aatccaactt atccggtatt agctaccgtt tccggtagtt atcccagtct    1380
aaagggtagg ttgcccacgt gttactcacc cgtccgccgc tcgattgtaa ggagcaagct    1440
ccttacgctc gcgctcgact tgcatgtatt aggcacgccg ccagcgttca tcctgagcca    1500
ggatcaa                                                              1507

<210> SEQ ID NO 28
<211> LENGTH: 10
<212> TYPE: PRT
<213> ORGANISM: Unknown
<220> FEATURE:
<223> OTHER INFORMATION: Description of Unknown: Carboxylic acid
      thioesterase peptide motif
<220> FEATURE:
<221> NAME/KEY: MOD_RES
<222> LOCATION: (2)..(2)
<223> OTHER INFORMATION: Asp, Asn or Thr
<220> FEATURE:
<221> NAME/KEY: MOD_RES
<222> LOCATION: (4)..(4)
<223> OTHER INFORMATION: Leu, Cys or Gln
<220> FEATURE:
<221> NAME/KEY: MOD_RES
<222> LOCATION: (5)..(9)
<223> OTHER INFORMATION: Any naturally-occurring amino acid
```

```
<220> FEATURE:
<221> NAME/KEY: MOD_RES
<222> LOCATION: (10)..(10)
<223> OTHER INFORMATION: Met, Cys, Asp, Leu, Asn, Thr or Val

<400> SEQUENCE: 28

Gly Xaa Ser Xaa Xaa Xaa Xaa Xaa Xaa Xaa
1               5                   10

<210> SEQ ID NO 29
<211> LENGTH: 9
<212> TYPE: PRT
<213> ORGANISM: Unknown
<220> FEATURE:
<223> OTHER INFORMATION: Description of Unknown: Carboxylic acid
      thioesterase peptide motif
<220> FEATURE:
<221> NAME/KEY: MOD_RES
<222> LOCATION: (1)..(1)
<223> OTHER INFORMATION: Val or Leu
<220> FEATURE:
<221> NAME/KEY: MOD_RES
<222> LOCATION: (2)..(3)
<223> OTHER INFORMATION: Any naturally-occurring amino acid
<220> FEATURE:
<221> NAME/KEY: MOD_RES
<222> LOCATION: (5)..(5)
<223> OTHER INFORMATION: Any naturally-occurring amino acid
<220> FEATURE:
<221> NAME/KEY: MOD_RES
<222> LOCATION: (6)..(6)
<223> OTHER INFORMATION: Asn, Val, Leu, Cys, Ala, Gly, His, Ile, Thr or
      Trp
<220> FEATURE:
<221> NAME/KEY: MOD_RES
<222> LOCATION: (7)..(7)
<223> OTHER INFORMATION: Asp or Glu
<220> FEATURE:
<221> NAME/KEY: MOD_RES
<222> LOCATION: (8)..(8)
<223> OTHER INFORMATION: Any naturally-occurring amino acid
<220> FEATURE:
<221> NAME/KEY: MOD_RES
<222> LOCATION: (9)..(9)
<223> OTHER INFORMATION: Leu, Ile, Trp, Phe, Thr, Met, Ala, Glu, Asn or
      Val

<400> SEQUENCE: 29

Xaa Xaa Xaa Gly Xaa Xaa Xaa Xaa Xaa
1               5

<210> SEQ ID NO 30
<211> LENGTH: 13
<212> TYPE: PRT
<213> ORGANISM: Unknown
<220> FEATURE:
<223> OTHER INFORMATION: Description of Unknown: Carboxylic acid
      thioesterase peptide motif
<220> FEATURE:
<221> NAME/KEY: MOD_RES
<222> LOCATION: (2)..(3)
<223> OTHER INFORMATION: Any naturally-occurring amino acid
<220> FEATURE:
<221> NAME/KEY: MOD_RES
<222> LOCATION: (5)..(5)
<223> OTHER INFORMATION: Pro, Gly, Ala, Phe, Leu, Ser or Val
<220> FEATURE:
<221> NAME/KEY: MOD_RES
<222> LOCATION: (6)..(11)
<223> OTHER INFORMATION: Any naturally-occurring amino acid
<220> FEATURE:
<221> NAME/KEY: MOD_RES
<222> LOCATION: (12)..(12)
<223> OTHER INFORMATION: Ile, Leu or Val
```

<400> SEQUENCE: 30

Asp Xaa Xaa His Xaa Xaa Xaa Xaa Xaa Xaa Xaa Ile
1               5                   10

<210> SEQ ID NO 31
<211> LENGTH: 183
<212> TYPE: PRT
<213> ORGANISM: Escherichia coli

<400> SEQUENCE: 31

Met Ala Asp Thr Leu Leu Ile Leu Gly Asp Ser Leu Ser Ala Gly Tyr
1               5                   10                  15

Arg Met Ser Ala Ser Ala Ala Trp Pro Ala Leu Leu Asn Asp Lys Trp
            20                  25                  30

Gln Asn Lys Thr Ser Val Val Asn Ala Ser Ile Ser Gly Asp Thr Ser
        35                  40                  45

Gln Gln Gly Leu Ala Arg Leu Pro Ala Leu Leu Lys Gln His Gln Pro
    50                  55                  60

Arg Trp Val Leu Val Glu Leu Gly Gly Asn Asp Gly Leu Arg Gly Phe
65                  70                  75                  80

Gln Pro Gln Gln Thr Glu Gln Thr Leu Arg Gln Ile Leu Gln Asp Val
                85                  90                  95

Lys Ala Ala Asn Ala Glu Pro Leu Leu Met Gln Ile Arg Leu Pro Ala
            100                 105                 110

Asn Tyr Gly Arg Arg Tyr Asn Glu Ala Phe Ser Ala Ile Tyr Pro Lys
        115                 120                 125

Leu Ala Lys Glu Phe Asp Val Pro Leu Leu Pro Phe Phe Met Glu Glu
    130                 135                 140

Val Tyr Leu Lys Pro Gln Trp Met Gln Asp Asp Gly Ile His Pro Asn
145                 150                 155                 160

Arg Asp Ala Gln Pro Phe Ile Ala Asp Trp Met Ala Lys Gln Leu Gln
                165                 170                 175

Pro Leu Val Asn His Asp Ser
            180

<210> SEQ ID NO 32
<211> LENGTH: 552
<212> TYPE: DNA
<213> ORGANISM: Escherichia coli

<400> SEQUENCE: 32
atggcggaca cgttattgat tctgggtgat agcctgagcg ccgggtatcg aatgtctgcc      60
agcgcggcct ggcctgcctt gttgaatgat aagtggcaga gtaaaacgtc ggtagttaat     120
gccagcatca gcggcgacac ctcgcaacaa ggactggcgc gccttccggc tctgctgaaa     180
cagcatcagc cgcgttgggt gctggttgaa ctgggcggca tgacggtttt cgtggttttt     240
cagccacagc aaaccgagca acgctgcgc cagattttgc aggatgtcaa agccgccaac      300
gctgaaccat tgttaatgca aatacgtctg cctgcaaact atggtcgccg ttataatgaa     360
gcctttagcg ccatttaccc caaactcgcc aaagagtttg atgttccgct gctgcccttt     420
tttatggaag aggtctacct caagccacaa tggatgcagg atgacggtat tcatcccaac     480
cgcgacgccc agccgtttat tgccgactgg atggcgaagc agttgcagcc tttagtaaat     540
catgactcat aa                                                         552

<210> SEQ ID NO 33

```
<211> LENGTH: 66
<212> TYPE: DNA
<213> ORGANISM: Artificial Sequence
<220> FEATURE:
<223> OTHER INFORMATION: Description of Artificial Sequence: Synthetic
      control region of FabA oligonucleotide

<400> SEQUENCE: 33
tttattccga actgatcgga cttgttcagc gtacacgtgt tagctatcct gcgtgcttca      60
ataaaa                                                                66

<210> SEQ ID NO 34
<211> LENGTH: 66
<212> TYPE: DNA
<213> ORGANISM: Artificial Sequence
<220> FEATURE:
<223> OTHER INFORMATION: Description of Artificial Sequence: Synthetic
      control region of FabB oligonucleotide

<400> SEQUENCE: 34
tctttaaatg gctgatcgga cttgttcggc gtacaagtgt acgctattgt gcattcgaaa      60
cttact                                                                66

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
tcatatgcgc ccattacatc cg                                              22

<210> SEQ ID NO 36
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
tcctaggagg gctaatttag ccctttagtt                                      30

<210> SEQ ID NO 37
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
atagtttagc ggccgcaaat cgagctggat caggatta                             38

<210> SEQ ID NO 38
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
aggattcaga catcgtgatg taatgaaaca agcaaatcaa gataga                    46
```

<210> SEQ ID NO 39
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 39
cgcggatccg aatcactacg ccactgttcc        30

<210> SEQ ID NO 40
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 40
ttgatttgct tgtttcatta catcacgatg tctgaatcct tg        42

<210> SEQ ID NO 41
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 41
atatgacgtc ggcatccgct tacagaca        28

<210> SEQ ID NO 42
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 42
aattcttaag tcaggagagc gttcaccgac aa        32

<210> SEQ ID NO 43
<211> LENGTH: 71
<212> TYPE: DNA
<213> ORGANISM: Artificial Sequence
<220> FEATURE:
<223> OTHER INFORMATION: Description of Artificial Sequence: Synthetic primer

<400> SEQUENCE: 43
taaccggcgt ctgacgactg acttaacgct caggctttat tgtccacttt gtgtaggctg        60
gagctgcttc g        71

<210> SEQ ID NO 44
<211> LENGTH: 75
<212> TYPE: DNA
<213> ORGANISM: Artificial Sequence
<220> FEATURE:
<223> OTHER INFORMATION: Description of Artificial Sequence: Synthetic primer

<400> SEQUENCE: 44

```
catttggggt tgcgatcacg acgaacacgc attttagagg tgaagaattg catatgaata      60
tcctccttta gttcc                                                      75
```

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45

```
cgtccgtggt aatcatttgg                                                 20
```

<210> SEQ ID NO 46
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46

```
tcgcaacctt ttcgttgg                                                   18
```

<210> SEQ ID NO 47
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47

```
catatgtcga tcaacgatca gcgactgac                                       29
```

<210> SEQ ID NO 48
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48

```
cctaggtcac agcagcccga gcagtc                                          26
```

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49

```
catatgacga tcgaaacgcg                                                 20
```

<210> SEQ ID NO 50
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
cctaggttac agcaatccga gcatct                                            26

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
catatgacca gcgatgttca c                                                 21

<210> SEQ ID NO 52
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
cctaggtcag atcagaccga actcacg                                           27

<210> SEQ ID NO 53
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
gcgcctcaga tcagcgctgc gaatgatttt caaaaatcgg ctttcaacac tgtaggctgg       60
agctgcttcg                                                              70

<210> SEQ ID NO 54
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ctgccatgct ctacacttcc caaacaacac cagagaagga ccaaaaaatg attccgggga      60
tccgtcgacc                                                              70

<210> SEQ ID NO 55
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
gtgctggcga tacgacaaaa ca                                                22

<210> SEQ ID NO 56
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 56
ccccgccctg ccatgctcta cac                                                    23

<210> SEQ ID NO 57
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
cacgttattg attctgggta atagcctgag cgccgggtat cg                               42

<210> SEQ ID NO 58
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
cgatacccgg cgctcaggct attacccaga atcaataacg tg                               42

<210> SEQ ID NO 59
<211> LENGTH: 186
<212> TYPE: PRT
<213> ORGANISM: Pectobacterium atrosepticum

<400> SEQUENCE: 59

Met Ala Asp Thr Leu Leu Ile Leu Gly Asp Ser Leu Ser Ala Gly Tyr
1               5                   10                  15

Gln Met Pro Ala Ala Asn Ala Trp Pro Thr Leu Leu Asn Thr Gln Trp
            20                  25                  30

Gln Thr Gln Lys Lys Gly Ile Ala Val Val Asn Ala Ser Ile Ser Gly
        35                  40                  45

Asp Thr Thr Ala Gln Gly Leu Ala Arg Leu Pro Ala Leu Leu Lys Gln
    50                  55                  60

His Gln Pro Arg Trp Val Leu Ile Glu Leu Gly Gly Asn Asp Gly Leu
65                  70                  75                  80

Arg Gly Phe Pro Ala Pro Asn Ile Glu Gln Asp Leu Ala Lys Ile Ile
                85                  90                  95

Thr Leu Val Lys Gln Ala Asn Ala Lys Pro Leu Leu Met Gln Val Arg
            100                 105                 110

Leu Pro Thr Asn Tyr Gly Arg Arg Tyr Thr Glu Ser Phe Ser Asn Ile
        115                 120                 125

Tyr Pro Lys Leu Ala Glu Gln Phe Ala Leu Pro Leu Leu Pro Phe Phe
    130                 135                 140

Met Glu Gln Val Tyr Leu Lys Pro Glu Trp Ile Met Glu Asp Gly Ile
145                 150                 155                 160

His Pro Thr Arg Asp Ala Gln Pro Phe Ile Ala Glu Trp Met Ala Lys
                165                 170                 175

Gln Leu Glu Pro Leu Val Asn His Glu Ser
            180                 185

<210> SEQ ID NO 60
<211> LENGTH: 561

```
<212> TYPE: DNA
<213> ORGANISM: Pectobacterium atrosepticum

<400> SEQUENCE: 60
atggctgata cattattaat tctgggtgat agcctcagtg cgggctacca gatgccggcc      60
gctaacgcct ggccaacgct gctgaacacg cagtggcaga cgcagaaaaa gggcatcgcc     120
gtggttaacg ccagcattag cggcgacacc accgcacagg gctggcgcg acttcctgcc     180
ttactgaaac aacatcagcc gcgttgggtg ttgattgaac tgggcggcaa tgacgggctt     240
cggggggttc cggcacccaa tatcgagcag atctggcga aaatcattac gctagtcaaa     300
caggctaacg ctaagcctct gctgatgcag gttcgtttgc caaccaacta tggccgccgc     360
tacaccgagt cattcagcaa catttacccc aaactcgcgg agcagtttgc gcttcctctg     420
ctgcctttct ttatggagca ggtgtatctt aaaccggagt ggatcatgga agatggcatc     480
catccaaccc gtgatgccca accgtttatc gcagaatgga tggcgaagca gctggaaccc     540
ttagttaacc atgagtctta a                                              561

<210> SEQ ID NO 61
<211> LENGTH: 184
<212> TYPE: PRT
<213> ORGANISM: Photobacterium profundum

<400> SEQUENCE: 61

Met Ala Trp Gly Asn Thr Leu Leu Val Val Gly Asp Ser Leu Ser Ala
1               5                   10                  15

Gly Tyr Gln Met Arg Ala Glu Gln Ser Trp Pro Val Leu Leu Gln Pro
            20                  25                  30

Ala Leu Lys Gln Gln Gly His Glu Ile Thr Val Val Asn Ala Ser Ile
        35                  40                  45

Ser Gly Asp Thr Thr Gly Asn Gly Leu Ala Arg Leu Pro Thr Leu Leu
    50                  55                  60

Gln Gln His Lys Pro Ala Tyr Val Ile Ile Glu Leu Gly Ala Asn Asp
65                  70                  75                  80

Gly Leu Arg Gly Phe Pro Gln Gly Thr Ile Arg Asn Asn Leu Ser Gln
                85                  90                  95

Met Ile Thr Glu Ile Gln Asn Ala Asp Ala Lys Pro Met Leu Val Gln
            100                 105                 110

Ile Lys Val Pro Pro Asn Tyr Gly Lys Arg Tyr Ser Asp Met Phe Ser
        115                 120                 125

Ser Ile Tyr Pro Gln Leu Ser Lys Glu Leu Ala Thr Pro Leu Leu Pro
    130                 135                 140

Phe Phe Leu Glu Gln Ile Ile Leu Lys Gln Glu Trp Met Met Asn Asp
145                 150                 155                 160

Gly Leu His Pro Lys Ser Asp Ala Gln Pro Trp Ile Ala Glu Tyr Met
                165                 170                 175

Ala Glu Asn Ile Ala Pro Tyr Leu
            180

<210> SEQ ID NO 62
<211> LENGTH: 549
<212> TYPE: DNA
<213> ORGANISM: Photobacterium profundum

<400> SEQUENCE: 62
atgggcaaca cattactggt tgtcggtgat agcttgagcg cgggctatca aatgcgggca      60
```

```
gaacaaagct ggccggtgtt actgcaaccc gcattaaagc aacaaggtca cgaaatcacc    120
gttgtaaatg ccagtatttc aggcgataca acaggaaacg gcttggctcg attgcctaca    180
ttattacaac aacataaacc agcttacgtc ataattgaac tcggggcgaa tgatggctta    240
cgtggtttcc ctcaaggtac tatacgtaac aatctcagcc aaatgatcac tgaaattcaa    300
aatgctgatg ccaagccaat gctcgtgcag ataaaagtgc cgcccaatta cggcaaacgc    360
tacagtgata tgttcagttc tatttaccct caactcagta agagttagc cacaccactg     420 ttacctttct ttttagagca gatcatttta aaacaagaat ggatgatgaa tgacggtttg    480
catcctaaat ctgatgctca gccatggatt gccgaatata tggctgagaa tatcgcgcct    540
tatttataa                                                            549
```

<210> SEQ ID NO 63
<211> LENGTH: 185
<212> TYPE: PRT
<213> ORGANISM: Photorhabdus luminescens

<400> SEQUENCE: 63

```
Met Ala Asp Thr Leu Leu Ile Leu Gly Asp Ser Leu Ser Ala Gly Tyr
1               5                   10                  15

His Leu Pro Ile Glu Gln Ser Trp Pro Ala Leu Met Glu Lys Lys Trp
                20                  25                  30

Gln Lys Ser Gly Asn Lys Ile Thr Val Ile Asn Gly Ser Ile Ser Gly
            35                  40                  45

Asn Thr Ala Ala Gln Gly Leu Glu Arg Leu Pro Glu Leu Leu Lys Gln
        50                  55                  60

His Lys Pro Arg Trp Val Leu Ile Glu Leu Gly Ala Asn Asp Gly Leu
65                  70                  75                  80

Arg Gly Phe Pro Pro Gln His Thr Glu Gln Asp Leu Gln Gln Ile Ile
                85                  90                  95

Thr Leu Val Lys Gln Ala Asn Ile Gln Pro Leu Leu Met Gln Ile Arg
            100                 105                 110

Leu Pro Pro Asn Tyr Gly Arg Arg Tyr Thr Glu Ser Phe Ala Lys Ile
        115                 120                 125

Tyr Pro Lys Leu Ala Glu Tyr Asn Gln Ile Pro Leu Leu Pro Phe Tyr
    130                 135                 140

Met Glu Gln Val Ala Ile Lys Pro Glu Trp Val Gln Gln Asp Gly Leu
145                 150                 155                 160

His Pro Asn Leu Ala Ala Gln Pro Phe Ile Ala Asp Trp Met Ser Asp
                165                 170                 175

Thr Leu Ser Ala His Leu Asn Tyr Ser
            180                 185
```

<210> SEQ ID NO 64
<211> LENGTH: 558
<212> TYPE: DNA
<213> ORGANISM: Photorhabdus luminescens

<400> SEQUENCE: 64

```
atggctgata cccttctgat tctcggtgat agccttagtg ccggttacca tctgcctatt     60
gagcagtcat ggcctgcttt gatggaaaaa aagtggcaaa atccggcaa taaaatcacg     120 gtcatcaacg gcagcatcag cggcaacacc gccgctcagg gccttgagcg gctacctgaa    180
ttacttaaac aacataaacc ccgttgggta ctgatagagc tgggtgccaa cgatggatta    240
cgcggttttc ctccacaaca caccgaacaa gatctacaac agatcattac tttagtgaaa    300
```

```
caagctaata ttcagccttt attgatgcag atccgtctac caccaaacta tgggcgccgt    360
tataccgagt cttttgccaa gatttacccc aaactggcag aatataatca aattcccctg    420
ctcccgtttt atatggagca agtcgccatt aaaccggagt gggtgcaaca agatgggtta    480
catcctaatc tggcagccca accatttatc gccgattgga tgtctgacac actatcagca    540
catcttaatt attcttaa                                                   558

<210> SEQ ID NO 65
<211> LENGTH: 182
<212> TYPE: PRT
<213> ORGANISM: Pseudomonas putida

<400> SEQUENCE: 65

Met Ala Gly Thr Leu Leu Val Val Gly Asp Ser Ile Ser Ala Gly Phe
1               5                   10                  15

Gly Leu Asp Ser Arg Gln Gly Trp Val Ser Leu Leu Gln Ala Arg Leu
            20                  25                  30

Arg Asp Glu Gly Phe Asp Asp Lys Val Val Asn Ala Ser Ile Ser Gly
        35                  40                  45

Asp Thr Ser Ala Gly Gly Gln Ala Arg Leu Pro Ala Leu Leu Ala Ala
    50                  55                  60

His Lys Pro Ser Leu Val Val Leu Glu Leu Gly Gly Asn Asp Gly Leu
65                  70                  75                  80

Arg Gly Gln Pro Pro Ala Gln Leu Gln Asn Leu Ala Ser Met Ile
                85                  90                  95

Glu Arg Ser Arg Gln Ala Gly Ala Lys Val Leu Leu Leu Gly Met Arg
            100                 105                 110

Leu Pro Pro Asn Tyr Gly Val Arg Tyr Thr Thr Ala Phe Ala Lys Val
        115                 120                 125

Tyr Glu Gln Leu Ala Ala Asp Lys Gln Val Pro Leu Val Pro Phe Phe
    130                 135                 140

Leu Glu Gly Val Gly Gly Val Pro Glu Leu Met Gln Ala Asp Gly Ile
145                 150                 155                 160

His Pro Ala Gln Gly Ala Gln Gln Arg Leu Leu Glu Asn Ala Trp Pro
                165                 170                 175

Ala Ile Lys Pro Leu Leu
            180

<210> SEQ ID NO 66
<211> LENGTH: 549
<212> TYPE: DNA
<213> ORGANISM: Pseudomonas putida

<400> SEQUENCE: 66
atggcaggaa cactgctggt tgttggcgat agtatcagcg ccggttttgg cctggatagc     60
cgtcagggct gggtgtctct cttgcaggcc cgtctcaggg acgaaggttt tgacgacaaa    120
gtggtcaatg cttcgatcag tggcgatacc agcgcaggtg gccaggcgcg gctgccggcg    180
ctgcttgcag cacataaacc gagcctggtg gtgctggagc tgggcggcaa cgatggcctg    240
cgcgggcagc cgcctgcaca attgcaacaa aatcttgcct cgatgatcga gcgttcgcgt    300
caggcagggg ccaaggtgct gctattgggc atgcgcctgc cgcccaatta tggtgtgcgt    360
tacaccaccg cctttgccaa ggtgtatgaa cagctggcag cggacaaaca ggttcccttg    420
gtgccgtttt tcctcgaagg ggtagggggc gtacctgaac tgatgcaggc tgatggcatc    480
```

```
catccggccc aggggggctca gcagcgcctg ctggaaaatg cctggccagc gataaaaccc      540
ttgctgtga                                                              549
```

<210> SEQ ID NO 67
<211> LENGTH: 182
<212> TYPE: PRT
<213> ORGANISM: Vibrio harveyi

<400> SEQUENCE: 67

```
Met Ser Glu Lys Leu Leu Val Leu Gly Asp Ser Leu Ser Ala Gly Tyr
1               5                   10                  15

Gln Met Pro Ile Glu Glu Ser Trp Pro Ser Leu Leu Pro Gly Ala Leu
            20                  25                  30

Leu Glu His Gly Gln Asp Val Lys Val Val Asn Gly Ser Ile Ser Gly
        35                  40                  45

Asp Thr Thr Gly Asn Gly Leu Ala Arg Leu Pro Ser Leu Leu Glu Gln
    50                  55                  60

His Thr Pro Asp Leu Val Leu Ile Glu Leu Gly Ala Asn Asp Gly Leu
65                  70                  75                  80

Arg Gly Phe Pro Pro Lys Leu Ile Thr Leu Asn Leu Ser Lys Met Ile
                85                  90                  95

Thr Met Ile Lys Asp Ser Gly Ala Asp Val Val Met Met Gln Ile Arg
            100                 105                 110

Val Pro Pro Asn Tyr Gly Lys Arg Tyr Ser Asp Met Phe Tyr Asp Ile
        115                 120                 125

Tyr Pro Lys Leu Ala Glu His Gln Gln Val Ala Leu Met Pro Phe Phe
    130                 135                 140

Leu Glu His Val Ile Ile Lys Pro Glu Trp Met Met Asp Asp Gly Leu
145                 150                 155                 160

His Pro Lys Pro Glu Ala Gln Pro Tyr Ile Ala Asp Phe Val Ala Gln
                165                 170                 175

Glu Leu Val Lys His Leu
            180
```

<210> SEQ ID NO 68
<211> LENGTH: 549
<212> TYPE: DNA
<213> ORGANISM: Vibrio harveyi

<400> SEQUENCE: 68

```
atgagcgaaa agctacttgt tttgggcgac agcctgagcg ctggttatca atgcctata       60 gaggagagtt ggcctagctt actcccaggc gcgttattag aacatggcca agatgtaaaa     120
gttgtaaacg gtagcatctc tggtgacacc acaggcaatg ccttgcacg gttaccttct     180 ctccttgagc aacacacgcc cgatttggta ctgattgagc ttggcgctaa cgatggccta     240
cgcggtttcc cacctaaact tattacgtta acctatcga aaatgattac catgatcaaa     300
gattctggtg cggatgtcgt catgatgcaa atccgcgtcc caccaaatta tggtaagcgt     360
tacagcgata tgttctacga catctaccct aaactggcag aacatcagca agtagcgcta     420
atgccgttct tcttagagca tgtcatcatt aaaccagaat ggatgatgga cgatggcttg     480
cacccaaaac cggaagctca acctacatt gctgactttg tcgctcaaga attggttaaa     540
catctctaa                                                            549
```

<210> SEQ ID NO 69
<211> LENGTH: 70

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
aaaaacagca acaatgtgag ctttgttgta attatattgt aaacatattg attccgggga    60
tccgtcgacc                                                           70

<210> SEQ ID NO 70
<211> LENGTH: 69
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
aaacggagcc tttcgggctc cgttattcat ttacgcggct tcaactttcc tgtaggctgg    60
agctgcttc                                                            69

<210> SEQ ID NO 71
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
cgggcaggtg ctatgaccag gac                                            23

<210> SEQ ID NO 72
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
cgcggcgttg accggcagcc tgg                                            23

<210> SEQ ID NO 73
<211> LENGTH: 182
<212> TYPE: PRT
<213> ORGANISM: Escherichia coli

<400> SEQUENCE: 73

Ala Asp Thr Leu Leu Ile Leu Gly Asp Ser Leu Ser Ala Gly Tyr Arg
1               5                   10                  15

Met Ser Ala Ser Ala Ala Trp Pro Ala Leu Leu Asn Asp Lys Trp Gln
            20                  25                  30

Ser Lys Thr Ser Val Val Asn Ala Ser Ile Ser Gly Asp Thr Ser Gln
        35                  40                  45

Gln Gly Leu Ala Arg Leu Pro Ala Leu Leu Lys Gln His Gln Pro Arg
    50                  55                  60

Trp Val Leu Val Glu Leu Gly Gly Asn Asp Gly Leu Arg Gly Phe Gln
65                  70                  75                  80

Pro Gln Gln Thr Glu Gln Thr Leu Arg Gln Ile Leu Gln Asp Val Lys
                85                  90                  95
```

```
Ala Ala Asn Ala Glu Pro Leu Leu Met Gln Ile Arg Leu Pro Ala Asn
            100                 105                 110

Tyr Gly Arg Arg Tyr Asn Glu Ala Phe Ser Ala Ile Tyr Pro Lys Leu
            115                 120                 125

Ala Lys Glu Phe Asp Val Pro Leu Leu Pro Phe Phe Met Glu Glu Val
            130                 135                 140

Tyr Leu Lys Pro Gln Trp Met Gln Asp Asp Gly Ile His Pro Asn Arg
145                 150                 155                 160

Asp Ala Gln Pro Phe Ile Ala Asp Trp Met Ala Lys Gln Leu Gln Pro
                165                 170                 175

Leu Val Asn His Asp Ser
            180

<210> SEQ ID NO 74
<211> LENGTH: 190
<212> TYPE: PRT
<213> ORGANISM: Artificial Sequence
<220> FEATURE:
<223> OTHER INFORMATION: Description of Artificial Sequence: Synthetic
      1J00_A polypeptide
<220> FEATURE:
<221> NAME/KEY: MOD_RES
<222> LOCATION: (10)..(10)
<223> OTHER INFORMATION: Chemically modified-Ser

<400> SEQUENCE: 74

Ala Asp Thr Leu Leu Ile Leu Gly Asp Ser Leu Ser Ala Gly Tyr Arg
1               5                   10                  15

Met Ser Ala Ser Ala Ala Trp Pro Ala Leu Leu Asn Asp Lys Trp Gln
            20                  25                  30

Ser Lys Thr Ser Val Val Asn Ala Ser Ile Ser Gly Asp Thr Ser Gln
            35                  40                  45

Gln Gly Leu Ala Arg Leu Pro Ala Leu Leu Lys Gln His Gln Pro Arg
        50                  55                  60

Trp Val Leu Val Glu Leu Gly Gly Asn Asp Gly Leu Arg Gly Phe Gln
65                  70                  75                  80

Pro Gln Gln Thr Glu Gln Thr Leu Arg Gln Ile Leu Gln Asp Val Lys
                85                  90                  95

Ala Ala Asn Ala Glu Pro Leu Leu Met Gln Ile Arg Leu Pro Ala Asn
            100                 105                 110

Tyr Gly Arg Arg Tyr Asn Glu Ala Phe Ser Ala Ile Tyr Pro Lys Leu
            115                 120                 125

Ala Lys Glu Phe Asp Val Pro Leu Leu Pro Phe Phe Met Glu Glu Val
            130                 135                 140

Tyr Leu Lys Pro Gln Trp Met Gln Asp Asp Gly Ile His Pro Asn Arg
145                 150                 155                 160

Asp Ala Gln Pro Phe Ile Ala Asp Trp Met Ala Lys Gln Leu Gln Pro
                165                 170                 175

Leu Val Asn His Asp Ser Leu Glu His His His His His
            180                 185                 190

<210> SEQ ID NO 75
<211> LENGTH: 190
<212> TYPE: PRT
<213> ORGANISM: Artificial Sequence
<220> FEATURE:
<223> OTHER INFORMATION: Description of Artificial Sequence: Synthetic
      1JRL_A polypeptide

<400> SEQUENCE: 75
```

```
Ala Asp Thr Leu Leu Ile Leu Gly Asp Ser Leu Ser Ala Gly Tyr Arg
1               5                   10                  15

Met Ser Ala Ser Ala Ala Trp Pro Ala Leu Leu Asn Asp Lys Trp Gln
            20                  25                  30

Ser Lys Thr Ser Val Val Asn Ala Ser Ile Ser Gly Asp Thr Ser Gln
        35                  40                  45

Gln Gly Leu Ala Arg Leu Pro Ala Leu Leu Lys Gln His Gln Pro Arg
    50                  55                  60

Trp Val Leu Val Glu Leu Gly Gly Asn Asp Gly Leu Arg Gly Phe Gln
65                  70                  75                  80

Pro Gln Gln Thr Glu Gln Thr Leu Arg Gln Ile Leu Gln Asp Val Lys
                85                  90                  95

Ala Ala Asn Ala Glu Pro Leu Leu Met Gln Ile Arg Pro Pro Ala Asn
            100                 105                 110

Tyr Gly Arg Arg Tyr Asn Glu Ala Phe Ser Ala Ile Tyr Pro Lys Leu
        115                 120                 125

Ala Lys Glu Phe Asp Val Pro Leu Leu Pro Phe Phe Met Glu Glu Val
    130                 135                 140

Tyr Leu Lys Pro Gln Trp Met Gln Asp Asp Gly Ile His Pro Asn Arg
145                 150                 155                 160

Asp Ala Gln Pro Phe Ile Ala Asp Trp Met Ala Lys Gln Leu Gln Pro
                165                 170                 175

Leu Val Asn His Asp Ser Leu Glu His His His His His His
                180                 185                 190

<210> SEQ ID NO 76
<211> LENGTH: 208
<212> TYPE: PRT
<213> ORGANISM: Escherichia coli

<400> SEQUENCE: 76

Met Met Asn Phe Asn Asn Val Phe Arg Trp His Leu Pro Phe Leu Phe
1               5                   10                  15

Leu Val Leu Leu Thr Phe Arg Ala Ala Ala Ala Asp Thr Leu Leu Ile
            20                  25                  30

Leu Gly Asp Ser Leu Ser Ala Gly Tyr Arg Met Ser Ala Ser Ala Ala
        35                  40                  45

Trp Pro Ala Leu Leu Asn Asp Lys Trp Gln Ser Lys Thr Ser Val Val
    50                  55                  60

Asn Ala Ser Ile Ser Gly Asp Thr Ser Gln Gln Gly Leu Ala Arg Leu
65                  70                  75                  80

Pro Ala Leu Leu Lys Gln His Gln Pro Arg Trp Val Leu Val Glu Leu
                85                  90                  95

Gly Gly Asn Asp Gly Leu Arg Gly Phe Gln Pro Gln Gln Thr Glu Gln
            100                 105                 110

Thr Leu Arg Gln Ile Leu Gln Asp Val Lys Ala Ala Asn Ala Glu Pro
        115                 120                 125

Leu Leu Met Gln Ile Arg Leu Pro Ala Asn Tyr Gly Arg Arg Tyr Asn
    130                 135                 140

Glu Ala Phe Ser Ala Ile Tyr Pro Lys Leu Ala Lys Glu Phe Asp Val
145                 150                 155                 160

Pro Leu Leu Pro Phe Leu Met Glu Glu Val Tyr Leu Lys Pro Gln Trp
                165                 170                 175

Met Gln Asp Asp Gly Ile His Pro Asn Arg Asp Ala Gln Pro Phe Ile
```

```
                    180                 185                 190

Ala Asp Trp Met Ala Lys Gln Leu Gln Pro Leu Val Asn His Asp Ser
            195                 200                 205

<210> SEQ ID NO 77
<211> LENGTH: 208
<212> TYPE: PRT
<213> ORGANISM: Shigella boydii

<400> SEQUENCE: 77

Met Met Asn Phe Asn Asn Val Phe Arg Trp His Leu Pro Phe Leu Phe
1               5                   10                  15

Leu Val Leu Leu Thr Phe Arg Ala Ala Ala Asp Thr Leu Leu Ile
            20                  25                  30

Leu Gly Asn Ser Leu Ser Ala Gly Tyr Arg Met Ser Ala Ser Ala Ala
            35                  40                  45

Trp Pro Ala Leu Leu Asn Asp Lys Trp Gln Ser Lys Thr Ser Val Val
    50                  55                  60

Asn Ala Ser Ile Ser Gly Asp Thr Ser Gln Gln Gly Leu Ala Arg Leu
65                  70                  75                  80

Pro Ala Leu Leu Lys Gln His Gln Pro Arg Trp Val Leu Val Glu Leu
                85                  90                  95

Gly Gly Asn Asp Gly Leu Arg Gly Phe Gln Pro Gln Gln Thr Glu Gln
            100                 105                 110

Thr Leu Arg Gln Ile Leu Gln Asp Val Lys Ala Ala Asn Ala Glu Pro
        115                 120                 125

Leu Leu Met Gln Ile Arg Leu Pro Ala Asn Tyr Gly Arg Arg Tyr Asn
    130                 135                 140

Glu Ala Phe Ser Ala Ile Tyr Pro Lys Leu Ala Lys Glu Phe Asp Val
145                 150                 155                 160

Pro Leu Leu Pro Phe Phe Met Glu Glu Val Tyr Leu Lys Pro Gln Trp
                165                 170                 175

Met Gln Asp Asp Gly Ile His Pro Asn Arg Asp Ala Gln Pro Phe Ile
            180                 185                 190

Ala Asp Trp Met Ala Lys Gln Leu Gln Pro Leu Val Asn His Asp Ser
        195                 200                 205

<210> SEQ ID NO 78
<211> LENGTH: 207
<212> TYPE: PRT
<213> ORGANISM: Escherichia coli

<400> SEQUENCE: 78

Met Asn Phe Asn Asn Val Phe Arg Trp His Leu Pro Phe Leu Phe Leu
1               5                   10                  15

Val Leu Leu Thr Phe Arg Ala Ala Ala Ala Asp Thr Leu Leu Ile Leu
            20                  25                  30

Gly Asp Ser Leu Ser Ala Gly Tyr Arg Met Ser Ala Ser Ala Ala Trp
            35                  40                  45

Pro Ala Leu Leu Asn Asp Lys Trp Gln Ser Lys Thr Ser Val Val Asn
    50                  55                  60

Ala Ser Ile Ser Gly Asp Thr Ser Gln Gln Gly Leu Ala Arg Leu Pro
65                  70                  75                  80

Ala Leu Leu Lys Gln His Gln Pro Arg Trp Val Leu Val Glu Leu Gly
                85                  90                  95

Gly Asn Asp Gly Leu Arg Gly Phe Gln Pro Gln Gln Thr Glu Gln Thr
```

```
              100                 105                 110
Leu Arg Gln Ile Leu Gln Asp Val Lys Ala Ala Asn Ala Glu Pro Leu
            115                 120                 125

Leu Met Gln Ile Arg Leu Pro Ala Asn Tyr Gly Arg Arg Tyr Asn Glu
        130                 135                 140

Ala Phe Ser Ala Ile Tyr Pro Lys Leu Ala Lys Glu Phe Asp Val Pro
145                 150                 155                 160

Leu Leu Pro Phe Leu Met Glu Glu Val Tyr Leu Lys Pro Gln Trp Met
                165                 170                 175

Gln Asp Asp Gly Ile His Pro Asn Arg Asp Ala Gln Pro Phe Ile Ala
            180                 185                 190

Asp Trp Met Ala Lys Gln Leu Gln Pro Leu Val Asn His Asp Ser
        195                 200                 205
```

<210> SEQ ID NO 79
<211> LENGTH: 207
<212> TYPE: PRT
<213> ORGANISM: Escherichia albertii

<400> SEQUENCE: 79

```
Met Asn Phe Asn Val Phe Arg Trp His Leu Pro Phe Leu Phe Leu
1               5                   10                  15

Val Leu Leu Thr Phe Arg Ala Ala Ala Ala Asp Thr Leu Leu Ile Leu
            20                  25                  30

Gly Asp Ser Leu Ser Ala Gly Tyr Arg Met Ser Ala Ser Ala Ala Trp
        35                  40                  45

Pro Ala Leu Leu Asn Asp Lys Trp Gln Ser Lys Thr Ser Val Val Asn
    50                  55                  60

Ala Ser Ile Ser Gly Asp Thr Ser Gln Gln Gly Leu Ala Arg Leu Pro
65                  70                  75                  80

Ala Leu Leu Lys Gln His Gln Pro Arg Trp Val Leu Val Glu Leu Gly
                85                  90                  95

Gly Asn Asp Gly Leu Arg Gly Phe Gln Pro Gln Gln Thr Glu Gln Thr
            100                 105                 110

Leu Arg Gln Ile Leu Gln Asp Val Lys Ala Ala Asn Ala Glu Pro Leu
        115                 120                 125

Leu Met Gln Ile Arg Leu Pro Ala Asn Tyr Gly Arg Arg Tyr Asn Glu
    130                 135                 140

Ala Phe Ser Ala Ile Tyr Pro Lys Leu Ala Lys Glu Phe Asp Ile Pro
145                 150                 155                 160

Leu Leu Pro Phe Phe Met Glu Glu Val Tyr Leu Lys Pro Gln Trp Met
                165                 170                 175

Gln Asp Asp Gly Ile His Pro Asn Arg Asp Ala Gln Pro Phe Ile Ala
            180                 185                 190

Asp Trp Met Ala Lys Gln Leu Gln Pro Leu Val Asn His Asp Ser
        195                 200                 205
```

<210> SEQ ID NO 80
<211> LENGTH: 197
<212> TYPE: PRT
<213> ORGANISM: Escherichia coli

<400> SEQUENCE: 80

```
Met Pro Phe Leu Phe Leu Val Leu Leu Thr Phe Arg Ala Ala Ala Ala
1               5                   10                  15

Asp Thr Leu Leu Ile Leu Gly Asp Ser Leu Ser Ala Gly Tyr Arg Met
```

```
            20                  25                  30
Ser Ala Ser Ala Ala Trp Pro Ala Leu Leu Asn Asp Lys Trp Gln Ser
        35                  40                  45

Lys Thr Ser Val Val Asn Ala Ser Ile Ser Gly Asp Thr Ser Gln Gln
    50                  55                  60

Gly Leu Ala Arg Leu Pro Ala Leu Leu Lys Gln His Gln Pro Arg Trp
65                  70                  75                  80

Val Leu Val Glu Leu Gly Gly Asn Asp Gly Leu Arg Gly Phe Gln Pro
                85                  90                  95

Gln Gln Thr Glu Gln Thr Leu Arg Gln Ile Leu Gln Asp Val Lys Ala
            100                 105                 110

Ala Asn Ala Glu Pro Leu Leu Met Gln Ile Arg Leu Pro Ala Asn Tyr
        115                 120                 125

Gly Arg Arg Tyr Asn Glu Ala Phe Ser Ala Ile Tyr Pro Lys Leu Ala
    130                 135                 140

Lys Glu Phe Asp Val Pro Leu Leu Pro Phe Leu Met Glu Val Tyr
145                 150                 155                 160

Leu Lys Pro Gln Trp Met Gln Asp Asp Gly Ile His Pro Asn Arg Asp
                165                 170                 175

Ala Gln Pro Phe Ile Ala Asp Trp Met Ala Lys Gln Leu Gln Pro Leu
            180                 185                 190

Val Asn His Asp Ser
        195

<210> SEQ ID NO 81
<211> LENGTH: 208
<212> TYPE: PRT
<213> ORGANISM: Shigella dysenteriae

<400> SEQUENCE: 81

Met Met Asn Phe Asn Asn Val Phe Arg Trp His Leu Pro Phe Leu Phe
1               5                   10                  15

Leu Val Leu Leu Thr Phe Arg Ala Ala Ala Asp Thr Leu Leu Ile
                20                  25                  30

Leu G

Ala Asp Trp Met Ala Lys Gln Leu Gln Pro Leu Val Asn His Asp Ser
        195                 200                 205

<210> SEQ ID NO 82
<211> LENGTH: 197
<212> TYPE: PRT
<213> ORGANISM: Citrobacter koseri

<400> SEQUENCE: 82

Met Pro Phe Leu Phe Leu Val Leu Leu Thr Phe Arg Ala Ala Ala
1               5                   10                  15

Asp Thr Leu Leu Ile Leu Gly Asp Ser Leu Ser Ala Gly Tyr Arg Met
            20                  25                  30

Ser Ala Ser Ala Ala Trp Pro Ala Leu Leu Asn Asp Lys Trp Gln Asp
        35                  40                  45

Lys Thr Pro Val Ile Asn Ala Ser Ile Ser Gly Asp Thr Ser Gln Gln
50                  55                  60

Gly Leu Ala Arg Leu Pro Ala Leu Leu Lys Gln His Gln Pro Arg Trp
65                  70                  75                  80

Val Leu Val Glu Leu Gly Gly Asn Asp Gly Leu Arg Gly Phe Gln Pro
                85                  90                  95

Gln Gln Thr Glu Gln Thr Leu Arg Lys Ile Leu Leu Asp Val Lys Ala
            100                 105                 110

Ala Asn Ala Glu Pro Leu Leu Met Gln Ile Arg Leu Pro Ala Asn Tyr
        115                 120                 125

Gly Arg Arg Tyr Asn Glu Thr Phe Ser Ala Ile Tyr Pro Arg Leu Ala
    130                 135                 140

Lys Glu Phe Asp Ile Pro Leu Leu Pro Phe Phe Met Glu Glu Val Tyr
145                 150                 155                 160

Leu Lys Pro Gln Trp Met Gln Asp Asp Gly Ile His Pro Asn Arg Asp
                165                 170                 175

Ala Gln Pro Phe Ile Ala Asp Trp Met Ala Gln Gln Leu Thr Pro Leu
            180                 185                 190

Val Asn His Asp Ser
        195

<210> SEQ ID NO 83
<211> LENGTH: 218
<212> TYPE: PRT
<213> ORGANISM: Unknown
<220> FEATURE:
<223> OTHER INFORMATION: Description of Unknown: Marine metagenome
      polypeptide

<400> SEQUENCE: 83

Val Leu Pro Leu Thr Asp Gly Leu Leu Lys Met Met Asn Phe Asn Asn
1               5                   10                  15

Val Phe Arg Trp His Leu Pro Ile Leu Phe Leu Ile Leu Phe Thr Cys
            20                  25                  30

Arg Ala Ala Ala Ala Asp Thr Leu Ile Leu Gly Asp Ser Leu Ser
        35                  40                  45

Ala Gly Tyr Arg Met Ser Ala Ser Ala Ala Trp Pro Ala Leu Leu Asn
    50                  55                  60

Asp Lys Trp Gln Ser Lys Thr Val Val Asn Ala Ser Ile Ser Gly
65                  70                  75                  80

Asp Thr Ser Gln Gln Ala Leu Ala Arg Leu Pro Ala Leu Leu Lys Gln
                85                  90                  95

His Gln Pro Arg Trp Val Leu Val Glu Leu Gly Gly Asn Asp Gly Leu
            100                 105                 110

Arg Gly Phe Ala Pro Gln Gln Thr Glu Gln Thr Leu Arg Thr Ile Val
            115                 120                 125

Gln Asp Val Lys Thr Ala Asn Ala Glu Pro Leu Leu Met Gln Ile Arg
    130                 135                 140

Leu Pro Ala Asn Tyr Gly Arg Tyr Asn Glu Thr Phe Ser Ala Leu
145                 150                 155                 160

Tyr Pro Lys Leu Ala Lys Glu Phe Asp Ile Pro Leu Leu Pro Phe Phe
                165                 170                 175

Met Glu Glu Val Tyr Leu Lys Pro Gln Trp Met Gln Asp Asp Gly Ile
            180                 185                 190

His Pro Asn Arg Asp Ala Gln Pro Phe Ile Ala Asp Trp Met Ala Lys
            195                 200                 205

Gln Leu Ser Pro Leu Val Lys His Glu Ser
            210                 215

<210> SEQ ID NO 84
<211> LENGTH: 295
<212> TYPE: PRT
<213> ORGANISM: Enterobacter cloacae

<400> SEQUENCE: 84

Leu Lys Asp Lys Pro Asp Met Pro Gly Ser Gln Arg Gly Ala Gly Leu
1               5                   10                  15

Phe Ile Lys Arg Val Glu Gly Leu Ala Asp Gln Val His Phe Pro Thr
            20                  25                  30

Ala Ala Ile Val Gln Thr Gly Glu Asn Gly Gln Gln Arg Gly Leu Thr
            35                  40                  45

Gly Thr Gly Phe Thr Asn Gln Gly Asp Gly Phe Gly Thr Phe Asp Asn
    50                  55                  60

Glu Phe Asn Ser Gly Glu Asp Gly Lys Leu Val Phe Pro Leu Thr Asp
65                  70                  75                  80

Arg Leu Leu Lys Thr Met Asn Phe Asn Asn Val Phe Arg Trp His Leu
                85                  90                  95

Pro Phe Leu Phe Leu Met Leu Met Thr Phe Arg Ala Ala Ala Ala Asp
            100                 105                 110

Thr Leu Leu Ile Leu Gly Asp Ser Leu Ser Ala Gly Tyr Arg Met Ala
            115                 120                 125

Ala Ser Ala Ala Trp Pro Ala Leu Leu Asn Asp Lys Trp Gln Ser Arg
    130                 135                 140

Ala Ser Val Val Asn Gly Ser Ile Ser Gly Asp Thr Ser Gln Gln Gly
145                 150                 155                 160

Leu Ser Arg Leu Pro Ala Leu Leu Lys Gln His Gln Pro Arg Trp Val
                165                 170                 175

Leu Val Glu Leu Gly Gly Asn Asp Gly Leu Arg Gly Phe Gln Pro Gln
            180                 185                 190

Gln Thr Glu Gln Thr Leu Arg Thr Ile Leu Gln Thr Ile Lys Ala Ala
            195                 200                 205

Asp Ala Gln Pro Leu Leu Met Gln Ile Arg Leu Pro Ala Asn Tyr Gly
    210                 215                 220

Arg Arg Tyr Asn Glu Ala Phe Ser Ala Ile Tyr Pro Lys Leu Ala Lys
225                 230                 235                 240

Glu Phe Asp Ile Pro Leu Leu Pro Phe Phe Met Glu Glu Val Tyr Leu
                245                 250                 255

-continued

```
Lys Pro Gln Trp Met Gln Asp Asp Gly Ile His Pro Asn Arg Asp Ala
            260                 265                 270
Gln Pro Phe Ile Ala Asp Trp Met Ala Thr Arg Leu Ala Pro Leu Val
        275                 280                 285
Asn His Asp Ser Ser Asn Ser
    290                 295

<210> SEQ ID NO 85
<211> LENGTH: 197
<212> TYPE: PRT
<213> ORGANISM: Enterobacter cancerogenus

<400> SEQUENCE: 85

Met Pro Phe Leu Phe Leu Ile Leu Leu Thr Phe Arg Ala Ala Ala Ala
1               5                   10                  15
Asp Thr Leu Leu Ile Leu Gly Asp Ser Leu Ser Ala Gly Tyr Arg Met
            20                  25                  30
Ala Ala Ser Ala Ala Trp Pro Ala Leu Leu Asn Asp Lys Trp Gln Ser
        35                  40                  45
Gln Thr Thr Val Val Asn Gly Ser Ile Ser Gly Asp Thr Ser Gln Gln
    50                  55                  60
Gly Leu Ser Arg Leu Pro Ala Leu Leu Lys Gln His Gln Pro Arg Trp
65                  70                  75                  80
Val Leu Val Glu Leu Gly Gly Asn Asp Gly Leu Arg Gly Phe Gln Pro
                85                  90                  95
Gln Gln Thr Glu His Thr Leu Arg Thr Ile Leu Gln Glu Ile Lys Ala
            100                 105                 110
Ala Asn Ala Gln Pro Leu Leu Met Gln Ile Arg Leu Pro Ala Asn Tyr
        115                 120                 125
Gly Arg Arg Tyr Asn Glu Ala Phe Ser Ala Ile Tyr Pro Lys Leu Ala
    130                 135                 140
Lys Glu Phe Asp Ile Pro Leu Leu Pro Phe Phe Met Glu Glu Val Tyr
145                 150                 155                 160
Leu Lys Pro Gln Trp Met Gln Asp Asp Gly Ile His Pro Asn Arg Asp
                165                 170                 175
Ala Gln Pro Phe Ile Ala Asp Trp Met Ala Thr Arg Leu Ala Pro Leu
            180                 185                 190
Val Lys His Asp Ser
        195

<210> SEQ ID NO 86
<211> LENGTH: 467
<212> TYPE: PRT
<213> ORGANISM: Klebsiella pneumoniae

<400> SEQUENCE: 86

Gly Leu Ser Pro Ser Asp Arg Leu Ser Thr Pro Gly Pro Ala Arg Arg
1               5                   10                  15
Pro Arg Arg Gly Leu Thr Pro Ala Arg Arg Ser Ala Ala Thr Ala Ser
            20                  25                  30
Ala Ile Arg Ala Arg Thr Ser Gly Arg Ser Cys Phe Leu Pro Gln Leu
        35                  40                  45
Ala Ile Arg Gln Ala Gln Thr Ala Ile Ala Ala Arg Arg Gln Gln Arg
    50                  55                  60
Ile Val Ser Asp Glu Asp Gln Gly Gly Ala Val Phe Ala Ile Lys Arg
65                  70                  75                  80
```

Glu Gln Gln Ile Gly Asn Phe Val Pro Gly Leu Ala Ile Glu Val Ala
                85                  90                  95
Gly Gly Leu Ile Gly Glu Gln Asn Gly Arg Ala Pro Val Lys Gly Pro
            100                 105                 110
Gly Gln Arg His Pro Leu Leu Phe Ala Ala Gly Glu Leu Arg Arg Gln
        115                 120                 125
Val Val Gln Ala Phe Ala Lys Ser Gln Leu Leu Lys Gln Arg Ala Gly
    130                 135                 140
Ile Ala Pro Ala Leu Ala Ile Ala Gly Ala Ala Gln Gln Arg Arg Gln
145                 150                 155                 160
Leu Asp Val Leu Gln Gly Val Glu Arg Arg Asp Gln His Lys Arg Leu
                165                 170                 175
Lys Asn Lys Thr Asn Val Leu Arg Pro Gln Arg Arg Pro Arg Leu Phe
            180                 185                 190
Ile His Pro Val Gln Arg Phe Ala Gln His Arg Tyr Phe Pro Ala Ala
        195                 200                 205
Ala Ile Val Glu Ala Gly Glu Asp Arg Gln Gln Gly Arg Phe Thr Gly
    210                 215                 220
Thr Arg Leu Ala Asp Gln Gly Asp Gly Leu Pro Arg Phe Asp Asn Gln
225                 230                 235                 240
Leu Asn Ser Gly Lys Asp Gly Glu Leu Met Leu Pro Leu Thr Asp Gly
                245                 250                 255
Leu Leu Lys Met Met Asn Phe Lys Tyr Val Phe Arg Trp His Val Pro
            260                 265                 270
Phe Leu Leu Leu Phe Leu Phe Thr Cys Arg Ala Met Ala Ala Asp Thr
        275                 280                 285
Leu Leu Ile Leu Gly Asp Ser Leu Ser Ala Gly Tyr Arg Met Ala Ala
    290                 295                 300
Asn Ala Ala Trp Pro Ala Leu Leu Asn Glu Gln Trp Gln Ala Lys Thr
305                 310                 315                 320
Pro Val Val Asn Ala Ser Ile Ser Gly Asp Thr Ser Gln Gln Gly Leu
                325                 330                 335
Ala Arg Leu Pro Ala Leu Leu Lys Gln His Gln Pro Arg Trp Val Leu
            340                 345                 350
Val Glu Leu Gly Gly Asn Asp Gly Leu Arg Gly Phe Pro Pro Gln Gln
        355                 360                 365
Thr Glu Gln Thr Leu Arg Thr Ile Ile Lys Asp Ile Lys Ala Ala Asn
    370                 375                 380
Ala Glu Pro Leu Leu Met Gln Ile His Leu Pro Ala Asn Tyr Gly Arg
385                 390                 395                 400
Arg Tyr Asn Glu Ala Phe Gly Ala Ile Tyr Pro Ala Leu Ala Lys Glu
                405                 410                 415
Phe Ala Ile Pro Leu Leu Pro Phe Phe Met Glu Glu Val Tyr Leu Lys
            420                 425                 430
Pro Gln Trp Met Gln Asp Asp Gly Ile His Pro Asn Arg Asp Ala Gln
        435                 440                 445
Pro Phe Ile Ala Asp Trp Met Ala Lys Arg Leu Ala Pro Leu Val Asn
    450                 455                 460
His Asp Ser
465

<210> SEQ ID NO 87
<211> LENGTH: 208

<212> TYPE: PRT
<213> ORGANISM: Enterobacter sp.

<400> SEQUENCE: 87

```
Met Met Asn Cys Asn Asn Val Phe Arg Trp His Leu Pro Phe Leu Phe
1               5                   10                  15

Leu Ile Leu Met Thr Phe Arg Ala Ala Ala Ala Asp Thr Leu Leu Val
            20                  25                  30

Leu Gly Asp Ser Leu Ser Ala Gly Tyr Arg Met Ala Ala Thr Ala Ala
        35                  40                  45

Trp Pro Ala Leu Leu Asn Asp Lys Trp Gln Thr Lys Thr Pro Val Leu
    50                  55                  60

Asn Ala Ser Ile Ser Gly Asp Thr Ser Gln Gln Gly Leu Ala Arg Leu
65                  70                  75                  80

Pro Ala Leu Leu Lys Gln His Gln Pro Arg Trp Val Leu Val Glu Leu
                85                  90                  95

Gly Gly Asn Asp Gly Leu Arg Gly Phe Gln Pro Gln Gln Thr Glu Gln
            100                 105                 110

Thr Leu Arg Lys Ile Ile Gln Asp Ile Gln Ala Ala Asn Ala Gln Pro
        115                 120                 125

Leu Leu Met Gln Ile Arg Leu Pro Ala Asn Tyr Gly Arg Arg Tyr Asn
130                 135                 140

Glu Ser Phe Ser Ala Ile Tyr Pro Lys Leu Ala Lys Glu Phe Asp Ile
145                 150                 155                 160

Pro Leu Leu Pro Phe Phe Met Glu Glu Val Tyr Leu Lys Pro Gln Trp
                165                 170                 175

Met Gln Asp Asp Gly Ile His Pro Asn Arg Asp Ala Gln Pro Phe Ile
            180                 185                 190

Ala Asp Trp Met Ala Thr Arg Leu Ala Pro Leu Val Lys His Asp Ser
        195                 200                 205
```

<210> SEQ ID NO 88
<211> LENGTH: 197
<212> TYPE: PRT
<213> ORGANISM: Klebsiella pneumoniae

<400> SEQUENCE: 88

```
Met Pro Phe Leu Leu Leu Phe Leu Phe Thr Cys Arg Ala Met Ala Ala
1               5                   10                  15

Asp Thr Leu Leu Ile Leu Gly Asp Ser Leu Ser Ala Gly Tyr Arg Met
            20                  25                  30

Ala Ala Asn Ala Ala Trp Pro Ala Leu Leu Asn Glu Gln Trp Gln Ala
        35                  40                  45

Lys Thr Pro Val Val Asn Ala Ser Ile Ser Gly Asp Thr Ser Gln Gln
    50                  55                  60

Gly Leu Ala Arg Leu Pro Ala Leu Leu Lys Gln His Gln Pro Arg Trp
65                  70                  75                  80

Val Leu Val Glu Leu Gly Gly Asn Asp Gly Leu Arg Gly Phe Pro Pro
                85                  90                  95

Gln Gln Thr Glu Gln Thr Leu Arg Thr Ile Ile Lys Asp Ile Lys Ala
            100                 105                 110

Ala Asn Ala Glu Pro Leu Leu Met Gln Ile His Leu Pro Ala Asn Tyr
        115                 120                 125

Gly Arg Arg Tyr Asn Glu Ala Phe Gly Ala Ile Tyr Pro Ala Leu Ala
    130                 135                 140
```

Lys Glu Phe Ala Ile Pro Leu Leu Pro Phe Met Glu Glu Val Tyr
145                 150                 155                 160

Leu Lys Pro Gln Trp Met Gln Asp Asp Gly Ile His Pro Asn Arg Asp
            165                 170                 175

Ala Gln Pro Phe Ile Ala Asp Trp Met Ala Lys Arg Leu Ala Pro Leu
        180                 185                 190

Val Asn His Asp Ser
        195

<210> SEQ ID NO 89
<211> LENGTH: 207
<212> TYPE: PRT
<213> ORGANISM: Klebsiella pneumoniae

<400> SEQUENCE: 89

Met Asn Phe Lys Tyr Val Phe Arg Trp His Val Pro Phe Leu Phe Leu
1               5                   10                  15

Phe Leu Phe Thr Cys Arg Ala Met Ala Ala Asp Thr Leu Leu Ile Leu
            20                  25                  30

Gly Asp Ser Leu Ser Ala Gly Tyr Arg Met Ala Ala Asn Ala Ala Trp
        35                  40                  45

Pro Ala Leu Leu Asn Glu Lys Trp Gln Ala Lys Thr Pro Val Val Asn
50                  55                  60

Ala Ser Ile Ser Gly Asp Thr Ser Gln Gln Gly Leu Ala Arg Leu Pro
65                  70                  75                  80

Ala Leu Leu Lys Gln His Gln Pro Arg Trp Val Leu Val Glu Leu Gly
                85                  90                  95

Gly Asn Asp Gly Leu Arg Gly Phe Pro Pro Gln Gln Thr Glu Gln Thr
            100                 105                 110

Leu Arg Thr Ile Ile Lys Asp Ile Lys Ala Ala Asn Ala Glu Pro Leu
        115                 120                 125

Leu Met Gln Ile His Leu Pro Ala Asn Tyr Gly Arg Arg Tyr Asn Glu
    130                 135                 140

Ala Phe Gly Ala Ile Tyr Pro Ala Leu Ala Lys Glu Phe Asp Ile Pro
145                 150                 155                 160

Leu Leu Pro Phe Phe Met Glu Glu Val Tyr Leu Lys Pro Gln Trp Met
                165                 170                 175

Gln Asp Asp Gly Ile His Pro Asn Arg Asp Ala Gln Pro Phe Ile Ala
            180                 185                 190

Asp Trp Met Ala Asn Arg Leu Ala Pro Leu Val Asn His Asp Ser
        195                 200                 205

<210> SEQ ID NO 90
<211> LENGTH: 204
<212> TYPE: PRT
<213> ORGANISM: Salmonella enterica

<400> SEQUENCE: 90

Met Asn Phe Asn Thr Val Phe Arg Trp His Leu Pro Phe Leu Phe Leu
1               5                   10                  15

Ile Leu Leu Thr Phe Arg Ala Ala Ala Ala Asp Thr Leu Leu Ile Leu
            20                  25                  30

Gly Asp Ser Leu Ser Ala Gly Tyr Arg Met Thr Ala Ser Ala Ala Trp
        35                  40                  45

Pro Ser Leu Leu Asn Asp Lys Trp Gln Asn Lys Thr Ser Val Val Asn
50                  55                  60

Ala Ser Ile Ser Gly Asp Thr Ser Gln Gln Gly Leu Ala Arg Leu Pro
65                  70                  75                  80

Ala Leu Leu Gln Gln His His Pro Arg Trp Val Val Glu Leu Gly
                85                  90                  95

Gly Asn Asp Gly Leu Arg Gly Phe Ala Pro Ala Gln Thr Glu Gln Thr
            100                 105                 110

Leu Arg Lys Ile Ile Gln Thr Val Lys Ala Ala Asp Ala Gln Pro Leu
            115                 120                 125

Leu Met Gln Ile His Leu Pro Ala Asn Tyr Gly Arg Arg Tyr Asn Glu
        130                 135                 140

Ser Phe Ser Ala Ile Tyr Pro Lys Leu Ala Lys Glu Phe Asp Ile Pro
145                 150                 155                 160

Leu Leu Pro Phe Phe Met Glu Glu Val Tyr Leu Lys Pro Gln Trp Met
                165                 170                 175

Gln Asp Asp Gly Ile His Pro Asn Arg Asp Ala Gln Pro Phe Ile Ala
            180                 185                 190

Asp Trp Met Ala Lys Gln Leu Thr Pro Phe Leu Ser
            195                 200

<210> SEQ ID NO 91
<211> LENGTH: 204
<212> TYPE: PRT
<213> ORGANISM: Salmonella typhimurium

<400> SEQUENCE: 91

Met Asn Phe Asn Thr Val Phe Arg Trp His Leu Pro Phe Leu Phe Leu
1               5                   10                  15

Ile Leu Leu Thr Phe Arg Ala Ala Ala Asp Thr Leu Leu Ile Leu
            20                  25                  30

Gly Asp Ser Leu Ser Ala Gly Tyr Arg Met Ala Ala Ser Ala Ala Trp
        35                  40                  45

Pro Ser Leu Leu Asn Asp Lys Trp Gln Asn Lys Thr Ser Val Val Asn
    50                  55                  60

Ala Ser Ile Ser Gly Asp Thr Ser Gln Gln Gly Leu Ala Arg Leu Pro
65                  70                  75                  80

Ala Leu Leu Gln Gln His His Pro Arg Trp Val Val Glu Leu Gly
                85                  90                  95

Gly Asn Asp Gly Leu Arg Gly Phe Ala Pro Ala Gln Thr Glu Gln Thr
            100                 105                 110

Leu Arg Lys Ile Ile Gln Thr Val Lys Ala Ala Asp Ala Gln Pro Leu
            115                 120                 125

Leu Met Gln Ile His Leu Pro Ala Asn Tyr Gly Arg Arg Tyr Asn Glu
        130                 135                 140

Ser Phe Ser Ala Ile Tyr Pro Lys Leu Ala Lys Glu Phe Asp Ile Pro
145                 150                 155                 160

Leu Leu Pro Phe Phe Met Glu Glu Val Tyr Leu Lys Pro Gln Trp Met
                165                 170                 175

Gln Asp Asp Gly Ile His Pro Asn Arg Asp Ala Gln Pro Phe Ile Ala
            180                 185                 190

Asp Trp Met Ala Lys Gln Leu Thr Pro Phe Leu Ser
            195                 200

<210> SEQ ID NO 92
<211> LENGTH: 204
<212> TYPE: PRT
<213> ORGANISM: Salmonella enterica

```
<400> SEQUENCE: 92

Met Asn Phe Asn Thr Val Phe Arg Trp His Leu Pro Phe Leu Phe Leu
1               5                   10                  15

Ile Leu Leu Thr Phe Arg Ala Ala Ala Ala Asp Thr Leu Leu Ile Leu
                20                  25                  30

Gly Asp Ser Leu Ser Ala Gly Tyr Arg Met Ala Ala Ser Ala Ala Trp
            35                  40                  45

Pro Ser Leu Leu Asn Asp Lys Trp Gln Asn Lys Thr Ser Val Val Asn
50                  55                  60

Ala Ser Ile Ser Gly Asp Thr Ser Gln Gln Gly Leu Ala Arg Leu Pro
65                  70                  75                  80

Ala Leu Leu Gln Gln His His Pro Arg Trp Val Val Glu Leu Gly
                85                  90                  95

Gly Asn Asp Gly Leu Arg Gly Phe Ala Pro Ala Gln Thr Glu Gln Thr
                100                 105                 110

Leu Arg Lys Ile Ile Gln Thr Val Lys Ala Ala Asp Ala Gln Pro Leu
                115                 120                 125

Leu Met Gln Ile His Leu Pro Ala Asn Tyr Gly Arg Arg Tyr Asn Glu
130                 135                 140

Ser Phe Ser Ala Ile Tyr Pro Lys Leu Ala Lys Glu Phe Asp Ile Pro
145                 150                 155                 160

Leu Leu Pro Phe Phe Met Glu Glu Ile Tyr Leu Lys Pro Gln Trp Met
                165                 170                 175

Gln Asp Asp Gly Ile His Pro Asn Arg Asp Ala Gln Pro Phe Ile Ala
                180                 185                 190

Asp Trp Met Ala Lys Gln Leu Thr Pro Phe Leu Ser
                195                 200

<210> SEQ ID NO 93
<211> LENGTH: 215
<212> TYPE: PRT
<213> ORGANISM: Salmonella enterica

<400> SEQUENCE: 93

Met Leu Thr Leu Thr Asp Gly Leu Pro Glu Thr Met Asn Phe Asn Thr
1               5                   10                  15

Val Phe Arg Trp His Leu Pro Phe Leu Phe Leu Ile Leu Leu Thr Phe
                20                  25                  30

Arg Ala Ala Ala Ala Asp Thr Leu Leu Ile Leu Gly Asp Ser Leu Ser
            35                  40                  45

Ala Gly Tyr Arg Met Ala Ala Ser Ala Ala Trp Pro Ser Leu Leu Asn
50                  55                  60

Asp Lys Trp Gln Asn Lys Thr Ser Val Val Asn Ala Ser Ile Ser Gly
65                  70                  75                  80

Asp Thr Ser Gln Gln Gly Leu Ala Arg Leu Pro Ala Leu Leu Gln Gln
                85                  90                  95

His His Pro Arg Trp Val Val Glu Leu Gly Gly Asn Asp Gly Leu
                100                 105                 110

Arg Gly Phe Ala Pro Ala Gln Thr Glu Gln Thr Leu Arg Lys Ile Ile
                115                 120                 125

Gln Thr Val Lys Ala Ala Asp Ala Gln Pro Leu Leu Met Gln Ile His
                130                 135                 140

Leu Pro Ala Asn Tyr Gly Arg Arg Tyr Asn Glu Ser Phe Ser Ala Ile
145                 150                 155                 160
```

```
Tyr Pro Lys Leu Ala Lys Phe Asp Ile Pro Leu Pro Phe Phe
                165                 170                 175

Met Glu Glu Val Tyr Leu Lys Pro Gln Trp Met Gln Asp Gly Ile
            180                 185                 190

His Pro Asn Arg Asp Ala Gln Pro Phe Ile Ala Asp Trp Met Ala Lys
        195                 200                 205

Gln Leu Thr Pro Phe Leu Ser
        210                 215

<210> SEQ ID NO 94
<211> LENGTH: 204
<212> TYPE: PRT
<213> ORGANISM: Salmonella enterica

<400> SEQUENCE: 94

Met Asn Phe Asn Thr Val Phe Arg Trp His Leu Pro Phe Leu Phe Leu
1               5                   10                  15

Ile Leu Leu Thr Phe Arg Ala Ala Ala Asp Thr Leu Leu Ile Leu
            20                  25                  30

Gly Asp Ser Leu Ser Ala Gly Tyr Arg Met Ala Ala Ser Ala Ala Trp
        35                  40                  45

Pro Ser Leu Leu Asn Asp Lys Trp Gln Asn Lys Thr Ser Val Val Asn
50                  55                  60

Ala Ser Ile Ser Gly Asp Thr Ser Gln Gln Gly Leu Ala Arg Leu Pro
65                  70                  75                  80

Ala Leu Leu Gln Gln His His Pro Arg Trp Val Val Val Glu Leu Gly
                85                  90                  95

Gly Asn Asp Gly Leu Arg Gly Phe Ala Pro Ala Gln Thr Glu Gln Thr
            100                 105                 110

Leu Arg Lys Ile Ile Gln Thr Val Lys Ala Ala Asp Ala Gln Pro Leu
        115                 120                 125

Leu Met Gln Ile His Leu Pro Ala Asn Tyr Gly Arg Arg Tyr Asn Glu
        130                 135                 140

Ser Phe Ser Ala Ile Tyr Pro Lys Leu Ala Lys Glu Phe Asp Ile Pro
145                 150                 155                 160

Leu Leu Pro Phe Phe Met Lys Glu Val Tyr Leu Lys Pro Gln Trp Met
                165                 170                 175

Gln Asp Asp Gly Ile His Pro Asn Arg Asp Ala Gln Pro Phe Ile Ala
            180                 185                 190

Asp Trp Met Ala Lys Gln Leu Thr Pro Phe Leu Ser
        195                 200

<210> SEQ ID NO 95
<211> LENGTH: 204
<212> TYPE: PRT
<213> ORGANISM: Salmonella enterica

<400> SEQUENCE: 95

Met Asn Phe Asn Thr Val Phe Arg Trp His Leu Pro Phe Leu Phe Leu
1               5                   10                  15

Ile Leu Leu Thr Phe Arg Ala Ala Ala Asp Thr Leu Leu Ile Leu
            20                  25                  30

Gly Asp Ser Leu Ser Ala Gly Tyr Arg Met Ala Ala Ser Ala Ala Trp
        35                  40                  45

Pro Ser Leu Leu Asn Asp Lys Trp Gln Asn Lys Thr Ser Val Val Asn
50                  55                  60
```

```
Ala Ser Ile Ser Gly Asp Thr Ser Gln Gln Gly Leu Ala Arg Leu Pro
 65                  70                  75                  80

Thr Leu Leu Gln Gln His His Pro Arg Trp Val Val Glu Leu Gly
                 85                  90                  95

Gly Asn Asp Gly Leu Arg Gly Phe Ala Pro Ala Gln Thr Glu Gln Thr
                100                 105                 110

Leu Arg Lys Ile Ile Gln Thr Val Lys Ala Ala Asp Ala Gln Pro Leu
            115                 120                 125

Leu Met Gln Ile His Leu Pro Ala Asn Tyr Gly Arg Arg Tyr Asn Glu
            130                 135                 140

Ser Phe Ser Ala Ile Tyr Pro Lys Leu Ala Lys Glu Phe Asp Ile Pro
145                 150                 155                 160

Leu Leu Pro Phe Phe Met Glu Glu Val Tyr Leu Lys Pro Gln Trp Met
                165                 170                 175

Gln Asp Asp Gly Ile His Pro Asn Arg Asp Ala Gln Pro Phe Ile Ala
                180                 185                 190

Asp Trp Met Ala Lys Gln Leu Thr Pro Phe Leu Ser
            195                 200

<210> SEQ ID NO 96
<211> LENGTH: 204
<212> TYPE: PRT
<213> ORGANISM: Salmonella enterica

<400> SEQUENCE: 96

Met Asn Phe Asn Thr Val Phe Arg Trp His Leu Pro Phe Leu Phe Leu
  1               5                  10                  15

Ile Leu Leu Thr Phe Arg Ala Ala Ala Asp Thr Leu Leu Ile Leu
                 20                  25                  30

Gly Asp Ser Leu Ser Ala Gly Tyr Arg Met Ala Ala Ser Ala Ala Trp
                 35                  40                  45

Pro Ser Leu Leu Asn Asp Lys Trp Gln Asn Lys Thr Ser Val Val Asn
 50                  55                  60

Ala Ser Ile Ser Gly Asp Thr Ser Gln Gln Gly Leu Ala Arg Leu Pro
 65                  70                  75                  80

Ala Leu Leu Gln Gln His His Pro Arg Trp Val Val Val Glu Leu Gly
                 85                  90                  95

Gly Asn Asp Gly Leu Arg Gly Phe Ala Pro Ala Gln Thr Glu Gln Thr
                100                 105                 110

Leu Arg Lys Ile Ile Gln Thr Val Lys Ala Ala Asp Ala Gln Pro Leu
            115                 120                 125

Leu Met Gln Ile His Leu Pro Ala Asn Tyr Gly Arg Arg Tyr Asn Glu
            130                 135                 140

Ser Phe Ser Ala Ile Tyr Leu Lys Leu Ala Lys Glu Phe Asp Ile Pro
145                 150                 155                 160

Leu Leu Pro Phe Phe Met Glu Glu Val Tyr Leu Lys Pro Gln Trp Met
                165                 170                 175

Gln Asp Asp Gly Ile His Pro Asn Arg Asp Ala Gln Pro Phe Ile Ala
                180                 185                 190

Asp Trp Met Ala Lys Gln Leu Thr Pro Phe Leu Ser
            195                 200

<210> SEQ ID NO 97
<211> LENGTH: 204
<212> TYPE: PRT
```

<213> ORGANISM: Salmonella enterica

<400> SEQUENCE: 97

| Met | Asn | Phe | Asn | Thr | Val | Phe | Arg | Trp | His | Leu | Pro | Phe | Leu | Phe | Leu |
|---|---|---|---|---|---|---|---|---|---|---|---|---|---|---|---|
| 1 | | | | 5 | | | | | 10 | | | | | 15 | |

| Ile | Leu | Leu | Thr | Phe | Arg | Ala | Ala | Ala | Asp | Thr | Leu | Leu | Ile | Leu |
|---|---|---|---|---|---|---|---|---|---|---|---|---|---|---|
| | | | 20 | | | | | 25 | | | | | 30 | |

| Gly | Asp | Ser | Leu | Ser | Ala | Gly | Tyr | Arg | Met | Ala | Ala | Ser | Ala | Ala | Trp |
|---|---|---|---|---|---|---|---|---|---|---|---|---|---|---|---|
| | | 35 | | | | | 40 | | | | | 45 | | | |

| Pro | Ser | Leu | Leu | Asn | Asp | Lys | Trp | Gln | Asn | Lys | Thr | Ser | Val | Val | Asn |
|---|---|---|---|---|---|---|---|---|---|---|---|---|---|---|---|
| | 50 | | | | | 55 | | | | | 60 | | | | |

| Ala | Ser | Ile | Ser | Gly | Asp | Thr | Ser | Gln | Gln | Gly | Leu | Ala | Arg | Leu | Pro |
|---|---|---|---|---|---|---|---|---|---|---|---|---|---|---|---|
| 65 | | | | | 70 | | | | | 75 | | | | | 80 |

| Ala | Leu | Leu | Gln | Gln | His | His | Pro | Arg | Trp | Val | Val | Val | Glu | Leu | Gly |
|---|---|---|---|---|---|---|---|---|---|---|---|---|---|---|---|
| | | | | 85 | | | | | 90 | | | | | 95 | |

| Gly | Asn | Asp | Gly | Leu | Arg | Gly | Phe | Ala | Pro | Ala | Gln | Thr | Glu | Gln | Thr |
|---|---|---|---|---|---|---|---|---|---|---|---|---|---|---|---|
| | | | 100 | | | | | 105 | | | | | 110 | | |

| Leu | Arg | Lys | Ile | Ile | Gln | Thr | Val | Lys | Ala | Ala | Asp | Ala | Gln | Pro | Leu |
|---|---|---|---|---|---|---|---|---|---|---|---|---|---|---|---|
| | | 115 | | | | | 120 | | | | | 125 | | | |

| Leu | Met | Gln | Ile | His | Leu | Pro | Ala | Asn | Tyr | Gly | Arg | Arg | Tyr | Asn | Glu |
|---|---|---|---|---|---|---|---|---|---|---|---|---|---|---|---|
| | 130 | | | | | 135 | | | | | 140 | | | | |

| Ser | Phe | Ser | Ala | Ile | Tyr | Pro | Lys | Leu | Ala | Lys | Glu | Phe | Asp | Ile | Pro |
|---|---|---|---|---|---|---|---|---|---|---|---|---|---|---|---|
| 145 | | | | | 150 | | | | | 155 | | | | | 160 |

| Leu | Leu | Pro | Phe | Phe | Met | Glu | Glu | Val | Tyr | Leu | Lys | Pro | Gln | Trp | Met |
|---|---|---|---|---|---|---|---|---|---|---|---|---|---|---|---|
| | | | | 165 | | | | | 170 | | | | | 175 | |

| Gln | Asp | Asp | Gly | Ile | His | Pro | Asn | His | Asp | Ala | Gln | Pro | Phe | Ile | Ala |
|---|---|---|---|---|---|---|---|---|---|---|---|---|---|---|---|
| | | | 180 | | | | | 185 | | | | | 190 | | |

| Asp | Trp | Met | Ala | Lys | Gln | Leu | Thr | Pro | Phe | Leu | Ser |
|---|---|---|---|---|---|---|---|---|---|---|---|
| | | 195 | | | | | 200 | | | | |

<210> SEQ ID NO 98
<211> LENGTH: 194
<212> TYPE: PRT
<213> ORGANISM: Salmonella enterica

<400> SEQUENCE: 98

| Met | Pro | Phe | Leu | Phe | Leu | Phe | Leu | Leu | Thr | Phe | Arg | Val | Ala | Ala | Ala |
|---|---|---|---|---|---|---|---|---|---|---|---|---|---|---|---|
| 1 | | | | 5 | | | | | 10 | | | | | 15 | |

| Asp | Thr | Leu | Leu | Val | Leu | Gly | Asp | Ser | Leu | Ser | Ala | Gly | Tyr | Arg | Met |
|---|---|---|---|---|---|---|---|---|---|---|---|---|---|---|---|
| | | | 20 | | | | | 25 | | | | | 30 | | |

| Ala | Ala | Asn | Ala | Ala | Trp | Pro | Ser | Leu | Leu | Asn | Asp | Lys | Trp | Gln | Asn |
|---|---|---|---|---|---|---|---|---|---|---|---|---|---|---|---|
| | | 35 | | | | | 40 | | | | | 45 | | | |

| Gln | Thr | Pro | Val | Val | Asn | Ala | Ser | Ile | Ser | Gly | Asp | Thr | Ser | Leu | Gln |
|---|---|---|---|---|---|---|---|---|---|---|---|---|---|---|---|
| | 50 | | | | | 55 | | | | | 60 | | | | |

| Gly | Leu | Thr | Arg | Leu | Pro | Ala | Leu | Leu | Gln | Gln | His | Gln | Pro | Arg | Trp |
|---|---|---|---|---|---|---|---|---|---|---|---|---|---|---|---|
| 65 | | | | | 70 | | | | | 75 | | | | | 80 |

| Val | Leu | Val | Glu | Leu | Gly | Gly | Asn | Asp | Gly | Leu | Arg | Gly | Phe | Ala | Pro |
|---|---|---|---|---|---|---|---|---|---|---|---|---|---|---|---|
| | | | | 85 | | | | | 90 | | | | | 95 | |

| Ala | Gln | Thr | Glu | Gln | Thr | Leu | Arg | Lys | Ile | Ile | Gln | Ala | Val | Lys | Ala |
|---|---|---|---|---|---|---|---|---|---|---|---|---|---|---|---|
| | | | 100 | | | | | 105 | | | | | 110 | | |

| Ala | Asn | Ala | Gln | Pro | Leu | Leu | Met | Gln | Ile | His | Leu | Pro | Ala | Asn | Tyr |
|---|---|---|---|---|---|---|---|---|---|---|---|---|---|---|---|
| | | 115 | | | | | 120 | | | | | 125 | | | |

| Gly | Arg | Arg | Tyr | Asn | Glu | Ser | Phe | Ser | Ala | Ile | Tyr | Pro | Lys | Leu | Ala |
|---|---|---|---|---|---|---|---|---|---|---|---|---|---|---|---|
| | 130 | | | | | 135 | | | | | 140 | | | | |

| Lys | Glu | Phe | Asp | Ile | Pro | Leu | Leu | Pro | Phe | Phe | Met | Glu | Glu | Val | Tyr |

```
         145                 150                 155                 160
Leu Lys Pro Gln Trp Met Gln Asp Asp Gly Ile His Pro Asn Arg Asp
                 165                 170                 175

Ala Gln Pro Phe Ile Ala Asp Trp Met Ala Lys Gln Leu Thr Pro Phe
                 180                 185                 190

Leu Ser

<210> SEQ ID NO 99
<211> LENGTH: 272
<212> TYPE: PRT
<213> ORGANISM: Klebsiella sp.

<400> SEQUENCE: 99

Met Gln Arg Phe Ala Gln His Arg Tyr Phe Pro Ala Ala Ile Val
1                 5                  10                  15

Gln Ala Gly Glu Asp Arg Gln Gly Arg Phe Thr Gly Ala Arg Leu
                 20                  25                  30

Ala Asp Gln Gly Asp Gly Leu Pro Arg Phe Asp Asn Gln Leu Asn Ser
                 35                  40                  45

Gly Lys Asp Gly Glu Leu Met Leu Pro Leu Thr Asp Gly Leu Leu Lys
 50                  55                  60

Met Met Asn Phe Lys Tyr Val Phe Arg Trp His Val Pro Phe Leu Phe
 65                  70                  75                  80

Leu Phe Leu Phe Thr Cys Arg Ala Met Ala Ala Asp Thr Leu Leu Ile
                 85                  90                  95

Leu Gly Asp Ser Leu Ser Ala Gly Tyr Arg Met Ala Ala Asn Ala Ala
                 100                 105                 110

Trp Pro Ala Leu Leu Asn Glu Lys Trp Gln Ala Lys Thr Pro Val Val
                 115                 120                 125

Asn Ala Ser Ile Ser Gly Asp Thr Ser Gln Gln Gly Leu Ala Arg Leu
 130                 135                 140

Pro Ala Leu Leu Lys Gln His Gln Pro Arg Trp Val Leu Val Glu Leu
145                 150                 155                 160

Gly Gly Asn Asp Gly Leu Arg Gly Phe Pro Pro Gln Gln Thr Glu Gln
                 165                 170                 175

Thr Leu Arg Thr Ile Ile Gln Thr Ile Lys Ala Ala Asn Ala Glu Pro
                 180                 185                 190

Leu Leu Met Gln Ile His Leu Pro Ala Asn Tyr Gly Arg Arg Tyr Asn
                 195                 200                 205

Glu Ala Phe Gly Ala Ile Tyr Pro Ala Leu Ala Lys Glu Phe Ala Ile
         210                 215                 220

Pro Leu Leu Pro Phe Phe Met Glu Glu Val Tyr Leu Lys Pro Gln Arg
225                 230                 235                 240

Met Glu Glu Asp Gly Ile His Pro Asn Arg Asp Ala Gln Pro Asn Ile
                 245                 250                 255

Ala Ala Trp Met Glu Asn Arg Leu Ala Pro Leu Asp Lys His Val Ser
                 260                 265                 270

<210> SEQ ID NO 100
<211> LENGTH: 219
<212> TYPE: PRT
<213> ORGANISM: Cronobacter sakazakii

<400> SEQUENCE: 100

Met Phe Pro Leu Thr Asp Gly Phe Ile Lys Met Met Asn Phe Lys Asn
1                 5                  10                  15
```

-continued

Val Phe Arg Trp His Phe Pro Phe Leu Leu Ala Leu Leu Ser Phe
            20                  25                  30

Arg Ala Ala Ala Ala Asp Thr Leu Leu Val Leu Gly Asp Ser Leu Ser
            35                  40                  45

Ala Gly Tyr Arg Met Ala Ala Asp Ala Ala Trp Pro Ala Leu Leu Asn
 50                  55                  60

Asp Lys Trp Gln Gln Arg Asp Val Arg Val Val Asn Ala Ser Ile Ser
65                  70                  75                  80

Gly Asp Thr Ala Gln Gln Gly Leu Ser Arg Leu Pro Ala Leu Leu Lys
                85                  90                  95

Gln His Gln Pro Arg Trp Val Leu Ile Glu Leu Gly Gly Asn Asp Gly
            100                 105                 110

Leu Arg Gly Phe Pro Pro Asp Thr Leu Ser Ala Thr Leu Arg Lys Ile
            115                 120                 125

Ile Glu Gln Val Lys Thr Ala Gly Ala Glu Pro Leu Leu Met Gln Ile
    130                 135                 140

Arg Leu Pro Ala Asn Tyr Gly Arg Arg Tyr Asn Gln Ala Phe Glu Ala
145                 150                 155                 160

Ile Tyr Pro Glu Leu Ala Gln Ser Phe Ser Ile Pro Leu Leu Pro Phe
                165                 170                 175

Phe Met Glu Glu Val Tyr Leu Lys Pro Gln Trp Met Gln Asp Asp Gly
            180                 185                 190

Ile His Pro Asn Arg Asp Ala Gln Pro Phe Ile Ala Asp Trp Met Ala
            195                 200                 205

Gln Arg Leu Ala Pro Leu Val Lys His Asp Ser
    210                 215

<210> SEQ ID NO 101
<211> LENGTH: 227
<212> TYPE: PRT
<213> ORGANISM: Pectobacterium atrosepticum

<400> SEQUENCE: 101

Met Met Asn Phe Lys Asn Val Phe Tyr Val Arg Ser Phe Ala Trp Arg
1               5                   10                  15

Ser Thr Arg Trp Ala Gly Leu Arg Lys His Val Phe Val Leu Leu Leu
            20                  25                  30

Leu Gly Leu Cys Ser Val Arg Ala Phe Ala Ala Asp Thr Leu Leu Ile
        35                  40                  45

Leu Gly Asp Ser Leu Ser Ala Gly Tyr Gln Met Pro Ala Ala Asn Ala
 50                  55                  60

Trp Pro Thr Leu Leu Asn Thr Gln Trp Gln Thr Gln Lys Lys Gly Ile
65                  70                  75                  80

Ala Val Val Asn Ala Ser Ile Ser Gly Asp Thr Thr Ala Gln Gly Leu
                85                  90                  95

Ala Arg Leu Pro Ala Leu Leu Lys Gln His Gln Pro Arg Trp Val Leu
            100                 105                 110

Ile Glu Leu Gly Gly Asn Asp Gly Leu Arg Gly Phe Pro Ala Pro Asn
            115                 120                 125

Ile Glu Gln Asp Leu Ala Lys Ile Ile Thr Leu Val Lys Gln Ala Asn
        130                 135                 140

Ala Lys Pro Leu Leu Met Gln Val Arg Leu Pro Thr Asn Tyr Gly Arg
145                 150                 155                 160

Arg Tyr Thr Glu Ser Phe Ser Asn Ile Tyr Pro Lys Leu Ala Glu Gln

```
                     165                 170                 175

Phe Ala Leu Pro Leu Pro Phe Phe Met Glu Gln Val Tyr Leu Lys
            180                 185                 190

Pro Glu Trp Ile Met Glu Asp Gly Ile His Pro Thr Arg Asp Ala Gln
        195                 200                 205

Pro Phe Ile Ala Glu Trp Met Ala Lys Gln Leu Glu Pro Leu Val Asn
210                 215                 220

His Glu Ser
225

<210> SEQ ID NO 102
<211> LENGTH: 200
<212> TYPE: PRT
<213> ORGANISM: Erwinia tasmaniensis

<400> SEQUENCE: 102

Met Ala Phe Met Thr Leu Arg Ala Ala Ala Asp Thr Leu Leu Val
1               5                   10                  15

Leu Gly Asp Ser Leu Ser Ala Gly Tyr Arg Met Ser Ala Ser Ala Ala
            20                  25                  30

Trp Pro Ala Leu Leu Asn Glu Lys Trp Gln Lys Ser Pro Ala Ile Ile
        35                  40                  45

Asn Gly Ser Ile Ser Gly Asp Thr Thr Ala Gln Gly Leu Ala Arg Leu
    50                  55                  60

Ser Ala Leu Leu Glu Gln His Gln Pro Arg Trp Val Leu Ile Glu Leu
65                  70                  75                  80

Gly Gly Asn Asp Gly Leu Arg Gly Phe Pro Pro Gln Val Glu Gln
                85                  90                  95

Asp Leu Asn Gln Ala Ile Ala Gln Ile Gln Ala Ala Lys Ala Gln Pro
            100                 105                 110

Leu Leu Met Gln Val Arg Leu Pro Ala Asn Tyr Gly Lys Arg Tyr Thr
        115                 120                 125

Asp Ser Phe Ala Ala Ile Tyr Pro Arg Leu Ala Ser Gln His Ala Ile
    130                 135                 140

Pro Leu Val Pro Phe Phe Met Glu Gln Val Tyr Leu Lys Pro Glu Trp
145                 150                 155                 160

Met Gln Asp Asp Gly Ile His Pro Asn Pro Ser Ala Gln Pro Phe Ile
                165                 170                 175

Ala Asp Leu Met Ala Lys Gln Leu Ala Pro Leu Val Lys His Glu Ala
            180                 185                 190

Ser Arg Ser Val Gly Asn Asp Gly
        195                 200

<210> SEQ ID NO 103
<211> LENGTH: 190
<212> TYPE: PRT
<213> ORGANISM: Yersinia pestis

<400> SEQUENCE: 103

Met Arg Ala Ala Ala Thr Asp Thr Leu Leu Ile Leu Gly Asp Ser Leu
1               5                   10                  15

Ser Ala Gly Tyr Arg Leu Pro Ile Ala Gln Ala Trp Pro Ser Leu Leu
            20                  25                  30

Asp Lys Lys Trp Gln Ala Thr Pro Ser Leu Pro Lys Val Val Asn Ala
        35                  40                  45

Ser Ile Ser Gly Asp Thr Ala Ala Gln Gly Leu Ala Arg Leu Pro Ala
```

```
    50                  55                  60

Leu Leu Lys Gln His Gln Pro Arg Trp Val Leu Ile Glu Leu Gly Ala
65                  70                  75                  80

Asn Asp Ala Leu Arg Gly Phe Pro Thr Gln Asp Ile Gln Arg Asp Leu
                85                  90                  95

Ser Glu Ile Ile Asn Gln Ile Thr Ala Ala Lys Ala Gln Pro Leu Leu
            100                 105                 110

Met Gln Ile Arg Ile Pro Pro Asn Tyr Gly Arg Arg Tyr Thr Asp Ala
        115                 120                 125

Phe Thr Ala Ile Tyr Pro Gln Leu Ala Gln Gln Phe Asp Ile Pro Leu
    130                 135                 140

Leu Pro Phe Phe Met Glu Gln Val Ala Val Lys Pro Glu Trp Met Gln
145                 150                 155                 160

Asp Asp Gly Leu His Pro Asn Gly Asp Ala Gln Pro Phe Ile Ala Asp
                165                 170                 175

Trp Met Ala Gln Gln Leu Lys Pro Leu Val Val Asp Pro Lys
            180                 185                 190

<210> SEQ ID NO 104
<211> LENGTH: 212
<212> TYPE: PRT
<213> ORGANISM: Yersinia pestis

<400> SEQUENCE: 104

Met Met Asn Phe Lys Asn Val Phe Arg Trp His Leu Pro Phe Leu Leu
1               5                   10                  15

Leu Leu Gly Leu Phe Ser Leu Arg Ala Ala Ala Thr Asp Thr Leu Leu
            20                  25                  30

Ile Leu Gly Asp Ser Leu Ser Ala Gly Tyr Arg Leu Pro Ile Ala Gln
        35                  40                  45

Ala Trp Pro Ser Leu Leu Asp Lys Lys Trp Gln Ala Thr Pro Ser Leu
    50                  55                  60

Pro Lys Val Val Asn Ala Ser Ile Ser Gly Asp Thr Ala Ala Gln Gly
65                  70                  75                  80

Leu Ala Arg Leu Pro Ala Leu Leu Lys Gln His Gln Pro Arg Trp Val
                85                  90                  95

Leu Ile Glu Leu Gly Ala Asn Asp Ala Leu Arg Gly Phe Pro Thr Gln
            100                 105                 110

Asp Ile Gln Arg Asp Leu Ser Glu Ile Ile Asn Gln Ile Thr Ala Ala
        115                 120                 125

Lys Ala Gln Pro Leu Leu Met Gln Ile Arg Ile Pro Pro Asn Tyr Gly
    130                 135                 140

Arg Arg Tyr Thr Asp Ala Phe Thr Ala Ile Tyr Pro Gln Leu Ala Gln
145                 150                 155                 160

Gln Phe Asp Ile Pro Leu Leu Pro Phe Phe Met Glu Gln Val Ala Val
                165                 170                 175

Lys Pro Glu Trp Met Gln Asp Asp Gly Leu His Pro Asn Gly Asp Ala
            180                 185                 190

Gln Pro Phe Ile Ala Asp Trp Met Ala Gln Gln Leu Lys Pro Leu Val
        195                 200                 205

Val Asp Pro Lys
    210

<210> SEQ ID NO 105
<211> LENGTH: 222

<212> TYPE: PRT
<213> ORGANISM: Yersinia pestis

<400> SEQUENCE: 105

```
Met Leu Thr Leu Thr Asp Val Leu Ile Lys Met Met Asn Phe Lys Asn
1               5                   10                  15

Val Phe Arg Trp His Leu Pro Phe Leu Leu Leu Gly Leu Phe Ser
            20                  25                  30

Leu Arg Ala Ala Ala Thr Asp Thr Leu Leu Ile Leu Gly Asp Ser Leu
                35                  40                  45

Ser Ala Gly Tyr Arg Leu Pro Ile Ala Gln Ala Trp Pro Ser Leu Leu
    50                  55                  60

Asp Lys Lys Trp Gln Ala Thr Pro Ser Leu Pro Lys Val Val Asn Ala
65                  70                  75                  80

Ser Ile Ser Gly Asp Thr Ala Ala Gln Gly Leu Ala Arg Leu Pro Ala
                85                  90                  95

Leu Leu Lys Gln His Gln Pro Arg Trp Val Leu Ile Glu Leu Gly Ala
                100                 105                 110

Asn Asp Ala Leu Arg Gly Phe Pro Thr Gln Asp Ile Gln Arg Asp Leu
            115                 120                 125

Ser Glu Ile Ile Asn Gln Ile Thr Ala Ala Lys Ala Gln Pro Leu Leu
    130                 135                 140

Met Gln Ile Arg Ile Pro Pro Asn Tyr Gly Arg Arg Tyr Thr Asp Ala
145                 150                 155                 160

Phe Thr Ala Ile Tyr Pro Gln Leu Ala Gln Gln Phe Asp Ile Pro Leu
                165                 170                 175

Leu Pro Phe Phe Met Glu Gln Val Ala Val Lys Pro Glu Trp Met Gln
            180                 185                 190

Asp Asp Gly Leu His Pro Asn Gly Asp Ala Gln Pro Phe Ile Ala Asp
            195                 200                 205

Trp Met Ala Gln Gln Leu Lys Pro Leu Val Val Asp Pro Lys
210                 215                 220
```

<210> SEQ ID NO 106
<211> LENGTH: 211
<212> TYPE: PRT
<213> ORGANISM: Yersinia pseudotuberculosis

<400> SEQUENCE: 106

```
Met Asn Phe Lys Asn Val Phe Arg Trp His Leu Pro Phe Leu Leu Leu
1               5                   10                  15

Leu Gly Leu Phe Ser Leu Arg Ala Ala Ala Thr Asp Thr Leu Leu Ile
            20                  25                  30

Leu Gly Asp Ser Leu Ser Ala Gly Tyr Arg Leu Pro Ile Ala Gln Ala
                35                  40                  45

Trp Pro Ser Leu Leu Asp Lys Lys Trp Gln Ala Thr Pro Ser Leu Pro
    50                  55                  60

Lys Val Val Asn Ala Ser Ile Ser Gly Asp Thr Ala Ala Gln Gly Leu
65                  70                  75                  80

Ala Arg Leu Pro Ala Leu Leu Lys Gln His Gln Pro Arg Trp Val Leu
                85                  90                  95

Ile Glu Leu Gly Ala Asn Asp Ala Leu Arg Gly Phe Pro Thr Gln Asp
            100                 105                 110

Ile Gln Arg Asp Leu Ser Glu Ile Ile Asn Gln Ile Thr Ala Ala Lys
            115                 120                 125
```

```
Ala Gln Pro Leu Leu Met Gln Ile Arg Ile Pro Pro Asn Tyr Gly Arg
    130                 135                 140

Arg Tyr Thr Asp Ala Phe Thr Ala Ile Tyr Pro Gln Leu Ala Gln Gln
145                 150                 155                 160

Phe Asp Ile Pro Leu Leu Pro Phe Phe Met Glu Gln Val Ala Val Lys
                165                 170                 175

Pro Glu Trp Met Gln Asp Asp Gly Leu His Pro Asn Gly Asp Ala Gln
            180                 185                 190

Pro Phe Ile Ala Asp Trp Met Ala Gln Gln Leu Lys Pro Leu Val Val
        195                 200                 205

Asp Pro Lys
    210

<210> SEQ ID NO 107
<211> LENGTH: 196
<212> TYPE: PRT
<213> ORGANISM: Serratia proteamaculans

<400> SEQUENCE: 107

Met Gly Leu Phe Ser Leu Arg Ala Val Ala Ala Asp Thr Leu Leu Ile
1               5                   10                  15

Leu Gly Asp Ser Leu Ser Ala Gly Tyr Arg Leu Pro Val Ala Gln Ala
            20                  25                  30

Trp Pro Thr Leu Leu Ala Asp Gln Trp Gln Lys Lys Pro Gly Asp Pro
        35                  40                  45

Gln Leu Val Asn Ala Ser Ile Ser Gly Asp Thr Ala Ala Gln Gly Leu
    50                  55                  60

Ala Arg Leu Pro Glu Leu Leu Lys Gln His Gln Pro Arg Trp Val Leu
65                  70                  75                  80

Ile Glu Leu Gly Ala Asn Asp Gly Leu Arg Gly Phe Pro Ala Gln Asp
                85                  90                  95

Leu Gln Arg Asp Leu Ser Gln Ile Ile Thr Leu Val Gln Gln Ala Gly
            100                 105                 110

Ala Gln Pro Leu Leu Met Gln Ile Arg Ile Pro Pro Asn Tyr Gly Arg
        115                 120                 125

Arg Tyr Thr Glu Ala Phe Ser Ala Ile Tyr Pro Gln Leu Ala Lys Gln
    130                 135                 140

Phe Asp Ile Pro Leu Leu Pro Phe Tyr Met Glu Gln Val Val Val Lys
145                 150                 155                 160

Ala Glu Trp Met Gln Asp Asp Gly Leu His Pro Asn Lys Asp Ala Gln
                165                 170                 175

Pro Phe Ile Ala Thr Trp Met Ala Glu Arg Leu Glu Pro Leu Val Lys
            180                 185                 190

His Glu Ser Asn
        195

<210> SEQ ID NO 108
<211> LENGTH: 216
<212> TYPE: PRT
<213> ORGANISM: Yersinia pestis

<400> SEQUENCE: 108

Met Leu Ile Lys Met Met Asn Phe Lys Asn Val Phe Arg Trp His Leu
1               5                   10                  15

Pro Phe Leu Leu Leu Leu Gly Leu Phe Ser Leu Arg Ala Ala Ala Thr
            20                  25                  30
```

```
                                -continued

Asp Thr Leu Leu Ile Leu Gly Asp Ser Leu Ser Ala Gly Tyr Arg Leu
    35                  40                  45

Pro Ile Ala Gln Ala Trp Pro Ser Leu Leu Asp Lys Lys Trp Gln Ala
    50                  55                  60

Thr Pro Ser Leu Pro Lys Val Val Asn Ala Ser Ile Ser Gly Asp Thr
65                  70                  75                  80

Ala Ala Gln Gly Leu Ala Arg Leu Pro Ala Leu Leu Lys Gln His Gln
                85                  90                  95

Pro Arg Trp Val Leu Ile Glu Leu Gly Ala Asn Asp Ala Leu Arg Gly
            100                 105                 110

Phe Pro Thr Gln Asp Ile Gln Arg Asp Leu Ser Glu Ile Ile Asn Gln
        115                 120                 125

Ile Thr Ala Ala Lys Ala Gln Pro Leu Leu Met Gln Ile Arg Ile Pro
    130                 135                 140

Pro Asn Tyr Gly Arg Arg Tyr Thr Asp Ala Phe Thr Ala Ile Tyr Pro
145                 150                 155                 160

Gln Leu Ala Gln Gln Phe Asp Ile Pro Leu Leu Pro Phe Phe Met Glu
                165                 170                 175

Gln Val Ala Val Lys Pro Glu Trp Met Gln Asp Asp Gly Leu His Pro
            180                 185                 190

Asn Gly Asp Ala Gln Pro Phe Ile Ala Asp Trp Met Ala Gln Gln Leu
        195                 200                 205

Lys Pro Leu Val Val Asp Ser Lys
    210                 215
```

METHODS AND COMPOSITIONS RELATED TO THIOESTERASE ENZYMES

CROSS REFERENCE TO RELATED APPLICATIONS

This application is a continuation of U.S. application Ser. No. 15/439,053, filed Feb. 22, 2017, which is a continuation of U.S. application Ser. No. 14/826,657, filed Aug. 14, 2015, which is a divisional of U.S. application Ser. No. 12/645,497, filed Dec. 23, 2009, now issued as U.S. Pat. No. 9,175,234, which claims the benefit of U.S. Provisional Application No. 61/140,600, filed Dec. 23, 2008, the entire contents of which are hereby incorporated by reference.

FIELD OF THE INVENTION

The present invention relates to novel thioesterase compositions, novel recombinant host cells comprising thioesterases, novel methods of production of fatty acid derivatives, and fatty acid derivatives produced thereby and uses thereof. One particular aspect of the present invention relates to the production of industrial chemicals and fuels.

BACKGROUND OF THE INVENTION

Developments in technology have been accompanied by an increased reliance on fuel and industrial chemicals from petrochemical sources. Such fuel sources are becoming increasingly limited and difficult to acquire. With the burning of fossil fuels taking place at an unprecedented rate, it is likely that the world's demand for fuel and petrochemical derived chemicals will soon outweigh current supplies.

As a result, efforts have been directed toward harnessing sources of renewable energy, such as sunlight, water, wind, and biomass. The use of biomass to produce new sources of fuel and chemicals which are not derived from petroleum sources (e.g., biofuel) has emerged as one alternative option.

Biofuel is a biodegradable, clean-burning combustible fuel which can be comprised of alkanes and/or esters. An exemplary biofuel is biodiesel. Biodiesel can be used in most internal combustion diesel engines in either a pure form, which is referred to as "neat" biodiesel, or as a mixture in any concentration with regular petroleum diesel or other biodiesels.

Biodiesel offers a number of beneficial properties compared to petroleum-based diesel, including reduced emissions (e.g., carbon monoxide, sulphur, aromatic hydrocarbons, soot particles, etc.) during combustion. Biodiesel also maintains a balanced carbon dioxide cycle because it is based on renewable biological materials. Biodiesel is typically completely biodegradable, and has good safety profile due to its relative high flash point and low flammability. Furthermore, biodiesel provides good lubrication properties, thereby reducing wear and tear on engines.

Current methods of making biodiesel involve transesterification of triacylglycerides from vegetable oil feedstocks, such as from rapeseed in Europe, from soybean in North America, and from palm oil in South East Asia. Industrial-scale biodiesel production is thus geographically and seasonally restricted to areas where vegetable oil feedstocks are produced. The transesterification process leads to a mixture of fatty esters which can be used as biodiesel, but also to an undesirable byproduct, glycerin. To be usable as biodiesel, the fatty esters must be further purified from the heterogeneous product. This increases costs and the amount of energy required for fatty ester production and, ultimately, biodiesel production as well. Furthermore, vegetable oil feedstocks are inefficient sources of energy because they require extensive acreage for cultivation. For example, the yield of biodiesel from rapeseed is only 1300 L/hectare because only the seed oil is used for biodiesel production, and not the rest of the rapeseed biomass. Additionally, cultivating some vegetable oil feedstocks, such as rapeseed and soybean, requires frequent crop rotation to prevent nutrient depletion of the land.

PCT Publication No. WO 2007/136762 discloses recombinant microorganisms that are capable of synthesizing products derived from the fatty acid synthetic pathway, including, inter alia, fatty acid esters and fatty alcohols. In particular, certain fatty acid derivatives are described having defined carbon chain length, branching and saturation levels. The '762 publication describes recombinant cells that utilize endogenous overexpression or heterologous expression of thioesterase proteins in the production of fatty acid derivatives.

PCT Publication No. WO 2008/119082 discloses genetically engineered cells and microorganisms that produce products from the fatty acid biosynthetic pathway, including, inter alia, fatty acid esters and fatty alcohols. The '082 publication describes recombinant cells that utilize overexpression of acyl-CoA synthetase enzymes to more efficiently produce fatty acid derivatives.

U.S. Pat. No. 5,955,329 discloses genetically engineered plant acyl-ACP thioesterase proteins having altered substrate specificity. In particular, the '329 patent discloses producing engineered plant acyl-ACP thioesterases, wherein the engineered plant acyl-ACP thioesterases demonstrate altered substrate specificity with respect to the acyl-ACP substrates hydrolyzed by the plant thioesterases as compared to the native acyl-ACP thioesterase.

While the prior art discloses certain useful disclosures regarding the production of certain fatty acid derivatives, a need exists in the field for improved methods and processes for more efficient and economical production of such fatty acid derivatives, and also for technology facilitating the production of compositions that have altered product specifications. As a specific example, a need exists for the production of fatty acid compositions having pre-designed, or "tailored," specifications and properties for particular applications such as fuels, detergents, lubricants, industrial precursor molecule and other valuable applications of fatty acid derivatives.

SUMMARY OF THE INVENTION

It is an object of the present invention to provide useful mutant and naturally-occurring thioesterase enzymes, polynucleotides encoding these enzymes, vectors comprising polynucleotides encoding the useful thioesterase enzymes, recombinant host cells comprising mutated endogenous thioesterase enzymes, recombinant host cells transformed with the vectors, recombinant host cells having polynucleotides encoding useful thioesterase enzymes chromosomally integrated therein, thioesterases produced by the host cells, fatty acid derivative compositions (such as industrial chemicals and biofuels) produced in vitro and/or in vivo, methods for producing fatty acid derivative compositions in vitro and/or in vivo, and methods of using the produced fatty acid derivative compositions.

It is an object of the present invention to provide methods of producing fatty acid derivative compositions through microbial fermentations that have predetermined product profiles with regard to carbon chain lengths and proportional yields. These compositions are well suited for applications in the fuel and chemical industries because their properties can be tailored to the particular applications for which they are intended. For example, it is possible to tailor a fatty ester product, according to the methods described herein, such that it can be used as an automobile fuel, and/or to design a composition to have, for example, improved fuel characteristics such as cloud point, lubricity, cetane number, kinematic viscosity, acid number, boiling point, oxidative stability, cold filter-plugging point, impurity profile, sulfated ash level, and/or flash point. Similarly, it is possible to produce industrial chemicals in accordance with the methods described herein that can replace current chemicals sourced from petroleum, and that are tailored to particular applications, for example, to produce fatty alcohols that are optimally suited for use as surfactants and/or detergents.

It is an object of the invention to provide for alternative methods of making fatty esters without the presence of (or in the absence of) an ester synthase. This method is energetically more favorable than the heretofore disclosed methods for producing fatty ester compositions through microbial fermentation processes, which required at least both a thioesterase enzyme and an ester synthase enzyme. As such, the novel thioesterases of the invention provide further advantages.

In one embodiment of the invention, mutant thioesterases (or naturally-occurring equivalents thereof) are provided that derive from a precursor thioesterase, wherein each of the mutants (or the naturally-occurring equivalents) has at least one altered property in vitro and/or in vivo, as compared to the properties of the precursor thioesterase. The altered property can be, for example, a biophysical property such as thermal stability (melting point $T_m$); solvent, solute, and/or oxidative stability; lipophilicity; hydrophilicity; quaternary structure; dipole moment; and/or isoelectric point. The altered property can also be, for example, a biochemical property such as pH optimum, temperature optimum, and/or ionic strength optimum. The altered property can further be, for example, an enzyme catalytic parameter such as product distribution (including, for example, a higher or lower percentage or proportional yield for a particular product vs. other products in the product mixture), specific activity, substrate preference, substrate affinity, substrate inhibition, product affinity, turnover rate or catalytic rate, product inhibition, kinetic mechanism, $K_M$, $k_{cat}$, $k_{cat}/K_m$, and/or $V_{Max}$. The altered property can additionally be, for example, an increase or a decrease in activity or a changed preference for alcoholysis vs. hydrolysis, acyl-CoA vs. acyl-acyl carrier protein substrates, ester vs. thioester substrates, saturated vs. unsaturated substrates, straight-chain vs. branched substrates; changes in positions of unsaturations, ranges of cetane numbers, or specific carbon chain lengths, branched substrates, position of branching, hydroxy-acyl substrates, keto-acyl substrates; and/or products with a changed range of or specific cetane numbers, octane rating, oxidative stability, lubricity, flash point, viscosity, boiling point, melting point, pour point, cloud point, cold filter plugging point, cold flow characteristics, aromaticity, and/or iodine number. Altered properties can also include, for example, a decrease in activity or an attenuation of ester hydrolysis, such that the hydrolysis of desired product molecules is reduced or eliminated. Altered properties can further include, for example, a decrease in the protein's toxicity to the cell and/or a change in the protein's expression level in the cell, as compared to the precursor protein's toxicity to and/or expression level in the same cell. In an exemplary embodiment, an altered property can include a change in the ability to catalyze the synthesis of fatty acyl derivatives directly or indirectly in vivo or in vitro. In another exemplary embodiment, an altered property is the improvement or increase of in vitro and/or in vivo yield or proportional yield of a particularly desirable fatty acid derivative.

In one embodiment of the invention, a mutant thioesterase (or a naturally-occurring equivalent thereof) is derived from a precursor thioesterase. In a particular embodiment of the invention, the precursor thioesterase is a naturally-occurring thioesterase, a previously modified thioesterase, or a synthetic thioesterase.

In one embodiment of the invention, the mutant thioesterase (or a naturally-occurring equivalent thereof) is derived from a precursor thioesterase that is a naturally-occurring thioesterase. The naturally-occurring precursor thioesterase can be obtained from, for example, a plant, animal, bacterial, fungal, yeast, or other microbial sources. The mutant thioesterase (or a naturally-occurring equivalent thereof) can be derived from a precursor thioesterase from *Acidovorax, Acinetobacter, Aeromonas, Alcanivorax, Aliivibrio, Alkalilimnicola, Alteromonadales, Alteromonas, Aurantimonas, Azoarcus, Azorhizobium, Azotobacter, Beggiatoa, Beijerinckia, Bordetella, Bradyrhizobium, Burkholderia, Caulobacter, Cellvibrio, Chromobacterium, Citrobacter, Comamonas, Cupriavidus, Dechloromonas, Delftia, Desulfovibrio, Enterobacter, Erwinia, Escherichia, Geobacter, Hahella, Halorhodospira, Herminiimonas, Idiomarina, Janthinobacterium, Klebsiella, Leptospira, Leptothrix, Limnobacter, Magnetospirillum, Marinobacter, Marinomonas, Methylibium, Methylobacillus, Methylobacterium, Methylocella, Methylococcus, Moritella, Nitrobacter, Nitrococcus, Nitrosomonas, Nitrosospira, Oceanospirillum, Oligotropha, Pectobacterium, Photobacterium, Photorhabdus, Polaromonas, Proteus, Providencia, Pseudoalteromonas, Pseudomonas, Psychromonas, Ralstonia, Reinekea, Rhodobacterales, Rhodoferax, Rhodopseudomonas, Rhodospirillum, Saccharophagus, Salmonella, Serratia, Shewanella, Shigella, Stenotrophomonas, Streptococcus, Thauera, Thioalkalivibrio, Thiobacillus, Vibrio, Xanthomonas,* or *Yersinia.*

In a particular embodiment, the precursor thioesterase of the invention can be derived from any one of *Acidovorax avenae* subsp. *citrulli* AAC00-1, *Acidovorax* sp. JS42, *Acinetobacter baumannii* ACICU, *Acinetobacter baumannii* ATCC 17978, *Aeromonas hydrophila* subsp. *Hydrophila* ATCC 7966, *Aeromonas salmonicida* subsp. *salmonicida* A449, *Alcanivorax borkumensis* SK2, *Alcanivorax* sp. DG881, *Aliivibrio salmonicida* LFI1238, *Alkalilimnicola ehrlichei* MLHE-1, alpha proteobacterium HTCC2255, Alteromonadales bacterium TW-7, *Alteromonas macleodii* deep ecotype, *Aurantimonas* sp. SI85-9A1, *Azoarcus* sp. BH72, *Azorhizobium caulinodans* ORS 571, *Azotobacter vinelandii* AvOP, *Beggiatoa* sp. PS, *Beijerinckia indica* subsp. indica ATCC 9039, *Bordetella avium* 197N, *Bordetella bronchiseptica* RB50, *Bordetella parapertussis* 12822, *Bordetella pertussis* Tohama I, *Bordetella petrii* DSM 12804, *Bradyrhizobium* sp. BTAi1, *Bradyrhizobium* sp. ORS278, *Burkholderia ambifaria* AMMD, *Burkholderia ambifaria* IOP40-10, *Burkholderia ambifaria* MC40-6, *Burkholderia ambifaria* MEX-5, *Burkholderia cenocepacia* AU 1054, *Burkholderia cenocepacia* H12424, *Burkholderia cenocepacia* J2315, *Burkholderia cenocepacia* MCO-3, *Burkholderia cenocepacia* PC184, *Burkholderia dolosa* AU0158, *Burkholderia graminis* C4D1M, *Burkholderia mallei* ATCC 23344, *Burkholderia mallei* GB8 horse 4, *Burkholderia mallei* NCTC 10229, *Burkholderia multivorans* ATCC 17616, *Burkholderia oklahomensis* C6786, *Burkholderia oklahomensis* E0147, *Burkholderia phymatum*

STM815, *Burkholderia pseudomallei* 1106a, *Burkholderia pseudomallei* 1106b, *Burkholderia pseudomallei* 14, *Burkholderia pseudomallei* 1655, *Burkholderia pseudomallei* 1710b, *Burkholderia pseudomallei* 305, *Burkholderia pseudomallei* 406e, *Burkholderia pseudomallei* 668, *Burkholderia pseudomallei* 7894, *Burkholderia pseudomallei* K96243, *Burkholderia pseudomallei* NCTC 13177, *Burkholderia* sp. 383, *Burkholderia thailandensis* Bt4, *Burkholderia thailandensis* E264, *Burkholderia thailandensis* MSMB43, *Burkholderia thailandensis* TXDOH, *Burkholderia ubonensis* Bu, *Burkholderia vietnamiensis* G4, *Caulobacter crescentus* CB15, *Cellvibrio japonicus* Ueda107, *Chromobacterium violaceum* ATCC 12472, *Chromohalobacter salexigens* DSM 3043, *Citrobacter koseri* ATCC BAA-895, *Comamonas testosteroni* KF-1, *Cupriavidus taiwanensis, Dechloromonas aromatica* RCB, *Delftia acidovorans* SPH-1, *Desulfovibrio desulfuricans* subsp. *desulfuricans* str. G20, *Desulfovibrio desulfuricans* subsp. *desulfuricans* str. G20, *Enterobacter cancerogenus* ATCC 35316, *Enterobacter sakazakii* ATCC BAA-894, *Enterobacter* sp. 638, *Erwinia tasmaniensis, Escherichia albertii* TWO7627, *Escherichia coli* O157:H7 EDL933, *Escherichia coli* O157:H7 str.EC4024, *Escherichia coli* O157:H7 str. EC4196, gamma proteobacterium HTCC5015, gamma proteobacterium KT 71, Geobacter sp. M21, *Hahella chejuensis* KCTC 2396, *Halorhodospira halophila* SL1, *Herminiimonas arsenicoxydans, Idiomarina baltica* OS145, *Idiomarina loihiensis L2*TR, *Janthinobacterium* sp. *Marseille, Klebsiella pneumoniae* 342, *Klebsiella pneumoniae* subsp. *pneumoniae* MGH 78578, *Klebsiella* sp. ZD414, *Leptospira interrogans serovar Copenhageni str.* Fiocruz L1-130, *Leptospira interrogans serovar Lai str.* 56601, *Leptothrix cholodnii* SP-6, *Limnobacter* sp. MED105, *Magnetospirillum magneticum* AMB-1, marine gamma proteobacterium HTCC2080, marine gamma proteobacterium HTCC2143, marine gamma proteobacterium HTCC2207, marine metagenome, *Marinobacter algicola* DG893, *Marinobacter aquaeolei* VT8, *Marinobacter* sp. ELB17, Marinomonas sp. MWYL1, *Methylibium petroleiphilum* PM1, *Methylobacillus flagellates* KT, *Methylobacterium chloromethanicum* CM4, *Methylobacterium extorquens* PA1, *Methylobacterium populi* BJ001, *Methylocella silvestris* BL2, *Methylococcus capsulatus* str. Bath, Moritella sp. PE36, *Nitrobacter* sp. Nb-311A, *Nitrobacter winogradskyi* Nb-255, *Nitrococcus mobilis* Nb-231, *Nitrosococcus oceani ATCC* 19707, *Nitrosococcus oceani C*-27, *Nitrosomonas europaea* ATCC 19718, *Nitrosomonas eutropha C*91, *Nitrosospira multiformis ATCC* 25196, *Oceanospirillum* sp. MED92, *Oligotropha carboxidovorans* 0*M*5, *Pectobacterium atrosepticum* SCRI1043, *Photobacterium profundum* 3TCK, *Photobacterium profundum* SS9, *Photobacterium* sp. SKA34, *Photorhabdus luminescens, Photorhabdus luminescens* subsp. *laumondii* 1101, *Polaromonas naphthalenivorans* CJ2, *Polaromonas* sp. JS666, *Polynucleobacter* sp. QLW-P1DMWA-1, *Proteus mirabilis* HI4320, *Providencia stuartii* ATCC 25827, *Pseudoalteromonas atlantica T*6c, *Pseudoalteromonas haloplanktis* TAC125, *Pseudoalteromonas* sp. 643*A*, *Pseudoalteromonas tunicata* D2, *Pseudomonas aeruginosa* PA7, *Pseudomonas aeruginosa* PACS2, *Pseudomonas aeruginosa PA*01, *Pseudomonas aeruginosa* UCBPP-PA14, *Pseudomonas entomophila* L48, *Pseudomonas fluorescens* Pf0-1, *Pseudomonas fluorescens* Pf-5, *Pseudomonas mendocina* ymp, *Pseudomonas putida* F1, *Pseudomonas putida* GB-1, *Pseudomonas putida* KT2440, *Pseudomonas putida W*619, *Pseudomonas stutzeri A*1501, *Pseudomonas syringae* pv. *Phaseolicola* 1448A, *Pseudomonas syringae* pv. *syringae* B728a, *Pseudomonas syringae* pv. *tomato str.* DC3000, *Psychromonas ingrahamii* 37, *Ralstonia eutropha* H16, *Ralstonia eutropha* JMP134, *Ralstonia metallidurans* CH34, *Ralstonia pickettii* 12D, *Ralstonia pickettii* 12J, *Ralstonia solanacearum* GMI1000, *Ralstonia solanacearum* IP01609, *Ralstonia solanacearum* MolK2, *Ralstonia solanacearum* UW551, *Reinekea* sp. MED297, *Rhodobacterales bacterium Y*4I, *Rhodoferax ferrireducens* T118, *Rhodopseudomonas palustris* BisA53, *Rhodopseudomonas palustris* BisB18, *Rhodopseudomonas palustris* BisB5, *Rhodopseudomonas palustris* CGA009, *Rhodopseudomonas palustris* HaA2, *Rhodopseudomonas palustris* TIE-1, *Rhodospirillum centenum* SW, *Saccharophagus degradans* 2-40, *Salmonella enterica* subsp. *arizonae serovar* 62:z4,z23:--, *Salmonella enterica* subsp. *enterica serovar Choleraesuis str. SC-B*67, *Salmonella enterica* subsp. *enterica serovar allinarum str.* 287/91, *Salmonella enterica* subsp. *enterica serovar Hadar str.* RI_05P066, *Salmonella enterica* subsp. *enterica serovar Javiana str.* GA_MM04042433, *Salmonella enterica* subsp. *enterica serovar Saintpaul* str. SARA23, *Salmonella enterica* subsp. *enterica serovar Saintpaul* str. SARA29, *Salmonella enterica* subsp. *enterica serovar Typhi str.* CT18, *Salmonella typhimurium* LT2, *Serratia proteamaculans* 568, *Shewanella amazonensis* SB2*B*, *Shewanella baltica* OS155, *Shewanella baltica* OS185, *Shewanella baltica* OS195, *Shewanella baltica* OS223, *Shewanella benthica* KT99, *Shewanella denitrificans* OS217, *Shewanella frigidimarina* NCIMB 400, *Shewanella halifaxensis* HAW-EB4, *Shewanella loihica PV*-4, *Shewanella oneidensis* MR-1, *Shewanella pealeana* ATCC 700345, *Shewanella putrefaciens* 200, *Shewanella sediminis* HAW-EB3, *Shewanella* sp. ANA-3, *Shewanella* sp. MR-4, *Shewanella* sp. MR-7, *Shewanella* sp. W3-18-1, *Shewanella woodyi* ATCC 51908, *Shigella boydii* Sb227, *Shigella dysenteriae* Sd197, *Stenotrophomonas maltophilia* K279a, *Stenotrophomonas maltophilia* R551-3, *Streptococcus* sp. (N1), synthetic construct, *Thauera* sp. MZ1T, *Thioalkalivibrio* sp. HL-EbGR7, *Thiobacillus denitrificans* ATCC25259, *Thiomicrospira crunogena* XCL-2, *Vibrio alginolyticus* 12G01, *Vibrio angustum* S14, *Vibrio campbellii* AND4, *Vibrio cholerae* 2740-80, *Vibrio cholerae* MZO-2, *Vibrio cholerae* 01 *biovar eltor str. N*16961, *Vibrio cholerae* V51, *Vibrio fischeri* ES114, *Vibrio fischeri* MJ11, *Vibrio harveyi* ATCC BAA-1116, *Vibrio mimicus, Vibrionales bacterium* SWAT-3, *Vibrio parahaemolyticus* AQ3810, *Vibrio parahaemolyticus* RIMD 2210633, *Vibrio shilonii* AK1, *Vibrio splendidus* 12B01, *Vibrio* sp. MED222, *Vibrio vulnificus* CMCP6, *Vibrio vulnificus* YJO16, *Xanthomonas axonopodis* pv. *citri str.* 306, *Xanthomonas campestris* pv. *campestris str.* ATCC 33913, *Xanthomonas campestris* pv. *campestris str.* B100, *Xanthomonas campestris* pv. *Vesicatoria str.* 85-10, *Xanthomonas oryzae* pv. *oryzae* KACC10331, *Xanthomonas oryzae* pv. *oryzae* PXO99A, *Xanthomonas oryzae* pv. *oryzicola* BLS256, *Yersinia bercovieri* ATCC 43970, *Yersinia enterocolitica* subsp. *enterocolitica* 8081, *Yersinia frederiksenii* ATCC 33641, *Yersinia intermedia* ATCC 29909, *Yersinia mollaretii* ATCC 43969, *Yersinia pestis Angola, Yersinia pestis biovar Orientalis str.* F1991016, *Yersinia pestis* C092, *Yersinia pestis* KIM or *Yersinia pseudotuberculosis IP* 31758.

In one embodiment of the invention, the precursor thioesterase is a thioesterase that has an analogous sequence to that of 'TesA (e.g., a TesA enzyme sans the signal peptide). In a preferred embodiment, the precursor thioesterase has at least about 20%, for example, at least about 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% sequence identity to 'TesA. In yet another example, the precursor thioesterase has at least about 20%, for example, at least about 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% sequence identity to a 'TesA that is obtained from an *E. coli.*, such as an *E. coli* K12. In a further example, the precursor thioesterase is a thioesterase that has an analogous sequence to the sequence of SEQ ID NO:31 in FIG. 58, and preferably at least about 20%, for example, at least about 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% sequence identity to SEQ ID NO:31 in FIG. 58. The analogous sequence can be from a naturally-occurring protein or can be from a previously modified protein.

In one embodiment of the invention, the precursor thioesterase is a thioesterase that comprises the amino acid strings:

G-D-S-L-X(5)-M (SEQ ID NO:28), wherein:
the "X" refers to any amino acid residue; the number in the parenthetical adjacent thereto,
when present, refers to the number of X residues in the stretch of amino acid residues;
the S residue at position 3 is a catalytic residue;
the D residue at position 2 may be substituted with N or T;
the L residue at position 4 may be substituted with C or Q;
the M residue at position 10 may be substituted with C, D, L, N, T, or V;
and/or
V-X(2)-G-X-N-D-X-L (SEQ ID NO:29), wherein:
each "X" refers to any amino acid residue; the number in the parentheses adjacent thereto,
when present, refers to the number of X residues in the stretch of amino acid residues;
the N residue at position 6 is in the oxyanion hole;
the V residue at position 1 may be substituted with L;
the N residue at position 6 may be substituted with V, L, C, A, G, H, I, T, or W;
the D residue at position 7 may be substituted with E;
the L residue at position 9 may be substituted with I, W, F, T, M, A, E, N, or V;
and/or
D-X(2)-H-P-X(7)-I (SEQ ID NO:30), wherein:
each "X" refers to any amino acid residue; each number in the parentheses adjacent thereto, when present, refers to the number of X residues in the respective stretch of amino acid residues;
the D and H residues at positions 1 and 4 respectively are the catalytic residues;
the P residue at position 5 may be substituted with G, A, F, L, S, or V;
the I residue at position 13 may be substituted with L or V.

In one embodiment of the invention, the precursor thioesterase is a thioesterase having immunological cross-reactivity with a 'TesA obtained from an *E. coli*. In a particular embodiment, the precursor thioesterase has immunological cross-reactivity with the 'TesA obtained from an *E. coli* K-12. In a particular embodiment, the precursor thioesterase has immunological cross-reactivity with a thioesterase comprising the amino acid sequence of SEQ ID NO:31 as set forth in FIG. 58. In a particular embodiment, the precursor thioesterase has cross-reactivity with fragments (or portions) of any of the thioesterases obtained from an *E. coli*, or from an *E. coli* K-12, and/or of any thioesterase that comprises the amino acid sequence of SEQ ID NO:31 as set forth in FIG. 58. The precursor enzyme having immunological cross-reactivity with 'TesA can be a naturally-occurring protein, a previously modified protein, or a synthetic protein.

In another particular example, the precursor thioesterase is a 'TesA from an *E. coli*, or is a homolog, a paralog or an ortholog of a 'TesA from an *E. coli*, such as a 'TesA from an *E. coli* K12. The thioesterase precursor from which a mutant of the present invention is derived can also be an enzymatically active portion or a fragment of any one of the aforedescribed thioesterases.

In one embodiment of the invention, a mutant thioesterase (or a naturally-occurring equivalent thereof) is provided that comprises an amino acid sequence having at least one substitution of an amino acid, as compared to a precursor thioesterase, such that the mutant thioesterase has at least one altered property in relation to the precursor thioesterase. In an exemplary embodiment of the invention, a mutant thioesterase is provided that has an amino acid sequence with a single substitution mutation, and exhibits at least one altered property as compared to the precursor thioesterase from which the mutant is derived. In an exemplary embodiment of the invention, a mutant thioesterase is provided that comprises an amino acid sequence having two or more substitution mutations from the sequence of its precursor thioesterase, and the mutant thioesterase has at least one altered property as compared to the precursor thioesterase.

In one embodiment of the invention, a mutant thioesterase (or a naturally-occurring equivalent thereof) is provided, which is a variant of a precursor thioesterase, and which has at least one altered property in vitro or in vivo in relation to such a precursor thioesterase, wherein the precursor thioesterase is a thioesterase that comprises an analogous sequence to SEQ ID NO:31 in FIG. 58 and accordingly comprises corresponding amino acid residues 1-182 of SEQ ID NO:31, and wherein the precursor thioesterase is modified at one or more amino acid positions selected from positions corresponding to one or more residues 1-182 of SEQ ID NO:31 in FIG. 58.

In one embodiment of the invention, a mutant thioesterase (or a naturally-occurring equivalent thereof) is provided, which is a variant of a precursor thioesterase that comprises an analogous sequence to SEQ ID NO:31 in FIG. 58 and accordingly comprises corresponding amino acid residues 1-182 of SEQ ID NO:31, and which has at least one altered property in vitro or in vivo in relation to such precursor thioesterase, wherein the precursor thioesterase is mutated at one or more positions corresponding to one or more amino acid positions of SEQ ID NO:31 in FIG. 58 selected from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 158, 159, 160, 161, 162, 163, 164, 165, 166, 167, 168, 169, 170, 171, 172, 173, 174, 175, 176, 177, 178, 179, 180, 181, and/or 182.

In one embodiment of the invention, a mutant thioesterase (or a naturally-occurring equivalent) is provided, which is a variant of a precursor thioesterase that comprises an analogous sequence to SEQ ID NO:31 of FIG. 58 and accordingly comprises corresponding amino acid residues 1-182 of SEQ ID NO:31, and which has at least one altered property in vitro or in vivo in relation to such precursor thioesterase, wherein the precursor thioesterase is mutated with one or more substitutions selected from A1C, A1F, A1L, A1Q, A1R, A1S, A1V, A1Y, D2E, D2H, D2K, D2L, D2M, D2P, D2R, D2W, T3E, T3G, T3K, T3L, T3R, T3W, L4A, L4G, L4M, L4N, L4S, L4V, L4Y, L5C, L5E, L5F, L5G, L5H, L5K, L5N, L5Q, L5S, L5W, L5Y, I6A, I6L, I6T, I6V, L7A, L7C, L7E, L7K, L7M, L7N, L7S, L7T, L7V, L7W, L7Y, G8A, G8K, G8S, D9N, D9T, S10C, L11A, L11C, L11I, L11M, L11Q, L11V, S12A, S12I, S12L, S12M, S12N, S12T, S12V, S12Y, A13C, A13D, A13G, A13H, A13I, A13L, A13N, A13S, A13T, A13V, A13W, A13Y, G14A, G14C, G14E, G14F, G14I, G14K, G14M, G14N, G14P, G14Q, G14R, G14S, G14T, G14V, Y15A, Y15C, Y15D, Y15E, Y15G, Y15I, Y15L, Y15M, Y15N, Y15Q, Y15R, Y15S, Y15V, R16A, R16D, R16E, R16G, R16H, R16I, R16L, R16M, R16N, R16P, R16Q, R16S, R16T, R16V, R16W, M17A, M17C, M17D, M17E, M17G, M17K, M17L, M17N, M17P, M17Q, M17R, M17S, M17T, M17V, S18E, S18M, S18N, S18T, A19C, A19E, A19L, A19V, S20A, S20C, S20D, S20G, S20L, S20T, S20W, A21G, A21I, A21L, A21P, A21Y, A22C, A22D, A22E, A22F, A22G, A22H, A22I, A22K, A22L, A22M, A22N, A22P, A22R, A22S, A22T, A22Y, W23A, W23H, W23N, W23P, W23Y, P24A, P24C, P24D, P24E, P24F, P24G, P24I, P24M, P24N, P24S, P24T, P24V, P24W, A25D, A25E, A25L, A25N, A25P, A25Q, A25R, A25S, A25V, L26C, L26D, L26E, L26F, L26G, L26H, L26I, L26K, L26N, L26P, L26Q, L26R, L26S, L26V, L26W, L26Y, L27A, L27C, L27F, L27H, L27M, L27R, L27S, L27T, L27V, L27W, L27Y, N28A, N28G, N28I, N28K, N28M, N28P, N28R, N28W, D29M, D29P, D29V, K30P, W31D, W31E, W31G, W31L, W31N, W31P, W31R, W31S, W31T, Q32V, Q32Y, S33F, S33G, S33I, S33M, S33R, K34A, K34H, K34M, K34R, T35F, T35G, T35K, T35L, T35M, T35Q, T35V, T35Y, S36A, S36F, S36H, S36I, S36L, S36W, V37A, V37F, V37G, V37H, V37L, V37N, V37S, V37Q, V37S, V37W, V37Y, V38D, V38E, V38F, V38G, V38K, V38L, V38P, V38R, V38S, N39A, N39C, N39E, N39F, N39G, N39K, N39M, N39P, N39Q, N39R, N39T, N39V, N39W, N39Y, A40D, A40G, A40H, A40L, A40M, A40P, A40T, A40V, A40Y, S41C, S41P, S41T, I42A, I42C, I42D, I42E, I42G, I42K, I42L, I42M, I42P, I42S, I42T, I42W, I42Y, S43A, S43C, S43D, S43E, S43F, S43G, S43H, S43L, S43M, S43N, S43P, S43R, S43T, S43V, S43W, G44A, G44C, G44E, G44F, G44H, G44K, G44L, G44M, G44N, G44Q, G44R, G44S, G44W, G44Y, D45A, D45C, D45E, D45F, D45G, D45H, D45I, D45K, D45L, D45M, D45P, D45Q, D45S, D45T, D45V, D45W, T46A, T46C, T46D, T46E, T46F, T46G, T46I, T46K, T46L, T46N, T46R, T46S, T46V, T46W, S47A, S47C, S47E, S47F, S47G, S47L, S47M, S47P, S47Q, S47R, S47T, S47V, S47W, S47Y, Q48C, Q48D, Q48E, Q48F, Q48G, Q48I, Q48M, Q48S, Q48T, Q48V, Q48W, Q48Y, Q49A, Q49C, Q49D, Q49E, Q49G, Q49H, Q49I, Q49K, Q49L, Q49M, Q49P, Q49R, Q49S, Q49V, Q49W, Q49Y, G50A, G50C, G50E, G50F, G50I, G50K, G50L, G50M, G50N, G50P, G50Q, G50R, G50S, G50T, G50W, G50Y, L51A, L51C, L51D, L51F, L51H, L51N, L51P, L51S, L51T, L51V, L51W, L51Y, A52C, A52D, A52H, A52I, A52L, A52M, A52P, A52R, A52V, A52W, A52Y, R53A, R53C, R53D, R53E, R53F, R53G, R53I, R53K, R53L, R53N, R53S, R53T, R53V, R53W, R53Y, L54A, L54C, L54E, L54F, L54G, L54M, L54N, L54S, L54T, L54W, L54Y, P55A, P55G, P55Y, A56P, A56R, A56W, A56Y, L57A, L57C, L57F, L57G, L57H, L57I, L57K, L57N, L57P, L57Q, L57R, L57S, L57T, L57V, L57W, L57Y, L58A, L58D, L58E, L58F, L58G, L58H, L58I, L58M, L58N, L58R, L58S, L58V, L58W, L58Y, K59E, K59R, K59V, Q60E, Q60M, Q60P, H61A, H61D, H61E, H61G, H61P, H61W, Q62G, Q62M, Q62P, Q62W, P63D, P63E, P63G, P63I, P63K, P63L, P63M, P63N, P63Q, P63R, P63S, P63T, P63V, P63W, R64D, R64E, R64F, R64L, R64M, R64P, R64Q, R64W, R64Y, W65A, W65E, W65G, W65K, W65L, W65M, W65N, W65P, W65R, W65V, V66C, V66G, V66I, V66M, V66N, V66Q, V66S, V66W, V66Y, L67A, L67C, L67E, L67G, L67M, L67Q, L67Q, L67S, L67T, L67W, V68A, V68E, V68G, V68L, V68M, V68N, V68P, V68Q, V68S, V68T, E69A, E69C, E69D, E69F, E69G, E69H, E69K, E69L, E69M, E69N, E69P, E69Q, E69S, E69V, E69W, E69Y, L70A, L70C, L70E, L70F, L70G, L70H, L70I, L70K, L70Q, L70S, L70T, L70V, L70W, G71A, G71C, G71S, G72A, G72C, G72M, G72P, G72S, N73A, N73C, N73G, N73H, N73I, N73L, N73P, N73R, N73S, N73T, N73V, N73W, D74A, D74C, D74E, D74F, D74G, D74Q, D74S, D74W, D74Y, G75A, G75C, G75D, G75E, G75F, G75I, G75K, G75L, G75M, G75N, G75P, G75R, G75T, G75V, G75W, G75Y, L76A, L76C, L76D, L76E, L76F, L76G, L76I, L76K, L76M, L76N, L76P, L76Q, L76R, L76T, L76V, L76W, R77A, R77C, R77D, R77E, R77F, R77G, R77H, R77K, R77L, R77N, R77Q, R77S, R77V, R77W, G78A, G78C, G78D, G78E, G78F, G78M, G78N, G78P, G78Q, G78R, G78S, G78T, G78V, G78Y, F79A, F79D, F79E, F79G, F79H, F79K, F79M, F79N, F79P, F79Q, F79S, F79V, F79W, F79Y, Q80A, Q80E, Q80G, Q80L, Q80M, Q80S, Q80W, Q80Y, P81A, P81E, P81K, P81L, P81M, P81N, P81T, P81W, P81Y, Q82A, Q82F, Q82I, Q82M, Q82N, Q82P, Q82R, Q82S, Q82T, Q82V, Q82W, Q82Y, Q83A, Q83C, Q83F, Q83G, Q83K, Q83L, Q83M, Q83N, Q83R, Q83S, Q83T, Q83V, Q83W, Q83Y, T84A, T84D, T84E, T84F, T84G, T84H, T84K, T84L, T84M, T84N, T84Q, T84R, T84S, T84V, T84W, T84Y, E85A, E85C, E85D, E85F, E85G, E85L, E85P, E85Q, E85R, E85S, E85T, E85V, E85W, E85Y, Q86A, Q86G, Q86H, Q86K, Q86P, Q86T, Q86V, Q86W, Q86Y, T87A, T87C, T87D, T87E, T87F, T87G, T87H, T87L, T87M, T87P, T87R, T87S, T87V, T87W, L88A, L88C, L88E, L88F, L88G, L88H, L88Q, L88S, L88W, L88Y, R89A, R89G, R89H, R89L, R89P, R89T, R89V, R89W, Q90E, Q90L, Q90N, Q90P, Q90W, Q90Y, I91E, I91G, I91L, I91M, I91N, I91Q, I91S, I91V, I91Y, L92A, L92C, L92E, L92G, L92H, L92N, L92Q, L92R, L92S, L92T, L92V, L92Y, Q93A, Q93E, Q93F, Q93G, Q93H, Q93I, Q93L, Q93M, Q93N, Q93P, Q93S, Q93V, Q93W, Q93Y, D94C, D94E, D94F, D94G, D94H, D94K, D94L, D94N, D94P, D94Q, D94R, D94S, D94V, V95A, V95C, V95D, V95E, V95F, V95G, V95I, V95L, V95M, V95N, V95P, V95Q, V95T, V95W, V95Y, K96A, K96C, K96L, K96N, K96P, K96Q, K96R, K96V, K96Y, A97C, A97E, A97F, A97K, A97N, A97P, A97R, A97V, A97W, A98E, A98G, A98K, A98L, A98P, A98V, A98W, A98Y, N99A, N99C, N99D, N99G, N99L, N99M, N99P, N99Q, N99R, N99S, N99W, N99Y, A100D, A100E, A100G, A100H, A100I, A100K, A100L, A100M, A100Q, A100R, A100S, A100T, A100V, A100W, A100Y, E101A, E101D, E101G, E101L, E101M, E101P, E101S, E101T, E101V, P102E, P102F, P102G, P102H, P102I, P102L, P102Q, P102R, P102S, P102V, P102W, P102Y, L103A, L103C, L103E, L103G, L103I, L103K, L103N, L103Q, L103R, L103S, L103T, L103V, L103W, L104A, L104C, L104E, L104G, L104I, L104N, L104P, L104Q, L104S, L104W, L104Y, M105A, M105C, M105E, M105F, M105G, M105I, M105K, M105L, M105P, M105T, M105V, M105W, Q106A, Q106C, Q106D, Q106G, Q106H, Q106K, Q106L, Q106M, Q106R, Q106S, Q106T, Q106V, Q106W, Q106Y, I107A, I107C, I107E, I107F, I107G, I107K, I107L, I107M, I107Q, I107S, I107T, I107V, I107Y, R108A, R108C, R108D, R108E, R108F, R108G, R108H, R108I, R108L, R108M, R108S, R108V, R108W, R108Y, L109A, L109C, L109D, L109E, L109F, L109G, L109K, L109M, L109P, L109Q, L109R, L109S, L109T, L109V, L109Y, P110A, P110C, P110D, P110E, P110F, P110G, P110H, P110K, P110L, P110M, P110N, P110R, P110S, P110V, P110W, A111C, A111E, A111L, A111M, A111N, A111P, A111Q, A111R, A111S, A111V, A111W, A111Y, N112A, N112F, N112G, N112I, N112K, N112L, N112P, N112R, N112V, N112W, N112Y, Y113A, Y113C, Y113D, Y113E, Y113G, Y113I, Y113M, Y113P, Y113Q, Y113S, Y113S, Y113W, G114A, G114F, G114K, G114L, G114M, G114P, G114W, G114Y, R115A, R115C, R115E, R115G, R115I, R115N, R115P, R115Q, R115S, R115V, R115W, R115Y, R116C, R116D, R116E, R116H, R116T, R116V, R116W, Y117A, Y117C, Y117D, Y117E, Y117G, Y117H, Y117I, Y117L, Y117M, Y117N, Y117P, Y117Q, Y117R, Y117S, Y117T, Y117V, Y117W, N118A, N118C, N118E, N118F, N118G, N118H, N118I, N118K, N118L, N118M, N118P, N118Q, N118S, N118T, N118V, N118W, E119C, E119D, E119F, E119G, E119K, E119L, E119M, E119P, E119Q, E119R, E119T, E119W, E119Y, A120D, A120E, A120G, A120I, A120L, A120P, A120T, A120W, F121A, F121C, F121D, F121E, F121G, F121K, F121L, F121M, F121N, F121P, F121Q, F121R, F121S, F121V, F121W, F121Y, S122A, S122C, S122D, S122E, S122F, S122G, S122I, S122L, S122M, S122P, S122R, S122V, S122W, S122Y, A123C, A123E, A123F, A123H, A123L, A123R, A123T, A123V, A123W, A123Y, I124A, I124C, I124D, I124E, I124G, I124H, I124K, I124L, I124R, I124S, I124T, I124W, I124Y, Y125C, Y125F, Y125G, Y125H, Y125I, Y125L, Y125P, Y125Q, Y125R, Y125S, Y125T, Y125V, Y125W, P126C, P126F, P126H, P126K, P126R, P126T, P126V, P126Y, K127A, K127I, K127P, K127S, L128A, L128C, L128E, L128F, L128G, L128Q, L128R, L128S, L128T, L128V, L128W, A129D, A129F, A129H, A129I, A129K, A129L, A129N, A129W, A129Y, K130E, K130I, K130P, K130V, E131A, E131C, E131D, E131F, E131G, E131I, E131K, E131L, E131N, E131P, E131V, E131W, F132C, F132D, F132E, F132K, F132L, F132N, F132P, F132T, F132V, D133C, D133K, D133R, D133S, D133T, D133V, D133Y, V134C, V134D, V134E, V134I, V134K, V134M, V134N, V134P, V134Q, V134R, V134S, V134W, V134Y, P135A, P135E, P135K, P135Q, L136A, L136C, L136D, L136E, L136F, L136G, L136H, L136K, L136M, L136N, L136P, L136Q, L136R, L136S, L136T, L137A, L137C, L137D, L137E, L137G, L137H, L137K, L137P, L137Q, L137R, L137S, L137Y, P138E, P138F, P138G, P138N, P138R, P138T, P138V, F139A, F139C, F139D, F139E, F139G, F139H, F139L, F139M, F139N, F139S, F139T, F139V, F139W, F140A, F140C, F140G, F140I, F140L, F140M, F140N, F140P, F140S, F140T, F140V, F140W, M141A, M141C, M141D, M141E, M141F, M141G, M141K, M141L, M141P, M141Q, M141R, M141T, M141V, M141W, M141Y, E142A, E142C, E142G, E142I, E142L, E142M, E142N, E142P, E142Q, E142R, E142S, E142T, E142V, E142W, E142Y, E143A, E143D, E143F, E143G, E143I, E143M, E143P, E143W, V144A, V144D, V144E, V144G, V144H, V144N, V144P, V144Q, V144R, V144S, V144W, V144Y, Y145A, Y145C, Y145D, Y145E, Y145G, Y145I, Y145L, Y145M, Y145N, Y145Q, Y145R, Y145S, Y145T, Y145W, L146A, L146C, L146D, L146E, L146G, L146H, L146P, L146S, L146W, K147G, K147P, K147R, K147W, P148D, P148E, P148W, Q149L, W150C, W150D, W150E, W150G, W150L, W150P, W150Q, W150R, W150T, M150V, M151A, M151C, M151D, M151E, M151F, M151G, M151I, M151L, M151Q, M151R, M151S, M151T, M151V, M151W, Q152A, Q152D, Q152E, Q152F, Q152H, Q152I, Q152K, Q152L, Q152N, Q152P, Q152R, Q152S, Q152T, Q152V, Q152Y, D153A, D153E, D153F, D153I, D153K, D153M, D153P, D153Q, D153V, D153W, D154A, D154C, D154E, D154F, D154G, D154H, D154I, D154K, D154L, D154M, D154N, D154P, D154R, D154S, D154T, D154V, D154W, G155A, G155F, G155H, G155I, G155P, G155V, G155W, G155Y, I156A, I156C, I156E, I156F, I156G, I156K, I156L, I156M, I156Q, I156R, I156S, I156T, I156V, I156Y, H157C, H157E, P158A, P158F, P158G, P158H, P158I, P158L, P158Q, P158S, P158T, P158V, P158W, N159C, N159E, N159G, N159I, N159K, N159L, N159M, N159P, N159Q, N159R, N159T, N159V, N159W, R160A, R160C, R160D, R160E, R160G, R160H, R160I, R160K, R160N, R160Q, R160S, R160W, D161E, D161G, D161I, D161K, D161L, D161M, D161N, D161Q, D161R, D161S, D161V, D161W, A162G, A162I, A162K, A162L, A162N, A162R, A162T, A162V, A162Y, Q163A, Q163C, Q163D, Q163E, Q163F, Q163G, Q163I, Q163L, Q163M, Q163S, Q163T, Q163V, Q163W, Q163Y, P164A, P164C, P164D, P164K, P164L, P164M, P164N, P164R, P164T, P164V, P164W, F165D, F165E, F165G, F165H, F165I, F165K, F165L, F165R, F165S, F165T, F165V, F165W, F165Y, I166A, I166C, I166F, I166L, I166M, I166S, I166V, I166Y, A167C, A167D, A167E, A167F, A167G, A167K, A167L, A167M, A167N, A167Q, A167R, A167T, A167V, A167W, A167Y, D168A, D168G, D168H, D168L, D168M, D168P, D168R, D168T, D168V, D168W, W169A, W169D, W169E, W169G, W169K, W169M, W169Q, W169R, W169S, W169T, W169V, M170A, M170E, M170F, M170G, M170H, M170L, M170N, M170Q, M170S, M170T, M170V, M170W, M170Y, A171E, A171F, A171I, A171S, A171V, A171W, K172A, K172M, K172P, Q173D, Q173I, Q173N, Q173P, Q173W, Q173Y, L174A, L174F, L174G, L174Q, L174S, L174T, L174W, L174W, L174Y, Q175F, Q175I, Q175L, Q175M, Q175Y, P176D, P176H, P176K, P176L, P176N, P176Q, P176R, P176V, P176W, P176Y, L177D, L177F, L177G, L177M, L177S, L177T, V178A, V178F, V178G, V178K, V178L, V178R, V178S, V178T, V178W, N179G, N179H, N179R, N179T, N179V, N179W, N179Y, H180A, H180E, H180G, H180L, H180P, H180R, H180S, H180V, H180W, D181A, D181C, D181E, D181G, D181H, D181I, D181L, D181P, D181Q, D181R, D181S, D181T, D181W, S182A, S182C, S182D, S182E, S182G, S182I, S182K, S182L, S182N, S182P, S182Q, S182R, S182T, and/or S180V, wherein the numbers in the substitution mutation designations refer to amino acid positions of SEQ ID NO:31.

In one embodiment of the invention, a mutant thioesterase (or a naturally-occurring equivalent thereof) is provided, which has an increased substrate specificity for, and/or activity (e.g., catalytic rate) with respect to $C_{10}$ substrates (i.e., substrates, the carbon chains of which are 10 carbons in length), and which is a variant of a precursor thioesterase that comprises an analogous sequence to SEQ ID NO:31 in FIG. 58, wherein the precursor thioesterase is mutated at one or more amino acid positions corresponding to one or more of residues selected from 5-30, 35-60, 65-98, 102-139, and/or 140-180 of SEQ ID NO:31. The increased substrate specificity for, and/or activity with respect to $C_{10}$ substrates can be measured in vitro and/or in vivo.

In one embodiment of the invention, a mutant thioesterase (or a naturally-occurring equivalent thereof) is provided, which has an increased substrate specificity for, and/or activity (e.g., catalytic rate) with respect to $C_{10}$ substrates, and which is a variant of a precursor thioesterase that comprises an analogous sequence to SEQ ID NO:31 in FIG. 58, wherein the precursor thioesterase is mutated at one or more amino acid positions corresponding to one or more residues of SEQ ID NO:31 selected from 1, 3, 4, 7, 9, 12, 13, 14, 16, 17, 20, 22, 24, 25, 28, 32, 38, 39, 40, 42, 43, 46, 47, 48, 49, 50, 51, 52, 54, 56, 59, 60, 64, 68, 72, 75, 76, 77, 78, 79, 80, 81, 82, 83, 84, 85, 86, 87, 89, 90, 91, 92, 93, 94, 95, 96, 98, 99, 100, 101, 102, 103, 105, 106, 107, 108, 109, 110, 111, 112, 113, 114, 115, 116, 117, 118, 119, 120, 121, 122, 123, 124, 125, 126, 127, 128, 130, 132, 133, 134, 138, 139, 140, 141, 142, 144, 145, 146, 147, 148, 150, 151, 152, 156, 158, 159, 160, 161, 162, 163, 164, 165, 166, 167, 168, 169, 170, 171, 172, 173, 175, 176, 177, 178, 179, 180, 18I, and/or 182. The increased substrate specificity for, and/or activity with respect to $C_{10}$ substrates can be measured in vitro and/or in vivo.

In one embodiment of the invention, a mutant thioesterase (or a naturally-occurring equivalent) is provided, which has an increased substrate specificity for, and/or activity (e.g., catalytic rate) with respect to $C_{10}$ substrates, and which is a variant of a precursor thioesterase that comprises an analogous sequence to SEQ ID NO:31 in FIG. 58, wherein the precursor thioesterase is mutated with one or more substitutions selected from A1L, A1S, T3K, L4A, L7M, L7V, D9N, S12A, A13D, G14A, G14E, G14P, G14Q, G14R, G14S, G14V, R16G, R16L, R16M, R16N, R16P, R16Q, R16T, M17C, M17L, M17T, M17V, S20A, S20C, S20D, S20G, S20L, S20T, S20W, A22C, A22D, A22E, A22G, A22H, A22I, A22K, A22N, P24A, P24C, P24D, P24F, P24I, P24S, P24T, P24V, P24W, A25E, A25L, A25N, A25Q, A25V, N28A, N28R, Q32V, Q32Y, V38E, V38K, V38R, N39A, N39T, A40D, A40H, I42A, I42E, I42L, I425, I42T, I42W, I42Y, S43A, S43C, S43D, S43E, S43L, S43N, S43P, T46E, T46F, T46I, T46L, T46V, S47A, S47C, S47F, S47G, S47L, S47M, S47T, S47V, Q48D, Q48E, Q48G, Q48S, Q48T, Q48V, Q48W, Q49A, Q49C, Q49D, Q49G, Q49H, Q49L, Q49M, Q49S, G50A, G50Q, L51A, L51F, L51H, L51Y, A52D, A52M, L54T, A56P, K59P, Q60M, R64D, R64E, R64Q, V68L, G72A, G72C, G72P, G72S, G75A, G75C, G75D, G75E, G75F, G75I, G75K, G75L, G75M, G75N, G75P, G75T, G75V, G75W, G75Y, L76A, L76D, L76G, L76I, L76K, L76M, L76N, L76P, L76Q, L76R, L76W, R77G, R77L, R77Q, G78A, G78C, G78E, G78F, G78M, G78N, G78Q, G78R, G78S, G78T, G78V, G78Y, F79A, F79D, F79E, F79G, F79H, F79N, F79Q, F79W, F79Y, Q80E, P81N, P81T, P81Y, Q82R, Q82S, Q82T, Q83A, Q83C, Q83F, Q83G, Q83K, Q83L, Q83M, Q83N, Q83R, Q83S, Q83T, Q83V, Q83W, Q83Y, T84A, T84F, T84L, T84M, T84N, T84Q, T84V, T84Y, E85A, E85C, E85L, E85Q, E85R, E85S, E85T, E85W, E85Y, Q86A, Q86G, Q86K, Q86T, T87D, T87P, R89A, R89G, Q90E, Q90Y, I91V, L92V, Q93A, Q93E, Q93G, Q93H, Q93I, Q93L, Q93S, Q93W, Q93Y, D94E, D94F, D94G, D94H, D94K, D94N, D94Q, D94R, D94S, D94V, V95L, V95T, K96V, K96Y, A98W, N99G, N99L, N99P, N99Q, N99R, N99Y, A100G, A100V, E101A, E101D, E101G, E101L, E101M, E101S, E101T, E101V, P102S, L103G, M105C, M105I, M105V, Q106A, Q106D, Q106H, Q106W, I107Y, R108A, R108D, R108E, R108F, R108G, R108H, R108I, R108L, R108M, R108S, R108W, R108Y, L109A, L109D, L109E, L109F, L109G, L109K, L109P, L109R, L109S, L109Y, P110C, P110D, P110E, P110F, P110G, P110H, P110K, P110L, P110M, P110N, P110R, P110S, P110V, P110W, A111C, A111E, A111L, A111M, A111P, A111Q, A111R, A111V, A111W, A111Y, N112A, N112F, N112G, N112K, N112R, N112W, Y113A, Y113C, Y113G, Y113I, Y113M, G114K, G114L, G114P, R115A, R115C, R115E, R115G, R115N, R115S, R115W, R115Y, R116D, R116E, R116W, Y117A, Y117C, Y117E, Y117I, Y117L, Y117N, Y117Q, Y117R, Y117S, Y117T, Y117V, N118C, N118G, N118I, N118K, N118S, N118T, N118V, N118W, E119C, E119F, E119G, E119K, E119M, E119R, E119W, E119Y, A120D, A120E, A120G, A120W, F121A, F121D, F121E, F121M, F121P, F121Q, F121R, F121S, F121Y, S122D, S122E, S122F, S122I, S122L, S122M, S122V, S122W, S122Y, A123H, A123L, A123V, I124I, Y125C, Y125F, Y125G, Y125P, Y125S, Y125V, Y125W, P126R, P126T, P126V, P126Y, K127S, L128C, L128T, L128V, K130E, K130I, K130V, F132D, F132E, F132N, F132T, D133K, D133R, D133S, D133T, D133V, D133Y, V134I, V134M, V134S, P138E, P138N, P138R, P138T, P138V, F139A, F139D, F139G, F139H, F139M, F139S, F139W, F140C, F140G, F140M, F140N, F140P, F140S, M141A, M141C, M141D, M141E, M141F, M141G, M141K, M141L, M141P, M141Q, M141R, M141T, M141V, M141W, M141Y, E142A, E142C, E142P, E142Q, E142W, E142Y, V144D, V144E, V144G, V144H, V144N, V144P, V144Q, V144R, V144S, V144W, V144Y, Y145A, Y145C, Y145D, Y145E, Y145G, Y145I, Y145L, Y145M, Y145N, Y145Q, Y145T, Y145W, L146A, L146C, L146D, L146E, L146G, L146H, L146S, L146W, K147G, K147P, K147W, P148D, P148E, W150C, W150D, W150E, W150G, W150L, W150Q, W150T, M151A, M151C, M151E, M151F, M151G, M151I, M151Q, M151S, M151T, M151V, M151W, Q152D, Q152F, Q152I, Q152L, Q152I, I156P, P158A, P158F, P158G, P158H, P158I, P158L, P158Q, P158T, P158V, N159C, N159E, N159G, N159I, N159K, N159L, N159M, N159R, N159T, N159V, R160A, R160C, R160D, R160E, R160G, R160H, R160N, R160Q, R160S, R160W, D161E, D161G, D161I, D161K, D161L, D161M, D161Q, D161R, D161W, A162I, A162L, A162T, A162V, A162Y, Q163G, Q163L, Q163M, Q163S, P164A, P164C, P164D, P164M, P164N, P164R, P164V, P164W, F165D, F165E, F165G, F165H, F165I, F165K, F165L, F165M, F165R, F165S, F165T, F165V, F165Y, I166F, I166L, I166M, I166V, A167C, A167M, A167R, A167T, D168G, D168P, D168R, W169E, W169K, W169Q, M170F, M170H, M170L, M170T, M170V, M170Y, A171E, A171F, A171V, A171W, K172A, K172M, Q173N, Q175I, P176H, P176K, P176N, P176W, L177M, L177T, V178T, V178W, N179G, N179H, N179R, N179T, N179V, N179Y, H180E, H180G, H180R, H180V, H180W, D181A, D181H, D181I, D181L, D181P, D181R, D181W, S182A, S182G, S182K, S182L, S182P, and/or S182R, wherein the numbers in the substitution mutation designations refer to amino acid positions of SEQ ID NO:31. The increased substrate specificity for, and/or activity with respect to $C_{10}$ substrates can be measured in vitro and/or in vivo.

In one embodiment of the invention, a mutant thioesterase (or a naturally-occurring equivalent thereof) is provided, which has an increased substrate specificity for, and/or activity (e.g., catalytic rate) with respect to $C_{12}$ substrates (i.e., substrates, the carbon chains of which are 12 carbons in length), and which is a variant of a precursor thioesterase that comprises an analogous sequence to SEQ ID NO:31 in FIG. 58, wherein the precursor thioesterase is mutated at one or more amino acid positions corresponding to residues 10-25, 35-85, 90-103, 110-143, 146-180 of SEQ ID NO:31. The increased substrate specificity for, and/or activity with respect to $C_{12}$ substrates can be measured in vitro and/or in vivo.

In one embodiment of the invention, a mutant thioesterase (or a naturally-occurring equivalent) is provided, which has an increased substrate specificity for, and/or activity (e.g., catalytic rate) with respect to $C_{12}$ substrates, and which is a variant of a precursor thioesterase that comprises an analogous sequence to SEQ ID NO:31 in FIG. 58, wherein the precursor thioesterase is mutated at one or more amino acid positions corresponding one or more residues of SEQ ID NO:31 selected from 1, 2, 3, 4, 5, 6, 7, 9, 11, 12, 13, 14, 15, 16, 17, 18, 19, 20, 21, 22, 24, 25, 26, 27, 28, 29, 30, 31, 35, 37, 38, 39, 40, 41, 42, 43, 44, 45, 46, 47, 48, 49, 50, 51, 52, 53, 54, 55, 57, 58, 60, 61, 62, 63, 64, 65, 66, 67, 68, 69, 70, 71, 72, 73, 74, 76, 77, 78, 79, 80, 81, 82, 83, 84, 86, 87, 88, 89, 90, 91, 92, 93, 94, 95, 96, 97, 98, 99, 100, 101, 102, 103, 104, 105, 106, 107, 108, 109, 111, 112, 113, 114, 115, 116, 117, 119, 120, 122, 123, 124, 125, 126, 127, 128, 129, 130, 131, 133, 134, 136, 137, 140, 141, 142, 145, 149, 152, 153, 155, 156, 158, 159, 160, 161, 162, 163, 164, 166, 167, 168, 169, 170, 172, 173, 174, 175, 176, 177, 179, 180, 181, and/or 182. The increased substrate specificity for, and/or activity with respect to $C_{12}$ substrates can be measured in vitro and/or in vivo.

In one embodiment of the invention, a mutant thioesterase (or a naturally-occurring equivalent thereof) is provided, which has an increased substrate specificity for, and/or activity (e.g., catalytic rate) with respect to $C_{12}$ substrates, and which is a variant of a precursor thioesterase that comprises an analogous sequence to SEQ ID NO:31 in FIG. 58, wherein the precursor thioesterase is mutated with one or more substitutions selected from A1Q, A1S, A1V, D2E, D2K, D2P, D2W, T3R, T3W, L4A, L4Y, L5F, L5G, L5S, L5Y, I6T, I6V, L7A, L7C, L7M, L7N, L7S, L7T, L7V, L7Y, D9N, L11M, S12A, S12I, S12V, A13C, A13G, A13H, A13I, A13L, A13N, A13T, A13W, G14F, G14I, G14K, G14M, G14V, Y15A, Y15C, Y15D, Y15E, Y15G, Y15I, Y15L, Y15M, Y15N, Y15Q, Y15R, Y15S, Y15V, R16D, R16E, R16G, R16H, R16I, R16L, R16N, R16P, R16S, R16T, R16V, R16W, M17A, M17C, M17G, M17K, M17N, M17P, M17Q, M17R, M17S, M17T, S18M, S18N, A19L, S20A, S20C, S20D, S20G, S20L, S20T, S20W, A21I, A21L, A21P, A21Y, A22F, A22L, A22M, A22N, A22R, A22Y, P24G, P24V, A25D, A25E, A25L, A25N, A25Q, A25R, A25V, L26D, L26E, L26F, L26G, L26H, L26I, L26K, L26N, L26R, L26S, L26W, L26Y, L27A, L27C, L27F, L27M, L27W, L27Y, N28R, N28W, D29P, K30P, W31E, W31N, T35L, T35Y, V37F, V37S, V37W, V38D, V38F, V38G, V38P, N39P, N39C, N39E, N39G, N39Q, N39W, A40D, A40L, A40M, A40P, A40V, A40Y, S41C, S41T, I42A, I42C, I42D, I42E, I42G, I42K, I42L, I42M, I42P, I42S, I42T, I42W, I42Y, S43A, S43D, S43E, S43F, S43G, S43H, S43L, S43M, S43N, S43R, S43T, S43V, G44C, G44E, G44H, G44K, G44L, G44N, G44Q, G44R, G44S, D45A, D45C, D45E, D45F, D45H, D45I, D45K, D45L, D45M, D45P, D45Q, D45S, D45T, D45V, D45W, T46A, T46C, T46D, T46G, T46K, T46N, T46R, T46S, S47P, S47Q, Q48E, Q48V, Q48W, Q48Y, Q49A, Q49C, Q49D, Q49E, Q49G, Q49H, Q49I, Q49K, Q49L, Q49M, Q49P, Q49R, Q49S, Q49V, Q49W, Q49Y, G50A, G50C, G50F, G50I, G50K, G50L, G50M, G50N, G50P, G50Q, G50R, G50S, G50T, G50Y, L51A, L51D, L51N, L51T, L51V, L51W, A52C, A52M, A52P, A52W, R53A, R53C, R53D, R53E, R53F, R53G, R53I, R53K, R53L, R53N, R53S, R53T, R53V, R53W, R53Y, L54A, L54C, L54E, L54F, L54G, L54M, L54N, L54S, L54W, L54Y, P55Y, L57A, L57C, L57F, L57K, L57P, L57Q, L57R, L57Y, L58A, L58D, L58E, L58G, L58H, L58N, L58R, L58S, L58W, L58Y, Q60P, H61D, H61G, H61P, Q62P, Q62W, P63I, P63L, P63N, P63S, P63T, P63V, P63W, R64F, R64P, R64W, R64Y, W65A, W65E, W65G, W65K, W65M, W65N, W65V, V66M, V66S, L67A, L67T, V68A, V68L, V68M, V68S, V68T, E69A, E69C, E69D, E69G, E69H, E69K, E69L, E69M, E69N, E69P, E69V, E69Y, L70A, L70C, L70E, L70F, L70H, L70I, L70K, L70Q, L70S, L70T, L70V, G71A, G72A, N73G, N73H, N73L, N73R, N73S, N73T, D74E, D74G, L76I, L76M, L76W, R77C, R77D, R77E, R77G, R77K, R77L, R77Q, R77S, R77V, R77W, G78D, F79P, Q80G, Q80M, Q80S, Q80Y, P81A, P81E, P81K, P81L, P81M, P81W, P81Y, Q82F, Q82V, Q82W, Q82Y, Q83A, T84E, T84R, T84W, Q86A, Q86T, T87E, T87G, T87L, L88C, R89L, R89P, Q90N, Q90P, Q90W, I91G, I91M, I91S, I91V, I91Y, L92A, L92C, L92G, L92H, L92N, L92S, L92T, L92V, L92Y, Q93A, Q93G, Q93H, Q93I, Q93P, Q93Y, D94P, V95F, V95G, V95L, V95N, V95Q, V95T, V95W, K96A, K96L, K96P, K96Y, A97K, A97P, A98L, A98P, A98V, A98W, A98Y, N99C, N99D, N99G, N99L, N99M, N99P, N99Q, N99R, N99W, N99Y, A100D, A100E, A100G, A100H, A100I, A100K, A100L, A100Q, A100R, A100V, A100W, A100Y, E101G, E101L, E101M, E101P, E101S, E101T, E101V, P102E, P102F, P102H, P102L, P102Q, P102R, P102S, P102W, P102Y, L103E, L103K, L103N, L103Q, L103R, L104C, L104P, L104S, L104W, M105C, M105E, M105G, M105V, Q106A, Q106C, Q106G, Q106K, Q106R, Q106S, Q106T, I107C, I107E, I107K, I107L, I107M, I107S, I107V, R108F, R108W, L109M, A111C, A111Q, A111W, N112A, N112G, N112W, Y113A, Y113D, Y113G, Y113I, G114K, G114L, G114M, G114Y, R115A, R115C, R115E, R115G, R115N, R115S, R115Y, R116H, R116W, Y117C, Y117H, Y117I, Y117L, Y117M, Y117N, Y117S, Y117T, Y117V, E119C, E119F, E119K, E119M, E119R, E119W, E119Y, A120D, A120G, A120I, A120T, A120W, S122F, S122I, S122L, S122M, S122V, S122W, S122Y, A123C, A123F, A123H, A123L, A123R, A123T, A123V, A123W, A123Y, I124G, I124H, I124K, I124L, I124R, I124S, I124Y, Y125F, Y125R, P126C, P126F, P126H, P126Y, K127I, K127P, L128A, L128S, L128T, A129H, A129I, A129K, A129N, A129W, A129Y, K130P, E131A, E131C, E131F, E131G, E131K, E131L, E131N, E131V, E131W, D133K, V134D, V134E, V134K, V134N, V134Q, V134R, V134W, V134Y, L136A, L136D, L136E, L136F, L136G, L136H, L136K, L136N, L136P, L136Q, L136R, L136S, L136T, L137E, L137G, L137H, L137P, L137Q, L137S, L137Y, F140M, M141A, M141C, M141L, M141P, E142C, Y145E, Q149L, Q152A, Q152D, Q152E, Q152H, Q152K, Q152R, Q152Y, D153K, G155F, G155W, G155Y, I156C, I156F, I156M, I156V, P158A, P158G, N159G, N159Q, N159T, N159V, R160A, R160D, R160E, R160G, R160H, R160N, R160Q, R160S, R160W, D161I, D161K, D161L, D161M, D161N, D161Q, D161W, A162G, Q163A, Q163C, Q163G, Q163L, Q163M, Q163S, Q163T, P164C, P164M, I166L, I166V, A167C, A167E, A167F, A167G, A167K, A167L, A167N, A167Q, A167R, A167T, A167V, A167Y, D168G, D168H, D168L, D168R, D168V, D168W, W169A, W169D, W169E, W169G, W169K, W169Q, W169S, M170F, M170G, M170N, M170Q, M170S, M170V, M170W, K172M, K172P, Q173N, L174A, L174F, L174G, L174T, L174W, Q175I, P176H, P176K, P176L, P176N, P176W, L177D, L177G, N179H, N179R, N179Y, H180A, H180G, D181H, D181I, D181L, D181R, D181W, S182K, S182L, S182P, and/or S182R, wherein the numbers in the substitution mutation designations refer to amino acid positions of SEQ ID NO:31. The increased substrate specificity for, and/or activity with respect to $C_{12}$ substrates can be measured in vitro and/or in vivo.

In one embodiment of the invention, a mutant thioesterase (or a naturally-occurring equivalent thereof) is provided, which has an increased substrate specificity for, and/or activity (e.g., catalytic rate) with respect to $C_{14}$ substrates (i.e., substrates, the carbon chains of which are 14 carbons in length), and which is a variant of a precursor thioesterase that comprises an analogous sequence to SEQ ID NO:31 in FIG. 58, wherein the precursor thioesterase is mutated at one or more amino acid positions corresponding to residues 5-20, 35-58, 65-80, 83-90, 110-130, 140-145, 155-160, 165-180 of SEQ ID NO:31. The increased substrate specificity for, and/or activity with respect to $C_{14}$ substrates can be measured in vitro and/or in vivo.

In one embodiment of the invention, a mutant thioesterase (or a naturally-occurring equivalent thereof) is provided, which has an increased substrate specificity for, and/or activity (e.g., catalytic rate) with respect to $C_{14}$ substrates, and which is a variant of a precursor thioesterase that comprises an analogous sequence to SEQ ID NO:31 in FIG. 58, wherein the precursor thioesterase is mutated at one or more amino acid positions corresponding one or more residues of SEQ ID NO:31 selected from 1, 4, 5, 7, 8, 9, 11, 12, 13, 14, 15, 16, 17, 20, 21, 22, 23, 25, 26, 28, 29, 33, 36, 37, 38, 39, 40, 41, 42, 43, 44, 45, 46, 47, 48, 49, 50, 51, 52, 53, 54, 56, 57, 58, 66, 68, 69, 70, 72, 73, 74, 75, 76, 77, 78, 79, 80, 81, 82, 83, 84, 85, 86, 87, 89, 91, 92, 93, 95, 96, 97, 98, 99, 100, 101, 102, 105, 106, 107, 108, 109, 110, 111, 112, 113, 114, 115, 116, 117, 118, 119, 120, 121, 122, 123, 124, 125, 126, 131, 133, 134, 136, 137, 138, 139, 140, 141, 142, 143, 147, 148, 151, 152, 153, 155, 156, 158, 159, 160, 161, 162, 163, 164, 165, 166, 167, 168, 169, 170, 171, 173, 174, 175, 176, 178, 179, 180, 181, and/or 182. The increased substrate specificity for, and/or activity with respect to $C_{14}$ substrates can be measured in vitro and/or in vivo.

In one embodiment of the invention, a mutant thioesterase (or a naturally-occurring equivalent thereof) is provided, which has an increased substrate specificity for, and/or activity (e.g., catalytic rate) with respect to $C_{14}$ substrates, and which is a variant of a precursor thioesterase that comprises an analogous sequence to SEQ ID NO:31 in FIG. 58, wherein the precursor thioesterase is mutated with one or more substitutions selected from A1S, L4S, L4Y, L5H, L5Y, L7C, L7M, L7N, L7S, L7T, L7Y, G8S, D9N, D9T, L11C, L11I, L11M, L11Q, L11V, S12I, S12L, S12M, S12T, S12V, A13H, A13I, A13L, A13T, A13V, G14F, G14I, G14R, G14T, G14V, Y15A, Y15C, Y15D, Y15E, Y15G, Y15I, Y15L, Y15M, Y15N, Y15Q, Y15R, Y15S, Y15V, R16G, R16N, R16P, R16W, M17C, M17D, M17G, M17K, M17N, M17P, M17R, M17S, M17T, S20A, S20D, S20G, S20L, S20T, S20W, A21G, A22L, A22N, A22Y, W23Y, A25E, A25N, A25Q, A25V, L26C, L26F, L26H, L26Q, L26V, L26Y, N28K, N28P, D29V, S33F, S36H, V37H, V37Q, V38F, N39F, N39M, N39Q, N39V, N39W, N39Y, A40G, A40P, A40T, A40V, S41P, S41T, I42A, I42D, I42E, I42G, I42L, I42M, I42P, I42S, I42T, I42W, I42Y, S43A, S43D, S43E, S43F, S43G, S43H, S43L, S43M, S43N, S43T, S43V, S43W, G44A, G44C, G44E, G44F, G44H, G44K, G44L, G44M, G44N, G44Q, G44R, G44S, G44W, G44Y, D45A, D45C, D45E, D45F, D45G, D45H, D45M, D45P, D45Q, D45S, D45T, D45V, D45W, T46A, T46C, T46D, T46G, T46K, T46N, T46S, T46W, S47E, S47P, S47Q, S47W, S47Y, Q48C, Q48F, Q48I, Q48M, Q48V, Q48W, Q48Y, Q49A, Q49C, Q49D, Q49E, Q49G, Q49H, Q49I, Q49K, Q49L, Q49M, Q49P, Q49R, Q49S, Q49V, Q49W, Q49Y, G50A, G50C, G50E, G50F, G50I, G50K, G50L, G50M, G50N, G50P, G50Q, G50R, G50S, G50T, G50W, G50Y, L51A, L51C, L51D, L51S, L51V, A52H, A52I, A52L, A52M, A52P, A52R, A52V, A52W, A52Y, R53A, R53C, R53D, R53E, R53F, R53G, R53I, R53K, R53L, R53N, R53S, R53T, R53V, R53W, R53Y, L54W, L54Y, A56R, A56W, A56Y, L57F, L58F, L58I, L58Y, V66I, V68L, E69A, E69C, E69D, E69F, E69G, E69H, E69K, E69L, E69M, E69N, E69Q, E69S, E69V, E69Y, L70A, L70C, L70E, L70F, L70H, L70Q, L70S, L70T, L70V, L70W, G72A, G72C, G72P, G72S, N73A, N73C, N73G, N73H, N73I, N73L, N73P, N73R, N73S, N73T, N73V, N73W, D74E, D74G, G75A, G75C, G75D, G75E, G75F, G75I, G75K, G75L, G75M, G75N, G75P, G75T, G75W, G75Y, L76A, L76C, L76D, L76E, L76F, L76G, L76I, L76K, L76M, L76N, L76P, L76Q, L76R, L76T, L76V, L76W, R77A, R77C, R77D, R77E, R77F, R77G, R77H, R77K, R77L, R77N, R77Q, R77S, R77V, R77W, G78P, F79M, F79P, F79V, Q80A, Q80G, Q80L, Q80M, Q80S, Q80W, Q80Y, P81A, P81E, P81K, P81L, P81M, P81W, P81Y, Q82F, Q82I, Q82N, Q82P, Q82V, Q82W, Q82Y, Q83A, T84S, E85D, Q86A, Q86T, Q86V, Q86W, T87A, T87C, T87E, T87F, T87G, T87H, T87L, T87M, T87S, T87V, T87W, R89H, R89T, R89V, R89W, I91L, I91V, I91Y, L92V, Q93A, Q93G, Q93H, Q93I, Q93P, Q93Y, V95L, V95M, V95T, V95W, K96A, K96L, K96P, K96Y, A97W, A98K, A98L, A98W, N99L, N99P, N99Q, N99Y, A100G, A100H, A100I, A100K, A100L, A100M, A100R, A100T, A100V, A100Y, E101G, E101L, E101M, E101S, E101T, E101V, P102S, M105A, M105C, M105E, M105G, M105I, M105L, M105V, Q106A, Q106C, Q106D, Q106G, Q106H, Q106K, Q106L, Q106M, Q106R, Q106S, Q106T, Q106V, Q106W, Q106Y, I107C, I107E, I107G, I107L, I107M, I107Q, I107V, R108A, R108C, R108D, R108F, R108I, R108L, R108S, R108V, R108W, R108Y, L109C, L109M, L109Q, L109T, L109V, L109Y, P110A, P110E, P110H, P110N, P110R, P110V, A111C, A111L, A111Q, A111R, A111V, A111W, N112A, N112F, N112G, N112I, N112L, N112P, N112V, N112W, N112Y, Y113A, Y113D, Y113G, Y113I, Y113M, Y113W, G114F, G114K, G114L, G114M, G114W, G114Y, R115A, R115C, R115E, R115G, R115I, R115N, R115P, R115Q, R115S, R115V, R115W, R115Y, R116C, R116H, R116T, R116V, R116W, Y117C, Y117H, Y117I, Y117L, Y117M, Y117N, Y117S, Y117W, N118A, N118C, N118E, N118G, N118H, N118I, N118L, N118M, N118P, N118Q, N118T, N118V, N118W, E119C, E119D, E119F, E119K, E119M, E119P, E119R, E119T, E119W, E119Y, A120D, A120G, A120I, A120L, A120T, A120W, F121A, F121C, F121D, F121E, F121K, F121L, F121M, F121P, F121Q, F121R, F121S, F121V, F121Y, S122A, S122C, S122D, S122E, S122F, S122G, S122I, S122L, S122M, S122P, S122V, S122W, S122Y, A123C, A123E, A123F, A123H, A123L, A123T, A123V, A123W, A123Y, I124A, I124C, I124G, I124L, I124Y, Y125C, Y125F, Y125G, Y125I, Y125L, Y125P, Y125Q, Y125R, Y125S, Y125T, Y125V, P126C, P126H, P126Y, E131I, E131L, D133K, D133Y, V134S, L136C, L136M, L136Q, L136S, L137P, P138E, P138R, P138T, F139M, F140M, M141A, M141C, M141L, M141P, E142A, E142C, E142L, E142M, E142N, E142P, E142Q, E142S, E142Y, E143I, E143P, K147R, P148W, M151I, M151Q, M151V, Q152A, Q152K, Q152S, D153I, D153K, D153M, D153W, G155F, G155H, G155W, G155Y, I156C, I156F, I156M, I156Q, I156R, I156S, I156V, P158A, P158G, P158S, N159G, N159T, R160A, R160G, R160H, R160N, R160W, D161G, D161I, D161K, D161L, D161M, D161N, D161Q, D161R, D161S, D161V, D161W, A162G, Q163G, Q163L, Q163M, Q163S, P164A, P164C, P164K, P164L, P164M, P164N, P164R, P164T, P164W, F165G, F165H, F165S, F165W, F165Y, I166L, I166V, A167T, D168A, D168G, D168H, D168P, D168R, D168T, W169A, W169E, W169K, W169M, W169Q, W169R, W169S, W169T, W169V, M170A, M170F, M170V, A171I, Q173N, Q173W, Q173Y, L174Q, L174W, Q175I, Q175Y, P176H, P176K, P176L, P176R, P176W, P176Y, V178A, V178T, V178W, N179H, N179R, N179T, N179V, N179Y, H180G, H180R, H180S, H180W, D181A, D181H, D181I, D181L, D181Q, D181R, D181S, D181W, S182A, S182E, S182G, S182I, S182K, S182L, S182P, S182Q, S182R, and/or S182T, wherein the numbers in the substitution mutation designations refer to amino acid positions of SEQ ID NO:31. The increased substrate specificity for, and/or activity with respect to $C_{14}$ substrates can be measured in vitro and/or in vivo.

In one embodiment of the invention, a mutant thioesterase (or a naturally-occurring equivalent thereof) is provided, which has a preference for ester substrates (e.g., acyl-PNP) over thioester substrates (e.g., acyl-CoA), and which is a variant of a precursor thioesterase that comprises an analogous sequence to SEQ ID NO:31 in FIG. 58, wherein the precursor thioesterase is mutated at one or more amino acid positions corresponding to residues selected from 95, 96, 97, 98, 99, 100, 101, 102, 104, 105, 106, 107, 108, 109, and/or 110 of SEQ ID NO:31. The preference for ester substrates over thioester substrates can be measured in vitro and/or in vivo.

In one embodiment of the invention, a mutant thioesterase (or a naturally-occurring equivalent thereof) is provided, which has a preference for ester substrates (e.g., acyl-PNP) over thioester substrates (e.g., acyl-CoA), and which is a variant of a precursor thioesterase that comprises an analogous sequence to SEQ ID NO:31 in FIG. 58, wherein the precursor thioesterase is mutated with one or more substitutions selected from V95L, V95M, V95T, K96A, K96L, K96W, K96Y, A97F, A97K, A97S, A97T, A97W, A98E, A98F, A98K, A98L, A98Q, A98W, N99Y, A100K, A100V, E101L, P102S, L104C, M105F, Q106A, Q106C, Q106T, Q106Y, I107A, I107C, I107G, I107L, I107M, I107Q, I107V, R108A, R108C, R108D, R108F, R108I, R108L, R108S, R108V, R108W, R108Y, L109M, L109V, P110A, P110F, P110H, P110N, P110V, and/or P110W, wherein the numbers in the substitution mutation designations refer to amino acid positions of SEQ ID NO:31. The preference for ester substrates over thioester substrates can be measured in vitro and/or in vivo.

In one embodiment of the invention, a mutant thioesterase (or a naturally-occurring equivalent thereof) is provided, which has a preference for thioester substrates (e.g., acyl-CoA) over ester substrates (e.g., acyl-PNP), and which is a variant of a precursor thioesterase that comprises an analogous sequence to SEQ ID NO:31 in FIG. 58, wherein the precursor thioesterase is mutated at one or more amino acid positions corresponding to residues selected from 95, 96, 97, 101, 102, 103, 104, 105, 107, 109, and/or 110 of SEQ ID NO:31. The preference for thioester substrates over ester substrates can be measured in vitro and/or in vivo.

In one embodiment of the invention, a mutant thioesterase (or a naturally-occurring equivalent thereof) is provided, which has a preference for thioester substrates (e.g., acyl-CoA) over ester substrates (e.g., acyl-PNP), and which is a variant of a precursor thioesterase that comprises an analogous sequence to SEQ ID NO:31 in FIG. 58, wherein the precursor thioesterase is mutated with one or more substitutions selected from V95E, V95I, V95W, V95Y, K96P, A97E, A97M, E101P, P102D, P102K, P102Y, L103E, L103K, L103N, L104A, L104D, L104E, L104N, L104Q, L104W, L104Y, M105W, I107E, I107K, I107P, L109A, L109C, L109D, L109E, L109G, L109K, L109N, L109P, L109Q, L109S, L109T, L109Y, and/or P110R, wherein the numbers in the substitution mutation designations refer to amino acid positions of SEQ ID NO:31. The preference for thioester substrates over ester substrates can be measured in vitro and/or in vivo.

In one embodiment of the invention, a mutant thioesterase (or a naturally-occurring equivalent thereof) is provided, which is capable of producing an increased proportional or percentage yield of fatty esters over other non-fatty ester products (e.g., free fatty acids and/or fatty acid derivatives other than fatty esters), and which is a variant of a precursor thioesterase that comprises an analogous sequence to SEQ ID NO:31 in FIG. 58, wherein the precursor thioesterase is mutated at one or more amino acid positions corresponding to residues of SEQ ID NO:31 selected from 1-14, 22-29, 33-58, 65-100, 103-109, 114-117, 119-121, 127-136, 139-144, 150-151, 155-170, and/or 173-174. The increased proportional or percentage yield of fatty esters over other products (e.g., fatty acid derivatives other than fatty esters) can be observed or determined in vitro and/or in vivo. Preferably, the increased proportional or percentage yield of fatty esters over other products is determined in vivo.

In one embodiment of the invention, a mutant thioesterase (or a naturally-occurring equivalent thereof) is provided, which is capable of producing an increased proportional or percentage yield of fatty esters over other products (e.g., free fatty acids and/or fatty acid derivatives other than fatty esters), and which is a variant of a precursor thioesterase that comprises an analogous sequence to SEQ ID NO:31 in FIG. 58, wherein the precursor thioesterase is mutated at one or more amino acid positions corresponding to residues of SEQ ID NO:31 selected from 1, 2, 4, 5, 6, 7, 8, 12, 13, 14, 22, 23, 24, 25, 26, 28, 29, 33, 34, 35, 36, 37, 38, 39, 40, 41, 44, 45, 46, 47, 49, 50, 53, 58, 65, 67, 68, 69, 70, 71, 72, 73, 74, 75, 76, 77, 79, 81, 84, 86, 87, 88, 89, 90, 91, 92, 93, 95, 96, 99, 100, 103, 104, 105, 106, 107, 108, 109, 114, 115, 117, 119, 120, 121, 127, 128, 129, 131, 132, 134, 135, 136, 139, 141, 142, 143, 144, 150, 151, 155, 156, 158, 159, 160, 161, 162, 163, 164, 165, 166, 169, 170, 173, and/or 174. The increased proportional or percentage yield of fatty esters over other products (e.g., fatty acid derivatives other than fatty esters) can be observed or determined in vitro and/or in vivo. Preferably, the increased proportional or percentage yield of fatty esters over other products (e.g., fatty acid derivatives other than fatty esters) is determined in vivo.

In one embodiment of the invention, a mutant thioesterase (or a naturally-occurring equivalent thereof) is provided, which is capable of producing an increased proportional or percentage yield of fatty esters over other products (e.g., free fatty acids and/or fatty acid derivatives other than fatty esters), and which is a variant of a precursor thioesterase that comprises an analogous sequence to SEQ ID NO:31 in FIG. 58, wherein the precursor thioesterase is mutated with one or more substitutions selected from A1R, D2H, D2R, L4G, L4M, L5Q, I6A, I6L, L7E, G8A, S12N, A13I, A13L, A13S, A13T, A13W, A13Y, G14K, G14R, G14S, G14T, A22D, A22E, A22H, A22Y, W23Y, P24C, P24G, P24T, A25P, L26C, L26D, L26E, L26G, L26N, N28A, N28M, D29V, S33G, S33M, K34A, K34H, K34M, T35G, T35M, S36A, V37A, V37G, V37H, V37S, V38D, V38G, V38P, N39E, N39Q, N39R, A40M, A40P, S41T, G44F, G44Y, D45P, D45Q, T46W, S47F, Q49I, G50A, G50K, G50M, G50S, R53S, L58D, L58M, L58R, W65L, L67G, V68G, V68M, V68N, E69P, E69Q, L70A, L70E, L70H, G71C, G72A, N73C, N73G, N73L, N73R, N73T, N73V, D74C, D74S, D74W, G75A, G75K, G75L, G75M, L76A, L76F, L76G, L76I, L76M, L76N, L76T, L76W, R77G, F79A, F79M, F79P, P81E, P81W, T84F, T84H, T84Y, Q86P, Q86W, T87M, T87S, T87W, L88C, L88F, L88G, L88H, L88Y, R89G, Q90P, Q90W, I91M, I91S, L92C, L92G, Q93F, Q93P, V95A, V95D, V95E, V95L, V95M, K96P, N99L, N99M, N99S, A100D, A100K, A100L, A100M, A100V, A100Y, L103A, L104A, L104C, L104P, L104Q, L104W, M105A, Q106A, Q106C, Q106T, Q106W, I107C, I107M, R108E, L109F, L109M, G114F, R115W, Y117P, E119D, E119P, A120P, F121A, F121C, F121W, K127P, L128F, A129L, A129Y, E131A, F132P, V134P, P135A, L136A, F139M, M141A, M141P, E142A, E143P, V144A, W150D, W150E, M151S, G155W, I156K, I156M, P158A, P158G, P158Q, P158S, N159E, N159I, R160H, R160I, R160K, D161G, A162T, A162Y, Q163A, Q163C, Q163E, Q163G, Q163I, Q163M, Q163S, Q163T, Q163V, P164C, F165D, F165S, I166A, I166L, W169M, M170E, M170G, M170N, M170S, Q173P, and/or L174A, wherein the numbers in the substitution mutation designations refer to amino acid positions of SEQ ID NO:31. The increased proportional or percentage yield of fatty esters over other products (e.g., fatty acid derivatives other than fatty esters) can be observed or determined in vitro and/or in vivo. Preferably, the increased proportional or percentage yield of fatty esters over other products (e.g., fatty acid derivatives other than fatty esters) is determined in vivo.

In one embodiment of the invention, a mutant thioesterase (or a naturally-occurring equivalent thereof) is provided, which is capable of producing a decreased proportional or percentage yield of fatty esters over other products (e.g., free fatty acids and/or fatty acid derivatives other than fatty esters) when fatty ester production is undesirable, and which is a variant of a precursor thioesterase that comprises an analogous sequence to SEQ ID NO:31 in FIG. 58, wherein the precursor thioesterase is mutated at one or more amino acid positions corresponding to residues of SEQ ID NO:31 selected from 3, 5, 15-18, 27-42, 46, 57-68, 77-78, 95-106, 121-123, 152-154, 167, and/or 175-182. The decreased proportional or percentage yield of fatty esters over other products (e.g., fatty acid derivatives other than fatty esters) can be observed or determined in vitro and/or in vivo. Preferably, the decreased proportional or percentage yield of fatty esters over other products (e.g., fatty acid derivatives other than fatty esters) is determined in vivo.

In one embodiment of the invention, a mutant thioesterase (or a naturally-occurring equivalent thereof) is provided, which is capable of producing a decreased proportional or percentage yield of fatty esters over other products (e.g., free fatty acids and/or fatty acid derivatives other than fatty esters) when fatty ester production is undesirable, and which is a variant of a precursor thioesterase that comprises an analogous sequence to SEQ ID NO:31 in FIG. 58, wherein the precursor thioesterase is mutated at one or more amino acid positions corresponding to residues of SEQ ID NO:31 selected from 3, 5, 15, 16, 18, 27, 28, 33, 34, 35, 36, 37, 38, 40, 42, 46, 57, 59, 60, 62, 65, 68, 77, 78, 95, 96, 97, 98, 99, 100, 102, 103, 105, 106, 121, 123, 152, 153, 154, 167, 175, 176, 178, 179, 180, 181, and/or 182. The decreased proportional or percentage yield of fatty esters over other products (e.g., fatty acid derivatives other than fatty esters) can be observed or determined in vitro and/or in vivo. Preferably, the decreased proportional or percentage yield of fatty esters over other products (e.g., fatty acid derivatives other than fatty esters) is determined in vivo.

In one embodiment of the invention, a mutant thioesterase (or a naturally-occurring equivalent thereof) is provided, which is capable of producing a decreased proportional or percentage yield of fatty esters over other products (e.g., free fatty acids and/or fatty acid derivatives other than fatty esters) when production of fatty esters is undesirable, and which is a variant of a precursor thioesterase that comprises an analogous sequence to SEQ ID NO:31 in FIG. 58, wherein the precursor thioesterase is mutated with one or more substitutions selected from T3E, T3G, T3K, T3L, L5C, L5G, Y15A, Y15L, Y15Q, Y15R, Y15V, R16D, R16E, R16G, R16I, R16V, S18E, L27V, N28G, N28I, S33I, S33R, K34R, T35F, T35K, T35L, T35Q, T35V, S36F, S36I, S36L, S36W, V37L, V38E, V38F, V38K, V38L, A40D, A40G, I42T, T46L, L57A, L57F, L57G, L57H, L57K, L57N, L57P, L57R, L57S, L57T, L57V, L57W, L57Y, K59V, Q60E, Q60P, Q62G, W65V, V68L, R77L, G78M, V95F, V95N, K96C, K96L, K96N, K96Q, K96R, K96Y, A97E, A97F, A97R, A97W, A98E, N99A, N99D, A100S, P102I, L103Q, L103W, M105L, Q106G, Q106H, Q106K, Q106S, Q106V, F121P, A123E, Q152D, Q152E, Q152F, Q152H, Q152I, Q152K, Q152L, Q152S, Q152T, Q152Y, D153P, D153V, D154E, A167V, Q175L, P176D, V178K, N179H, N179W, H180E, H180L, H180P, H180R, D181C, D181E, S182K, S182L, S182N, S182R, S182T, and/or S182V, wherein the numbers in the substitution mutation designations refer to amino acid positions of SEQ ID NO:31. The decreased proportional or percentage yield of fatty esters over other products (e.g., fatty acid derivatives other than fatty esters) can be observed or determined in vitro and/or in vivo. Preferably, the decreased proportional or percentage yield of fatty esters over other products (e.g., fatty acid derivatives other than fatty esters) is determined in vivo.

In one embodiment of the invention, a mutant thioesterase (or a naturally-occurring equivalent thereof) is provided, which is capable of increased and/or improved production of one or more fatty acid derivatives, and which is a variant of a precursor thioesterase that comprises an analogous sequence to SEQ ID NO:31 in FIG. 58, wherein the precursor thioesterase is mutated at one or more amino acid positions corresponding to residues of SEQ ID NO:31 selected from 2, 4, 11-22, 25-31, 37-45, 49-58, 63-80, 84-130, 136-146, and/or 150-174. An exemplary fatty acid derivative that is produced accordingly is a free fatty acid. The increased and/or improved production of fatty acid derivatives can be measured in vitro and/or in vivo. Preferably, the increased and/or improved production of fatty acid derivatives is measured in vivo.

In one embodiment of the invention, a mutant thioesterase (or a naturally-occurring equivalent thereof) is provided, which is capable of increased and/or improved production of one or more fatty acid derivatives, and which is a variant of a precursor thioesterase that comprises an analogous sequence of SEQ ID NO:31 in FIG. 58, wherein the precursor thioesterase is mutated at one or more amino acid positions corresponding to residues of SEQ ID NO:31 selected from 2, 4, 11, 12, 13, 14, 15, 16, 17, 19, 21, 22, 25, 26, 27, 28, 29, 30, 31, 37, 39, 41, 42, 43, 44, 45, 49, 50, 51, 53, 54, 58, 63, 65, 66, 67, 68, 69, 70, 71, 73, 74, 75, 76, 77, 78, 79, 80, 84, 87, 88, 90, 91, 92, 93, 94, 95, 96, 97, 98, 100, 102, 103, 104, 105, 106, 107, 108, 109, 110, 111, 112, 113, 115, 117, 118, 119, 120, 121, 122, 124, 127, 128, 129, 130, 136, 137, 138, 139, 140, 141, 143, 144, 145, 146, 150, 151, 152, 154, 155, 156, 158, 162, 163, 166, 167, 169, 170, 173, and/or 174. An exemplary fatty acid derivative that is produced accordingly is a free fatty acid. The increased and/or improved production of a fatty acid derivative can be measured in vitro and/or in vivo. Preferably, the increased and/or improved production of a fatty acid derivative is measured in vivo.

In one embodiment of the invention, a mutant thioesterase (or a naturally-occurring equivalent thereof) is provided, which is capable of increased and/or improved production of one or more fatty acid derivatives, and which is a variant of a precursor thioesterase that comprises an analogous sequence to SEQ ID NO:31 in FIG. 58, wherein the precursor thioesterase is mutated with one or more substitutions selected from: D2L, D2P, D2R, L5G, L11I, S12N, S12T, A13N, G14C, G14P, G14S, G14T, G14V, Y15C, Y15I, Y15V, R16T, M17D, M17E, M17N, M17R, M17S, M17V, A19C, A21G, A22L, A22R, A22T, A25P, L26D, L26G, L26W, L27C, L27F, L27W, L27Y, N28I, N28P, D29P, K30P, W31D, W31G, W31N, W31P, W31R, W31S, W31T, V37Y, N39P, S41C, I42D, I42G, S43E, G44K, G44R, G44W, D45G, Q49E, G50A, G50K, G50M, G50Q, L51D, L51T, R53A, R53G, R53L, R53N, R53S, R53V, L54E, L54F, L54G, L54N, L54S, L54W, L58R, P63G, P63M, P63N, P63T, P63W, W65E, W65G, V66G, V66S, L67T, V68S, E69F, E69V, L70C, L70F, L70Q, L70S, L70T, L70V, G71A, N73G, N73L, D74A, D74C, G75A, G75C, G75F, G75R, G75W, L76I, R77A, R77C, R77D, R77F, R77G, R77H, R77K, R77L, R77N, R77Q, R77S, R77W, G78D, G78E, F79K, Q80G, T84H, T84N, T84Q, T87A, T87F, T87H, T87W, L88A, L88C, L88H, Q90N, Q90W, I91G, I91L, I91M, I91S, L92G, L92N, L92Q, L92S, L92T, L92Y, Q93P, D94P, V95F, V95N, V95Q, K96P, A97C, A97P, A98P, A98V, A100D, A100E, A100Q, A100Y, P102L, P102Q, P102R, L103E, L103K, L104A, L104Q, L104W, L104Y, M105C, M105E, M105F, M105L, Q106D, Q106G, Q106L, Q106V, Q106W, Q106Y, I107A, I107C, I107E, I107G, I107K, I107L, I107Q, 1107S, 11071, R108G, L109F, L109V, L109Y, P110A, P110E, P110F, P110G, P110H, P110N, P110S, P110V, A111Y, N112F, N112P, Y113D, Y113E, Y113P, R115W, Y117A, Y117D, Y117E, Y117G, Y117P, Y117Q, N118F, E119P, A120P, F121C, F121L, F121M, F121N, F121Q, F121R, F121V, F121W, F121Y, S122D, S122F, S122L, S122P, S122W, S122Y, I124A, I124G, I124H, I124K, I124R, K127P, L128S, A129I, A129W, A129Y, K130P, L136A, L136D, L136E, L136G, L136K, L136N, L136P, L136Q, L136S, L136T, L137A, L137C, L137H, L137K, L137Q, L137S, L137Y, P138F, F139L, F139M, F140C, F1401, F140L, F140M, F140V, M141T, E143P, V144H, Y145I, L146G, L146P, W150G, W150I, W150V, M151F, M151L, M151N, M151S, M151T, M151W, Q152N, Q152V, Q152Y, D154C, D154E, G155I, I156C, I156K, 1156I, I156V, P158G, P158T, A162T, Q163A, Q163C, Q163E, Q163I, Q163S, Q163T, Q163V, I166C, A167E, A167F, A167L, A167N, A167R, A167V, A167Y, W169K, M170N, M170S, Q173D, L174A, L174T, and/or L174W, wherein the numbers in the substitution mutation designations refer to amino acid positions of SEQ ID NO:31. An exemplary fatty acid derivative produced accordingly is a free fatty acid. The increased and/or improved production of a fatty acid derivative can be measured in vitro and/or in vivo. Preferably, the increased and/or improved production of a fatty acid derivative is measured in vivo.

In one embodiment, a mutant thioesterase (or a naturally-occurring equivalent thereof) is provided, which is capable of producing an increased proportional or percentage yield of short-chain (e.g., $C_8$, $C_9$, $C_{10}$, $C_{11}$, $C_{12}$, $C_{13}$, $C_{14}$) fatty acid derivatives (e.g., short-chain fatty acids, short-chain fatty esters, short-chain fatty alcohols, etc.) vs. other products (e.g., non-short-chain fatty acid derivatives, including, for example, long-chain (e.g., $C_{15}$, $C_{16}$, $C_{17}$, $C_{18}$, $C_{19}$, $C_{20}$) fatty acids, long-chain fatty esters, long-chain fatty alcohols, etc.), and which is a variant of a precursor thioesterase that comprises an analogous sequence to SEQ ID NO:31 in FIG. 58, wherein the precursor thioesterase is mutated at one or more amino acid positions corresponding to one or more residues of SEQ ID NO:31 selected from 13, 16-17, 25-38, 55-67, 78-98, 105-119, 122, 126, 132-145, 153, and/or 161-182. An exemplary short-chain fatty acid derivative is a $C_{12}$ fatty acid derivative. An alternative short-chain fatty acid derivative is a $C_{14}$ fatty acid derivative. In certain circumstances, the increased proportional or percentage yield of short-chain fatty acid derivative can be correlated to a decreased proportional yield of long-chain fatty acid derivatives. The increased proportional or percentage yield of short-chain fatty acid derivatives and/or the corresponding decreased proportional or percentage yield of long-chain fatty acid derivatives can be measured in vitro or in vivo. Preferably, the increased proportional yield of short-chain fatty acid derivatives or the corresponding decreased proportional or percentage yield of long-chain fatty acid derivatives is measured in vivo.

In one embodiment, a mutant thioesterase (or a naturally-occurring equivalent thereof) is provided, which is capable of producing an increased proportional or percentage yield of short-chain (e.g., $C_8$, $C_9$, $C_{10}$, $C_{11}$, $C_{12}$, $C_{13}$, $C_{14}$) fatty acid derivatives (e.g., short-chain fatty acids, short-chain fatty esters, short-chain fatty alcohols, etc.) vs. other products (e.g., non-short-chain fatty acid derivatives, including, for example, long-chain fatty acids, long-chain fatty esters, long-chain fatty alcohols, etc.), and which is a variant of a precursor thioesterase that comprises an analogous sequence to SEQ ID NO:31 in FIG. 58, wherein the precursor thioesterase is mutated at one or more amino acid positions corresponding to one or more residues of SEQ ID NO:31 selected from 13, 16, 17, 25, 29, 31, 35, 36, 38, 55, 57, 58, 59, 61, 62, 63, 64, 65, 66, 67, 78, 79, 82, 83, 84, 85, 86, 87, 89, 90, 93, 94, 95, 96, 97, 98, 105, 106, 108, 111, 113, 114, 117, 119, 122, 126, 132, 135, 136, 139, 142, 144, 145, 153, 161, 162, 165, 168, 173, 175, 176, 178, 179, 180, 181, and/or 182. An exemplary short-chain fatty acid derivative is a $C_{12}$ fatty acid derivative. An alternative short-chain fatty acid derivative is a $C_{14}$ fatty acid derivative. In certain circumstances, the increased proportional or percentage yield of short-chain fatty acid derivatives can be correlated to a decreased proportional yield of long-chain fatty acid derivatives. The increased proportional or percentage yield of short-chain fatty acid derivatives and/or the corresponding decreased proportional or percentage yield of long-chain fatty acid derivatives can be measured in vitro or in vivo. Preferably, the increased proportional yield of short-chain fatty acid derivatives or the corresponding decreased proportional yield of long-chain fatty acid derivatives is measured in vivo.

In one embodiment, a mutant thioesterase (or a naturally-occurring equivalent thereof) is provided, which is capable of producing an increased proportional or percentage yield of short-chain (e.g., $C_8$, $C_9$, $C_{10}$, $C_{11}$, $C_{12}$, $C_{13}$, $C_{14}$) fatty acid derivatives (e.g., short-chain fatty acids, short-chain fatty esters, short-chain fatty alcohols, etc.) vs. other products (e.g., non-short-chain fatty acid derivatives including, for example, long-chain fatty acids, long-chain fatty esters, long-chain fatty alcohols, etc.), and which is a variant of a precursor thioesterase that comprises an analogous sequence to SEQ ID NO:31 in FIG. 58, wherein the precursor thioesterase is mutated with one or more substitution selected from: A13V, R16A, M17T, A25S, D29M, W31L, T35Y, S36W, V38S, P55A, P55G, L57I, L58M, L58V, K59E, H61W, Q62M, P63V, R64M, W65L, V66C, L67C, L67M, G78F, G78M, G78R, G78T, G78V, F79K, F79Y, Q82A, Q82M, Q82R, Q83G, Q83K, T84M, T84V, E85A, E85C, E85G, E85Q, E85S, E85T, E85V, E85W, E85Y, Q86H, Q86Y, T87R, R89V, Q90L, Q93M, Q93N, Q93V, D94C, D94L, V95G, K96C, A97N, A97V, A98G, A98Y, M105I, Q106K, Q106R, R108W, A111E, A111N, A111S, A111W, A111Y, Y113A, Y113S, Y113V, G114K, G114Y, Y117R, E119M, E119Q, E119R, S122F, 5122I, S122M, S122R, P126K, F132C, F132D, F132K, F132L, F132N, F132V, P135A, P135E, P135K, P135Q, L136H, F139L, E142W, V144Y, Y145A, Y145C, Y145D, Y145E, Y145G, Y145I, Y145L, Y145M, Y145N, Y145R, Y145S, Y145T, D153K, D153Q, D161K, A162I, F165K, D168W, Q173I, Q175M, P176Q, P176R, P176V, V178F, V178G, V178L, V178R, V178S, V178T, N179H, H180E, H180P, H180R, H180S, H180V, H180W, D181R, D181T, S182C, S182D, S182G, and/or S182R, wherein the numbers in the substitution mutation designations refer to amino acid positions of SEQ ID NO:31. An exemplary short-chain fatty acid derivative is a $C_{12}$ fatty acid derivative. An alternative short-chain fatty acid derivative is a $C_{14}$ fatty acid derivative. In certain circumstances, the increased proportional or percentage yield of short-chain fatty acid derivatives can be correlated to a decreased proportional yield of long-chain fatty acid derivatives. The increased proportional or percentage yield of short-chain fatty acid derivatives and/or the corresponding decreased proportional yield of long-chain fatty acid derivatives can be measured in vitro or in vivo. Preferably, the increased proportional yield of short-chain fatty acid derivatives or the corresponding decreased proportional yield of long-chain fatty acid derivatives is measured in vivo.

In one embodiment, a mutant thioesterase (or a naturally-occurring equivalent thereof) is provided, which is capable of producing a decreased proportional or percentage yield of short-chain (e.g., $C_8$, $C_9$, $C_{10}$, $C_{11}$, $C_{12}$, $C_{13}$, $C_{14}$) fatty acid derivatives (e.g., short-chain fatty acids, short-chain fatty esters, short-chain fatty alcohols, etc.) vs. other products (e.g., non-short-chain fatty acid derivatives including, for example, long-chain (e.g., $C_{15}$, $C_{16}$, $C_{17}$, $C_{18}$, $C_{19}$, $C_{20}$) fatty acids, long-chain fatty esters, long-chain fatty alcohols, etc.), and which is a variant of a precursor thioesterase that comprises an analogous sequence to SEQ ID NO:31 in FIG. 58, wherein the precursor thioesterase is mutated at one or more amino acid positions corresponding to one or more residues of SEQ ID NO:31 selected from 1-31, 36-81, 84-159, 162-177, and/or 181. An exemplary short-chain fatty acid derivative is a $C_{12}$ fatty acid derivative. An alternative short-chain fatty acid derivative is a $C_{14}$ fatty acid derivative. In certain circumstances, the decreased proportional or percentage yield of short-chain fatty acid derivatives can be correlated to an increased proportional yield of long-chain fatty acid derivatives. The decreased proportional or percentage yield of short-chain fatty acid derivatives and/or the corresponding increased proportional yield of long-chain fatty acid derivatives can be measured in vitro or in vivo. Preferably, the decreased proportional yield of short-chain fatty acid derivatives or the corresponding increased proportional yield of long-chain fatty acid derivatives is measured in vivo.

In one embodiment, a mutant thioesterase (or a naturally-occurring equivalent thereof) is provided, which is capable of producing a decreased proportional or percentage yield of short-chain (e.g., $C_8$, $C_9$, $C_{10}$, $C_{11}$, $C_{12}$, $C_{13}$, $C_{14}$) fatty acid derivatives (e.g., short-chain fatty acids, short-chain fatty esters, short-chain fatty alcohols, etc.) vs. other products (e.g., non-short-chain fatty acid derivatives including, for example, long-chain fatty acids, long-chain fatty esters, long-chain fatty alcohols, etc.), and which is a variant of a precursor thioesterase that comprises an analogous sequence to SEQ ID NO:31 in FIG. 58, wherein the precursor thioesterase is mutated at one or more amino acid positions corresponding to one or more residues of SEQ ID NO:31 selected from 1, 2, 3, 4, 5, 6, 7, 8, 9, 11, 12, 13, 14, 15, 16, 17, 18, 19, 21, 22, 23, 24, 26, 27, 30, 31, 36, 37, 38, 42, 44, 45, 46, 47, 48, 50, 51, 52, 53, 54, 55, 57, 61, 63, 64, 65, 66, 67, 68, 69, 70, 71, 72, 73, 74, 75, 76, 77, 78, 79, 81, 84, 85, 86, 87, 88, 89, 90, 91, 92, 93, 94, 95, 96, 97, 99, 100, 102, 103, 104, 105, 106, 107, 108, 109, 110, 111, 112, 113, 114, 115, 117, 118, 119, 120, 121, 122, 124, 125, 127, 128, 129, 130, 131, 132, 133, 134, 136, 137, 138, 139, 140, 141, 142, 143, 144, 145, 146, 150, 151, 152, 153, 154, 155, 156, 157, 158, 159, 162, 163, 165, 166, 167, 168, 170, 171, 173, 174, 175, 176, 177, and/or 181. An exemplary short-chain fatty acid derivative is a $C_{12}$ fatty acid derivative. An alternative short-chain fatty acid derivative is a $C_{14}$ fatty acid derivative. In certain circumstances, the decreased proportional or percentage yield of short-chain fatty acid derivatives can be correlated to an increased proportional yield of long-chain fatty acid derivatives. The decreased proportional or percentage yield of short-chain fatty acid derivatives and/or the corresponding increased proportional yield of long-chain fatty acid derivatives can be measured in vitro or in vivo. Preferably, the decreased proportional yield of short-chain fatty acid derivatives or the corresponding increased proportional yield of long-chain fatty acid derivatives is measured in vivo.

In one embodiment, a mutant thioesterase (or a naturally-occurring equivalent thereof) is provided, which is capable of producing a decreased proportional or percentage yield of short-chain (e.g., $C_8$, $C_9$, $C_{10}$, $C_{11}$, $C_{12}$, $C_{13}$, $C_{14}$) fatty acid derivatives (e.g., short-chain fatty acids, short-chain fatty esters, short-chain fatty alcohols, etc.) vs. other products (e.g., non-short-chain fatty acid derivatives including, for example, long-chain fatty acids, long-chain fatty esters, long-chain fatty alcohols, etc.), and which is a variant of a precursor thioesterase that comprises an analogous sequence to SEQ ID NO:31 in FIG. 58, wherein the precursor thioesterase is mutated with one or more substitution selected from: A1C, A1F, A1L, A1Y, D2L, D2M, D2P, D2W, T3R, L4A, L4M, L4N, L4S, L4V, L4Y, L5E, L5F, L5G, L5K, L5N, L5S, L5W, I6T, L7A, L7E, L7K, L7M, L7W, G8K, D9N, D9T, L11A, L11C, L11I, L11M, L11Q, L11V, 5121, S12L, S12M, 512N, 512T, 512V, 512Y, A13C, G14C, G14E, G14I, G14M, G14N, G14P, G14S, G14T, G14V, Y15C, Y15E, Y15G, Y15I, Y15N, Y15V, R16T, M17D, M17E, M17G, M17L, M17N, M17P, M17R, M175, M17V, S18M, S18N, S18T, A19E, A19L, A19V, A21P, A22D, A22E, A22F, A22H, A22I, A22K, A22L, A22P, A22R, A22S, A22T, A22Y, W23A, W23H, W23N, W23P, P24A, P24C, P24D, P24E, P24F, P24G, P24I, P24M, P24N, P24S, P24T, P24V, P24W, L26P, L27A, L27C, L27F, L27H, L27R, L27S, L27T, L27W, L27Y, K30P, W31D, W31P, W31R, S36F, S36L, V37G, V37H, V37N, V37Q, V37W, V37Y, V38P, N39E, N39G, N39K, N39M, N39P, N39Q, N39Y, I42D, I42G, I42P, G44A, G44E, G44K, G44M, G44N, G44R, G44S, G44W, G44Y, D45G, D45M, T46D, S47E, S47P, S47Q, S47R, S47Y, Q48Y, G50C, G50E, G50F, G50I, G50K, G50L, G50M, G50N, G50P, G50Q, G50R, G50S, G50T, G50W, G50Y, L51D, L51P, L51T, A52P, R53A, R53C, R53D, R53E, R53F, R53G, R53I, R53K, R53L, R53N, R535, R53T, R53V, R53W, R53Y, L54C, L54E, L54G, L54N, L54Y, P55Y, L57P, H61A, H61D, H61E, P63D, P63E, P63G, P63K, P63M, P63N, P63Q, P63R, R64L, W65G, W65P, W65R, V66N, V66Q, V66S, V66W, V66Y, L67E, L67G, L67Q, L67R, L67S, L67W, V68E, V68G, V68N, V68P, V68Q, E69A, E69C, E69D, E69F, E69G, E69H, E69K, E69L, E69M, E69N, E69P, E69Q, E69S, E69V, E69W, E69Y, L70A, L70C, L70E, L70F, L70G, L70H, L70K, L70Q, L70S, L70T, L70W, G71C, G71S, G72A, G72M, G72P, N73A, N73G, N73H, N73I, N73L, N73P, N73R, N73S, N73T, N73W, D74A, D74C, D74F, D74G, D74Q, D74S, D74W, D74Y, G75A, G75C, G75D, G75E, G75F, G75I, G75K, G75L, G75M, G75N, G75P, G75R, G75T, G75V, G75W, G75Y, L76A, L76C, L76D, L76E, L76F, L76G, L76I, L76K, L76M, L76N, L76P, L76Q, L76R, L76T, L76V, L76W, R77A, R77C, R77D, R77E, R77F, R77G, R77H, R77N, R77S, R77V, R77W, G78A, G78C, G78D, G78E, G78N, G78P, G78Q, G78Y, F79P, F79Q, F79S, F79V, P81E, P81W, T84D, T84E, T84G, T84H, T84K, T84L, T84N, T84Q, T84R, T84W, T84Y, E85F, E85P, Q86A, T87F, L88A, L88E, L88G, L88H, L88Q, L88S, L88W, L88Y, R89P, Q90P, Q90W, I91E, I91L, I91M, I91N, I91Q, I91S, I91Y, L92C, L92E, L92G, L92H, L92N, L92Q, L92R, L92S, L92Y, Q93P, D94P, D94V, V95A, V95C, V95D, V95E, V95F, V95I, V95P, V95Q, V95W, V95Y, K96P, A97C, A97P, N99D, A100Q, A100Y, P102E, P102G, P102H, P102L, P102R, P102V, P102W, L103C, L103E, L103I, L103K, L103N, L103R, L103S, L103T, L103V, L104A, L104C, L104E, L104G, L104I, L104N, L104P, L104Q, L104S, L104W, L104Y, M105A, M105C, M105E, M105F, M105G, M105K, M105L, M105P, M105T, M105W, Q106D, Q106G, Q106H, Q106L, Q106W, I107A, I107E, I107F, I107G, I107K, I107L, I107Q, I107S, I107T, I107Y, R108A, R108C, R108D, R108E, R108F, R108G, R108H, R108I, R108L, R108M, R108S, R108V, R108Y, L109C, L109F, L109G, L109K, L109Q, L109R, L109T, L109V, L109Y, P110A, P110C, P110D, P110E, P110F, P110G, P110H, P110K, P110L, P110M, P110N, P110R, P110S, P110V, P110W, A111C, A111L, A111P, A111Q, A111R, A111V, N112I, N112L, N112P, N112Y, Y113D, Y113E, Y113Q, G114A, R115W, Y117D, Y117G, Y117P, N118F, E119C, E119L, A120P, F121A, F121C, F121D, F121E, F121G, F121K, F121L, F121N, F121P, F121Q, F121R, F121S, F121V, F121W, F121Y, S122D, S122E, S122L, S122P, I124D, I124E, I124G, I124H, I124K, I124R, I124W, I124Y, Y125C, Y125G, Y125H, Y125I, Y125L, Y125P, Y125Q, Y125R, Y125S, Y125T, Y125V, K127A, L128E, L128F, L128G, L128K, L128Q, L128R, L128S, L128W, A129D, A129F, A129L, A129W, A129Y, K130P, K130V, E131A, E131C, E131D, E131P, E131V, F132P, D133C, V134C, V134D, V134N, V134P, V134W, L136A, L136D, L136E, L136G, L136N, L136P, L136T, L137D, L137E, L137G, L137H, L137K, L137P, L137Q, L137R, L137S, P138G, P138N, P138V, F139A, F139C, F139D, F139E, F139G, F139H, F139M, F139N, F139S, F139T, F139V, F139W, F140A, F140C, F140G, F140I, F140L, F140M, F140N, F140P, F140S, F140T, F140V, F140W, M141C, M141D, M141E, M141F, M141G, M141K, M141L, M141P, M141Q, M141R, M141T, M141W, M141Y, E142A, E142C, E142G, E142I, E142L, E142M, E142P, E142Q, E142R, E142T, E142V, E143A, E143D, E143F, E143G, E143I, E143M, E143P, E143W, V144A, V144D, V144E, V144G, V144H, V144N, V144P, V144Q, V144R, V144S, Y145Q, Y145W, L146C, L146P, W150P, W150R, M151A, M151C, M151D, M151E, M151F, M151G, M151I, M151L, M151Q, M151R, M151S, M151T, M151V, M151W, Q152P, D153A, D153E, D153F, D154A, D154C, D154E, D154F, D154G, D154H, D154I, D154K, D154L, D154N, D154P, D154R, D154S, D154T, D154V, D154W, G155A, G155P, G155V, I156A, I156C, I156E, I156F, I156G, I156K, I156M, I156Q, I156R, I156S, I156T, I156Y, H157C, H157E, P158F, P158H, P158I, P158L, P158Q, P158V, P158W, N159P, N159W, A162K, A162L, A162N, A162R, A162Y, Q163A, Q163D, Q163E, Q163F, Q163I, Q163V, Q163W, Q163Y, F165L, I166A, I166F, I166M, I166S, I166Y, A167C, A167D, A167E, A167F, A167L, A167N, A167R, A167V, A167W, A167Y, D168M, D168R, M170E, M170F, M170G, M170N, M170S, M170T, A171S, Q173D, Q173P, L174A, L174G, L174S, L174T, L174W, L174Y, Q175F, P176L, P176Y, L177F, L177M, L177S, D181C, D181E, and/or D181G, wherein the numbers in the substitution mutation designations refer to amino acid positions of SEQ ID NO:31. An exemplary short-chain fatty acid derivative is a $C_{12}$ fatty acid derivative. An alternative short-chain fatty acid derivative is a $C_{14}$ fatty acid derivative. In certain circumstances, the decreased proportional or percentage yield of short-chain fatty acid derivatives can be correlated to an increased proportional yield of long-chain fatty acid derivatives. The decreased proportional or percentage yield of short-chain fatty acid derivatives and/or the corresponding increased proportional yield of long-chain fatty acid derivatives can be measured in vitro or in vivo. Preferably, the decreased proportional yield of short-chain fatty acid derivatives or the corresponding increased proportional yield of short-chain fatty acid derivatives is measured in vivo.

In one embodiment of the invention, a polynucleotide (or a gene) encoding a mutant thioesterase (or a naturally-occurring equivalent thereof) of the invention is provided. In another embodiment of the invention, a vector is provided comprising the polynucleotide (or the gene) according to the invention.

In one embodiment of the invention, the precursor thioesterase is encoded by a gene that is selectively hybridizable to the polynucleotide sequence of 'tesA, or an ortholog, paralog or homolog thereof. FIG. 56 lists GenBank Accession Numbers of protein homologs of 'TesA having at least 40% amino acid sequence identity to 'TesA. The precursor thioesterase can be encoded by a polynucleotide that is selectively hybridizable under conditions of intermediate stringency, under high stringency, or under maximum stringency.

In one embodiment of the invention, a polynucleotide encoding a precursor thioesterase is provided wherein the precursor thioesterase comprises the amino acid sequence of 'TesA, an ortholog thereof, a paralog thereof, or a homolog thereof. For example, the precursor thioesterase comprises the amino acid sequence of a 'TesA obtained from an *E. coli*, such as an *E. coli* K12. In a particular embodiment, a polynucleotide encoding the precursor thioesterase is provided wherein the precursor thioesterase comprises the amino acid sequence, a variant, or a fragment of SEQ ID NO:31 of FIG. 58. In a particular embodiment, the gene encoding the precursor thioesterase comprises the polynucleotide sequence of SEQ ID NO:32 in FIG. 59, or a fragment thereof.

In one embodiment of the invention, a polynucleotide encoding a precursor thioesterase is provided wherein the precursor thioesterase comprises a protein having at least about 20%, for example, at least about 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% identity to the sequence SEQ ID NO:31 of FIG. 58. In one embodiment, a polynucleotide encoding a precursor thioesterase is provided wherein the precursor thioesterase comprises a protein having at least about 20%, for example, at least about 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% identity to the sequence of an *E. coli* K12 'TesA. In one embodiment of the invention, a polynucleotide is provided, which comprises a sequence having at least about 20%, for example, at least about 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% identity to SEQ ID NO:32 in FIG. 59.

In one embodiment of the invention, a vector is provided that comprises a gene (or a polynucleotide) encoding a mutant thioesterase or a naturally-occurring equivalent thereof. Vectors according to the invention can be transformed into suitable host cells to produce recombinant host cells.

In one embodiment of the invention, a probe is provided that comprises a polynucleotide of about 4 to about 150 nucleotides long, which is substantially identical to a corresponding fragment of SEQ ID NO:32 in FIG. 59, wherein the probe is useful for detecting and/or identifying polynucleotide sequences encoding enzymes that have thioesterase activity. A probe according to the invention can be used to detect and isolate potential precursor thioesterases from sources not known to produce such precursor thioesterases or for which the amino acid or nucleic sequence is unknown.

In certain embodiments of the invention, a recombinant host cell is provided comprising a polynucleotide encoding a mutant thioesterase or a naturally-occurring equivalent thereof. In one embodiment, known genomic alteration or modification techniques can be employed to alter or modify the endogenous thioesterases of the host cell, effectuating one or more of the aforementioned mutations, such that at least one of the mutant endogenous thioesterases has at least one altered property. In another embodiment, the recombinant host cell is engineered to include a plasmid comprising a polynucleotide encoding a mutant thioesterase or a naturally-occurring equivalent thereof. In yet another embodiment, the recombinant host cell expresses the thioesterase after the polynucleotide encoding the thioesterase is integrated into the chromosome of the host cell.

In one embodiment of the invention, the recombinant host cell of the invention can be selected from any cell capable of expressing a recombinant gene construct, and can be selected from a microbial, plant or animal cell. In a particular embodiment, the host cell is bacterial, cyanobacterial, fungal, yeast, algal, human or mammalian in origin. In a particular embodiment, the host cell is selected from any of Gram positive bacterial species such as Actinomycetes; Bacillaceae, including *Bacillus alkalophilus, Bacillus subtilis, Bacillus licheniformis, Bacillus lentos, Bacillus brevis, Bacillus stearothennophilus, Bacillus alkalophilus, Bacillus amyloliquefaciens, Bacillus coagulans, Bacillus circulans, Bacillus lautus, Bacillus megaterium, B. thuringiensis;* Brevibacteria sp., including *Brevibacterium flavum, Brevibacterium lactofennentum, Brevibacterium ammoniagenes, Brevibacterium butanicum, Brevibacterium divaricatum, Brevibacterium healii, Brevibacterium ketoglutamicum, Brevibacterium ketosoreductum, Brevibacterium lactofennentum, Brevibacterium linens, Brevibacterium paraffinolyticum; Corynebacterium* spp. such as *C. glutamicum* and *C. melassecola, Corynebacterium herculis, Corynebacterium lilium, Corynebactertium acetoacidophilum, Corynebacterium acetoglutamicum, Corynebacterium acetophilum, Corynebacterium ammoniagenes, Corynebacterium fujiokense, Corynebacterium nitrilophilus*; or lactic acid bacterial species including *Lactococcus* spp. such as *Lactococcus lactis; Lactobacillus* spp. including *Lactobacillus reuteri; Leuconostoc* spp.; *Pediococcus* spp.; *Serratia* spp. such as *Serratia marcescens; Streptomyces* species, such as *Streptomyces lividans, Streptomyces murinus, S. coelicolor* and *Streptococcus* spp. Alternatively, strains of a Gram negative bacterial species belonging to Enterobacteriaceae including *E. coli, Cellulomonas* spp.; or to Pseudomonadaceae including *Pseudomonas aeruginosa, Pseudomonas alcaligenes, Pseudomonas fluorescens, Pseudomonas putida, Pseudomonas syringae* and *Burkholderia cepacia, Salmonella* sp., *Stenotrophomonas* spp., and *Stenotrophomonas maltophilia*. Oleaginous microorganisms such as *Rhodococcus* spp, *Rhodococcus opacus, Ralstonia* spp., and *Acetinobacter* spp. are useful as well. Furthermore, yeasts and filamentous fungal strains can be useful host cells, including *Absidia* spp.; *Acremonium* spp.; *Agaricus* spp.; *Anaeromyces* spp.; *Aspergillus* spp., including *A. aculeates, A. awamori, A. flavus, A. foetidus, A. fumaricus, A. fumigatus, A. nidulans, A. niger, A. oryzae, A. terreus; A. tubingensis* and *A. versicolor; Aeurobasidium* spp.; *Cephalosporum* spp.; *Chaetomium* spp.; *Coprinus* spp.; *Dactyllum* spp.; *Fusarium* spp., including *F. conglomerans, F. decemcellulare, F. javanicum, F. lini, F. oxysporum* and *F. solani; Gliocladium* spp.; *Kluyveromyces* sp.; *Hansenula* sp.; *Humicola* spp., including *H. insolens* and *H. lanuginosa; Hypocrea* spp.; *Mucor* spp.; *Neurospora* spp., including *N. crassa* and *N. sitophila; Neocallimastix* spp.; *Orpinomyces* spp.; *Penicillium* spp.; *Phanerochaete* spp.; *Phlebia* spp.; *Pichia* sp.; *Piromyces* spp.; *Rhizopus* spp.; *Rhizomucor* species such as *Rhizomucor miehei; Schizophyllum* spp.; *Schizosaccharomyces* such as, for example, *S. pombe* species; *chytalidium* sp., *Sulpholobus* sp., *Thermoplasma* sp., *Thermomyces* sp.; *Trametes* spp.; *Trichoderma* spp., including *T. reesei, T. reesei (longibrachiatum)* and *T. viride; Yarrowinia* sp.; and *Zygorhynchus* spp and in particular include oleaginous yeast just *Phafia* spp., *Rhorosporidium toruloides* Y4, *Rhodotorula Glutinis* and *Candida* 107.

In one embodiment of the invention, a recombinant host cell is provided, which expresses or overexpresses a gene encoding the mutant thioesterase (or a naturally-occurring equivalent thereof), and which also expresses (or overexpresses) one or more genes encoding one or more enzymes that utilize, as a substrates, reaction products of the mutant thioesterase (e.g., fatty acids, fatty acyl-CoAs, fatty acyl-phosphate esters, fatty aldehydes, fatty esters, or fatty alcohols) or reaction products of one or more other enzymes that are parts of a metabolic pathway, including reaction products of the mutant thioesterase (e.g., fatty acids) as precursors and/or substrates.

In one embodiment of the invention, a recombinant host cell is provided, which expresses or overexpresses a gene encoding a mutant thioesterase (or a naturally-occurring equivalent thereof) and which also expresses (or overexpresses) one or more genes encoding one or more enzymes that react with a substrate that is necessary as a precursor to a reaction in a fatty acid biosynthetic pathway. In a particular embodiment, the recombinant host cell includes a gene that encodes thioesterase and a gene that encodes an enzyme that reacts with a substrate that is necessary as a precursor to a reaction in a fatty acid synthetic pathway, which comprises the overexpression or modification of a gene selected from pdh, panK, aceEF, fabH, fabD, fabG, acpP, and/or fabF.

In one embodiment of the invention, the recombinant host cell comprises a gene (or a polynucleotide) that encodes a mutant thioesterase (or a naturally-occurring equivalent thereof) and also comprises the attenuation or deletion of a gene that reduces carbon flowthrough, or a gene that competes for substrates, cofactors, or energy requirements within a fatty acid biosynthetic pathway. In a particular embodiment, the attenuated gene comprises at least one of fadE, gpsA, ldhA, pflB, adhE, pta, poxB, ackA, ackB, plsB, and/or sfa.

In one embodiment of the invention, a recombinant host cell comprises a gene (or a polynucleotide) encoding a mutant thioesterase (or a naturally-occurring equivalent thereof) and a heterologously-introduced exogenous gene encoding at least one fatty acid derivative enzyme. In certain embodiments, the exogenous gene or polynucleotide encodes, for example, an acyl-CoA synthase, an ester synthase, an alcohol acyltransferase, an alcohol dehydrogenase, an acyl-CoA reductase, a fatty-alcohol-forming acyl-CoA reductase, a carboxylic acid reductase, a decarboxylase, an aldehyde reductase, a fatty alcohol acetyl transferase, an acyl condensing enzyme, an aminotransferase, or a decarbonylase.

In one embodiment of the invention, the recombinant host cell comprises a gene encoding a mutant thioesterase (or a naturally-occurring equivalent thereof) and at least two heterologously-introduced exogenous genes encoding fatty acid derivative enzymes. In certain embodiments, the exogenous genes or polynucleotides encode, for example, an acyl-CoA synthase, an ester synthase, an alcohol acyltransferase, an alcohol dehydrogenase, an acyl-CoA reductase, a fatty-alcohol-forming acyl-CoA reductase, a carboxylic acid reductase, a decarboxylase, an aldehyde reductase, a fatty alcohol acetyl transferase, an acyl condensing enzyme, an aminotransferase, or a decarbonylase.

In a preferred embodiment of the invention, a gene encoding the mutant thioesterase (or a naturally-occurring equivalent thereof) and/or a fatty acid derivative enzyme, for example, an acyl-CoA synthase, an ester synthase, an alcohol acyltransferase, an alcohol dehydrogenase, an acyl-CoA reductase, a fatty-alcohol forming acyl-CoA reductase, a carboxylic acid reductase, a decarboxylase, an aldehyde reductase, a fatty alcohol acetyl transferase, an acyl condensing enzyme, an alcohol acetyltransferase, an aminotransferase, an additional thioesterase or a decarbonylase that is overexpressed.

In one embodiment of the invention, genes encoding mutant thioesterases (or naturally-occurring equivalents thereof), fatty acid derivative enzymes and/or other recombinantly expressed genes in a recombinant host cell are modified to optimize at least one codon for expression in the recombinant host cell.

In one embodiment of the invention, the recombinant host cell comprises at least one gene encoding a mutant thioesterase (or a naturally-occurring equivalent thereof) and a gene encoding an acyl-CoA synthase. The acyl-CoA synthase can be any of fadD, fadK, BH3103, yhfL, Pfl-4354, EAV15023, fadD1, fadD2, RPC_4074, fadDD35, fadDD22, faa3p, or the gene encoding the protein ZP_01644857. Other examples of acyl-CoA synthase genes include fadDD35 from *M. tuberculosis* HR7Rv [NP_217021], yhfL from *B. subtilis* [NP_388908], fadD1 from *P. aeruginosa* PAO1 [NP_251989], the gene encoding the protein ZP_01644857 from *Stenotrophomonas maltophilia* R551-3, or faa3p from *Saccharomyces cerevisiae* [NP_012257].

In one embodiment of the invention, a recombinant host cell is provided comprising at least one gene or polynucleotide encoding a mutant thioesterase (or a naturally-occurring equivalent thereof) and a gene or polynucleotide encoding an ester synthase, such as an ester synthase gene obtained from *Acinetobacter* spp., *Alcanivorax borkumensis*, *Arabidopsis thaliana*, *Saccharomyces cerevisiae*, *Homo sapiens*, *Simmondsia chinensis*, *Mortierella alpina*, *Cryptococcus curvatus*, *Alcanivorax jadensis*, *Alcanivorax borkumensis*, *Acinetobacter* sp. HO1-N, or *Rhodococcus opacus*. Examples of ester synthase genes include wax/dgat, encoding a bifunctional ester synthase/acyl-CoA: diacylglycerol acyltransferase from *Simmondsia chinensis*, *Acinetobacter* sp. strain ADP1, *Alcanivorax borkumensis*, *Pseudomonas aeruginosa*, *Fundibacter jadensis*, *Arabidopsis thaliana*, or *Alkaligenes eutrophus*. In a preferred embodiment, the gene encoding the ester synthase is overexpressed.

In one embodiment of the invention, the recombinant host cell comprises at least one gene encoding a fatty aldehyde biosynthetic enzyme. A fatty aldehyde biosynthetic gene can be, for example, a carboxylic acid reductase gene (e.g., a car gene), having a polynucleotide sequence and/or polypeptide motif listed in FIGS. 32 and 33, or a variant thereof. In some instances, the fatty aldehyde biosynthetic gene encodes one or more of the amino acid motifs depicted in FIG. 33.

In one embodiment of the invention, the recombinant host cell comprises at least one fatty alcohol production gene. Fatty alcohol production genes include, for example, acr1. Fatty alcohol production genes are described in, for example, PCT Publication Nos. 2008/119082 and 2007/136762, the disclosures of which are herein incorporated by reference.

In one embodiment of the invention, the recombinant host cell comprises a gene encoding a mutant thioesterase (or a naturally-occurring equivalent thereof) and a gene encoding at least one olefin producing gene. The gene may be a terminal olefin producing gene or an internal olefin producing gene. As examples of terminal olefin producing genes, those described in PCT Publication No. 2009/085278, including orf880, are appropriate. As examples of internal olefin producing genes, those described in PCT Publication No. 2008/147781 A2 are appropriate. The disclosures of PCT Publication Nos. 2009/085278 and 2008/147781 A2 are herein incorporated by reference.

In one embodiment of the invention, a recombinant host cell is provided comprising at least one gene or polynucleotide encoding a mutant thioesterase (or a naturally-occurring equivalent thereof), and at least one of (a) a gene or polynucleotide encoding a fatty acid derivative enzyme and (b) a gene or polynucleotide encoding an acyl-CoA dehydrogenase enzyme that is attenuated. Preferably that gene encoding a fatty acid derivative enzyme that is attenuated or deleted is endogenous to the host cell, encoding, for example, an acyl-CoA synthase, an ester synthase, an alcohol acyltransferase, an alcohol dehydrogenase, an acyl-CoA reductase, a carboxylic acid reductase, a decarbonylase, a fatty alcohol acetyl transferase, a fatty acid decarboxylase, or a fatty-alcohol-forming acyl-CoA reductase. In one embodiment, the attenuated gene encodes an acyl-CoA synthase or an ester synthase.

In one embodiment of the invention, a recombinant host cell is provided that expresses, or preferably overexpresses, a thioesterase enzyme under conditions that result in the direct synthesis of fatty esters from acyl-ACP or acyl-CoA, such as fatty acid methyl esters (FAME) and fatty acid ethyl esters (FAEE), by such thioesterase. In this embodiment, the thioesterase directly converts acyl-ACP or acyl-CoA to fatty ester without necessarily expressing an enzyme that is a fatty acyl CoA synthase or an ester synthase to produce fatty esters. Nonetheless, while expression or overexpression of a fatty acyl-CoA synthase or ester synthase is unnecessary, such enzymes may be desirable to increase product yields. In this embodiment, the thioesterase enzyme can be any of an endogenous thioesterase, a heterologously-expressed thioesterase, a mutant thioesterase, or a naturally-occurring equivalent thereof.

In one embodiment of the invention, the recombinant host cell has an endogenous gene encoding an acyl-CoA dehydrogenase enzyme that is deleted or attenuated.

In one embodiment of the invention, a method is provided wherein the recombinant host cell according to the invention is cultured under conditions that permit expression or overexpression of one or more thioesterase enzymes, which can be selected from endogenous thioesterases, heterologously-expressed thioesterases, mutant thioesterases (or naturally-occurring equivalents thereof), or a combination of these thioesterases. In a particular embodiment, the thioesterase enzyme that is expressed or overexpressed can be recovered, and more preferably substantially purified, after the host cell is harvested and/or lysed.

In one embodiment of the invention, a method is provided wherein the recombinant host cell according to the invention is cultivated under conditions that permit production of fatty acid derivatives. In a preferred embodiment, the fatty acid derivative can be recovered, and more preferably the fatty acid derivative is substantially purified. In a particularly preferred embodiment, the fatty acid derivative composition is substantially purified from other components produced during cultivation by centrifugation.

In one aspect of the invention, a method is provided for producing a fatty acid derivative, comprising cultivating a recombinant host cell of the invention under conditions suitable to ensure expression or overexpression of a mutant thioesterase (or a naturally-occurring equivalent thereof), and recovering the fatty acid derivative that is produced.

In one embodiment, a method is provided for extracellularly producing a fatty acid derivative in vitro, comprising cultivating a recombinant host cell under conditions suitable for expression or overexpression of a thioesterase enzyme (including, for example, an endogenous thioesterase, a heterologously-expressed thioesterase, a mutant thioesterase, or a naturally-occurring equivalent thereof), harvesting the cells, and lysing the cells, such that the thioesterase enzyme that is produced can be recovered and used to produce fatty acid derivatives in vitro. In an exemplary embodiment, the thioesterase enzyme is substantially purified. In another exemplary embodiment, the thioesterase enzyme is not purified from the cell lysate. The purified thioesterase enzyme or the cell lysate comprising such an enzyme can then be subject to suitable thioesterase substrates under conditions that allow the production of fatty acid derivatives extracellularly. Techniques for introducing substrates to enzymes are well known in the art. A non-limiting example is adding the substrate(s) in a solution form to the enzyme solution or the cell lysate, and allowing the mixture to incubate. Another non-limiting example involves incubating the substrate(s) and enzyme solution or cell lysate by either attaching the substrate(s) or the enzyme to a solid medium (e.g., beads, resins, plates, etc.) and pass the enzyme solution/lysate or the substrate(s), respectively through the solid medium in a speed that allows for sufficient contact between the substrate(s) and the enzyme.

In another embodiment of the invention, a method is provided for producing a fatty acid derivative, which comprises cultivating a recombinant host cell under conditions suitable to ensure expression of a thioesterase enzyme (including, for example, an endogenous thioesterase, a heterologously-expressed thioesterase, a mutant thioesterase, or a naturally-occurring equivalent thereof), and recovering the fatty acid derivative that is secreted or released extracellularly. Accordingly, the fatty acid derivative product is recovered from, for example, the supernatant of a fermentation broth wherein the host cell is cultured.

In one embodiment of the invention, a method is provided for obtaining a fatty acid derivative composition extracellularly by cultivating a recombinant host cell that has been transformed with a polynucleotide encoding a thioesterase enzyme (including, for example, an endogenous thioesterase, a heterologous thioesterase, a mutant thioesterase, or a naturally-occurring equivalent thereof), cultivating under conditions that permit production of a fatty acid derivative, a major or minor portion of which is secreted or released extracellularly, and recovering the fatty acid derivative that is produced. In an exemplary embodiment, the fatty acid derivative is produced within the cell, but a portion of it is released by the host cell. Accordingly, the method further comprises harvesting the cells, lysing the cells, and recovering the fatty acid derivative.

In one embodiment of the invention, a method of producing fatty acid derivatives is provided wherein a recombinant host cell that expresses, or preferably overexpresses, a thioesterase enzyme under conditions that result in the synthesis of fatty esters from acyl-ACP or acyl-CoA by such thioesterase is cultured under conditions that permit such direct production of fatty esters.

In one embodiment of the invention, a method of producing fatty acid derivatives is provided comprising: modifying one or more endogenous thioesterases of the host cell using suitable genomic alteration techniques such that the endogenous thioesterases comprise one or more mutations and have one or more altered properties, as compared to the endogenous thioesterase precursors; and cultivating the host cell under conditions suitable for said host cell to express or overexpress such mutant thioesterases; and recovering the fatty acid derivatives. In an exemplary embodiment, the fatty acid derivative that is produced can be secreted or released extracellularly, such that it can be recovered from, for example, the supernatant of the fermentation broth wherein the host cell is cultured.

In one embodiment of the invention, a method of producing fatty acid derivatives is provided comprising: transforming the host cell with a polynucleotide sequence encoding a mutant thioesterase (or a naturally-occurring equivalent thereof), such that the production of fatty acid derivatives in the host cell is altered relative to a cell that has not been transformed with the mutant thioesterase gene (or a naturally-occurring equivalent thereof).

In one embodiment of the invention, a method of producing fatty acid derivatives is provided comprising: providing a polynucleotide sequence comprising a gene encoding a mutant thioesterase (or a naturally-occurring equivalent thereof); transforming a suitable host cell under conditions wherein said polynucleotide sequence is incorporated into said chromosome of said cell and said gene is expressible within said host cell; cultivating the transformed host cell under conditions suitable for said host cell to express said gene and produce a mutant thioesterase protein (or a naturally-occurring equivalent thereof); and recovering the fatty acid derivatives.

In any of the embodiments above, derivatives of a certain carbon chain length can be recovered at a greater proportional yield, in comparison with the production of such fatty acid derivatives of the same carbon chain length in the same host cell in the absence of the mutant thioesterase (or a naturally-occurring equivalent thereof). In a particular embodiment, the fatty acid derivatives that are recovered at an increased or decreased yield comprise a primary chain length of $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$ or $C_{39}$ fatty acyl chain. The fatty acid derivatives that are recovered at an increased or decreased yield in the composition can be selected from all types of fatty acid derivatives, including, for example, hydrocarbons, fatty acids, fatty esters, fatty aldehydes, fatty alcohols terminal olefins, internal olefins, alkanes, diols, fatty amines, dicarboxylic acids, or ketones, or combinations thereof.

Alternatively, in any of the embodiments above, a particular fatty acid derivative can be produced at an increased or decreased proportional or percentage yield relative to the other fatty acid derivatives, when compared to the proportional or percentage yield of that particular fatty acid derivative in the same host cell in the absence of the mutant thioesterase (or a naturally-occurring equivalent thereof). In a particular embodiment, the fatty acid derivative that is produced at an increased proportional or percentage yield is a fatty ester. In another embodiment, the fatty acid derivative that is produced at a decreased proportional or percentage yield is a fatty ester.

Alternatively, in any of the embodiments above, fatty acid derivatives can be produced at an increased yield, or at an increased proportional yield of short-chain (e.g., $C_8$, $C_9$, $C_{10}$, $C_{11}$, $C_{12}$, $C_{13}$, or $C_{14}$) products. Conversely, in any of the embodiments above, fatty acid derivatives can be produced at a decreased yield, or at a decreased proportional yield of short-chain (e.g., $C_8$, $C_9$, $C_{10}$, $C_{11}$, $C_{12}$, $C_{13}$, or $C_{14}$) products.

In one embodiment of the invention, a method of producing fatty acid derivatives is provided wherein the yield of fatty acid derivatives produced by the method of the invention is at least about 0.001 g of fatty acid derivative product/g of carbon source, for example, at least about 0.01 g of fatty acid derivative product/g of carbon source, about 0.1 g of fatty acid derivative product/g of carbon source, about 0.2 g of fatty acid derivative product/g of carbon source, about 0.3 g of fatty acid derivative product/g of carbon source, about 0.4 g of fatty acid derivative product/g of carbon source, or about 0.45 g of fatty acid derivative product/g of carbon source.

In one embodiment of the invention, a method of producing fatty acid derivatives is provided wherein the method results in a titer of at least about 0.5 g/L, for example, at least about 1 g/L, 2 g/L, 5 g/L, 10 g/L, 20 g/L, 30 g/L, 40 g/L, 50 g/L, 75 g/L, 100 g/L, 150 g/L or 200 g/L.

In one embodiment of the invention, a method of producing fatty acid derivatives is provided wherein the productivity of the method is such that at least about 0.1 g/L.h, for example, at least about 0.5 g/L.h, 1 g/L.h, 2 g/L.h, 3 g/L.h, 4 g/L.h, 5 g/L.h, 6 g/L.h, 7 g/L.h or 8 g/L.h is produced.

In one embodiment of the invention, fatty acid derivative compositions are provided that are produced by the host cells of the invention. Such compositions can comprise hydrocarbons, esters, alcohols, ketones, aldehydes, fatty acids, dicarboxylic acids, internal olefins, terminal olefins, and/or combinations thereof. Such compositions are useful in applications in the chemical industry, for example in the production of surfactants and detergents, or as a biofuel and a substitute for petroleum, heating oil, kerosene, diesel, jet fuel or gasoline.

In one embodiment of the invention, fatty acid derivative compositions are provided comprising less than or equal to about 50 ppm arsenic, about 30 ppm, about 25 ppm, or between about 10 and about 50 ppm arsenic; less than or equal to about 200 ppm calcium, about 150 ppm calcium, about 119 ppm calcium or between about 50 and about 200 ppm calcium; less than or equal to about 200 ppm chlorine, about 150 ppm chlorine, about 119 ppm chlorine or between about 50 and about 200 ppm chlorine; less than or equal to about 50 ppm copper, about 30 ppm copper, about 23 ppm copper, or between about 10 and about 50 ppm copper; less than or equal to about 300 ppm iron, about 200 ppm iron, about 136 ppm iron, or between about 50 and about 250 ppm iron; less than or equal to about 50 ppm lead, about 30 ppm lead, about 25 ppm lead, or between about 10 and about 50 ppm lead; less than or equal to about 50 ppm manganese, about 30 ppm manganese, about 23 ppm manganese, or between about 10 and about 50 ppm manganese; less than or equal to about 50 ppm magnesium, about 30 ppm magnesium, about 23 ppm magnesium, or between about 10 and about 50 ppm magnesium; less than or equal to about 0.5 ppm mercury, about 0.1 ppm mercury, about 0.06 ppm mercury or between about 0.01 and about 0.2 ppm mercury; less than or equal to about 50 ppm molybdenum, about 30 ppm molybdenum, about 23 ppm molybdenum or between about 10 and about 50 ppm molybdenum; less than or equal to about 2% nitrogen; about 1% nitrogen, about 0.5% nitrogen, or between about 0.1-1% nitrogen; less than or equal to about 200 ppm potassium, about 150 ppm potassium, about 103 ppm potassium, or between about 50 and about 200 ppm potassium; less than or equal to about 300 ppm sodium, 200 ppm sodium, about 140 ppm sodium, or between about 50 and about 300 ppm sodium; less than or equal to about 1 ppm sulfur, less than or equal to about 1% sulfur, about 0.14% sulfur, or between about 0.05 and about 0.3% sulfur; less than or equal to about 50 ppm zinc, about 30 ppm zinc, about 23 ppm zinc, or between about 10 and about 50 ppm zinc; or less than or equal to about 700 ppm phosphorus, about 500 ppm phosphorus, about 350 ppm phosphorus, or between about 100 and about 700 ppm phosphorus.

In one embodiment of the invention, fatty acid derivatives having fractions of modern carbon of about 1.003 to about 1.5 are provided.

In one embodiment of the invention, a fatty acid derivative composition is provided wherein the composition includes constituents comprising an acyl group that has a double bond at position 7 in the carbon chain (between carbon number 7 on the carbon chain and carbon number 8 on the carbon chain) from its reduced end.

In a particular embodiment, the fatty acid derivative composition comprises $C_5$-$C_{25}$ (i.e., a carbon chain length of 5 to 25 carbons) fatty esters, $C_5$-$C_{25}$ fatty acids, $C_5$-$C_{25}$ fatty aldehydes, $C_5$-$C_{25}$ fatty alcohols; or $C_{10}$-$C_{20}$ (i.e., a carbon chain length of 10 to 20 carbons) fatty esters, $C_{10}$-$C_{20}$ fatty acids, $C_{10}$-$C_{20}$ fatty aldehydes, $C_{10}$-$C_{20}$ fatty alcohols; or $C_{12}$-$C_{18}$ (i.e., a carbon chain length of 12 to 18 carbons) fatty esters, $C_{12}$-$C_{18}$ fatty acids, $C_{12}$-$C_{18}$ fatty aldehydes, $C_{12}$-$C_{18}$ fatty alcohols.

In a particular embodiment, the fatty acid derivatives of the invention comprise straight chain fatty acid derivatives, branched chain fatty acid derivatives, and/or cyclic moieties. In a particular embodiment, the fatty acid derivatives are unsaturated (e.g., monounsaturated) or saturated.

In one embodiment of the invention, the fatty acid derivative composition comprises a fatty ester that is produced from an alcohol and an acyl-CoA, wherein the alcohol is at least about 1, for example, at least about 2, about 3, about 4, about 5, about 6, about 7, about 8, about 10, about 12, about 14, about 16, or about 18 carbons in length, and the acyl-CoA is at least about 2, for example, at least about 4, about 6, about 8, about 10, about 12, about 14, about 16, about 18, about 20, about 22, about 24, or about 26 carbons in length. In some embodiments, the alcohol and acyl-CoA from which the fatty ester are produced vary by about 2, about 4, about 6, about 8, about 10, about 12, or about 14 carbon atoms.

In another embodiment, the fatty acid derivative composition comprises a fatty ester that is produced from an alcohol and an acyl-ACP, wherein the alcohol is at least about 1, for example, at least about 2, about 3, about 4, about 5, about 6, about 7, about 8, about 10, about 12, about 14, about 16, or about 18 carbons in length, and the acyl-ACP is at least about 2, for example, about 4, about 6, about 8, about 10, about 12, about 14, about 16, about 18, about 20, about 22, about 24, or about 26 carbons in length. In some embodiments, the alcohol and acyl-ACP from which the fatty ester are produced vary by about 2, about 4, about 6, about 8, about 10, about 12 or about 14 carbon atoms.

In one embodiment of the invention, the fatty acid derivative composition comprises a mixture of derivatives including free fatty acids. In one embodiment, the percentage of free fatty acids by weight is at least about 0.5%, for example, at least about 1%, about 2%, about 3%, about 4%, about 5%, about 6%, about 7%, about 8%, about 9%, about 10%, about 15%, about 20%, or about 25%. In a certain embodiment, the percentage of fatty esters produced by weight is at least about 50%, for example, at least about 55%, about 60%, about 65%, about 70%, about 75%, about 80%, about 85%, or about 90%. In a further embodiment, the ratio of fatty acid derivatives other than free fatty acids to free fatty acids is greater than about 90:1, for example, greater than about 80:1, about 50:1, about 20:1, about 10:1, about 9:1, about 8:1, about 7:1, about 5:1, about 2:1 or about 1:1, by weight.

In one embodiment, the fatty acid derivative composition comprises a mixture of derivatives including free fatty acids. In one embodiment, the percentage of free fatty acids by weight is at least about 50%, for example, at least about 55%, about 60%, about 65%, about 70%, about 75%, about 80%, about 85%, or about 90%. In a certain embodiment, the percentage of fatty ester produced by weight is at least about at least about 0.5%, for example, at least about 1%, about 2%, about 3%, about 4%, about 5%, about 6%, about 7%, about 8%, about 9%, about 10%, about 15%, about 20%, about 25%, about 30%, about 35%, about 40%, about 45%, or about 50%. In a further embodiment, the ratio of the fatty acid derivative produced other than free fatty acids to free fatty acids is less than about 60:1, for example, less than about 50:1, about 40:1, about 30:1, about 20:1, about 10:1, about 1:1, about 1:2; about 1:3, about 1:5, or about 1:10, by weight.

In one embodiment of the invention, the fatty acid derivative composition includes one or more fatty esters selected from: ethyl decanoate, ethyl dodecanoate, ethyl tridecanoate, ethyl tetradecanoate, ethyl pentadecanoate, ethyl cis-9-hexadecenoate, ethyl hexadecanoate, ethyl heptadecanoate, ethyl cis-11-octadecenoate, ethyl octadecanoate, methyl decanoate, methyl dodecanoate, methyl tridecanoate, methyl tetradecanoate, methyl pentadecanoate, methyl cis-9-hexadecenoate, methyl hexadecanoate, methyl heptadecanoate, methyl cis-11-octadecenoate, methyl octadecanoate, or a combination thereof.

In one embodiment of the invention, the fatty acid derivative composition includes one or more free fatty acids selected from: octanoic acid, decanoic acid, dodecanoic acid, tetradecanoic acid, pentadecanoic acid, cis-9-hexadecenoic acid, hexadecanoic acid, cis-11-octadecenoic acid, or combinations thereof.

Compositions comprising the fatty acid derivatives of the invention can be used as fuels. For example, the fatty acid derivatives can be used as, or as a component of, a biodiesel, a fatty alcohol, a fatty ester, a triacylglyceride, a gasoline, a diesel, or a jet fuel. A gasoline or a biodiesel composition can be used in an internal combustion engine. A jet fuel can be used in a jet engine. Accordingly, fuel compositions comprising the fatty acid derivatives prepared according to the present disclosures are provided herein.

Compositions comprising fatty acid derivatives of the invention can be used as fuel additives. For example, they can be added to a petroleum-based diesel or biodiesel to improve its renewable fuel content, lubricity, kinematic viscosity, acid number, boiling point, oxidative stability, cold filter-plugging point, impurity profiles, sulfated ash level, cetane number, cloud point, or pour point. Accordingly, fuel additive compositions comprising fatty acid derivatives produced according to the present disclosures are also provided.

Compositions comprising fatty acid derivatives of the invention can also be used as biocrude compositions, which can serve as feedstocks for making other petroleum-derivative compounds. For example, long chain hydrocarbons, internal or terminal olefins, alkanes, fatty aldehydes and fatty esters made according to the current invention can be further processed to produce fuels, fuel additives, fuel blends, and/or chemical products. Accordingly, biocrude compositions comprising fatty acid derivatives prepared according to the present disclosures are provided.

Compositions comprising fatty acid derivatives of the invention can be used as feedstocks in manufacturing detergents and surfactants, nutritional supplements, polymers, paraffin replacements, lubricants, solvents, personal care products, rubber processing additives, corrosion inhibitors, emulsifiers, plastics, textiles, cosmetics, paper products, coatings, metalworking fluids, dielectrics, oiling agents, and/or emollients. Accordingly, feedstock compositions comprising fatty acid derivatives prepared according to the present disclosures are also provided.

DESCRIPTION OF THE FIGURES

FIG. 1 (FIG. 1) is a table identifying various genes that can be over-expressed or attenuated to increase fatty acid derivative production. The table also identifies various genes that can be modulated to alter the structure of the fatty acid derivative product. Certain of the genes that are used to alter the structure of the fatty acid derivative will also increase the production of fatty acid derivatives.

FIG. 8A is a GC-MS spectrum showing ethyl acetate extract of strain C41(DE3, ΔfadE/pHZ1.43)/pRSET B+pAS004.114B) wherein the pHZ1.43 plasmid expressed ADP1 ester synthase (EC 2.3.1.20, 2.3.1.75). FIG. 8B is a GC-MS spectrum showing ethyl acetate extract of strain C41(DE3, ΔfadE/pHZ1.43)/pRSET B+pAS004.114B) wherein the pHZ1.43 plasmid expressed SAAT. FIG. 8C is a GC-MS spectrum showing acetyl acetate extract of strain C41(DE3, ΔfadE/pHZ1.43)/pRSET B+pAS004.114B) wherein the pHZ1.43 plasmid did not contain ADP1 (an ester synthase) or SAAT. FIG. 8D is a GC-MS spectrum showing the mass spectrum and fragmentation pattern of $C_8C_8$ produced by C41(DE3, ΔfadE/pHZ1.43)/pRSET B+pAS004.114B wherein the pHZ1.43 plasmid expressed SAAT).

FIGS. 15A-B (FIGS. 15A-B) are chromatograms depicting GC/MS analysis. FIG. 15A is a chromatogram depicting the components of an ethyl acetate extract of the culture of *E. coli* LS9001 strain transformed with plasmids pCDF-Duet-1-fadD-WSadp1, pETDuet-1-'TesA. FIG. 15B is a chromatogram depicting the ethyl hexadecanoate and the ethyl oleate, which were used as references.

FIG. 17 (FIG. 17) is the full DNA sequence of the pOP-80 plasmid (SEQ ID NO:1)

FIG. 18 (FIG. 18) is the DNA sequence (SEQ ID NO:2) for the *E. coli* codon-optimized fadD35 gene (GenBank Accession No. NP_217021).

FIG. 19 (FIG. 19) is the DNA sequence (SEQ ID NO:3) for the *E. coli* codon-optimized fadD1 gene (GenBank Accession No. NP_251989).

FIG. 20 (FIG. 20) is the BsyhfLBspHIF primer (SEQ ID NO:4) based on the DNA sequence deposited at NCBI with GenBank Accession No. NC_000964.

FIG. 21 (FIG. 21) is the BsyhfLEcoR primer (SEQ ID NO:5) based on the DNA sequence deposited at NCBI with GenBank Accession No. NC_000964.

FIG. 22 (FIG. 22) is the DNA sequence (SEQ ID NO:6) for the yhfL gene from *Bacillus subtilis*.

FIG. 23 (FIG. 23) is the Scfaa3pPciF primer (SEQ ID NO:7) based on the DNA sequence deposited at NCBI with GenBank Accession No. NC_001141.

FIG. 24 (FIG. 24) is the Scfaa3pPciI primer (SEQ ID NO:8) based on the DNA sequence deposited at NCBI with GenBank Accession No. NC_001141.

FIG. 25 (FIG. 25) is the DNA sequence (SEQ ID NO:9) for the faa3 gene from *Saccharomyces cerevisiae* (GenBank Accession No. NP_012257).

FIG. 26 (FIG. 26) is the Smprk59BspF primer (SEQ ID NO:10) based on the DNA sequence deposited at NCBI with GenBank Accession No. NZ_AAVZ01000044.

FIG. 27 (FIG. 27) is the Smprk59HindR primer (SEQ ID NO:11) based on the DNA sequence deposited at NCBI with GenBank Accession No. NZ_AAVZ01000044.

FIG. 28 (FIG. 28) is the PrkBsp primer (SEQ ID NO:12).

FIG. 29 (FIG. 29) is the DNA sequence encoding the protein ZP_01644857 from *Stenotrophomonas maltophilia* R551-3 (SEQ ID NO:13).

FIG. 30 (FIG. 30) is the protein sequence of ZP_01644857 from *Stenotrophomonas maltophilia* ATCC 17679 (SEQ ID NO:14).

FIG. 32 (FIG. 32) is a listing of the nucleotide sequence (SEQ ID NO:15) and the corresponding amino acid sequence (SEQ ID NO:16) of *Nocardia* sp. NRRL 5646 car gene.

FIG. 33 (FIG. 33) is a listing of amino acid sequence motifs for CAR homologs.

FIGS. 34A-B (FIGS. 34A-B) are GC/MS traces of olefins produced by *Jeotgalicoccus* sp. ATCC 8456 cells and *Jeotgalicoccus halotolerans* DSMZ 17274 cells, respectively.

FIGS. 41A-B (FIGS. 41A-B) are orf880 nucleotide (SEQ ID NO:25) and amino acid (SEQ ID NO:26) sequences, respectively. FIG. 41C is the partial 16s rRNA sequence (SEQ ID NO:27) of *Jeotgalicoccus* sp. ATCC8456.

FIG. 44 (FIG. 44) describes amino acid motifs for identifying precursor thioesterases useful in the present invention.

FIGS. 45A-B (FIGS. 45A-B) include a tables listing the results of assays identifying mutant thioesterases with altered properties. In particular, FIG. 45A includes lists of mutants with Z scores of at least 3 for activity (i.e., catalytic rate) with respect to the named substrate or specificity for the named substrate; and FIG. 45B is a table of mutants having improved and/or increased yield/production of fatty acid derivatives with Z scores of at least 3.

FIGS. 46A-E (FIGS. 46A-E) include tables listing the results of assays identifying mutant thioesterases with altered proportional yield of fatty esters vs. other products (e.g., fatty acid derivatives other than fatty esters). In particular, FIG. 46A is a table showing mutants having Z scores of at least 3 with respect to the proportional or percentage yield of fatty esters vs. free fatty acids. FIG. 46B is a table showing mutants having Z scores of less than −3 with respect to the proportional or percentage yield of fatty esters vs. free fatty acids. FIG. 46C is a table showing mutants having Z scores of at least 3 with respect to the in vivo yield of fatty acid derivatives. FIG. 46D is a table showing mutants having Z scores of at least 3 with respect to the proportional yield of short-chain (e.g., $C_8$, $C_9$, $C_{10}$, $C_{11}$, $C_{12}$, $C_{13}$, and/or $C_{14}$) fatty acid derivatives vs. other fatty acid derivatives (e.g., fatty acid derivatives other than short-chain fatty acid derivatives including, for example, long-chain (e.g., $C_{15}$, $C_{16}$, $C_{17}$, $C_{18}$, $C_{19}$, and/or $C_{20}$) fatty acid derivatives). FIG. 46E is a table showing mutants having Z scores of less than −3 with respect to the proportional yield of short-chain (e.g., $C_8$, $C_9$, $C_{10}$, $C_{11}$, $C_{12}$, $C_{13}$, and/or $C_{14}$) fatty acid derivatives vs. other fatty acid derivatives (e.g., fatty acid derivatives other than short-chain fatty acid derivatives including, for example, long-chain (e.g., $C_{15}$, $C_{16}$, $C_{17}$, $C_{18}$, $C_{19}$, and/or $C_{20}$) fatty acid derivatives).

FIG. 55 (FIG. 55) compares the relevant sequence regions of naturally-occurring thioesterases that comprise residues at positions that correspond to mutations in 'TesA that introduce altered properties. The relevant residue is highlighted in dark color, and aligned with corresponding residues in naturally-occurring thioesterases.

FIG. 56 (FIG. 56) lists GenBank Accession numbers of 'TesA homologs.

FIGS. 57A-F (FIG. 57A-F) are graphs depicting substrate specificity (Z score) vs. amino acid residue positions corresponding to 'TesA sequence of SEQ ID NO:31 with symbols to represent levels of conservation in the cons70 alignment for $C_{10}$ specificity (FIG. 57A and FIG. 57D), $C_{12}$ specificity (FIG. 57B and FIG. 57E) and $C_{14}$ specificity (FIG. 57C and FIG. 57F).

FIG. 58 (FIG. 58) shows the amino acid sequence of an *E. coli* 'TesA (SEQ ID NO:31).

FIG. 59 (FIG. 59) shows a nucleotide sequence encoding an *E. coli* 'TesA (SEQ ID NO:32).

DETAILED DESCRIPTION OF THE INVENTION

Figure 2:
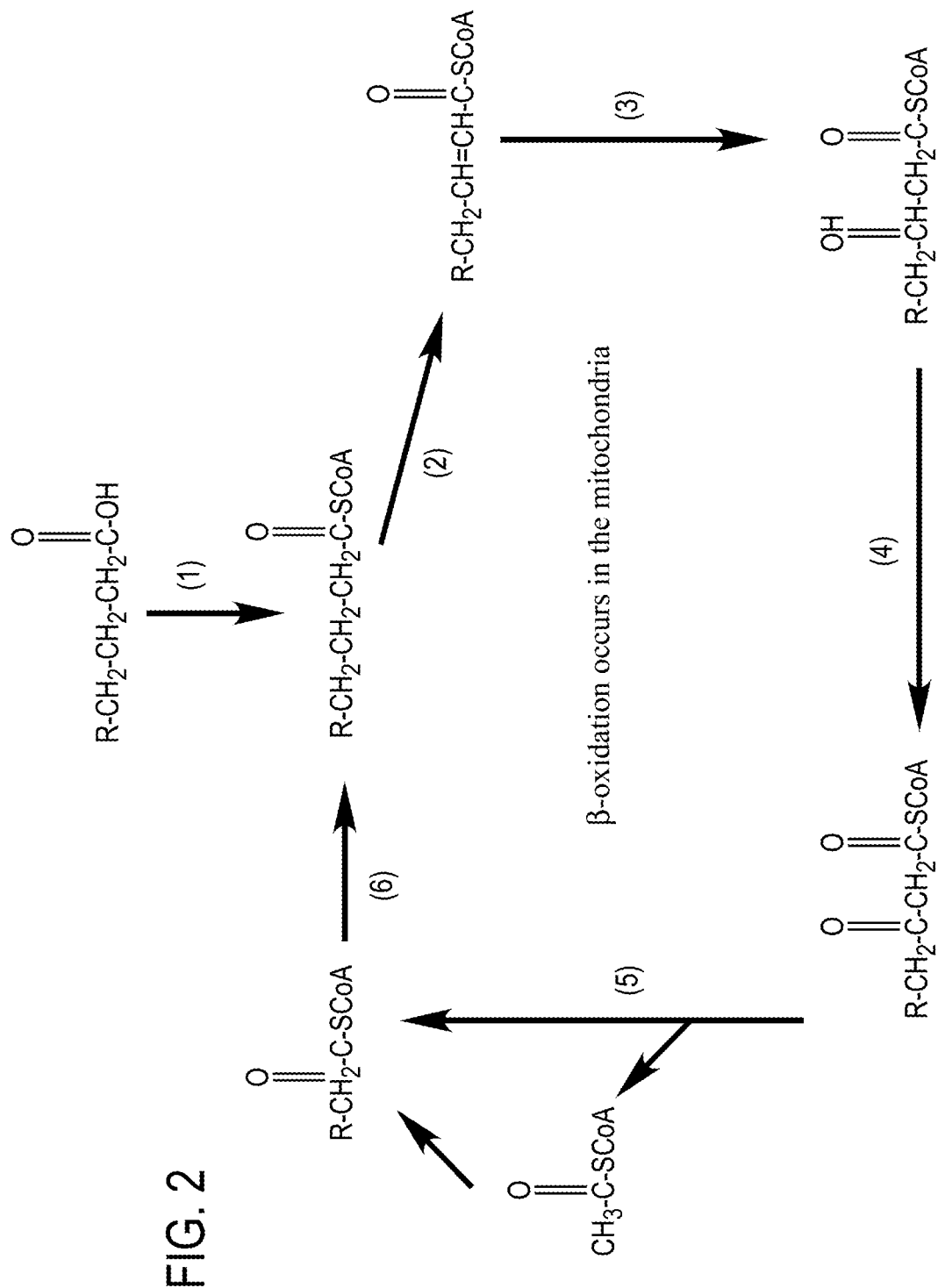
FIG. 2 (FIG. 2) is a diagram illustrating the beta-oxidation pathway, including steps catalyzed by the following enzymes (1) acyl-CoA synthase (EC 6.2.1.-). (2) acyl-CoA dehydrogenase (EC 1.3.99.3), (3) enoyl-CoA hydratase (EC 4.2.1.17); (4) 3-hydroxybutyryl-CoA epimerase (EC 5.1.2.3), and (5) 3-ketoacyl-CoA thiolase (EC 2.3.1.16). This final reaction of the β-oxidation cycle, releases acetyl-CoA and an acyl-CoA fatty acid two carbons shorter, ready to go through β-oxidation reactions again.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein, including GenBank database sequences, are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

Definitions

Throughout the specification, a reference may be made using an abbreviation of a gene name or a polypeptide name, but it is understood that such an abbreviated gene or polypeptide name represents the genus of genes or polypeptides, respectively. Such gene names include all genes encoding the same polypeptide and homologous polypeptides having the same physiological function. Polypeptide names include all polypeptides that have the same activity (e.g., that catalyze the same fundamental chemical reaction).

Unless otherwise indicated, the accession numbers referenced herein are derived from the NCBI database (National Center for Biotechnology Information) maintained by the National Institute of Health, U.S.A. Unless otherwise indicated, the accession numbers are as provided in the database as of March 2008.

EC numbers are established by the Nomenclature Committee of the International Union of Biochemistry and Molecular Biology (NC-IUBMB) (available at http://www.chem.qmul/ac/uk/iubmb/enzyme/). The EC numbers referenced herein are derived from the KEGG Ligand database, maintained by the Kyoto Encyclopedia of Genes and Genomics, sponsored in part by the University of Tokyo. Unless otherwise indicated, the EC numbers are as provided in the database as of March 2008.

The articles "a" and "an" are used herein to refer to one or more than one (i.e., to at least one) of the grammatical object of the article. By way of example, "an element" means one element or more than one element.

The term "about" is used herein to mean a value±20% of a given numerical value. Thus, "about 60%" refers to a value of 60±(20% of 60) (i.e., between 48 and 70).

As used herein, the term "alcohol dehydrogenase" (EC 1.1.1.*) is a polypeptide capable of catalyzing the conversion of a fatty aldehydes to an alcohol (e.g., a fatty alcohol). Additionally, one of ordinary skill in the art will appreciate that some alcohol dehydrogenases will catalyze other reactions as well. For example, some alcohol dehydrogenases will accept other substrates in addition to fatty aldehydes. Such non-specific alcohol dehydrogenases are, therefore, also included in this definition. Polynucleotide sequences encoding alcohol dehydrogenases are known in the art, and such dehydrogenases are publicly available.

The term "altered property" refers to a modification in one or more properties of a mutant polynucleotide or mutant protein with reference to a precursor polynucleotide or precursor protein. Properties that can be advantageously altered with respect to proteins made according to the present invention include oxidative stability, substrate specificity, substrate selectivity, catalytic activity, thermal stability, pH stability, pH activity profile, resistance to proteolytic degradation, $K_m$, $k_{cat}$, $k_{cat}/k_m$ ratio, protein folding, inducing an immune response, ability to bind to a ligand, ability to bind to a receptor, ability to be secreted, ability to translocate in an active manner into a membrane, ability to be displayed on the surface of a cell, ability to oligomerize, ability to signal, ability to stimulate cell proliferation, ability to inhibit cell proliferation, ability to induce apoptosis, ability to be modified by phosphorylation or glycosylation, ability to treat disease. In one embodiment of the invention, mutant thioesterases are provided that derive from a precursor thioesterase, wherein the mutant has at least one altered property either in vitro or in vivo, as compared to the properties of the precursor thioesterase. In one embodiment, the altered property can be a biophysical property such as thermal stability (melting point $T_m$), solvent stability, solute stability, oxidative stability, lipophilicity, hydrophilicity, quaternary structure, dipole moment, or isoelectric point. In one embodiment, the altered property can be a biochemical property such as pH optimum, temperature optimum, ionic strength optimum, and/or an enzyme catalytic parameter (such as, for example, product distribution, product proportional or percentage yield, specific activity, substrate preference, substrate affinity, substrate inhibition, product affinity, turnover rate, product inhibition, kinetic mechanism, $K_M$, $k_{cat}$, $k_{cat}/K_m$, and/or $V_{MAX}$). In one embodiment, the altered property is a changed preference for particular substrates, as reflected in, for example, a changed preference for alcoholysis or hydrolysis, acyl-CoA or acyl-acyl carrier protein substrates, ester or thioester substrates, saturated or unsaturated substrates, position of unsaturations, broad or narrow specificity (e.g., the ability to catalyze a range of substrates or only substrates of a specific carbon chain length). In one embodiment, the altered property can be an increased preference or activity for branched substrates, substrates having a specific position of branching, hydroxyacyl substrates, keto-acyl substrates, substrates that result in a product having desirable fuel attributes (i.e., cetane number, octane rating, oxidative stability, lubricity, flash point, viscosity, boiling point, melting point, pour point, cloud point, cold filter plugging point, cold flow characteristics, aromaticity, and/or iodine number). Altered properties also include a decrease in activity or attenuation of ester hydrolysis, such as hydrolysis of desired product molecules, or a decrease in the toxicity of the protein to the cell and/or a change in the expression level of the protein in the cell. In a particular embodiment, the at least one altered property is, for example, a change in the ability of the thioesterase to catalyze the synthesis of fatty acyl esters directly or indirectly, in vivo or in vitro, such as by transesterification.

As used herein, an "analogous sequence" is one wherein the function of the gene is essentially the same as a reference gene such as, for example, a 'tesA gene from E. coli. Additionally, analogous genes include at least about 20%, for example, at least about 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% sequence identity with the sequence of a reference gene or polynucleotide such as, for example, the polynucleotide or polypeptide sequence of a 'tesA gene or a 'TesA thioesterase, respectively. In additional embodiments more than one of the above properties applies to the sequence. Analogous sequences are determined by known methods of sequence alignment.

The term "alignment" refers to a method of comparing two or more polynucleotides or polypeptide sequences for the purpose of determining their relationship to each other. Alignments are typically performed by computer programs that apply various algorithms, however it is also possible to perform an alignment by hand. Alignment programs typically iterate through potential alignments of sequences and score the alignments using substitution tables, employing a variety of strategies to reach a potential optimal alignment score. Commonly-used alignment algorithms include, but are not limited to, CLUSTALW, (see, Thompson J. D., Higgins D. G., Gibson T. J., CLUSTAL W: improving the sensitivity of progressive multiple sequence alignment through sequence weighting, position-specific gap penalties and weight matrix choice, Nucleic Acids Research 22: 4673-4680, 1994); CLUSTALV, (see, Larkin M. A., et al., CLUSTALW2, ClustalW and ClustalX version 2, Bioinformatics 23(21): 2947-2948, 2007); Jotun-Hein, Muscle et al., MUSCLE: a multiple sequence alignment method with reduced time and space complexity, BMC Bioinformatics 5: 113, 2004); Mafft, Kalign, ProbCons, and T-Coffee (see Notredame et al., T-Coffee: A novel method for multiple sequence alignments, Journal of Molecular Biology 302: 205-217, 2000). Exemplary programs that implement one or more of the above algorithms include, but are not limited to MegAlign from DNAStar (DNAStar, Inc. 3801 Regent St. Madison, Wis. 53705), MUSCLE, T-Coffee, CLUSTALX, CLUSTALV, JalView, Phylip, and Discovery Studio from Accelrys (Accelrys, Inc., 10188 Telesis Ct, Suite 100, San Diego, Calif. 92121). In a non-limiting example, MegAlign is used to implement the CLUSTALW alignment algorithm with the following parameters: Gap Penalty 10, Gap Length Penalty 0.20, Delay Divergent Seqs (30%) DNA Transition Weight 0.50, Protein Weight matrix Gonnet Series, DNA Weight Matrix IUB.

The term "antibodies" refers to immunoglobulins. Antibodies include but are not limited to immunoglobulins obtained directly from any species from which it is desirable to produce antibodies. In addition, the present invention encompasses modified antibodies. The term also refers to antibody fragments that retain the ability to bind to the same epitope to which the intact antibody also binds, and include polyclonal antibodies, monoclonal antibodies, chimeric antibodies, anti-idiotype (anti-ID) antibodies. Antibody fragments include, but are not limited to the complementarity-determining regions (CDRs), single-chain fragment variable regions (scFv), heavy chain variable region (VH), light chain variable region (VL). Polyclonal and monoclonal antibodies are also encompassed by the present invention. Preferably, the antibodies are monoclonal antibodies.

The term "attenuate" means to weaken, reduce or diminish. In one example, the sensitivity of a particular enzyme to feedback inhibition or inhibition caused by a composition that is not a product or a reactant (non-pathway specific feedback) is reduced such that the enzyme activity is not impacted by the presence of a compound. In a particular example, the expression of fabH gene is temperature sensitive and its sequence can be altered to decrease the sensitivity to temperature fluctuations. Also, expression of the fabH gene can be attenuated when branched amino acids are desired. In another example, an enzyme that has been modified to be less active can be referred to as attenuated. A functional modification of the sequence encoding an enzyme can be used to attenuate expression of an enzyme. Sequence modifications may include, for example, a mutation, deletion, or insertion of one or more nucleotides in a gene sequence or a sequence controlling the transcription or translation of a gene sequence, which modification results in a reduction or inhibition of production of the gene product, or renders the gene product non-functional. For example, functional deletion of fabR in E. coli reduces the repression of the fatty acid biosynthetic pathway and allows E. coli to produce more unsaturated fatty acids (UFAs). In some instances a functional deletion is described as a knock-out mutation. Other methods are available for attenuating expression of an enzyme. For example, attenuation can be accomplished by modifying the sequence encoding the gene as described above; placing the gene under the control of a less active promoter, expressing interfering RNAs, ribozymes, or antisense sequences that target the gene of interest; by changing the physical or chemical environment, such as temperature, pH, or solute concentration, such that the optimal activity of the gene or gene product is not realized; or through any other techniques known in the art.

The term "biocrude" refers to a biofuel that can be used as a substitute of petroleum-based fuels. In addition, biocrude, like petroleum crude, can be converted into other fuels, for example gasoline, diesel, jet fuel, or heating oil. Moreover, biocrude, like petroleum crude, can be converted into other industrially useful chemicals for use in, for example, pharmaceuticals, cosmetics, consumer goods, industrial processes, etc. A biocrude composition can comprise, for example, hydrocarbons, hydrocarbon products, fatty acid esters, and/or aliphatic ketones, or a combination thereof. In a preferred embodiment, a biocrude composition is comprised of hydrocarbons, for example, aliphatic (e.g., alkanes, alkenes, alkynes) or aromatic hydrocarbons.

The term "biodiesel" refers to a particular kind of biofuel that can be used in diesel engines. Biodiesel can be a substitute for traditional diesel, which is typically derived from petroleum. Biodiesel can be used in internal combustion diesel engines in either a pure form, which is referred to as "neat" biodiesel, or as a mixture in any concentration with a petroleum-based diesel. A biodiesel composition can also comprise various suitable additives. Biodiesel can be comprised of hydrocarbons or esters. In one embodiment, biodiesel is comprised of fatty esters, such as fatty acid methyl esters (FAME) or fatty acid ethyl esters (FAEE). In a preferred embodiment, these FAME and FAEE are comprised of fatty acyl moieties having a carbon chain length of about 8-20, 10-18, or 12-16. Fatty esters used as biodiesel may contain carbon chains that are straight, branched, saturated, or unsaturated.

The term "biofuel" refers to any fuel derived from biomass. Biomass is a biological material that can be converted into a biofuel. One exemplary source of biomass is plant matter. For example, corn, sugar cane, and switchgrass can be used as biomass. Another non-limiting example of biomass is animal matter, for example cow manure. Biomass also includes waste products from industry, agriculture, forestry, and households. Examples of such waste products include, without limitation, fermentation waste, straw, lumber, sewage, garbage and food leftovers and glycerol. Biomass also includes sources of carbon, such as carbohydrates (e.g., sugars). Biofuels can be substituted for petroleum based fuels. For example, biofuels are inclusive of transportation fuels (e.g., gasoline, diesel, jet fuel, etc.), heating fuels, and electricity-generating fuels. A biofuel is a renewable energy source. Non-limiting examples of biofuels include biodiesel, hydrocarbons (e.g., alkanes, alkenes, alkynes, or aromatic hydrocarbons), and alcohols derived from biomass.

The term "carbon chain length" is defined herein as the number of carbon atoms in a carbon chain of a thioesterase substrate or a fatty acid derivative. The carbon chain length of a particular molecule is marked as $C_x$, wherein the subscript "x" refers to the number of carbons in the carbon chain. As used herein, the term "long-chain" refers to those molecules that have a carbon chain of about 15 to about 20 carbons long (e.g., $C_{15}$, $C_{16}$, $C_{17}$, $C_{18}$, $C_{19}$, or $C_{20}$). The term "short-chain" refers to those molecules that have a carbon chain of about 8 to about 14 carbons long (e.g., $C_8$, $C_9$, $C_{10}$, $C_{11}$, or $C_{12}$).

The term "carbon source" means a substrate or compound suitable to be used as a source of carbon for prokaryotic or simple eukaryotic cell growth. Carbon sources can be in various forms, including, but not limited to polymers, carbohydrates, acids, alcohols, aldehydes, ketones, amino acids, peptides, gases (e.g., CO and $CO_2$), and the like. These include, for example, various monosaccharides such as glucose, fructose, mannose and galactose; oligosaccharides such as fructo-oligosaccharide and galacto-oligosaccharide; polysaccharides such as xylose, and arabinose; disaccharides such as sucrose, maltose and turanose; cellulosic material such as methyl cellulose and sodium carboxymethyl cellulose; saturated or unsaturated fatty acid esters such as succinate, lactate and acetate; alcohols such as ethanol, etc., or mixtures thereof. The carbon source can additionally be a product of photosynthesis, including, but not limited to glucose. Glycerol can be an effective carbon source as well. Suitable carbon sources can be generated from any number of natural and renewable sources, including particularly biomass from agricultural, municipal and industrial waste, so long as the material can be used as a component of a fermentation to provide a carbon source. Biomass sources include corn stover, sugarcane, switchgrass, animal matter, or waste materials.

The term "chromosomal integration" means the process whereby an incoming sequence is introduced into the chromosome of a host cell. The homologous regions of the transforming DNA align with homologous regions of the chromosome. Then, the sequence between the homology boxes can be replaced by the incoming sequence in a double crossover (i.e., homologous recombination). In some embodiments of the present invention, homologous sections of an inactivating chromosomal segment of a DNA construct align with the flanking homologous regions of the indigenous chromosomal region of the microbial chromosome. Subsequently, the indigenous chromosomal region is deleted by the DNA construct in a double crossover.

The term "cloud point" refers to the temperature of a liquid at which the dissolved solids are no longer completely soluble, precipitating as a second phase and giving the fluid a cloudy appearance. This term is relevant to a number of applications with somewhat or completely different consequences. In the petroleum industry, cloud point refers to the temperature below which wax or other heavy hydrocarbons crystalize in a crude oil, refined oil or fuel to form a cloudy appearance. The presence of solidified wax influences the flowing behavior of the fluid, raising the tendency to clog fuel filters/injectors and other machine parts, causing accumulation of wax on cold surfaces (e.g., on pipeline surfaces or heat exchanger surfaces), and changing even the emulsion characteristics with water. Cloud point is an indication of the tendency of the oil to plug filters or small orifices at cold operating temperatures. The cloud point of a nonionic surfactant or glycol solution is the temperature at which the mixture starts to separate into two or more phases, thus becoming cloudy. This behavior is characteristic of non-ionic surfactants containing polyoxyethylene chains, which can exhibit reverse solubility versus temperature behavior in water, and therefore can "cloud out" at some point as the temperature is raised. Glycols demonstrating this behavior are known as "cloud-point glycols" and are used as shale inhibitors. The cloud point is typically also affected by salinity, being generally lower in more saline fluids.

The term "cloud point lowering additive" refers to an additive that can be added to a composition to decrease or lower the cloud point of the composition, as described above.

The term "conditions that permit product production" refers to any fermentation conditions that allow a production host to produce a desired product, such as acyl-CoA or fatty acid derivatives including, for example, fatty acids, hydrocarbons, fatty alcohols, waxes, or fatty esters. Fermentation conditions usually comprise many parameters. Exemplary conditions include, but are not limited to, temperature ranges, levels of aeration, pH ranges, and media composition (e.g., solvents and solutes). Each of these conditions, individually and in combination, allows the production host to grow. Exemplary media include broths or gels. Generally, a suitable medium includes a carbon source, such as glucose, fructose, cellulose, or the like, which can be metabolized by the microorganism directly. In addition, enzymes can be used in the medium to facilitate the mobilization (e.g., the depolymerization of starch or cellulose to fermentable sugars) and subsequent metabolism of the carbon source. To determine if the culture conditions are suitable for product production, the production host can be cultured for about 4, 8, 12, 24, 36, 48, or 72 hours. During culturing or after culturing, samples can be obtained and analyzed to determine if the culture conditions permit product production. For example, the production hosts in the sample or the medium in which the production hosts were grown can be tested for the presence of the desired product. When testing for the presence of a product, assays, such as, but not limited to, TLC, HPLC, GC/FID, GC/MS, LC/MS, MS, as well as those provided in the examples herein, can be used.

The term "consensus sequence" or "canonical sequence" refers to an archetypical amino acid sequence against which all variants of a particular protein or sequence of interest are compared. Either term also refers to a sequence that sets forth the nucleotides that are most often present in a polynucleotide sequence of interest. For each position of a protein, the consensus sequence gives the amino acid that is most abundant in that position in the sequence alignment.

As used herein, the term "consensus mutation" refers to a difference in the sequence of a starting gene and a consensus sequence. Consensus mutations are identified by comparing the sequences of the starting gene and the consensus sequence resulting from a sequence alignment. In some embodiments, consensus mutations are introduced into the starting gene such that it becomes more similar to the consensus sequence. Consensus mutations also include amino acid changes that change an amino acid in a starting gene to an amino acid that is more frequently found in a multiple sequence alignment (MSA) at that position relative to the frequency of that amino acid in the starting gene. Thus, the term "consensus mutation" refers to any amino acid change that replaces an amino acid of the starting gene with an amino acid that is more abundant in the MSA than the native amino acid.

The term "conservative substitutions" or "conserved substitutions" refers to, for example, a substitution wherein one or more of the following amino acid substitutions are made: replacement of an aliphatic amino acid, such as alanine, valine, leucine, and isoleucine, with another aliphatic amino acid; replacement of a serine with a threonine; replacement of a threonine with a serine; replacement of an acidic residue, such as aspartic acid and glutamic acid, with another acidic residue; replacement of a residue bearing an amide group, such as asparagine and glutamine, with another residue bearing an amide group; exchange of a basic residue, such as histidine, lysine and arginine, with another basic residue; and replacement of an aromatic residue, such as tryptophan, phenylalanine and tyrosine, with another aromatic residue; or replacement of small amino acids, such as glycine, alanine, serine, threonine and methionine, with another small amino acid. Amino acid substitutions which do not generally alter the specific activity are known in the art and are described, for example, by H. Neurath and R. L. Hill, in The Proteins, Academic Press, New York, 1979. Useful conservative modifications include Alanine to Cysteine, Glycine, or Serine; Arginine to Isoleucine, Lysine, Methionine, or Ornithin; Asparagine to Aspartic acid, Glutamine, Glutamic acid, or Histidine; Aspartic acid to Asparagine, Glutamine, or Glutamic acid; Cysteine to Methionine, Serine, or Threonine; Glutamine to Asparagine, Aspartic acid, or Glutamic acid; Glutamic acid to Asparagine, Aspartic acid, or Glatmine; Glycine to Aspartic acid, Alanine, or Proline; Histidine to Asparagine, or Glutamine; Isoleucine to Leucine, Methionine, or Valine; Leucine to Isoleucine, Methionine, or Valine; Lysine to Arginine, Glutamine, Glutamic acid, Isoleucine, Methionine, or Ornithin; Methionine to Cysteine, Isoleucine, Leucine, or Valine; Phenylalanine to Histidine, L-Dopa, Leucine, Methionine, Threonine, Tryptophan, Tyrosine, 3-phenylproline, 4-phenylproline, or 5-phenylproline; Proline to L-1-thioazolidine-4-carboxylic acid or D- or L-1-oxazolidine-4-carboxylic acid; Serine to Cysteine, Methionine, or Threonine; Threonine to Methionine, Serine, or Valine; Tryptophan to Tyrosine; Tyrosine to L-Dopa, Histidine, or Phenylalanine; and Valine to Isoleucine, Leucine, or Methionine.

Figure 47:
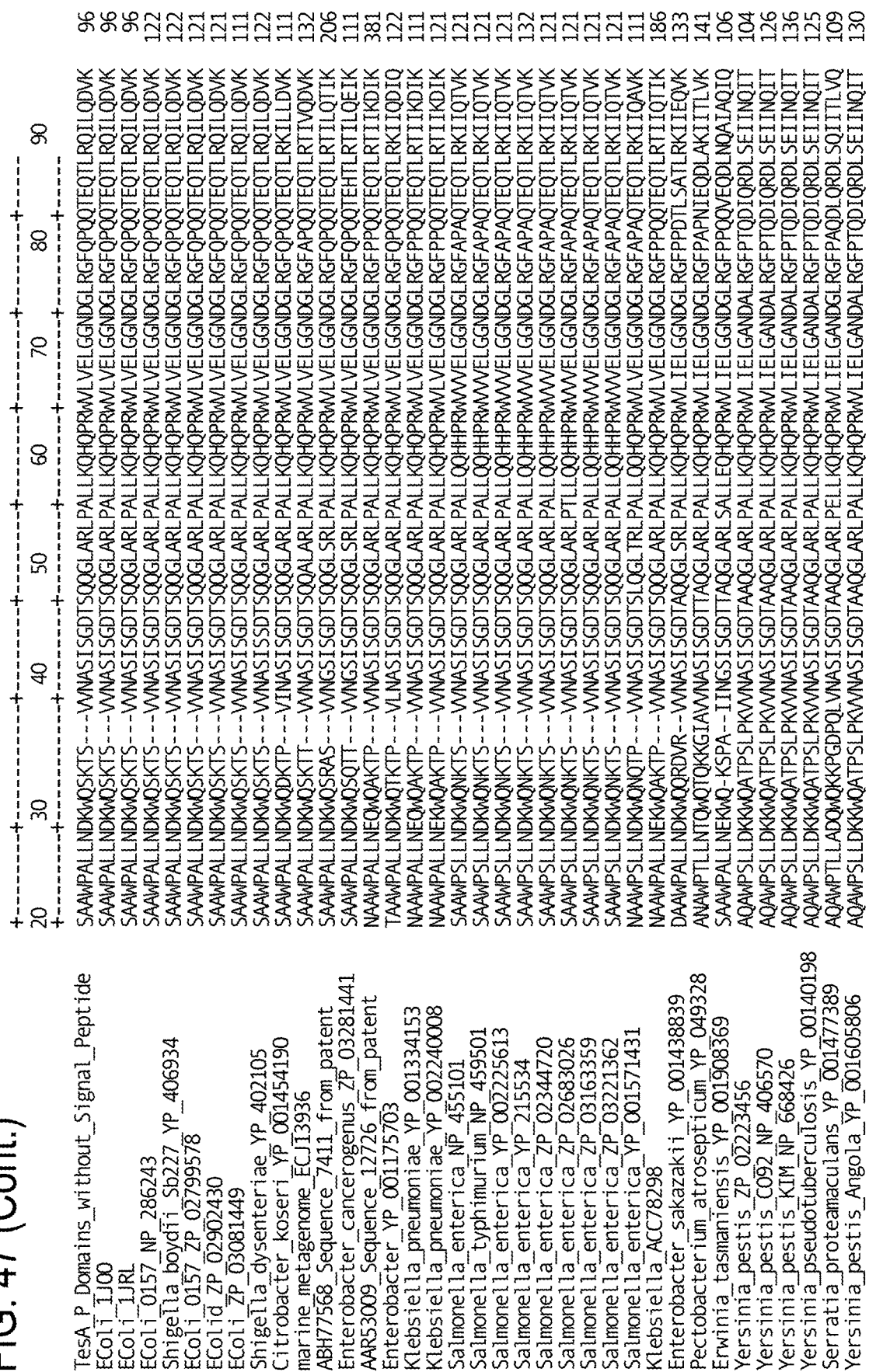
FIG. 47 (FIG. 47) is a sequence alignment of homologs of 'TesA using the amino acid residues of an *E. coli* 'TesA (i.e., TesA without the signal peptide) as a reference sequence for numbering purposes. In order, the figure sets forth SEQ ID NOs: 73-108.
Figure 47:
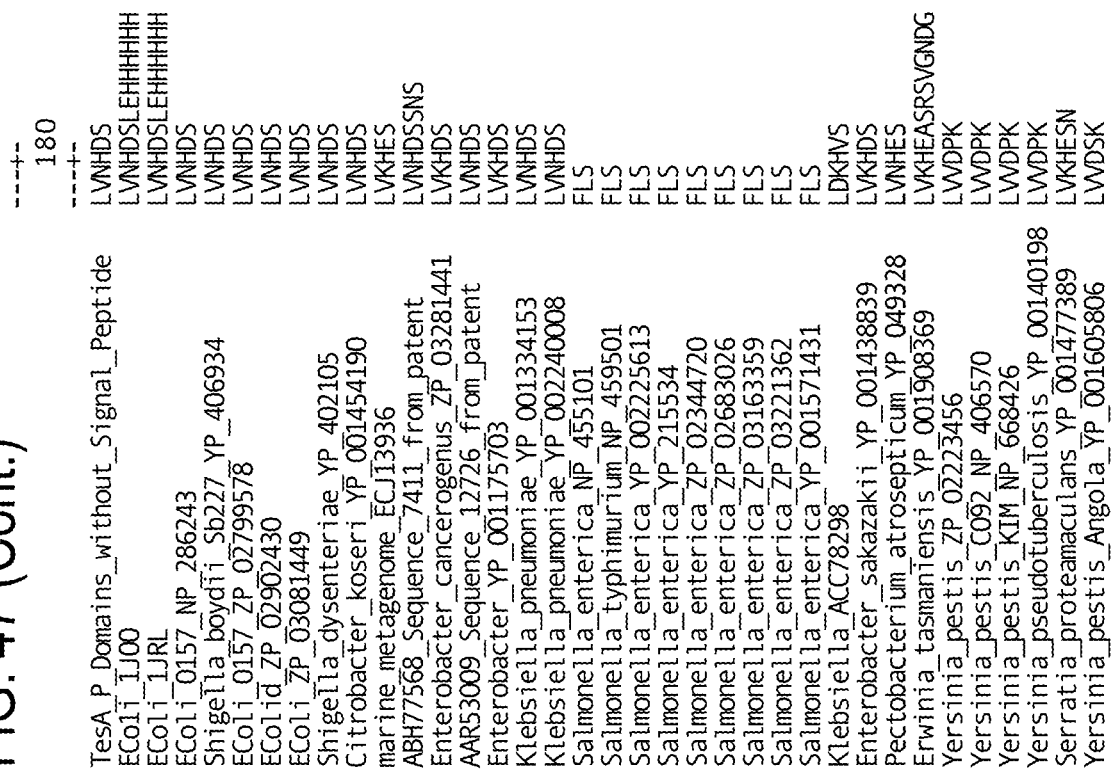

The term "corresponds to" refers to an amino acid residue in a first protein sequence being positionally equivalent to an amino acid residue in a second reference protein sequence by virtue of the fact that the residue in the first protein sequence lines up with the residue in the reference sequence using bioinformatic techniques, for example, using the methods described herein for preparing a sequence alignment. The corresponding residue in the first protein sequence is then assigned the residue number in the second reference protein sequence. The first protein sequence can be analogous to the second protein sequence or non-analogous to the second protein sequence, although it is preferred that the two protein sequences are analogous sequences. For example, when the amino acid sequence of an E. coli 'TesA, SEQ ID NO:31 in FIG. 58, is used as a reference sequence, each of the amino acid residues in another aligned protein of interest or analogous protein can be assigned a residue number corresponding to the residue numbers 1-182 of SEQ ID NO:31. For example, in FIG. 47, the aligned amino acid sequences are referenced or corresponded to the sequence of an E. coli 'TesA. Accordingly, a given position in another thioesterase of interest, either a precursor or a mutant thioesterase, can be assigned a corresponding position in the 'TesA sequence, using known bioinformatic techniques such as those described herein.

The term "deletion," when used in the context of an amino acid sequence, means a deletion in or a removal of a residue from the amino acid sequence of a precursor protein, resulting in a mutant protein having one less amino acid residue as compared to the precursor protein. The term can also be used in the context of a nucleotide sequence, which means a deletion in or removal of a residue from the polynucleotide sequence of a precursor polynucleotide.

The term "derived from" and "obtained from" refer to, in the context of a precursor thioesterase, a thioesterase produced or producible by a strain of the organism in question, and also a thioesterase encoded by a polynucleotide sequence isolated from such strain and produced in a host organism containing such a polynucleotide sequence. Additionally, the terms refer to a thioesterase that is encoded by a polynucleotide sequence of synthetic and/or cDNA origin and that has the identifying characteristics of the thioesterase in question. To exemplify, "thioesterases derived from Enterobacteriacaea" refers to those enzymes having thioesterase activity that are naturally produced by Enterobacteriacaea, as well as to thioesterases like those produced by Enterobacteriacaea sources but that, through the use of genetic engineering techniques, are produced by non-Enterobacteriocaea organisms transformed with a polynucleotide encoding said thioesterase.

The term "DNA construct" and "transforming DNA" are used interchangeably herein to refer to a DNA used to introduce sequences into a host cell or organism. Typically a DNA construct is generated in vitro by PCR or other suitable technique(s) known to those in the art. In certain embodiments, the DNA construct comprises a sequence of interest (e.g., an incoming sequence). In some embodiments, the sequence is operably linked to additional elements such as control elements (e.g., promoters, etc.). A DNA construct can further comprise a selectable marker. It can also comprise an incoming sequence flanked by homology boxes. In a further embodiment, the DNA construct comprises other non-homologous sequences, added to the ends (e.g., stuffer sequences or flanks). In some embodiments, the ends of the incoming sequence are closed such that the DNA construct forms a closed circle. The transforming sequences may be wildtype, mutant or modified. In some embodiments, the DNA construct comprises sequences homologous to the host cell chromosome. In other embodiments, the DNA construct comprises non-homologous sequences. Once the DNA construct is assembled in vitro it may be used to: 1) insert heterologous sequences into a desired target sequence of a host cell; 2) mutagenize a region of the host cell chromosome (i.e., replace an endogenous sequence with a heterologous sequence); 3) delete target genes; and/or (4) introduce a replicating plasmid into the host.

A polynucleotide is said to "encode" an RNA or a polypeptide if, in its native state or when manipulated by methods known to those of skill in the art, it can be transcribed and/or translated to produce the RNA, the polypeptide, or a fragment thereof. The antisense strand of such a polynucleotide is also said to encode the RNA or polypeptide sequences. As is known in the art, a DNA can be transcribed by an RNA polymerase to produce an RNA, and an RNA can be reverse transcribed by reverse transcriptase to produce a DNA. Thus a DNA can encode an RNA, and vice versa.

The phrase "equivalent," in this context, refers to thioesterase enzymes that are encoded by a polynucleotide capable of hybridizing to the polynucleotide having the sequence of SEQ ID NO:31 in FIG. 58, under conditions of medium to maximum stringency. For example, being equivalent means that an equivalent mature thioesterase comprises at least 70%, at least 75%, at least 80%, at least 85%, at least 90%, at least 91%, at least 92%, at least 93%, at least 94%, at least 95%, at least 96%, at least 97%, at least 98%, and/or at least 99% sequence identity to the amino acid sequence of SEQ ID NO:31 in FIG. 58.

An "ester synthase" is a peptide capable of catalyzing a biochemical reaction to producing esters. For example, an ester synthase is a peptide that is capable of participating in converting a thioester to a fatty ester. In certain embodiments, an ester synthase converts a thioester, acyl-CoA, to a fatty ester. In an alternate embodiment, an ester synthase uses a thioester and an alcohol as substrates to produce a fatty ester. Ester synthases are capable of using short and long chain acyl-CoAs as substrates. In addition, ester synthases are capable of using short and long chain alcohols as substrates. Non-limiting examples of ester synthases include wax synthases, wax-ester synthases, acyl-CoA: alcohol transacylases, acyltransferases, fatty acyl-coenzyme A:fatty alcohol acyltransferases, fatty acyl-ACP transacylase, and alcohol acetyltransferase. An ester synthase that converts an acyl-CoA thioester to a wax is called a wax synthase. Exemplary ester synthases include those classified under the enzyme classification number EC 2.3.1.75. The term "ester synthase" does not comprise enzymes that also have thioesterase activity. The ones that have both ester synthase activity and thioesterase activity are categorized as thioesterases herein.

The term "expressed genes" refers to genes that are transcribed into messenger RNA (mRNA) and then translated into protein, as well as genes that are transcribed into types of RNA, such as transfer RNA (tRNA), ribosomal RNA (rRNA), and regulatory RNA, which are not translated into protein.

The terms "expression cassette" or "expression vector" refers to a polynucleotide construct generated recombinantly or synthetically, with a series of specified elements that permit transcription of a particular polynucleotide in a target cell. A recombinant expression cassette can be incorporated into a plasmid, chromosome, mitochondrial DNA, plasmid DNA, virus, or polynucleotide fragment. Typically, the recombinant expression cassette portion of an expression vector includes, among other sequences, a polynucleotide sequence to be transcribed and a promoter. In particular embodiments, expression vectors have the ability to incorporate and express heterologous polynucleotide fragments in a host cell. Many prokaryotic and eukaryotic expression vectors are commercially available. Selection of appropriate expression vectors is within the knowledge of those of skill in the art. The term "expression cassette" is also used interchangeably herein with "DNA construct," and their grammatical equivalents.

The term "fatty acid derivative," as used herein, refers to a composition that is derived from a metabolic pathway, which pathway includes a thioesterase reaction. Thus, fatty acid derivative products can be products that are, or are derived from, fatty acid or fatty esters that are products of a thioesterase reaction. Fatty acid derivatives thus include, for example, products that are, or that are derived from, fatty acids that are the direct reaction product of a thioesterase, and/or a fatty ester that is a direct reaction product of a thioesterase. Exemplary fatty acid derivatives include, for example, short and long chain alcohols, hydrocarbons, and fatty alcohols and esters, including waxes, fatty acid esters, and/or fatty esters. Specific non-limiting examples of fatty acid derivatives include fatty acids, fatty acid methyl esters, fatty acid ethyl esters, fatty alcohols, fatty alkyl-acetates, fatty aldehydes, fatty amines, fatty amides, fatty sulfates, fatty ethers, ketones, alkanes, internal olefins, terminal olefins, dicarboxylic acids, w-dicarboxylic acids, diols and terminal and/or internal fatty acids.

The term "fatty acid derivative enzymes" refers to, collectively and individually, enzymes that may be expressed or overexpressed in the production of fatty acid derivatives. These enzymes may be parts of a fatty acid biosynthetic pathway. Non-limiting examples of fatty acid derivative synthases include fatty acid synthases, thioesterases, acyl-CoA synthases, acyl-CoA reductases, alcohol dehydrogenases, alcohol acyltransferases, fatty alcohol-forming acyl-CoA reductase, fatty acid decarbonylases, carboxylic acid reductases, fatty alcohol acetyl transferases, and ester synthases. Fatty acid derivative enzymes convert substrates into fatty acid derivatives. In certain circumstances, a suitable substrate may be a first fatty acid derivative, which is converted by a fatty acid derivative enzyme into a different, second fatty acid derivative.

The term "fatty alcohol" refers to an alcohol having the formula ROH. In certain embodiments, a fatty alcohol is an alcohol made from a fatty acid or fatty acid derivative. In one embodiment, the R group is at least about 5, 6, 7, 8, 9, 10, 11, 12, 13, 14, 15, 16, 17, 18, 19, or 20 carbons in length. R can be straight or branched chain. The branched chains may have one or more points of branching. In addition, the branched chains may include cyclic branches, such as cyclopropane or epoxide moieties. Furthermore, R can be saturated or unsaturated. If unsaturated, R can have one or more points of unsaturation. In one embodiment, the fatty alcohol is produced biosynthetically. Fatty alcohols have many uses. For example, fatty alcohols can be used to produce specialty chemicals. Specifically, fatty alcohols can be used as biofuels; as solvents for fats, waxes, gums, and resins; in pharmaceutical salves, emollients and lotions; as lubricating-oil additives; in detergents and emulsifiers; as textile antistatic and finishing agents; as plasticizers; as nonionic surfactants; and in cosmetics, for example as thickeners.

The term "fatty alcohol forming peptides" refers to peptides capable of catalyzing the conversion of acyl-CoA to fatty alcohol, including fatty alcohol forming acyl-CoA reductase (FAR, EC 1.1.1.*), acyl-CoA reductase (EC 1.2.1.50) or alcohol dehydrogenase (EC 1.1.1.1). Additionally, one of ordinary skill in the art will appreciate that some fatty alcohol forming peptides will catalyze other reactions as well. For example, some acyl-CoA reductase peptides will accept substrates other than fatty acids. Such non-specific peptides are, therefore, also included. Polynucleotide sequences encoding fatty alcohol forming peptides are known in the art and such peptides are publicly available.

The term "fatty aldehyde" refers to an aldehyde having the formula RCHO characterized by an unsaturated carbonyl group (C=O). In certain embodiments, a fatty aldehyde is an aldehyde made from a fatty acid or fatty acid derivative. In one embodiment, the R group is at least about 1, 2, 3, 4, 5, 6, 7, 8, 9, 10, 11, 12, 13, 14, 15, 16, 17, 18, 19, or 20 carbons in length. R can be straight or branched chain. The branched chains may have one or more points of branching. In addition, the branched chains can be cyclic branches.

Furthermore, R can be saturated or unsaturated. If unsaturated, R can have one or more points of unsaturation. In one embodiment, the fatty aldehyde is produced biosynthetically. Fatty aldehydes have many uses. For example, fatty aldehydes can be used to produce specialty chemicals. Specifically, fatty aldehydes can be used to produce polymers, resins, dyes, flavorings, plasticizers, perfumes, pharmaceuticals, and other chemicals. Some are used as solvents, preservatives, or disinfectants. Some natural and synthetic compounds, such as vitamins and hormones, are also aldehydes.

The terms "fatty aldehyde biosynthetic polypeptide," "carboxylic acid reductase," and "CAR" are used interchangeably herein.

The term "fatty ester" refers to an ester having greater than 5 carbon atoms. In certain embodiments, a fatty ester is an ester made from a fatty acid, for example a fatty acid ester. In one embodiment, a fatty ester contains an A side (i.e., the carbon chain attached to the carboxylate oxygen) and a B side (i.e., the carbon chain comprising the parent carboxylate). In a particular embodiment, when a fatty ester is derived from the fatty acid biosynthetic pathway, the A side is contributed by an alcohol, and the B side is contributed by a fatty acid. Any alcohol can be used to form the A side of the fatty esters. For example, the alcohol can be derived from the fatty acid biosynthetic pathway. Alternatively, the alcohol can be produced through non-fatty acid biosynthetic pathways. Moreover, the alcohol can be provided exogenously. For example, the alcohol can be supplied to the fermentation broth in instances where the fatty ester is produced by an organism. Alternatively, a carboxylic acid, such as a fatty acid or acetic acid, can be supplied exogenously in instances where the fatty ester is produced by an organism that can also produce alcohol. The carbon chains comprising the A side or B side can be of any length. In one embodiment, the A side of the ester is at least about 1, 2, 3, 4, 5, 6, 7, 8, 10, 12, 14, 16, 18, or 20 carbons in length. The B side of the ester is at least about 4, 6, 8, 10, 12, 14, 16, 18, 20, 22, 24, or 26 carbons in length. The A side and/or the B side can be straight or branched chain. The branched chains may have one or more points of branching. In addition, the branched chains may include cyclic branches, such as cyclopropane or epoxide moieties. Furthermore, the A side and/or B side can be saturated or unsaturated. If unsaturated, the A side and/or B side can have one or more points of unsaturation. In one embodiment, the fatty ester is produced biosynthetically. In this embodiment, first the fatty acid is "activated." Non-limiting examples of activated fatty acids are acyl-CoA, acyl ACP, acyl-AMP, and acyl phosphate. Acyl-CoA can be a direct product of fatty acid biosynthesis or degradation. In addition, acyl-CoA can be synthesized from a free fatty acid, a CoA, and an adenosine nucleotide triphosphate (ATP). An example of an enzyme that produces acyl-CoA is an acyl-CoA synthase. After the fatty acid is activated, it can be readily transferred to a recipient nucleophile. Exemplary nucleophiles are alcohols, thiols, amines, or phosphates. In another embodiment, the fatty ester can be derived from a fatty acyl-thioester and an alcohol. In one embodiment, the fatty ester is a wax. The wax can be derived from a long chain fatty alcohol and a long chain fatty acid. In another embodiment, the fatty ester is a fatty acid thioester, for example fatty acyl Coenzyme A (acyl-CoA). In other embodiments, the fatty ester is a fatty acyl panthothenate, an acyl acyl carrier protein (acyl-ACP), a fatty acyl enzyme ester, or a fatty phosphate ester. An ester can be formed from an acyl enzyme ester intermediate through the alcoholysis of the ester bond to form a new ester and the free enzyme. Fatty esters have many uses. For example, fatty esters can be used as, or as a component of, a biofuel or a surfactant.

The term "fatty ester vs. other fatty acid derivatives" as used herein refers to the proportional yield of fatty ester in comparison with the total amount of other fatty acid derivatives that are not fatty esters. In other words, the amount of fatty esters is compared with the amount of fatty acid derivatives other than fatty esters.

The term "fermentation productivity" or "productivity" refers to the rate of product production and is expressed g $L^{-1}h^{-1}$. Specific Productivity is the productivity normalized for catalyst concentration and is expressed as g/g $L^{-1}h^{-1}$ g (catalyst)$^{-1}$.

The term "fermentation titer" or "titer" refers to the concentration of a reaction product, usually expressed as g/L but also in other units (i.e., molar, mass/mass, mass/volume, or volume/volume).

The term "fermentation yield" or "yield" refers to the amount of product produced from a given amount of raw material and is usually expressed as the ratio of mass of the product produced divided by the mass of raw material consumed (g product/g raw material). It can also be expressed a molar yield (moles product/moles raw material).

The term "fraction of modern carbon" refers to the parameter "$f_M$" as defined by National Institute of Standards and Technology (NIST) Standard Reference Materials (SRMs) 4990B and 4990C, known as oxalic acids standards HOxI and HOxII, respectively. The fundamental definition relates to 0.95 times the $^{14}C/^{12}C$ isotope ratio HOxI (referenced to AD 1950). This is roughly equivalent to decay-corrected pre-Industrial Revolution wood. For the current living biosphere (plant material), $f_M$ is about 1.1.

The term "functional assay" refers to an assay that provides an indication of a protein's activity. In particularly preferred embodiments, the term refers to an assay system in which a protein is analyzed for its ability to function in its natural capacity. For example, in the case of enzymes, a functional assay involves determining the effectiveness of the enzyme in catalyzing a reaction.

"Gene" refers to a polynucleotide (e.g., a DNA segment), which encodes a polypeptide, and includes regions preceding and following the coding regions as well as intervening sequences (introns) between individual coding segments (exons).

The term "homologous genes" refers to a pair of genes from different but related species, which correspond to each other and which are identical or similar to each other. The term encompasses genes that are separated by the speciation process during the development of new species) (e.g., orthologous genes), as well as genes that have been separated by genetic duplication (e.g., paralogous genes).

The term "endogenous protein" refers to a protein that is native to or naturally occurring in a cell. "Endogeneous polynucleotide" refers to a polynucleotide that is in the cell and was not introduced into the cell using recombinant engineering techniques. For example, a gene that was present in the cell when the cell was originally isolated from nature. A gene is still considered endogenous if the control sequences, such as a promoter or enhancer sequences that activate transcription or translation, have been altered through recombinant techniques. Conversely, the term "heterologous" is also used herein, and refers to a protein or a polynucleotide that does not naturally occur in a host cell.

The term "homologous recombination" refers to the exchange of DNA fragments between two DNA molecules or paired chromosomes at sites of identical or nearly identical nucleotide sequences. In certain embodiments, chromosomal integration is homologous recombination.

The term "homologous sequences" as used herein refers to a polynucleotide or polypeptide sequence having, for example, about 100%, about 99% or more, about 98% or more, about 97% or more, about 96% or more, about 95% or more, about 94% or more, about 93% or more, about 92% or more, about 91% or more, about 90% or more, about 88% or more, about 85% or more, about 80% or more, about 75% or more, about 70% or more, about 65% or more, about 60% or more, about 55% or more, about 50% or more, about 45% or more, or about 40% or more sequence identity to another polynucleotide or polypeptide sequence when optimally aligned for comparison. In particular embodiments, homologous sequences can retain the same type and/or level of a particular activity of interest. In some embodiments, homologous sequences have between 85% and 100% sequence identity, whereas in other embodiments there is between 90% and 100% sequence identity. In particular embodiments, there is 95% and 100% sequence identity.

"Homology" refers to sequence similarity or sequence identity. Homology is determined using standard techniques known in the art (see, e.g., Smith and Waterman, Adv. Appl. Math., 2:482, 1981; Needleman and Wunsch, J. Mol. Biol., 48:443, 1970; Pearson and Lipman, Proc. Natl. Acad. Sci. USA 85:2444, 1988; programs such as GAP, BESTFIT, FASTA, and TFASTA in the Wisconsin Genetics Software Package (Genetics Computer Group, Madison, Wis.); and Devereux et al., Nucl. Acid Res., 12:387-395, 1984). A non-limiting example includes the use of the BLAST program (Altschul et al., Gapped BLAST and PSI-BLAST: a new generation of protein database search programs, Nucleic Acids Res. 25:3389-3402, 1997) to identify sequences that can be said to be "homologous." A recent version such as version 2.2.16, 2.2.17, 2.2.18, 2.2.19, or the latest version, including sub-programs such as blastp for protein-protein comparisons, blastn for nucleotide-nucleotide comparisons, tblastn for protein-nucleotide comparisons, or blastx for nucleotide-protein comparisons, and with parameters as follows: Maximum number of sequences returned 10,000 or 100,000; E-value (expectation value) of 1e-2 or 1e-5, word size 3, scoring matrix BLOSUM62, gap cost existence 11, gap cost extension 1, may be suitable. An E-value of 1e-5, for example, indicates that the chance of a homologous match occurring at random is about 1 in 10,000, thereby marking a high confidence of true homology.

The term "host strain" or "host cell" refers to a suitable host for an expression vector comprising a DNA of the present invention.

The term "hybridization" refers to the process by which a strand of polynucleotide joins with a complementary strand through base pairing, as known in the art. A polynucleotide sequence is considered to be "selectively hybridizable" to a reference polynucleotide sequence if the two sequences specifically hybridize to one another under moderate to high stringency hybridization and wash conditions. Hybridization conditions are based on the melting temperature ($T_m$) of the polynucleotide binding complex or probe. For example, "maximum stringency" typically occurs at about $T_m$–5° C. (5° C. below the $T_m$ of the probe); "high stringency" at about 5-10° C. below the $T_m$; "intermediate stringency" at about 10-20° C. below the $T_m$ of the probe; and "low stringency" at about 20-25° C. below the $T_m$. Functionally, maximum stringency conditions may be used to identify sequences having strict identity or near-strict identity with the hybridization probe; while an intermediate or a low stringency hybridization can be used to identify or detect polynucleotide sequence homologs. Moderate and high stringency hybridization conditions are well known in the art. An example of high stringency conditions includes hybridization at about 42° C. in 50% formamide, 5×SSC, 5×Denhardt's solution, 0.5% SDS and 100 pg/mL denatured carrier DNA followed by washing two times in 2×SSC and 0.5% SDS at room temperature and two additional times in 0.1×SSC and 0.5% SDS at 42° C. An example of moderate stringent conditions includes an overnight incubation at 37° C. in a solution comprising 20% formamide, 5×SSC (150 mM NaCl, 15 mM trisodium citrate), 50 mM sodium phosphate (pH 7.6), 5×Denhardt's solution, 10% dextran sulfate and 20 mg/mL denatured sheared salmon sperm DNA, followed by washing the filters in 1×SSC at about 37° C. to about 50° C. Those of skill in the art know how to adjust the temperature, ionic strength, and other conditions as necessary to accommodate factors such as probe length and the like.

The term "hydrocarbon" refers to chemical compounds that contain the elements carbon (C) and hydrogen (H). All hydrocarbons consist of a carbon backbone and atoms of hydrogen attached to that backbone. Sometimes, the term is used as a shortened form of the term "aliphatic hydrocarbon." There are essentially three types of hydrocarbons: (1) aromatic hydrocarbons, which have at least about one aromatic ring; (2) saturated hydrocarbons, also known as alkanes, which lack double, triple or aromatic bonds; and (3) unsaturated hydrocarbons, which have one or more double or triple bonds between carbon atoms and include, for example, alkenes (e.g., dienes), and alkynes.

The term "identical," in the context of two polynucleotide or polypeptide sequences, means that the residues in the two sequences are the same when aligned for maximum correspondence, as measured using a sequence comparison or analysis algorithm such as those described herein. For example, if when properly aligned, the corresponding segments of two sequences have identical residues at 5 positions out of 10, it is said that the two sequences have a 50% identity. Most bioinformatic programs report percent identity over aligned sequence regions, which are typically not the entire molecules. If an alignment is long enough and contains enough identical residues, an expectation value can be calculated, which indicates that the level of identity in the alignment is unlikely to occur by random chance.

The term "improving mutation" or "performance-enhancing mutation" refers to a mutation in a protein that lead to altered properties, which confer improved performance in terms of a target and/or desired property of a protein as compared to a precursor protein.

The term "insertion," when used in the context of a polypeptide sequence, refers to an insertion in the amino acid sequence of a precursor polypeptide, resulting in a mutant polypeptide having an amino acid that is inserted between two existing contiguous amino acids, i.e., adjacent amino acids residues, which are present in the precursor polypeptide. The term "insertion," when used in the context of a polynucleotide sequence, refers to an insertion of one or more nucleotides in the precursor polynucleotide between two existing contiguous nucleotides, i.e., adjacent nucleotides, which are present in the precursor polynucleotides.

The term "introduced" refers to, in the context of introducing a polynucleotide sequence into a cell, any method suitable for transferring the polynucleotide sequence into the cell. Such methods for introduction include but are not limited to protoplast fusion, transfection, transformation, conjugation, and transduction (see, e.g., Ferrari et al., Genetics, in Hardwood et al, (eds.), *Bacillus*, Plenum Publishing Corp., pp. 57-72, 1989).

The term "isolated" or "purified" means a material that is removed from its original environment, for example, the natural environment if it is naturally occurring, or a fermentation broth if it is produced in a recombinant host cell fermentation medium. A material is said to be "purified" when it is present in a particular composition in a higher or lower concentration than the concentration that exists prior to the purification step(s). For example, with respect to a composition normally found in a naturally-occurring or wild type organism, such a composition is "purified" when the final composition does not include some material from the original matrix. As another example, where a composition is found in combination with other components in a recombinant host cell fermentation medium, that composition is purified when the fermentation medium is treated in a way to remove some component of the fermentation, for example, cell debris or other fermentation products, through, for example, centrifugation or distillation. As another example, a naturally-occurring polynucleotide or polypeptide present in a living animal is not isolated, but the same polynucleotide or polypeptide, separated from some or all of the coexisting materials in the natural system, is isolated, whether such process is through genetic engineering or mechanical separation. Such polynucleotides can be parts of vectors. Alternatively, such polynucleotides or polypeptides can be parts of compositions. Such polynucleotides or polypeptides can be considered "isolated" because the vectors or compositions comprising thereof are not part of their natural environments. In another example, a polynucleotide or protein is said to be purified if it gives rise to essentially one band in an electrophoretic gel or a blot.

The term "mature," in the context of a protein, means a form of a protein or peptide that is in its final functional form. To exemplify, a mature form of a thioesterase of the present invention comprises the amino acid residues 1-182 of SEQ ID NO:31 in FIG. 58.

The term "modified fatty acid derivatives" refers to products made, at least in part, from a part of the fatty acid biosynthetic pathway of a recombinant host cell, wherein the product differs from the product made by such host cell in the absence of the mutant thioesterase of the invention. Thus, where a mutant thioesterase (or naturally-occurring equivalent thereof) is introduced into a recombinant host cell, resulting in the production of a fatty acid derivative that has a different product profile, for example, a higher or lower concentration of certain fatty acid derivatives having a specific chain length, or a higher or lower concentration of a certain type of fatty acid derivative, that fatty acid material is "modified" within the context of this invention.

The term "mutant thioesterase" or "variant thioesterase" refers to a thioesterase that comprises a mutation with reference to a precursor thioesterase.

The term "mutation" refers to, in the context of a polynucleotide, a modification to the polynucleotide sequence resulting in a change in the sequence of a polynucleotide with reference to a precursor polynucleotide sequence. A mutant polynucleotide sequence can refer to an alteration that does not change the encoded amino acid sequence, for example, with regard to codon optimization for expression purposes, or that modifies a codon in such a way as to result in a modification of the encoded amino acid sequence. Mutations can be introduced into a polynucleotide through any number of methods known to those of ordinary skill in the art, including random mutagenesis, site-specific mutagenesis, oligonucleotide directed mutagenesis, gene shuffling, directed evolution techniques, combinatorial mutagenesis, site saturation mutagenesis among others.

"Mutation" or "mutated" means, in the context of a protein, a modification to the amino acid sequence resulting in a change in the sequence of a protein with reference to a precursor protein sequence. A mutation can refer to a substitution of one amino acid with another amino acid, an insertion or a deletion of one or more amino acid residues. Specifically, a mutation can also be the replacement of an amino acid with a non-natural amino acid, or with a chemically-modified amino acid or like residues. A mutation can also be a truncation (e.g., a deletion or interruption) in a sequence or a subsequence from the precursor sequence. A mutation may also be an addition of a subsequence (e.g., two or more amino acids in a stretch, which are inserted between two contiguous amino acids in a precursor protein sequence) within a protein, or at either terminal end of a protein, thereby increasing the length of (or elongating) the protein. A mutation can be made by modifying the DNA sequence corresponding to the precursor protein. Mutations can be introduced into a protein sequence by known methods in the art, for example, by creating synthetic DNA sequences that encode the mutation with reference to precursor proteins, or chemically altering the protein itself. A "mutant" as used herein is a protein comprising a mutation. For example, it is also possible to make a mutant by replacing a portion of a thioesterase with a wild type sequence that corresponds to such portion but includes a desired variation at a specific position that is naturally-occurring in the wild type sequence.

A "naturally-occurring equivalent," in the context of the present invention, refers to a naturally-occurring thioesterase, or a portion thereof, that comprises a naturally-occurring residue, wherein the naturally-occurring residue corresponds to a mutation in 'TesA (e.g., a mutation in SEQ ID NO:31 of FIG. 58) that has introduced a desirable altered property to 'TesA. Examples of naturally-occurring equivalent thioesterases having such modifications are provided in FIG. 55.

The term "operably linked," in the context of a polynucleotide sequence, refers to the placement of one polynucleotide sequence into a functional relationship with another polynucleotide sequence. For example, a DNA encoding a secretory leader (e.g., a signal peptide) is operably linked to a DNA encoding a polypeptide if it is expressed as a preprotein that participates in the secretion of the polypeptide. A promoter or an enhancer is operably linked to a coding sequence if it affects the transcription of the sequence. A ribosome binding site is operably linked to a coding sequence if it is positioned so as to facilitate translation. Generally, "operably linked" means that the DNA sequences being linked are contiguous, and, in the case of a secretory leader, contiguous and in the same reading frame.

The term "operon region" refers to a group of contiguous genes that are transcribed as a single transcription unit from a common promoter, and are thereby subject to co-regulation. In some embodiments, the operon includes a regulator gene.

The term "optimal alignment" refers to the alignment giving the highest overall alignment score.

The term "orthologs" or "orthologous genes" refers to genes in different species that have evolved from a common ancestral gene by speciation. Typically, orthologs retain the same function during the course of evolution. Identification of orthologs finds use in the reliable prediction of gene function in newly sequenced genomes.

"Overexpressed" or "overexpression" in a host cell occurs if the enzyme is expressed in the cell at a higher level than the level at which it is expressed in a corresponding wild-type cell.

The term "paralog" or "paralogous genes" refers to genes that are related by duplication within a genome. While orthologs retain the same function through the course of evolution, paralogs evolve new functions, even though some functions are often related to the original one. Examples of paralogous genes include, but are not limited to, genes encoding myoglobin and hemoglobin, which arose from the same ancient ancestor but evolved to have different functions.

The term "partition coefficient" means the equilibrium concentration of a compound in an organic phase divided by the concentration at equilibrium in an aqueous phase (e.g., in a fermentation broth). In one embodiment of the bi-phasic system described herein, the organic phase is formed by the fatty acid derivative during the production process. In certain circumstances, an organic phase can also be provided, for example, a layer of octane can be provided to the fermentation broth to facilitate product separation. When describing a two phase system, the partition coefficient, P, is usually discussed in terms of log P. A compound with a log P of 1 would partition 10:1 to the organic phase. A compound with a log P of −1 would partition 1:10 to the organic phase. By choosing an appropriate fermentation broth and organic phase, a fatty acid derivative with a high log P value will separate into the organic phase even at very low concentrations in the fermentation vessel.

The terms "percent sequence identity," "percent amino acid sequence identity," "percent gene sequence identity," and/or "percent polynucleotide sequence identity," with respect to two polypeptides, polynucleotides and/or gene sequences (as appropriate), refer to the percentage of residues that are identical in the two sequences when the sequences are optimally aligned. Thus, 80% amino acid sequence identity means that 80% of the amino acids in two optimally aligned polypeptide sequences are identical.

The term "plasmid" refers to a circular double-stranded (ds) DNA construct used as a cloning vector, and which forms an extrachromosomal self-replicating genetic element in some eukaryotes or prokaryotes, or integrates into the host chromosome.

The term "precursor thioesterase" refers a thioesterase protein from which the mutant thioesterase of the invention can be derived, through, for example, recombinant or chemical means. Examples of precursor thioesterases are naturally-occurring or wildtype thioesterases from plant, animal or microbial sources. A precursor thioesterase can also be a thioesterase that is non-naturally-occurring. An example of a non-naturally-occurring thioesterase is a thioesterase made through, for example, random mutation, chemical synthesis, molecular evolution, or site directed mutagenesis, which can serve as a useful starting point from which to design and/or make the mutant thioesterases of the invention.

A "primer" is an oligonucleotide, whether occurring naturally as in a purified restriction digest sample, or produced synthetically, which is capable of acting as a point of initiation of synthesis when placed under conditions in which the synthesis of a primer extension product that is complementary to a reference polynucleotide strand is induced. Suitable conditions include, for example, the presence of nucleotides and an inducing agent such as a DNA polymerase, and a suitable temperature and pH. A primer is preferably single stranded for maximum efficiency in amplification, but can alternatively be double stranded. If double stranded, a primer can be first treated to separate its strands before it is used to prepare extension products. In particular embodiments, a primer is an oligodeoxyribonucleotide. In certain preferred embodiments, a primer is sufficiently long to prime the synthesis of extension products in the presence of an inducing agent. The exact lengths of primers will depend on a number of factors, including temperature, source of primer, and the methods used for amplification.

The term "probe" refers to an oligonucleotide, whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA or other enzyme-based histochemical assays), fluorescent, radioactive, and luminescent systems. It is not intended that the present invention be limited to any particular detection system or label.

A "production host" is a cell used to produce products. As disclosed herein, a production host is modified to express or overexpress selected genes, or to have attenuated expression of selected genes. Non-limiting examples of production hosts include plant, animal, human, bacteria, yeast, cyanobacteria, algae, and/or filamentous fungi cells.

A "promoter" is a polynucleotide sequence that functions to direct transcription of a downstream gene. In preferred embodiments, the promoter is appropriate to the host cell in which the target gene is being expressed. The promoter, together with other transcriptional and translational regulatory polynucleotide sequences (also termed "control sequences") is necessary to express a given gene. In general, the transcriptional and translational regulatory sequences include, but are not limited to, promoter sequences, ribosomal binding sites, transcriptional start and stop sequences, translational start and stop sequences, and enhancer or activator sequences.

The term "promoters" or "enhancers" refers to transcriptional control signals in eukaryotes. Promoters and enhancers consist of short arrays of DNA sequences that interact specifically with cellular proteins involved in transcription (Maniatis et al., Science, 236:1237, 1987). Promoter and enhancer elements have been isolated from a variety of eukaryotic sources including genes in yeast, insect, mammalian and plant cells. Promoter and enhancer elements have also been isolated from viruses. Analogous control elements, such as promoters and enhancers, are also found in prokaryotes. The selection of a particular promoter and enhancer depends on the cell type used to express the protein of interest. Some eukaryotic and prokaryotic promoters and enhancers have a broad production host cell range while others are functional in a limited subset of production host cells (see, e.g., Voss et al., Trends Biochem. Sci., 11:287, 1986; Maniatis et al., 1987, supra). The term "promoter element," "promoter," or "promoter sequence" refers to a DNA sequence that functions as a switch which activates the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA.

The term "property" refers to, in the context of a polynucleotide, any characteristic or attribute of a polynucleotide that can be selected or detected. These properties include, but are not limited to, a property affecting binding to a polypeptide, a property conferred on a cell comprising a particular polynucleotide, a property affecting gene transcription (e.g., promoter strength, promoter recognition, promoter regulation, enhancer function), a property affecting RNA processing (e.g., RNA splicing, RNA stability, RNA conformation, and post-transcriptional modification), a property affecting translation (e.g., level, regulation, binding of mRNA to ribosomal proteins, post-translational modification). For example, a binding site for a transcription factor, polymerase, regulatory factor, and the like, of a polynucleotide may be altered to produce desired characteristics or to identify undesirable characteristics.

The term "property" refers to, in the context of a protein, any characteristic or attribute of a protein that can be selected or detected.

The terms "protein" and "polypeptide" are used interchangeably herein. The 3-letter code as well as the 1-letter code for amino acid residues as defined in conformity with the IUPAC-IUB Joint Commission on Biochemical Nomenclature (JCBN) is used throughout this disclosure. It is also understood that a polypeptide may be coded for by more than one polynucleotide sequence due to the degeneracy of the genetic code. An enzyme is a protein.

The terms "proportional yield" and "percentage yield" are used interchangeably herein. It refers to the amount of a desired product in relation to other products that are within the same mixture produced by a recombinant host of the present invention. For example, the proportional yield of a desired product can be improved such that it is more predominant over the other components in the product mixture to reduce the burden of purification. In another example, the proportional yield of an undesired product (i.e., a component that will need to be removed from the desired product) can be reduced such that it is less predominant over the desired component in the product mixture to achieve the same end. Proportional yields are expressed herein in the form of "X vs. other fatty acid derivatives," which compares the amount of X, which is a type of fatty acid derivative (e.g., a fatty ester, a fatty acid derivative of a particular chain length), and the term "other fatty acid derivatives" means the aggregate amount of all other fatty acid derivatives other than X that are produced in the same experiment, culture, or fermentation run.

The term "prosequence" refers to an amino acid sequence between the signal sequence and mature protein that is necessary for the secretion of the protein. Cleavage of the prosequence can lead to a mature active protein/enzyme under certain circumstances and suitable conditions.

The term "recombinant," when used to modify the term "cell" or "vector" herein, refers to a cell or a vector that has been modified by the introduction of a heterologous polynucleotide sequence, or that the cell is derived from a cell so modified. Thus, for example, recombinant cells express genes that are not found in identical form within the native (non-recombinant) form of the cells or express, as a result of deliberate human intervention, native genes that are otherwise abnormally expressed, underexpressed or not expressed at all. The terms "recombination," "recombining," and generating a "recombined" polynucleotide refer generally to the assembly of two or more polynucleotide fragments wherein the assembly gives rise to a chimeric polynucleotide made from the assembled parts.

The term "regulatory segment," "regulatory sequence," or "expression control sequence" refers to a polynucleotide sequence that is operatively linked with another polynucleotide sequence that encodes the amino acid sequence of a polypeptide chain to effect the expression of that encoded amino acid sequence. The regulatory sequence can inhibit, repress, promote, or even drive the expression of the operably-linked polynucleotide sequence encoding the amino acid sequence.

The term "selectable marker" or "selective marker" refers to a polynucleotide (e.g., a gene) capable of expression in a host cell, which allows for ease of selection of those hosts containing the vector. Examples of selectable markers include but are not limited to antimicrobial markers. Thus, the term "selectable marker" refers to a gene that provides an indication when a host cell has taken up an incoming sequence of interest or when some other reaction has taken place. Typically, selectable markers are genes that confer antimicrobial resistance or a metabolic advantage on the host cells to allow the cells containing the exogenous sequences to be distinguished from the cells that have not received the exogenous sequences. A "residing selectable marker" is one that is located on the chromosome of the microorganism to be transformed. A residing selectable marker encodes a gene that is different from the selectable marker on the transforming construct. Selective markers are known to those of skill in the art. As indicated above, suitably the marker is an antimicrobial resistant marker, including, for example, $amp^R$; $phleo^R$; $spec^R$; $kan^R$; $ery^R$; $tet^R$; $cmp^R$; and $neo^R$. See, e.g., Guerot-Fleury, Gene, 167: 335-337, 1995; Palmeros et al., Gene, 247:255-264, 2000; and Trieu-Cuot et al., *Gene,* 23:331-341, 1983. Other markers useful in accordance with the invention include, but are not limited to, auxotrophic markers, such as tryptophan; and detection markers, such as 6-galactosidase.

The term "selectable marker-encoding nucleotide sequence" refers to a polynucleotide sequence that is capable of expression in the host cells and where the expression of the selectable marker confers to the cells containing the expressed gene the ability to grow in the presence of a corresponding selective agent or in the absence of one or more essential nutrients.

A "signal sequence" or "signal peptide" refers to a polynucleotide or amino acid sequence that participates in the secretion of the mature or precursor forms of a protein. This definition of signal sequence is a functional one, meant to include all those amino acid sequences encoded by the N-terminal portion of the protein gene, which participate in the effectuation of the secretion of protein. They are often, but not universally, bound to the N-terminal portion of a protein or to the N-terminal portion of a precursor protein. The signal sequence can be endogenous or exogenous. The signal sequence can be one that is normally associated with the protein (e.g., thioesterase), or can be one originated or derived from a gene encoding another secreted protein. An exemplary exogenous signal sequence comprises the first seven amino acid residues of the signal sequence from *Bacillus subtilis* subtilisin fused to the remainder of the signal sequence of the subtilisin from *Bacillus* lentos (ATCC 21536). Another exemplary signal sequence comprises the signal sequence for TesA that is removed to produce 'TesA.

The term "substantially identical," in the context of two polynucleotides or two polypeptides refers to a polynucleotide or polypeptide that comprises at least 70% sequence identity, for example, at least 75%, at least 80%, at least 85%, at least 90%, at least 91%, at least 92%, at least 93%, at least 94%, at least 95%, at least 96%, at least 97%, at least 98%, or at least 99% sequence identity as compared to a reference sequence using the programs or algorithms (e.g., BLAST, ALIGN, CLUSTAL) using standard parameters.

One indication that two polypeptides are substantially identical can be that the first polypeptide is immunologically cross-reactive with the second polypeptide. Typically, polypeptides that differ by conservative amino acid substitutions are immunologically cross-reactive. Thus, a polypeptide is substantially identical to a second polypeptide, for example, when the two peptides differ only by a conservative substitution. Another indication that two polynucleotide sequences are substantially identical is that the two molecules hybridize to each other under stringent conditions (e.g., within a range of medium to maximum stringency).

"Substantially purified" means molecules that are at least about 60% free, preferably at least about 75% free, about 80% free, about 85% free, and more preferably at least about 90% free from other components with which they are naturally associated. As used herein, the term "purified" or "to purify" also refers to the removal of contaminants from a sample. For example, the removal of contaminants can result in an increase in the percentage of fatty acid derivatives of interest in a sample. For example, after fatty acid derivatives are expressed in plant, bacterial, yeast, or mammalian production host cells, the fatty acid derivatives can be purified by, e.g., the removal of production host cell proteins. This step, also called recovery, involves separating and processing the fatty acid derivative composition such that the composition is useful in industrial applications, for example, as a fuel or a chemical. After purification, the percentage of fatty acid derivatives in the sample is increased. The term purified does not require absolute purity; rather, it is intended as a relative term. Thus, for example, a purified fatty acid derivative preparation is one in which the product is more concentrated than the product is in its environment within a cell. For example, a purified fatty ester is one that is substantially separated from cellular components (e.g., polynucleotides, lipids, carbohydrates, and other peptides) that can accompany it. In another example, a purified fatty ester preparation is one in which the fatty ester is substantially free from contaminants, such as those that might be present following fermentation. For example, a fatty ester is said to be "purified" when at least about 50% by weight of a sample is composed of the fatty ester. In another example when at least about 60%, 70%, 80%, 85%, 90%, 91%, 92%, 93%, 94%, 95%, 96%, 97%, 98%, or 99% or more by weight of a sample is composed of the fatty ester.

"Substitution" means replacing an amino acid in the sequence of a precursor protein with another amino acid at a particular position, resulting in a mutant of the precursor protein. The amino acid used as a substitute can be a naturally-occurring amino acid, or can be a synthetic or non naturally-occurring amino acid.

The term "surfactants" refers to substances that are capable of reducing the surface tension of a liquid in which they are dissolved. They are typically composed of a water-soluble head and a hydrocarbon chain or tail. The water-soluble head is hydrophilic and can be either ionic or nonionic. The hydrocarbon chain is hydrophobic. Surfactants are used in a variety of products, including detergents and cleaners, and are also used as auxiliaries for textiles, leather and paper, in chemical processes, in cosmetics and pharmaceuticals, in the food industry, in agriculture, and in oil recovery. In addition, they can be used to aid in the extraction and isolation of crude oils which are found in hard-to-access environments or in water emulsions. There are four types of surfactants characterized by varying uses. Anionic surfactants have detergent-like activity and are generally used for cleaning applications. Cationic surfactants contain long chain hydrocarbons and are often used to treat proteins and synthetic polymers or are components of fabric softeners and hair conditioners. Amphoteric surfactants also contain long chain hydrocarbons and are typically used in shampoos. Non-ionic surfactants are often used in cleaning products.

The term "synthase" refers to an enzyme that catalyzes a synthesis process. As used herein, the term "synthase" includes synthases and synthetases.

The term "target property" refers to a property of the starting gene that is intended to be altered.

The term "thioesterase" refers to an enzyme that has thioesterase activity. Thioesterases include thioester hydrolases, which are identified as members of Enzyme Classification E.C. 3.1.2 and are obtainable from a variety of sources. Plant thioesterases are described in, for example, Voelker and Davies, J. Bact., Vol., 176, No. 23, pp. 7320-27, 1994, U.S. Pat. Nos. 5,667,997, 5,455,167. Thioesterases are also obtainable from microbial sources, such as those described in Akoh et al., Prog. Lipid Res., vol. 43, no. 6, pp. 534-52, 2004; Diczfalusy and Alexson, Arch. Biochem. Biophys., vol. 334, no. 1, pp. 104-12, 1996; Larson and Kolattukudy, Arch. Biochem. Biophys., vol. 237, no. 1, pp. 27-37, 1985; Lawson et al., Biochemistry, vol. 33, no. 32, pp. 9382-88, 1994; Lee et al., Eur. J. Biochem., vol. 184, no. 1, pp. 21-28, 1989; Naggert et al., J. Biol. Chem., vol. 266, no. 17, pp. 11044-50, 1991; Nie et al., Biochemistry, vol. 47, no. 29, pp. 7744-51, 2008; Seay and Lueking, Biochemistry, vol. 25, no. 9, pp. 2480-85, 1986; Spencer et al., J. Biol. Chem., vol. 253, no. 17, pp. 5922-26, 1978; and Zhuang et al., Biochemistry, vol. 47, no. 9, pp. 2789-96, 2008. Thioesterases are also obtainable from, for example, cyanobacterial, algal, mammalian, insect, and fungal sources. A thioesterase can have activity other than thioesterase activity, for example proteolytic activity or oxygen ester hydrolysis activity. A particularly useful thioesterase is the 'TesA (or thioesterase I) enzyme from E. coli, which is a truncated version of the full-length TesA serine thioesterase enzyme that is described in Cho and Cronan, J. Biol. Chem., vol., 268, no. 13, pp. 9238-45, 1992. An E. coli 'TesA polypeptide comprises 182 amino acids, and is the product of a cleavage reaction wherein the 26 amino acid leader sequence of E. coli TesA is removed. E. coli 'Tes A, for example, has the amino acid sequence of SEQ ID NO:31 in FIG. 58.

The term "thioesterase activity" refers to the capacity to catalyze a thioester cleavage reaction, which usually involves the hydrolysis of a thioester at a thiol group into an acid and a thiol, but can also include a transesterification step in which a thioester bond is cleaved and a new ester bond is formed. In general, an acyl-ACP thioesterase is capable of catalyzing the hydrolytic cleavage of fatty acyl-acyl carrier protein thioesters and/or fatty acyl-coenzyme A thioesters. Examples of enzymes having thioesterase activity include acetyl-CoA hydrolase, palmitoyl-CoA hydrolase, succinyl-CoA hydrolase, formyl-CoA hydrolase, acyl-CoA hydrolase, palmitoyl-protein thioesterase, and ubiquitin thiolesterase. Thioesterase activity can be established by any of the following assays:

Acyl-CoA Hydrolysis Assay:
  A Tris-HCl buffer, 0.1 M, pH 8.0; Palmitoyl-CoA, 5 µM; DTNB, 0.01 M in 0.1 M potassium phosphate buffer, pH 7.0 are used to prepare a complete assay mixture. The assay mixture thus contains a final concentration of 10 µmol of Tris-HCl buffer, pH 8.0, 0.05 µmol of DTNB, and 0.01 µmol of palmitoyl-CoA. The complete assay mixture is then mixed with the thioesterase, in a final volume of 2.0 mL.

The rate of cleavage of the acyl-CoA substrate is measured by monitoring the change in absorbance at 405 nm, using a molar extinction coefficient of 13,600 M$^{-1}$ cm$^{-1}$.

In Vivo Assay:

The thioesterase of interest is expressed in a suitable host, such as an *E. coli*. Following expression of the protein, the culture is acidified with 1 N HCl to a final pH of about 2.5 and then extracted with an equal volume of ethyl acetate. Free fatty acids in the organic phase are derivatized with tetramethylammonium hydroxide (TMAH) to generate the respective methyl esters, which are then analyzed on a gas chromatograph equipped with a flame ionization detector.

Thiolactone Hydrolysis Assay:

A reagent solution containing 25 mM L-homocysteine thiolactone (L-HcyT) and 0.5 mM 5,5-dithio-bis-2-nitrobenzoic acid (DTNB) in 0.1 M HEPES buffer (pH 7.3) is first prepared. Enzyme is then added to the reagent solution and L-HcyT hydrolysis is monitored by detecting the free thiol group with DTNB at 412 nm (ε=13,600 M$^{-1}$ cm$^{-1}$ for 5-thio-2-nitrobenzoic acid).

4-MU-6S-Palm-βGlc Assay:

A reaction mixture containing 10 μL of thioesterase enzyme and 20 μL of substrate solution is first prepared. The substrate solution contains 0.64 mM MU-6S-Palm-β-Glc, 15 mM dithiothreitol (DTT), 0.375% (w/v) Triton X-100, and 0.1 U β-glucosidase from almonds in McIlvain's phosphate/citrate buffer, pH 4.0. The reaction mixture is incubated for 1 hour at 37° C. Exogenous almond β-glucosidase is added to hydrolyze the reaction intermediate, MU-6-thio-β-glucoside, quantitatively. The hydrolysis reaction is terminated by the addition of 200 μL of 0.5 M sodium carbonate, pH 10.7, containing 0.025% Triton X-100, and the fluorescence of the released 4-methylumbelliferone (MU) is measured in a fluorometer ($\lambda_{ex}$=372, $\lambda_{em}$=445 nm).

Lysophospholipase Assay:

A reaction mixture containing 10 μL of thioesterase mixed with 10 μL of 3 mM 1-oleoyl-phosphatidylethanolamine, 25 μL of 100 mM Tris-HCl (pH 7.0), and 5 μL of 5 mM EDTA is prepared. The reaction is terminated with the addition of 1.5 mL CHCE:CH$_3$OH (1:2), followed by the addition of water to bring the total aqueous volume to 0.9 mL. The organic phase is then analyzed by thin layer chromatography together with suitable standards, using plates prepared from 40 g Silica Gel H suspended in 95 mL of 1 mM sodium tetraborate. The solvent system consists of CHCE:CH$_3$OH:H$_2$O (95:35:5).

Protease Substrate Assay:

A reaction mixture containing 10 μL of enzyme mixed with 800 μL 12.5 mM Tris-HCl (pH 8.0) containing 0.25% Triton X-100 and 10 μL of Cbz-Phe-ONp dissolved in DMSO is prepared. The p-nitrophenol released via cleavage of the substrate is measured by monitoring the absorbance at 405 nm.

Fatty Acyl-PNP Hydrolysis Assay:

A reagent solution containing 2% Triton X-100 in 50 mM sodium phosphate, pH 7.0, and 10 mM C$_{12}$-p-nitrophenol (acyl-PNP) in acetone is first prepared. Then a C$_{12}$-PNP working solution is prepared by mixing 600 μL 10 mM C$_{12}$-PNP into a 9.4-mL phosphate buffer. The assay is performed by adding 40 μL of the acyl-PNP working solution to each well of a 96-well plate, followed by the rapid addition of 40 μL of enzyme. The solution is mixed for 15 seconds, and the absorbance change is read at 405 nm in a microtiter plate reader at 25° C.

Ester Formation from Thioester:

A reaction mixture containing 1.5 μM thioesterase enzyme, 100 μM myristoyl-CoA, 10% (v/v) methanol, and 50 mM sodium phosphate, pH 7.0 is prepared. The reaction mixture is incubated for 1 hour at 20° C. and terminated with the addition of 1 N HCl to decrease the pH to about 2.5. The mixture is extracted with an equal volume of ethyl acetate and the amount of fatty ester produced is determined via GC-MS or other standard methods such as GC-FID, LC-MS, or thin layer chromatography.

Ester Formation from Ester:

A reaction mixture containing 1.5 μM thioesterase enzyme, 300 μM lauroyl-CoA, 10% (v/v) methanol, and 50 mM sodium phosphate, pH 7.0 is prepared. The reaction mixture is incubated for 1 hour at 20° C. and terminated with the addition of 1 N HCl to decrease the pH to about 2.5. The mixture is extracted with an equal volume of ethyl acetate and the amount of lauryl ester produced is determined via GC-MS or other standard methods such as GC-FID, LC-MS, or thin layer chromatography.

The term "transformed" or "stably transformed" cell refers to a cell that has a non-native (heterologous) polynucleotide sequence integrated into its genome or as an episomal plasmid that is maintained for at least two generations.

The term "transport protein" refers to a protein that facilitates the movement of one or more compounds in and/or out of an organism or organelle. In some embodiments, an exogenous DNA sequence encoding an ATP-Binding Cassette (ABC) transport protein will be functionally expressed by the production host so that the production host exports the fatty acid derivative into the culture medium. ABC transport proteins are found in many organisms, such as *Caenorhabditis elegans, Arabidopsis thalania, Alcaligenes eutrophus* (later renamed *Ralstonia eutropha*), or *Rhodococcus erythropolis*. Non-limiting examples of ABC transport proteins include CER5, AtMRP5, AmiS2 and AtPGP1. In a preferred embodiment, the ABC transport protein is CER5 (e.g., AY734542). In other embodiments, the transport protein is an efflux protein selected from: AcrAB, TolC, or AcrEF from *E. coli* or tll1618, tll1619, and tll0139 from *Thermosynechococcus elongatus* BP-1. In further embodiments, the transport protein is a fatty acid transport protein (FATP) selected from *Drosophila melanogaster, Caenorhabditis elegans, Mycobacterium tuberculosis*, or *Saccharomyces cerevisiae* or any one of the mammalian FATPs known in the art. Transport proteins are useful, for example, for enhancing the secretion or release of products that are otherwise not capable of spontaneously secret the product. They are also useful when the engineered host cells are capable of spontaneously secret or release the product, but either release it slowly or incompletely. Under those circumstances, the transport proteins can enhance the secretion by accelerating the secretion step or driving the secretion to completion.

"Variant" is used interchangeably herein with "mutant."

"Vector" refers to a polynucleotide construct designed to introduce polynucleotides into one or more cell types. Vectors include cloning vectors, expression vectors, shuttle vectors, plasmids, cassettes and the like. In some embodiments, the polynucleotide construct comprises a polynucleotide sequence encoding a thioesterase (e.g., a precursor or a mature thioesterase) that is operably linked to a suitable prosequence (e.g., a secretory pro-sequence) capable of effecting the expression of the polynucleotide or gene in a suitable host.

A "wax" is a substance comprising, at least in part, fatty esters. In certain embodiments, a fatty ester has an A side and a B side, each comprising medium to long carbon chains. In addition to fatty esters, a wax may comprise other components. For example, a wax can comprise hydrocarbons, sterol esters, aliphatic aldehydes, alcohols, ketones, beta-diketones, triacylglycerols and the like. Typically a wax is a solid at room temperature, for example, at 20° C.

"Wild-type" means, in the context of gene or protein, a polynucleotide or protein sequence that occurs in nature. In some embodiments, the wild-type sequence refers to a sequence of interest that is a starting point for protein engineering.

Production of Fatty Acid Derivatives

According to an embodiment of the present invention, the novel thioesterases of the invention are expressed in a host cell that is capable of converting a carbon source to a fatty acid derivative. The invention pertains to two distinct embodiments: (1) the discovery that a mutant thioesterase can be used to optimize and/or "design" a fatty acid derivative composition so as to make such compositions more useful and that different mutations will provide different target properties; and (2) the discovery that thioesterase will act in a recombinant host cell to directly produce fatty ester products, without the presence of a wax synthase or ester synthase enzyme.

According to an embodiment of the invention, the fatty acid derivative compositions produced in accordance with the methods, vectors, and cells herein have modified or altered properties as compared to the fatty acid derivatives produced using host cells that do not comprise the thioesterase variants of the invention. For example, as also described herein, using the thioesterases of the present invention, it is possible to develop manufacturing processes that produce fatty acid derivatives, which, in comparison with a similar process involving a wildtype thioesterase, have altered compositional profiles, for example, altered percentages of a range of or a specific carbon chain length acyl group, saturated or unsaturated acyl groups, position of unsaturations, branched acyl groups, position of branching, hydroxyl-acyl groups, keto-acyl groups, proportion of esters or free fatty acids in the product, proportion of short-chain (e.g., $C_8$, $C_9$, $C_{10}$, $C_{11}$, $C_{12}$, $C_{13}$, and/or $C_{14}$) vs. long-chain (e.g., $C_{15}$, $C_{16}$, $C_{17}$, $C_{18}$, $C_{19}$, and/or $C_{20}$) fatty acid derivatives, or yield of fatty acid derivatives. Accordingly, products with various desirable properties can be engineered such that they have optimized cetane numbers, octane ratings, oxidative stability, lubricity, flash points, viscosity, boiling points, melting points, pour points, cloud points, cold filter plugging points, cold flow characteristics, aromaticity, and/or iodine numbers.

Fatty acid derivatives are useful as, or as components of, biofuels and specialty chemicals. Fatty acid derivatives and products made therefrom include fuels, fuel additives, fuel blends, detergents and surfactants, nutritional supplements, polymers, paraffin replacements, lubricants, solvents, personal care products, rubber processing additives, corrosion inhibitors, emulsifiers, plastics, textiles, cosmetics, paper products, coatings, metalworking fluids, dielectrics, oiling agents and emollients. The methods and compositions disclosed herein allow for the production of fatty acid derivatives with particular branch points, levels of saturation, and carbon chain length. The methods and compositions herein also allow for the production of a higher proportion of fatty esters vs. other products, or alternatively, a lower proportion of fatty esters vs. other products, depending on whether a higher proportional or percentage yield of fatty esters or a lower proportional or percentage yield of fatty esters is desirable. Specifically, for example, the methods and compositions herein allow for the production of a larger proportion of fatty acid esters vs. free fatty acids, or in other words, allows for a higher proportional or percentage yield of fatty acid esters vs. free fatty acids. Alternatively, for example, the methods and compositions herein allow for the production of a smaller proportion of fatty acid esters vs. free fatty acids, when large amounts of fatty acid esters are undesirable. Furthermore, the methods and compositions herein allow for the production of an improved yield of fatty acid derivatives.

Non-limiting examples of microorganisms which can be used as production hosts to produce fatty acid derivatives include cyanobacteria, algae, bacteria, yeast, or filamentous fungi. Further non-limiting examples of suitable production hosts include plant, animal, or human cells.

Alcohols (short chain, long chain, branched, or unsaturated) can be produced by the production hosts described herein. Such alcohols can be used as fuels directly or they can be used to create a fatty ester. Fatty esters, alone or in combination with other fatty acid derivatives described herein, are also useful as, or as components of, fuels.

Similarly, hydrocarbons produced from the production hosts described herein can be used as, or as components of, biofuels. Such hydrocarbon-based fuels can be designed to contain branch points, defined degrees of saturation, and specific carbon lengths utilizing the teachings provided herein. When used as biofuels alone or in combination with other fatty acid derivatives, the hydrocarbons can be combined with suitable additives or other traditional fuels (e.g., alcohols, diesel derived from triglycerides, and petroleum-based fuels).

The cetane number (CN), viscosity, melting point, and heat of combustion for various fatty esters have been characterized in Knothe, Fuel Processing Technology 86:1059-1070, 2005, which is herein incorporated by reference in its entirety. A production host can be engineered to produce any of the fatty esters described in Knothe, using the teachings provided herein.

I. Production of Fatty Acid Derivatives and Modifications for Improving Production/Yield The production host used to produce acyl-CoA and/or fatty acid derivatives can be recombinantly modified to include polynucleotide sequences that over-express peptides. For example, the production host can be modified to increase the production of acyl-CoA and reduce the catabolism of fatty acid derivatives and intermediates in the fatty acid biosynthetic pathway, or to reduce feedback inhibition at specific points in the fatty acid biosynthetic pathway. In addition to modifying the genes described herein, additional cellular resources can be diverted to over-produce fatty acids. For example, the lactate, succinate, and/or acetate pathways can be attenuated, and acetyl-CoA carboxylase (acc) can be over-expressed. The modifications to the production host described herein can be through genomic alterations, addition of recombinant expression systems, or combinations thereof. For example, one or more endogenous thioesterases of a particular production host can be modified using suitable techniques such that the mutant thioester has at least one altered property as compared to the endogenous thioesterase precursor, or such that the host cell exhibits at least one altered property, as compared to the same host cell before it is subject to the genomic alteration steps.

The fatty acid biosynthetic pathways involved are illustrated in FIGS. 2-5. Subsections A-G below describe the steps in these pathways. Various enzymes catalyze various steps in the pathway. Accordingly, each step is a potential place for overexpression of the gene to produce more enzyme(s) and thus drive the production of more fatty acids and fatty acid derivatives. Genes encoding the enzymes required for the pathway may also be recombinantly added to a production host lacking such enzymes. Finally, steps that would compete with the pathway leading to production of fatty acids and fatty acid derivatives can be attenuated or blocked in order to increase the production of the desired products.

According to the disclosures herein, a person of ordinary skill in the art can use the thioesterases of the invention to prepare microorganisms that produce fatty acid derivatives and to manufacture various fatty acid derivatives using such microorganisms, wherein such fatty acid derivatives have altered properties. It is further possible to prepare microorganisms that produce such fatty acid derivatives more efficiently by having the desired levels of yield, productivity, or titer during fermentations.

A. Acetyl-CoA-Malonyl-CoA to Acyl-ACP

Fatty acid synthase (FAS) is a group of peptides that catalyze the initiation and elongation of acyl chains (Marrakchi et al., Biochemical Society, 30:1050-1055, 2002). The acyl carrier protein (ACP) along with the enzymes in the FAS pathway control the length, degree of saturation, and branching of the fatty acids produced. The steps in this pathway are catalyzed by enzymes of the fatty acid biosynthesis (fab) and acetyl-CoA carboxylase (acc) gene families. Depending upon the desired product, one or more of these genes can be attenuated or over-expressed.

I. Fatty Acid Biosynthetic Pathway: Acetyl-CoA or Malonyl-CoA to Acyl-ACP

The fatty acid biosynthetic pathway in the production host uses the precursors acetyl-CoA and malonyl-CoA. The steps in this pathway are catalyzed by enzymes of the fatty acid biosynthesis (fab) and acetyl-CoA carboxylase (acc) gene families. This pathway is described in Heath et al., Prog. Lipid Res., 40(6):467-97, 2001, which is incorporated herein by reference.

Acetyl-CoA is carboxylated by acetyl-CoA carboxylase (Acc, a multi-subunit enzyme encoded by four separate genes, accABCD) to form malonyl-CoA. The malonate group is transferred to ACP by malonyl-CoA:ACP transacylase (FabD) to form malonyl-ACP. A condensation reaction then occurs, where malonyl-ACP merges with acetyl-CoA, resulting in β-ketoacyl-ACP. β-ketoacyl-ACP synthase III (FabH) initiates the FAS cycle, while β-ketoacyl-ACP synthase I (FabB) and β-ketoacyl-ACP synthase II (FabF) are involved in subsequent cycles.

Next, a cycle of steps is repeated until a saturated fatty acid of the appropriate length is made. First, the β-ketoacyl-ACP is reduced by NADPH to form β-hydroxyacyl-ACP. This step is catalyzed by β-ketoacyl-ACP reductase (FabG). β-hydroxyacyl-ACP is then dehydrated to form trans-2-enoyl-ACP. β-hydroxyacyl-ACP dehydratase/isomerase (FabA) or β-hydroxyacyl-ACP dehydratase (FabZ) catalyze this step. NADPH-dependent trans-2-enoyl-ACP reductase I, II, or III (FabI, FabK, or FabL, respectively) reduces trans-2-enoyl-ACP to form acyl-ACP. Subsequent cycles are started by the condensation of malonyl-ACP with acyl-ACP by β-ketoacyl-ACP synthase I or β-ketoacyl-ACP synthase II (FabB or FabF, respectively).

II. Modifying the Fatty Acid Biosynthetic Pathway to Increase Acyl-ACP Production Production host organisms may be engineered to overproduce acetyl-CoA and malonyl-CoA. Such production host organisms include plant, animal, or human cells. Microorganisms such as cyanobacteria, algae, bacteria, yeast, or filamentous fungi can be used as production hosts. Non-limiting examples of microorganisms that may be used as production hosts include *E. coli, Saccharomyces cerevisiae, Candida lipolytica, Synechococcus, Synechocystis, Clamydomonas, Arthrobacter* AK 19, *Rhodotorula* glutinins, *Acinetobacter* sp. strain M-1, *Candida lipolytica*, and other oleaginous microorganisms. Several different modifications can be made, either in combination or individually, to the production host to obtain increased acetyl-CoA/malonyl-CoA/fatty acid and fatty acid derivative production.

For example, to increase acetyl-CoA production, one or more of the following genes can be expressed in a production host: pdh, panK, aceEF (which encodes the E1p dehydrogenase component and the E2p dihydrolipoamide acyltransferase component of the pyruvate and 2-oxoglutarate dehydrogenase complexes), fabH, fabD, fabG, acpP, and fabF. In other examples, additional genes encoding fatty-acyl-CoA reductases and aldehyde decarbonylases can be expressed in the production host. It is known in the art that a plasmid containing one or more of the aforementioned genes, all under the control of a constitutive, or otherwise controllable promoter, can be constructed. Exemplary GenBank Accession numbers for these genes are listed in the parentheticals: pdh (BAB34380, AAC73227, AAC73226), panK (also known as coaA, AAC76952), aceEF (AAC73227, AAC73226), fabH (AAC74175), fabD (AAC74176), fabG (AAC74177), acpP (AAC74178), and fabF (AAC74179).

Additionally, the expression levels of fadE, gpsA, ldhA, pflb, adhE, pta, poxB, ackA, and/or ackB can be attenuated or knocked-out in the engineered microorganism by transformation with conditionally replicative or non-replicative plasmids containing null or deletion mutations of the corresponding genes, or by substituting the promoter or enhancer sequences. Exemplary GenBank Accession numbers for these genes are listed in the parentheticals: fadE (AAC73325), gspA (AAC76632), ldhA (AAC74462), pflb (AAC73989), adhE (AAC74323), pta (AAC75357), poxB (AAC73958), ackA (AAC75356), and ackB (BAB81430). The resulting engineered production hosts have increased acetyl-CoA production levels when grown in an appropriate environment.

Moreover, malonyl-CoA overproduction can be affected by engineering the production host as described above with accABCD (e.g., GenBank Accession number AAC73296, EC 6.4.1.2) included in the plasmid synthesized de novo. Fatty acid overproduction can be achieved by further including a gene encoding lipase (e.g., GenBank Accession Nos. CAA89087 and CAA98876) in the plasmid synthesized de novo.

As a result, in some examples, an acetyl-CoA carboxylase is overexpressed to increase the intracellular concentration thereof by at least about 2-fold, at least about 5-fold, or at least about 10-fold, relative to the native expression levels.

In addition, a PlsB (e.g., GenBank Accession number AAC77011) D311E mutant can be used to increase the amount of available acyl-CoA.

In addition, overexpression of an sfa gene (suppressor of FabA, e.g., GenBank Accession No. AAN79592) can be included in the production host to increase production of monounsaturated fatty acids (Rock et al., J. Bacteriology, 178:5382-5387, 1996).

B. Acyl-ACP and/or Acyl-CoA to Fatty Ester Using Thioesterase

In a typical microbial process model for fatty acid synthesis, acetyl-CoA and malonyl-CoA are converted through a series of steps to form the acyl-ACP chains. Acyl-ACP is then converted via a series of alternative enzymatic steps to various end products, including fatty acid derivatives. For example, typically acyl-ACP is converted to fatty esters by the combined consecutive reactions of a thioesterase, an acyl-CoA ligase/synthetase and an ester synthase. A limitation to the commercial use of these enzymes in a metabolic pathway is the need to produce the fatty acyl CoA substrate from a fatty acyl ACP precursor, which requires at least two enzymatic steps and the expenditure of metabolic energy from two phosphoanhydride bonds. Direct production of fatty esters with thioesterase mitigates the loss of ATP caused by these two enzymatic steps. Recently it has been demonstrated that lipases (whose natural "alcohol" substrate is water) can also be used in vitro to catalyze the transesterification reaction that makes biodiesel (i.e. the conversion of triacyl glyceride and methanol to fatty acid methyl ester and glycerol). However, lipases are generally toxic to the cells when produced intracellularly.

Despite having a published specificity for water, the present invention describes the discovery that, in the presence of a sufficient amount of an alcohol, the alcohol can become an acceptable substrate for a thioesterase. In that case, thioesterases can catalyze the alcoholysis of the fatty acyl enzyme intermediates, just like a lipase does in vitro. Thus, under the right conditions, an enzyme that accepts a fatty ester as substrate to form a fatty enzyme intermediate that is subsequently cleaved through either hydrolysis or transesterification can be used to synthesize desired fatty acid esters if a sufficient level of a suitable alcohol is provided to drive alcoholysis. Examples of enzymes having this capability, which can produce esters directly from acyl-ACP include, in addition to thioesterases, acyltransferases, lipases, esterases, and proteases. Useful thioesterases can be naturally-occurring and/or precursor thioesterases as defined herein, or can be mutant thioesterases prepared in accordance with the disclosures herein. One of ordinary skill in the art is capable of determining the fitness of using a particular enzyme to directly produce fatty esters from Acyl-ACP. For example, the assays provided in Example 32 are useful in determining direct ester production.

According to this aspect of the invention, the thioesterase can be utilized to directly produce fatty esters either in the presence or the absence of an ester synthase and/or a fatty acyl CoA ligase/synthetase. For example, expression of a thioesterase that can catalyze the direct production of fatty esters in a recombinant host strain can be used to supplement fatty ester production where the strain also expresses an ester synthase. Additionally, expression of a thioesterase that can catalyze the direct production of fatty esters in a recombinant host cell can be used where there is no or low ester synthase expression.

A mutant thioesterase can be utilized that has been modified to have altered properties compared to the precursor thioesterase.

C. Acyl-ACP to Fatty Acid

I. Fatty Acid Biosynthetic Pathway: Acyl-ACP to Fatty Acids

As described above, acetyl-CoA and malonyl-CoA are processed in several steps to form acyl-ACP chains. The enzyme sn-glycerol-3-phosphate acyltransferase (PlsB) catalyzes the transfer of an acyl group from acyl-ACP or acyl-CoA to the sn-1 position of glycerol-3-phosphate. Thus, PlsB is a key regulatory enzyme in phospholipid synthesis, which is a part of the fatty acid pathway. Inhibiting PlsB leads to an increase in the levels of long chain acyl-ACP, which feedback will inhibit early steps in the pathway, which involve genes such as, for example, accABCD, fabH, and fabI. Uncoupling of this regulation, for example by thioesterase overexpression, leads to increased fatty acid production.

II. Modifying the Fatty Acid Biosynthetic Pathway to Produce the Desired Types or Proportions of Fatty Acids According to the invention, the expressed thioesterase has altered properties as compared to the native or endogenous thioesterase in the host strain. To engineer a production host for the production of a homogeneous population of fatty acid derivatives, one or more endogenous genes can be attenuated or functionally deleted and, as a result, one or more thioesterases according to the invention can be expressed. For example, $C_{10}$ fatty acid derivatives (i.e., fatty acid derivatives each comprising a carbon chain that is 10 carbons long) can be produced by attenuating thioesterase $C_{18}$ (e.g., GenBank Accession Nos. AAC73596 and POADA1), which uses $C_{18:1}$-ACP, and by expressing an altered thioesterase that has increased specificity for and/or activity (e.g., catalytic rate) with regard to $C_{10}$ substrates (i.e., substrates each comprising a carbon chain that is 10 carbons long). This results in a more homogeneous population of fatty acid derivatives that have an increase in fatty acids having a carbon chain length of 10. In another example, $C_{12}$ fatty acid derivatives can be produced by attenuating endogenous thioesterases that produce non-$C_{12}$ fatty acids and expressing an altered thioesterase that has increased specificity for and/or activity (i.e., catalytic rate) with regard to $C_{12}$ substrates. In another example, $C_{14}$ fatty acid derivatives can be produced by attenuating endogenous thioesterases that produce non-$C_{14}$ fatty acids and expressing an altered thioesterase that has increased specificity for and/or activity (i.e., catalytic rate) with regard to $C_{14}$ substrates. In another example, a higher proportional yield of short-chain (e.g., $C_8$, $C_9$, $C_{10}$, $C_{11}$, $C_{12}$, $C_{13}$, and/or $C_{14}$) fatty acid derivatives vs. other non-short-chain fatty acid derivatives in the product mixture. In yet another example, a lower proportional yield of short chain (e.g., $C_8$, $C_9$, $C_{10}$, $C_{11}$, $C_{12}$, $C_{13}$, and/or $C_{14}$) fatty acid derivatives vs. other non-short-chain fatty acid derivatives in the product mixture can also be achieved. In a further example, a higher and/or improved yield of free fatty acid derivatives can be produced by expressing an altered thioesterase that has improved catalytic rate and/or production or yield in vivo. In yet another example, a higher or lower proportional or percentage yield of fatty esters vs. other products, such as free fatty acids, can be produced by applying one or more of certain thioesterase mutants. Acetyl-CoA, malonyl-CoA, and fatty acid overproduction can be verified using methods known in the art, for example by radioactive precursors, HPLC, LC-MS, and GC-MS subsequent to cell lysis.

In an alternative embodiment, a thioesterase of the invention can be expressed within the host strain in combination with an endogenous thioesterase. In yet another alternative embodiment, one or more endogenous thioesterases can be modified using suitable genomic alternation techniques that are known to those skilled in the art, such that the mutant thioesterases has at least one altered property as compared to the endogenous thioesterase precursors, and/or such that the host cell exhibits at least one altered property as compared to the host cell before such genomic alteration techniques are applied.

D. Fatty Acid to Acyl-CoA

I. Conversion of fatty acids to acyl-CoA

Acyl-CoA synthase (ACS) esterifies free fatty acids to acyl-CoA by a two-step mechanism. The free fatty acid first is converted to an acyl-AMP intermediate (an adenylate) through the pyrophosphorolysis of ATP. The activated carbonyl carbon of the adenylate is then coupled to the thiol group of CoA, releasing AMP and the acyl-CoA final product. See Shockey et al., Plant Physiol. 129:1710-1722, 2002.

The E. coli ACS enzyme FadD and the fatty acid transport protein FadL are typically important components of a fatty acid uptake system. FadL mediates the transportation of fatty acids into the bacterial cell, and FadD mediates the formation of acyl-CoA esters. When no other carbon source is available, exogenous fatty acids are taken up by bacteria and converted to acyl-CoA esters, which bind to the transcription factor FadR and derepress the expression of the fad genes that encode proteins responsible for fatty acid transport (FadL), activation (FadD), and β-oxidation (FadA, FadB, FadE, and FadH). When alternative sources of carbon are available, bacteria synthesize fatty acids as acyl-ACPs, which are then used for phospholipid synthesis, rather than serving as substrates for β-oxidation. Thus, acyl-CoA and acyl-ACP are independent sources of fatty acids that lead to different end-products. See Caviglia et al., J. Biol. Chem., 279(12):1163-1169, 2004.

II. Modifying the Fatty Acid Biosynthetic Pathway to Increase Conversion of Fatty Acids to Acyl-CoA Production hosts can be engineered using known peptides to produce fatty acids of various lengths which can be converted to acyl-CoA. One method of making fatty acid derivatives involves increasing the expression of, or expressing more active forms of, one or more acyl-CoA synthase peptides (EC 6.2.1.-).

A list of acyl-CoA synthases that can be expressed to produce acyl-CoA and fatty acid derivatives is shown in Table 1. These Acyl-CoA synthases can be examined to optimize any pathway that uses fatty-acyl-CoAs as substrates. Using bioinformatics and synthetic genes, heterologous fadD genes can be expressed in production strains and evaluated for their capacity to produce biodiesel and potentially biocrude.

Based on their degree of similarity to E. coli fadD, the following homologous genes are selected to be synthesized and evaluated:

fadDD35 from M. tuberculosis HR7Rv [NP_217021].
yhfL from B. subtilis [NP_388908].
fadD1 from P. aeruginosa PAO1 [NP_251989].
fadD homolog, encoding Faa3p from Saccharomyces cerevisiae [NP_012257].

Additional fatty acid acyl-CoA synthases from eukaryotic organisms, which can be used to produce acyl-CoA as well as fatty acid derivatives, include those described in Shockey et al., Plant Physiol., 129: 1710-1722, 2002 (Arabidopsis), Caviglia et al., J. Biol. Chem., 279: 1163-1169, 2004 (rat), and Knoll et al., J. Biol. Chem., 269(23):16348-56, 1994 (yeast). Gene sequences encoding these synthetases are known in the art. See, e.g., Johnson et al., J. Biol. Chem., 269: 18037-18046, 1994; Shockey et al., Plant Physiol., 129: 1710-1722, 2002; Black et al., J. Biol. Chem., 267: 25513-25520, 1992. These eukaryotic acyl-CoA synthases, despite lacking in high homology to E. coli FadD sequences, can complement FadD activity in E. coli FadD knockouts.

A. Acyl-CoA to Fatty Alcohol

1. Conversion of Acyl-CoA to Fatty Alcohol

Acyl-CoA is reduced to a fatty aldehyde by an NADH-dependent acyl-CoA reductase (e.g., Acr1). The fatty aldehyde is then reduced to a fatty alcohol by an NADPH-dependent alcohol dehydrogenase (e.g., YqhD). Alternatively, fatty alcohol forming acyl-CoA reductase (FAR) catalyzes the reduction of an acyl-CoA into a fatty alcohol and CoASH. FAR uses NADH or NADPH as a cofactor in this four-electron reduction. Although the alcohol-generating FAR reactions proceed through an aldehyde intermediate, a free aldehyde is not released. Thus, the alcohol-forming FARs are distinct from the enzymes that carry out two-electron reductions of acyl-CoA and yield free fatty aldehyde as a product. (See Cheng and Russell, J. Biol. Chem., 279(36):37789-37797, 2004; Metz et al., Plant Physiol., 122:635-644, 2000).

2. Modifying the Fatty Acid Biosynthetic Pathways to Increase Conversion of Acyl-CoA to Fatty Alcohol Production hosts can be engineered using known polypeptides to produce fatty alcohols from acyl-CoA. One

TABLE 1

Acyl-CoA synthases

| Gene Name/Locus | Source | GenBank Accession No. | % Identity to E. coli FadD | % Similarity to E. coli FadD |
|---|---|---|---|---|
| fadD | E. coli | NP_416319 | — | — |
| fadK | E. coli | YP_416216 | 28 | 46 |
| fadD | Acinetobacter sp. ADP1 | YP_045024 | 51 | 70 |
| fadD | Haemophilus influenza RdKW20 | NP_438551 | 64 | 78 |
| BH3103 | Bacillus halodurans C-125 | NP_243969 | 40 | 58 |
| yhfL | Bacillus subtilis | NP_388908 | 39 | 57 |
| pfl-4354 | Pseudomonas fluorescens Pfo-1 | YP_350082 | 52 | 71 |
| EAV15023 | Comamonas testosterone KF-1 | ZP_01520072 | 55 | 72 |
| fadD1 | Pseudomonas aeruginosa | NP_251989 | 54 | 72 |
| fadD2 | Pseudomonas aeruginosa PAO1 | NP_251990 | 55 | 72 |
| fadD | Rhizobium etli CFN42 | YP_533919 | 55 | 72 |
| RPC_4074 | Rhodopseudomonas palustris Bis B18 | YP_533919 | 56 | 72 |
| fadD1 | Rasltonia solanacearum GMI 1000 | NP_520978 | 56 | 72 |
| fadDD35 | Mycobacterium tuberculosis H37Rv | NP_217021 | 28 | 46 |
| fadDD22 | Mycobacterium tuberculosis H37Rv | NP_217464 | 23 | 42 |
| PRK0059 | Stenotrophomonas maltophilia R551-3 | ZP_01644857 | 59 | 75 | method of making fatty alcohols involves increasing the expression of, or expressing more active forms of, fatty alcohol forming acyl-CoA reductases (encoded by a gene such as acr1, EC 1.2.1.50/1.1.1), acyl-CoA reductases (EC 1.2.1.50), and/or alcohol dehydrogenases (EC 1.1.1.1).

Fatty alcohols are often described as hydrocarbon-based surfactants. They also serve as suitable components of surfactants. For surfactant production, the production host is modified so that it produces a surfactant from a renewable carbon source. Such a production host includes a first exogenous polynucleotide sequence encoding a protein capable of converting a fatty acid to a fatty aldehyde and a second exogenous polynucleotide sequence encoding a protein capable of converting a fatty aldehyde to an alcohol. In some examples, the first exogenous polynucleotide sequence encodes a fatty acid reductase. In one embodiment, the second exogenous polynucleotide sequence encodes mammalian microsomal aldehyde reductase or long-chain aldehyde dehydrogenase. In a further example, the first and second exogenous polynucleotide sequences are from *Arthrobacter* AK 19, *Rhodotorula glutinins, Acinetobacter* sp. strain M-1, or *Candida lipolytica*. In one embodiment, the first and second heterologous polynucleotide sequences form a multienzyme complex from *Acinetobacter* sp. strain M-1 or from *Candida lipolytica*.

Additional sources of heterologous DNA sequences encoding fatty acid to long chain alcohol converting proteins that can be used in surfactant production include, but are not limited to, *Mortierella alpina* (ATCC 32222), *Cryptococcus curvatus*, (also referred to as *Apiotricum curvatum*), *Alcanivorax jadensis* (T9T=DSM 12718=ATCC 700854), *Acinetobacter* sp. HO1-N (ATCC 14987) and *Rhodococcus opacus* (PD630 DSMZ 44193).

In one example, the fatty acid derivative is a saturated or unsaturated surfactant product having a carbon chain length of about 6 to about 36 carbon atoms, about 8 to about 30 carbon atoms, about 10 to about 26 carbon atoms, about 12 to about 20 carbon atoms, or about 12 to about 16 carbon atoms. In another example, the surfactant product has a carbon chain length of about 10 to about 18 carbon atoms, or about 12 to about 14 carbon atoms.

Suitable production hosts for producing surfactants include eukaryotic or prokaryotic microorganisms. Exemplary production hosts include *Arthrobacter* AK 19, *Rhodotorula glutinins, Acinetobacter* sp. strain M-1, *Arabidopsis thalania, Candida lipolytica, Saccharomyces cerevisiae*, cyanobacteria such as *Synechocystis* spp. and *Synechococcus* spp., Algae such as *Clamydomonas*, and *E. coli* engineered to overexpress acetyl-CoA carboxylase. Production hosts that demonstrate an innate ability to synthesize high levels of surfactant precursors in the form of lipids and oils, such as *Rhodococcus opacus, Arthrobacter* AK 19, *Rhodotorula* glutinins, *E. coli* engineered to express acetyl CoA carboxylase, and other oleaginous cyanobacteria, bacteria, yeast, and fungi can also be used.

B. Fatty Alcohols to Fatty Esters

Production hosts can be engineered using known polypeptides to produce fatty esters of various lengths. One method of making fatty esters includes increasing the expression of, or expressing more active forms of, one or more alcohol O-acetyltransferase peptides (EC 2.3.1.84). These peptides catalyze the acetylation of an alcohol by converting an acetyl-CoA and an alcohol to a CoA and an ester. In some examples, the alcohol O-acetyltransferase peptides can be expressed in conjunction with selected thioesterase peptides, FAS peptides, and fatty alcohol forming peptides, thus allowing the control of carbon chain lengths, saturation levels, and degrees of branching. In some cases, the bkd operon can be coexpressed in order to produce branched fatty acid precursors.

As used herein, alcohol O-acetyltransferase peptides include peptides in enzyme classification number EC 2.3.1.84, as well as any other peptides capable of catalyzing the conversion of an acetyl-CoA and an alcohol to form a CoA and an ester. Additionally, one of ordinary skill in the art will appreciate that alcohol O-acetyltransferase peptides can also catalyze other reactions.

For example, some alcohol O-acetyltransferase peptides can accept other substrates in addition to fatty alcohols and/or acetyl-CoA thioesters, such as other alcohols and other acyl-CoA thioesters. Such non-specific or divergent-specificity alcohol O-acetyltransferase peptides are, therefore, also included. Various alcohol O-acetyltransferase peptide sequences are publicly available. Assays for measuring the activity of alcohol O-acetyltransferase peptides are known in the art. Moreover, O-acyltransferases can be engineered to impart new activities and/or specificities for the donor acyl group or acceptor alcohol moiety. Engineered enzymes can be generated through well documented rational and evolutionary approaches.

C. Acyl-CoA to Fatty Esters

1. Production of Fatty Esters

Fatty esters are synthesized by an acyl-CoA:fatty alcohol acyltransferase (e.g., ester synthase), which conjugates a long chain fatty alcohol to a fatty acyl-CoA via an ester linkage. Ester synthases and the encoding genes are known from the jojoba plant and the bacterium *Acinetobacter* sp. strain ADP1 (formerly *Acinetobacter calcoaceticus* ADP1). The bacterial ester synthase is a bifunctional enzyme, exhibiting ester synthase activity and the ability to form triacylglycerols from diacylglycerol substrates and fatty acyl-CoAs (acyl-CoA:diglycerol acyltransferase (DGAT) activity). The gene wax/dgat encodes both ester synthase and DGAT. See Cheng et al., J. Biol. Chem., 279(36):37798-37807, 2004; Kalscheuer and Steinbuchel, J. Biol. Chem., 278:8075-8082, 2003. Ester synthases can also be used to produce certain fatty esters that can be used as a fuel, such as biodiesel, as described herein.

2. Modifying the Fatty Acid Biosynthetic Pathway to Produce Fatty Esters Using Ester Synthase The production of fatty esters, including waxes, from acyl-CoA and alcohols, can be engineered using known polypeptides. One method of making fatty esters includes increasing the expression of, or expressing more active forms of, one or more ester synthases (EC 2.3.1.20, 2.3.1.75). Various ester synthase peptide sequences are publicly available. Methods of determining ester synthase activity are provided in U.S. Pat. No. 7,118,896, which is herein incorporated by reference in its entirety.

In certain embodiments, if the desired product is an ester-based biofuel, a production host can be modified such that it produces an ester from a renewable energy source. Such a production host includes an exogenous genes encoding an ester synthase that is expressed so as to confer upon said production host the ability to synthesize a saturated, unsaturated, or branched fatty ester from a renewable energy source. In some embodiments, the organism can also express genes encoding the following exemplary proteins: fatty acid elongases, acyl-CoA reductases, acyltransferases, ester synthases, fatty acyl transferases, diacylglycerol acyltransferases, thioesterases, and/or acyl-coA wax alcohol acyltransferases. In an alternate embodiment, the organism expresses a gene encoding a bifunctional ester synthase/acyl-CoA: diacylglycerol acyltransferase. For example, the bifunctional ester synthase/acyl-CoA:diacylglycerol acyltransferase can be selected from the multi-enzyme complexes from *Simmondsia chinensis, Acinetobacter* sp. strain ADP1 (formerly *Acinetobacter calcoaceticus* ADP1), *Alcanivorax borkumensis, Pseudomonas aeruginosa, Fundibacter jadensis, Arabidopsis thaliana*, or *Alcaligenes eutrophus* (later renamed *Ralstonia eutropha*). In one embodiment, the fatty acid elongases, acyl-CoA reductases, or wax synthases are obtained and/or derived from a multi-enzyme complex from *Alcaligenes eutrophus* (later renamed *Ralstonia eutropha*) or other organisms known in the literature to produce esters such as wax or fatty esters.

Additional sources of heterologous DNA sequences encoding ester synthesis proteins useful in fatty ester production include, but are not limited to, *Mortierella alpina* (e.g., ATCC 32222), *Cryptococcus curvatus* (also referred to as *Apiotricum curvatum*), *Alcanivorax jadensis* (e.g., T9T=DSM 12718=ATCC 700854), *Acinetobacter* sp. HO1-N, (e.g., ATCC 14987) and *Rhodococcus opacus* (e.g., PD630, DSMZ 44193).

Useful production hosts for producing fatty esters can be eukaryotic or prokaryotic microorganisms. Non-limiting examples of production hosts for producing fatty esters include *Saccharomyces cerevisiae, Synechococcus, Synechocystis, Clamydomonas, Candida lipolytica, E. coli, Arthrobacter* AK 19, *Rhodotorula glutinins, Acinetobacter* sp. strain M-1, *Candida lipolytica*, and other oleaginous microorganisms.

In one example, the ester synthase from *Acinetobacter* sp. ADP1 at locus AAO17391 (described in Kalscheuer and Steinbuchel, J. Biol. Chem., 278:8075-8082, 2003, herein incorporated by reference) is used. In another example, the ester synthase from *Simmondsia chinensis* at locus AAD38041 is used.

In certain embodiments, the esters produced in accordance with the methods and compositions herein are secreted or released from the host cells, and thus can be recovered extracellularly. Optionally, an ester exporter such as a member of the FATP family can be used to facilitate the release of esters into the extracellular environment. A non-limiting example of a suitable ester exporter is fatty acid (long chain) transport protein CG7400-PA, isoform A, from *Drosophila melanogaster*, at locus NP_524723.

D. Acyl-ACP, Acyl-CoA to Hydrocarbon

1. Hydrocarbons from Particular Microorganisms

A diverse set of microorganisms are known to produce hydrocarbons, such as alkanes, olefins, and isoprenoids. Many of these hydrocarbons are derived from fatty acid biosynthesis. The production of these hydrocarbons can be controlled by controlling the genes associated with fatty acid biosynthesis in the native production hosts.

For example, hydrocarbon biosynthesis in the algae *Botryococcus braunii* occurs via the decarbonylation of fatty aldehydes. The fatty aldehydes are produced by the reduction of fatty acyl thioesters by an enzyme such as a fatty acyl-CoA reductase. Thus, the structure of the final alkanes can be controlled by engineering *B. braunii* to express specific genes, such as thioesterases, which control the chain length of the fatty acids being channeled into alkane biosynthesis. Expressing the enzymes that result in branched chain fatty acid biosynthesis in *B. braunii* will result in the production of branched chain alkanes. Introduction of genes affecting the production of desaturated fatty acids will result in the production of olefins. Further combinations of these genes can provide further control over the final structure of the hydrocarbons that will be produced.

To produce higher levels of native or engineered hydrocarbons, the genes involved in the biosynthesis of fatty acids and their precursors, or the degradation of other products can be expressed, overexpressed, or attenuated. Each of these approaches can be applied to the production of alkanes in *Vibrio fumissii* M1 and other *Vibrio fumissii* strains, which produce alkanes through the reduction of fatty alcohols. In addition to *Vibrio fumissii*, other alkane producing organisms that utilize the fatty acid pathway can be used.

Each of these approaches can also be applied to the production of the olefins produced by strains of *Micrococcus leuteus, Stenotrophomonas maltophilia*, and related microorganisms. These microorganisms produce long chain olefins that are derived from the head-to-head condensation of fatty acid precursors. Controlling the structure and level of the fatty acid precursors using the methods described herein will result in the formation of olefins of different chain lengths, branching characteristics, and levels of saturation.

Cyanobacteria can also be used as suitable production hosts for the production of fatty acid derivatives such as fatty alcohols, fatty esters, and hydrocarbons. For example, *Synechocystis* sp. PCC6803 and *Synechococcus elongates* PCC7942 can serve as production hosts and can be engineered using standard molecular biology techniques (Thiel, Genetic analysis of cyanobacteria, in THE MOLECULAR BIOLOGY OF CYANOBACTERIA, ADVANCES IN PHOTOSYNTHESIS AND RESPIRATION 581-611 (Kluwer Academic Publishers), 1994; Koksharova and Wolk, Appl. Microbiol. Biotechnol., 58: 123-137, 2002, the contents of which are incorporated by reference herein. Fatty acid biosynthesis genes can be readily identified and isolated in these organisms.

Furthermore, many cyanobacteria are natural producers of hydrocarbons, such as heptadecane, and therefore contain hydrocarbon biosynthesis genes that can be deregulated and overexpressed in conjunction with manipulating their fatty acid biosynthesis genes, in order to increase hydrocarbon production.

Unlike other bacteria, some cyanobacteria (e.g., *Synechocystis* sp. PCC6803) contain polyunsaturated fatty acids in their lipids (Murata, Plant cell Physiol., 33: 933-941, 1992), and thus have the inherent capability to produce polyunsaturated fatty acid derivatives. Most importantly, cyanobacteria are photosynthetic organisms that synthesize all cellular carbon by harvesting sun light and fixing carbon dioxide. Therefore, fatty acid derivatives produced in cyanobacteria are directly derived from $CO_2$.

2. Producing Hydrocarbons from Reduction of Primary Alcohols

Hydrocarbons can also be produced using evolved oxidoreductases for the reduction of primary alcohols. Using primary fatty alcohols to produce alkanes in microorganisms, such as *Vibrio fumissii* M1, is known. See, e.g., Park, J. Bacteriol., 187:1426-1429, 2005, the content of which is incorporated herein by reference. One example of an oxidoreductase that can be used to produce hydrocarbons from fatty alcohols is NAD(P)H-dependent oxidoreductase. Synthetic NAD(P)H dependent oxidoreductases can be produced through the use of evolutionary engineering and can be expressed in production hosts to produce fatty acid derivatives.

The process of "evolving" a fatty alcohol reductase to have the desired activity is known and practiced by those skilled in the art (Kolkman and Stemmer, Nat. Biotechnol., 19:423-8, 2001; Ness et al., Adv. Protein Chem., 55:261-92, 2000; Minshull and Stemmer, Curr. Opin. Chem. Biol., 3:284-90, 1999; Huisman and Gray, Curr. Opin. Biotechnol., 13:352-8, 2002; U.S. Patent Publication No. 2006/0195947), the contents of all of which are incorporated herein by reference.

A library of NAD(P)H-dependent oxidoreductases is generated by standard methods, such as error-prone PCR, site-specific random mutagenesis, site-specific saturation mutagenesis, or site-directed specific mutagenesis. Additionally, a library can be created through the "shuffling" of naturally-occurring NAD(P)H-dependent oxidoreductase encoding sequences. The library is expressed in a suitable production host, such as an *E. coli*. Individual colonies expressing a different member of the oxidoreductase library are then analyzed for expression of an oxidoreductase that can catalyze the reduction of a fatty alcohol.

For example, each cell can be assayed as a whole cell bioconversion, a cell extract, or a permeabilized cell. Enzymes purified from the cell can be analyzed as well. Fatty alcohol reductases are identified by spectrophotometrically or fluorometrically monitoring the fatty alcohol-dependent oxidation of NAD(P)H. Production of alkanes is monitored by GC-MS, TLC, or other suitable methods.

An oxidoreductase identified in this manner is used to produce alkanes, alkenes, and related branched hydrocarbons. This is achieved either in vitro or in vivo. The latter is achieved by expressing the evolved fatty alcohol reductase gene in an organism that produces fatty alcohols, such as the ones described herein. The fatty alcohols act as substrates for the alcohol reductase, which produces alkanes. Other oxidoreductases can also be engineered to catalyze this reaction, such as those that use molecular hydrogen, glutathione, FADH, or other reductive coenzymes.

3. Conversion of Acyl-ACP to Ketone and/or Olefins

Acyl-ACP can be converted to a ketone and/or an internal olefin by the action of acyl condensing enzymes, as described in PCT Publication No. 2008/147781 A2, the disclosures of which are incorporated herein by reference. As described in the '781 publication, acyl-condensing peptides include peptides that are capable of catalyzing the condensation of acyl-ACP, acyl-CoA, acyl-AMP, fatty acids, and mixtures thereof using the methods described therein. In some embodiments, these acyl-condensing peptides have high, medium, or low substrate specificity. In certain examples, the acyl-condensing peptides are more substrate specific and will only accept substrates of a specific chain length. Additionally, one of ordinary skill in the art will appreciate that some acyl-condensing peptides will catalyze other reactions as well. Examples of acyl-condensing enzymes are disclosed in the '781 publication. In addition, the '781 publication describes adenylating proteins, dehydratases, and dehydrogenases that can be used in the production of hydrocarbons such as internal olefins.

Recombinant organisms can be engineered using polynucleotides and proteins, for example, those disclosed in the '781 publication, to produce hydrocarbons and aliphatic ketones that have defined structural characteristics (e.g., degrees of branching, levels of saturation, or carbon chain lengths). One method of making hydrocarbons involves increasing the expression of, or expressing more active forms of, one or more acyl-condensing enzymes (enzymes that condense two or more of acyl-CoA, acyl-ACP, acyl-AMP, acyl-ester, fatty acid, or mixtures thereof). One of ordinary skill in the art will appreciate that the products produced from such condensation reactions vary depending on the acyl chain that is condensed. Products that can be produced include, for example, hydrocarbons and hydrocarbon intermediates, such as aliphatic ketones. The aliphatic ketones, hydrocarbons, and hydrocarbon intermediates can be engineered to have specific carbon chain characteristics by expressing various enzymes or attenuating the expression of various enzymes in the recombinant organism. According to the present invention, the mutant thioesterases of the invention can be used to manipulate the range of acyl species carbon chain lengths. Thus, by using a mutant thioesterase having a particular substrate specificity or selectivity, it is possible to affect the downstream reactions so as to result in a predetermined olefin or ketone product profile.

4. Conversion of Fatty Acid to Aldehyde

Fatty acids resulting from thioesterase cleavage can be converted to an aldehyde by the action of the carboxylic acid reductase gene. Aldehydes can be useful products in themselves, or they can serve as substrates for further enzymatic catalysis reactions, for example, in the production of fatty alcohols via an enzymatic reaction of alcohol dehydrogenase, or in the production of alkanes via an enzymatic reaction of decarbonylases. According to the compositions and methods herein, the fatty acid substrates of the carboxylic acid reductase can be manipulated so as to achieve a predetermined product profile in the aldehyde or fatty alcohol product.

E. Release of Fatty Acid Derivatives—with or without Transport Proteins

As described herein, the fatty acid derivatives produced in accordance with the methods, compositions, vectors, and host cells herein can be secreted or spontaneously released so as to allow the recovery of the fatty acid derivative products extracellularly. The speed of spontaneous secretion may or may not be sufficiently fast, and the level of release may or may not be sufficiently complete. Therefore, optionally, transport proteins can be used to facilitate export of fatty acid derivatives out of the production host. Transport and efflux proteins are known to excrete a large variety of compounds, and can naturally be modified to be selective for particular types of fatty acid derivatives. Non-limiting examples of suitable transport proteins are ATP-Binding Cassette (ABC) transport proteins, efflux proteins, and fatty acid transporter proteins (FATP). Additional non-limiting examples of suitable transport proteins include the ABC transport proteins from organisms such as *Caenorhabditis elegans, Arabidopsis thalania, Alkaligenes eutrophus*, and *Rhodococcus erythropolis*. Exemplary ABC transport proteins include CER5, AtMRP5, AmiS2, or AtPGP1. In a preferred embodiment, the ABC transport protein is a CER5 (e.g., AY734542)). Vectors containing genes that express suitable transport proteins can be inserted into protein production hosts to increase or drive the release of fatty acid derivatives.

Production of fatty acid derivative products according to the present invention does not require transport or efflux protein modification and it is possible to select production hosts for their endogenous ability to release fatty acid derivatives. Furthermore, simply by constructing host cells according to the present disclosure, for example, fatty acid derivative products that are otherwise not known to be secreted can be secreted or spontaneously released. The efficiency of product production and release into the fermentation broth can be expressed as a ratio of intracellular product to extracellular product. In some examples, the ratio can be about 100:1, 50:1, 20:1, 10:1, 5:1, 4:1, 3:1, 2:1, 1:1, 1:2, 1:3, 1:4, 1:5, 1:10, 1:20, 1:30, 1:40 or 1:50.

II. Selection of Carbon Chain Characteristics of Fatty Acid Derivatives

Fatty acid derivatives with particular branch points, levels of saturation, carbon chain lengths, and ester characteristics can be produced as desired. Microorganisms that naturally produce particular derivatives can be selected as production hosts, and in certain circumstances, endogenous enzymes therein can be manipulated to produce fatty acid derivatives of desirable characteristics. Alternatively, genes that express enzymes that will produce particular fatty acid derivatives can be suitably inserted into the production host microorganisms.

In some examples, expression of exogenous FAS genes originating from different species or engineered variants can be achieved in a production host, resulting in the biosynthesis of fatty acids that are structurally different (in, for example, lengths, levels of branching, degrees of unsaturation, etc.) from those of the native production host. These heterologous gene products can also be selected or engineered to be unaffected by the natural regulatory mechanisms in the production host cells, and as such allowing control of the production of the desired commercial product. For example, the FAS enzymes from *Bacillus subtilis, Saccharomyces cerevisiae, Streptomyces* spp., *Ralstonia, Rhodococcus, Corynebacteria, Brevibacteria, Mycobacteria*, oleaginous yeast, or the like can be expressed in a suitable production host. The expression of such exogenous enzymes will alter the structure of the fatty acid produced.

When a production host is engineered to produce a fatty acid with a specific level of unsaturation, branching, or carbon chain length, the resulting engineered fatty acid can be used in the production of fatty acid derivatives. Fatty acid derivatives generated from such production hosts can display the characteristics of the engineered fatty acid.

For example, a production host can be engineered to make branched, short chain fatty acids, which can then be used by the production host to produce branched, short chain fatty alcohols. Similarly, a hydrocarbon can be produced by engineering a production host to produce a fatty acid having a defined level of branching, unsaturation, and/or carbon chain length, and thus producing a homogeneous hydrocarbon population. Additional steps can be employed to improve the homogeneity of the resulting product. For example, when an unsaturated alcohol, fatty ester, or hydrocarbon is desired, the production host organism can be engineered to produce low levels of saturated fatty acids, and in addition can be modified to express an additional desaturase and thus lessen the production of saturated product.

A. Branched and Cyclic Moieties

1. Engineering Branched and Cyclic Fatty Acid Derivatives

Fatty acids are key intermediates in the production of fatty acid derivatives. Fatty acid derivatives containing branch points, cyclic moieties, and combinations thereof can be prepared using branched or cyclic fatty acids.

For example, *E. coli* naturally produces straight chain fatty acids (sFAs). To engineer *E. coli* to produce branched chain fatty acids (brFAs), several genes that provide branched precursors (e.g., a bkd operon) can be introduced into the production host and expressed to allow initiation of fatty acid biosynthesis from branched precursors (e.g., fabH). The bkd, ilv, icm, and fab gene families can be expressed or overexpressed to produce branched chain fatty acid derivatives. Similarly, to produce cyclic fatty acids, genes that provide cyclic precursors can be introduced into the production host and expressed to allow initiation of fatty acid biosynthesis from cyclic precursors. The ans, chc, and plm gene families can be expressed or overexpressed to produce cyclic fatty acids.

Additionally, a production host can be engineered to express genes encoding proteins for the elongation of brFAs (e.g., genes encoding ACP, FabF, etc.) and/or to delete or attenuate the corresponding *E. coli* genes that normally lead to sFAs. In this regard, endogenous genes that would compete with the introduced genes (e.g., fabH, fabF) are deleted or attenuated.

The branched acyl-CoA (e.g., 2-methyl-butyryl-CoA, isovaleryl-CoA, isobutyryl-CoA, etc.) are the precursors of brFA. In most microorganisms containing brFA, the brFA are synthesized in two steps from branched amino acids (e.g., isoleucine, leucine, or valine) (Kadena, Microbiol. Rev., 55:288, 1991). A production host can be engineered to express or overexpress one or more of the enzymes involved in these two steps to produce brFAs, or to over-produce brFAs. For example, the production host may have an endogenous enzyme that can accomplish one step leading to brFA, therefore only genes encoding enzymes involved in the second step need to be introduced recombinantly.

The mutant thioesterases of the invention can be engineered to have one or more altered properties, for example, altered specificity and/or increased activity (e.g., catalytic rate), with regard to branched or cyclic chain acyl-CoA or acyl-ACP compounds described herein. Accordingly the recombinant cell producing fatty acid derivatives can be made to preferentially produce a desired branched or cyclic chain fatty acid derivative product that may have high value as an end product.

2. Formation of Branched Fatty Acids and Branched Fatty Acid Derivatives

The first step in forming brFAs is the production of the corresponding α-keto acids by a branched-chain amino acid aminotransferase. Production hosts can endogenously include genes encoding such enzymes, or alternatively, such genes can be recombinantly introduced. *E. coli*, for example, endogenously expresses such an enzyme, IlvE (EC 2.6.1.42; GenBank Accession No. YP_026247). In some production hosts, a heterologous branched-chain amino acid aminotransferase may not be expressed. However, *E. coli* IlvE or any other branched-chain amino acid aminotransferase (e.g., IlvE from *Lactococcus lactis* (GenBank Accession No. AAF34406), IlvE from *Pseudomonas putida* (GenBank Accession No. NP_745648), or IlvE from *Streptomyces coelicolor* (GenBank Accession No. NP_629657)), if not endogenous, can be introduced. If the aminotransferase reaction is rate limiting in brFA biosynthesis in the chosen production host organism, then the aminotransferase can be overexpressed.

The second step is the oxidative decarboxylation of the α-keto acids to the corresponding branched-chain acyl-CoA. This reaction can be catalyzed by a branched-chain α-keto acid dehydrogenase complex (bkd; EC 1.2.4.4.) (Denoya et al., J. Bacteriol., 177:3504, 1995), which consists of E1α/β (decarboxylase), E2 (dihydrolipoyl transacylase) and E3 (dihydrolipoyl dehydrogenase) subunits. These branched-chain α-keto acid dehydrogenase complexes are similar to pyruvate and α-ketoglutarate dehydrogenase complexes. Every microorganism that possesses brFAs and/or grows on branched-chain amino acids can be used as a source to isolate bkd genes for expression in production hosts such as, for example, *E. coli*. Furthermore, *E. coli* has the E3 component as part of its pyruvate dehydrogenase complex (encoded by, for example, lpd, EC 1.8.1.4, GenBank Accession No. NP_414658), thus it can be sufficient to only express the E1 α/β and E2 bkd genes. Table 2 recites non-limiting examples of bkd genes from several microorganisms that can be recombinantly introduced and expressed in a production host to provide branched-chain acyl-CoA precursors. Microorganisms having such bkd genes can also be used as production hosts.

TABLE 2

Bkd genes from selected microorganisms

| Organism | Gene | GenBank Accession No. |
|---|---|---|
| Streptomyces coelicolor | bkdA1 (E1α) | NP_628006 |
| | bkdB1 (E1β) | NP_628005 |
| | bkdC1 (E2) | NP_638004 |
| Streptomyces coelicolor | bkdA2 (E1α) | NP_733618 |
| | bkdB2 (E1β) | NP_628019 |
| | bkdC2 (E2) | NP_628018 |
| Streptomyces avermitilis | bkdA (E1α) | BAC72074 |
| | bkdB (E1β) | BAC72075 |
| | bkdC (E2) | BAC72076 |
| Streptomyces avermitilis | bkdF (E1α) | BAC72088 |
| | bkdG (E1β) | BAC72089 |
| | bkdH (E2) | BAC72090 |
| Bacillus subtilis | bkdAA ((E1α) | NP_390288 |
| | bkdAB (E1β) | NP_390288 |
| | bkdB (E2) | NP_390288 |
| Pseudomonas putida | bkdA1 (E1α) | AAA65614 |
| | bkdA2 (E1β) | AAA65615 |
| | bkdC (E2) | AAA65617 |

In another example, isobutyryl-CoA can be made in a production host, for example in E. coli, through the coexpression of a crotonyl-CoA reductase (Ccr, EC 1.6.5.5, 1.1.1.1) and isobutyryl-CoA mutase (large subunit IcmA, EC 5.4.99.2; small subunit IcmB, EC 5.4.99.2) (Han and Reynolds, J. Bacteriol., 179:5157, 1997). Crotonyl-CoA is an intermediate in fatty acid biosynthesis in E. coli and other microorganisms. Non-limiting examples of ccr and icm genes from selected microorganisms are given in Table 3.

TABLE 3 ccr and icm genes from selected microorganisms

| Organism | Gene | GenBank Accession No. |
|---|---|---|
| Streptomyces coelicolor | ccr | NP_630556 |
| | icmA | NP_629554 |
| | icmB | NP_630904 |
| Streptomyces cinnamonensis | ccr | AAD53915 |
| | icmA | AAC08713 |
| | icmB | AJ246005 |

In addition to expression of the bkd genes, the initiation of brFA biosynthesis utilizes β-ketoacyl-acyl-carrier-protein synthase III (FabH, EC 2.3.1.41) with specificity for branched chain acyl-CoAs (Li et al., J. Bacteriol., 187:3795-3799, 2005). Non-limiting examples of such FabH enzymes are listed in Table 4. fabH genes that are involved in fatty acid biosynthesis of any brFA-containing microorganism can be expressed in a production host. The Bkd and FabH enzymes from production hosts that do not naturally make brFA may not support brFA production, therefore Bkd and FabH can be expressed recombinantly. Vectors containing the bkd and fabH genes can be inserted into such a production host. Similarly, the endogenous level of Bkd and FabH production may not be sufficient to produce brFA, therefore, they can be over-expressed. Additionally, other components of fatty acid biosynthesis pathway can be expressed or over-expressed, such as acyl carrier proteins (ACPs) and β-ketoacyl-acyl-carrier-protein synthase II (encoded by fabF, EC 2.3.1.41) (non-limiting examples of candidates are listed in Table 4). In addition to expressing these genes, some genes in the endogenous fatty acid biosynthesis pathway may be attenuated in the production host. Genes encoding enzymes that compete for substrate(s) with the enzymes of the pathway that result in brFA production can be attenuated to increase brFA production. For example, in E. coli the most likely candidates to interfere with brFA biosynthesis are fabH (GenBank Accession No. NP_415609) and/or fabF genes (GenBank Accession No. NP_415613).

TABLE 4 fabH, ACP and fabF genes from selected microorganisms with brFAs

| Organism | Gene | GenBank Accession No. |
|---|---|---|
| Streptomyces coelicolor | fabH1 | NP_626634 |
| | ACP | NP_626635 |
| | fabF | NP_626636 |
| Streptomyces avermitilis | fabH3 | NP_823466 |
| | fabC3 (ACP) | NP_823467 |
| | fabF | NP_823468 |
| Bacillus subtilis | fabH_A | NP_389015 |
| | fabH_B | NP_388898 |
| | ACP | NP_389474 |
| | fabF | NP_389016 |
| Stenotrophomonas maltophilia | SmalDRAFT_0818 (fabH) | ZP_01643059 |
| | SmalDRAFT_0821 (ACP) | ZP_01643063 |
| | SmalDRAFT_0822 (fabF) | ZP_01643064 |
| Legionella pneumophila | FabH | YP_123672 |
| | ACP | YP_123675 |
| | fabF | YP_123676 |

As mentioned above, branched chain alcohols can be produced through the combination of expressing genes that support brFA synthesis and alcohol synthesis. For example, when a gene encoding an alcohol reductase, such as acr1 from Acinetobacter baylyi ADP1, is coexpressed with a bkd operon in an E. coli host cell, the host cell can synthesize isopentanol, isobutanol, or 2-methyl butanol. Similarly, when acr1 is coexpressed with ccr/icm genes in an E. coli host cell, the host cell can synthesize isobutanol.

3. Formation of Cyclic Fatty Acids and Cyclic Fatty Acid Derivatives

To convert a production host such as an E. coli into an organism capable of synthesizing ω-cyclic fatty acids (cyFA), a gene that provides the cyclic precursor cyclohexylcarbonyl-CoA (CHC-CoA) (Cropp et al., Nature Biotech., 18:980-983, 2000) is introduced and expressed in the production host. A similar conversion is possible for other production hosts, for example, bacteria, yeast and filamentous fungi.

Non-limiting examples of genes that provide CHC-CoA in E. coli include: ansJ, ansK, ansL, chcA, and ansM from the ansatrienin gene cluster of Streptomyces collinus (Chen et al., Eur. J. Biochem., 261: 98-107, 1999), or plmJ, plmK, plmL, chcA, and plmM from the phoslactomycin B gene cluster of Streptomyces sp. HK803 (Palaniappan et al., J. Biol. Chem., 278:35552-35557, 2003) together with the chcB gene (Patton et al., Biochem., 39:7595-7604, 2000) from S. collinus, S. avermitilis, or S. coelicolor (see Table 5 for GenBank Accession numbers). The genes listed above in Table 4 can then be expressed to allow initiation and elongation of co-cyclic fatty acids. Alternatively, the homologous genes can be isolated from microorganisms that make cyFA and expressed in E. coli.

TABLE 5

Genes for the synthesis of CHC-CoA

| Organism | Gene | GenBank Accession No. |
|---|---|---|
| Streptomyces collinus | ansJK | U72144* |
| | ansL | |
| | chcA | |
| | ansM | |
| | chcB | AF268489 |
| Streptomyces sp. HK803 | pmlJK | AAQ84158 |
| | pmlL | AAQ84159 |
| | chcA | AAQ84160 |
| | pmlM | AAQ84161 |
| Streptomyces coelicolor | chcB/caiD | NP_629292 |
| Streptomyces avermitilis | chcB/caiD | NP_629292 |

*Only chcA is annotated in GenBank entry U72144, ansJKLM are according to Chen et al., Eur. J. Biochem., 261:98-107, 1999.

The genes listed in Table 4 (fabH, ACP, and fabF) are sufficient to allow initiation and elongation of ω-cyclic fatty acids because they typically have broad substrate specificity. If the coexpression of any of these genes with the ansJKLM/chcAB or pmlJKLM/chcAB genes from Table 5 does not yield cyFA, then fabH, ACP, and/or fabF homologs from microorganisms that make cyFAs can be isolated (e.g., by using degenerate PCR primers or heterologous DNA sequence probes) and coexpressed. Table 6 lists non-limiting examples of microorganisms that contain ω-cyclic fatty acids.

TABLE 6

Non-limiting examples of microorganisms that contain ω-cyclic fatty acids

| Organism | Reference |
|---|---|
| Curtobacterium pusillum | ATCC19096 |
| Alicyclobacillus acidoterrestris | ATCC49025 |
| Alicyclobacillus acidocaldarius | ATCC27009 |
| Alicyclobacillus cycloheptanicus * | Moore, J. Org. Chem., 62: pp. 2173, 1997. |

* Uses cycloheptylcarbonyl-CoA and not cyclohexylcarbonyl-CoA as precursor for cyFA biosynthesis.

B. Saturation

Fatty acids are key intermediates in the production of fatty acid derivatives. The degrees of saturation in fatty acid derivatives can be controlled by regulating the degrees of saturation of the fatty acid intermediates. The sfa, gns, and fab families of genes can be expressed or overexpressed to control the saturation of fatty acids.

Production hosts can be engineered to produce unsaturated fatty acids by engineering the production host to overexpress fabB, or by growing the production host at low temperatures (e.g., less than 37° C.). FabB has preference for cis-$\delta^3$ decenoyl-ACP, and results in unsaturated fatty acid production in E. coli. Overexpression of the fabB gene results in the production of a significant percentage of unsaturated fatty acids (de Mendoza et al., J. Biol. Chem., 258:2098-101, 1983). The fabB gene can be inserted into and expressed in production hosts not naturally having the gene. These unsaturated fatty acids can then be used as intermediates in the production hosts that are engineered to produce fatty acid derivatives, such as fatty alcohols, fatty esters, waxes, olefins, alkanes, and the like.

Alternatively, repressors of fatty acid biosynthesis, for example, a repressor (GenBank Accession No. NP_418398) encoded by fabR, can be deleted. This will also result in increased unsaturated fatty acid production in E. coli (Zhang et al., J. Biol. Chem., 277:15558, 2002). Similar deletions can be made in other production hosts. Further increase in unsaturated fatty acids may be achieved, for example, by overexpression of fabM (encoding trans-2, cis-3-decenoyl-ACP isomerase, GenBank Accession No. DAA05501) and controlled expression of fabK (encoding trans-2-enoyl-ACP reductase II, GenBank Accession No. NP_357969) from Streptococcus pneumoniae (Marrakchi et al., J. Biol. Chem., 277: 44809, 2002), while deleting E. coli fabI (encoding trans-2-enoyl-ACP reductase, GenBank Accession No. NP_415804). Additionally, to increase the percentage of unsaturated fatty esters, the production host can also overexpress fabB (encoding 3-ketoacyl-ACP synthase I, GenBank Accession No. BAA16180, EC:2.3.1.41), sfa (encoding a suppressor of fabA, GenBank Accession No. AAC44390), and gnsA and gnsB (both encoding secG null mutant suppressors, GenBank Accession No. ABD18647.1 and GenBank Accession No. AAC74076.1, respectively). In some examples, the endogenous fabF gene can be attenuated, thus increasing the percentage of palmitoleate ($C_{16:1}$) produced.

The mutant thioesterases of the invention can be engineered to have altered properties, for example, altered specificity and/or increased activity, with regard to substituted or unsubstituted acyl-CoA or acyl-ACP compounds that are prepared as described herein. Accordingly the recombinant cell producing the fatty acid derivatives can be made to preferentially produce a desired saturation profile in a fatty acid derivative product that may have high value as an end product.

C. Chain Lengths and Ester Characteristics

1. Chain Lengths and Production of Odd-Numbered Chains

The methods described herein permit production of fatty esters and fatty acid derivatives of varied chain lengths by selecting a suitable mutant thioesterase that has specificity and/or selectivity for a substrate of a specific carbon chain length. By expressing the specific thioesterases, fatty acids and fatty acid derivatives having desired carbon chain lengths can be produced. In some embodiments, an endogenous thioesterase can be mutated using known genomic alteration techniques. Or, a gene encoding a particular thioesterase can be heterologously introduced into a production host such that a fatty acid or fatty acid derivative of a particular carbon chain length is produced. In certain embodiments, expression of endogenous thioesterases is suppressed. The mutant thioesterases of the invention can be engineered to have altered properties, for example, altered specificity and/or increased activity, with regard to specific chain lengths of acyl-CoA or acyl-ACP compounds described herein. Accordingly, the recombinant cell producing the fatty acid derivatives can be made to preferentially produce a fatty acid derivative product with the desired chain length and/or high value as an end product.

In one embodiment, the fatty acid derivative contains a carbon chain of about 4 to 36 carbon atoms, about 6 to 32 carbon atoms, about 10 to 30 carbon atoms, about 10 to 18 carbon atoms, about 24 to 32 carbon atoms, about 26 to 30 carbon atoms, about 26 to 32 carbon atoms, about 5 to 10 carbon atoms, about 10 to 16 carbon atoms, or about 12 to 18 carbon atoms. In an alternate embodiment, the fatty acid derivative contains a carbon chain less than about 20 carbon atoms, less than about 18 carbon atoms, or less than about 16 carbon atoms. In another embodiment, the fatty ester product is a saturated or unsaturated fatty ester product having a carbon atom content between 24 and 46 carbon atoms. In one embodiment, the fatty ester product has a carbon atom content between 24 and 32 carbon atoms. In another embodiment, the fatty ester product has a carbon content of 14 and 20 carbons. In another embodiment, the fatty ester is the methyl ester of $C_{18:1}$. In another embodiment, the fatty ester is the ethyl ester of $C_{16:1}$. In another embodiment, the fatty ester is the methyl ester of $C_{16:1}$. In yet another embodiment, the fatty ester is octadecyl ester of octanol.

Certain microorganisms preferentially produce even- or odd-numbered carbon chain fatty acids and fatty acid derivatives. For example, *E. coli* normally produce even-numbered carbon chain fatty acids and fatty acid ethyl esters (FAEE). Surprisingly, the methods disclosed herein can be used to alter that production. For example, *E. coli* can be made to produce odd-numbered carbon chain fatty acids and FAEE under certain circumstances.

2. Ester Characteristics

An ester typically includes what may be designated an "A" side and a "B" side. The B side may be contributed by a fatty acid produced from de novo synthesis in the production host organism. In some embodiments, where the production host is additionally engineered to make alcohols, including fatty alcohols, the A side is also produced by the production host organism. In yet other embodiments, the A side can be provided by the growth medium. By selecting the desired thioesterase genes, the B side (and the A side when fatty alcohols are being made) can be designed to be have certain desirable carbon chain characteristics. These characteristics include, for example, points of branching, points of unsaturation, and desired carbon chain lengths. Thus, the mutant thioesterases of the invention can be engineered to have altered properties, for example, altered specificity and/or increased activity, with regard to preference for accepting certain acyl-CoA or acyl-ACP compounds as an A side chain as described herein. Accordingly the recombinant cell producing the fatty acid derivatives can be made such that it preferentially produces a desired fatty acid derivative product that is valuable as an end product.

When particular thioesterase genes are selected, the A and B sides will have similar carbon chain characteristics when they are both contributed by the production host using fatty acid biosynthetic pathway intermediates. For example, at least about 50%, 60%, 70%, or 80% of the fatty esters produced will have A and B sides that vary by about 2, 4, 6, 8, 10, 12, or 14 carbons in length. The A side and the B side can also display similar branching and saturation levels.

In addition to producing fatty alcohols that contribute to the A side, the production host can produce other short chain alcohols such as ethanol, propanol, isopropanol, isobutanol, and butanol for incorporation on the A side using techniques well known in the art. For example, butanol can be made by the production host organism. To create butanol producing cells, the LS9001 strain, for example, can be further engineered to express atoB (acetyl-CoA acetyltransferase) from *Escherichia coli* K12, β-hydroxybutyryl-CoA dehydrogenase from *Butyrivibrio fibrisolvens*, crotonase from *Clostridium beijerinckii*, butyryl CoA dehydrogenase from *Clostridium beijerinckii*, CoA-acylating aldehyde dehydrogenase (ALDH) from *Cladosporium flavum*, and adhE encoding an aldehyde-alcohol dehydrogenase of *Clostridium acetobutylicum* in the pBAD24 expression vector under the prpBCDE promoter system. Other production host organisms may be similarly modified to produce butanol or other short chain alcohols. For example, ethanol can be produced in a production host using the methods described by Kalscheuer et al., Microbiology, 152:2529-2536, 2006, which is herein incorporated by reference.

III. Genetic Engineering of Production Strain to Increase/Improve Fatty Acid Derivative Production/Yield Heterologous polynucleotide sequences involved in a biosynthetic pathway for the production of fatty acid derivatives can be introduced stably or transiently into a production host cell using techniques known in the art. Non-limiting examples of such techniques include electroporation, calcium phosphate precipitation, DEAE-dextran mediated transfection, liposome-mediated transfection, conjugation, transduction, and genomic integration. For stable transformation, a DNA sequence can further include a selectable marker, including, for example, markers for antibiotic resistance, and genes that complement auxotrophic deficiencies. On the other hand, endogenous polynucleotides involved in the biosynthetic pathway for the production of fatty acid derivatives can also be mutated using known genomic alteration techniques. These strategies can be applied separately or in combination.

Various embodiments herein utilize an expression vector that includes a heterologous DNA sequence encoding a protein involved in a metabolic or biosynthetic pathway. Suitable expression vectors include, but are not limited to, viral vectors (such as baculovirus vectors), phage vectors (such as bacteriophage vectors), plasmids, phagemids, cosmids, fosmids, bacterial artificial chromosomes, viral vectors (e.g., viral vectors based on vaccinia virus, poliovirus, adenovirus, adeno-associated virus, SV40, herpes simplex virus, and the like), P1-based artificial chromosomes, yeast plasmids, yeast artificial chromosomes, and any other vectors for specific production hosts of interest (such as *E. coli*, *Pseudomonas pisum*, and *Saccharomyces cerevisiae*).

Useful expression vectors can include one or more selectable marker genes to provide a phenotypic trait for selection of transformed production host cells. The selectable marker gene encodes a protein necessary for the survival or growth of transformed production host cells grown in a selective culture medium. Production host cells not transformed with the vector containing the selectable marker gene will not survive in the culture medium. Typical selection genes encode proteins that (a) confer resistance to antibiotics or other toxins (e.g., ampicillin, neomycin, methotrexate, or tetracycline); (b) complement auxotrophic deficiencies; or (c) supply critical nutrients not available from complex media (e.g., the gene that encodes D-alanine racemate for Bacilli). In alternative embodiments, the selectable marker gene is one that encodes dihydrofolate reductase or confers neomycin resistance (for use in eukaryotic cell culture), or one that confers tetracycline or ampicillin resistance (for use in a prokaryotic production host cell, such as in *E. coli*).

In the expression vector, the DNA sequence encoding the gene in the biosynthetic pathway is operably linked to an appropriate expression control sequence (e.g., promoters, enhancers, and the like) to direct synthesis of the encoded gene product. Such promoters can be derived from microbial or viral sources, including, for example, from CMV and SV40. Depending on the production host/vector system utilized, any number of suitable transcription and translation control elements can be used in the expression vector, including constitutive and inducible promoters, transcription enhancer elements, transcription terminators, and the like. See, e.g., Bitter et al., Methods in Enzymology, 153:516-544, 1987.

Suitable promoters for use in prokaryotic production host cells include, but are not limited to, promoters capable of recognizing the T4, T3, Sp6 and T7 polymerases, the $P_R$ and P_L promoters of bacteriophage lambda, the trp, recA, heat shock, and lacZ promoters of *E. coli*, the alpha-amylase and the sigma-specific promoters of *B. subtilis*, the promoters of the bacteriophages of *Bacillus, Streptomyces* promoters, the int promoter of bacteriophage lambda, the bla promoter of the beta-lactamase gene of pBR322, and the CAT promoter of the chloramphenicol acetyl transferase gene. Prokaryotic promoters are reviewed by Glick, J. Indust. Microbiol., 1:277, 1987; Watson et al., MOLECULAR BIOLOGY OF THE GENE, 4th Ed. (1987), Benjamin Cummins (1987); and Sambrook et al., MOLECULAR CLONING: A LABORATORY MANUAL, 2nd Ed. (Cold Spring Harbor Laboratory Press, 1989), the disclosures of which are incorporated herein by reference. Non-limiting examples of suitable eukaryotic promoters for use within a eukaryotic production host are viral in origin and include the promoter of the mouse metallothionein I gene (Hamer et al., J. Mol. Appl. Gen., 1:273, 1982); the TK promoter of herpes virus (McKnight, Cell, 31:355, 1982); the SV40 early promoter (Benoist et al., Nature, 290:304, 1981); the cytomegalovirus promoter (Foecking et al., Gene, 45:101, 1980); the yeast gal4 gene promoter (Johnston et al., PNAS (USA), 79:6971, 1982; Silver et al., PNAS (USA), 81:5951, 1984); and the IgG promoter (Orlandi et al., PNAS (USA), 86:3833, 1989), the contents of which are incorporated herein by reference.

The production host can be genetically modified with a heterologous gene sequence encoding a biosynthetic pathway gene product that is operably linked to an inducible promoter. Inducible promoters are known in the art. Non-limiting examples of suitable inducible promoters include promoters that are affected by proteins, metabolites, or chemicals. These include, but are not limited to: a bovine leukemia virus promoter, a metallothionein promoter, a dexamethasone-inducible MMTV promoter, an SV40 promoter, an MRP polIII promoter, a tetracycline-inducible CMV promoter (such as the human immediate-early CMV promoter) as well as those from the trp and lac operons.

In some examples, a production host is genetically modified with a heterologous gene sequence encoding a biosynthetic pathway gene product that is operably linked to a constitutive promoter. Suitable constitutive promoters are known in the art and include constitutive adenovirus major late promoter, a constitutive MPSV promoter, or a constitutive CMV promoter.

In some examples, a modified production host is one that is genetically modified with an exogenous gene sequence encoding a single protein involved in a biosynthesis pathway. In other embodiments, a modified production host is one that is genetically modified with exogenous gene sequences encoding two or more proteins involved in a biosynthesis pathway, for example, the first and second enzymes in a biosynthetic pathway.

When a production host is genetically modified to express two or more proteins involved in a biosynthetic pathway, those gene sequences can each be contained in a single or in separate expression vectors. When those gene sequences are contained in a single expression vector, in some embodiments, the polynucleotide sequences will be operably linked to a common control element wherein the common control element controls expression of all of the biosynthetic pathway protein-encoding gene sequences in the single expression vector (e.g., a promoter).

When a modified production host is genetically modified with heterologous DNA sequences encoding two or more proteins involved in a biosynthesis pathway, one of the DNA sequences can be operably linked to an inducible promoter, and one or more of the DNA sequences can be operably linked to a constitutive promoter.

In some embodiments, the intracellular concentration (i.e., the concentration within the genetically modified production host) of a biosynthetic pathway intermediate can be increased to further boost the yield of the final product. The intracellular concentration of the intermediate can be increased in a number of ways, including, but not limited to, increasing the concentration in the culture medium of a substrate for a biosynthetic pathway; increasing the catalytic activity of an enzyme that is active in the biosynthetic pathway; increasing the intracellular amount of a substrate (e.g., a primary substrate) for an enzyme that is active in the biosynthetic pathway; and the like.

In some examples, the fatty acid derivative or intermediate is produced in the cytoplasm of the production host. The cytoplasmic concentration can be increased in a number of ways, including, but not limited to, binding of the fatty acid to coenzyme A to form an acyl-CoA thioester. Additionally, the concentration of acyl-CoA can be increased by increasing the biosynthesis of CoA in the cell, such as by over-expressing genes associated with pantothenate biosynthesis (e.g., panD) or knocking out genes associated with glutathione biosynthesis (e.g., glutathione synthase).

Regulatory sequences, coding sequences, and combinations thereof, can be introduced or altered in the chromosome of the production host. In some examples, the integration of the desired recombinant sequence into the production host genomic sequence does not require the use of a selectable marker such as an antibiotic. In some examples, the genomic alterations include changing the control sequence of the target genes by replacing the native promoter(s) with a promoter that is insensitive to regulation. There are numerous approaches for doing this. For example, Valle and Flores, in *Methods Mol. Biol.*, 267:113-122, 2006, describe a PCR-based method to overexpress chromosomal genes in *E. coli*. The content of Valle and Flores is incorporated by reference herein. Another approach is based on the use of single-stranded oligonucleotides to create specific mutations directly in the chromosome, using the technique developed by Court et al., PNAS (USA), 100:15748-15753, 2003, the content of which is also incorporated herein by reference. This technique is based on the use of the overexpression of the Beta protein from the bacteriophage lambda to enhance genetic recombination. The advantages of this approach include that synthetic oligonucleotides 70 bases long (or more) can be used to create point mutations, insertions, and deletions, thus eliminating any cloning steps. Furthermore, the system is sufficiently efficient that no markers are necessary to isolate the desired mutations.

With this approach the regulatory region of a gene can be changed to create a stronger promoter and/or eliminate the binding site of a repressor. Accordingly, a desired gene can be overexpressed in the production host organism.

IV. Fermentation

A. Maximizing Production Efficiency

Production and isolation of fatty acid derivatives can be enhanced by employing specific fermentation techniques. One method for maximizing production while reducing costs is increasing the percentage of the carbon source that is converted to hydrocarbon products.

During normal cellular lifecycles, carbon is used in cellular functions to produce lipids, saccharides, proteins, organic acids, and polynucleotides. Reducing the amount of carbon necessary for growth-related activities can increase the efficiency of carbon source conversion to output. This can be achieved by first growing microorganisms to a desired density, which is achieved at the peak of the growth log phase. Then, replication checkpoint genes can be harnessed to stop the growth of cells. Specifically, quorum sensing mechanisms (as reviewed in Camilli and Bassler, Science, 311:1113, 2006; Venturi, FEMS Microbio. Rev., 30:274-291, 2006; and Reading and Sperandio, FEMS Microbiol. Lett., 254:1-11, 2006, the disclosures of which are incorporated by reference herein) can be used to activate genes associated with the stationary phase.

Genes that can be activated to stop cell replication and growth in *E. coli* include umuDC genes, the over-expression of which stops the progression from stationary phase to exponential growth (Murli et al., J. of Bact., 182:1127, 2000). UmuC is a DNA polymerase that can carry out translesion synthesis over non-coding lesions—the mechanistic basis of most UV and chemical mutagenesis. The umuDC gene products are used for the process of translesion synthesis and also serve as polynucleotide sequence damage checkpoints. The umuDC gene products include UmuC, UmuD, umuD', UmuD'$_2$C, UmuD'$_2$, and/or UmuD$_2$. In the mean time, the product-producing genes can be activated, thus minimizing the need for replication and maintenance pathways to be used while the fatty acid derivative is being made. Production host microorganisms can also be engineered to express umuC and/or umuD from *E. coli* in pBAD24 under the prpBCDE promoter system through de novo synthesis of these genes with the appropriate end-product production genes.

The percentage of input carbons converted to fatty esters or hydrocarbon products is a cost driver. The more efficient the process is (i.e., the higher the percentage of input carbons converted to fatty esters or hydrocarbon products), the less expensive the process is. For oxygen-containing carbon sources (e.g., glucose and other carbohydrate based sources), the oxygen is released in the form of carbon dioxide. For every 2 oxygen atoms released, a carbon atom is also released, leading to a maximal theoretical metabolic efficiency of about 34% (w/w) (for fatty acid derived products). This figure, however, changes for other hydrocarbon products and carbon sources. Typical efficiencies in the literature are about <5%. Production hosts engineered to produce hydrocarbon products can have greater than about 1%, for example, greater than about 3%, 5%, 10%, 15%, 20%, 25%, or 30% efficiency. In one example, production hosts will exhibit an efficiency of about 10% to about 25%. In other examples, such production hosts will exhibit an efficiency of about 25% to about 30%. In other examples, such production hosts will exhibit >30% efficiency.

The production host can be additionally engineered to express recombinant cellulosomes, such as those described in PCT application number PCT/US2007/003736, incorporated herein by reference in its entirety, which can allow the production host to use cellulosic material as a carbon source. For example, the production host can be additionally engineered to express invertases (EC 3.2.1.26) so that sucrose can be used as a carbon source.

Similarly, the production host can be engineered using the teachings described in U.S. Pat. Nos. 5,000,000; 5,028,539; 5,424,202; 5,482,846; and 5,602,030, all incorporated herein by reference in their entirety, so that the production host can assimilate carbon efficiently and use cellulosic materials as carbon sources.

In one example, the fermentation chamber encloses a fermentation run/mixture that is undergoing a continuous reduction. In this instance, a stable reductive environment is created. The electron balance is maintained by the release of carbon dioxide (in gaseous form). Efforts to augment the NAD/H and NADP/H balance can also facilitate in stabilizing the electron balance.

The availability of intracellular NADPH can also be enhanced by engineering the production host to express an NADH:NADPH transhydrogenase. The expression of one or more NADH:NADPH transhydrogenases converts the NADH produced in glycolysis to NADPH which enhances the production of fatty acid derivatives.

B. Small-Scale Hydrocarbon Production

For small scale hydrocarbon product production, *E. coli* BL21(DE3) cells harboring pBAD24 (with ampicillin resistance and the end-product synthesis pathway) as well as pUMVC1 (with kanamycin resistance and the acetyl CoA/malonyl CoA over-expression system) are incubated overnight in 2 Liter flasks at 37° C., shaken at >200 rpm in 500 mL LB medium supplemented with 75 µg/mL ampicillin and 50 µg/mL kanamycin until the cultures reach an OD$_{600}$ of >0.8. Upon achieving an OD$_{600}$ of >0.8, cells are supplemented with 25 mM sodium propionate (at pH 8.0) to activate the engineered gene systems for production, and to stop cellular proliferation by activating UmuC and UmuD proteins. The induction step is performed for 6 hours at 30° C. After incubation, the medium is examined for hydrocarbon product using GC-MS.

C. Large-Scale Hydrocarbon Production

For large scale product production, the engineered production hosts are grown in batches of 10 Liter, 100 Liter, or larger; fermented; and induced to express the desired products based on the specific genes encoded in the appropriate plasmids therein.

For example, *E. coli* BL21(DE3) cells harboring pBAD24 (with ampicillin resistance and the end-product synthesis pathway) as well as pUMVC1 (with kanamycin resistance and the acetyl-CoA/malonyl-CoA overexpression) are incubated from a 500-mL seed culture for a 10-Liter fermentation run (or a 5-Liter seed culture for a 100-Liter fermentation) in an LB medium (glycerol free) containing 50 µg/mL kanamycin and 75 µg/mL ampicillin at 37° C., which is shaken at >200 rpm until the culture reaches an OD$_{600}$ of >0.8, a process that typically takes about 16 hours. The fermentation medium is continuously supplemented so as to maintain a sodium pohosphate of 25 mM, at pH 8.0, in order to activate the engineered gene systems for production, and to stop cellular proliferation by activating UmuC and UmuD proteins. The medium is also continuously supplemented with glucose to maintain a concentration of 25 g/100 mL.

After the first hour of induction, an aliquot of no more than 10% of the total cell volume is removed each hour and allowed to settle without agitation, which in turn allows the hydrocarbon product(s) to rise to the surface, undergoing a spontaneous phase separation. The hydrocarbon component is collected and the aqueous phase returned to the reaction chamber. The reaction chamber is operated continuously. When the OD$_{600}$ drops below about 0.6, the cells are replaced with a new batch grown from a seed culture.

For wax ester production, the wax esters are isolated, washed briefly in 1 M HCl, and returned to pH 7 through extensive washing with distilled water.

V. Post-Production Processing

The fatty acid derivatives produced during fermentation can be separated from the fermentation media. Any technique known for separating fatty acid derivatives from aqueous media can be used. An exemplary separation process is a two-phase (bi-phasic) separation process. This process involves fermenting the genetically engineered production hosts under conditions sufficient to produce a fatty acid derivative, allowing the derivative to collect in an organic phase, and separating the organic phase from the aqueous fermentation broth. This method can be practiced in both a batch and continuous fermentation setting.

Bi-phasic separation takes advantage of the relative immiscibility of fatty acid derivatives to facilitate separation. "Immiscibility" refers to the relative inability of a compound to dissolve in water and is defined and/or determined by the compounds partition coefficient. One or ordinary skill in the art will appreciate that by choosing a fermentation broth and organic phase such that the fatty acid derivative being produced has a high log P value, the fatty acid derivative will separate into the organic phase in the fermentation vessel, even at low concentrations.

The fatty acid derivatives produced in accordance to the compositions, vectors, cells, and methods herein will be relatively immiscible in the fermentation broth, as well as in the cytoplasm. Therefore, the fatty acid derivative will collect in an organic phase either intracellularly and/or extracellularly. The collection of the products in the organic phase will lessen the impact of the fatty acid derivatives on cellular function, and will allow the production host to produce greater amount of product for longer.

The fatty alcohols, fatty esters, waxes, and hydrocarbons produced in accordance to the disclosures herein allow for the production of homogeneous compounds wherein at least about 60%, 70%, 80%, 90%, 91%, 92%, 93%, 94%, or 95% of the fatty alcohols, fatty esters, and waxes produced suitably have carbon chain lengths that vary by less than about 6, less than about 4 carbons, or less than about 2 carbons. These compounds can also be produced so that they have a relatively uniform degree of saturation, for example, at least about 60%, 70%, 80%, 90%, 91%, 92%, 93%, 94%, or 95% of the fatty alcohols, fatty esters, hydrocarbons and waxes are monounsaturated, diunsaturated, or triunsaturated. These compounds can be used directly as products or components of products, for example, as fuels, detergents, lubricants, personal care additives, nutritional supplements etc. These compounds can also be used as feedstock for subsequent reactions to make other products, including, for example transesterification, hydrogenation, catalytic cracking (via hydrogenation, pyrolysis, or both), or epoxidation reactions.

The fatty alcohols, fatty esters, waxes, and hydrocarbons produced in accordance to the compositions, vectors, cells, and methods herein contain low levels of unwanted or undesired elements, including, but not limited to, heavy metals. In some embodiments, the fatty alcohols, fatty esters, waxes, and hydrocarbons produced as described herein suitably contain less than about 50 ppm arsenic; less than about 300 ppm calcium; less than about 200 ppm chlorine; less than about 50 ppm cobalt; less than about 50 ppm copper; less than about 300 ppm iron; less than about 2% by weight of water; less than about 50 ppm lead; less than about 50 ppm manganese; less than about 0.2 ppm mercury; less than about 50 ppm molybdenum; less than about 1% by weight of nitrogen; less than about 200 ppm potassium; less than about 300 ppm sodium; less than about 3% by weight of sulfur; less than 50 ppm zinc; and/or less than 700 ppm phosphorus.

In some embodiments, the fatty alcohols, fatty esters, waxes, and hydrocarbons produced in accordance to the disclosures herein contain between about 50% and about 90% carbon; between about 5% and about 25% hydrogen; or between about 5% and about 25% oxygen. In other embodiments, the fatty alcohols, fatty esters, waxes, and hydrocarbons produced as described herein contain between about 65% and about 85% carbon; between about 10% and about 15% hydrogen; or between about 10% and about 20% oxygen.

VI. Fuel Compositions

As provided herein, certain fatty acid derivatives made according to the methods and compositions described herein possess various advantageous characteristics for use as a fuel. One of ordinary skill in the art will appreciate that, depending upon the intended purpose of the fuel, different fatty acid derivatives may have advantages as compared to others fatty acid derivatives. For example, branched fatty acid derivatives may be more desirable as automobile fuels or components of automobile fuels that are intended for uses in cold climates. Similarly, for certain applications, it may be advantageous to produce a fuel that is either more or less oxygenated or more or less saturated.

Using the methods described herein, fuels comprising relatively homogeneous fatty acid derivatives that at the same time have the desired characteristics/qualities can be produced. Such fatty acid derivative-based fuels can be characterized by carbon fingerprinting, and their lack of impurities, when compared to petroleum derived fuels or biodiesel derived from triglyceride, is also advantageous. The fatty acid derivative-based fuels can be combined with other fuels or fuel additives to produce fuels having desired properties.

The production hosts and methods disclosed herein can be used to produce free fatty acids and fatty esters. In some embodiments, the production hosts and methods disclosed herein can be used to produce a higher and/or improved titer or yield of fatty acid derivatives, including, for example, free fatty acids and/or fatty esters. In some embodiments, the percentage of free fatty acids in the product produced by the production host is at least about 1%, for example, at least about 2%, 3%, 4%, 5%, 6%, 7%, 8%, 9%, 10%, 15%, 20%, or 25%. In some embodiments, the percentage of fatty esters in the product produced by the production host is at least about 50%, for example, at least about 55%, 60%, 65%, 70%, 75%, 80%, 85%, or 90%. In some embodiments, the ratio of fatty esters to free fatty acids in the product produced by the production host is about 10:1, 9:1, 8:1, 7:1, 5:1, 2:1, or 1:1. In certain embodiments, the fatty ester produced by the production host is ethyl dodecanoate, ethyl tridecanoate, ethyl tetradecanoate, ethyl pentadecanoate, ethyl cis-9-hexadecenoate, ethyl hexadecanoate, ethyl heptadecanoate, ethyl cis-11-octadecenoate, ethyl octadecanoate, or combinations thereof. In certain other embodiments, the fatty ester produced by the production is methyl dedecanoate, methyl tridecanoate, methyl tetradecanoate, methyl pentadecanoate, methyl cis-9-hexadecenoate, methyl hexadecanoate, methyl heptadecanoate, methyl cis-11-octadecenoate, methyl octadecanoate, or combinations thereof. In certain embodiments, the free fatty acid produced by the production host is dodecanoic acid, tetradecanoic acid, pentadecanoic acid, cis-9-hexadecenoic acid, hexadecanoic acid, cis-11-octadecenoic acid, or combinations thereof.

The production hosts and methods disclosed herein can be used to produce different proportions of free fatty acids and fatty esters. In some embodiments, the proportion of free fatty acids in the product can be modified according to the methods, compositions, vectors and cells described herein such that the proportion is higher or lower vs. the fatty esters that are produced. In certain related embodiments, the proportion of fatty esters in the product can also be modified according to the disclosures herein, such that the proportion is higher or lower vs. the other products, for example, the free fatty acids, that are produced. In certain other embodiments, the proportional yield of fatty acid derivative with certain carbon chain lengths can be increased or decreased.

A. Carbon Fingerprinting

Biologically produced fatty acid derivatives represent a new source of fuels, such as alcohols, diesel, and gasoline. Biofuels made according to the methods and compositions described herein have not heretofore been produced from renewable sources and are new compositions of matter. These new fuels can be distinguished from fuels derived from petrochemical carbon on the basis of dual carbon-isotopic fingerprinting. Additionally, the specific source of biosourced carbon (e.g., glucose vs. glycerol) can be determined by dual carbon-isotopic fingerprinting (see U.S. Pat. No. 7,169,588, which is herein incorporated by reference in its entirety, in particular, at col. 4, line 31, to col. 6, line 8).

The fatty acid derivatives and the associated biofuels, chemicals, and mixtures can be distinguished from their petrochemical derived counterparts on the basis of $^{14}C$ ($f_M$) and dual carbon-isotopic fingerprinting.

The fatty acid derivatives described herein have utility in the production of biofuels and chemicals. The new fatty acid derivative-based products provided by the instant invention additionally can be distinguished on the basis of dual carbon-isotopic fingerprinting from those materials derived solely from petrochemical sources. The ability to distinguish these products is beneficial in tracking these materials in commerce. For example, fuels or chemicals comprising both "new" and "old" carbon isotope profiles can be distinguished from fuels and chemicals made only of "old" materials. Thus, the instant materials can be followed or "tracked" in commerce or identified in commerce as a biofuel on the basis of their unique profile. In addition, other competing materials can be identified as being biologically derived or derived from a petrochemical source.

In some examples, a biofuel composition is made, which includes a fatty acid derivative having $\delta^{13}C$ of from about −10.9 to about −15.4, wherein the fatty acid derivative accounts for at least about 85% of biosourced material (i.e., derived from a renewable resource such as, for example, cellulosic materials and sugars) in the composition. In other examples, the biofuel composition includes a fatty acid derivative having the formula:

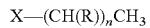

wherein

X=CH$_3$, —CH$_2$OR$^1$; —C(O)OR$^2$; or —C(O)NR$^3$R$^4$;

R=for each n, independently absent, an H, or a lower aliphatic;

n=an integer from about 8 to about 34, preferably an integer from about 10 to about 24;

R$^1$, R$^2$, R$^3$, R$^4$=independently selected from an H or a lower alkyl.

Typically, when R is a lower aliphatic group, R represents a branched, unbranched or cyclic lower alkyl or lower alkenyl moiety. Exemplary R groups include, without limitation, methyl, isopropyl, isobutyl, sec-butyl, cyclopentenyl, and the like. The fatty acid derivative is additionally characterized as having a $\delta^{13}C$ of from about −10.9 to about −15.4, and the fatty acid derivative accounts for at least about 85% of biosourced material in the composition. In some examples the fatty acid derivative in the biofuel composition is characterized by having a fraction of modern carbon ($f_M$ $^{14}C$) of at least about 1.003, 1.010, or 1.5.

B. Impurities

The fatty acid derivatives prepared in accordance with the disclosures herein are useful as components of or for making biofuels as well as other industrial chemicals. These fatty acid derivatives are made directly from fatty acids and not from the chemical processing of triglycerides. Accordingly, fuels and other industrial chemicals comprising the disclosed fatty acid derivatives often contain fewer impurities than are normally associated with, for example, products derived from triglycerides such as fuels derived from vegetable oils and fats.

The crude fatty acid derivative biofuels prepared in accordance with the disclosures herein (prior to mixing the fatty acid derivative with other fuels such as petroleum-based fuels) contain less transesterification catalysts than petroleum-based diesel or other biodiesel produced via one or more transesterification steps. The fatty acid derivative can contain less than about 2.0%, for example, less than about 1.5%, 1.0%, 0.5%, 0.3%, 0.1%, 0.05%, or 0% of a transesterification catalyst or an impurity resulting from a transesterification catalyst. Non-limiting examples of transesterification catalysts include hydroxide catalysts, such as NaOH, KOH, and LiOH; and acidic catalysts, such as mineral acid catalysts and Lewis acid catalysts. Non-limiting examples of catalysts and impurities resulting from transesterification catalysts include tin, lead, mercury, cadmium, zinc, titanium, zirconium, hafnium, boron, aluminum, phosphorus, arsenic, antimony, bismuth, calcium, magnesium, strontium, uranium, potassium, sodium, lithium, and combinations thereof.

The crude fatty acid derivative biofuels prepared in accordance with the disclosures herein (prior to mixing the fatty acid derivatives with one or more other fuels) tend to have a low gelling point, especially when the fatty acid derivative product comprises a $C_{16:1}$ ethyl ester or a $C_{18:1}$ ethyl ester, as compared to the gelling points of other types of biofuels.

Similarly, the crude fatty acid derivative biofuels prepared in accordance with the disclosures herein (prior to mixing the fatty acid derivative(s) with one or more other fuels such as petroleum-based diesels or other biodiesels) contain less glycerol (or glycerin) than biofuels made from triglycerides. The fatty acid derivative(s) can contain less than about 2.0%, for example, less than about 1.5%, 1.0%, 0.5%, 0.3%, 0.1%, 0.05%, or 0% by weight of glycerol.

Crude biofuels derived from the fatty acid derivatives herein also contain less free alcohol(s) (e.g., alcohols that are used to create the ester) than biodiesels made from triglycerides. This is due in part to the efficiency of utilization of the alcohols by the production hosts of the present disclosure. For example, the fatty acid derivative(s) can contain less than about 2.0%, 1.5%, 1.0%, 0.5%, 0.3%, 0.1%, 0.05%, or 0% by weight of free alcohol.

Biofuel derived from the disclosed fatty acid derivatives can be additionally characterized by its low concentration of sulfur as compared to petroleum-derived diesel. Biofuel derived from fatty acid derivatives herein can have less than about 2.0%, for example, less than about 1.5%, 1.0%, 0.5%, 0.3%, 0.1%, 0.05%, or 0% by weight of sulfur.

C. Additives and Fuel Compositions

Fuel additives are used to enhance the performance of a fuel or engine. For example, fuel additives can be used to alter the freezing/gelling points, cloud points, lubricity, viscosity, oxidative stability, ignition quality, octane levels, and flash points. In the United States, all fuel additives must be registered with Environmental Protection Agency. The names of fuel additives and the companies that sell the fuel additives are publicly available by contacting the EPA or by viewing the agency's website. One of ordinary skill in the art will appreciate that the fatty acid derivatives described herein can be mixed with one or more fuel additives to impart a desired quality.

The fatty acid derivatives described herein can be formulated into suitable fuel additives, which enhances the performance of fuels or engines. For example, the fatty acid derivatives described herein can be formulated into lubricity improvers, which impart desirable properties such as wear protection to the engine parts. Accordingly, additive compositions comprising the fatty acid derivatives produced in accordance with the disclosures herein are provided. In another example, the fatty acid derivatives described herein can be formulated into corrosion inhibitors.

The fatty acid derivatives described herein can be mixed with other fuels such as one or more biodiesels derived from triglycerides, various alcohols such as ethanol and butanol, and petroleum-derived products such as gasoline or diesel. Under certain circumstances, a fatty acid derivative with a low gelling point, such as a $C_{16:1}$ ethyl ester or a $C_{18:1}$ ethyl ester, is produced. This low gelling point fatty acid derivative can be mixed with one or more biodiesels made from triglycerides to reduce gelling point of the resulting fuel when compared to a fuel containing only the one or more biodiesels made from triglycerides. Similarly, a fatty acid derivative, such as a $C_{16:1}$ ethyl ester or a $C_{18:1}$ ethyl ester, can be mixed with a petroleum-derived diesel to provide a mixture that contains at least about, and often greater than about, 5% by weight of biodiesel. In some examples, the fuel mixture includes at least about 10%, 15%, 20%, 30%, 40%, 50%, and 60% by weight of the fatty acid derivative.

In some embodiments, the fuel composition can further comprise a synthetic fuel. Any synthetic fuel obtained from coal, natural gas, or biomass can be suitably used. In a further embodiments, the synthetic fuel comprises a Fischer-Tropsch based fuel, a Bergius-based fuel, a Mobil-based fuel, a Karrick-based fuel, or a combination thereof. In still further embodiments, the synthetic fuel comprises a Coal-To-Liquids based fuel (CTL-based fuel), a Gas-To-Liquids based fuel (GTL-based fuel), a Biomass-To-Liquids based fuel (BTL-based fuel), a Coal and Biomass-To-Liquids based fuel (CBTL-based fuel), or a combination thereof. In an exemplary embodiment, the synthetic fuel comprises a Fischer-Tropsch-based fuel.

The amount of synthetic fuel in the fuel composition disclosed herein may be from about 5% to about 90%, from about 5% to about 80%, from about 5% to about 70%, from about 5% to about 60%, or from about 5% to about 50%.

In certain embodiments, a biofuel composition can be made that includes at least about 5%, 10%, 20%, 30%, 40%, 50%, 60%, 70%, 80%, 85%, 90% or 95% of a fatty acid derivative that includes a carbon chain that is 8:0, 10:0, 12:0, 14:0, 14:1, 16:0, 16:1, 18:0, 18:1, 18:2, 18:3, 20:0, 20:1, 20:2, 20:3, 22:0, 22:1 or 22:3. Such biofuel compositions can additionally include at least one additive selected from a cloud point lowering additive that can lower the cloud point to less than about 5° C., or less than about 0° C.; a surfactant; a microemulsion; at least about 5%, 10%, 15%, 20%, 30%, 40%, 50%, 60%, 70%, 80%, 85%, 90%, or 95% diesel fuel from triglycerides; a petroleum-derived gasoline; or a diesel fuel from petroleum.

In some embodiments, the fuel composition comprising the fatty esters produced in accordance with the methods, vectors, cells and compositions herein further comprises one or more diesel fuel additives. Suitable additives are desirably those that afford improved performance but also compatibility with the components in the fuel composition and devices that are typically associated with diesel engines. Illustrative examples of other suitable fuel additives include ignition improvers or cetane number improvers, detergents, dispersants, antiwear agents, viscosity index modifiers, friction modifiers, lubricity improvers, stabilizers, antioxidants, corrosion inhibitors, biocides, metal deactivators, and minor amounts of other optional additives, including, without limitation, antifoaming agents and seal fixes.

In particular embodiments, ignition improvers or cetane number improvers are often added to improve diesel engine performance. Exemplary cetane number improvers include 2'-ethylhexyl nitrate, and other alkyl nitrates. Cetane number improvers can be added to a fuel composition in an amount that is about 0.01 wt. % to about 1.0 wt. %, for example, about 0.05 wt. % to about 0.5 wt. %, based on the total weight of the fuel composition.

In certain embodiments, various detergents and/or dispersants can be included in the fuel composition comprising the fatty ester produced in accordance with the present disclosures to associate and disperse or remove harmful deposits from diesel engine parts. Suitable detergents typically comprise a polar head comprising a metal salt of an acidic organic compound and a long hydrophobic tail. Exemplary detergents include borated carbonate salts, borated sulfonate salts, which are preferably overbased. See, e.g., U.S. Pat. Nos. 4,744,920, 4,965,003, the disclosures of which are incorporated herein. Exemplary dispersants include, without limitation, carboxylic dispersants, succinimide dispersants, amine dispersants, and Mannich dispersants. See, e.g., U.S. Pat. Nos. 3,172,892, 3,438,757, 3,980,569, and 6,165,235, the disclosures of which are incorporated by reference herein. Dispersants can be present in the fuel composition in an amount of about 0.01 wt. % to about 0.1 wt. %, for example, 0.03 to about 0.05 wt. %, based on the total weight of the fuel composition.

In certain embodiments, antiwear agents, including for example, dihydrocarbyl dithiophosphate metal salts, can be added to the fuel composition to provide both antiwear and antioxidation benefits. See, e.g., U.S. Pat. No. 5,898,023, the disclosures of which are incorporated herein by reference.

In particular embodiments, the amount of lubricity improver in the fuel composition can range from about 1 ppm to about 50,000 ppm, for example, about 10 ppm to about 20,000 ppm, or about 25 ppm to about 10,000 ppm. Non-limiting examples of lubricity improvers include esters and fatty acids, which may or may not be the same as those produced in accordance to the methods described herein.

In particular embodiments, the amount of stabilizers, which improves the storage stability of the fuel composition, can range from about 0.001 wt. % to about 2 wt. %, for example about 0.01 wt. % to about 1 wt. %, based on the total weight of the fuel composition. An exemplary stabilizer is a tertiary alkyl primary amine.

Antioxidants prevent the formation of gum depositions on fuel system components due to oxidation of the fuels in storage and/or inhibit the formation of peroxide compounds in certain fuel compositions. The amount of antioxidants can be ranged from about 0.001 wt. % to about 5 wt. %, for example, from about 0.01 wt. % to about 1 wt. %, based on the total weight of the fuel composition.

Corrosion inhibitors protect ferrous metals in fuel handling systems, such as pipelines and storage tanks, from corrosion. Certain corrosion inhibitors are also known to impart additional lubricity, and as such are particularly suitable when additional lubricity is desired. The corrosion inhibitor may be present in the fuel composition in an amount of about 0.001 wt. % to about 5 wt. %, for example, from about 0.01 wt. % to about 1 wt. %, based on the total weight of the fuel composition.

Biocides are used to combat microbial growth in the fuel composition, which may be present in the fuel composition at a concentration of about 0.001 wt. % to about 5 wt. %, for example, from about 0.01 wt. % to about 1 wt. %, based on the total weight of the fuel composition.

Metal deactivators suppress the catalytic effects of some metals, particularly copper, have on fuel oxidation, which can be present in the fuel composition in an amount of about 0.001 wt. % to about 5 wt. %, for example, at 0.01 wt. % to about 1 wt. %, based on the total weight of the fuel composition.

In addition, viscosity improvers, which are typically polymeric materials of number average molecular weights of from about 5,000 to about 250,000, and friction modifiers, which are typically sulfur-containing organo-molybdenum compounds can be added in minor amounts. Foam inhibitors, which typically include alkyl methacrylate polymers or dimethyl silicon polymers, can also be added to the fuel composition in an amount of less than about 10 ppm. Furthermore, seal fixes can be added to insure proper elastomer sealing and prevent premature seal failure can be included in the fuel composition.

EXAMPLES

The examples that follow illustrate the engineering of production hosts to produce specific fatty acid derivatives. The biosynthetic pathways involved in the production of fatty acid derivatives are illustrated in the figures.

Figure 3:
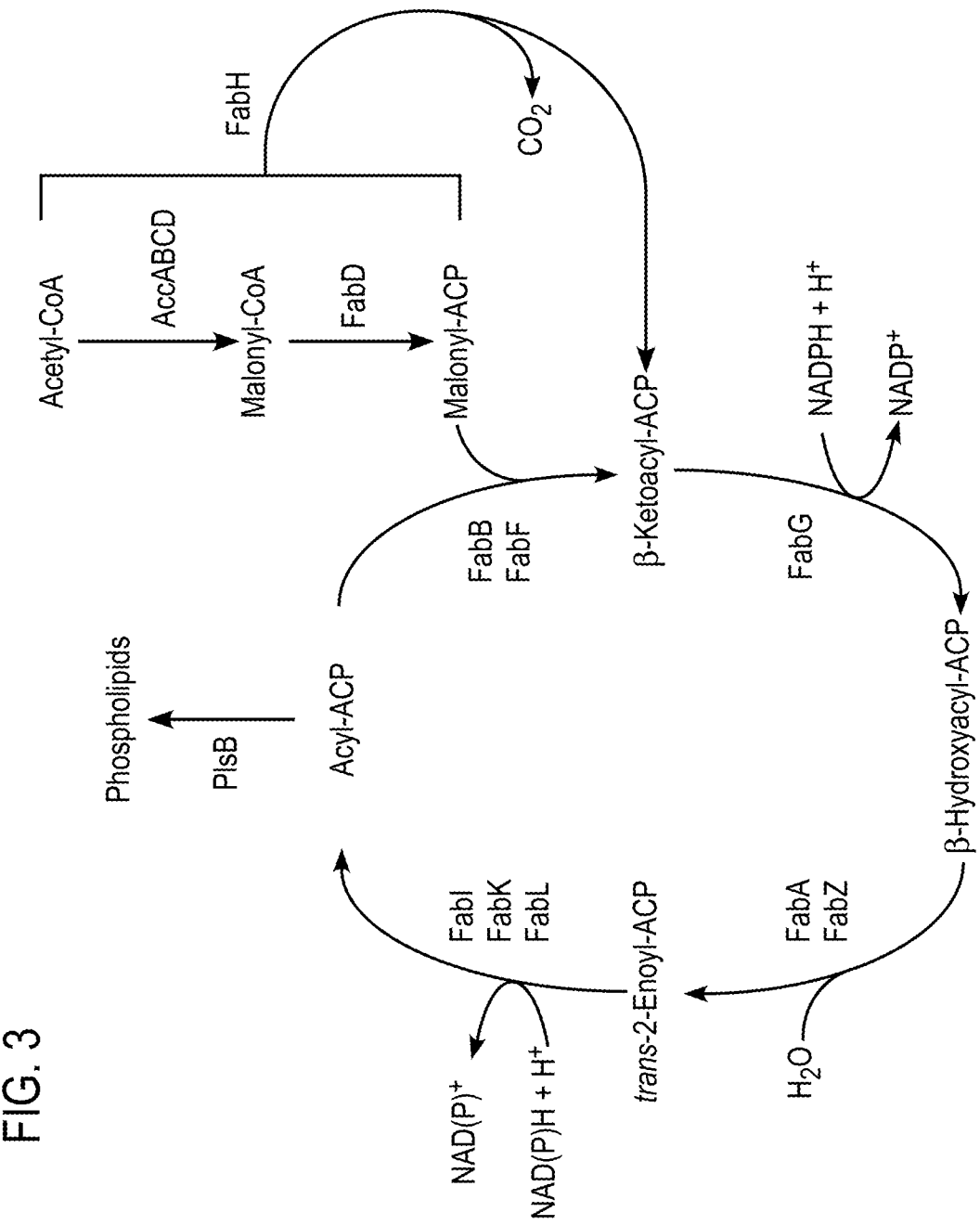
FIG. 3 (FIG. 3) is a diagram illustrating the FAS biosynthetic pathway.

For example, FIG. 3 is a diagram of the FAS pathway depicting the enzymes directly involved in the synthesis of acyl-ACP. To increase the production of fatty acid derivatives, such as waxes, fatty esters, fatty alcohols, and hydrocarbons, one or more of the enzymes described therein can be over expressed or mutated to reduce feedback inhibition, in order to increase the amount of acyl-ACP produced. Additionally, enzymes that metabolize the intermediates to make non-fatty acid based products (e.g., side reactions) can be functionally deleted or attenuated to increase the flux of carbon through the fatty acid biosynthetic (FAS) pathway. In the examples below, many production hosts are described that have been modified to increase fatty acid production.

Figure 4:
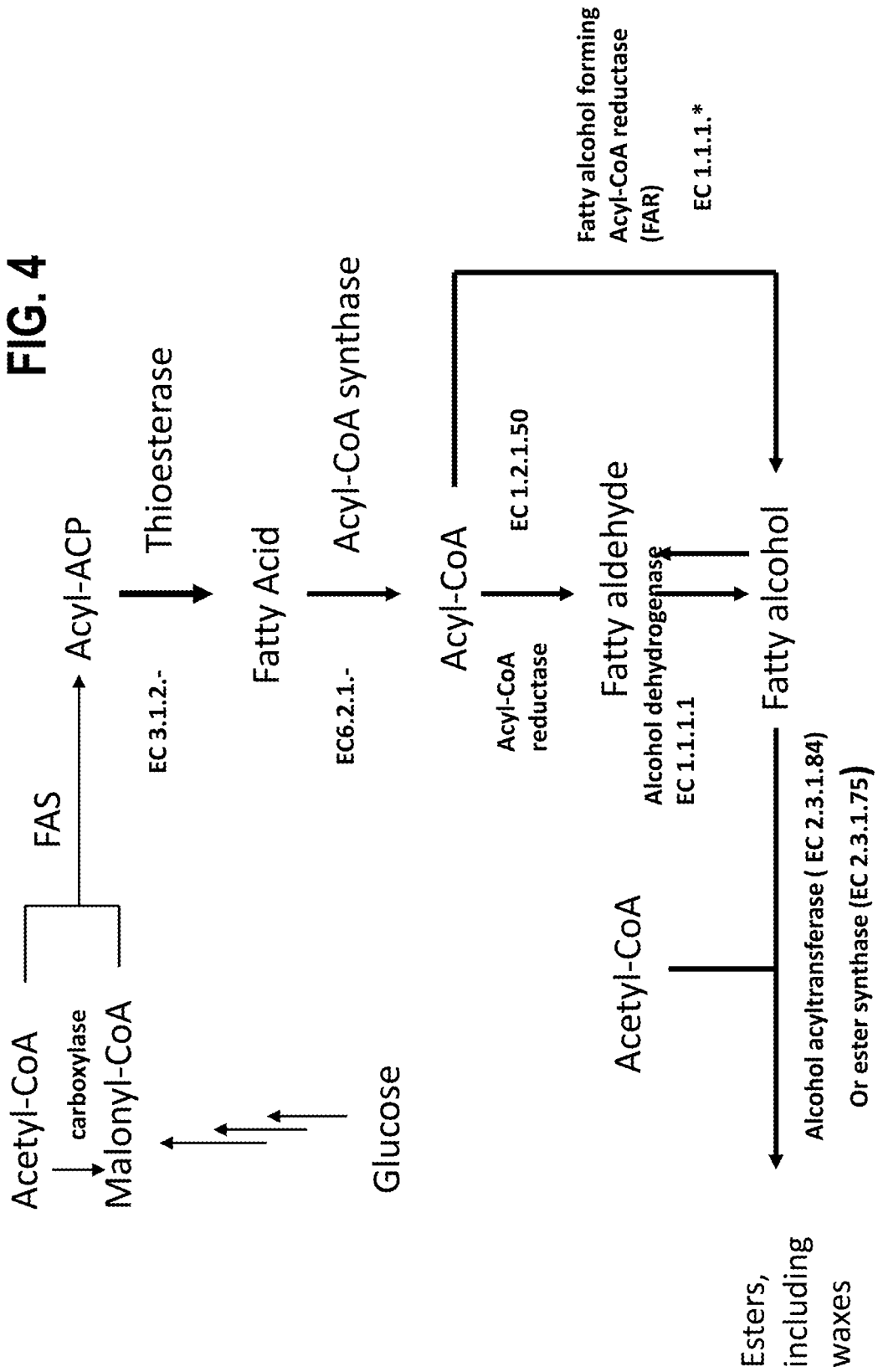
FIG. 4 (FIG. 4) is a diagram illustrating biosynthetic pathways that produce fatty esters depending upon the substrates provided.
Figure 5:
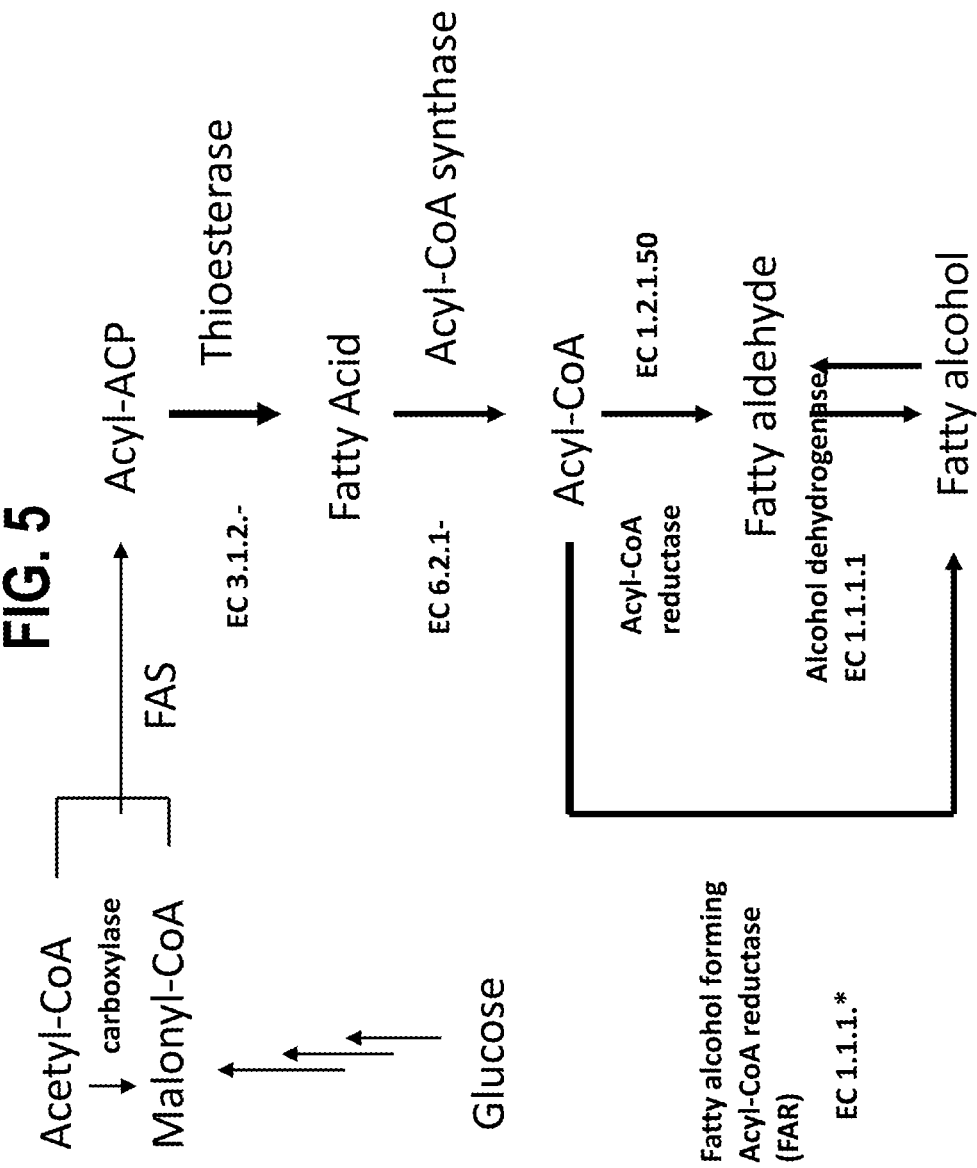
FIG. 5 (FIG. 5) is a diagram illustrating biosynthetic pathways that produce fatty alcohols.

FIGS. 4 and 5 depict biosynthetic pathways that can be engineered to make fatty esters and fatty alcohols, respectively. The conversion of each substrate (e.g., acetyl-CoA, malonyl-CoA, acyl-ACP, fatty acid, and acyl-CoA) to each product (e.g., acetyl-CoA, malonyl-CoA, acyl-ACP, fatty acid, acyl-CoA, fatty aldehydes, fatty esters, and fatty alcohols) can be accomplished using several different polypeptides that are members of the enzyme classes indicated.

The examples below describe microorganisms that have been engineered or can be engineered to produce specific fatty alcohols, fatty esters, and hydrocarbons.

Example 1. Production Host Construction

An exemplary production host is LS9001. LS9001 was produced by modifying C41(DE3) from Overexpress (Saint Beausine, France) to knockout the fadE gene (acyl-CoA dehydrogenase).

Briefly, the fadE knockout strain of *E. coli* was prepared using primers YafV_NotI and Ivry_Ol to amplify about 830 bp upstream of fadE and primers Lpcaf of and LpcaR_Bam to amplify about 960 bp downstream of fadE. Overlap PCR was used to create a construct for in-frame deletion of the complete fadE gene. The fadE deletion construct was cloned into the temperature-sensitive plasmid pKOV3, which contained a sacB gene for counterselection, and a chromosomal deletion of fadE was made according to the method of Link et al., J. Bact. 179:6228-6237, 1997. The resulting strain was not capable of degrading fatty acids and fatty acyl-CoAs. This knockout strain is herein designated as *E. coli* (DE3, ΔfadE).

Another fadE deletion strain, MG1655, was constructed according to the procedures described by Datsenko et al., PNAS (USA), 97:6640-6645 (2000), with the modifications described below. The two primers used to create the deletion were:

```
Del-fadE-F:
                                          (SEQ ID NO: 69)
5'-
AAAAACAGCAACAATGTGAGCTTTGTTGTAATTATATTGTAAACATATTG ATTCCGGGGATCCGTCGACC;
and Del-fadE-R:
                                          (SEQ ID NO: 70)
5'-
AAACGGAGCCTTTCGGCTCCGTTATTCATTTACGCGGCTTCAACTTTCCT

GTAGGCTGGAGCTGCTTC.
```

The Del-fadE-F and Del-fadE-R primers each contain 50 bases of homology to the *E. coli* fadE gene and were used to amplify the Kanamycin resistance cassette from plasmid pKD13 by PCT as described. The resulting PCR product was used to transform electrocompetent *E. coli* MG1655 cells containing pKD46. The cells were previously induced with arabinose for 3-4 hours as described by Datsenko, supra. Following 3 hours of outgrowth in an SOC medium at 37° C., the cells were plated on Luria agar plates containing 50 μg/mL of Kanamycin. Resistant colonies were isolated after an overnight incubation at 37° C. Disruption of the fadE gene was confirmed in some of the colonies by PCR amplication using primers fadE-L2 and fadE-R1, which were designed to flank the fadE gene.

```
                                          (SEQ ID NO: 71)
    fadE-L2    5'-CGGGCAGGTGCTATGACCAGGAC;
    and (SEQ ID NO: 72)
    fadE-R1    5'-CGCGGCGTTGACCGGCAGCCTGG
```

After the proper fadE deletion was confirmed, one colony was used to remove the Km$^R$ marker using the pCP20 plasmid. The resulting strain is designed as MG1655 (ΔfadE).

The fadE-deleted hosts were subject to further adjustments. A plasmid carrying the four genes that are responsible for acetyl-CoA carboxylase activity in *E. coli* (accA, accB, accC, and accD, GenBank Accession Nos: NP_414727, NP_417721, NP_417722, NP_416819, EC 6.4.1.2) were introduced. The accABCD genes were cloned in two steps as bicistronic operons into the NcoI/HindIII and NdeI/AvrII sites of pACYCDuet-1 (Novagen, Madison, Wis.), and the resulting plasmid was designated as pAS004.126. Alternatively, the production host was engineered to express accABCD from *Lactobacillus plantarum*.

Additional modifications that were included in a production host included the following: overexpression of aceEF (encoding the E1p dehydrogenase component and the E2p dihydrolipoamide acyltransferase component of the pyruvate and 2-oxoglutarate dehydrogenase complexes); and fabH/fabD/fabG/acpP/fabF (encoding FAS) from *E. coli*, Nitrosomonas europaea (ATCC 19718), Bacillus subtilis, Saccharomyces cerevisiae, Streptomyces spp, Ralstonia, Rhodococcus, Corynebacteria, Brevibacteria, Mycobacteria, and oleaginous yeast. Similarly, production hosts were engineered to express accABCD (encoding acetyl CoA carboxylase) from Pisum savitum. However, when the production host was also producing butanol it was found less desirable to express the Pisum savitum homolog.

In some production hosts, genes were knocked out or attenuated using the method of Link, et al., J. Bacteriol. 179:6228-6237, 1997. Genes that were knocked out or attenuated included gpsA (encoding biosynthetic sn-glycerol 3-phosphate dehydrogenase, GenBank Accession No. NP_418065, EC: 1.1.1.94); ldhA (encoding lactate dehydrogenase, GenBank Accession No. NP_415898, EC: 1.1.1.28); pflb (encoding formate acetyltransferase 1, GenBank Accession No. P09373, EC: 2.3.1.54); adhE (encoding alcohol dehydrogenase, GenBank Accession No. CAA47743, EC: 1.1.1.1, 1.2.1.10); pta (encoding phosphotransacetylase, GenBank Accession No. NP_416800, EC: 2.3.1.8); poxB (encoding pyruvate oxidase, GenBank Accession No. NP_415392, EC: 1.2.2.2); ackA (encoding acetate kinase, GenBank Accession No. NP_416799, EC: 2.7.2.1), and combinations thereof.

Similarly, the PlsB[D311E] mutation was introduced into LS9001 to attenuate plsB for the fadE deletion. This mutation decreased the amount of carbon diverted to phospholipid production. An allele encoding PlsB[D311E] was made by replacing the GAC codon for aspartate 311 with a GAA codon for glutamate. The altered allele was prepared by gene synthesis and the chromosomal plsB wildtype allele was exchanged for the mutant plsB [D311E] allele using the method of Link et al. (see supra).

Example 2. Production Host Modifications

The following plasmids were constructed for the expression of various proteins that are used in the synthesis of fatty acid derivatives. The constructs were prepared using standard molecular biology methods. All the cloned genes were put under the control of IPTG-inducible promoters (e.g., a T7 promoter, a tac promoter, or a lac promoter).

The 'tesA gene (thioesterase A gene, GenBank Accession No. NP_415027 without leader sequence (SEQ ID NO:31) (Cho and Cronan, J. Biol. Chem., 270:4216-9, 1995, EC: 3.1.1.5, 3.1.2.-)) of E. coli was cloned into an NdeI/AvrII digested pETDuet-1 vector (pETDuet-1 described herein is available from Novagen, Madison, Wis.). Genes encoding FatB-type plant thioesterases (TEs) from Umbellularia californica, Cuphea hookeriana, and Cinnamonum camphorum (GenBank Accession Nos: UcFatB1=AAA34215, ChFatB2=AAC49269, ChFatB3=AAC72881, CcFatB=AAC49151) were individually cloned into three different vectors: (i) NdeI/AvrII digested pETDuet-1; (ii) XhoI/HindIII digested pBluescript KS+(Stratagene, La Jolla, Calif., to create N-terminal lacZ::TE fusion proteins); and (iii) XbaI/HindIII digested pMAL-c2X (New England Lab, Ipswich, Mass.) (to create n-terminal malE::TE fusions). The fadD gene (encoding acyl-CoA synthase) from E. coli was cloned into a NcoI/HindIII digested pCDF-Duet-1 derivative, which contained the acr1 gene (acyl-CoA reductase) from Acinetobacter baylyi ADP1 within its NdeI/AvrII sites.

Table 7 provides a summary of the plasmids generated to make several exemplary production hosts.

TABLE 7

Summary of plasmids used in production hosts

| Plasmid | Source Organism Gene Product | GenBank Accession No. & EC number |
|---|---|---|
| pETDuet-1-'TesA | E. coli | Accessions: NP_415027, |
|  | 'TesA | EC: 3.1.1.5, 3.1.2.- |
| pETDuet-1-TEuc | Umbellularia californica | Q41635 |
| pBluescript-TEuc | UcFatB1 |  |
| pMAL-c2X-TEuc |  | AAA34215 |
| pETDuet-1-TEch | Cuphea hookeriana | ABB71581 |
| pBluescript-TEch | ChFatB2 | AAC49269 |
| pMAL-c2X-TEch | ChFatB3 | AAC72881 |
| pETDuet-1-TEcc | Cinnamonum camphorum |  |
| pBluescript-TEcc TEci | CcFabB | AAC49151 |
| pETDuet-1-atFatA3 | Arabidopsis thaliana | NP_189147 |
| pETDuet-1-HaFatA1 | Helianthus annuus | AAL769361 |
| pCDFDuet-1-fadD-acr1 | E. coli | fadD:Accessions NP_416319, EC 6.2.1.3 acr1:Accessions YP_047869 |
| pETDuet-1-'TesA | E. coli | Accessions: NP_415027, |
|  | 'TesA | EC: 3.1.1.5, 3.1.2.- |
| pETDuet-1-TEuc | Umbellularia californica | Q41635 |
| pBluescript-TEuc | UcFatB1 | AAA34215 |
| pMAL-c2X-TEuc |  |  |
| pETDuet-1-TEch | Cuphea hookeriana | ABB71581 |
| pBluescript-TEch | ChFatB2 | AAC49269 |
| pMAL-c2X-TEch | ChFatB3 | AAC72881 |
| pETDuet-1-TEcc | Cinnamonumcamphorum |  |
| pBluescript-TEcc TEci | CcFatB | AAC49151 |
| pCDFDuet-1-fadD-acr1 | E. coli | fadD: Accessions NP_416319, EC 6.2.1.3 acr1: Accessions YP_047869 |

One of ordinary skill in the art will appreciate that different plasmids and genomic modifications can be used to achieve similar strains.

The selected expression plasmids contained compatible replicons and antibiotic resistance markers to produce a four-plasmid expression system.

In some embodiments, LS9001 can be co-transformed with: (i) any of the TE-expressing plasmids; (ii) the fadD-expressing plasmid, which also expresses acr1; and (iii) ester synthase expression plasmid.

As will be clear to one of ordinary skill in the art, when LS9001 is induced with IPTG, the resulting strain will produce increased concentrations of fatty alcohols from carbon sources such as glucose.

Example 3. Production of Fatty Alcohol in the Recombinant E. coli Strain

Fatty alcohols were produced by expressing a thioesterase gene and an acyl-CoA reductase gene exogenously in a production host. More specifically, plasmids pCDFDuet-1-fadD-acr1 (acyl-CoA reductase) and pETDuet-1-'TesA (thioesterase) were transformed into E. coli strain LS9001 and corresponding transformants were selected using LB plates supplemented with 100 mg/L spectinomycin and 50 mg/L carbenicillin. Four transformants of LS9001/pCDF-Duet-1-fadD-acr1 were independently inoculated into 3 mL of an M9 medium supplemented with 50 mg/L carbenicillin and 100 mg/L spectinomycin. The samples containing the transformants were cultured at 25° C. in a shaker (shaking at about 250 rpm) until they reached 0.5 $OD_{600}$. Next, 1.5 mL of each sample was transferred into a 250 mL flask containing 30 mL of the M9 medium described above. The resulting culture was grown at 25° C. in a shaker until it reached an $OD_{600}$ of between 0.5-1.0. IPTG was then added to a final concentration of 1 mM. Cell growth continued for 40 hours.

The cells were then centrifuged and pelleted at 4,000 rpm. The cell pellet was suspended in 1.0 mL of methanol. 3 mL of ethyl acetate was then mixed with the suspended cells, followed by the addition of 3 mL of $H_2O$. Next, the mixture was sonicated for 20 minutes. The resulting sample was centrifuged at 4,000 rpm for 5 minutes. Then the organic phase (the upper phase), which contained fatty alcohol(s), was subjected to GC/MS analysis. The total alcohol (including tetradecanol, hexadecanol, hexadecenol, and octadecenol) titer was about 1-10 mg/L. When an *E. coli* strain carrying only empty vectors was cultured under the same conditions and following the same protocol, a fatty alcohols titer of only 0.2-0.5 mg/L was obtained.

Example 4. Production of Fatty Acids (FA) and Fatty Acid Ethyl Esters (FAEE) Containing Odd-Numbered Carbon Chains without Heavy Metals 1. Production of Biodiesel Sample #23-30

Biodiesel sample #23-30 ("sample #23-30") was produced by bioreactor cultivation of an *E. coli* strain (C41 DE3 ΔfadE ΔfabR 'TesA fadD adp1ws) engineered to produce fatty esters. A two-stage inoculum protocol was utilized for expansion of the culture. The first stage consisted of the inoculation of a 50 mL LB medium (supplemented with 100 µg/L carbenicillin and 100 µg/L spectinomycin) in a 250 mL baffled shake flask with a 1 mL frozen stock vial of the *E. coli* ester production strain. This seed flask was incubated at 37° C. for about 7 hours (final $OD_{600}$=4.5, pH 6.7), after which 3 mL of the primary culture was transferred to each of three 2 L baffled flasks containing 350 mL buffered F1 minimal medium that also contained 100 µg/L carbenicillin and 100 µg/L spectinomycin. The shake flask buffer used was Bis-Tris propane at a final concentration of 200 mM (pH 7.2). These secondary seed flasks were incubated at 37° C. for about 18 hours (final $OD_{600}$=12, pH 5.5) and the contents were used to inoculate three 14 L bioreactors with a starting volume of 6.5 liters of buffered F1 minimal medium following inoculation. These bioreactors also contained 100 µg/L carbenicillin and 100 g/L spectinomycin.

These 14 L bioreactors were initially cultivated at 37° C., and the dissolved oxygen levels were maintained at 30% of saturation, using the agitation and oxygen enrichment cascade loops. The pH of the fermentation mix was maintained at 7.2, using 1 M $H_2SO_4$ and anhydrous ammonia gas. A nutrient feed consisting primarily of 43% (w/v) glucose was initiated in each bioreactor when the original 5 g/L glucose charge in the basal medium was exhausted. The glucose solution feed rate was then manually adjusted for the duration of the fermentation run to keep the residual glucose at a low (but non-zero) value for the duration of the fermentation run. Cultures were induced with a final concentration of 1 mM IPTG when the $OD_{600}$ of the cultures reached 30. At this induction point, the bioreactor cultivation temperature was reduced to 30° C., and about 15 mL/L (on a 6.5 to 7-Liter volume basis) of ethanol was added to the culture and monitored by HPLC throughout. Additional ethanol was added periodically to the bioreactors to maintain the residual concentrations at about 20 mL/L. The contents of the bioreactors were harvested after about 60 hours of cultivation, with about 10 L of the broth harvested from each of the three bioreactors.

These harvest broths were combined and extracted with an equivalent volume of ethyl acetate with stirring at room temperature for two hours. The broth extracts were then centrifuged (3,500 rpm, 30 minutes) to separate the liquid layers, followed by the removal of the organic layer for further processing. Ethyl acetate was almost completely removed (<0.3% residual, as determined by GC/FID) from the organic layer using rotary evaporation (Büchi, R-200), leaving about 90 mL of a dark, oily liquid. This liquid was referred to as sample #23-30.

2. Quantification of FA and FAEE in Sample #23-30

GC-MS was performed using an Agilent 5975B MSD system equipped with a 30 m×0.25 mm (0.10 µm film) DB-5 column. The column temperature was 3-minute isothermal at 100° C. The temperature of the column was programmed to rise from 100° C. to 320° C. at a rate of 20° C./min. When the final temperature of 320° C. was reached, the column remained isothermal for 5 minutes at that temperature. The injection volume was 1 µL. The carrier gas, helium, was released at 1.3 mL/min. The mass spectrometer was equipped with an electron impact ionization source. The ionization source temperature was set at 300° C. FAEE standards (e.g., ethyl dodecanoate, ethyl tetradecanoate, ethyl cis-9-hexadecenoate, ethyl hexadecanoate, ethyl octadecanoate, all >99%); fatty acid methyl ester (FAME) standards (e.g., methyl dodecanoate, methyl tetradecanoate, methyl pentadecanoate, methyl cis-9-hexadecenoate, methyl hexadecanoate, methyl cis-11-octadecenoate, all >99%); trimethylsilyl diazomethane (TMSD, 2 M in hexane); hydrochloric acid (37%); methanol (>99.9%); and ethyl acetate (>99.9%) were purchased from Sigma-Aldrich and applied without prior purification.

Sample #23-30 was derivatized by adding 50 µL trimethylsilyldiazomethane (TMSD), 8 µl HCl, and 36 µl methanol to 1 mL of sample (1 mg/mL in ethyl acetate). The mixture was incubated at room temperature for 1 hour.

Prior to quantitation, the FAEE and FAME in sample #23-30 were identified using two methods. First, the GC retention time of each compound was compared to the retention time of a known standard. Second, identification of each compound was confirmed by matching the compound's mass spectrum to a standard's mass spectrum in the mass spectra library.

When a standard for a FAEE or FAME was available, the quantification of the FAEE or FAME was determined by generating a calibration curve (concentration vs. instrument response). A linear relationship between the instrument response and the analyte concentration was then obtained. The concentration of the compound in the sample was determined by taking its instrument response and referring to the calibration curve.

When a standard for an FAEE was not available, an average instrument response was used to determine the compound's concentrations. The slope and the intercept for all existing calibration curves were averaged. From these averages, a linear relationship between concentration and instrument response was determined. The concentrations of unknown compounds were then determined by referencing the instrument responses to the linear relationship between instrument response and concentration using Equation 1.

concentration=(instrument response−average interception)/average slope    Equation 1:

After identifying and quantifying the FAME, the concentration of the associated free fatty acids was determined based upon the concentration of FAME and the molecular weight ratio of FA to FAME. Finally, the concentration of FAEE and FA in mg/L was converted into percentage in the biodiesel sample (w/w %).

The concentrations of FAEE and FA in sample #23-30 are listed in Table 8. The total concentration of FAEEs and FAs was 80.7%. The rest of the unknown compounds may be analyzed by LC/MS/MS method. Ethyl pentadecanoate, ethyl cis-9-hexadecenoate, ethyl hexadecanoate and ethyl cis-11-octadecenoate were the major component of sample #23-30.

TABLE 8

Percentage of FAEE and FA in sample #23-30

| Name | Structure | MW | Percentage, % |
|---|---|---|---|
| Ethyl dodecanoate | 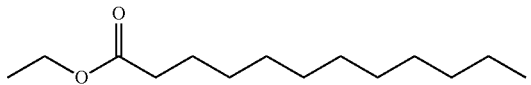 [SMILES: CCCCCCCCCCCC(=O)OCC] | 228.2 | 1.82 ± 0.03 |
| Ethyl tridecanoate | 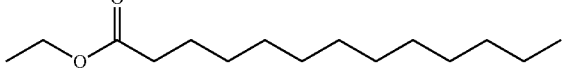 | 242.2 | 0.16 ± 0.01 |
| Ethyl tetradecanoate | 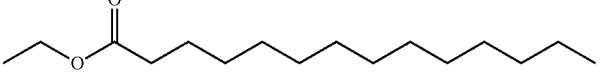 | 256.2 | 12.88 ± 0.16 |
| Ethyl pentadecanoate | 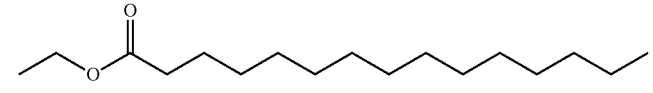 [SMILES: CCCCCCCCCCCCCCC(=O)OCC] | 270.3 | 0.62 ± 0.02 |
| Ethyl cis-9-hexadecenoate | 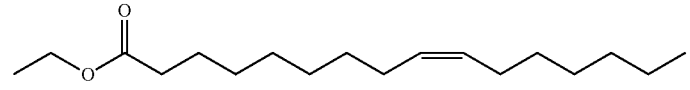 [SMILES: CCCCCC/C=C\CCCCCCCC(=O)OCC] | 282.3 | 24.12 ± 0.20 |
| Ethyl hexadecanoate | 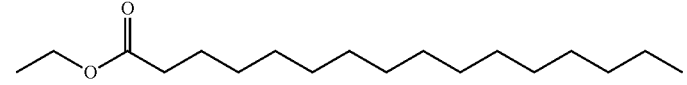 [SMILES: CCCCCCCCCCCCCCCC(=O)OCC] | 284.3 | 9.04 ± 0.11 |
| Ethyl heptadecanoate | 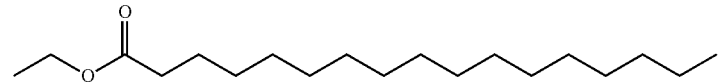 [SMILES: CCCCCCCCCCCCCCCCC(=O)OCC] | 298.3 | 0.11 ± 0.01 |
| Ethyl cis-11-octadecenoate | 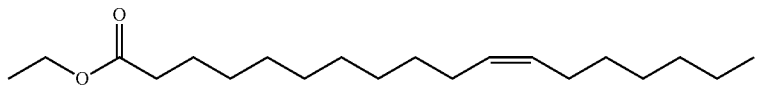 [SMILES: CCCCCC/C=C\CCCCCCCCCC(=O)OCC] | 310.3 | 23.09 ± 0.33 |
| Ethyl octadecanoate | 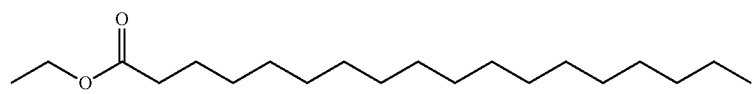 [SMILES: CCCCCCCCCCCCCCCCCC(=O)OCC] | 312.3 | 0.19 ± 0.03 |
| Dodecanoic acid | 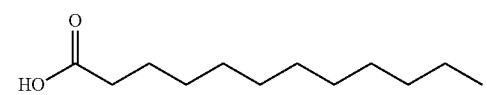 | 200.2 | 0.94 ± 0.02 |
| Tetradecanoic acid | 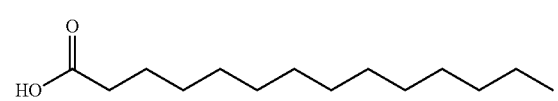 [SMILES: CCCCCCCCCCCCCC(=O)O] | 228.2 | 2.63 ± 0.03 |
| Pentadecanoic acid | 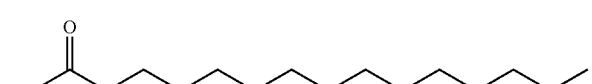 | 242.2 | 0.10 ± 0.01 |
| cis-9-hexadecenoic acid | 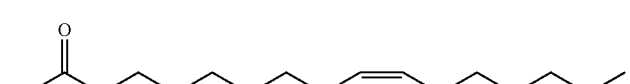 | 254.2 | 1.97 ± 0.01 |

TABLE 8-continued

Percentage of FAEE and FA in sample #23-30

| Name | Structure | MW | Percentage, % |
|---|---|---|---|
| Hexadecanoic acid | 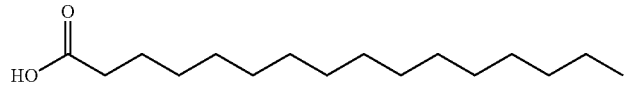 [SMILES: CCCCCCCCCCCCCCCC(=O)O] | 256.2 | 1.01 ± 0.01 |
| cis-11-octadecenoic acid | 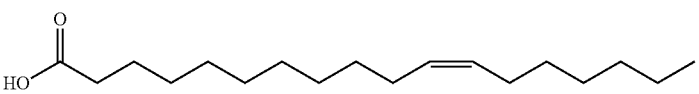 [SMILES: CCCCCC/C=C\CCCCCCCCCC(=O)O] | 282.3 | 2.00 ± 0.02 |

*Percentage is w/w %.

Surprisingly, sample #23-30 contained odd-numbered FA and FAEE.

3. Quantitative Elemental Analysis of Sample #23-30

Heavy metals are known to poison the catalysts used in catalytic cracking. To measure the levels of heavy metals in sample #23-30, sample #23-30 was sent to Galbraith Laboratories, Inc., for quantitative elemental analysis of arsenic, calcium, carbon, chlorine, cobalt, copper, hydrogen, iron, Karl Fisher water, lead, manganese, magnesium, mercury, molybdenum, nitrogen, potassium, sodium, sulfur, zinc, oxygen, and phosphorus. Preparatory and analytical methods are described below. Results are shown in Table 9. All amounts in Table 9 were below the level of quantitation (LOQ) except for carbon (73.38%), chlorine (91 ppm), hydrogen (12.1%), Karl Fisher water (0.998%), mercury (0.057 ppm), oxygen (14.53%), and phosphorus (343 ppm). Therefore, sample #23-30 did not contain high levels of the heavy metals of concern.

Method G-52, Rev 6: Microwave Digestion of Samples for Metals Analysis

An appropriate amount of sample was weighed into a microwave vessel to the nearest 0.001 g. The appropriate reagents were then added to the microwave vessel. If a visible reaction was observed the reaction was allowed to cease before capping the vessel. The vessel was then sealed and placed in the microwave according to the manufacturer's directions. The temperature of each vessel reached a minimum of 180±10° C. in 5 minutes. It remained at a minimum of 180±10° C. for 10 minutes. At the end of the microwave program the vessels were allowed to cool for a minimum of 5 minutes before removal. The vessels were then uncapped and transferred to volumetric flasks for analysis by the proper technique.

Method G-55, Rev 3: Parr Oxygen Bomb Combustion for the Determination of Halogens Samples were weighed into a combustion cup, and mineral oil was added as a combustion aid. For chlorine (Cl) and bromine (Br) measurements, 1% hydrogen peroxide solution was added into the bomb. For sulfur (S) measurements, a 0.01 N sodium hydroxide solution was added. The sample and cup were sealed into a Parr oxygen combustion bomb along with a suitable absorbing solution. The bomb was purged with oxygen, then pressurized to 25-30 atm of oxygen pressure, and ignited. Afterwards, the contents of the bomb were well mixed and transferred to a beaker for subsequent analysis.

Method G-30B, Rev 7: Wet Ash Digestion of Inorganic and Organic Compounds for Metals Analysis The sample was charred using $H_2SO_4$. If analyzing for metals that form insoluble sulfates, $HClO_4$ and $HNO_3$ were used to char the organic material. After charring the sample, $HNO_3$ was added and the sample was refluxed to solubilize the metals present. If the solution became cloudy, HCl was added to aid complete digestion. HF can be used if silicon was present in the sample but only if silicon was not an analyte of interest. All HF used was restricted to Teflon vessels. The clear digestate was quantitatively transferred to a Class A volumetric flask and brought to final volume. The sample was then analyzed.

Method ME-4A Rev 2: Determination of Anions Suppressed by Ion Chromatography

| | |
|---|---|
| Instrument | Dionex Model DX500 |
| Chromatograph Column | Dionex IonPac AS9-SC 4 × 250 mm |
| Eluent | 2.4 mM $Na_2CO_3$ 1.8 mM $NaHCO_3$ |
| Preparation | Aqueous samples may be analyzed as is. Water-soluble samples are typically transferred by weight to a known volume. Other solid materials that are not water-soluble may be extracted to determine extractable quantities of various anions or combusted to determine total quantities of an element such as Cl or Br. |
| Calibration | Standards to bracket sample concentration. 0.2 mg/L-4.0 mg/L |
| Sample Intro | Auto injection (Hitachi Model AS7200) |
| Determination | Conductivity detection/linear regression |
| Quantitation Limit | Typically 0.2 mg/L in solution. |
| Interferences | Anions with similar retention times; overlapping peaks from major constituent anions. |

Method S-300 Rev 7: Determination of Water by Coulometric Titration (Karl Fischer)

This method combined coulometry with the Karl Fischer titration. The sample was mixed with an amine-methanol mixture containing predominantly iodide ion (I−) and sulfur dioxide. The iodine produced at the anode through the electrolysis was allowed to react with water. In such cases, iodine was produced in direct proportion to the quantity of electricity according to Faraday's Law. Also, because 1 mole of water stoichiometrically reacts with 1 mole of iodine, 1 mg of water was equivalent to 10.71 coulombs of electricity. Utilizing this principle, the Moisture Meter determined the amount of water directly from the number of coulombs required for the electrolysis. This procedure included both direct introduction and a vaporizer pre-treatment technique.

| | |
|---|---|
| Preparation | Weigh to obtain 100 μg to 3 mg H2O; Protect samples from atmospheric moisture during weighing and transfer. |
| Instrument | Mitsubishi Moisture Meter MCI Model CA-06 (Inst. #569) |
| | Mitsubishi Moisture Vaporizer, Model CA/VA-06 (Inst. #568) |
| Control | Sodium tartrate monohydrate (15.66%); |
| | Frequency: every 10 samples, one each day minimum, 95-105% recovery |
| Sample Intro | A. Entry port, Direct transfer; capillary, syringe, or scoop |
| | B. Furnace, tin capsules (Water Vaporizer VA-06); Temperature varies, 200° C. is default value used for standards. Most samples analyzed at 160° C. Other temperatures upon request. |
| Determination | Coulometric titration of Karl Fischer reagent via automatic titrator |
| Quantitation Limit | 100 μg $H_2O$ |
| Precision & Accuracy | RSD    RE    INSTR# |
| Sodium Tartrate | 1.35%    −0.54%    569 |
| Monohydrate | 1.34%    −2.13%    568 |
| Equations | ($2I^- - 2e^- \rightarrow I_2$); ($I_2 + SO_2 + 3C_5H_5N + H_2O \rightarrow 2C_5H_5N\ HI + C_5H_5N\ SO_3$) |
| | μg $H_2O$/spl wt (g) = ppm $H_2O$ |
| | μg $H_2O$ × 0.1/spl wt (mg) = % $H_2$) |
| Interferences | (direct transfer only) free alkali; oxidizing, reducing agent; mercaptans |

Method E16-2, Rev 9 (Trace E16-2A): Sulfur Determination Using the LECO SC-432DR The SC-432DR Sulfur Analyzer is a non-dispersive infrared, digitally controlled instrument designed to measure sulfur content in a variety of organic and inorganic materials. The sample was combusted at 1350±50° C. in an atmosphere of pure oxygen. The sulfur was oxidized to sulfur dioxide and quantitated by infrared absorption. The SC-432DR was equipped with two detectors, a high-range and a low-range infrared cell.

| | |
|---|---|
| Instrument | LECO SC-432DR Sulfur Analyzer |
| Sample Intro | Weigh sample to nearest 0.01 mg. Weigh samples directly into sample boat tared on electronic balance. Weight automatically transferred to SC432 database. Cover sample with LECO Com-Cat combustion accelerator as called for by sample type. |
| Calibration | Three conditioners of 5-10 mg cystine. Seven calibration standards of 30-175 mg NIST SRM 8415 Whole Egg Powder (0.512% S). Internal calibration using a quadratic regressed curve. |
| Control | NIST SRM 1549 Milk Powder (0.351%); others to match sample type. |
| | Frequency: one for every ten samples. |
| Determination | Combustion in $O_2$ atmosphere at 1350° C. Determination of resulting $SO_2$ by infrared detector. |
| Quantitation Limit | 0.08 mg S |
| Calculations | Internal |
| Precision & Accuracy | RSD (%)    Mean Recovery (%) |
| (milk powder) | 2.60    97.97 |

Method ME-2, Rev 14: Carbon, Hydrogen, and Nitrogen Determination

This instrument burns sample in pure oxygen at 950° C. under static conditions to produce combustion products of $CO_2$, $H_2O$, and $N_2$. The PE-240 automatically analyzes these products in a self-integrating, steady state thermal conductivity analyzer. Tungstic anhydride may be added to aid combustion. An extended combustion time (e.g., burn hard mode) may be employed for difficult to combust samples.

| Instrument | PerkinElmer 240 Elemental Analyzer (Instrument # 409, 410) |
|---|---|
| Sample intro | Weigh 1.0-2.5 mg into Al capsule; crimp (see GLI Procedure G-6) for liquids; washed with solvent prior to weighing upon request |
| Decomposition | Combustion at ≥950° C., reduction at ≥675° C. = $CO_2$, $H_2O$, $N_2$ |
| Calibration | Cyclohexanone-2,4-dinitropheylhydrazone (1-2.5 mg) |
| Control | s-1409, 2-1410: Cyclohexanone-2,4-dinitropheylhydrazone (51.79% C, 5.07% H, 20.14% N) |
| Determination | $CO_2$, $H_2O$, $N_2$ by thermal conductivity analyzer |
| Quantitation | 0.5% C, 0.5% H, 0.5% N |

| | Instrument #409 | | | Instrument #410 | | |
|---|---|---|---|---|---|---|
| Precision & accuracy | C | H | N | C | H | N |
| RSD % | 0.28 | 1026 | 0.39 | 0.35 | 1.12 | 0.41 |
| Mean recovery (%) | 99.94 | 101.25 | 99.86 | 100.13 | 100.40 | 100.04 |

| Interferences | Metals and some halogens cause incomplete combustion. Combustion aids and/or an extended combustion time can be used to alleviate this problem. |
|---|---|
| Calculations | Instrument calculates & prints w/w results for % C, % H, and % N. For samples crimped in an aluminum capsule, the % N is corrected with a factor; (μV/μg sample/K) × 100 = % Element, where K = calibration = μV/μg of C, or H, or N |

Method ME-70, Rev 4: Inductively Coupled Plasma Atomic Emission Spectrometry

This method describes multi-elemental determinations by ICP-AES using simultaneous optical systems and axial or radial viewing of the plasma. The instrument measures characteristic emission spectra by optical spectrometry. Samples were nebulized and the resulting aerosol was transported to the plasma torch. Element-specific emission spectra were produced by radio-frequency inductively coupled plasma. The spectra were dispersed by a grating spectrometer, and the intensities of the emission lines were monitored by photosensitive devices. Background correction was required for trace element determination. Background was measured adjacent to analyte lines on samples during analysis. The position selected for the background-intensity measurement, on either or both sides of the analytical line, was determined by the complexity of the spectrum adjacent to the analyte line. In one mode of analysis, the position used should be as free as possible from spectral interference and should reflect the same change in background intensity as occurs at the analyte wavelength measured. Background correction is not required in cases of line broadening where a background correction measurement would actually degrade the analytical result.

| Instrument | ICP-OES Optima 5300, 3300DV and 4300DV, or equivalent |
|---|---|
| Decomposition | Prior to analysis, samples must be acidified or digested using appropriate Sample Preparation Methods. |
| Calibration | 0.01 ppm-60 ppm plus matrix specific calibrations |
| Sample Intro | Peristaltic pump, cross flow nebulizer, gemcone nebulizer, scott ryton spray chamber and quartz cylonic spray chamber |
| Determination | Atomic emission by radio frequency inductively coupled plasma of element-specific emission spectra through a grating spectrometer monitored by photosensitive devices. |
| Quantitation Limit | Element and calibration specific ranging from 0.01-2 ppm |
| Precision & Accuracy | ±10% RSD |
| Interferences | Spectral, chemical, physical, memory |
| Calculations | wt % = (fc × v/10 × D)/spl<br>ppm = (fc × v × D)/SPL<br>Where fc = final concentration in μg/mL; v = sample volume in mL; D = dilution factor; spl = sample mass in mg; SPL = sample mass in g |

Method E80-2, Rev 4: Determination of Mercury (Automated Cold Vapor Technique)

This procedure is based on EPA SW846 Method 7471A. Cold Vapor Atomic Absorption is based on the general theory of atomic absorption, which holds that free atoms of the analyte absorb energy from a lamp source that is proportional to the concentration of analyte. By using a lamp containing the metal to be measured, the exact wavelength needed for absorption was produced and interferences were greatly reduced. Cold Vapor Atomic Absorption uses this principle, and the mercury atoms were liberated by reducing mercury ions with Tin (II) Chloride ($SnCl_2$). Nitrogen gas carried the atoms through an optical cell, with the Hg lamp on one end and the detector on the other end. Because the cold vapor method was employed, instead of a flame method, undigested organic compounds were an interference concern, because of their wide band of absorption wavelengths.

| | |
|---|---|
| Instrument | PerkinElmer FIMS 400 Automated Mercury Analyzer or equivalent |
| Decomposition | Variable, usually microwave digestion or permanganate hot water bath digestion |
| Calibration | 0.1-5.0 µg/L |
| Sample Introduction | Autosampler, peristaltic pump |
| Determination | Primary wavelength 253.7 nm, using a solid state detector |
| Detection Limit | Varies with preparation method and sample matrix |
| Precision & Accuracy | For microwave digestion:     For $MnO_4^-$ digestion: |
| RE | −2.47%                           4.90% |
| RSD | 7.48%                             5.20% |
| Interferences | Undigested organic compounds |
| Calculations | $ppb\ Hg = \dfrac{\mu g/L\ in\ solution \times volume\ (mL) \times dilution\ factor}{sample\ weight\ (g)}$ |

TABLE 9

Quantitative elemental analysis of sample #23-30

| Element | Preparation Method | Analytical Method | Result |
|---|---|---|---|
| Arsenic | G-52 | ME-70 | <25 ppm |
| Calcium | G-30B | ME-70 | <119 ppm |
| Carbon | N/A | ME-2 | 73.38% |
| Chlorine | G-55 | ME-4A | 91 ppm |
| Cobalt | G-30B | ME-70 | <23 ppm |
| Copper | G-30B | ME-70 | <23 ppm |
| Hydrogen | N/A | ME-2 | 12.1% |
| Iron | G-30B | ME-70 | <136 ppm |
| Karl Fisher water | N/A | S-300 | 0.998% |
| Lead | G-52 | ME-70 | <25 ppm |
| Manganese | G-30B | ME-70 | <23 ppm |
| Magnesium | G-30B | ME-70 | <23 ppm |
| Mercury | G-52 | E80-2 | 0.057 ppm |
| Molybdenum | G-30B | ME-70 | <23 ppm |
| Nitrogen | N/A | ME-2 | <0.5% |
| Potassium | G-30B | ME-70 | <103 ppm |
| Sodium | G-30B | ME-70 | <140 ppm |
| Sulfur | N/A | E16-2A | <0.140% |
| Zinc | G-30B | ME-70 | <23 ppm |
| Oxygen | N/A | Subtraction* | 14.53% |
| Phosphorus | G-30B | ME-70 | 343 ppm |

Results presented as "<" are below LOQ.
*Oxygen content was determined by subtracting the observed results for all other elements from 100%.

Example 5. Production and Release of Fatty Alcohol from Production Host acr1 (encoding acyl-CoA reductase) was expressed in *E. coli* cultured with glucose as the sole carbon and energy source. The *E. coli* produced small amounts of fatty alcohols such as dodecanol ($C_{12:0}$-OH), tetradecanol ($C_{14:0}$-OH), and hexadecanol ($C_{16:0}$-OH). In other samples, FadD (acyl-CoA synthase) was expressed together with acr1 in *E. coli*. A five-fold increase in fatty alcohol production was observed.

Figure 6:
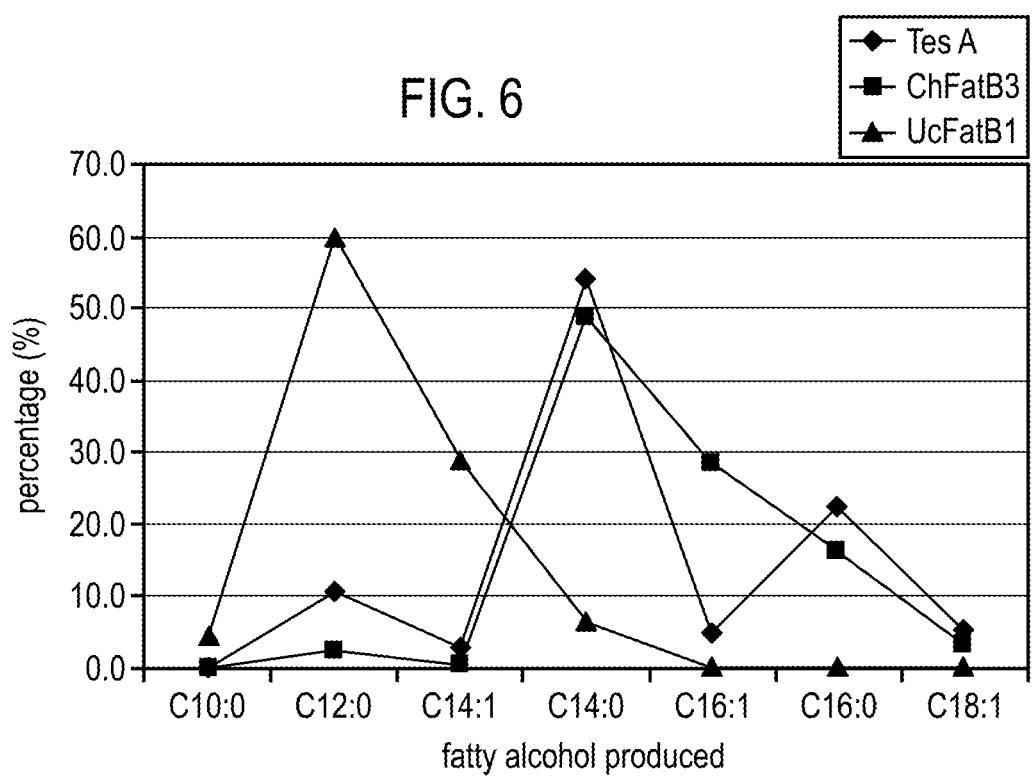
FIG. 6 (FIG. 6) is a graph depicting fatty alcohol production by the strain co-transformed with pCDFDuet-1-fadDacr1 and plasmids containing various thioesterase genes. Saturated $C_{10}$, $C_{12}$, $C_{14}$, $C_{16}$ and $C_{18}$ fatty alcohol were identified.

In other samples, acr1, fadD, and accABCD (acetyl-CoA carboxylase), in a plasmid carrying accABCD constructed as described in EXAMPLE 1, were expressed along with various individual thioesterases (TEs) in wild-type *E. coli* C41 (DE3) and an *E. coli* C41 (DE3 ΔfadE, a strain lacking acyl-CoA dehydrogenase). This resulted in further increases in fatty alcohol production and modulation of the profiles of fatty alcohols (see FIG. 6). For example, over-expression of *E. coli* 'TesA (pETDuet-1-'TesA) in this system achieved about a 60-fold increase in $C_{12:0}$-OH, $C_{14:0}$-OH and $C_{16:0}$-OH, with $C_{14:0}$-OH being the major fatty alcohol. A very similar result was obtained when the ChFatB3 enzyme (FatB3 from *Cuphea hookeriana* in pMAL-c2X-TEcu) was expressed. When the UcFatB1 enzyme (FatB1 from *Umbellularia californicain* in pMAL-c2X-TEuc) was expressed, fatty alcohol production increased about 20-fold and $C_{12:0}$-OH was the predominant fatty alcohol.

Figure 7:
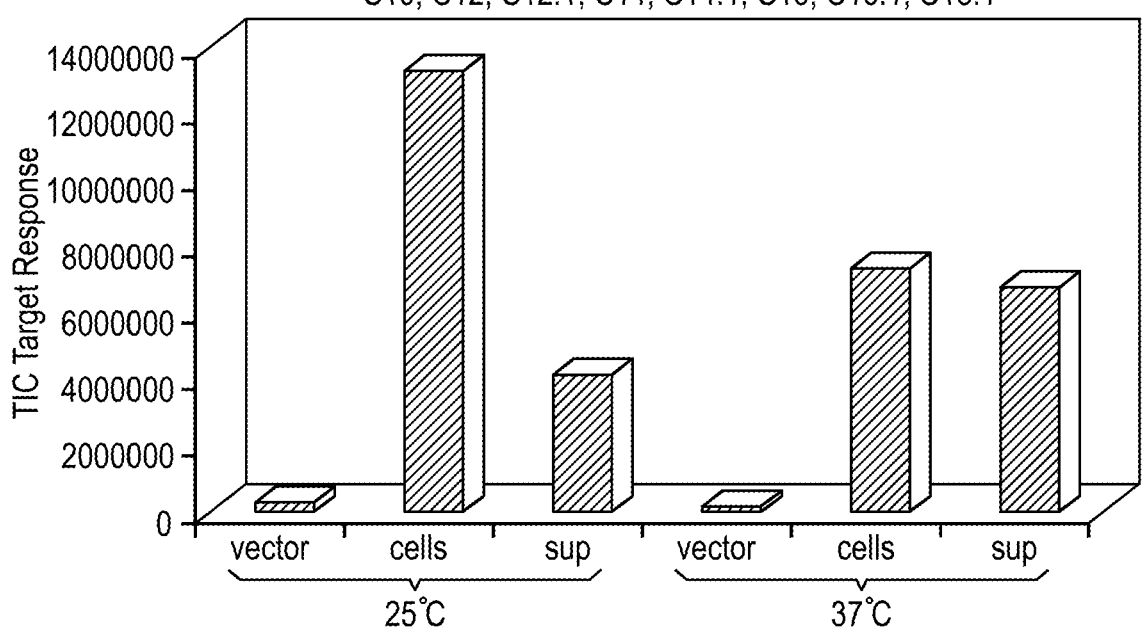
FIG. 7 (FIG. 7) is a graph depicting fatty alcohol production by the strain described in Example 3, co-transformed with pCDFDuet-1-fadD-acr1 and plasmids containing various thioesterase genes. The strains were grown aerobically at 25° C. or 37° C. in an M9 mineral medium containing 0.4% glucose in shake flasks. Fatty alcohols were detected in the cell pellets as well as in the supernatants, indicating a substantial extracellular production of such alcohols. Cultivation at 25° C. resulted in the release of about 25% of the product from the cells, whereas cultivation at 37° C. resulted in the release of about 50% of the product from the cell.
Figure 8A:
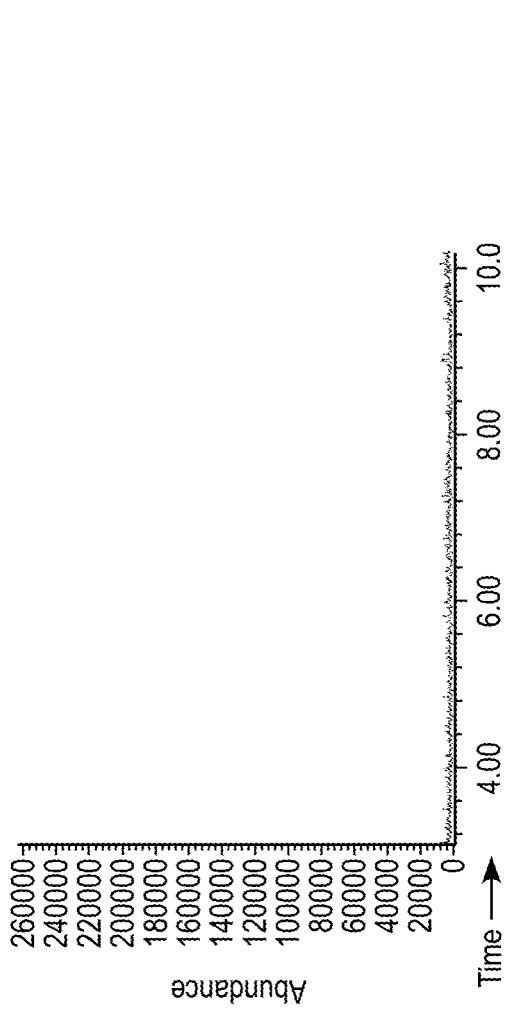
FIG. 8A-D (FIGS. 8A-D) are plots depicting GC-MS spectra of octyl octanoate ($C_8C_8$) produced by a production host expressing alcohol acetyl transferase (AATs, EC 2.3.1.84) and production hosts expressing ester synthase (EC 2.3.1.20, 2.3.1.75).
Figure 8B:
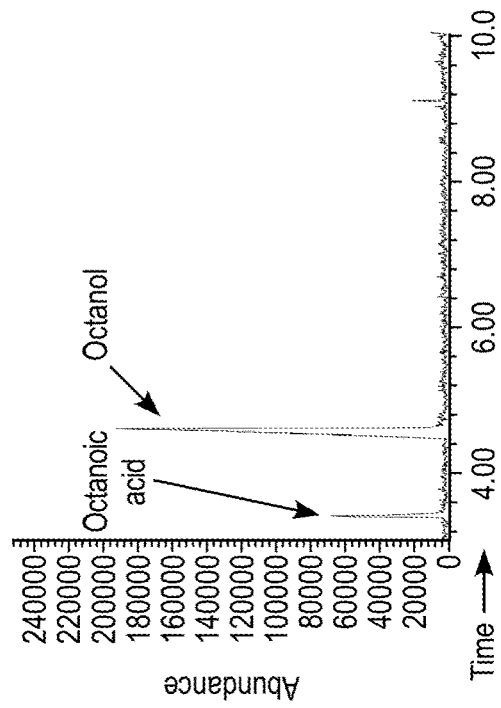
Figure 8C:
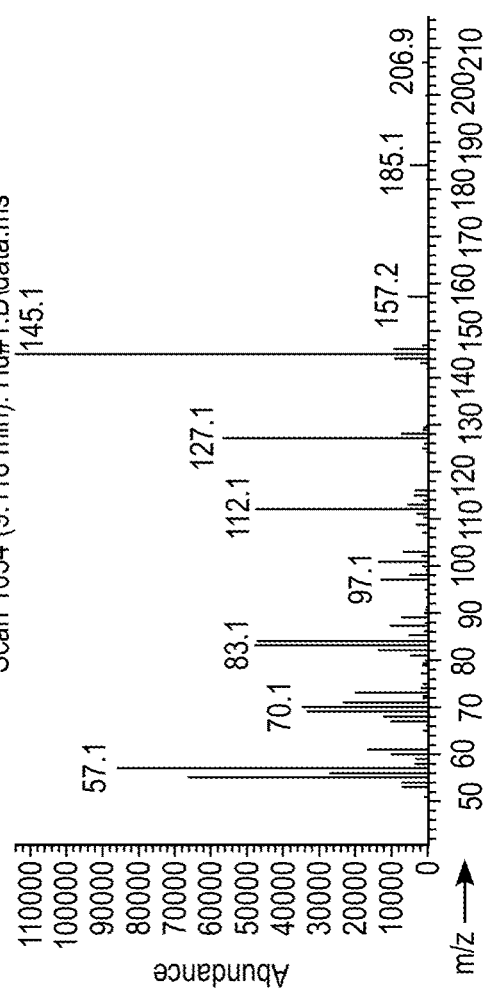
Figure 8D:
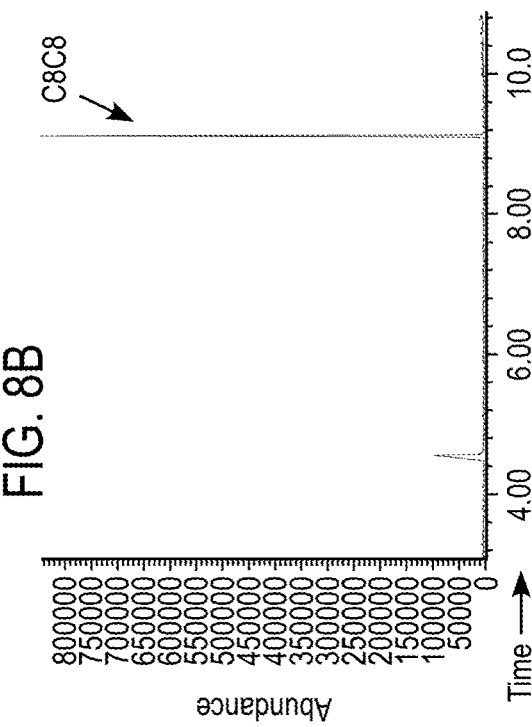

Expression of ChFatB3 and UcFatB1 also led to the production of significant amounts of the unsaturated fatty alcohols $C_{16:1}$-OH and $C_{14:1}$-OH, respectively. Fatty alcohols were also found in the supernatant of samples generated from the expression of 'tesA. At 37° C., about equal amounts of fatty alcohols were found in the supernatant and in the cell pellet. Whereas at 25° C., about 25% of the fatty alcohols was found in the supernatant. See FIG. 7.

Example 6. Production of Fatty Alcohol Using a Variety of Acyl-CoA Reductases This example describes fatty alcohol production using a variety of acyl-CoA reductases. Fatty alcohols can be the final product. Alternatively, the production host cells can be engineered to additionally express/overexpress ester synthases to produce fatty esters.

Each of four genes encoding fatty acyl-CoA reductases (Table 10) from various sources were codon-optimized for *E. coli* expression and synthesized by Codon Devices, Inc. (Cambridge, Mass.). Each of the synthesized genes was cloned as an NdeI-AvrII fragment into pCDFDuet-1-fadD vector (described in Example 2). Each of the plasmids carrying these acyl-CoA reductase genes with the *E. coli* fadD gene was transformed into *E. coli* strain C41 (DE) strain (purchased from Over-expression).

The recombinant strains were cultured in 3 mL of an LB broth (supplemented with 100 mg/L spectinomycin) at 37° C. overnight. 0.3 mL of the overnight culture was transferred to 30 mL of a fresh M9 medium (containing 100 mg/L spectinomycin) and cultured at 25° C. When the cultures reached $OD_{600}$ of 0.5, 1 mM IPTG was added. Each culture was fed 0.1% of one of three fatty acids dissolved in $H_2O$ at pH 7.0. The three fatty acids fed were sodium dodecanoate, sodium myristate, or sodium palmitate. A culture without the addition of fatty acid was also included as a control. After induction, the cultures were allowed to grow at the same temperature for an additional 40 hours at 25° C.

The quantification of fatty alcohol yield at the end of fermentation was performed using GC-MS as described above in EXAMPLE 3 and/or EXAMPLE 4. The resulting fatty alcohol produced from the corresponding fatty acid is shown in Table 11. The results indicated that three acyl-CoA reductases—Acr1, AcrM, and BmFAR—were able to convert all three fatty acids into corresponding fatty alcohols. The results also indicated that hFAR and JjFAR had activity when myristate and palmitate were the substrates. However, there was little or no activity when dodecanoate was the substrate. mFAR1 and mFAR2 only demonstrated low activity with myristate and demonstrated no activity with the other two fatty acids.

TABLE 10

Acyl-CoA reductases

| Acyl-CoA reductase | Protein ID Accession number | Protein sources |
|---|---|---|
| mFAR1 | AAH07178 | Mus musculus |
| mFAR2 | AAH55759 | Mus musculus |
| JjFAR | AAD38039 | Simmondsia chinensis |
| BmFAR | BAC79425 | Bombyx mori |
| Acr1 | AAC45217 | Acinetobacter baylyi ADP1 |
| AcrM | BAB85476 | Acinetobacter sp. M1 |
| hFAR | AAT42129 | Homo sapiens |

TABLE 11

Fatty alcohol production

| E. coli C41(DE3) | Acyl-CoA reductase genes | Peak Area[c] | | | |
|---|---|---|---|---|---|
| | | Dodecanoate/ dodecanol[b] | Myristate/ tetradecanol[b] | Palmitate/ hexadecanol[b] | No fatty acid feeding [a]/ hexadecanol |
| | mFAR1 | 7,400 | 85,700 | 8,465 | 70,900 |
| | mFAR2 | 2,900 | 14,100 | 32,500 | 25,800 |
| | JjFAR | 5,200 | 8,500 | 53,112 | 33,800 |
| | BmFAR | 35,800 | 409,000 | 407,000 | 48,770 |
| | acr1 | 202,000 | 495,000 | 1,123,700 | 58,515 |
| | acrM | 42,500 | 189,000 | 112,448 | 36,854 |
| | hFAR1 | 5,050 | 59,500 | 109,400 | 94,400 |
| vector control | | 4,000 | 1,483 | 32,700 | 27,500 |
| media control | | 10,700 | 1,500 | 25,700 | 25,000 |

Note:
[a] Only hexadecanol was quantified in this case.
[b] Fatty acid fed/fatty alcohol produced.
[c] The area peak of fatty alcohol produced.

Example 7. Medium Chain Fatty Esters

Alcohol acetyl transferases (AATs, EC 2.3.1.84), which is responsible for acyl acetate production in various plants, can be used to produce medium chain length fatty esters, such as octyl octanoate, decyl octanoate, decyl decanoate, and the like. Fatty esters, synthesized from medium chain alcohol (such as $C_6$ and $C_8$) and medium chain acyl-CoA or fatty acids (such as $C_6$ and $C_8$) have relatively low melting points. For example, hexyl hexanoate has a melting point of about −55° C. and octyl octanoate has a melting point of about −18° C. to about −17° C. The low melting points of these compounds make them suitable for use as biofuels.

In this example, an SAAT gene encoding a thioesterase was co-expressed in a production host E. coli C41(DE3, ΔfadE) (as described in International Application No. PCT/US08/058788, the disclosures of which is incorporated herein by reference) with fadD from E. coli and acr1 (alcohol reductase from A. baylyi ADP1). Octanoic acid was provided in the fermentation broth. This resulted in the production of octyl octanoate. Similarly, when the ester synthase gene from A. baylyi ADP1 was expressed in the production host instead of the SAAT gene, octyl octanoate was produced.

A recombinant SAAT gene was synthesized by DNA 2.0 (Menlo Park, Calif. 94025). The synthesized DNA sequence was based on the published gene sequence (GenBank Accession No. AF193789), but modified to eliminate the NcoI site. The synthesized SAAT gene (as a BamHI-HindIII fragment) was cloned in pRSET B (Invitrogen, Carlsbad, Calif.), linearized with BamHI and HindIII. The resulting plasmid, pHZ1.63A was cotransformed into an E. coli production host with pAS004.114B, which carries a fadD gene from E. coli and acr1 gene from A. baylyi ADP1. The transformants were cultured in 3 mL of an M9 medium containing 2% glucose. After IPTG induction and the addition of 0.02% octanoic acid, the culture was allowed to grow at 25° C. for 40 hours. 3 mL of acetyl acetate was then added to the whole culture and mixed several times using a mixer. The acetyl acetate phase was analyzed by GC/MS.

Surprisingly, no acyl acetate was observed in the acetyl acetate extract. However, octyl octanoate was observed. However, the control strain without the SAAT gene (C41 (DE3, ΔfadE)/pRSET B+pAS004.114B) did not produce octyl octanoate. Furthermore, the strain (C41(DE3, ΔfadE)/pHZ1.43 B+pAS004.114B) in which the ester synthase gene from A. baylyi ADP1 was carried by pHZ1.43 produced octyl octanoate (see FIGS. 8A-D).

The finding that SAAT activity produces octyl octanoate makes it possible to produce medium chain fatty esters, such as octyl octanoate and octyl decanoate, which have low melting points and are suitable for use as biofuels and for replacing triglyceride based biodiesel.

Example 8. Production of Fatty Esters in E. coli Strain LS9001

Fatty esters were produced by engineering an E. coli production host to express a fatty alcohol forming acyl-CoA reductase, thioesterase, and an ester synthase. Thus, the production host produced both the A and the B side of the ester and the structure of both sides was influenced by the expression of the thioesterase gene.

The LS9001 strain was transformed with plasmids carrying an ester synthase gene from A. baylyi ADP1 (plasmid pHZ1.43), a thioesterase gene from Cuphea hookeriana (plasmid pMAL-c2X-Tech), and a fadD gene from E. coli (plasmid pCDFDuet-1-fad).

Plasmid pHZ1.43 carrying the ester synthase (WSadp1, GenBank Accession No. AA017391, EC 2.3.175) was constructed as follows. First the gene for WSadp1 was amplified with the following primers using genomic DNA sequence from A. baylyi ADP1 as template:

```
                                      (SEQ ID NO: 35)
WSadp1_NdeI,  5'-TCATATGCGCCCATTACATCCG-3';
and
                                      (SEQ ID NO: 36)
WSadp1_Avr,   5'-TCCTAGGAGGGCTAATTTAGCCCTTTAGTT-3'.
```

Then, the PCR product was digested with NdeI and AvrII and cloned into pCOLADuet-1 to give pHZ 1.43. The plasmid carrying wSadp1 was then co-transformed into E. coli strain LS9001 with both pETDuet-1'TesA and pCDF-Duet-1-fadD-acr1, and transformants were selected on LB plates supplemented with 50 mg/L of kanamycin, 50 mg/L of carbenicillin and 100 mg/L of spectinomycin.

Three transformants were inoculated in 3 mL of LBKCS (LB broth supplement with 50 mg/L kanamycin, 50 mg/L carbenicillin, 100 mg/L spectinomycin, and 10 g/L glucose) and incubated at 37° C. in a shaker (shaking at 250 rpm). When the cultures reached an $OD_{600}$ of about 0.5, 1.5 mL of each culture was transferred into 250 mL flasks containing 50 mL LBKCS. The flasks were then incubated in a shaker (250 rpm) at 37° C. until the culture reached an $OD_{600}$ of about 0.5 to about 1.0. IPTG was then added to a final concentration of 1 mM. The induced cultures were incubated at 37° C. in a shaker (250 rpm) for another 40-48 hours.

The cultures were then transferred into 50 mL conical tubes and the cells were centrifuged at 3,500×g for about 10 minutes. Each of the cell pellets was then mixed with 5 mL ethyl acetate. The ethyl acetate extracts were analyzed with GC/MS. The titer of fatty esters (including $C_{16}C_{16}$, $C_{14:1}C_{16}$, $C_{18:1}C_{18:1}$, $C_2C_{14}$, $C_2C_{16}$, $C_2C_{16:1}$, $C_{16}C_{16:1}$ and $C_2C_{18:1}$) was about 10 mg/L. When an E. coli strain only carrying empty vectors was cultured under the same conditions and following the same protocol, only 0.2 mg/L fatty esters was found in the ethyl acetate extract.

Example 9. Production and Release of Fatty-Ethyl Ester from Production Host

The LS9001 strain was transformed with plasmids carrying an ester synthase gene from A. baylyi (plasmid pHZ1.43), a thioesterase gene from Cuphea hookeriana (plasmid pMAL-c2X-TEcu) and a fadD gene from E. coli (plasmid pCDFDuet-1-fadD).

This recombinant strain was cultured at 25° C. in 3 mL of an M9 medium containing 50 mg/L kanamycin, 100 mg/L carbenicillin, and 100 mg/L spectinomycin. After IPTG induction, the medium was adjusted to a final concentration of 1% ethanol and 2% glucose.

The culture was allowed to grow for 40 hours after IPTG induction. The cells were separated from the spent medium by centrifugation at 3,500×g for 10 minutes. The cell pellet was re-suspended with 3 mL of the M9 medium. The cell suspension and the spent medium were then extracted with 1 volume of ethyl acetate. The resulting ethyl acetate phases from the cell suspension and the supernatant were subjected to GC-MS analysis.

Figure 9:
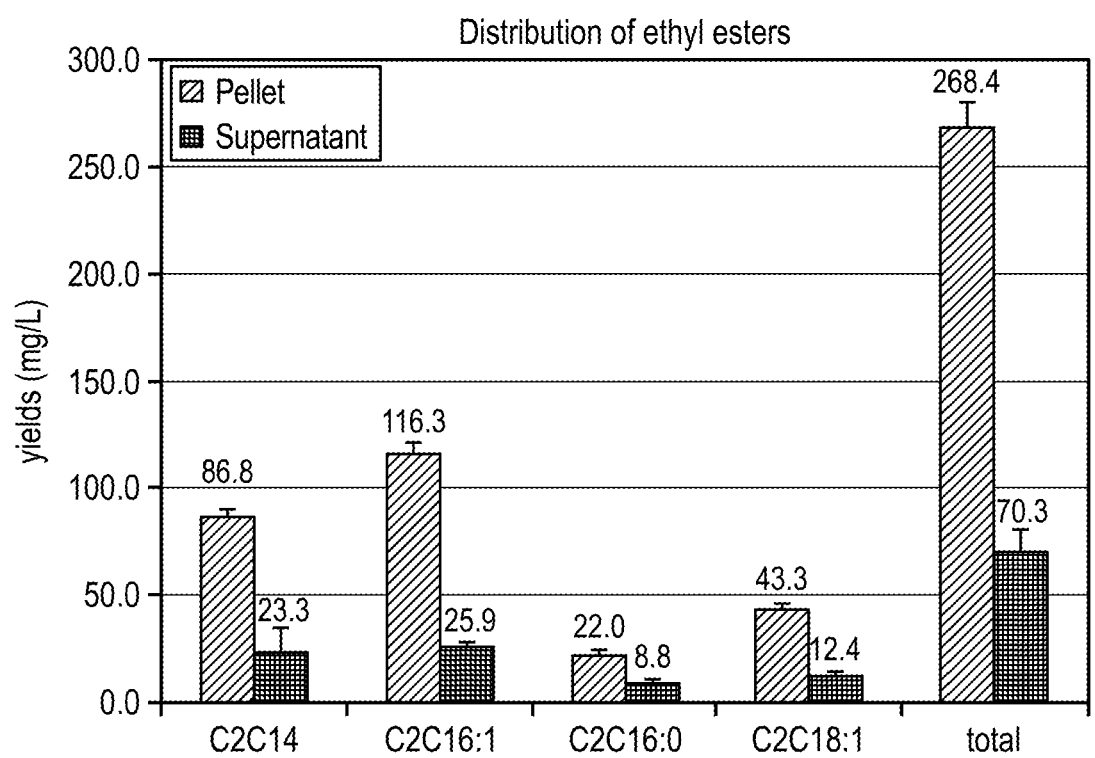
FIG. 9 (FIG. 9) is a graph depicting the distribution of ethyl esters made (in accordance with Example 9) when the ester synthase from *A. baylyi* ADP1 (WSadp1) was co-expressed with a thioesterase from *Cuphea hookeriana* in a production host.

The $C_{16}$ ethyl ester was the most prominent ester species for this thioesterase and 20% of the fatty ester produced was released from the cell. See FIG. 9. A control E. coli strain C41(DE3, ΔfadE) containing pCOLADuet-1 (empty vector for the ester synthase gene), pMAL-c2X-TEuc (containing fatB from U. california) and pCDFDuet-1-fadD (fadD gene from E. coli) failed to produce detectable amounts of fatty acid ethyl esters. The fatty acid esters were quantified using commercial palmitic acid ethyl ester as the reference.

Fatty esters were also made using the methods described herein except that methanol or isopropanol was added to the fermentation broth. The expected fatty esters were produced.

Example 8. The Influence of Various Thioesterases on the Composition of Fatty-Ethyl Esters Produced in Recombinant E. coli Strains The thioesterases FatB3 (C. hookeriana), 'TesA (E. coli), and FatB (U. california) were expressed simultaneously with ester synthase (from A. baylyi). A plasmid, pHZ1.61, which comprises a pCDFDuet-1 (Novagen, Madison, Wis.) backbone with the fadD gene, was constructed by replacing the NotI-AvrII fragment (carrying the acr1 gene) with the NotI-AvrII fragment from pHZ1.43 such that fadD and the ADP1 ester synthase were in one plasmid and each of the coding sequences was under the control of a separate T7 promoter. The construction of pHZ1.61 made it possible to use a two-plasmid system instead of the three-plasmid system. pHZ1.61 was then co-transformed into E. coli C41(DE3, ΔfadE) with one of the plasmids, each carrying a different thioesterase gene as described herein.

The total fatty acid ethyl esters (in both the supernatant and intracellular fatty acid ethyl fluid) produced by these transformants were evaluated using the technique described herein. The titers and the composition of fatty acid ethyl esters are summarized in Table 12.

TABLE 12

Titers (mg/L) and composition of fatty acid ethyl esters by recombinant E. coli
C41(DE3, ΔfadE)/pHZ1.61 and plasmids carrying various thioesterase genes.

| Thioesterases | $C_2C_{10}$ | $C_2C_{12:1}$ | $C_2C_{12}$ | $C_2C_{14:1}$ | $C_2C_{14}$ | $C_2C_{16:1}$ | $C_2C_{16}$ | $C_2C_{18:1}$ | Total |
|---|---|---|---|---|---|---|---|---|---|
| 'TesA | 0.0 | 0.0 | 6.5 | 0.0 | 17.5 | 6.9 | 21.6 | 18.1 | 70.5 |
| ChFatB3 | 0.0 | 0.0 | 0.0 | 0.0 | 10.8 | 12.5 | 11.7 | 13.8 | 48.8 |
| ucFatB | 6.4 | 8.5 | 25.3 | 14.7 | 0.0 | 4.5 | 3.7 | 6.7 | 69.8 |
| pMAL | 0.0 | 0.0 | 0.0 | 0.0 | 5.6 | 0.0 | 12.8 | 7.6 | 26.0 |

Note:
'TesA, pETDuet-1-'TesA; chFatB3, pMAL-c2X-TEcu; ucFatB, pMAL-c2X-TEuc; pMAL, pMAL-c2X, the empty vector for thioesterase genes used in the study.

Example 9. Use of Various Ester Synthases to Produce Biofuel

Four genes encoding ester synthases were synthesized based on corresponding polynucleotide sequences reported in NCBI GenBank with minor modifications. These modifications include the removal of internal NcoI, NdeI, HindIII, and AvrII restriction sites without introducing other changes to the corresponding amino acid sequence. The four genes of interest were each synthesized with an NdeI site on the 5' end and an AvrII at the 3' end. The sequences were then cloned into the NdeI and AvrII site of pCOLADuet-1 (Novagene) to produce pHZ1.97-376, pHZ1.97-377, pHZ1.97-atfA1 and pHZ1.97-atfA2. The plasmids carrying each of the four genes of interest along with the respective GenBank Accession numbers and the GenPeptide Accessions numbers are listed in Table 13 below.

TABLE 13

Ester synthases

| Plasmids | ID | DNA sequence original sources | GenBank Accession No. | GenPeptide accession No. |
|---|---|---|---|---|
| pHZ1.97-376 | FES376(376) | Marinobacter aquaeolei VT8 | CP000514.1 | ABM17275 |
| pHZ1.97-377 | FES377(377) | Marinobacter aquaeolei VT8 | CP000514.1 | ABM20141 |
| pHZ1.97-atfA1 | FESA1(AtfA1) | Alcanivorax borkumensis SK2 | NC_008260.1 | YP_94462 |
| pHZ1.97-atfA2 | FESA2(AtfA2) | Alcanivorax borkumensis SK2 | NC_008260.1 | YP_693524 |

Each of the four plasmids was transformed into E. coli C41 (DE3, ΔfadEΔfabR)/pETDuet-1-'TesA+pCDFDuet-1-fadD. Three transformants from each transformation were selected for fermentation studies to determine their abilities to synthesize fatty acid ethyl esters. The fermentation step was performed as described in EXAMPLE 6, but at two different temperatures, 25° C. or 37° C. Strain C41 (DE3, ΔfadEΔfabR)/pETDuet-1-'TesA+pCDFDuet-1-fadD+ pHZ1.43 (expressing ADP1 ester synthase) was used as a positive control and C41 (DE3, ΔfadEΔfabR)/pETDuet-1-'TesA+pCDFDuet-1-fadD as a negative control.

The expression of each of the four ester synthase genes in the E. coli strain with attenuated fadE and fabR activity and overexpressing 'tesA and fadD enabled each strain to produce about 250 mg/L of FAEE at 25° C. This was the same amount produced by the positive control that expressed ADP1 ester synthase. In contrast, the negative control strain produced less than 50 mg/L FAEE under the same conditions at 25° C. (see, FIG. 10). The fatty acyl composition of FAEE produced from these four ester synthases was similar to that from ADP1 ester synthases (see, FIG. 11)

Figure 12:
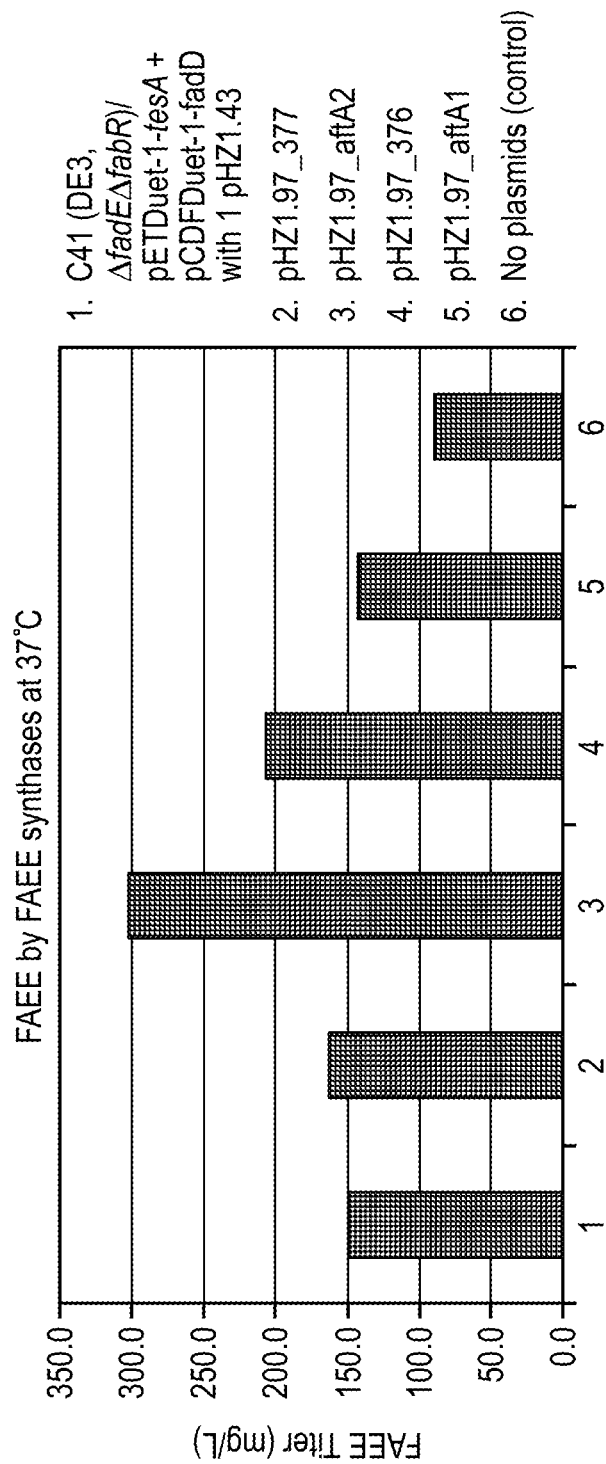
FIG. 12 (FIG. 12) is a graph depicting the production of ethyl esters by various ester synthases at 37° C. The ethyl esters were produced by recombinant *E. coli* strains carrying various ester synthase genes. The recombinant strains were (1) C41 (DE3, ΔfadEΔfabR)/pETDuet-1-'TesA+pCDF-Duet-1-fadD with 1 pHZ1.43; (2) pHZ1.97_377; (3) pHZ1.97_atfA2; (4) pHZ1.97_376; (5) pHZ1.97_atfA1; and (6) no plasmids (control).
Figure 13:
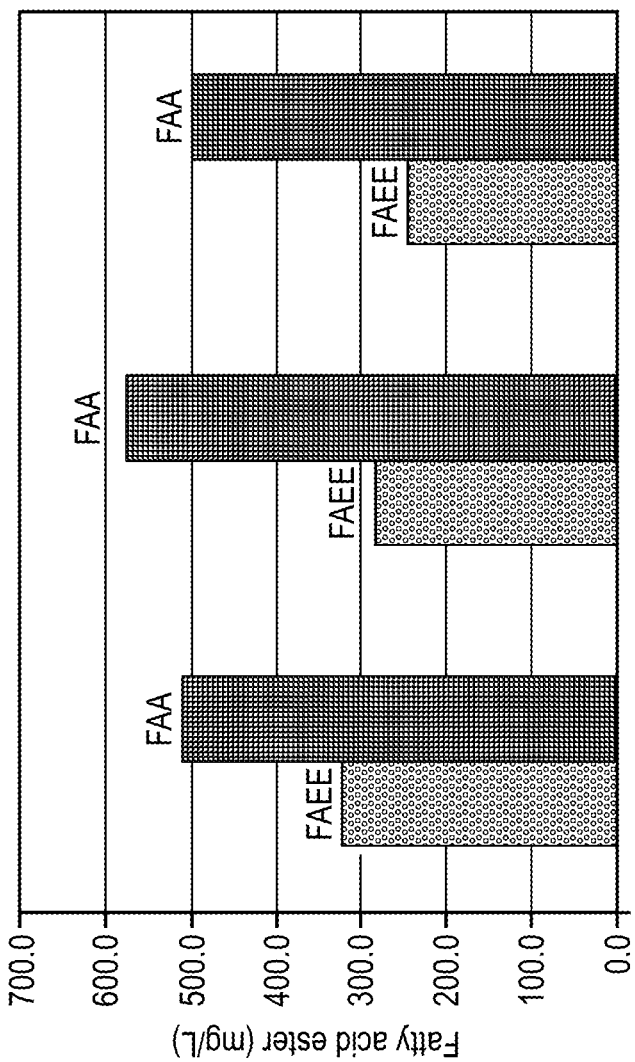
FIG. 13 (FIG. 13) is a graph depicting concentrations of free fatty acids (FFA) and fatty acid ethyl esters (FAEE) produced from three individual colonies from the transformants, C41 (DE3, ΔfadEΔfabR)/pETDuet-1-'TesA+pCDF-Duet-1-fadD+pHZ1.97_atfA2. The FFA was converted to fatty acid ethyl ester (FAEE) and quantified by GC/MS.

Results from fermentations performed at 37° C. indicated that strains carrying pHZ1.97_aftA2 and strains carrying pHZ1.97_376 produced more FAEE than the positive control carrying pHZ1.43 (see, FIG. 12). The strains carrying pHZ1.97_aftA2 and the strains carrying pHZ1.97_376 also produced large amount of free fatty acid (see, FIG. 13). Whereas the strain carrying pHZ.143 did not accumulate free fatty acid. The results demonstrated that these four ester synthases were capable of accepting ethanol and a broad range of acyl-CoA as substrates.

Example 12. Use of Eukaryotic Ester Synthase to Produce Biofuel

This example describes the cloning and expression of an ester synthase from Saccharomyces cerevisiae. Plasmids were generated using standard molecular biology techniques.

TABLE 14

Plasmids with eeb1

| Given Name | Vector Backbone | Construction |
|---|---|---|
| pGL10.59 | pCOLADuet-1 (Novagen) | eeb1* gene inserted between BamHI and HindIII sites (KanR) |
| pGL10.104 | pMAL c2x (NEB) | eeb1* gene inserted between BamHI and HindIII sites (AmpR) |

TABLE 14-continued

Plasmids with eeb1

| Given Name | Vector Backbone | Construction |
| --- | --- | --- |
| pMAL-c2X-TEuc | pMAL c2x (NEB) | See Table 7 above |
| pCDFDuet-1-acr1 | pCDFDuet-1 (Novagen) | See Table 7 above |

*The *Saccharomyces cerevisiae* gene eeb1 (GenBank Accession number YPL095C) was PCR-amplifed from *S. cerevisiae* genomic DNA sequence using primers that introduced the 5' BamHI and 3' HindIII sites.

An *E. coli* C41 (DE3 ΔfadE) production host was used to express the various plasmids. The *E. coli* cells were cultured in an M9 minimal medium (containing 6 g/L $Na_2HPO_4$, 3 g/L $KH_2PO_4$, 0.5 g/L NaCl, 1 g/L $NH_4Cl$, 1 mg/L thiamine (vit. B1), 1 mM $MgSO_4$, 0.1 mM $CaCl_2$, 0.4% (w/v) or 2% (w/v) glucose). All fatty acid stock solutions were prepared by dissolving the fatty acid sodium or potassium salt in distilled deinoized water at pH 7.0. Octanoic acid stock was purchased from Sigma, St. Louis, Mo.

Fermentations were performed using the C41 (DE3 ΔfadE) strain containing plasmids pCDFDuet-1-acr1, pMAL-c2X-TEuc (ucFatB), and pGL10.59 (eeb1). The control strain was C41 (DE3 ΔfadE) strain carrying pCDFDuet-1-acr1, pMAL-c2X-TEuc, and the empty pCOLADuet-1 vector. Each of the three colonies from each transformation were used to inoculate an M9+0.4% glucose starter culture supplemented with carbenicillin (100 µg/mL), spectinomycin (100 µg/mL), and kanamycin (50 µg/mL). The cultures were allowed to grow at 37° C. overnight. Production cultures were established by making a 1:100 dilution of starter culture to inoculate 3 mL M9 media+0.4% glucose. The production cultures were allowed to grow at 37° C. until $OD_{600}$=0.6 before being induced with 1 mM IPTG, fed 1% ethanol, and cultured for an additional 40 hours at 25° C. Whole cell cultures were extracted with an equal volume of ethyl acetate by vortexing vigorously for 30 seconds. The organic phase was taken and examined on the GC/MS using the method alkane_1_splitless_ctc.m for FAEE detection, which is described above in EXAMPLE 4, part 2, "Quantification of FA and FAEE in sample #23-30."

No FAEE peaks were detected in the samples. In order to determine whether eeb1 was correctly expressed, IPTG-induced and uninduced cultures were analyzed by SDS-PAGE. No band corresponding to the size of Eeb1 (about 52 kDa) was detected. This suggested that, for this particular plasmid system, Eeb1 was not well-expressed.

Additional expression experiments were performed using a different expression vector. The gene was cloned into the vector pMALc2x, which expressed the target protein as a maltose binding protein (MBP) fusion. SDS-PAGE analysis of whole-cell lysates revealed that cultures induced with 1 mM IPTG yielded an appropriately-sized band corresponding to the Eeb1-MBP fusion (about 92 kDa). The band was not present in uninduced cells. This experiment was described in detail in International Application No. PCT/US08/058788, the disclosures therein is incorporated by reference in the entirety.

Eeb1 enzymatic activity was assessed using the C41 (DE3 ΔfadE) *E. coli* strain carrying plasmids pCDFDuet-1-acr1 and pGL10.104 (eeb1). A C41 (DE3 ΔfadE) with pCDF-Duet-1-acr1 and pMALc2x served as the control strain. Three colonies were picked from each transformation and each was used to inoculate an M9+0.4% glucose overnight starter culture supplemented with carbenicillin (100 µg/mL) and spectinomycin (100 µg/mL). A 1:100 dilution of the starter culture was used to inoculate 10 mL of an M9+0.4% glucose production cultures. The production cultures were allowed to grow at 37° C. until $OD_{600}$=0.4-0.5 before inducing with 1 mM IPTG. The cultures were each fed about 1% ethanol, octanoic acid (to about 0.01% or about 0.02% of the final volume), and/or decanoic acid (to about 0.02% of the final volume). Fermentations were allowed to continue for 24 hours at 25° C. Extractions were carried out by adding 1/10 volume of 12 M HCl and an equal volume of ethyl acetate to the culture and vortexing for 30 seconds. Samples were analyzed by GC/MS as described above.

GC/MS data revealed a peak corresponding to the octanoic acid ethyl ester can be detected for cells expressing eeb1 and fed octanoic acid and ethanol. The vector control strain also showed a $C_2C_8$ peak, albeit a smaller peak than that of the eeb1-expressing cells.

Cells that were fed 0.02% decanoic acid did not grow well; therefore, the following studies were conducted using 0.01% or 0.005% decanoic acid. To test the ability of Eeb1 to utilize alcohols other than ethanol in synthesizing fatty acid esters, fermentations were carried out using the same strain: C41 (DE3 ΔfadE) with pCDFDuet-1-acr1 and pGL10.104. Cells were cultured as previously described. At induction, the cells were fed 0.02% octanoic acid along with 1% methanol, ethanol, propanol, or isopropanol. Cells were also fed 0.01% or 0.005% decanoic acid and 1% ethanol. Fermentations were allowed to continue post-induction for 24 hours at 25° C. To prepare for analysis by GC/MS, cultures were centrifuged to separate the pellet and the supernatant. The pellet was resuspended in an equal volume of a fresh M9+0.4% glucose medium. Both the resuspended pellets and supernatant samples were extracted as described above and analyzed by GC/MS.

All of the supernatant samples contained large amounts of fatty acid but no detectable fatty acid esters. Similarly, the vector control pellet samples contained no fatty acid ester peaks, as determined using GC/MS. However, cells fed a $C_{10}$ fatty acid showed peaks that were identified as representing decanoic acid.

The pellet samples derived from the cells expressing Eeb1 and fed a $C_8$ fatty acid and propanol or ethanol showed small peaks corresponding to propyl or ethyl esters. No peak was detected from the cells that were fed methanol or isopropanol. Cultures fed 0.01% or 0.005% of a $C_{10}$ fatty acid and ethanol also produced a $C_2C_{10}$ FAEE, but the FAEE was found in the pellet samples.

The results indicated that Eeb1 was capable of synthesizing FAEEs using octanoic or decanoic acids, and was also able to use methanol to generate the octanoic methyl ester. However, these compounds were highly volatile and as such the GC/MS data might not have accurately reflected the true titers. To more accurately measure product formation a hexadecane overlay was used to facilitate the capture of more volatile FAEEs.

Eeb1 activity with regard to fatty acid substrates was assessed using strain C41 (DE3 ΔfadE) with pCDFDuet-1-acr1 and pGL10.104, which was fed different chain-length fatty acids. Cells were cultured as described above, but were induced at $OD_{600}$=0.8-0.9 so as to promote better cell growth post-induction. At this point, cells were fed 1% ethanol and 0.02% of a $C_8$ fatty acid or 0.01% of a combination of the following fatty acids: $C_{10}$, $C_{12}$, $C_{14}$, and $C_{16}$. Cultures that were fed $C_8$ or $C_{10}$ fatty acids were overlaid with 20% total volume of hexadecane. Fermentations were carried out for an additional 24 hours at 25° C. post induction. For product analysis, whole cultures (without separating the supernatant from the pellet) were extracted as described herein, with 1/10 volume of HCl and an equal volume (to the volume of the culture) of ethyl acetate. Hexadecane-treated samples were injected directly into the GC/MS using the program hex_1_splitless_ctc.m, which is described above in EXAMPLE 4, part 2, "Quantification of FA and FAEE in sample #23-30."

None of the vector controls had any detectable FAEE peaks. For the $C_8$- and $C_{10}$-fed cells, large $C_2C_8$ and $C_2C_{10}$ peaks were detected in the hexadecane samples, but not in the ethyl acetate samples. This demonstrated that hexadecane was able to successfully trap the volatile FAEEs. For the rest of the ethyl acetate samples, small peaks were detected for $C_2C_{12}$ and $C_2C_{14}$ FAEEs, but no $C_2C_{16}$ FAEE was detected. Thus, Eeb1 generated ethyl esters using fatty acids with chain lengths from $C_8$ to $C_{14}$. Eeb1 favored $C_8$ and $C_{10}$ over the longer-chain fatty acids.

Figure 14:
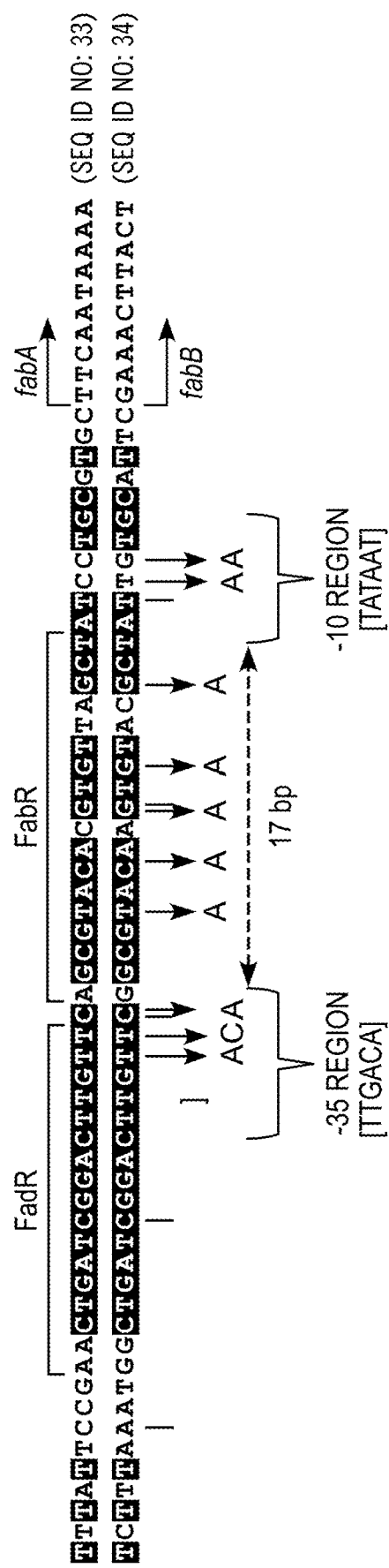
FIG. 14 (FIG. 14) is a diagram depicting the control regions for FabA (SEQ ID NO:33) and FabB (SEQ ID NO:34). The FadR and FabR consensus binding sites are shown in bold. Vertical arrows indicate the positions where mutations can be made to alter fabA expression. The proposed base for each position is also indicated by the brackets. The two regions that constitute the −35 and −10 regions of the typical *E. coli* promoter are indicated by the brackets. The proposed mutations that make the promoter closer to the consensus promoter sequence are also shown.

Example 13. Genomic Integration of Recombinant Sequences to Make a Host Strain that Over-Expresses *E. coli* FabA and/or FabB Genes It is known that the product of the fabR gene acts as a repressor of the expression of the fabA and fabB genes. It is also known that FadR works as an activator of the same genes. The FabR and predicted consensus binding sequences were previously published by Zhang et al., J. Biol. Chem. 277: 15558-15565, 2002. The consensus binding sequences and their locations relative to the fabA and fabB genes of *E. coli* is shown in FIG. 14.

A fabR knockout strain of *E. coli* was created. Primers TrmA_R_NotI and FabR_FOP were used to amplify about 1,000 bp upstream of fabR, and primers SthA_F_Bam and FabR_ROP were used to amplify about 1000 bp downstream of fabR. Overlap PCR was applied to create a construct for in-frame deletion of the complete fabR gene. The fabR deletion construct was cloned into a temperature-sensitive plasmid pKOV3, which contained SacB for counterselection. A chromosomal deletion of fabR was made according to the method described in Link et al., J. Bact., 179:6228-6237, 1997.

TABLE 15 fabR knock-out primers

| Primer Name | Primer Sequence (5' to 3') |
|---|---|
| TrmA_R_Not | ATAGTTTAGCGGCCGCAAATCGAGCTGGATCAGGATTA (SEQ ID NO: 37) |
| FabR_FOP | AGGATTCAGACATCGTGATGTAATGAAACAAGCAAATCAAGATAGA (SEQ ID NO: 38) |
| SthA_F_Bam | CGCGGATCCGAATCACTACGCCACTGTTCC (SEQ ID NO: 39) |
| FabR_ROP | TTGATTTGCTTGTTTCATTACATCACGATGTCTGAATCCTTG (SEQ ID NO: 40) |

Example 14. Production Host Construction

Table 16 identifies the homologs of certain genes described herein, which are known to be expressed in microorganisms that produce biodiesels, fatty alcohols, and hydrocarbons. To increase fatty acid production and, therefore, hydrocarbon production in production hosts such as those identified in Table 16, heterologous genes can be expressed, such as those from *E. coli*.

One of ordinary skill in the art will appreciate that genes that are endogenous to the microorganisms provided in Table 16 can also be expressed, over-expressed, or attenuated using the methods described herein. Moreover, genes that are described in Table 16 can be expressed, overexpressed, or attenuated in production hosts that endogenously produce hydrocarbons to allow for the production of specific hydrocarbons with defined carbon chain length, saturation points, and branch points.

TABLE 16

| Hydrocarbon production hosts | | | |
|---|---|---|---|
| Organism | Gene Name | Accession No./ SEQ ID/Loci | EC No. |
| *Desulfovibrio desulfuricans* G20 | accA | YP_388034 | 6.4.1.2 |
| *Desulfovibrio desulfuricans* G22 | accC | YP_388573/YP_388033 | 6.3.4.14, 6.4.1.2 |
| *Desulfovibrio desulfuricans* G23 | accD | YP_388034 | 6.4.1.2 |
| *Desulfovibrio desulfuricans* G28 | fabH | YP_388920 | 2.3.1.180 |
| *Desulfovibrio desulfuricans* G29 | fabD | YP_388786 | 2.3.1.39 |
| *Desulfovibrio desulfuricans* G30 | fabG | YP_388921 | 1.1.1.100 |
| *Desulfovibrio desulfuricans* G31 | acpP | YP_388922/YP_389150 | 3.1.26.3, 1.6.5.3, 1.6.99.3 |

TABLE 16-continued

Hydrocarbon production hosts

| Organism | Gene Name | Accession No./ SEQ ID/Loci | EC No. |
|---|---|---|---|
| Desulfovibrio desulfuricans G32 | fabF | YP_388923 | 2.3.1.179 |
| Desulfovibrio desulfuricans G33 | gpsA | YP_389667 | 1.1.1.94 |
| Desulfovibrio desulfuricans G34 | ldhA | YP_388173/YP_390177 | 1.1.1.27, 1.1.1.28 |
| Erwinia (micrococcus) amylovora | accA | 942060-943016 | 6.4.1.2 |
| Erwinia (micrococcus) amylovora | accB | 3440869-3441336 | 6.4.1.2 |
| Erwinia (micrococcus) amylovora | accC | 3441351-3442697 | 6.3.4.14, 6.4.1.2 |
| Erwinia (micrococcus) amylovora | accD | 2517571-2516696 | 6.4.1.2 |
| Erwinia (micrococcus) amylovora | fadE | 1003232-1000791 | 1.3.99.- |
| Erwinia (micrococcus) amylovora | plsB(D311E) | 333843-331423 | 2.3.1.15 |
| Erwinia (micrococcus) amylovora | aceE | 840558-843218 | 1.2.4.1 |
| Erwinia (micrococcus) amylovora | aceF | 843248-844828 | 2.3.1.12 |
| Erwinia (micrococcus) amylovora | fabH | 1579839-1580789 | 2.3.1.180 |
| Erwinia (micrococcus) amylovora | fabD | 1580826-1581749 | 2.3.1.39 |
| Erwinia (micrococcus) amylovora | fabG | CAA74944 | 1.1.1.100 |
| Erwinia (micrococcus) amylovora | acpP | 1582658-1582891 | 3.1.26.3, 1.6.5.3, 1.6.99.3 |
| Erwinia (micrococcus) amylovora | fabF | 1582983-1584221 | 2.3.1.179 |
| Erwinia (micrococcus) amylovora | gpsA | 124800-125810 | 1.1.1.94 |
| Erwinia (micrococcus) amylovora | ldhA | 1956806-1957789 | 1.1.1.27, 1.1.1.28 |
| Kineococcus radiotolerans SRS30216 | accA | ZP_00618306 | 6.4.1.2 |
| Kineococcus radiotolerans SRS30216 | accB | ZP_00618387 | 6.4.1.2 |
| Kineococcus radiotolerans SRS30216 | accC | ZP_00618040/ ZP_00618387 | 6.3.4.14, 6.4.1.2 |
| Kineococcus radiotolerans SRS30216 | accD | ZP_00618306 | 6.4.1.2 |
| Kineococcus radiotolerans SRS30216 | fadE | ZP_00617773 | 1.3.99.- |
| Kineococcus radiotolerans SRS30216 | plsB(D311E) | ZP_00617279 | 2.3.1.15 |
| Kineococcus radiotolerans SRS30216 | aceE | ZP_00617600 | 1.2.4.1 |
| Kineococcus radiotolerans SRS30216 | aceF | ZP_00619307 | 2.3.1.12 |
| Kineococcus radiotolerans SRS30216 | fabH | ZP_00618003 | 2.3.1.180 |
| Kineococcus radiotolerans SRS30216 | fabD | ZP_00617602 | 2.3.1.39 |
| Kineococcus radiotolerans SRS30216 | fabG | ZP_00615651 | 1.1.1.100 |
| Kineococcus radiotolerans SRS30216 | acpP | ZP_00617604 | 3.1.26.3, 1.6.5.3, 1.6.99.3 |
| Kineococcus radiotolerans SRS30216 | fabF | ZP_00617605 | 2.3.1.179 |
| Kineococcus radiotolerans SRS30216 | gpsA | ZP_00618825 | 1.1.1.94 |
| Kineococcus radiotolerans SRS30216 | ldhA | ZP_00618879 | 1.1.1.28 |
| Rhodospirillum rubrum | accA | YP_425310 | 6.4.1.2 |
| Rhodospirillum rubrum | accB | YP_427521 | 6.4.1.2 |
| Rhodospirillum rubrum | accC | YP_427522/YP_425144/YP_427028/YP_426209/ YP_427404 | 6.3.4.14, 6.4.1.2 |
| Rhodospirillum rubrum | accD | YP_428511 | 6.4.1.2 |
| Rhodospirillum rubrum | fadE | YP_427035 | 1.3.99.- |
| Rhodospirillum rubrum | aceE | YP_427492 | 1.2.4.1 |
| Rhodospirillum rubrum | aceF | YP_426966 | 2.3.1.12 |

TABLE 16-continued

Hydrocarbon production hosts

| Organism | Gene Name | Accession No./ SEQ ID/Loci | EC No. |
|---|---|---|---|
| Rhodospirillum rubrum | fabH | YP_426754 | 2.3.1.180 |
| Rhodospirillum rubrum | fabD | YP_425507 | 2.3.1.39 |
| Rhodospirillum rubrum | fabG | YP_425508/YP_425365 | 1.1.1.100 |
| Rhodospirillum rubrum | acpP | YP_425509 | 3.1.26.3, 1.6.5.3, 1.6.99.3 |
| Rhodospirillum rubrum | fabF | YP_425510/YP_425510/ YP_425285 | 2.3.1.179 |
| Rhodospirillum rubrum | gpsA | YP_428652 | 1.1.1.94 1.1.1.27 |
| Rhodospirillum rubrum | ldhA | YP_426902/YP_428871 | 1.1.1.28 |
| Vibrio furnissii | accA | 1, 16 | 6.4.1.2 |
| Vibrio furnissii | accB | 2, 17 | 6.4.1.2 |
| Vibrio furnissii | accC | 3, 18 | 6.3.4.14, 6.4.1.2 |
| Vibrio furnissii | accD | 4, 19 | 6.4.1.2 |
| Vibrio furnissii | fadE | 5, 20 | 1.3.99.- |
| Vibrio furnissii | plsB(D311E) | 6, 21 | 2.3.1.15 |
| Vibrio furnissii | aceE | 7, 22 | 1.2.4.1 |
| Vibrio furnissii | aceF | 8, 23 | 2.3.1.12 |
| Vibrio furnissii | fabH | 9, 24 | 2.3.1.180 |
| Vibrio furnissii | fabD | 10, 25 | 2.3.1.39 |
| Vibrio furnissii | fabG | 11, 26 | 1.1.1.100 |
| Vibrio furnissii | acpP | 12, 27 | 3.1.26.3, 1.6.5.3, 1.6.99.3 |
| Vibrio furnissii | fabF | 13, 28 | 2.3.1.179 |
| Vibrio furnissii | gpsA | 14, 29 | 1.1.1.94 |
| Vibrio furnissii | ldhA | 15, 30 | 1.1.1.27, 1.1.1.28 |
| Stenotrophomonas maltophilia R551-3 | accA | ZP_01643799 | 6.4.1.2 |
| Stenotrophomonas maltophilia R551-3 | accB | ZP_01644036 | 6.4.1.2 |
| Stenotrophomonas maltophilia R551-3 | accC | ZP_01644037 | 6.3.4.14, 6.4.1.2 |
| Stenotrophomonas maltophilia R551-3 | accD | ZP_01644801 | 6.4.1.2 |
| Stenotrophomonas maltophilia R551-3 | fadE | ZP_01645823 | 1.3.99.- |
| Stenotrophomonas maltophilia R551-3 | plsB(D311E) | ZP_01644152 | 2.3.1.15 |
| Stenotrophomonas maltophilia R551-3 | aceE | ZP_01644724 | 1.2.4.1 |
| Stenotrophomonas maltophilia R551-3 | aceF | ZP_01645795 | 2.3.1.12 |
| Stenotrophomonas maltophilia R551-3 | fabH | ZP_01643247 | 2.3.1.180 |
| Stenotrophomonas maltophilia R551-3 | fabD | ZP_01643535 | 2.3.1.39 |
| Stenotrophomonas maltophilia R551-3 | fabG | ZP_01643062 | 1.1.1.100 |
| Stenotrophomonas maltophilia R551-3 | acpP | ZP_01643063 | 3.1.26.3 1.6.5.3, 1.6.99.3 |
| Stenotrophomonas maltophilia R551-3 | fabF | ZP_01643064 | 2.3.1.179 |
| Stenotrophomonas maltophilia R551-3 | gpsA | ZP_01643216 | 1.1.1.94 |
| Stenotrophomonas maltophilia R551-3 | ldhA | ZP_01645395 | 1.1.1.28 |
| Synechocystis sp. PCC6803 | accA | NP_442942 | 6.4.1.2 |
| Synechocystis sp. PCC6803 | accB | NP_442182 | 6.4.1.2 6.3.4.14, |

TABLE 16-continued

Hydrocarbon production hosts

| Organism | Gene Name | Accession No./ SEQ ID/Loci | EC No. |
|---|---|---|---|
| Synechocystis sp. PCC6803 | accC | NP_442228 | 6.4.1.2 |
| Synechocystis sp. PCC6803 | accD | NP_442022 | 6.4.1.2 |
| Synechocystis sp. PCC6803 | fabD | NP_440589 | 2.3.1.39 |
| Synechocystis sp. PCC6803 | fabH | NP_441338 | 2.3.1.180 |
| Synechocystis sp. PCC6803 | fabF | NP_440631 | 2.3.1.179 |
| Synechocystis sp. PCC6803 | fabG | NP_440934 | 1.1.1.100, 3.1.26.3 |
| Synechocystis sp. PCC6803 | fabZ | NP_441227 | 4.2.1.60 |
| Synechocystis sp. PCC6803 | fabI | NP_440356 | 1.3.1.9 |
| Synechocystis sp. PCC6803 | acp | NP_440632 | |
| Synechocystis sp. PCC6803 | fadD | NP_440344 | 6.2.1.3 |
| Synechococcus elongates PCC7942 | accA | YP_400612 | 6.4.1.2 |
| Synechococcus elongates PCC7942 | accB | YP_401581 | 6.4.1.2 |
| Synechococcus elongates PCC7942 | accC | YP_400396 | 6.3.4.14, 6.4.1.2 |
| Synechococcus elongates PCC7942 | accD | YP_400973 | 6.4.1.2 |
| Synechococcus elongates PCC7942 | fabD | YP_400473 | 2.3.1.39 |
| Synechococcus elongates PCC7942 | fabH | YP_400472 | 2.3.1.180 |
| Synechococcus elongates PCC7942 | fabF | YP_399556 | 2.3.1.179 |
| Synechococcus elongates PCC7942 | fabG | YP_399703 | 1.1.1.100, 3.1.26.3 |
| Synechococcus elongates PCC7942 | fabZ | YP_399947 | 4.2.1.60 |
| Synechococcus elongates PCC7942 | fabI | YP_399145 | 1.3.1.9 |
| Synechococcus elongates PCC7942 | acp | YP_399555 | |
| Synechococcus elongates PCC7942 | fadD | YP_399935 | 6.2.1.3 |

The Accession Numbers of Table 16 are from GenBank, Release 159.0 as of Apr. 15, 2007, EC Numbers of Table 16 are from KEGG, Release 42.0 of April 2007 (plus daily updates up to and including May 9, 2007), results for *Erwinia amylovora* strain Ea273 were obtained from the Sanger sequencing center, completed shotgun sequence as of May 9, 2007, positions for *Erwinia* represent locations on the Sanger psuedo-chromosome, sequences from *Vibrio fumisii* M1 are from the VFM1 pseudo-chromosome, v2 build, as of Sep. 28, 2006, and include the entire gene, and may also include flanking sequence.

Example 15. Additional Exemplary Production Strains

Table 17 provides additional exemplary production strains. Two example biosynthetic pathways are described for producing fatty acids, fatty alcohols, and wax esters. For example, Table 17 provides examples 1 and 2 that produce fatty acids. The production host strain used to produce fatty acids in example 1 is a production host cell that is engineered to have the desired synthetic enzymatic activities. Each "x" marks the genes correlated to the activities, for example, acetyl-CoA carboxylase, thio-esterase, and acyl-CoA synthase activity. Production host cells can be selected from bacteria, yeast, and fungi. As provided in Table 17, additional production hosts can be created using the indicated exogenous genes.

Table 17: Combination of genes useful for making genetically engineered production strains

| Peptide | Sources of genes | Genes | II. Fatty acids | | III. Fatty alcohols | | IV. wax/fatty esters | |
|---|---|---|---|---|---|---|---|---|
| | | | example 1 | example 2 | example 1 | example 2 | example 1 | example 2 |
| acetyl-CoA carboxylase | E. coli | accABCD | X | X | X | X | X | X |
| thio-esterase | E. coli | 'TesA | X | | X | | X | X |
| | Cinnamomum camphora | ccFatB | | | | | | |
| | Umbellularia californica | umFatB | | X | | X | | |
| | Cuphea hookeriana | chFatB2 | | | | | | |
| | Cuphea hookeriana | chFatB3 | | | | | | |
| | Cuphea hookerian | chFatA | | | | | | |
| | Arabidopsis thaliana | AtFatA1 | | | | | | |
| | Arabidopsis thaliana | AtFatB1 [M141T] | | | | | | |

-continued

| Peptide | Sources of genes | Genes | II. Fatty acids example 1 | II. Fatty acids example 2 | III. Fatty alcohols example 1 | III. Fatty alcohols example 2 | IV. wax/fatty esters example 1 | IV. wax/fatty esters example 2 |
|---|---|---|---|---|---|---|---|---|
| acyl-CoA synthase | E. coli | fadD | X | X | X | X | X | X |
| acyl-CoA reductase | Bombyx mori | bFAR | | | | | | |
| | Acinetobacter baylyi ADP1 | acr1 | | | X | | X | |
| | Simmondsia chinesis | jjFAR | | | | X | | X |
| | Triticum aestivum | TTA1 | | | | | | |
| | Mus musculus | mFAR1 | | | | | | |
| | Mus musculus | mFAR2 | | | | | | |
| | Acinetobacter sp M1 | acrM1 | | | | | | |
| | Homo sapiens | hFAR | | | | | | |
| Ester synthase/ alcohol acyl-transferase | Fundibacter jadensis DSM 12178 | WST9 | | | | | | |
| | Acinetobacter sp. HO1-N | WSHN | | | | | X | |
| | Acinetobacter baylyl ADP1 | WSadp1 | | | | | | X |
| | Mus musculus | mWS | | | | | | |
| | Homo sapiens | hWS | | | | | | |
| | Fragaria x ananassa | SAAT | | | | | | |
| | Malus x domestica | MpAAT | | | | | | |
| | Simmondsia chinensis | JjWS (AAD38041) | | | | | | |
| Decarbonylase | Arabidopsis thaliana | cer1 | | | | | | |
| | Oryzasativa | cer1 | | | | | | |
| Transport protein | Acinetobacter sp. HO1-N | unknown | | | | | X | X |
| | Arabidopsis thaliana | Cer5 | | | | | | |

Example 16. Use of Additional Acyl-CoA Synthases to Over Produce Acyl-CoA

Homologs to E. coli fadD can be expressed in E. coli by synthesizing codon-optimized genes based on a desired sequence from M. tuberculosis HR7Rv (NP_217021, FadDD35), B. subtilis (NP_388908, YhfL), Saccharomyces cerevisiae (NP_012257, Faa3p) or P. aeruginosa PAO1 (NP_251989). The synthetic genes can be designed to include NcoI- and HindII-compatible overhangs. The acyl-CoA synthases can then be cloned into a NcoI/HindIII digested pTrcHis2 vector (Invitrogen Corp., Carlsbad, Calif.) as described above and expressed in E. coli strain MG1655 ΔfadE. The expression in E. coli may lead to an increased production of acyl-CoA.

Fatty acid derivatives such as an FAEE can also be produced by co-transformation of the E. coli strain MG1655 ΔfadE with various acyl-CoA synthases in the pTrcHis2 vector with a compatible plasmid derived from pCL1920, which contains the thioester gene from Cuphea hookeriana with or without an ester synthase from A. baylyi. The resulting production host will produce FAEE when cultured in a medium containing ethanol as described above.

Example 17. Use of Additional Acyl-CoA Synthases to Overproduce Acyl-CoA

DNA sequences or protein sequences of many E. coli FadD homologs are known. However the biochemical properties of only a few have been described. See, e.g., Knoll et al., J. Biol. Chem. 269(23):16348-56, 1994; Shockey et al., Plant Physiol. 132: 1065-1076, 2003. Furthermore, their capacity to be expressed in an active form at sufficiently high levels for commercial purposes is unknown. To explore the possibility of using heterologous acyl-CoA synthases for esters production, several acyl-CoA synthase genes were cloned and expressed as follows. Although this example describes transforming the production host with separate plasmids for the thioesterase, ester synthase, and acyl-CoA synthase genes, these genes may alternatively be incorporated in a single plasmid to transform the production host.

1. Construction of pOP-80 Plasmid

To over-express the genes, a low-copy plasmid based on the commercial vector pCL1920 (Lerner and Inouye, NAR 18: 4631, 1990) carrying a strong transcriptional promoter was constructed by digesting pCL1920 with restriction enzymes AflIII and SfoI (New England BioLabs Inc. Ipswich, Mass.). Three DNA sequence fragments were produced by this digestion. The 3737 bp fragment was gel-purified using a gel-purification kit (Qiagen, Inc. Valencia, Calif.). In parallel, a fragment containing the trc-promoter and lacI region from the commercial plasmid pTrcHis2 (Invitrogen, Carlsbad, Calif.) was amplified by PCR using primers LF302: 5'-ATATGACGTCGGCATCCGCTTACA-GACA-3'(SEQ ID NO:41); and LF303: 5'-AATTCT-TAAGTCAGGAGAGCGTTCACCGACAA-3'(SEQ ID NO:42). These two primers also introduced recognition sites for the restriction enzymes ZraI (gacgtc) and AflII (cttaag), respectively, at the end of the PCR products. After amplification, the PCR products were purified using a PCR-purification kit (Qiagen, Inc. Valencia, Calif.) and digested with ZraI and AflII following the conditions recommended by the manufacturer (New England BioLabs Inc., Ipswich, Mass.). After digestion, the PCR product was gel-purified and ligated with the 3737 bp DNA sequence fragment derived from pCL1920.

Figure 16:
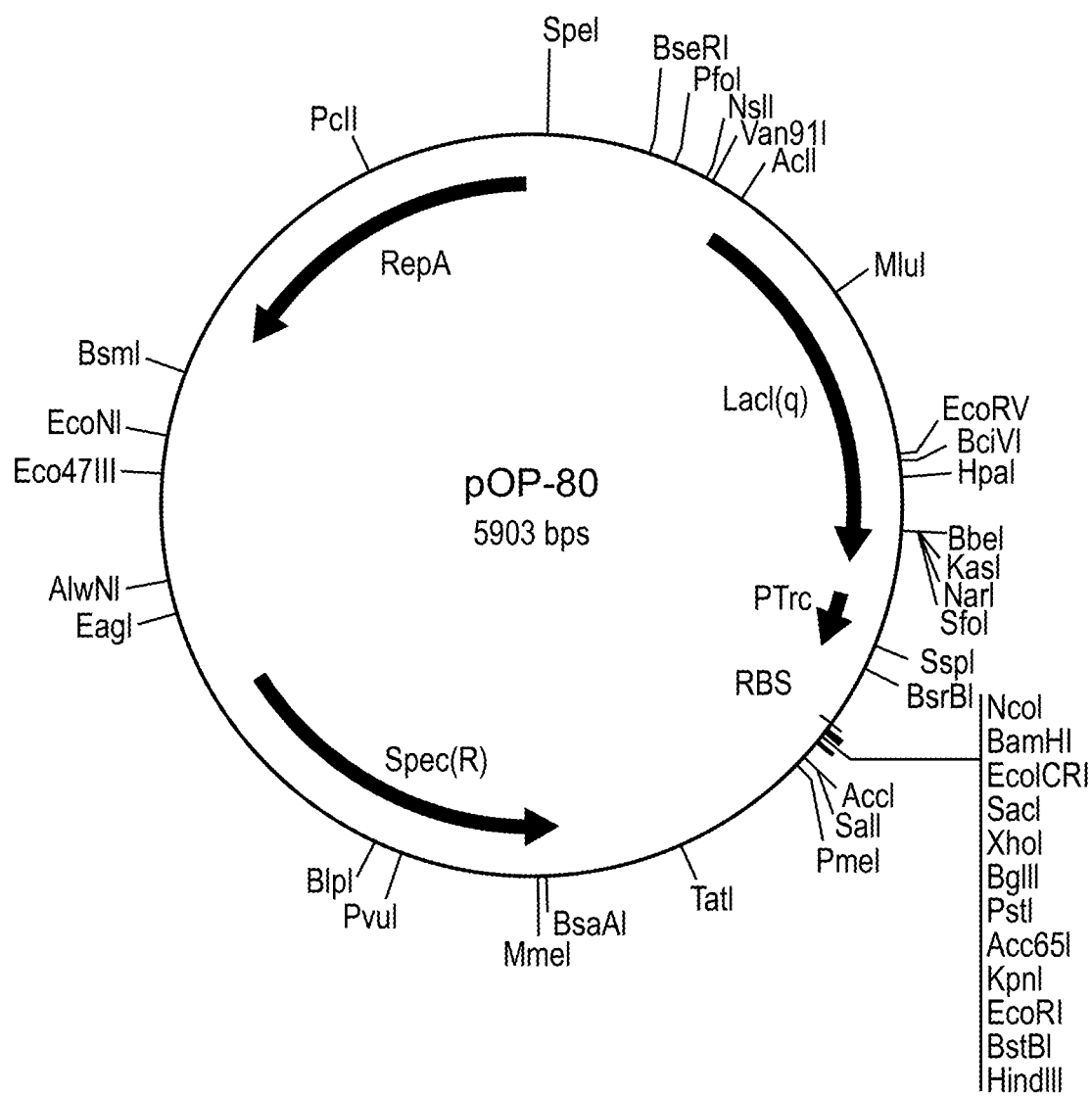
FIG. 16 (FIG. 16) is a map of the pOP-80 plasmid.
Figure 31:
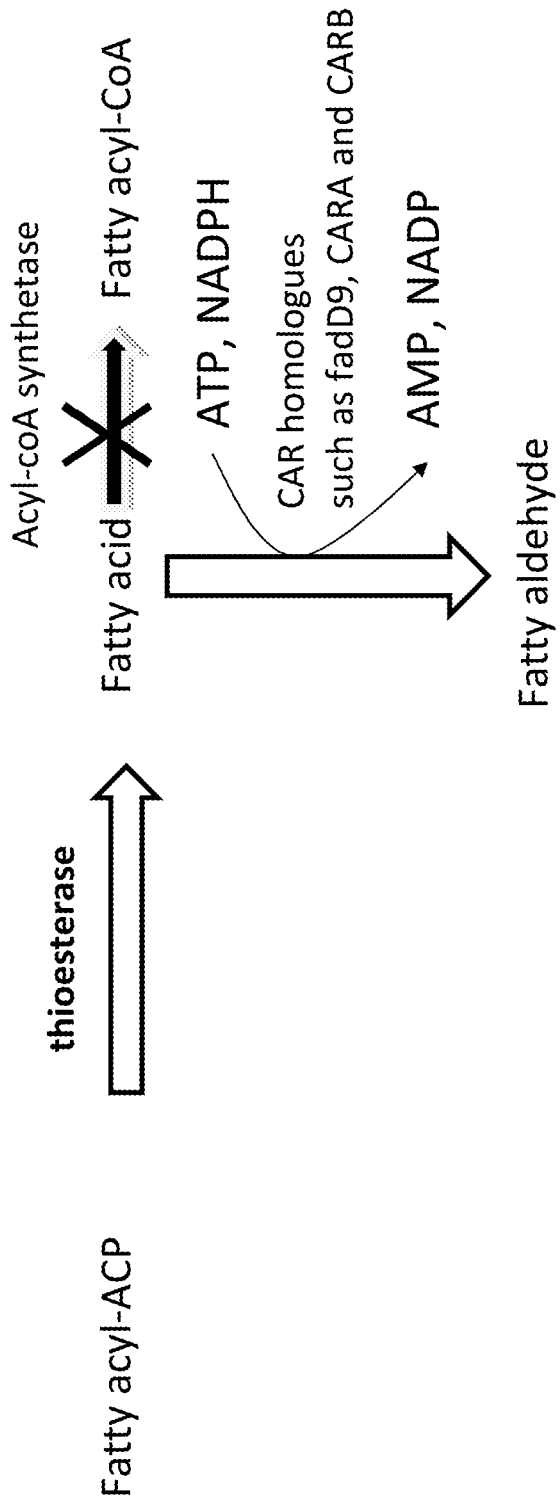
FIG. 31 (FIG. 31) is a schematic of a new pathway for fatty aldehyde production.
Figure 35A:
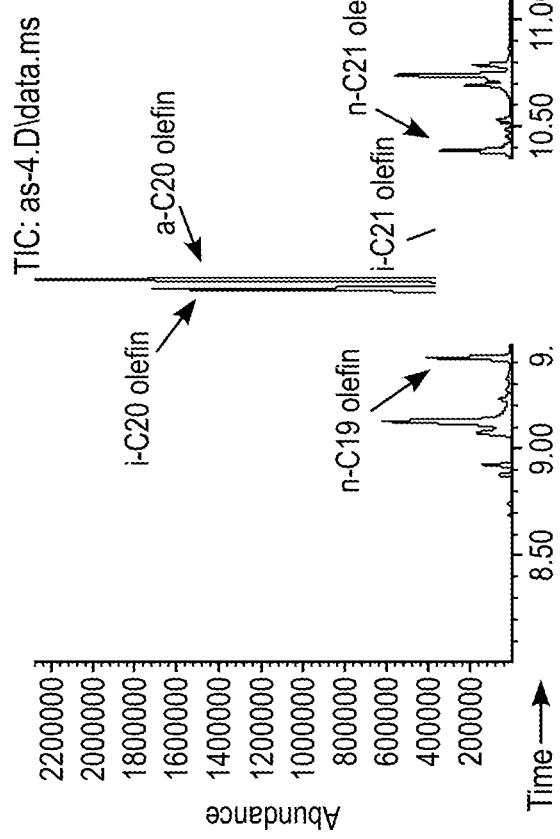
FIGS. 35A-B (FIGS. 35A-B) are GC/MS traces of olefins produced by *Jeotgalicoccus pinnipedalis* DSMZ 17030 cells and *Jeotgalicoccus psychrophiles* DSMZ 19085 cells, respectively.
Figure 35B:
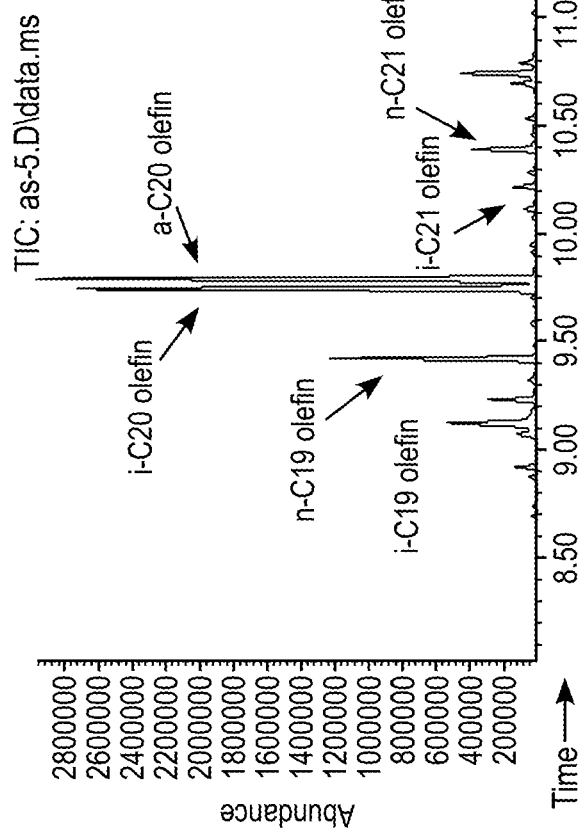

After transformation with the ligation mixture in TOP10 chemically competent cells (Invitrogen, Carlsbad, Calif.), transformants were selected on Luria agar plates containing 100 μg/mL spectinomycin. Many colonies were visible after overnight incubation at 37° C. Plasmids present in these colonies were purified, analyzed with restriction enzymes, and then sequenced. One plasmid produced in this way was retained, named pOP-80, and used for further experiments. A map of pOP-80 is shown in FIG. 16.

The DNA sequences of relevant regions of plasmid pOP-80 were verified. It was found in the junctions where the 2 fragments were ligated that 3 to 4 bases at each end were missing. This was probably caused by an exonuclease activity contaminating one of the restriction enzymes. It was likely that these small deletions did not affect any relevant plasmid function. The resulting plasmid was used for all expression experiments described in this example. The full sequence of the plasmid is disclosed as SEQ ID NO:1 in FIG. 17.

2. Cloning of fadD35 from *Mycobacterium tuberculosis* HR7Rv

An *E. coli* codon-optimized gene was synthesized by DNA 2.0 Inc. (Menlo Park, Calif.), using the protein sequence of the fadD35 gene deposited at NCBI with the GenBank Accession No. NP_217021 as a starting point. The synthetic gene contained a unique NcoI site at the 5'-end and a unique EcoRI site at the 3'-end. The synthetic gene was provided by DNA 2.0 Inc. cloned in plasmid pJ201:16084. The fad35 gene was released from this plasmid by digesting with NcoI and EcoRI. The sequence of this fragment is shown in SEQ ID NO:2 in FIG. 18. The resulting DNA sequence fragment is disclosed in SEQ ID NO:2 was ligated with pOP-80, which was previously digested with NcoI and EcoRI. The ligation mixture was transformed into TOP10 chemically competent cells (Invitrogen, Carlsbad, Calif.), which were then plated on Luria agar plates containing 100 µg/mL spectinomycin and incubated at 37° C. overnight. Colonies that appeared the next day were screened, and a strain containing the correct plasmid was identified. The plasmid was named pDS9.

3. Cloning of fadD1 from *Pseudomonas aeruginosa* PAO1

An *E. coli* codon-optimized gene was synthesized by DNA 2.0 Inc. (Menlo Park, Calif.) using the protein sequence of the fadD1 gene deposited at NCBI with the GenBank Accession No. NP_251989 as a starting point. The synthetic gene contained a unique BspHI site at the 5'-end and a unique EcoRI site at the 3'-end. The synthetic gene was provided by DNA 2.0, Inc. and cloned in plasmid pJ201:16083. The fadD1 gene was released from this plasmid by digesting with BspHI and EcoRI. The sequence of this fragment is shown in SEQ ID NO:3 in FIG. 19. The resulting DNA sequence fragment of SEQ ID NO:3 was ligated with pOP-80, which was previously digested with NcoI and EcoRI. The ligation mixture was transformed into TOP10 chemically competent cells (Invitrogen, Carlsbad, Calif.), which were then plated on Luria agar plates containing 100 µg/mL spectinomycin and incubated at 37° C. overnight. Colonies that appeared the next day were screened. A strain containing the correct plasmid was identified. The plasmid was named pDS8.

4. Cloning of yhfL from *Bacillus subtilis*

The yhfL gene was amplified by PCR using *Bacillus subtilis* 1168 chromosomal DNA sequence as a template, and two primers designed based on the DNA sequence deposited at NCBI with GenBank Accession No. NC_000964. The sequences of the 2 primers were:

```
                                      (SEQ ID NO: 4)
BsyhfLBspHIF:  5'-CATCATGAATCTTGTTTC-3'
               (FIG. 20)

(SEQ ID NO: 5)
BsyhfLEcoR:    5'-CGGAATTCTTATTGGGGCAAAATATC-3'
               (FIG. 21)
```

These two primers introduced a BspHI recognition site at the 5'-end and an EcoRI recognition site at the 3'-end. The PCR product was cloned directly into pCR-Blunt II-TOPO vector using the Zero Blunt TOPO PCR cloning kit (Invitrogen, Carlsbad, Calif.). A plasmid carrying the yhfL gene was named pDS1. To subclone yhfL, plasmid pDS1 was digested with BspHI and EcoRI. The resulting DNA sequence fragment SEQ ID NO:6 (FIG. 22) was gel-purified and cloned into pOP-80, which was previously digested with NcoI and EcoRI. The plasmid carrying the *B. subtilis* yhfL gene cloned into pOP-80 was named pDS4.

5. Cloning of faa3p from *Saccharomyces cerevisiae* (NP_012257)

The faa3p gene was amplified by PCR using commercial *Saccharomyces cerevisiae* chromosomal DNA sequence ATCC 204508D (American Type Culture Collection, Manassas, Va.) as a template, and two primers that were designed based on the DNA sequence deposited at NCBI with the GenBank Accession No. NC_001141 as a template. The sequences of the two primers were:

```
                                      (SEQ ID NO: 7)
Scfaa3pPciF:   5'-CGACATGTCCGAACAACAC-3'
               (FIG. 23)

(SEQ ID NO: 8)
Scfaa3pPciI:   5'-GCAAGCTTCTAAGAATTTTCTTTG-3'
               (FIG. 24)
```

These two primers introduced a PciI recognition site at the 5'-end and a HindIII recognition site at the 3'-end.

The PCR product was cloned directly into pCR-Blunt II-TOPO vector using the Zero Blunt TOPO PCR cloning kit (Invitrogen, Carlsbad, Calif.). A plasmid carrying the faa3p gene was named pDS2. To subclone faa3p, plasmid pDS2 was digested with PciI and HindIII. The DNA sequence fragment (SEQ ID NO:9) (FIG. 25) was gel-purified and cloned into pOP-80, which was previously digested with NcoI and HindIII. The plasmid carrying the *S. cerevisiae* faa3p gene cloned into pOP-80 was named pDS5.

6. Cloning of ZP 01644857 from *Stenotrophomonas maltophilia* R551-3

The structural gene sequence for the protein ZP_01644857 is available at NCBI as part of the locus NZ_AAVZ01000044. The gene was amplified by PCR using *Stenotrophomonas maltophilia* R551-3 chromosomal DNA sequence as template, and two primers designed based on the deposited DNA sequence. The sequences of the two primers were:

```
                                     (SEQ ID NO: 10)
Smprk59BspF:   5'-AGTCATGAGTCTGGATCG-3'
               (FIG. 26)

(SEQ ID NO: 11)
Smprk59HindR:  5'-GGAAGCTTACGGGGCGGGCG-3'
               (FIG. 27)
```

These two primers introduced a BspHI recognition site at the 5'-end and a HindIII recognition site at the 3'-end.

The PCR product was cloned directly into pCR-Blunt II-TOPO vector using the Zero Blunt TOPO PCR cloning kit (Invitrogen, Carlsbad, Calif.). A plasmid carrying the gene encoding the protein ZP_01644857 was named pDS3. To facilitate further subcloning of the gene, an internal BspHI site was removed by site directed mutagenesis using the primer PrkBsp:5'-GCGAACGGCCTGGTCTTTAT-GAAGTTCGGTGG-3'(SEQ ID NO:12) (FIG. 28) and the QuikChange Multi Site-Directed mutagenesis kit (Stratagene, La Jolla, Calif.). After the proper mutation was corroborated by DNA sequencing, the resulting plasmid was digested with BspHI and HindIII, and was named pDS6. The DNA sequence fragment was gel-purified and cloned into pOP-80 previously digested with NcoI and HindIII. The plasmid carrying the gene encoding the protein ZP_01644857 cloned into pOP-80 was named pDS7. The protein sequence of ZP_01644857 is disclosed in FIG. 29 (SEQ ID NO:13).

7. Construction of Strains to Produce Fatty Esters.

An *E. coli* BL21(DE3) strain was first transformed with plasmid pETDuet-1-'TesA (described in EXAMPLE 2) carrying the *E. coli* 'tesA gene, and plasmid pHZ1.97 (described in EXAMPLE 9) carrying the atfA2 ester synthetase gene, respectively. Both genes were under the control of a T7 promoter inducible by IPTG. Two independent transformants carrying both plasmids were transformed with each of the recombinant plasmids carrying the heterologous fadD genes, and selected on Luria agar plates containing 100 µg/mL carbenicillin, 50 µg/mL kanamycin, and 100 µg/mL spectinomycin. Three independent colonies carrying the three plasmids were evaluated for fatty-ester production.

8. Analysis of Fatty Esters Produced Using ZP 01644857 from *Stenotrophomonas maltophilia* R551-3

To evaluate the use of the protein ZP_01644857 from *Stenotrophomonas maltophilia* R551-3 in a production host to produce fatty esters, an *E. coli* BL21(DE3) strain was transformed with plasmid pETDuet-1-'TesA (described in EXAMPLE 2) carrying the *E. coli* 'tesA gene, plasmid pHZ1.97 (described in EXAMPLE 9) carrying the atfA2 ester synthetase gene, and plasmid pDS7 carrying the gene encoding the protein ZP_01644857 (described above in the instant example). This production host was fermented to produce fatty esters as described in EXAMPLE 4. As a control, a second *E. coli* strain BL21(DE3)ΔfadE containing plasmids pETDuet-1-'TesA, pHZ1.97, and pCL1920 was used as a production host to produce fatty esters.

Table 18 below indicates the fatty ester yields from these production hosts.

TABLE 18

Fatty ester yields from a production host that produced ZP_01644857

| Ester type: | $C_2C_{12:1}$ mg/L | $C_2C_{12:0}$ mg/L | $C_2C_{14:1}$ mg/L | $C_2C_{14:0}$ mg/L | $C_2C_{16:1}$ mg/L | $C_2C_{16:0}$ mg/L | $C_2C_{18:1}$ mg/L | $C_2C_{18:0}$ mg/L | Total mg/L[c] |
|---|---|---|---|---|---|---|---|---|---|
| Control[a] | 0.0 | 0.0 | 0.0 | 1.78 | 9.80 | 5.65 | 33.7 | 0.00 | 50.93 |
| fadD ZP_01644857[b] | 1.49 | 3.57 | 3.68 | 33.22 | 52.77 | 43.09 | 91.11 | 10.08 | 239.01 |

[a]Control: strain BL21(DE3) D fadE, containing plasmids pETDuet-1-'TesA, pHZ1.97 and pCL1920.
[b] Strain BL21(DE3) D fadE, containing plasmids pETDuet-1-'TesA, pHZ1.97 and pDS7.
[c]These values represent the average of 3 cultures.

Example 18. Down-Regulation of Beta-Oxidation

This example describes the creation of an *E. coli* strain MG1655 ΔfadE ΔydiO.

Fatty acid degradation can be eliminated or attenuated by attenuating any of the β-oxidation enzymatic reactions described herein (see, FIG. 2). For example, the *E. coli* strain MG1655 ΔfadE can be further engineered using primers to amplify up-stream of ydiO and additional primers to amplify downstream of ydiO. Overlap PCR can then be used to create a construct for in-frame deletion of the complete ydiO gene. The ydiO deletion construct is then cloned into a temperature sensitive plasmid pKOV3, which contains a sacB gene for counter-selection. A chromosomal deletion of ydiO is made according to the method of Link et al., J. Bact. 179:6228-6237, 1997. The resulting strain will not be capable of degrading fatty acids and fatty acyl-CoAs. Additional methods of generating a double knockout of fadE and ydiO are described, for example, in Campbell et al., Mol. Microbiol. 47:793-805, 2003.

It is also possible to avoid fatty acid degradation by selecting or employing a production host that does not contain the β-oxidation pathway. For example, several species of *Streptococcus* have been sequenced and no β-oxidation genes have been found.

Example 19. Identification of Additional Ester Synthases

This example provides additional ester synthases and methods of using such synthases for the production of fatty esters.

Using bioinformatics, additional ester synthases were identified. These ester synthases contain motifs that differ from other known motifs, such as the motifs found in ADP1. The differences in the motifs are noted in Table 19, below.

TABLE 19

Comparison of ester synthases motifs

| ADP1-motifs | HHAXVDG V | NDVVLGALRXY A L | PLXAMV P P | ISNVPG | REPLYXNG A |
|---|---|---|---|---|---|
| Hypothetical protein BCG_3544c [*Mycobacterium bovis* BCG str. Pasteur 1173P2] gi/121639399 | HHSLIDG Y | NDVALGGLRRF A L | SLIVVL P | VSNVPG P | EDVLYLRG S |

TABLE 19-continued

Comparison of ester synthases motifs

| Protein of unknown function UPF0089 [*Mycobacterium gilvum* PYR-GCK] gi/145221651 | HHALVDG Y | NDVALGGLRKF A L | SLIAFL P | VSNVPG P | REPLYFNG S |

TABLE 19-continued

Comparison of ester synthases motifs

| Protein of unknown function UPF0089 [Mycobacterium vanbaalenii PYR-1] gi/ 120406715 | HHALVDG Y | NDVALGGLRKF A L | SLIAFL P | VSNVPG P | REPLYFNG S |

The identified sequences can be cloned using standard molecular biology techniques. These sequences can be expressed using the vectors described herein and used to make various fatty esters. The motifs can also be used to identify other ester synthases.

Example 20. Product Characterization

To characterize and quantify the fatty alcohols and fatty esters, gas chromatography (GC) coupled with electron impact mass spectra (MS) detection was used. Fatty alcohol samples were first derivatized with an excess of N-trimethylsilyl (TMS) imidazole to increase detection sensitivity. Fatty esters did not require derivatization. Fatty alcohol-TMS derivatives and fatty esters were dissolved in an appropriate volatile solvent, such as, for example, ethyl acetate.

The samples were analyzed on a 30 m DP-5 capillary column using the following method. After a 1 µl splitless injection onto the GC/MS column, the oven was held at 100° C. for 3 minutes. The temperature was incrementally raised to 320° C. at a rate of 20° C./minute. The oven was held at 320° C. for an additional 5 minutes. The flow rate of the carrier gas helium was 1.3 mL/minute. The MS quadrapole scanned from 50 to 550 m/z. Retention times and fragmentation patterns of product peaks were compared with authentic references to confirm peak identity.

For example, hexadeconic acid ethyl ester eluted at 10.18 minutes (FIGS. 15A-B). The parent ion of 284 mass units was readily observed. More abundant were the daughter ions produced during mass fragmentation. The most prevalent daughter ion was of 80 mass units. The derivatized fatty alcohol hexadecanol-TMS eluted at 10.29 minutes and the parent ion of 313 were observed. The most prevalent ion was the M-14 ion of 299 mass units.

Quantification was carried out by injecting various concentrations of the appropriate authentic references using the GC/MS method as described herein. This information was used to generate a standard curve with response (total integrated ion count) versus concentration.

Example 21. Identification and Reclassification of a Microorganism Belonging to the Genus *Jeotgalicoccus* that is an α-Olefin Producer

Figure 36A:
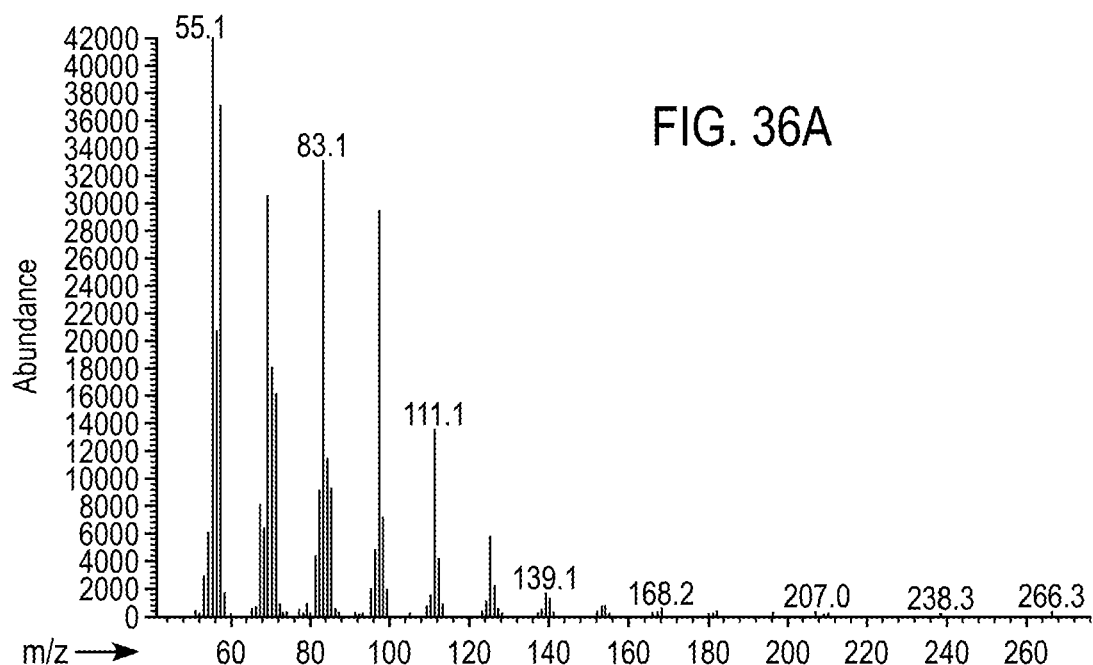
FIGS. 36A-B (FIGS. 36A-B) are mass spectrometry fragmentation patterns of two α-olefins produced by *Jeotgalicoccus* ATCC 8456 cells. Compound A was identified as 1-nonadecene and compound B as 18-methyl-1-nonadecene.
Figure 36B:
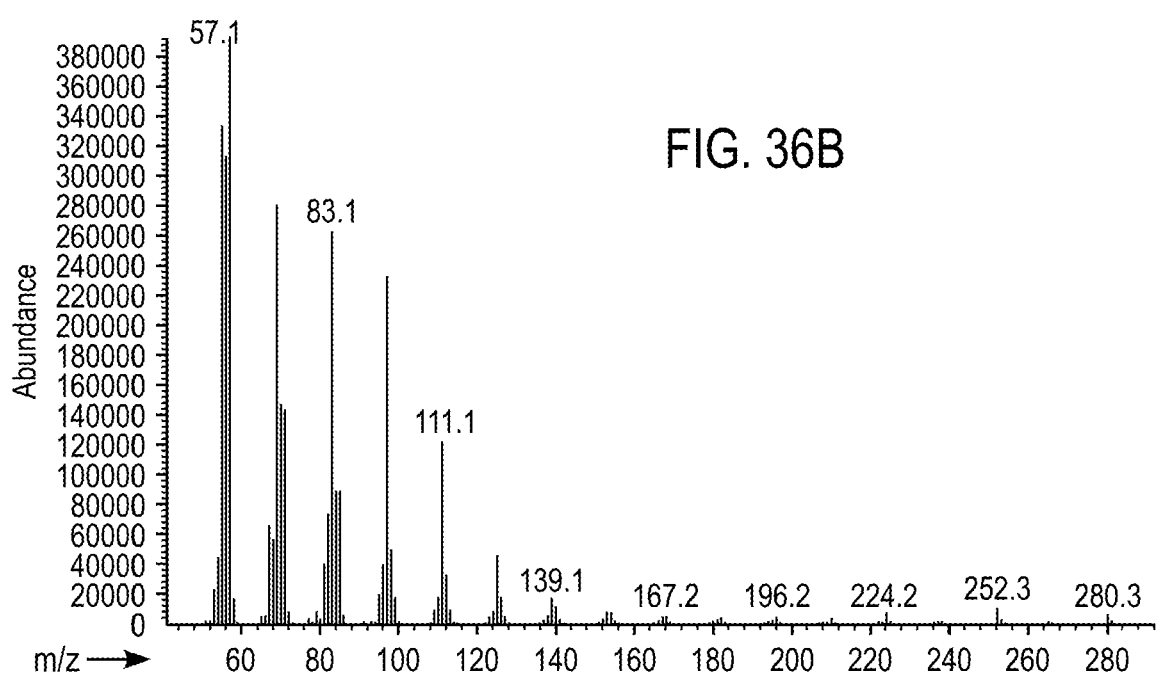

*Micrococcus candicans* ATCC 8456 was previously reported to synthesize aliphatic hydrocarbons with carbon chain lengths ranging from $C_{18}$ to $C_{20}$ (Morrison et al., J. Bacteriol. 108:353-358, 1971). To identify the hydrocarbons produced by this strain, ATCC 8456 cells were cultured in 15 mL TSBYE medium (3% Tryptic Soy Broth+0.5% Yeast Extract), for 40-48 hours at 30° C. Cells from 5 mL of culture were pelleted, resuspended in 1 mL methanol, sonicated for 30 minutes, and extracted with 4 mL hexane. After solvent evaporation, samples were resuspended in 0.1 mL hexane and analyzed by GC-MS. The hydrocarbons were identified to be the following α-olefins: 15-methyl-1-heptadecene (a-$C_{18}$), 16-methyl-1-heptadecene (i-$C_{18}$), 1-nonadecene (n-$C_{19}$), 17-methyl-1-nonadecene (a-$C_{20}$) and 18-methyl-1-nonadecene (i-$C_{20}$) (see FIG. 34 (i=iso, a=anteiso, n=straight chain) and FIG. 36).

Based upon the following analyses, it was determined that ATCC 8456 was previously misidentified as belonging to the genus Micrococci. The phylogenetic classification of ATCC 8456 was reassessed by amplifying and sequencing the partial 16s rRNA gene using primers Eubac27 and 1492R (see DeLong et al., PNAS 89:5685, 1992). The 16s rRNA sequence of ATCC8456 was analyzed using the classifier program of the Ribosomal Database Project II (http://rdp.cme.msu.edu/index.jsp). Based upon this analysis, the strain was identified as belonging to the genus *Jeotgalicoccus*. The genus *Jeotgalicoccus* has been previously described (Jung-Hoon et al., Int. J. Syst. Evol. Microbiol. 53:595-602, 2003).

Figure 37:
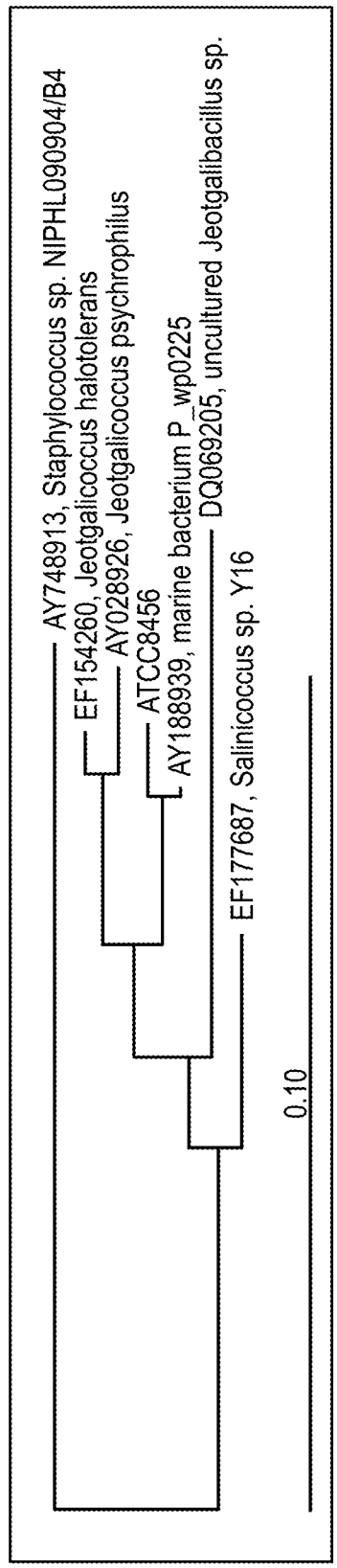
FIG. 37 (FIG. 37) is a schematic of a phylogenetic analysis of 16s rRNA of *Jeotgalicoccus* ATCC 8456.

Additional analysis using the G+C content of ATCC 8456 was conducted. *Jeotgalicoccus* is a low G+C Gram-positive bacteria related to the genus *Staphylococcus* (see FIG. 37). Micrococci, on the other hand, are high G+C Gram-positive bacteria. The ends of several clones from a cosmid library of ATCC 8456 genomic DNA were sequenced. Based upon a DNA sequence of about 4,000 bp, the G+C content was determined to be about 36%. Nucleotide sequence searches against a non-redundant protein database revealed that all sequences with a match to a database entry were similar to proteins from low G+C Gram-positive bacteria, such as species belonging to the genus *Staphylococcus* or *Bacillus*, but not species belonging to the genus *Micrococcus*.

Next, an analysis of the entire genome of ATCC 8456 was conducted. Based on a DNA sequence of about 2.1 MB, the G+C content of the entire genome was determined to be about 36.7%. In contrast, bacteria of the genus *Micrococcus* are known to have high G+C genomes, e.g., the genome of *Micrococcus luteus* NCTC 2665 has a G+C content of 72.9% (GenBank Accession No. ABLQ01000001-68). Based upon the G+C content analysis, it was determined that the ATCC 8456 microorganism does not belong to the genus *Micrococcus*.

Additional *Jeotgalicoccus* strains were also examined to determine if they produced α-olefins. The following strains of *Jeotgalicoccus* were examined: *Jeotgalicoccus halotolerans* DSMZ 17274, *Jeotgalicoccus psychrophiles* DSMZ 19085, and *Jeotgalicoccus pinnipedalis* DSMZ 17030. Each strain was cultured in 15 mL TSBYE medium (3% Tryptic Soy Broth+0.5% Yeast Extract) and the hydrocarbons were isolated and analyzed by GC-MS as described above. All three strains produced α-olefins similar to the ones produced by ATCC 8456 (FIGS. 34B, 34C and 34D depict GC-MS traces for hydrocarbons produced by *Jeotgalicoccus halotolerans* DSMZ 17274 cells, *Jeotgalicoccus pinnipedalis* DSMZ 17030 cells, and *Jeotgalicoccus psychrophiles* DSMZ 19085 cells, respectively). These data indicate that the ability to produce α-olefins is widespread among the genus *Jeotgalicoccus*.

Example 22. Production of Increased Levels of Olefins and α-Olefins not Normally Produced by ATCC 8456 Cells Using Fatty Acid Feeding The fatty acids eicosanoic acid (straight-chain $C_{20}$ fatty acid), 16-methyl octadecanoic acid and 17-methyl octadecanoic acid (branched-chain $C_{19}$ fatty acids) were identified as components of ATCC 8456's lipids. These fatty acids were deduced to be the direct precursors, after decarboxylation, for 1-nonadecene, 15-methyl-1-heptadecene and 16-methyl-1-heptadecene biosynthesis, respectively. In order to improve α-olefin production and to produce olefins not normally produced by ATCC 8456 cells, fatty acid feeding experiments were carried out as described below.

ATCC 8456 cells were cultured in 15 mL of a TSBYE medium (containing 3% Tryptic Soy Broth+0.5% Yeast Extract). Fatty acids were added to the culture medium at a final concentration of 0.5 g/L (0.05%). After growth for 40-48 hrs at 30° C., cells from 5 mL of culture were pelleted, resuspended in 1 mL methanol, sonicated for 30 minutes and extracted with 4 mL hexane. After solvent evaporation, samples were resuspended in 0.1 mL hexane and analyzed by GC-MS.

Figure 38A:
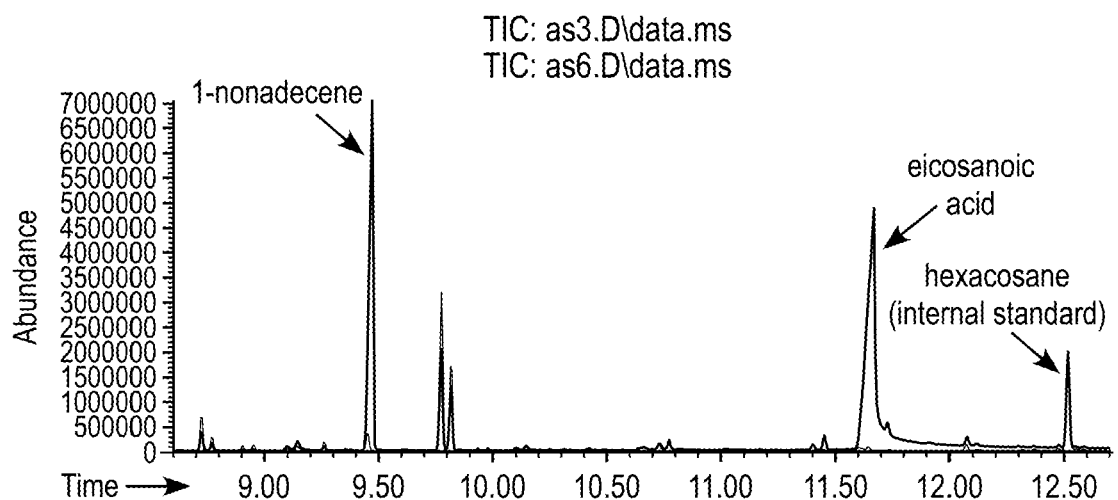
FIGS. 38A-B (FIGS. 38A-B) are GC/MS traces of α-olefins produced by *Jeotgalicoccus* sp. ATCC 8456 cells upon feeding with eicosanoic acid (FIG. 38A) or stearic acid (FIG. 38B).
Figure 38B:
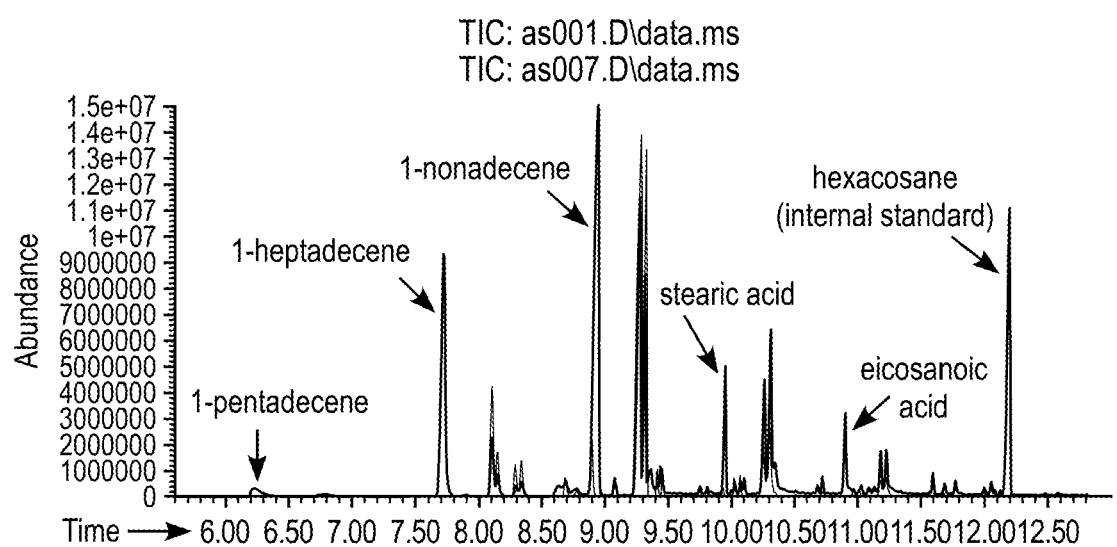

When cultures were fed eicosanoic acid, an increase in 1-nonadecene production of about 18-fold was observed (see FIG. 38A; black traces depict without and gray traces depict with fatty acid feeding). When cultures were fed stearic acid or palmitic acid, an increase in the production of the α-olefins 1-pentadecene and 1-heptadecene, respectively, was observed (see FIG. 38B). These olefins are not normally produced by ATCC 8456 cells. This indicated that fatty acids were the direct precursors for α-olefins and that *Jeotgalicoccus* bacteria can be used to enzymatically convert fatty acids into α-olefins in vivo.

Alternatively, resting *Jeotgalicoccus* cells can be fed with various fatty acids to achieve similar results.

Example 23. In Vitro Synthesis of α-Olefins Using Cell Extracts and Partially Purified Proteins A cell free extract of ATCC 8456 was used to convert free fatty acids into α-olefins. The cell free extract was generated using the following procedure: ATCC 8456 cells were cultured in a TSBYE medium (containing 3% Tryptic Soy Broth+0.5% Yeast Extract) at 30° C. for 24 hrs with shaking. The cells were then pelleted from the culture by centrifugation at 3,700 rpm for 20 minutes. The cell pellet was then resuspended in 50 mM Tris buffer pH 7.5 with 0.1 M NaCl and 2.0 mM dithiothreitol to a concentration of 0.1 g/mL cells. To this cell slurry, 200 units/mL of lysostaphin (Sigma) was added on ice. The cell lysis reaction continued for 30 minutes. The cells were then sonicated at 12 W on ice for three cycles of 1.5 seconds of sonication followed by 1.5 seconds of rest. Sonication lasted for a total of 9 seconds. This procedure was repeated 5 times with a 1-minute interval between sonication cycles. The lysed cells were then subjected to centrifugation at 12,000 rpm for 10 minutes to pellet the cell debris. The supernatant (cell free extract) was removed and used for the conversion of free fatty acids to α-olefins.

After obtaining the cell free extract, the free fatty acids stearic acid and eicosanoic acid were converted to α-olefins using the cell free extract as described below. First, a 5% stock solution of sodium or potassium stearate was made in 1% Tergitol solution (Sigma, St. Louis, Mo.). Next, 6 µl of the stock solution was added to 1 mL of the cell free extract at room temperature to obtain a final concentration of 1 mM free fatty acid salt. The reaction was conducted at room temperature for 3 hrs. The α-olefins were recovered by adding 200 µl of ethyl acetate to the mixture, vortexing briefly, centrifuging briefly, and then removing the organic phase. The α-olefins were identified and/or detected by GC/MS.

Figure 39:
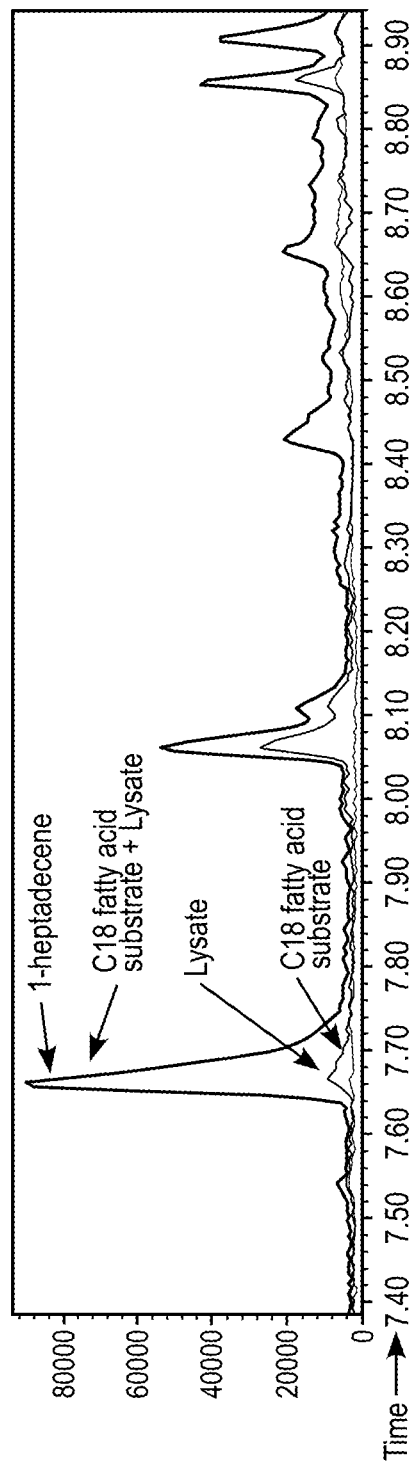
FIG. 39 (FIG. 39) is a GC/MS trace of α-olefins (1-heptadecene) produced by cell free lysates of *Jeotgalicoccus* sp. ATCC 8456 cells, as compared to a trace of cell-free lysate without the $C_{18}$ fatty acid substrate, and a trace of the $C_{18}$ fatty acid substrate itself.

FIG. 39 shows the GC/MS trace for the resulting products. In sample 1, no stearic acid was added to the cell free extract. In sample 2, the cell free extract was replaced with 50 mM Tris pH 7.5 buffer with 0.1 M sodium chloride to which stearic acid was added. In sample, stearic acid was added to the cell free extract. The peak at 7.62 minute had the same retention time and the same mass spectra as 1-heptadecene (Sigma). When eicosanoic acid was added under similar conditions, 1-nonadecene was formed.

Boiling the cell free extract eliminated the production of α-olefins upon the addition of free fatty acids. This data strongly suggested that the ATCC 8456 catalyst was protein based.

The ATCC 8456 cell free extract did not require additional co-factors to produce α-olefins. When the cell free extract was supplemented with several co-factors in 1 mM concentrations, no increase in α-olefin synthesis was observed. The co-factors examined were NAD+, NADP+, NADH, NADPH, $FADH_2$, SAM, ATP, and CoA. In addition, $Mg^{2+}$ was examined, but at a 10 mM concentration. The co-factor requirement was also tested by dialyzing the cell free extract with a 10 kDa cut-off membrane for 1.5 hrs in a volume that was 200-fold greater than the cell extract volume using a dialysis buffer: 50 mM Tris, pH 7.5 with 0.1 M sodium chloride. No decrease in α-olefin synthesis was observed after dialysis. Additionally, no decrease in α-olefin synthesis was observed when 10 mM EDTA pH 7.5 was added to the reaction mixture.

The ATCC 8456 cell free extract was further enriched by carrying out an ammonium sulfate precipitation. First, enough ammonium sulfate was added to the cell free extract to bring the concentration of ammonium sulfate to 50% (wt/vol) saturation. The mixture was stirred gently on ice for 60 minutes and then centrifuged at 13,000 rpm for 30 minutes. The supernatant was recovered and additional ammonium sulfate was added to bring the ammonium sulfate concentration to 65% (wt/vol). The mixture was allowed to mix on ice for 60 minutes and was centrifuged again for 30 minutes. The supernatant was discarded. The pellet was then resuspended in 50 mM Tris buffer pH 7.5 with 0.1 M sodium chloride. This mixture was then dialyzed in the aforementioned buffer to remove the ammonium sulfate. The cell free extract treated with ammonium sulfate had the same α-olefin synthesizing activity as the cell free extract.

Example 24. Purification and Identification of a Protein that Converts Fatty Acids into α-Olefins To isolate the protein necessary for α-olefin production from ATCC 8456 cells, the following protein purification procedure was carried out. First, 6 L of ATCC 8456 cells were cultured in a TSBYE medium at 30° C. for 24 hours with shaking. The cells were pelleted by centrifugation at 3,700 rpm for 20 minutes at 4° C., and the supernatant was discarded. The cell pellet was resuspended in a solution of 100 mL of 50 mM Tris pH 8.0, 0.1 M NaCl, 2.0 mM DTT, and bacterial protease inhibitors. The cell slurry was then passed through a French press one time at a pressure of 30,000 psi. Next, the cell slurry was sonicated as described in Example 3 to shear the DNA. The cell free extract was centrifuged at 10,000 rpm for 60 minutes at 4° C. The supernatant was then removed and ammonium sulfate was added to a final concentration of 50% (wt/vol). The mixture was gently stirred at 4° C. for 60 minutes and then centrifuged at 10,000 rpm for 30 minutes. The supernatant was then removed and additional ammonium sulfate was added to 65% (wt/vol) saturation. The mixture was stirred again for 60 minutes at 4° C. and centrifuged at 10,000 rpm for 30 mM. The supernatant was discarded. The remaining pellet was resuspended in 50 mL of 50 mM Tris pH 8.0 and 2.0 mM DTT.

The mixture was passed through a 5 mL HiTrap SP column (GE Healthcare) at 3 mL/min and 4° C. The following buffers were used as an elution gradient: buffer A contained 50 mM Tris pH 8.0 and 2.0 mM DTT; buffer B contained 50 mM Tris pH 8.0, 1.0 M NaCl, and 2.0 mM DTT. After the column was loaded with the mixture, the column was washed with 40% buffer B. Next a 20-minute gradient of 40% buffer B to 100% buffer B at 3.0 mL/min was carried out. 5 mL fractions were collected during the elution gradient. Each fraction was tested for activity as described in Example 3. Fractions containing α-olefin production activity typically eluted between 600 and 750 mM NaCl concentration. Fractions containing activity were then pooled and dialyzed into buffer A.

Figure 40:
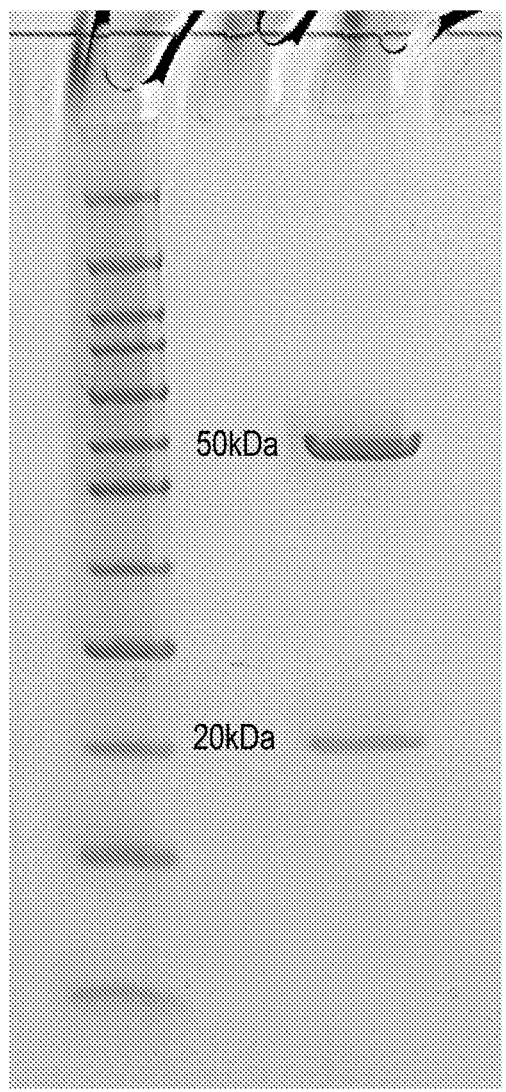
FIG. 40 (FIG. 40) is a digital representation of an SDS-PAGE gel of final purified α-olefins-producing protein fraction from *Jeotgalicoccus* sp. ATCC 8456 cells.

The dialyzed protein fraction was then loaded onto a 1 mL ResourceQ (GE Healthcare) column at 4 mL/min at 4° C. Buffer B used with the HiTrap SP column was also used for the ResourceQ column. A 7-minute elution gradient between 0% buffer B and 25% buffer B was run at 4 mL/min. 1.5 mL fractions were collected and assayed for activity. Active fractions eluted between 150 and 200 mM NaCl concentrations. Fractions containing activity were then pooled and concentrated with a Millipore Amicon protein concentrator (4 mL and 10 kDa exclusion size) to about 50 µL. The approximate protein concentration was determined with a Bradford assay (Bio-Rad). Final protein concentrations ranged from about 5 mg/mL to about 10 mg/mL. 30 µL of protein was then loaded onto a SDS PAGE gel (Invitrogen) along with an appropriate protein molecular weight marker. The gel was stained with Simple Safe Coomassie stain (Invitrogen). FIG. 40 depicts a representative gel. Two intense protein bands at 50 kDa and 20 kDa were observed.

To determine the identity of the protein bands, the bands were excised from the gel, digested with trypsin, and analyzed using LC/MS/MS. The LC/MS/MS data was analyzed using the program Mascot (Mann et al., Anal. Chem. 66:4390-4399, 1994). The ATCC 8456 genome was sequenced. The genomic data was used to interpret the LC/MS/MS data and to determine the identity of the protein bands. The 50 kDa band had a strong match with ORF880. The Mascot score assigned to this match was 919, a high score. Furthermore, ORF880 has a predicted molecular weight of 48,367 Da. The nucleotide and amino acid sequences of orf880 are presented in FIGS. 41A and 41B, respectively.

Figure 42:
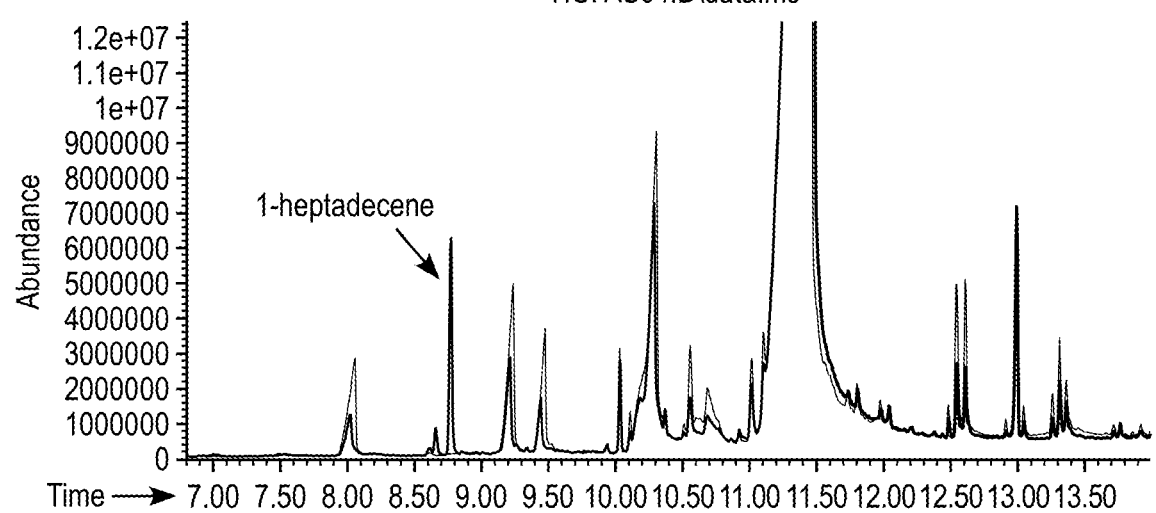
FIG. 42 (FIG. 42) is a GC/MS trace of α-olefins produced by *E. coli* upon expression of *Jeotgalicoccus* sp. 8456_orf880 and feeding of stearic acid.
Figure 43:
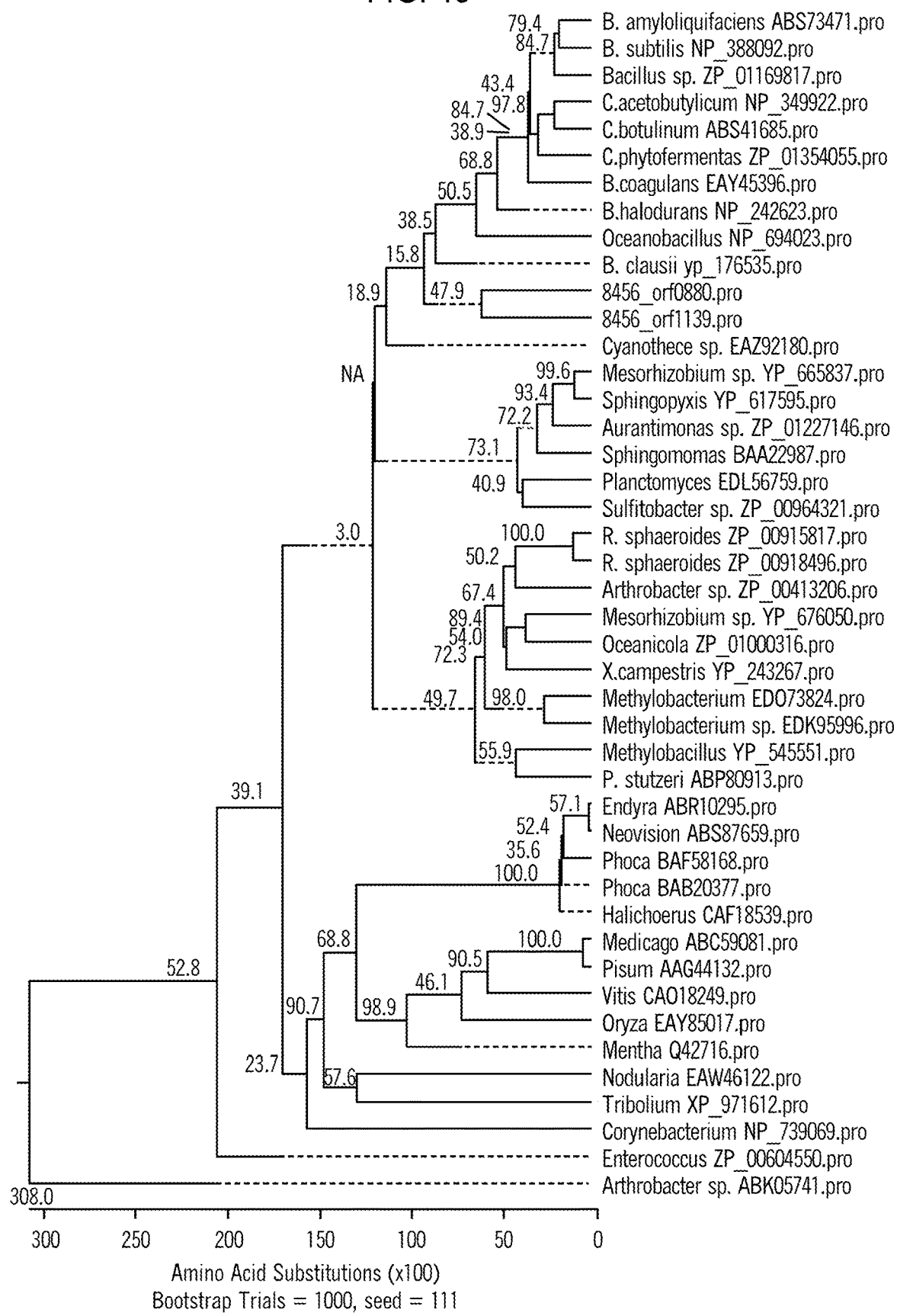
FIG. 43 (FIG. 43) is a schematic of a bootstrap phylogenetic analysis of 8456_orf880 homologs using ClustalW.

Example 25. Heterologous Expression of Jeotgalicoccus ATCC 8456 Orf880 in E. coli Jeotgalicoccus ATCC 8456 Orf880 was identified as one of the two major proteins in a highly purified enzyme fraction that catalyzed the conversion of free fatty acids to α-olefins. The genomic DNA encoding ATCC 8456_orf880 was cloned into pCDF-Duet1 under the control of the T7 promoter, and E. coli was transformed with various vectors, as described below. The E. coli cells were cultured and the hydrocarbons produced by the cells were analyzed as described in Example 23. When 0.05% stearic acid was fed to cultures of E. coli transformed with the 8456_orf880-containing vector, the expression of 8456_orf880 led to the formation of 1-heptadecene in E. coli (see FIG. 42, which depicts GC/MS traces of α-olefins from E. coli either without (black) or with (gray) 8456_orf880 expression). In contrast, adding 0.05% stearic acid to cultures of E. coli transformed with a vector control (not containing ATCC_orf880) did not result in the production of 1-heptadecene. This demonstrated that 8456_orf880 synthesized α-olefins from free fatty acids in an E. coli heterologous host. This result indicates that α-olefin biosynthesis can be performed in heterologous organisms. Additionally, when E. coli cells expressing 8456_orf880 protein were fed with 0.05% palmitic acid or 0.05% eicosanoic acid, the production of 1-pentadecene or 1-nonadecene, respectively, was observed.

Example 26. In Vitro Synthesis of α-Olefins Using Orf880 Heterologously Expressed in and Purified from E. coli The genomic DNA encoding ATCC8456_orf880 was cloned into the NdeI and XhoI sites of vector pET15b (Novagen) under the control of a T7 promoter for expression in and purification from E. coli. This plasmid expressed an N-terminal His-tagged version of 8456_orf880.

An E. coli BL21 strain (DE3) (Invitrogen) was transformed with pET15b-ORF 880 using routine chemical transformation techniques. Protein expression was carried out by first inoculating a colony of the E. coli strain in 5 mL of LB media supplemented with 100 mg/L carbenecillin and shaken overnight at 37° C. to produce a starter culture. This starter culture was used to inoculate 1 L of an LB medium supplemented with 100 mg/L carbenecillin. The culture was shaken at 37° C. until it reached an $OD_{600}$ value of 0.6. The culture was placed on ice for 10 minutes before IPTG was added to a final concentration of 250 µM. The culture was then shaken at 18° C. for about 18 hours. The culture was then centrifuged at 3,700 rpm for 20 minutes at 4° C. The pellet was resuspended in 30 mL of buffer containing 100 mM sodium phosphate buffer at pH 7.2, supplemented with Bacterial ProteaseArrest (GBiosciences). The cells were sonicated at 12 W on ice for 9 seconds with 1.5 seconds of sonication followed by 1.5 seconds of rest. This procedure was repeated 5 times with 1 minute intervals between each sonication cycle. The cell free extract was centrifuged at 10,000 rpm for 30 minutes at 4° C. 5 mL of Ni-NTA (Qiagen) was added to the supernatant and the mixture was gently stirred at 4° C. The slurry was passed through a column to remove the resin from the lysate. The resin was then washed with 30 mL of buffer containing 100 mM sodium phosphate buffer at pH 7.2, and 30 mM imidazole. Finally, the protein was eluted with 15 mL of 100 mM sodium phosphate buffer at pH 7.2 plus 250 mM imidazole. The protein solution was dialyzed with 200 volumes of 100 mM sodium phosphate buffer at pH 7.2. Protein concentration was determined using the Bradford assay (Bio-Rad). 125 µg/mL of protein was obtained.

To assay the in vitro fatty acid substrate specificity of ORF880, potassium salts of the following fatty acids were prepared: tetradecanoic acid, hexadecanoic acid, octadecanoic acid, eicosanoic acid, and behenic acid (Sigma). The fatty acid solutions were made with 2% ethanol and 2% Tergitol solution (Sigma, St. Louis, Mo.) to a final concentration of 20 mM.

The kinetics of the decarboxylation reaction and production was determined. A 200 µl reaction mixture was prepared containing the following reactants: 1.25 µM of ORF880, 200 µM of potassium octadecanoate, 200 µl dithiothreitol, and 100 mM sodium phosphate buffer at pH 7.2. The reaction mixture was incubated at room temperature and time points were taken in duplicate between 5 minute and 120 minute.

The reaction was quenched and extracted by adding 100 μl of ethyl acetate containing 1-octadecene at 5 mg/L as an internal reference. Samples were analyzed using GC/MS using the alkane 1 splitless method, using the following parameters: run time: 20 mM; column: HP-5-MS Part No. 19091S-433E (length of 30 meters; I.D.: 0.25 mm narrowbore; film: 0.25 μM); sample: standard ethyl acetate extraction; inject: 1 μl Agilent 6850 inlet; inlet: 300° C. splitless; carrier gas: helium; flow: 1.3 mL/min; oven temp: 100° C. hold 5 mM, 320 at 20° C./min, 320 hold 5 min; det: Agilent 5975B VL MSD; det. temp: 300° C.; scan: 50-500 M/Z. Calibration curves were generated using 1-heptadecene dissolved in ethyl acetate. Based upon this analysis, the product production was determined to be linear from 5 minute to 60 minute.

To assay the reaction rates of different fatty acid substrates, the following 200 μl reaction mixtures were prepared: 1.0 μM ORF 880 enzyme, 200 μM of a test fatty acid salt, 200 μL dithiothreitol, and 100 mM sodium phosphate buffer at pH 7.2. The reactions were carried out at room temperature and time points were taken in triplicates at 20 minute and 47 minute using the extraction and analysis procedures as described above. Reference curves were generated using available chemical standards. In some instances, the chemical standards were not available. Under those circumstances, for example, cis-9-heneicosene was used as a reference for 1-heneicosene, and 9-tricosene was used as a reference for 1-tricosene. Activities were calculated by taking the difference between the average α-olefin concentrations for each substrate at 47 minute and 20 minute and then dividing the difference by 27 minute. The results are summarized in Table 20.

TABLE 20

Activity of ORF880 with different fatty acid substrates

| Substrate | Activity (nM alkene produced/min) |
|---|---|
| tetradecanoic acid | 22.9 |
| hexadecanoic acid | 181.9 |
| octadecanoic acid | 77.2 |
| eicosanoic acid | 19.7 |
| behenic acid | 30.6 |

These results demonstrate that heterologously expressed ORF880 was able to convert fatty acid substrates to olefins in vitro. These data also show that ORF880 had greater activity when hexadecanoic acid was the fatty acid substrate.

Example 27. Production of α-Olefins from Glucose by Heterologous Expression of *Jeotgalicoccus* ATCC 8456 Orf880 in *E. coli* Mg1655 ΔfadD 1. Construction of fadD Deletion Strain The fadD gene of *E. coli* MG1655 was deleted using the lambda red system (Datsenko et al., Proc. Natl. Acad. Sci. USA. 97: 6640-6645, 2000) as follows:

The chloramphenicol acetyltransferase gene from pKD3 was amplified using the primers fad1:
(SEQ ID NO: 43)
5'-TAACCGGCGTCTGACGACTGACTTAACGCTCAGGCTTTATTGTCCACTTT
GTGTAGGCTGGAGCTGCTTCG-3';
and fad2:
(SEQ ID NO: 44)
5'-CATTTGGGGTTGCGATGACGACGAACACGCAT
TTTAGAGGTGAAGAATTGCATATGAATATCCTCCTTTAGTTCC-3'.

Figure 10:
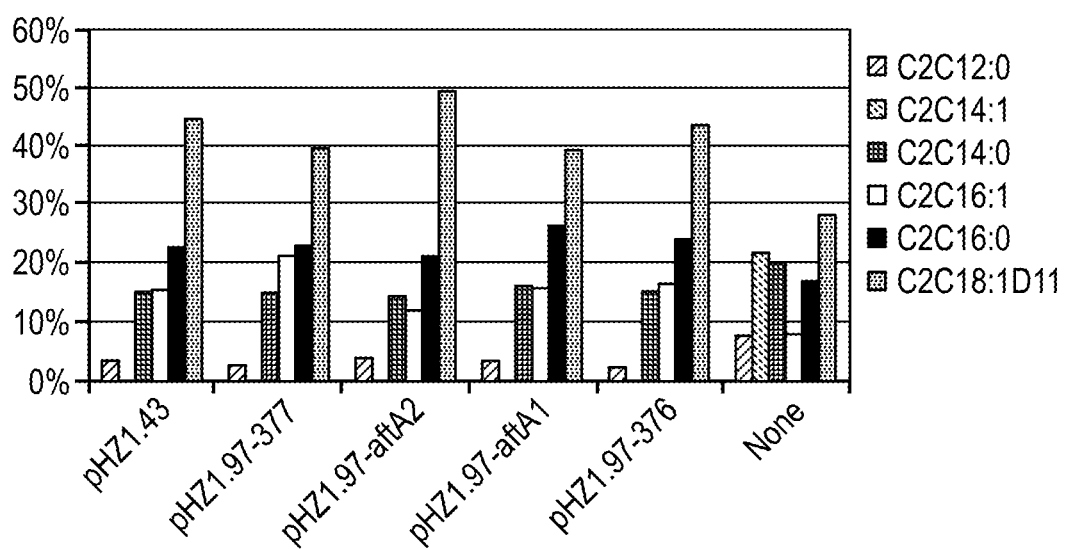
FIG. 10 (FIG. 10) is a graph depicting the production of ethyl esters by various ester synthases at 25° C. The ethyl esters were produced by recombinant *E. coli* strains carrying various ester synthase genes. The recombinant strains were (1) C41 (DE3, ΔfadEΔfabR)/pETDuet-1-'TesA+pCDF-Duet-1-fadD with 1 pHZ1.43; (2) pHZ1.97_377; (3) pHZ1.97_atfA2; (4) pHZ1.97_376; (5) pHZ1.97_atfA1; and (6) no plasmids (control).
Figure 11:
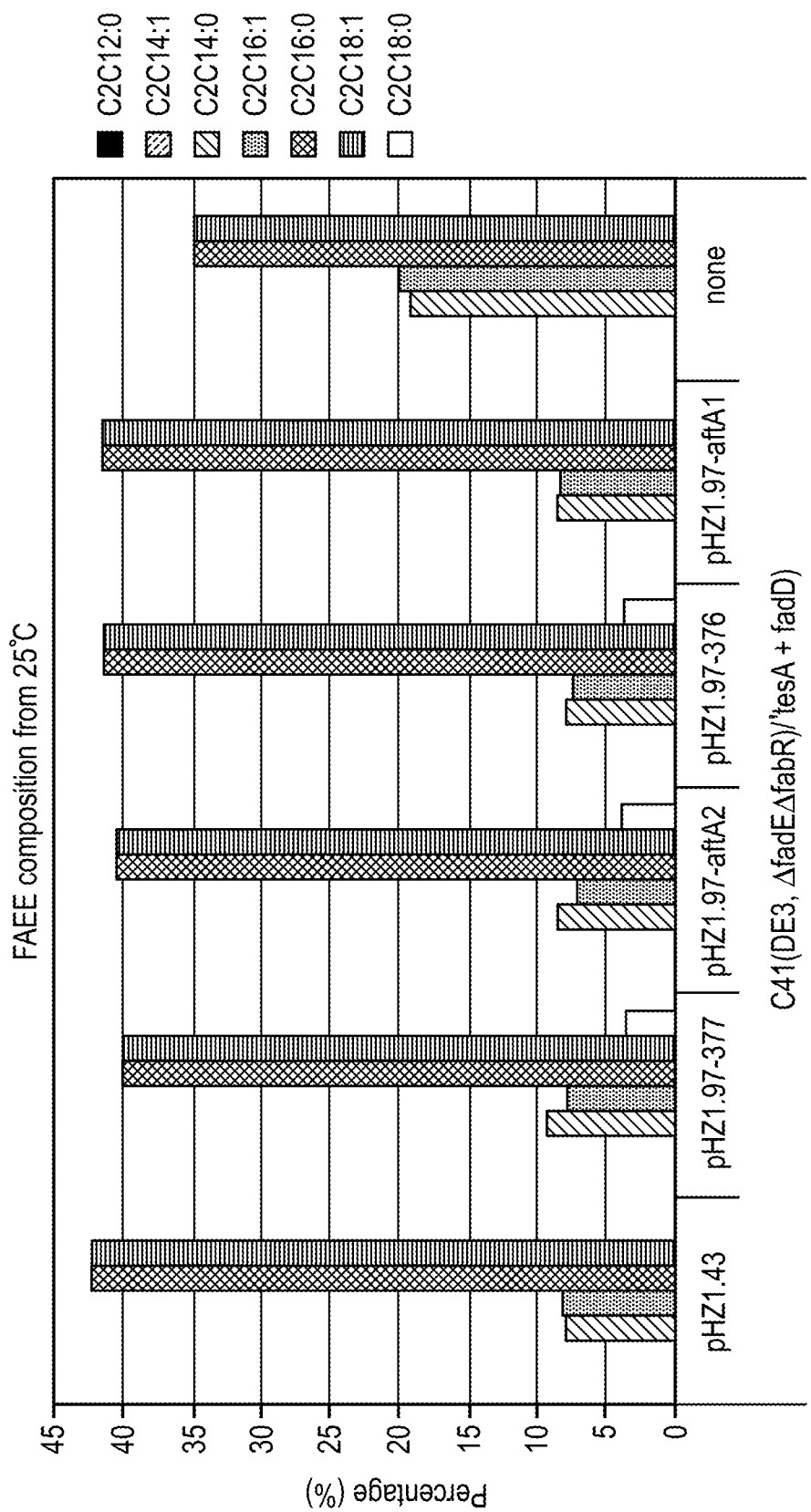
FIG. 11 (FIG. 11) is a graph depicting the acyl composition of fatty acid ethyl esters (FAEE) produced from various *E. coli* strains. The recombinant strains are (1) C41 (DE3, ΔfadEΔfabR)/pETDuet-1-'TesA+pCDFDuet-1-fadD with 1 pHZ1.43; (2) pHZ1.97_377; (3) pHZ1.97_atfA2; (4) pHZ1.97_376; (5) pHZ1.97_atfA1; and (6) no plasmids (control).

This PCR product was electroporated into *E. coli* MG1655 (pKD46). The cells were plated on L-chloramphenicol (30 μg/mL)(L-Cm) and cultured overnight at 37° C. Individual colonies were selected and plated onto another L-Cm plate and cultured at 42° C. These colonies were then patched to L-Cm and L-carbenicillin (100 mg/mL) (L-Cb) plates and cultured at 37° C. overnight. Colonies that were $Cm^R$ and $Cb^S$ were evaluated further by PCR to ensure the PCR product inserted at the correct site. PCR verification was performed on colony lysates of these bacteria using primers fadF: 5'-CGTCCGTGGTAATCATTTGG-3'(SEQ ID NO:45); and fadR: 5'-TCGCAACCTTTTCGTTGG-3'(SEQ ID NO:46). Expected size of the ΔfadD::Cm deletion was about 1200 bp (FIG. 10). The chloramphenicol resistance gene was eliminated using a FLP helper plasmid as described in Datsenko et al. Proc. Natl. Acad. Sci. USA. 97: 6640-6645, 2000. PCR verification of the deletion was performed with primers fadF and fadR. The MG1655 ΔfadD strain was unable to grow on M9+oleate agar plates (oleate as carbon source). It was also unable to grow in M9+oleate liquid media.

2. Expression of *Jeotgalicoccus* ATCC 8456 orf880 in *E. coli* MG1655 ΔfadD

The genomic DNA encoding ATCC 8456_orf880, which was codon-optimized for expression in *E. coli*, was cloned into vector OP80 (pCL1920 derivative) under the control of a $P_{trc}$ promoter, and *E. coli* MG1655 ΔfadD was transformed with the resulting vector. The *E. coli* cells were cultured at 37° C. in an M9 mineral medium supplemented with 20 μg/mL uracil and 100 μg/mL spectinomycin. Glucose (1%, w/v) was the only source of carbon and energy. When the culture reached an $OD_{600}$ of 0.8 to 1.0, IPTG (1 mM) was added and the temperature was shifted to 25° C. After growth for an additional 18 to 24 hours at 25° C., cells from 10 mL of culture were pelleted, resuspended in 1 mL methanol, sonicated for 30 minutes, and extracted with 4 mL hexane. After solvent evaporation, samples were resuspended in 0.1 mL hexane and analyzed by GC-MS. In contrast to the vector-only control, *E. coli* cells transformed with the orf880-bearing vector produced the α-olefins 1-pentadecene and heptadecadiene. This result indicates that expression of ORF880 confers the ability to biosynthesize α-olefins to *E. coli* when cultured on glucose, and that the direct precursors are the most abundant fatty acids in *E. coli*, namely hexadecanoic acid and vaccenic acid (11-cis-octadecenoic acid).

Example 28. Identification of Carboxylic Acid Reductase (CAR) Homologs

The carboxylic acid reductase (CAR) from *Nocardia* sp. strain NRRL 5646 can reduce carboxylic acids into corresponding aldehydes without separate activating enzymes, such as acyl-CoA synthases (Li et al., J. Bacteriol. 179:3482-3487, 1997; He et al., Appl. Environ. Microbiol. 70:1874-1881, 2004)). A BLAST search using the NRRL 5646 CAR amino acid sequence (Genpept Accession No. AAR91681) as the query sequence identified about 20 homologous sequences. Three homologs, listed in Table 21, were evaluated for their ability to convert fatty acids into fatty aldehydes in vivo when expressed in E. coli. At the nucleotide sequence level, carA, carB, and fadD9 (demonstrated 62.6%, 49.4%, and 60.5% homology, respectively, to the car gene (AY495697) of Nocardia sp. NRRL 5646. At the amino acid level, CARA, CARB, and FadD9 demonstrated 62.4%, 59.1% and 60.7% identity, respectively, to CAR of Nocardia sp. NRRL 5646.

TABLE 21

CAR-like Protein and the corresponding coding sequences.

| Genpept Accession | Locus_tag | Annotation in GenBank | Gene name |
|---|---|---|---|
| NP_217106 | Rv 2590 | Probable fatty-acid-CoA ligase (FadD9) | fadD9 |
| ABK75684 | MSMEG 2956 | NAD dependent epimerase/dehydratase family protein | carA |
| YP_889972.1 | MSMEG 5739 | NAD dependent epimerase/dehydratase family protein | carB |

Example 29. Expression of Car Homologs in E. coli

1. Plasmid Construction

Three E. coli expression plasmids were constructed to express the genes encoding the CAR homologs listed in Table 22, below. First, fadD9 was amplified from genomic DNA of Mycobacterium tuberculosis H37Rv (obtained from The University of British Columbia, and Vancouver, BC Canada) using the primers fadD9F and FadDR (see Table 22). The PCR product was first cloned into PCR-blunt (Invitrogen) and then released as an NdeI-AvrII fragment. The NdeI-AvrII fragment was then cloned between the NdeI and AvrII sites of pACYCDuet-1 (Novogen) to generate pACYCDuet-1-fadD9.

The carA and carB genes were amplified from the genomic DNA of Mycobacterium smegmatis MC2 155 (obtained from the ATCC (ATCC 23037D-5)) using primers CARMCaF and CARMCaR or CARMCbF and CARMCbR, respectively (see, Table 22). Each PCR product was first cloned into PCR-blunt and then released as an NdeI-AvrII fragment. Each of the two fragments was then subcloned between the NdeI and AvrII sites of pACYCDuet-1 (Novogen) to generate pACYCDUET-carA and pACYCDUET-carB.

TABLE 22

Primers used to amplify genes encoding CAR homologs

| | |
|---|---|
| fadD9F | CAT ATGTCGATCAACGATCAGCGACTGAC (SEQ ID NO: 47) |
| fadD9R | CCTAGG TCACAGCAGCCCGAGCAGTC (SEQ ID NO: 48) |
| CARMCaF | CAT ATGACGATCGAAACGCG (SEQ ID NO: 49) |
| CARMCaR | CCTAGG TTACAGCAATCCGAGCATCT (SEQ ID NO: 50) |
| CARMCbF | CAT ATGACCAGCGATGTTCAC (SEQ ID NO: 51) |
| CARMCbR | CCTAGG TCAGATCAGACCGAACTCACG (SEQ ID NO: 52) |

2. Evaluation of Fatty Aldehyde Production

Plasmids encoding the CAR homologs (pACYCDUET-fadD9, pACYCDUET-carA, and pACYCDUET-carB) were separately co-transformed into the E. coli strain C41 (DE3, ΔfadE) (described in PCT/US08/058788) together with pET-Duet-1-'TesA (described in PCT/US08/058788, the disclosures of which is incorporated by reference herein).

The E. coli transformants were cultured in 3 mL of an LB medium supplemented with carbenicillin (100 mg/L) and chloramphenicol (34 mg/L) at 37° C. After overnight growth, 15 µl of culture was transferred into 2 mL of a fresh LB medium supplemented with carbenicillin and chloramphenicol. After 3.5 hours of growth, 2 mL of culture were transferred into a 125 mL flask containing 20 mL of an M9 medium with 2% glucose and with carbenicillin and chloramphenicol. When the $OD_{600}$ of the culture reached 0.9, 1 mM of IPTG was added to each flask. After 20 hours of growth at 37° C., 20 mL of ethyl acetate (with 1% of acetic acid, v/v) was added to each flask to extract the organic compounds produced during the fermentation. The crude ethyl acetate extract was directly analyzed with GC/MS as described below. The co-expression of the leaderless 'TesA and any of the three car genes in E. coli resulted in detectable fatty aldehyde production. In one fermentation, LS9001/pACYCDUET carB+pETDuet-1-'TesA produced an average of 120 mg/L of fatty aldehydes. The retention times were 6.959 minutes for dodecanal, 8.247 minutes for 7-tetradecenal, 8.37 minutes for tetradecanal, 9.433 minutes for 9-hexadecenal, 9.545 minutes for hexadecanal, and 10.945 minutes for 11-octadecenal. The presence of large amounts of fatty aldehydes is consistent with CAR being an aldehyde-generating, fatty acid reductase (AFAR). This mechanism is different from the alcohol-generating fatty acyl-CoA reductases (FAR), for example, JjFAR, and fatty acyl-CoA reductases, such as Acr1.

3. Substrate Preferences of the CAR Homologs

Distinct substrate preferences were observed among the three CAR homologs evaluated. FadD9 exhibited a strong preference for $C_{12}$ fatty acids relative to other fatty acids with carbon chain lengths greater than 12. Both CarA and CarB demonstrated wider substrate ranges than FadD9.

4. Quantification and Identification of Fatty Aldehydes

A GC-MS experiment was performed using an Agilent 5975B MSD system equipped with a 30 m×0.25 mm (0.10 µm film) DB-5 column. The column temperature was 3-minute isothermal at 100° C. The column was programmed to rise from 100° C. to 320° C. at a rate of 20° C./min. When the final temperature was reached, the column remained isothermal for 5 minutes at 320° C. The injection volume was 1 µL. The carrier gas, helium, was released at 1.3 mL/min. The mass spectrometer was equipped with an electron impact ionization source. The ionization source temperature was set at 300° C.

Prior to quantification, various aldehydes were identified using two methods. First, the GC retention time of each compound was compared to the retention time of a known standard, such as laurylaldehyde (dodecanal). Second, identification of each compound was confirmed by matching the compound's mass spectrum to a standard's mass spectrum in the mass spectra library.

Example 30. Production of Fatty Alcohol by Heterologous Expression of Car Homologs in *E. coli* Mg1655 (De3, ΔfadD)

1. Construction of fadD Deletion Strain

The fadD gene of *E. coli* MG1655 was deleted using the lambda red system (Datsenko et al., PNAS (USA). 97: 6640-6645, 2000) as follows: The chloramphenicol acetyltransferase gene from pKD3 was amplified with primers fad1: 5'-TAACCGGCGTCTGACGACTGACTTAACGC-TCAGGCTTTATTGTCCACTTTGTGTAGGCTG GAGCTGCTTCG-3'(SEQ ID NO:43); and fad2: 5'-CAT-TTGGGGTTGCGATGACGACGAACACGCATTT-TAGAGGTGAAGAATTGCATATGAAT ATCCTCCTT-TAGTTCC-3'(SEQ ID NO:44). This PCR product was electroporated into *E. coli* MG1655 (pKD46). The cells were plated on L-chloramphenicol (30 μg/mL) (L-Cm) and cultured overnight at 37° C. Individual colonies were selected and plated onto another L-Cm plate and cultured at 42° C. These colonies were then patched to L-Cm and L-carbenicillin (100 mg/mL) (L-Cb) plates and cultured at 37° C. overnight. Colonies that were $Cm^R$ and $Cb^S$ were evaluated further by PCR to ensure the PCR product inserted at the correct site. PCR verification was performed on colony lysates of these bacteria using primers fadF: 5'-CGTCCGTGGTAATCATTTGG-3'(SEQ ID NO:45); and fadR: 5'-TCGCAACCTTTTCGTTGG-3'(SEQ ID NO:46). Expected size of the ΔfadD::Cm deletion was about 1200 bp. The chloramphenicol resistance gene was eliminated using a FLP helper plasmid as described in Datsenko et al., Proc. Natl. Acad. Sci. USA, 97:6640-6645, 2000. PCR verification of the deletion was performed using primers fadF and fadR. The MG1655 ΔfadD strain was unable to grow on M9+oleate agar plates (using oleate as carbon source). It was also unable to grow in M9+oleate liquid media. The growth defect was complemented by an *E. coli* fadD gene supplied in trans (in pCL1920-Ptrc).

2. Construction of MG1655(DE3, ΔfadD) Strain

To generate a T7-responsive strain, the λDE3 Lysogenization Kit (Novagen) was utilized, which is designed for site-specific integration of λDE3 prophage into an *E. coli* host chromosome, such that the lysogenized host can be used to express target genes cloned in T7 expression vectors. λDE3 is a recombinant phage carrying the cloned gene for T7 RNA polymerase under lacUV5 control. Briefly, the host strain was cultured in an LB medium supplemented with 0.2% maltose, 10 mM $MgSO_4$, and antibiotics at 37° C., to an $OD_{600}$ of 0.5. Next, $10^8$ pfu λDE3, $10^8$ pfu Helper Phage, and $10^8$ pfu Selection Phage were incubated with 10 μl host cells. The host/phage mixture was incubated at 37° C. for 20 minutes to allow the phage to be adsorbed into the host. Finally, the mixture was pipetted onto an LB plate supplemented with antibiotics. The mixture was spread evenly using plating beads, and the plates were inverted plates and incubated at 37° C. overnight.

λDE3 lysogen candidates were evaluated for their ability to support the growth of the T7 Tester Phage. T7 Tester Phage is a T7 phage deletion mutant that is completely defective unless active T7 RNA polymerase is provided by the host cell. The T7 Tester Phage makes very large plaques on authentic λDE3 lysogens in the presence of IPTG, while much smaller plaques are observed in the absence of inducer. The relative size of the plaques in the absence of IPTG is an indication of the basal level expression of T7 RNA polymerase in the lysogen, and can vary widely between different host cell backgrounds.

The following procedure was used to determine the presence of DE3 lysogeny. First, candidate colonies were cultured in LB media supplemented with 0.2% maltose, 10 mM $MgSO_4$, and antibiotics at 37° C., to an $OD_{600}$ of 0.5. An aliquot of T7 Tester Phage was then diluted in 1× Phage Dilution Buffer to a titer of $2\times10^3$ pfu/mL. In duplicate tubes, 100 μl host cells were mixed with 100 μL diluted phage. The host/phage mixture was incubated at room temperature for 10 minutes to allow the phage to be adsorb into the host. Next, 3 mL of molten top agarose was added to each tube containing host and phage. The contents of one duplicate were plated onto an LB plate and the other duplicate onto an LB plate supplemented with 0.4 mM IPTG (isopropyl-b-thiogalactopyranoside) to evaluate induction of T7 RNA polymerase. Plates were allowed to sit undisturbed for 5 minutes until the top agarose hardened. The plates were then inverted at 30° C. overnight.

3. Construction of MG1655(DE3, ΔfadD, yjgB::Kan) Strain

The yjgB knockout strain, MG1655(DE3, ΔfadD, yjgB::kan), was constructed using the following the protocol of the lambda red system (Datsenko et al., Proc. Natl. Acad. Sci. USA 97:6640-6645, 2000):

The kanamycin resistant gene from pKD13 was amplified with primers yjgBRn: 5'-GCGCCTCAGATCAGCGCTG-CGAATGATTTTCAAAAATCGGCTTTCAACACTG-TAGGCTG GAGCTGCTTCG-3'SEQ ID NO:53); and yjgBFn: 5'-CTGCCATGCTCTACACTTCCCAAACAAC-ACCAGAGAAGGACCAAAAAATGATTCCGGGG ATCCGTCGACC-3'(SEQ ID NO:54). The PCR product was then electroporated into *E. coli* MG1655 (DE3, ΔfadD)/pKD46. The cells were plated on kanamycin (50 μg/mL) (L-Kan) and cultured overnight at 37° C. Individual colonies were selected and plated onto another L-Kan plate and cultured at 42° C. These colonies were then patched to L-Kan and carbenicillin (100 mg/mL) (L-Cb) plates and cultured at 37° C. overnight. Colonies that were $kan^R$ and $Cb^S$ were evaluated further by PCR to ensure the PCR product was inserted at the correct site. PCR verification was performed on colony lysates of these bacteria using primers BF: 5'-GTGCTGGCGATACGACAAAACA-3'(SEQ ID NO:55); and BR: 5'-CCCCGCCCTGCCATGCTCTACAC-3'(SEQ ID NO:56). The expected size of the yjgB::kan knockout was about 1450 bp.

4. Evaluation of FadD on Fatty Alcohol Production Using MG1655 (DE3, ΔfadD) Strain In Example 2, a fadE deletion strain was used for fatty aldehyde and fatty alcohol production from 'TesA, CAR homologs, and endogenous alcohol dehydrogenase(s) in *E. coli*. To demonstrate that CAR homologs used fatty acids instead of acyl-CoA as a substrate, the gene encoding for acyl-CoA synthase in *E. coli* (fadD) was deleted so that the fatty acids produced were not activated with CoA. *E. coli* strain MG1655 (DE3, ΔfadD) was transformed with pET-Duet-1-'TesA and pACYCDuet-1-carB. The transformants were evaluated for fatty alcohol production using the methods described herein. These transformants produced about 360 mg/L of fatty alcohols (dodecanol, dodecenol, tetredecanol, tetredecenol, cetyl, hexadecenol, and octadecenol).

YjgB is an alcohol dehydrogenase. To confirm that YjgB was an alcohol dehydrogenase responsible for converting fatty aldehydes into their corresponding fatty alcohols, pET-Duet-1-'TesA and pACYCDuet-1-fadD9 were co-transformed into either MG1655(DE3, ΔfadD) or MG1655(DE3, ΔfadD, yjgB::kan). At the same time, MG1655(DE3, ΔfadD, yjgB::kan) was transformed with both pETDuet-1-'tesA-yjgB and pACYCDuet-1-fadD9.

The E. coli transformants were cultured in 3 mL of an LB medium supplemented with carbenicillin (100 mg/L) and chloramphenicol (34 mg/L) at 37° C. After overnight growth, 15 µL of culture was transferred into 2 mL of a fresh LB medium supplemented with carbenicillin and chloramphenicol. After 3.5 hrs of growth, 2 mL of culture was transferred into a 125 mL flask containing 20 mL of an M9 medium containing 2% glucose, carbenicillin, and chloramphenicol. When the $OD_{600}$ of the culture reached 0.9, 1 mM of IPTG was added to each flask. After 20 hours of growth at 37° C., 20 mL of ethyl acetate (with 1% of acetic acid, v/v) was added to each flask to extract the fatty alcohols produced during the fermentation. The crude ethyl acetate extract was directly analyzed using GC/MS as described herein.

The yjgB knockout strain resulted in significant accumulation of dodecanal and a lower fatty alcohol titer. The expression of yjgB from plasmid pETDuet-1-'tesA-yjgB in the yjgB knockout strain effectively removed the accumulation of dodecanal. The data indicated that YjgB was involved in converting dodecanal into dodecanol and that there may be other alcohol dehydrogenase(s) present in E. coli to convert other aldehydes into alcohols. Dodecanal accumulated in the yjgB knockout strain, but it was not observed in either the wild-type strain (MG1655(DE3, ΔfadD)) or the yjgB knockout strain with the yjgB expression plasmid.

Example 31. Generation of 'TesA Library

In this Example, methods are described for preparing a mutant library of 'TesA. A suitable expression vector such as pACYC-'TesA that encodes 'TesA, the truncated TesA lacking a signal peptide, enables production of the 'TesA protein in the host strain. The plasmid pACYC-'TesA includes the 'tesA sequence under the regulation of a trc promoter, a transcription terminator, a p15a origin of replication, an open reading frame encoding lacIq, and the beta-lactamase antibiotic resistance gene.

The 'TesA protein amino acid sequence is provided in FIG. 58 (SEQ ID NO:31).

The QuikChange Mutagenesis kit (Stratagene) enables the facile construction of large numbers of mutants. Use of this kit to construct each 'TesA mutant starts with two complementary primers containing one or more mismatched bases required to change the encoded amino acid at the desired position. The primers are 25-45 nucleotides in length, with melting temperature >78° C. as calculated using the formula:

$T_m = 81.5 + 0.41(\% \; GC) 675/N$ where $T_m$ is the melting temperature, % GC is the percent of residues in the primer that are guanosine or cytidine, and N is the number of nucleotides in the primer. For example, the primers:

```
                                                (SEQ ID NO: 57)
CACGTTATTGATTCTGGGTAATAGCCTGAGCGCCGGGTATCG
and
                                                (SEQ ID NO: 58)
CGATACCCGGCGCTCAGGCTATTACCCAGAATCAATAACGTG
``` were used to mutate the aspartic acid at residue 9 to asparagine, where the underlined bases indicate the codon that was changed.

The primers were used in a polymerase chain reaction with pACYC-'TesA as a template, using the following temperature cycling program: 1 minute at 95° C.; followed by 18 cycles of 50 seconds at 95° C., 50 seconds at 60° C., and 5 minutes at 68° C.; and 7 minutes at 68° C. The reaction products were then digested using the restriction enzyme DpnI, to selectively degrade the methylated template DNA. The remaining DNA was then transformed into E. coli for isolation of plasmid clones, which were then sequenced to verify that the desired substitutions have been obtained.

Example 32. Assays

In the following Examples, assays for determining protein content, free fatty acid levels, and hydrolysis of acyl-PNP and acyl-CoA substrates are described. Specific assays used herein are also set forth below.

1. Assay for Determination of Protein Content in Cell Lysates

Cell lysates of E. coli expression cultures producing 'TesA variants were prepared for characterization. To generate the expression cultures, seed cultures were grown overnight at 37° C. in an LB medium containing 1% (w/v) glucose and 100 µg/mL carbenicillin. The seed cultures were then diluted 1:100 into the same medium and grown for 3 hours at 37° C. with shaking (200 rpm). A 40 µL aliquot of each culture was then added to 360 µL of LS9-1 medium (described below) supplemented with 100 µg/mL carbenicillin and grown in a 96-well culture plate. After 3 additional hours of growth, isopropyl β-D-1-thiogalactopyranoside (IPTG, at 1 mM final concentration) and Bis-Tris Propane (pH 7.0, at 0.1 M final concentration) were added, and the cultures were allowed to grow overnight.

Cell pellets were harvested by centrifugation of the expression cultures (10 minutes at 3,500 rpm). The growth medium is discarded and the cell pellets stored at −80° C. To prepare soluble extracts, the frozen cell pellets are lysed in 50% BugBuster (EMD Biosciences, Cat. No. 70584-4) in 25 mM sodium phosphate, pH 7.0. Following 40 minutes of agitation, the cell lysates are clarified by centrifugation (10 minutes at 3,500 rpm). The concentration of protein in the supernatant of the cell lysate is then measured using the bicinchoninic acid (BCA) assay, according to the protocol provided by manufacturer (Thermo Scientific, Cat. No. 23225). The supernatant is then used in the assays described below.

Medium:

| 5x Salt Solution | | 1X final concentration |
|---|---|---|
| $Na_2HPO_4$ | 30 g | 6 g/L |
| $KH_2PO_4$ | 15 g | 3 g/L |
| NaCl | 2.5 g | 0.5 g/L |
| $NH_4Cl$ | 5 g | 1 g/L |
| $dH_2O$ | to 1 L | |

-continued

| stock solutions: | final concentration: |
|---|---|
| 10 mg/mL Thiamine (Vitamin B1) | 1 mg/L |
| 1M MgSO$_4$ | 1 mM |
| 1M CaCl$_2$ | 0.1 mM |
| 20% glucose | 2.00% |
| sterile water | |
| 20 mg/mL uracil | 20 µg/mL high pH |
| trace minerals 1000x | 1x |
| For 1 L L59-1 media with 1.0 % glucose: | |
| 200 mL 5x Salt Solution | |
| 100 µL Thiamine (B1) | |
| 1 ml MgSO$_4$ | |
| 100 µL CaCl$_2$ | |
| 50 mL 20% Glucose | |
| 1 mL trace minerals | |
| 1 mL Uracil | |
| Water to 1 L (premake it 750 mL) | |
| TM solution (filter sterilized): | |
| 27 g/L FeCl$_3$-6 H$_2$O | |
| 2 g/L ZnCl$_2$-4H$_2$O | |
| 2 g/L CaCl$_2$-6H$_2$O | |
| 2 g/L Na$_2$MoO$_4$-2H$_2$O | |
| 1.9 g/L CuSO$_4$-5H$_2$O | |
| 0.5 g/L H$_3$BO$_3$ | |
| 100 mL/L concentrated HCl | |
| q.s. w/Milli-Q water | |

2. Free Fatty Acid Analysis

'TesA variants are produced in *E. coli* expression cultures, and the free fatty acids produced by the cultures were analyzed. To generate the expression cultures, seed cultures were first grown overnight at 37° C. in an LB medium containing 1% (w/v) glucose and 100 µg/mL carbenicillin, and then diluted 1:100 into the same medium and grown for 3 hours at 37° C. with shaking (200 rpm). 40 µL of each culture was then added to 360 µL of LS9-1 medium supplemented with 100 µg/mL carbenicillin, and grown in a 96-well culture plate. After 3 additional hours of growth, isopropyl β-D-1-thiogalactopyranoside (IPTG, at 1 mM final concentration) and Bis-Tris Propane (pH 7.0, at 0.1 M final concentration) were added, and the cultures were allowed to grow overnight.

The cultures were then acidified with 1 N HCl to a final pH of about 2.5 and then extracted with 600 µL ethyl acetate. Free fatty acids in the organic phase were derivatized with tetramethylammonium hydroxide (TMAH) to generate the respective methyl esters, which were then analyzed on a gas chromatograph equipped with a flame ionization detector.

3. Fatty Acyl-PNP Hydrolysis Assay

In this assay system, the reagent solutions used were:
1. 2% Triton X-100 in 50 mM sodium phosphate, pH 7.0
2. 10 mM acyl-para-nitrophenol (acyl-PNP) in acetone To prepare an acyl-PNP working solution, 600 µL acyl-PNP stock was added to 9.4 mL phosphate buffer and mixed well.

The assay was performed by adding 40 µL of the acyl-PNP working solution to each well of a 96-well plate, followed by the rapid addition of 40 µL of clarified cell lysate. The solutions were mixed for 15 seconds, and the absorbance change was read at 405 nm in a microtiter plate reader at 25° C. The esterase activity was expressed as the ratio of $(\Delta A405/sec)_{mut}/(\Delta A405/sec)_{wt}$, wherein $(\Delta A405/sec)_{mut}$ was the change in absorbance at 405 nm per second in samples containing mutant 'TesA, and $(\Delta A405/sec)_{wt}$ was the change in absorbance at 405 nm per second in samples containing wildtype 'TesA.

4. Acyl-CoA Hydrolysis Assay

In this assay system, the reagent solutions used were:
10 mM acyl-coenzyme A (acyl-CoA) in 50 mM sodium phosphate, pH 7.0
50 mM sodium phosphate, pH 8.0, 50 mM monobromobimane (MBB) (Novagen, Cat. No. 596105) in acetonitrile. To prepare acyl-CoA working solution, 0.5 mL acyl-CoA stock and 0.5 mL MBB stock were added to 29 mL phosphate buffer followed by mixing.

The assay was performed by adding 60 µL of the acyl-CoA working solution to each well of a black 96-well plate, followed by the rapid addition of 40 µL of clarified cell lysate. After mixing for 15 seconds, the progress of the reaction was monitored by fluorescence ($\lambda_{ex}$=380 nm, $\lambda_{em}$=480 nm) in a microtiter plate reader at 25° C. The acyl-CoA thioesterase activity was expressed as the ratio of $(\Delta RFU/sec)_{mut}/(\Delta RFU/sec)_{wt}$, where $(\Delta RFU/sec)_{mut}$ was the change in relative fluorescence units per second in samples containing mutant 'TesA, and $(\Delta RFU/sec)_{wt}$ was the change in relative fluorescence units per second in samples containing wildtype 'TesA.

5. Applying the Z Score Methodology

A Z-score determination was conducted following the Z score methodology as follows.

The Z score for a sample is defined as the number of standard deviations the sample signal differs from the control population signal mean. The Z score has been used to rank the mutants according to properties of interest such as, for example, substrate chain length specificity, relative preference for ester over thioester bonds, relative preference for thioester bonds over ester bonds, and the proportion or percentage of ester produced. The Z score is measured using the following calculation:

$Z$=(sample value−control average)/Standard deviation of controls

The positive control used to generate the mutant 'TseA library herein was wild type 'TesA.

In a normal distribution, about 2.1% of the data will comprise 2 or more standard deviations above the mean, and about 0.1% of the data will comprise 3 or more standard deviations above the mean. Therefore Z scores of 2 or greater, 3 or greater, −2 or less, −3 or less and so forth are used to define more and more stringent classes of data that are unlikely to occur by random chance.

Those variants that have a Z score greater than 3 were marked as having an improved performance in terms of preference for substrates of certain chain lengths and/or catalytic rate. Also, those variants that have a Z score greater than 3 were marked, under other circumstances, as providing an improved or enhanced proportional or percentage yield for fatty esters vs. free fatty acids. Additionally, those variants that have a Z score of −3 or less were marked, in yet other circumstances, as providing a reduced proportional or percentage yield for fatty esters vs. free fatty acids.

Substrate specificity numbers are defined as the kinetic slope of a given mutant for one substrate, divided by the total of the kinetic slopes for the three substrates studied in the PNP assay ($C_{10}$, $C_{12}$, $C_{14}$), where the kinetic slope is the observed initial rate for the hydrolysis of a given ester substrate.

For example, to calculate a substrate specificity number for $C_{10}$:

$C_{10}$ SubsSpec=Mutant Slope $C_{10}$/(Mutant Slope $C_{10}$+$C_{12}$+$C_{14}$)

Next a substrate specificity Z score was calculated. The Average and Standard Deviations of the substrate specificity numbers for the positive controls were first calculated (for each plate), and the following formula was applied:

Mutant $C_{10}$ SubSpec Z score=(Mutant SubSpec $C_{10}$-AvgSubSpec)/SDSubSpec

As another example, to calculate an ester specificity number:

EsterSpec=Mutant Slope $C_{14}$-PNP/Mutant Slope $C_{14}$-CoA

Next an ester specificity Z score was calculated. The Average and Standard Deviations of the ester specificity numbers for the positive controls were first calculated (for each plate), and the following formula was applied:

Mutant Ester Specificity Z score=(Mutant EsterSpec–AvgEsterSpec)/SDEsterSpec Those variants which have an Ester Specificity Z score greater than 3 were defined and marked as having a preference for ester over thioester, and/or as having improved activity (i.e., catalytic rate) with regard to ester over thioester. Those variants which have an Ester Specificity Z score less than –3 were marked as having a preference for thioester over ester.

Example 33. Free Fatty Acid Analysis of 'TesA Variants

In this Example, assay results identifying various properties of 'TesA variants are provided. The analysis was conducted using the methods described above in Example 32. In the tables of FIGS. 45 and 46, the mutations are presented using "Variant Codes," each of which provides the wildtype amino acid, followed by the position in the amino acid sequence, followed by the replacement amino acid (e.g., "S10A" indicates that the serine at position 10 in the amino acid sequence has been replaced by alanine in this particular variant).

Example 34. Analysis of 'TesA Variants

Assay results for 'TesA variants are provided in FIGS. 45 and 46. The analysis was conducted using the methods described above in Example 32. As shown in FIG. 45, activity levels on $C_{10}$, $C_{12}$ and $C_{14}$ substrates and substrate specificities were analyzed.

FIG. 45 depicts performance indices of certain 'TesA variants of the mutant 'TesA library, which demonstrated improved performance compared to the wildtype enzyme. FIG. 45A-B depict performance indices of 'TesA mutants in terms of specificity for substrates of certain chain lengths.

FIG. 46A depicts 'TesA mutants that provided increased or enhanced proportional or percentage yield of fatty esters vs. free fatty acids. FIG. 46B depicts 'TesA mutants that provided reduced proportional or percentage yield of fatty esters vs. free fatty acids. Only mutants that had Z scores above 3 are illustrated in the table and other mutants having lesser activity are not included. Notwithstanding the presentation of data, it is submitted that a lower Z score may identify valuable mutants and the Z score cut-off of 3 provided in FIG. 45 is not intended to limit the scope of the invention.

Figure 57A:
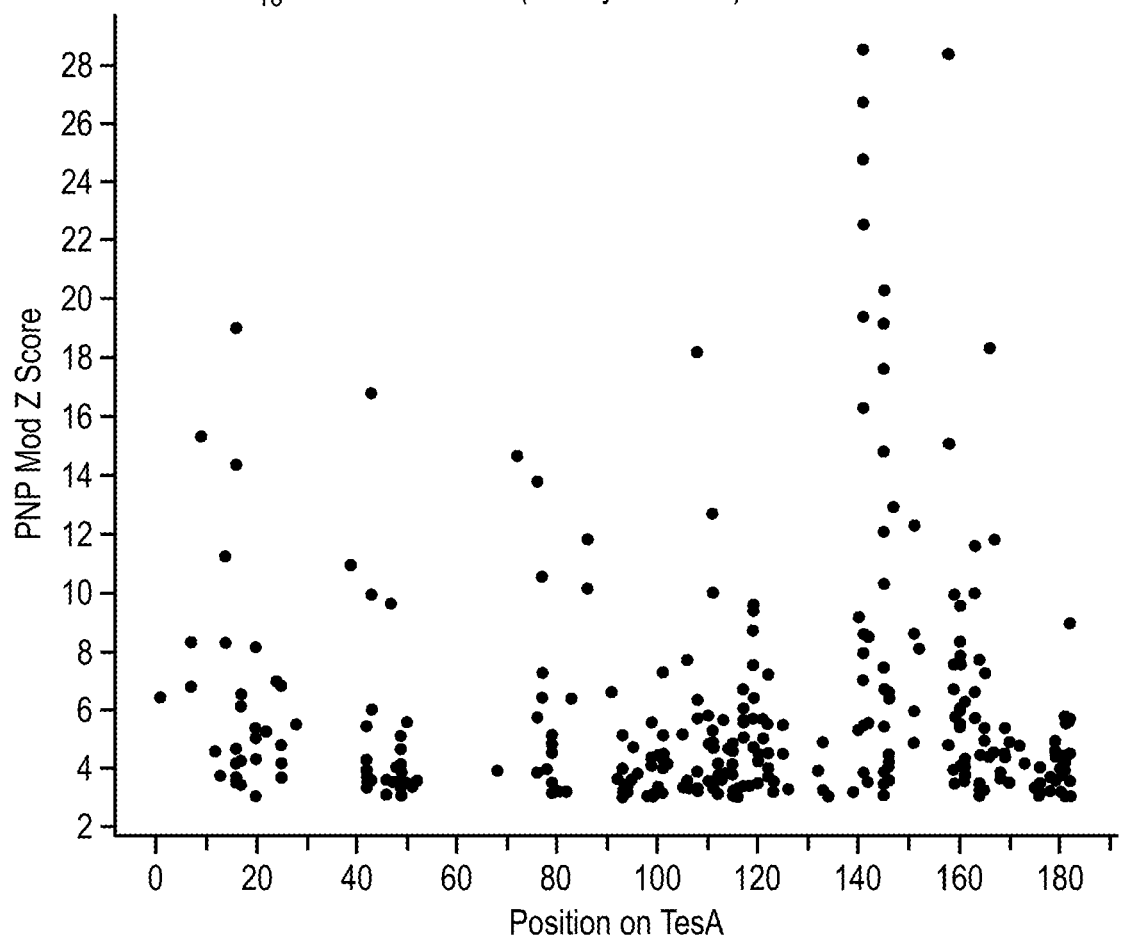
Figure 57B:
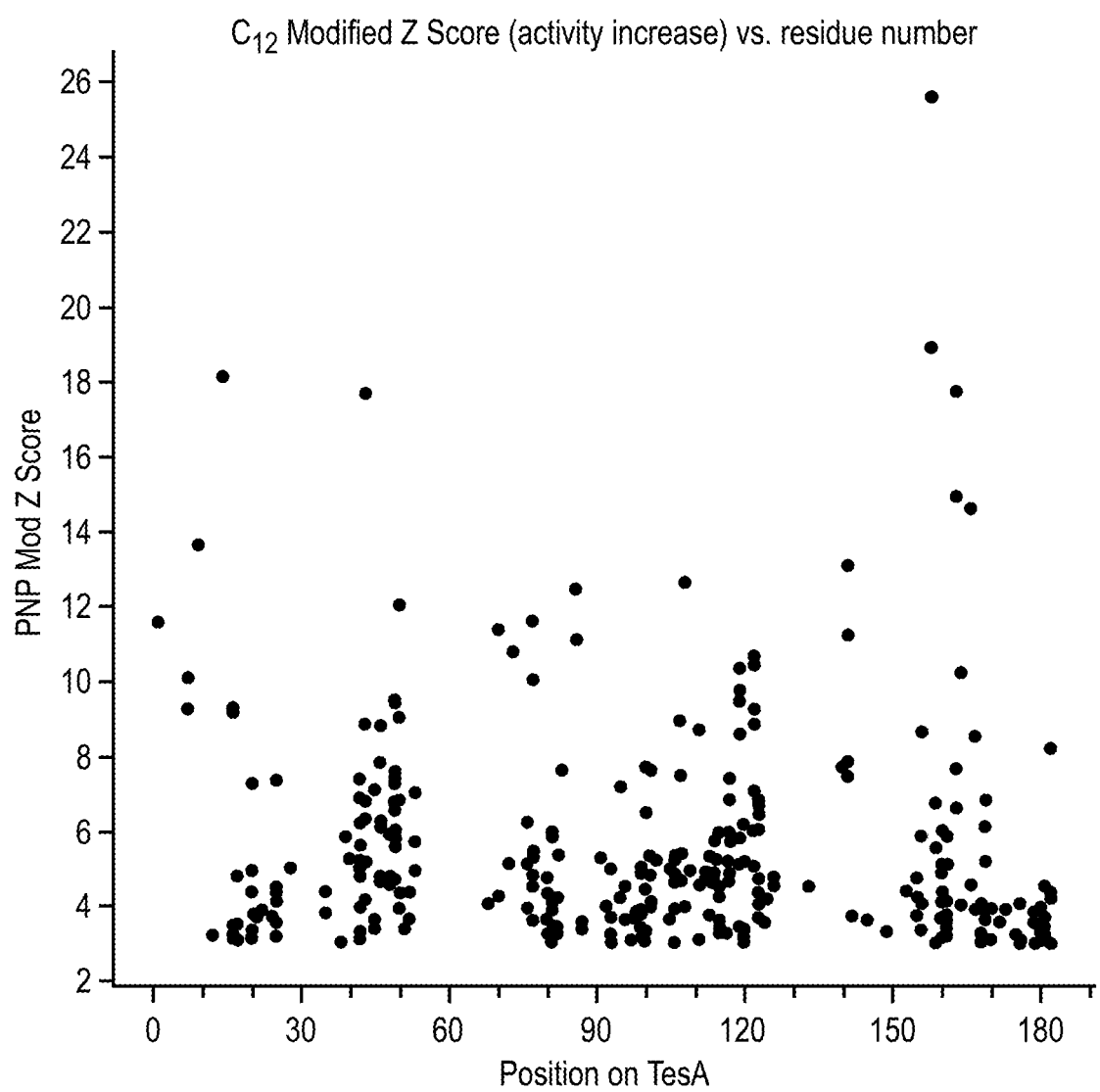
Figure 57E:
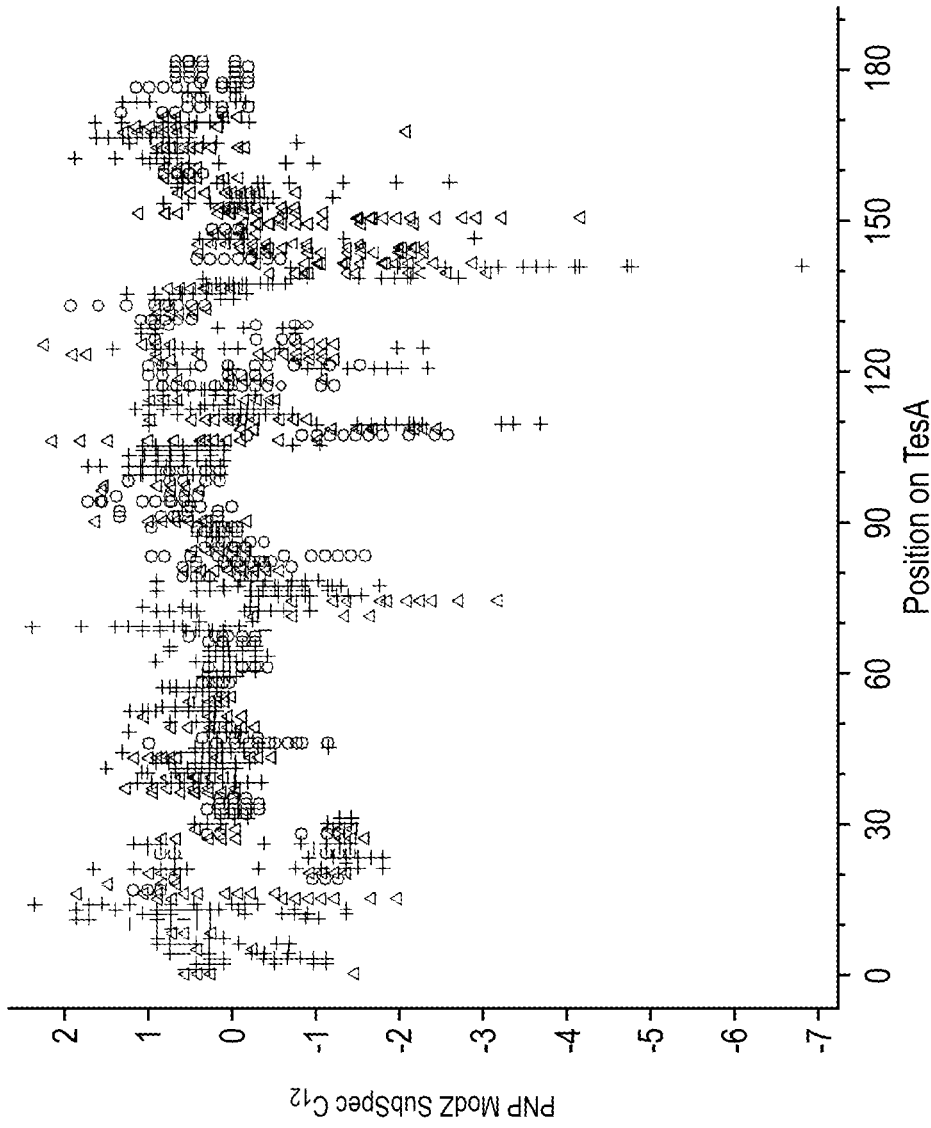

The results are represented graphically along the entire length of the 'TesA molecule in FIGS. 57A-C.

1. Fatty Acid Production Activity for 'TesA Variants

Assay results for fatty acid production activity in 'TesA variants are conducted using the methods described above in Example 32.

2. Fatty Acyl-PNP Assay of 'TesA Variants

Assay results for fatty acyl-PNP activity of 'TesA variants are provided in FIG. 45. The analysis was conducted using the methods described above in Example 32.

3. Acyl-CoA Analysis of 'TesA Variants

Assay results for acyl-CoA activity of 'TesA variants are provided in FIG. 45. The analysis was conducted using the methods described above in Example 32.

4. Preference for Thioester (Acyl-CoA) over Ester (Acyl-PNP)

Assay results for acyl-CoA activity and acyl-PNP activity of 'TesA variants are conducted using the methods described above in Example 32.

5. Preference for Ester (Acyl-CoA) over Thioester (Acyl-CoA)

Assay results for acyl-CoA activity and acyl-PNP activity of 'TesA variants are conducted using the methods described above in Example 32.

Example 35. Direct Production of Fatty Esters in the Absence of Ester Synthase

In this example, the ability of 'TesA to catalyze the transesterification of a fatty acyl-CoA into the corresponding fatty ester in the presence of an alcohol in vitro is demonstrated. *E. coli* 'TesA enzyme was recombinantly expressed and purified to homogeneity as an N-terminal 6×His-tagged protein. In particular, the 'TesA gene encoding thioesterase I enzyme from *E. coli* (SEQ ID NO:31 of FIG. 58) was inserted into a pET15-b vector (Novagen), which vector carried an N-terminal 6×His-tag, and transformed into BL21-DE3 cells for expression. Cells were cultured in LB media at 37° C., 200 rpm, until $OD_{600}$ reached 1.0, induced with 0.5 mM IPTG (final), and then allowed to grow at 28° C. for an additional 5 hours. After harvesting at 6,000 rpm, the pellet was resuspended in 40 mL of 100 mM Tris-HCl, pH 7.4, sonicated and centrifuged at 10,000 rpm for 20 minutes. Clarified lysate was then applied to a His-bind column (Calbiochem) and the protein was purified as per the manufacturer's instruction. Eluted protein was then dialyzed into a buffer containing 25 mM sodium phosphate, pH 7.2, and 10% glycerol for storage and use. Thioesterase activity of the purified 'TesA enzyme was determined.

Catalysis of fatty acyl-CoA to fatty ester by 'TesA involves a nucleophilic attack by an alcohol on the carbonyl center subsequent to the exit of the coenzyme A moiety from the active site. The rate of spontaneous transesterification of palmitic acid by ethanol in the absence of 'TesA was analyzed to prove that ethanol can replace water as the nucleophile to form fatty esters instead of fatty acids.

Accordingly, a 4 mM (about 1 mg/mL) aliquot of palmitic acid ($C_{16}$-COOH) (Sigma) was incubated with varying amounts of ethanol for different time periods at room temperature. Samples were extracted with a 1:1 volumetric ratio of ethyl acetate and the extract was analyzed using GC-MS for the presence of ethyl palmitate. The results are compiled in Table 23 below, which indicated that spontaneous transesterification between ethanol and palmitic acid occurs at a conversion rate of less than 0.01 mole/mole of palmitic acid.

TABLE 23

| % Ethanol (v/v) | $C_2C_{16}$ formed*, mg/L | % conversion (g/g) | % conversion (mole/mole) |
|---|---|---|---|
| 0 | 0 | 0 | 0 |
| 20 | 0.34 | 0.034 | 0.030 |

TABLE 23-continued

| % Ethanol (v/v) | $C_2C_{16}$ formed*, mg/L | % conversion (g/g) | % conversion (mole/mole) |
|---|---|---|---|
| 30 | 0.25 | 0.025 | 0.022 |
| 40 | 0.25 | 0.025 | 0.022 |
| 50 | 0.35 | 0.035 | 0.031 |

*Average of two data points.

The rate of in vitro transesterification catalyzed by 'TesA on palmitoyl-CoA substrate was analyzed. Reactions were carried out at room temperature for 1 hour in a buffer containing 100 μM of palmitoyl-CoA, 100 μM of Phosphate buffer pH 7.0 and 1 mM BSA, either in the presence or absence of 1.5 μM of purified 'TesA. Ethanol concentrations varied between 0-60% (v/v). 1:1 volumetric ratio of ethyl acetate was used for quenching and subsequent extraction. Formation of ethyl palmitate was monitored using GC-MS. Table 24 summarizes the results.

TABLE 24

| Ethanol | Ethyl palmitate (mg/L) | | Ethyl palmitate formed (mg/L) | % conversion (g/g of C16-CoA) | % conversion (mole/mole) |
|---|---|---|---|---|---|
| % v/v | −'TesA | +'TesA | | | |
| 0 | 0 | 0 | 0 | 0 | 0 |
| 5 | 0 | 0 | 0 | 0 | 0 |
| 10 | 0 | 4.12 | 4.12 | 4.12 | 14.57 |
| 20 | 0 | 6.64 | 6.64 | 6.64 | 23.49 |
| 40 | 0 | 1.88 | 1.88 | 1.88 | 6.65 |
| 60 | 0 | 1.74 | 1.74 | 1.74 | 6.15 |

The results indicate that 'TesA thioesterases efficiently catalyzes the transesterification of an acyl-CoA, palmitoyl-CoA, into ethyl palmitate in presence of ethanol. Maximum yield obtained was 23.5 mole/mole of palmitoyl-CoA. Given that yields for spontaneous conversion of palmitic acid to palmitic ester are extremely low compared to those in presence of 'TesA (i.e., indicating a >1,000-fold increase) the conversion occurs enzymatically. Based on our data, maximum transesterification yields occurred at 10-20% ethanol (v/v) levels. Higher alcohol concentrations affect enzyme stability and/or activity adversely and therefore result in lower ester yields.

From these results, a conclusion was reached that thioesterase can catalyze the direct esterification of an acyl-CoA substrate in the presence of alcohol. It will be possible to modify the ester product by changing the alcohol (e.g., by using methanol, propanol or butanol) and/or the alcohol concentration.

Example 36. In Vivo Production of Fatty Esters by Thioesterase

In this example, the ability of 'TesA to produce esters in vivo in the absence of heterologously expressed ester synthase was investigated. Ester formation in the absence of a heterologously expressed ester synthase was observed in the E. coli strain MG1655 (ΔfadE), which also carries an artificial operon containing 'tesA and fadD under the control of a trc promoter, along with a kanamycin marker gene. The operon was integrated into the chromosome, interrupting the native lacZ gene. This strain was tested in a shake flask fermentation using media comprising 6 g/L $Na_2HPO_4$, 3 g/L $KH_2PO_4$, 0.5 g/L NaCl, 1 g/L $NH_4Cl$, 1 mg/L thiamine, 1 mM $MgSO_4$, 0.1 mM CaCl, supplemented with extra $NH_4Cl$ (an additional 1 g/L), Bis-Tris buffer (0.2 M), Triton X-100 (0.1% v/v), and trace minerals (27 mg/L $FeCl_3$-$6H_2O$, 2 mg/L $ZnCl_2$-$4H_2O$, 2 mg/L $CaCl_2$-$6H_2O$, 2 mg/L $Na_2MoO_4$-$2H_2O$, 1.9 mg/L $CuSO_4$-$5H_2O$, 0.5 mg/L $H_3BO_3$, 100 mL/L concentrated HCl).

An LB+antibiotics pre-seed culture was inoculated with a scraping from a glycerol stock or from a single colony. It was cultured for 6 to 8 hours until the $OD_{600}$ reached >1.0. A fermentation medium plus 2% glucose (w/v)+antibiotics overnight seed culture was inoculated with the LB pre-seed culture to 4% (v/v). 15 mL fermentation media+3% glucose (w/v)+antibiotics production cultures were prepared in 125 mL baffled shake flasks. An appropriate amount of the overnight seed culture was used to inoculate the production culture such that the starting $OD_{600}$ in the production culture flask was about 0.5. The flasks were allowed to grow until the $OD_{600}$ therein reached 1.0, at which point the cultures were induced with 1 mM IPTG (final concentration) and fed methanol or ethanol (at 2% v/v). The fermentation runs were allowed to continue for the indicated amount of time post-induction. All culture steps were performed at 32° C. with shaking at 200 rpm.

Whole broth extractions were performed using a standard microextraction procedure. In brief, 500 μl of broth was transferred to a microcentrifuge tube, to which 100 μl of 1M HCl was added. The acidified cultures were extracted with 500 μl of ethyl acetate, vortexed for 5 minutes, and centrifuged at top speed for 1 minute. The organic layer was analyzed using GC-FID for both simultaneous fatty acid methyl ester (FAME) and free fatty acid (FFA) quantification and simultaneous fatty acid ethyl ester (FAEE) and FFA quantification.

In samples containing FAEE and FFA, the FFA were derivatized with Bis(trimethylsilyl)trifluoroacetamide before quantification.

Figure 48:
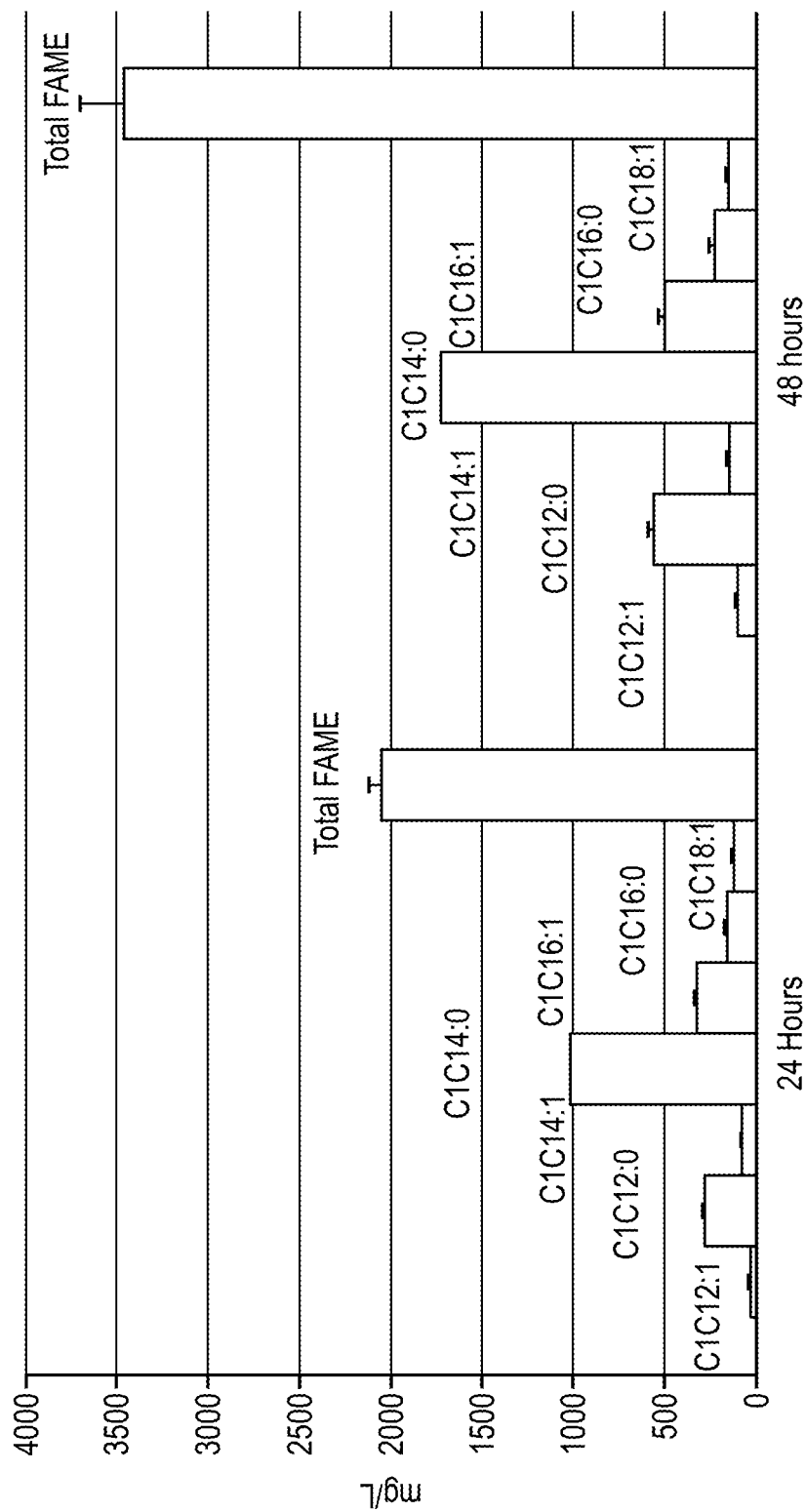
FIG. 48 (FIG. 48) is a graph depicting the FAME titers and composition for the MG1655 (ΔfadE) pTrc-'TesA_fadD strain.

The MG1655 (ΔfadE) pTrc-'TesA_fadD strain, which was cultured and fed 2% methanol at induction, produced 2 g/L total FAMEs by the 24 hour time point and 3.5 g/L total FAMEs by the end of the fermentation at 48 hours (FIG. 48). Minimal amounts of FFAs were detected, about 100 mg/L in total. The cultures reached their highest density, $OD_{600}$ about 11, after 24 hours and did not continue to grow in the following 24 hours. Specific productivity was calculated to be about 200 mg/L/OD at 24 hours, and about 300 mg/L/OD at 48 hours. These data indicated that, with the overexpression of 'tesA and fadD, even in the absence of a wax synthase, FAME production was observed.

Figure 49:
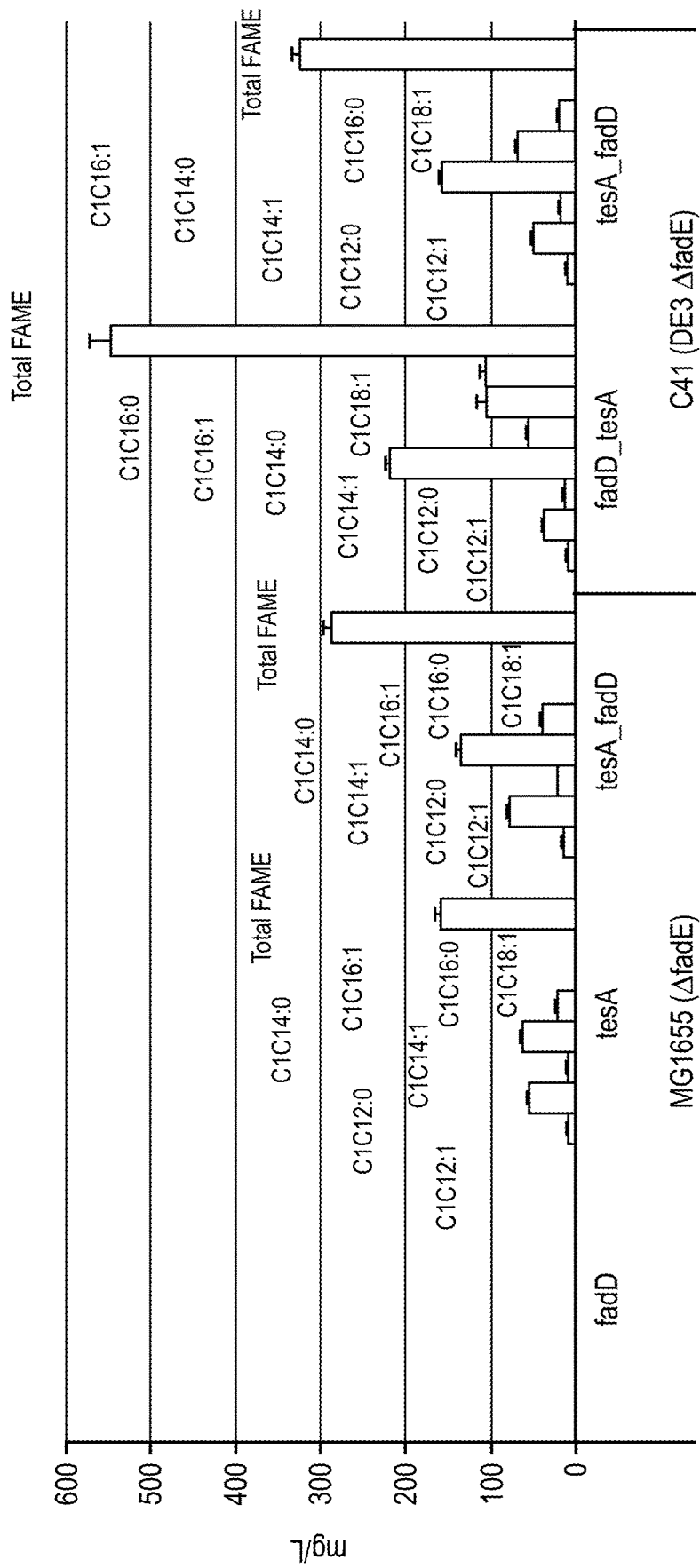
FIG. 49 (FIG. 49) is a graph depicting the FAME titers and composition for the MG1655 (ΔfadE) and C41(ΔfadE) strains expressing fadD and 'tesA on plasmids during a 25-hour fermentation run.
Figure 50:
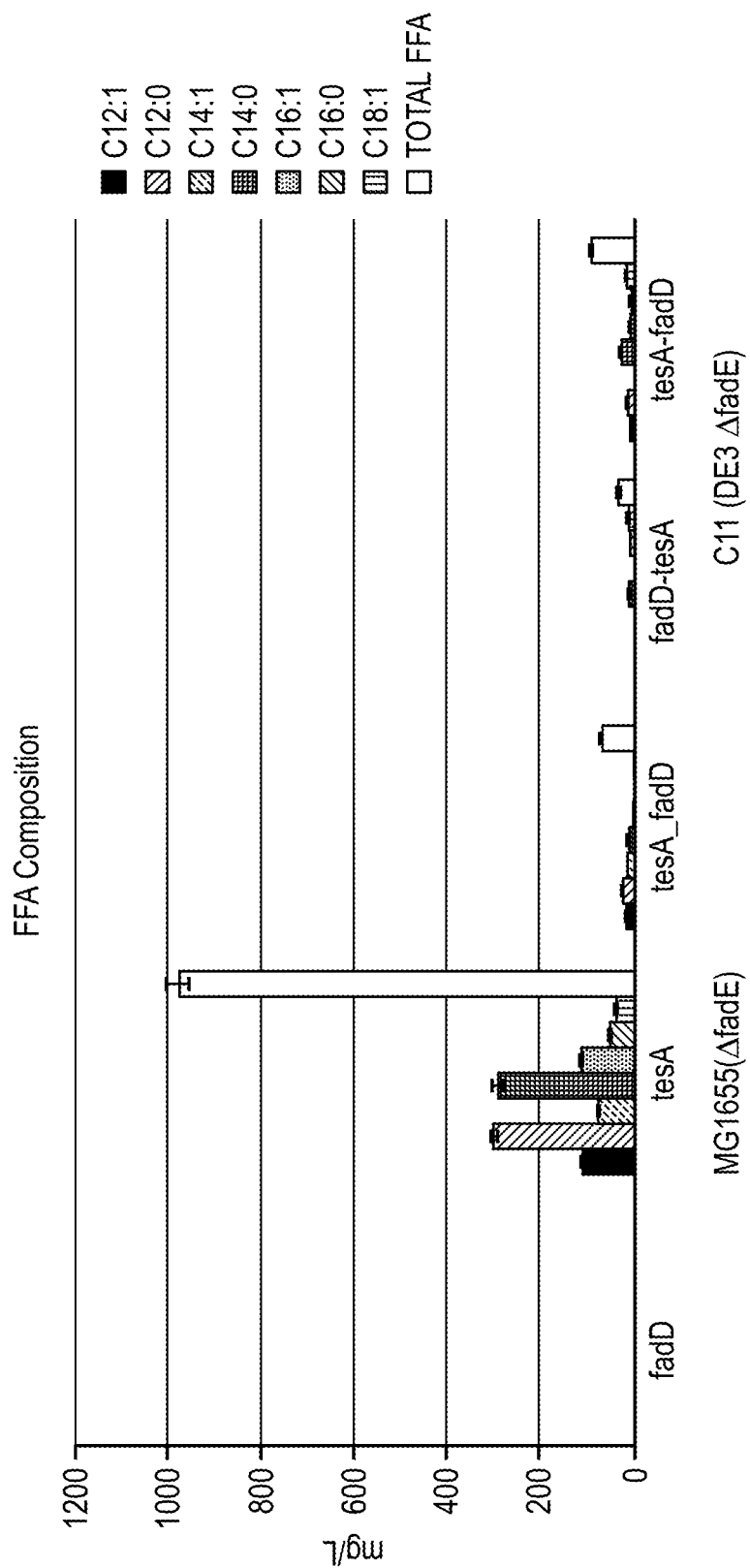
FIG. 50 (FIG. 50) is a graph depicting the FAME titers and composition for the MG1655 (ΔfadE) pTrc-'TesA_fadD strain.

To assess the ability of FadD or 'TesA to independently produce FAME, a second fermentation was carried out testing two different E. coli strains carrying plasmids with either fadD, 'tesA, or both fadD and 'tesA. The plasmids were all pACYC-based and expression was driven by a trc promoter. Three different MG1655 (ΔfadE) strains were tested, one with a fadD only plasmid, one with a 'tesA only plasmid, and one with 'tesA and fadD with 'tesA being located upstream of fadD. Two C41 (ΔfadE) were tested, both carrying 'tesA and fadD, but with the genes in different order relative to the promoter. These strains were cultured in the media described above and fed 2% methanol at induction and grown for an additional 25 hours post-induction. The strain expressing only fadD did not produce any FAMEs while the 'tesA strain produced only about 150 mg/L FAMEs (FIG. 49). Having both 'TesA and fadD improves upon FAME production over 'TesA alone. The two C41 strains produced a further increase in FAME production, as observed in the strain carrying a plasmid in which fadD is upstream of 'tesA, over the strain expressing 'tesA and fadD in the opposite order. This suggested that higher FadD expression enhanced the ability of 'TesA to produce esters. Since 'TesA can cleave both acyl-ACPs and acyl-CoAs, it is likely that the production of acyl-CoAs by FadD is allowing for the FFAs generated by 'TesA to be recycled back to the thioesterase to either be converted back into FFAs by hydrolysis or taken all the way to FAMEs by alcoholysis. Examination of the FFA titers leads to the conclusion that only the strain expressing 'TesA produced significant amounts of FFA, while the strains expressing fadD produced very little FFA (FIG. 50).

'TesA was tested for its ability to utilize ethanol for the direct formation of fatty acid ethyl ester (FAEE). The two MG1655 (ΔfadE) strains from the experiment described above, the fadD overexpression strain and the 'TesA overexpression strain, were tested. Also included in this experiment was the MG1655 (ΔfadE) with the integrated 'tesA_fadD operon under the control of a trc promoter. All strains were cultured using the protocol described above. At induction, all strains were fed 2% (v/v) of methanol or 2% (v/v) of ethanol. In addition, the MG1655 (ΔfadE)+fadD strain was fed 0.05% (w/v) of C14:0 fatty acid to ensure that sufficient free fatty acid substrate was available to FadD for catalyzing the potential alcoholysis reaction. The fermentations were allowed to continue for 24 hours.

Figure 51:
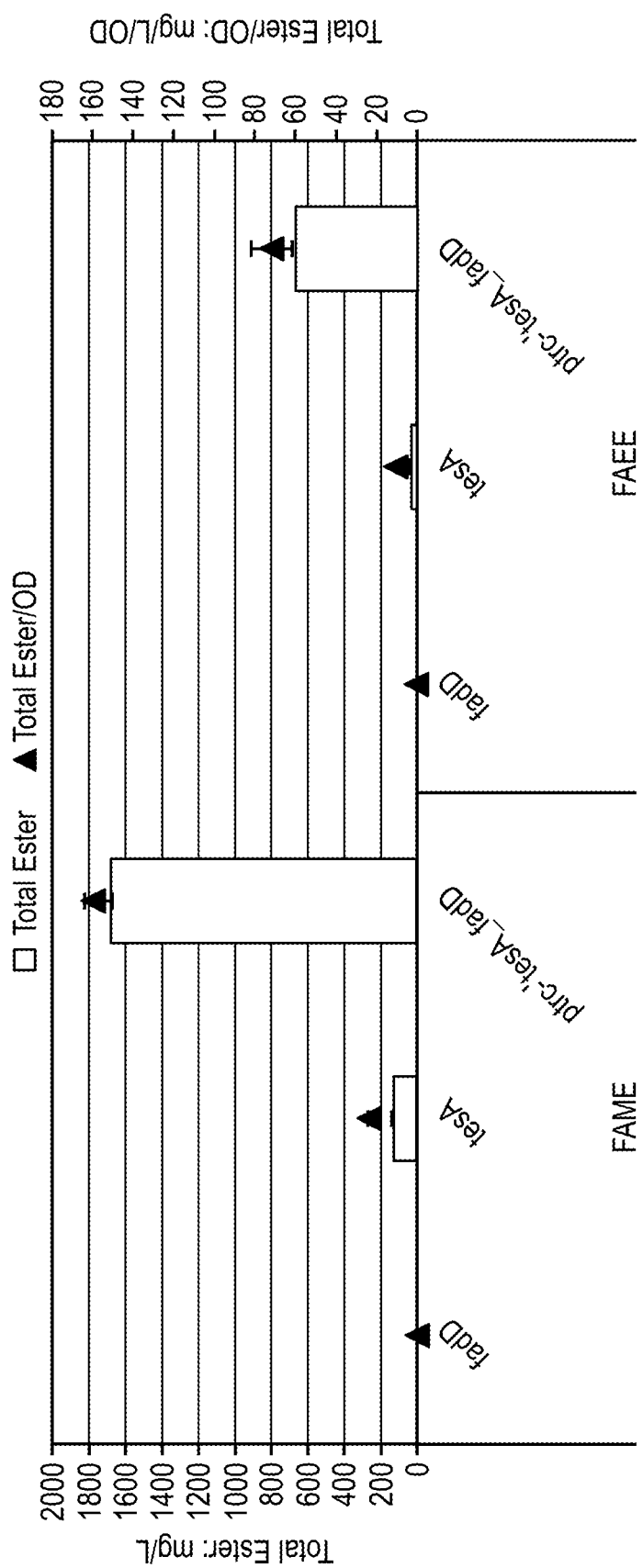
FIG. 51 (FIG. 51) is a graph depicting the FAME titers and composition for the MG1655 (ΔfadE) and C41 (ΔfadE) strains expressing fadD and 'tesA on plasmids during a 25-hour fermentation run.
Figure 52:
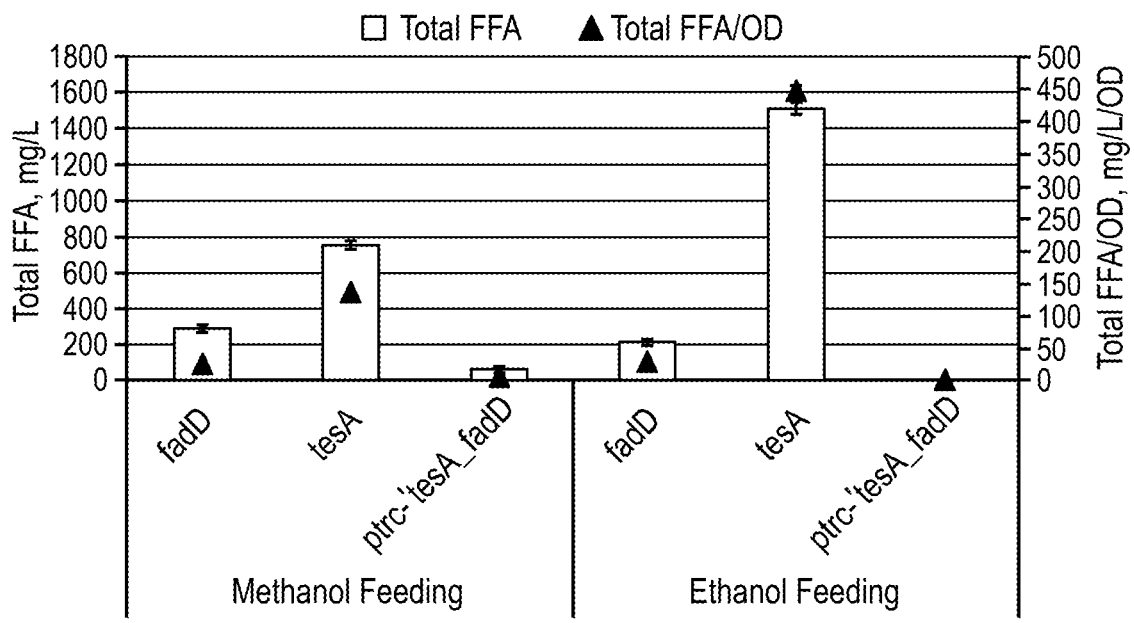
FIG. 52 (FIG. 52) is a graph depicting the FFA titers and composition for the MG1655 (ΔfadE) and C41 (ΔfadE) strains expressing fadD and 'tesA on plasmids during a 25-hour fermentation run.

Under these fermentation conditions, FadD alone was again unable to produce the requisite $C_1C_{14}$:0 FAME or the $C_2C_{14}$:0 FAEE, indicating that FadD was not sufficient for ester formation (FIG. 51). However, 'TesA alone was able to produce FAEEs and as before, overexpression of 'tesA and fadD boosts overall production of FAEEs over having 'tesA alone. While overall FAEE titers were lower than FAME titers, this data demonstrate that 'TesA can also use ethanol in addition to methanol for the formation of fatty esters. Analysis of FFA formation under these fermentation conditions indicates that the strains behaved similarly with ethanol feeding as they did with methanol feeding (FIG. 52).

The FFA present in the fadD samples was contributed almost entirely by the $C_{14}$:0 FFA fed during fermentation. The strain expressing 'tesA produced a large amount of FFA, while the strain expressing 'tesA and fadD showed very little accumulation of FFA. In the presence of 'TesA, only 14% conversion of FFA to FAME or a 2.3% of FFA to FAEE was observed. In the presence of 'TesA and FadD, nearly a 100% conversion of FFA to either FAME or FAEE was observed. These data suggest that 'TesA is necessary and sufficient for fatty acid alcohol ester formation, but the overexpression of FadD along with 'TesA is important for increased FAME and FAEE formation.

Figure 53:
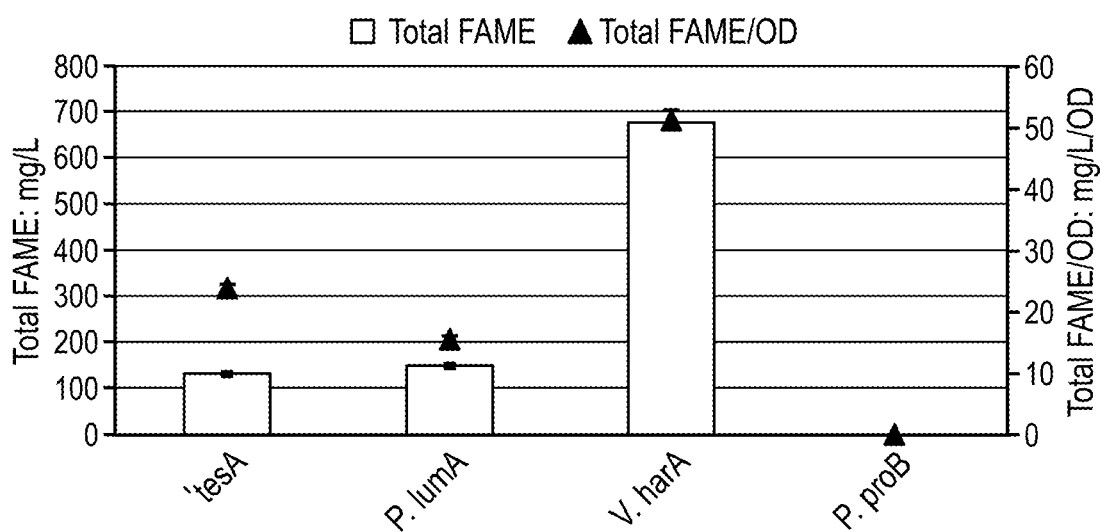
FIG. 53 (FIG. 53) is a graph depicting the FAME titers for the MG1655 (ΔfadE) strains expressing *E. coli* 'tesA, *P. luminescens* 'tesA, *V. harveyi* 'tesA and *P. profundum* tesB on plasmids, during a 24-hour fermentation run. Titers are represented in mg/L and mg/L/OD.
Figure 54:
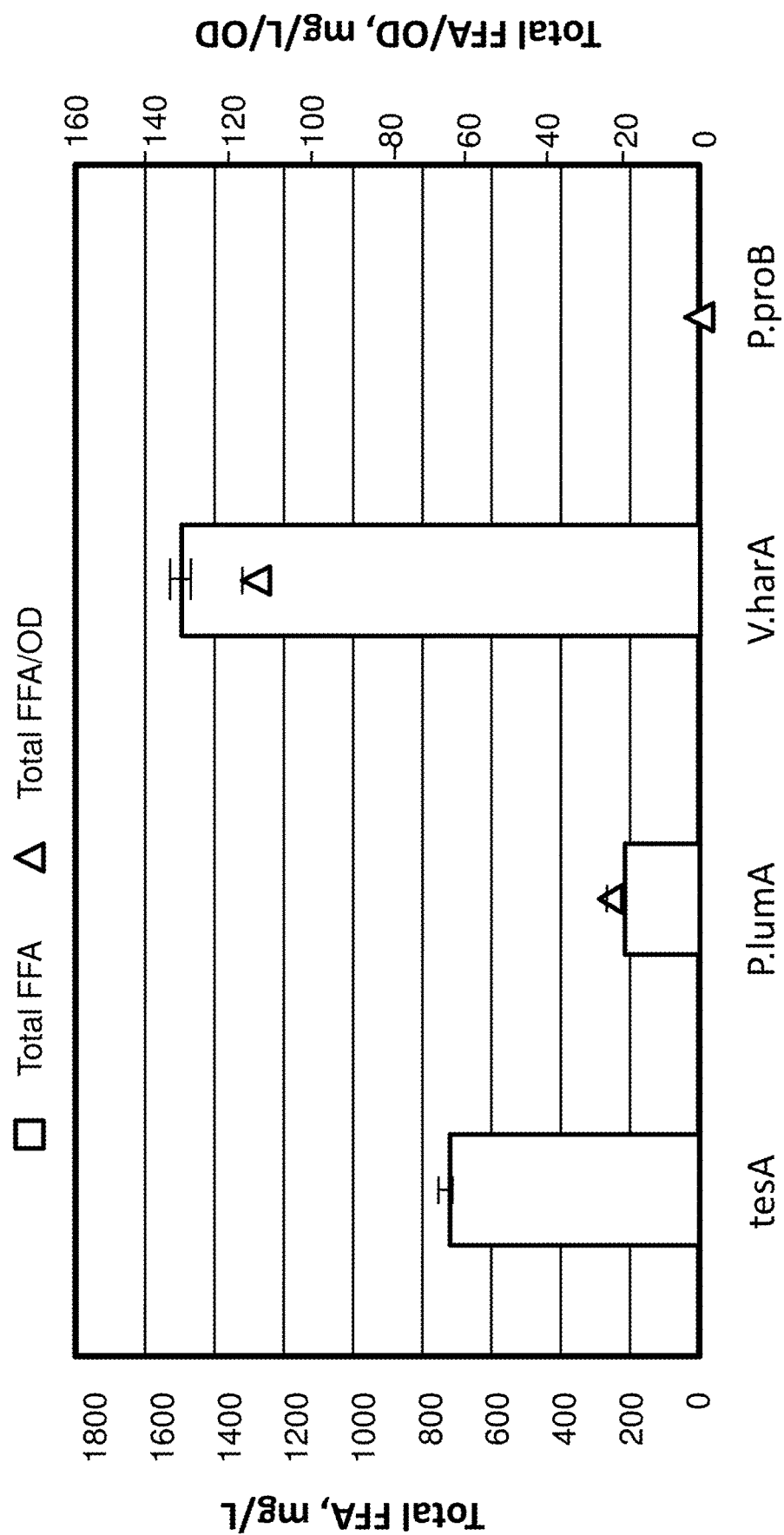
FIG. 54 (FIG. 54) is a graph of FFA titers for MG1655 (ΔfadE) strains expressing *E. coli* 'tesA, *P. luminescens* 'tesA, *V. harveyi* 'tesA and *P. profundum* tesB on plasmids, during a 24-hour fermentation run. Titers are represented in mg/L (bars) and mg/L/OD (triangles).

The previous results suggest that E. coli 'TesA can produce FAME and FAEE when fed the appropriate alcohols during fermentation. To determine whether this is a function unique to E. coli 'TesA, the ability of other heterologously expressed thioesterases to produce FAMEs was investigated. 'TesA homologs from Photorhabdus luminescens and Vibrio harveyi along with a TesB from Photobacterium profundum were overexpressed from pACYC-based plasmids in the strain MG1655 (ΔfadE) and tested alongside the E. coli 'TesA overexpression strain from the previous fermentations. Shake flask fermentations were carried out in fermentation media and allowed to continue for 24 hours post-induction. The results indicated that the two 'TesA homologs were also able to generate FAMEs (FIG. 53). P. luminescens 'TesA produced FAME at a level comparable to E. coli 'TesA, while the V. harveyi 'TesA was able to produce much more FAME than E. coli 'TesA. When looking at the FFA titers, the P. luminescens 'TesA produced less FFA than E. coli 'TesA, but again, the V. harveyi 'TesA produced much larger FFA titers when compared to its E. coli counterpart (FIG. 54). Interestingly, the V. harveyi 'TesA was highly active and was able to produce higher FAME and FFA titers than the control strain expressing E. coli 'TesA; moreover, its FFA to FAME conversion rate was over 30% to E. coli 'TesA's 14%. Additionally, despite producing lower total FAME titers, the strain expressing P. luminescens 'TesA showed that FAME constituted over 60% of the total FAME+ FFA titer.

1. Ester Synthase Activity in Other 'TesA Homologs

The 'TesA homologs from Escherichia coli, Pectobacterium atrosepticum, Photobacterium profundum, Photorhabdus luminescens, Pseudomonas putida, and Vibrio harveyi were cloned into the expression vector pACYC under the control of a trc promoter. All sequences were cloned as truncated genes lacking a signal peptide sequence, in order to achieve cytoplasmic expression. DNA and amino acid sequences for the homologs are shown in Table 26. An alignment of the amino acid sequences is shown in Table 27.

The plasmids were transformed into E. coli MG1655 ΔfadE and cultured overnight at 37° C. on LB agar plates containing 100 µg/mL carbenicillin. Individual colonies were selected and cultured at 37° C. in an LB broth containing 1% (w/v) glucose and 100 µg/mL carbenicillin until $OD_{600}$ reached a value of about 1.0. 200 µL of the culture was then diluted into 1.8 mL of an M9 medium containing 100 µg/mL carbenicillin. After growing the cultures for 3 hours at 37° C., IPTG (1 mM final concentration), as well as Bis-Tris Propane buffer (0.1 M, pH 7.0), and methanol (2% v/v) were added.

After 20 hours of growth at 37° C., 1 mL of culture was extracted by adding 100 µL 1 N HCl and 250 µL ethyl acetate. A C20 free fatty acid internal standard was included in the ethyl acetate solution.

Figure 60:
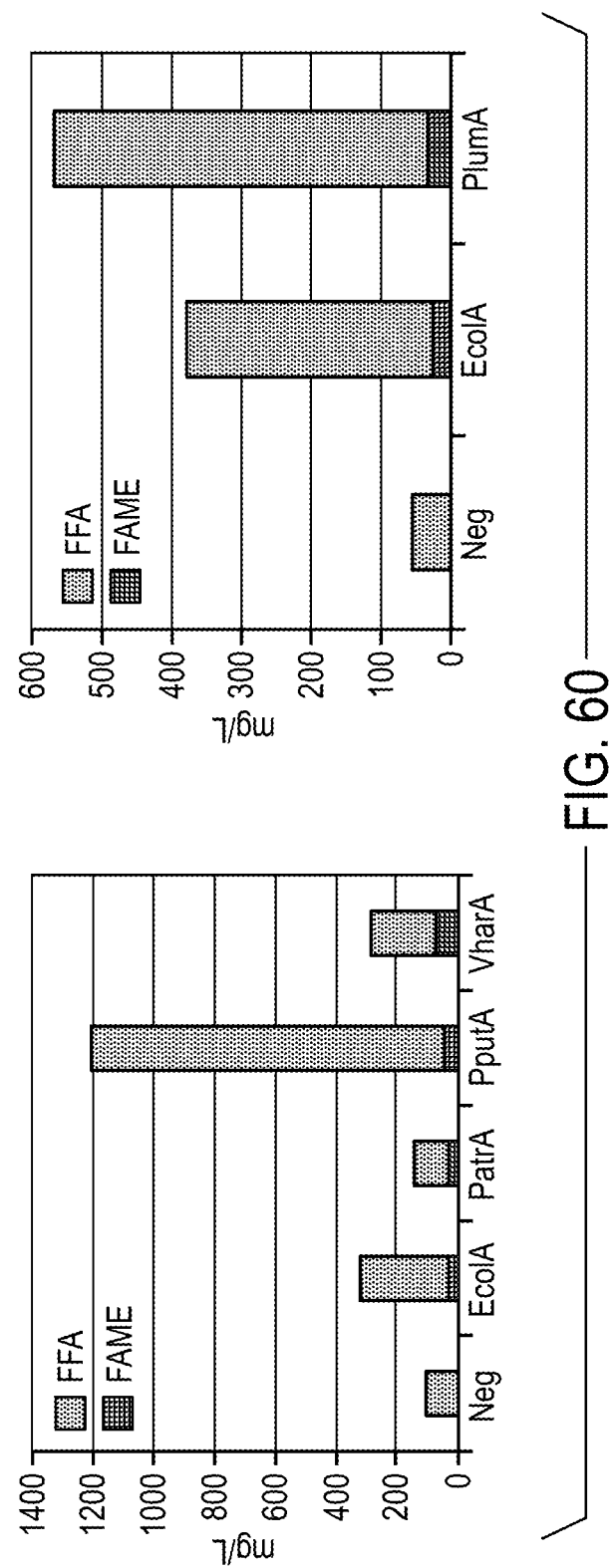
FIG. 60 (FIG. 60) is a graph of free fatty acid (FFA) and fatty acyl methyl ester (FAME) titers in cultures of *E. coli* MG1655 ΔfadE cells transformed with pACYC containing the 'tesA homologs from *E. coli* (EcolA), *Pectobacterium atrosepticum* (PatrA), *Pseudomonas putida* (PputA), *Vibrio harveyi* (VharA), *Photorhabdus luminescens* (PlumA), or with pACYC containing no insert (Neg).

The fatty acids and methyl esters were analyzed on a gas chromatograph Trace GC Ultra (Thermo Electron Corp) equipped with a flame ionization detector. The total amount of fatty acid (FFA) and fatty acyl methyl ester (FAME) produced varied among the homologs studied (see FIG. 60).

E. coli 'TesA produced about 300 mg/L in total fatty products, while the Pseudomonas putida homolog generated nearly 4 times that amount. The proportion of FAME produced was also dependent on which 'TesA homolog was expressed. Whereas only 3% of total product generated by 'TesA from Pseudomonas putida was FAME, more than 25% of total product generated by Vibrio harveyi 'TesA was FAME. These results indicate that ester formation is catalyzed and influenced by 'TesA, rather than being a purely chemical process that is not affected by the enzyme. It follows that this activity is a function of the amino acid sequence of the enzyme and that it can be engineered to increase or decrease the propensity for ester production.

To determine whether FadD overexpression would increase FAME titers, the plasmids were then transformed into E. coli MG1655 ΔfadE carrying the fadD gene on the pCL1920 plasmid, under the control of a trc promoter. The transformed cells were cultured overnight at 37° C. on LB agar plates containing 100 µg/mL carbenicillin and 100 µg/mL spectinomycin. Individual colonies were selected and cultured at 37° C. in LB broth containing 1% (w/v) glucose, 100 µg/mL carbenicillin, and 100 µg/mL spectinomycin until $OD_{600}$ reached a value of about 1.0. 200 µL of the culture was then diluted into 1.8 ml of an M9 medium containing 100 µg/mL carbenicillin and 100 µg/mL spectinomycin. After growing the cultures for 3 hours at 37° C., IPTG (1 mM final concentration), as well as Bis-Tris Propane buffer (0.1 M, pH 7.0) and methanol (2% v/v) were added.

After 20 hours of growth at 37° C., 1 ml of culture was extracted by adding 100 µL 1 N HCl and 250 µL ethyl acetate. A $C_{20}$ free fatty acid internal standard was included in the ethyl acetate solution.

Figure 61:
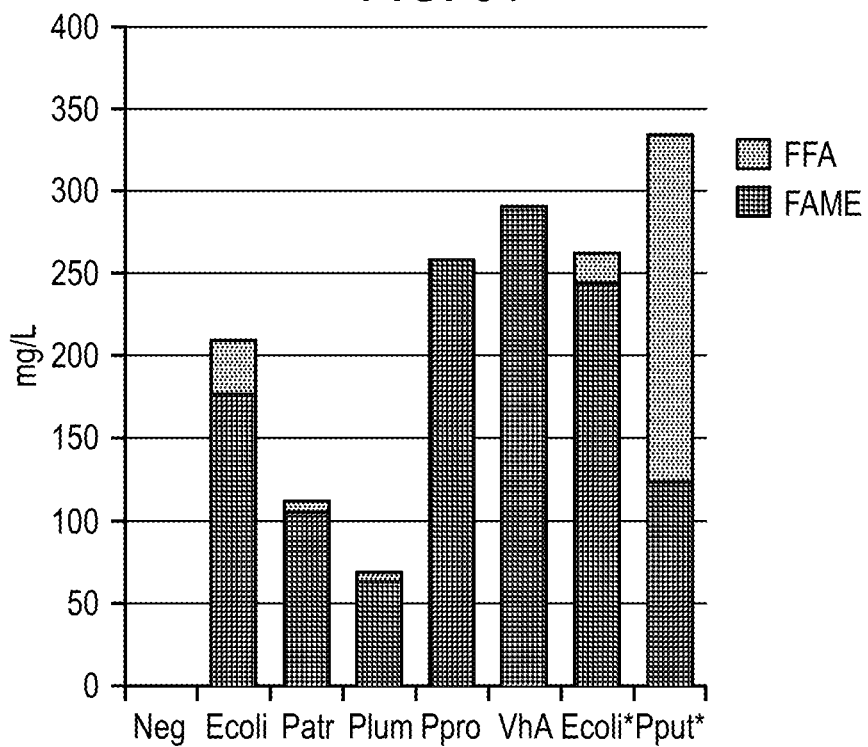
FIG. 61 (FIG. 61) is a graph of FFA and FAME titers in cultures of *E. coli* MG1655 ΔfadE cells overexpressing fadD and 'tesA from *E. coli* (Ecoli), *Pectobacterium atrosepticum* (Patr), *Photorhabdus luminescens* (Plum), Photobacterium *profundum* (Ppro), *Vibrio harveyi* (VhA), *Pseudomonas putida* (Pput), or no 'tesA (Neg). (Data marked with an asterisk (*) are from a separate experiment.)

The fatty acids and methyl esters were analyzed on a gas chromatograph Trace GC Ultra (Thermo Electron Corp) equipped with a flame ionization detector. As observed previously with *E. coli* 'TesA, coexpression of FadD increased the proportion of FAME produced for all homologs tested (See FIG. 61). Therefore, co-expression of an acyl-CoA synthase in conjunction with 'TesA homologs can be used to increase ester production. Interestingly, the total titer of FFA plus FAME produced by 'TesA from *P. putida* was much lower when FadD was co-expressed. This suggests that *P. putida* 'TesA may be more specific for acyl-ACP substrates than acyl-CoAs, and can be co-expressed with an ester synthase or other thioesterase with greater activity against acyl-CoAs to further increase ester production.

2. Enhanced Ester Synthesis by a 'TesA Mutant

As mentioned above, the studies of 'TesA homologs have indicated that ester synthase activity in 'TesA in an engineerable trait; that is, one can make changes in the amino acid sequence of the enzyme to improve the production of esters. To this end, a mutant of *E. coli* 'TesA was constructed with enhanced ester synthase activity. Replacing Ser10, the nucleophilic serine residue in the active site of 'TesA, with cysteine to generate the S10C mutant yields an improved 'TesA enzyme that produces a higher proportion of FAME.

Plasmids encoding wildtype *E. coli* 'TesA, the S10C mutant, or no 'TesA were transformed into *E. coli* MG1655 ΔfadE and cultured overnight at 37° C. on LB agar plates containing 100 µg/mL carbenicillin. Individual colonies were selected and cultured overnight at 37° C. in an LB broth containing 1% (w/v) glucose and 100 µg/ml carbenicillin. The cultures were then diluted 1:100 in a fresh LB medium supplemented with 1% (w/v) glucose and 100 µg/mL carbenicillin, and cultured at 37° C. until $OD_{600}$ reached a value of about 1.0. 200 µL of the culture was then diluted into 1.8 mL of an M9 medium containing 100 µg/mL carbenicillin. After growing the cultures for 3 hours at 37° C., IPTG (1 mM final concentration) was added, as well as Bis-Tris Propane buffer (0.1 M, pH 7.0) and methanol (2% v/v).

After 20 hours of growth at 37° C., 1 mL of culture was extracted by adding 100 µL 1 N HCl and 250 µL ethyl acetate. A $C_{20}$ free fatty acid internal standard was included in the ethyl acetate solution.

Figure 62:
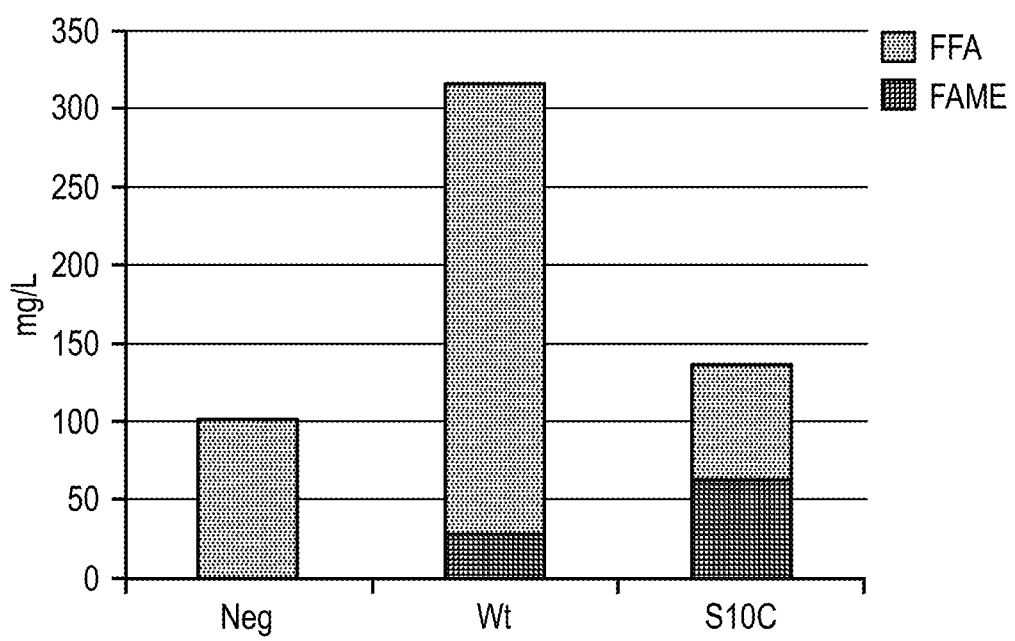
FIG. 62 (FIG. 62) is a graph of FFA and FAME titers in cultures of E. coli MG1655 ΔfadE expressing wildtype E. coli 'tesA(WT), the S10C mutant (S10C), or no 'tesA (Neg).

The fatty acids and methyl esters were analyzed on a gas chromatograph Trace GC Ultra (Thermo Electron Corp) equipped with a flame ionization detector. The total amount of fatty acid (FFA) and fatty acyl methyl ester (FAME) was greater in cultures of wildtype *E. coli* 'TesA (316 mg/L) compared to the S10C mutant (136 mg/L), but the proportion of FAME in S10C (47%) was greater than that observed with wildtype 'TesA (9%). This demonstrates that the sequence of 'TesA can be modified to affect the proportion of esters produced (See FIG. 62).

TABLE 26

Sequences of 'TesA homologs studied in Example 36

| Species | DNA Sequence | Amino Acid Sequence |
|---|---|---|
| Escherichia coli | ATGGCGGACACGTTATTGA TTCTGGGTGATAGCCTGAG CGCCGGGTATCGAATGTCT GCCAGCGCGGCCTGGCCTG CCTTGTTGAATGATAAGTG GCAGAGTAAAACGTCGGT AGTTAATGCCAGCATCAGC GGCGACACCTCGCAACAA GGACTGGCGCGCCTTCCGG CTCTGCTGAAACAGCATCA GCCGCGTTGGGTGCTGGTT GAACTGGGCGGCAATGAC GGTTTGCGTGGTTTTCAGC CACAGCAAACCGAGCAAA CGCTGCGCCAGATTTTGCA GGATGTCAAAGCCGCCAA CGCTGAACCATTGTTAATG CAAATACGTCTGCCTGCAA ACTATGGTCGCCGTTATAA TGAAGCCTTTAGCGCCATT TACCCCAAACTCGCCAAAG AGTTTGATGTTCCGCTGCT GCCCTTTTTTATGGAAGAG GTCTACCTCAAGCCACAAT GGATGCAGGATGACGGTA TTCATCCCAACCGCGACGC CCAGCCGTTTATTGCCGAC TGGATGGCGAAGCAGTTGC AGCCTTTAGTAAATCATGA CTCATAA (SEQ ID NO: 32) | MADTLLILGDSLSAGYRMSA SAAWPALLNDKWQSKTSVV NASISGDTSQQGLARLPALLK QHQPRWVLVELGGNDGLRG FQPQQTEQTLRQILQDVKAA NAEPLLMQIRLPANYGRRYN EAFSAIYPKLAKEFDVPLLPF FMEEVYLKPQWMQDDGIHP NRDAQPFIADWMAKQLQPL VNHDS (SEQ ID NO: 31) |
| Pectobacterium atrosepticum | ATGGCTGATACATTATTAA TTCTGGGTGATAGCCTCAG TGCGGGCTACCAGATGCCG GCCGCTAACGCCTGGCCAA CGCTGCTGAACACGCAGTG GCAGACGCAGAAAAAGGG CATCGCCGTGGTTAACGCC AGCATTAGCGGCGACACC ACCGCACAGGGGCTGGCG CGACTTCCTGCCTTACTGA AACAACATCAGCCGCGTTG GGTGTTGATTGAACTGGGC GGCAATGACGGGCTTCGG GGGTTTCCGGCACCCAATA TCGAGCAGGATCTGGCGA AAATCATTACGCTAGTCAA ACAGGCTAACGCTAAGCCT CTGCTGATGCAGGTTCGTT TGCCAACCAACTATGCCG CCGCTACACCGAGTCATTC AGCAACATTTACCCCAAAC TCGCGGAGCAGTTTGCGCT TCCTCTGCTGCCTTTCTTTA TGGAGCAGGTGTATCTTAA ACCGGAGTGGATCATGGA AGATGGCATCCATCCAACC CGTGATGCCCAACCGTTTA TCGCAGAATGGATGGCGA AGCAGCTGGAACCCTTAGT TAACCATGAGTCTTAA (SEQ ID NO: 60) | MADTLLILGDSLSAGYQMPA ANAWPTLLNTQWQTQKKGI AVVNASISGDTTAQGLARLP ALLKQHQPRWVLIELGGNDG LRGFPAPNIEQDLAKIITLVK QANAKPLLMQVRLPTNYGR RYTESFSNIYPKLAEQFALPL LPFFMEQVYLKPEWIMEDGI HPTRDAQPFIAEWMAKQLEP LVNHES (SEQ ID NO: 59) |
| Photobacterium profundum | ATGGGCAACACATTACTGG TTGTCGGTGATAGCTTGAG CGCGGGCTATCAAATGCGG GCAGAACAAAGCTGGCCG GTGTTACTGCAACCCGCAT TAAAGCAACAAGGTCACG AAATCACCGTTGTAAATGC CAGTATTTCAGGCGATACA ACAGGAAACGGCTTGGCTC GATTGCCTACATTATTACA ACAACATAAACCAGCTTAC GTCATAATTGAACTCGGGG | MAWGNTLLVVGDSLSAGYQ MRAEQSWPVLLQPALKQQG HEITVVNASISGDTTGNGLAR LPTLLQQHKPAYVIIELGAND GLRGFPQGTIRNNLSQMITEI QNADAKPMLVQIKVPPNYG KRYSDMFSSIYPQLSKELATP LLPFFLEQIILKQEWMMNDG LHPKSDAQPWIAEYMAENIA PYL (SEQ ID NO: 61) |

TABLE 26-continued

Sequences of 'TesA homologs studied in Example 36

| Species | DNA Sequence | Amino Acid Sequence |
|---|---|---|
| | CGAATGATGGCTTACGTGG<br>TTTCCCTCAAGGTACTATA<br>CGTAACAATCTCAGCCAAA<br>TGATCACTGAAATTCAAAA<br>TGCTGATGCCAAGCCAATG<br>CTCGTGCAGATAAAAGTGC<br>CGCCCAATTACGGCAAACG<br>CTACAGTGATATGTTCAGT<br>TCTATTTACCCTCAACTCA<br>GTAAAGAGTTAGCCACACC<br>ACTGTTACCTTTCTTTTTAG<br>AGCAGATCATTTTAAAACA<br>AGAATGGATGAATGA<br>CGGTTTGCATCCTAAATCT<br>GATGCTCAGCCATGGATTG<br>CCGAATATATGGCTGAGAA<br>TATCGCGCCTTATTTATAA<br>(SEQ ID NO: 62) | |
| Photo-<br>rhabdus<br>lumi-<br>nescens | ATGGCTGATACCCTTCTGA<br>TTCTCGGTGATAGCCTTAG<br>TGCCGGTTACCATCTGCCT<br>ATTGAGCAGTCATGGCCTG<br>CTTTTGATGGAAAAAAGTG<br>GCAAAAATCCGGCAATAA<br>AATCACGGTCATCAACGGC<br>AGCATCAGCGGCAACACC<br>GCCGCTCAGGGCCTTGAGC<br>GGCTACCTGAATTACTTAA<br>ACAACATAAACCCCGTTGG<br>GTACTGATAGAGCTGGGTG<br>CCAACGATGGATTACGCGG<br>TTTTCCTCCACAACACACC<br>GAACAAGATCTACAACAG<br>ATCATTACTTTAGTGAAAC<br>AAGCTAATATTCAGCCTTT<br>ATTGATGCAGATCCGTCTA<br>CCACCAAACTATGGGCGCC<br>GTTATACCGAGTCTTTTGC<br>CAAGATTTACCCCAAACTG<br>GCAGAATATAATCAAATTC<br>CCCTGCTCCCGTTTTATAT<br>GGAGCAAGTCGCCATTAA<br>ACCGGAGTGGGTGCAACA<br>AGATGGGTTACATCCTAAT<br>CTGGCAGCCCAACCATTTA<br>TCGCCGATTGGATGTCTGA<br>CACACTATCAGCACATCTT<br>AATTATTCTTAA<br>(SEQ ID NO: 64) | MADTLLILGDSLSAGYHLPIE<br>QSWPALMEKKWQKSGNKIT<br>VINGSISGNTAAQGLERLPEL<br>LKQHKPRWVLIELGANDGLR<br>GFPPPQHTEQDLQQIITLVKQA<br>NIQPLLMQIRLPPNYGRRYTE<br>SFAKIYPKLAEYNQIPLLPFY<br>MEQVAIKPEWVQQDGLHPN<br>LAAQPFIADWMSDTLSAHLN<br>YS<br>(SEQ ID NO: 63) |
| Pseudo-<br>monas<br>putida | ATGGCAGGAACACTGCTG<br>GTTGTTGGCGATAGTATCA<br>GCGCCGGTTTTGGCCTGGA<br>TAGCCGTCAGGGCTGGGTG<br>TCTCTCTTGCAGGCCCGTC<br>TCAGGGACGAAGGTTTTGA<br>CGACAAAGTGGTCAATGCT<br>TCGATCAGTGGCGATACCA<br>GCGCAGGTGGCCAGGCGC<br>GGCTGCCGGCGCTGCTTGC<br>AGCACATAAACCGAGCCT<br>GGTGGTGCTGGAGCTGGGC<br>GGCAACGATGGCCTGCGC<br>GGGCAGCCGCCTGCACAAT<br>TGCAACAAAATCTTGCCTC<br>GATGATCGAGCGTCGCGT<br>CAGGCAGGGGCCAAGGTG<br>CTGCTATTGGGCATGCGCC<br>TGCCGCCCAATTATGGTGT<br>GCGTTACACCACCGCTTT<br>GCCAAGGTGTATGAACAG<br>CTGGCAGGACAAACAG<br>GTTCCCTTGGTGCCGTTTTT<br>CCTCGAAGGGGTAGGGGG<br>CGTACCTGAACTGATGCAG | MAGTLLVVGDSISAGFGLDS<br>RQGWVSLLQARLRDEGFDD<br>KVVNASISGDTSAGGQARLP<br>ALLAAHKPSLVVLELGGNDG<br>LRGQPPAQLQQNLASMIERS<br>RQAGAKVLLLGMRLPPNYG<br>VRYTTAFAKVYEQLAADKQ<br>VPLVPFFLEGVGGVPELMQA<br>DGIHPAQGAQQRLLENAWP<br>AIKPLL<br>(SEQ ID NO: 65) |
| | GCTGATGGCATCCATCCGG<br>CCCAGGGGGCTCAGCAGC<br>GCCTGCTGGAAAATGCCTG<br>GCCAGCGGATAAAACCCTTG<br>CTGTGA<br>(SEQ ID NO: 66) | |
| Vibrio<br>harveyi | ATGAGCGAAAAGCTACTTG<br>TTTTGGGCGACAGCCTGAG<br>CGCTGGTTATCAAATGCCT<br>ATAGAGGAGAGTTGGCCT<br>AGCTTACTCCCAGGCGCGT<br>TATTAGAACATGGCCAAGA<br>TGTAAAAGTTGTAAACGGT<br>AGCATCTCTGGTGACACCA<br>CAGGCAATGGCCTTGCACG<br>GTTACCTTCTCTCCTTGAG<br>CAACACACGCCCGATTGG<br>TACTGATTGAGCTTGGCGC<br>TAACGATGGCCTACGCGGT<br>TTCCCACCTAAACTTATTA<br>CGTTAAACCTATCGAAAAT<br>GATTACCATGATCAAAGAT<br>TCTGGTGCGGATGTCGTCA<br>TGATGCAAATCCGCGTCCC<br>ACCAAATTATGGTAAGCGT<br>TACAGCGATATGTTCTACG<br>ACATCTACCCTAAACTGGC<br>AGAACATCAGCAAGTAGC<br>GCTAATGCCGTTCTTCTTA<br>GAGCATGTCATCATTAAAC<br>CAGAATGGATGATGGACG<br>ATGGCTTGCACCCAAAACC<br>GGAAGCTCAACCCTACATT<br>GCTGACTTTGTCGCTCAAG<br>AATTGGTTAAACATCTCTA<br>A<br>(SEQ ID NO: 68) | MSEKLLVLGDSLSAGYQMPI<br>EESWPSLLPGALLEHGQDVK<br>VVNGSISGDTTGNGLARLPSL<br>LEQHTPDLVLIELGANDGLR<br>GFPPKLITLNLSKMITMIKDS<br>GADVVMMQIRVPPNYGKRY<br>SDMFYDIYPKLAEHQQVAL<br>MPFFLEHVIIKPEWMMDDGL<br>HPKPEAQPYIADFVAQELVK<br>HL<br>(SEQ ID NO: 67) |

TABLE 27

Alignment of 'TesA sequences

'TesA    --MADTLLILGDSLSAGYRMSASAAWPALLNDKWQSKT---   55
         SVVNASISGDTSQQGLARL

PatrA    --MADTLLILGDSLSAGYQMPAANAWPTLLNTQWQTQKKGI
         AVVNASISGDTTAQGLARL

PlumA    --MADTLLILGDSLSAGYHLPIEQSWPALMEKKWQKSGNKI
         TVINGSISGNTAAQGLERL

PproA    MAWGNTLLVVGDSLSAGYQMRAEQSWPVLLQPALKQQGHEI
         TVVNASISGDTTGNGLARL

VhA      --MSEKLLVLGDSLSAGYQMPIEESWPSLLPGALLEHGQDV
         KVVNGSISGDTTGNGLARL

PputA    --MAGTLLVVGDSISAGFGLDSRQGWVSLLQARLRDEGFDD
         KVVNASISGDTSAGGQARL

'TesA    PALLKQHQPRWVLELGGNDGLRGFQPQQTEQTLRQILQDV   115
         KAANAEPLLMQIRLPANYG

PatrA    PALLKQHQPRWVLIELGGNDGLRGFPAPNIEQDLAKIITLV
         KQANAKPLLMQVRLPTNYG

PlumA    PELLKQHKPRWVLIELGANDGLRGFPPQHTEQDLQQIITLV
         KQANIQPLLMQIRLPPNYG

PproA    PTLLQQHKPAYVIIELGANDGLRGFPQGTIRNNLSQMITEI
         QNADAKPMLVQIKVPPNYG

TABLE 27-continued

Alignment of 'TesA sequences

| | |
|---|---|
| VhA | PSLLEQHTPDLVLIELGANDGLRGFPPKLITLNLSKMITMI KDSGADVVMMQIRVPPNYG |
| PputA | PALLAAHKPSLVVLELGGNDGLRGQPPAQLQQNLASMIERS RQAGAKVLLLGMRLPPNYG |
| 'TesA | RRYNEAFSAIYPKLAKEFDVPLLPFFMEEVYLKPQWMQDDG 175 IHPNRDAQPFIADWMAKQL |
| PatrA | RRYTESFSNIYPKLAEQFALPLLPFFMEQVYLKPEWIMEDG IHPTRDAQPFIAEWMAKQL |
| PlumA | RRYTESFAKIYPKLAEYNQIPLLPFYMEQVAIKPEWVQQDG LHPNLAAQPFIADWMSDTL |
| PproA | KRYSDMFSSIYPQLSKELATPLLPFFLEQIILKQEWMMNDG LHPKSDAQPWIAEYMAENI |
| VhA | KRYSDMFYDIYPKLAEHQQVALMPFFLEHVIIKPEWMMDDG LHPKPEAQPYIADFVAQEL |
| PputA | VRYTTAFAKVYEQLAADKQVPLVPFFLEGVGGVPELMQADG IHPAQGAQQRLLENAWPAI |
| 'TesA | QPLVNHDS 183 |
| PatrA | EPLVNHES |
| PlumA | SAHLNYS |
| PproA | APYL |
| VhA | VKHL |
| PputA | KPLL. |

Example 37. Production of Fame in the Absence of a Wax Synthase in Fermentors

This Example demonstrates that a process as described in Example 36, supra, can be scaled up to produce fatty acid esters at commercial scale in accordance with the present invention.

Cells from a frozen stock were revived in an LB broth for 4-8 hours and then cultured in a defined medium containing: 1.5 g/L of $KH_2PO_4$, 4.54 g/L of $K_2HPO_4$ trihydrate, 4 g/L of $(NH_4)_2SO_4$, 0.15 g/L of $MgSO_4$ heptahydrate, 20 g/L of glucose, 200 mM of Bis-Tris buffer (pH 7.2), 1.25, and 1.25 mL/L of a vitamin solution. The trace metals solution comprised 27 g/L of $FeCl_3 \cdot 6H_2O$, 2 g/L of $ZnCl_2 \cdot 4H_2O$, 2 g/L of $CaCl_2 \cdot 6H_2O$, 2 g/L of $Na_2MoO_4 \cdot 2H_2O$, 1.9 g/L of $CuSO_4 \cdot 5H_2O$, 0.5 g/L of $H_3BO_3$, and 100 mL/L of concentrated HCl. The vitamin solution comprised 0.42 g/L of riboflavin, 5.4 g/L of pantothenic acid, 6 g/L of niacin, 1.4 g/L of pyridoxine, 0.06 g/L of biotin, and 0.04 g/L of folic acid.

100 mL of a culture grown overnight was used to inoculate 2 liters of the same medium, but with only 2 g/L of glucose, in a fermentor under tightly controlled temperature, pH, agitation, aeration and dissolved oxygen. The conditions in the fermentor were 32° C., pH 6.8, and a dissolved oxygen (DO) level equal to 30% of saturation. The pH was maintained by addition of $NH_4OH$, which also acted as a nitrogen source for cell growth. When the initial glucose became almost consumed, a feed containing 60% glucose, 3.9 g/L $MgSO_4$ heptahydrate and 10 mL/L of the trace minerals solution was supplied to the fermentor. The feed rate was set up to match the cell growth rate to avoid accumulation of glucose in the fermentor. By avoiding glucose accumulation, it was possible to reduce or eliminate the formation of byproducts such as acetate, formate and ethanol, which are otherwise commonly produced by E. coli. During the first 16-24 hours, the feed was supplied exponentially, allowing the cells to grow at a fixed growth rate. Once the feed rate reached a desired maximum (from 6 to 10 g glucose/L fermentor/h) it was maintained at that level for the remainder of the fermentation run. In the early phases of the growth, the production of FAME was induced by the addition of 1 mM IPTG and 25 mL/L of pure methanol. The fermentation was allowed to continue for a period of 3 days. Methanol was added several times during the run to replenish what had been consumed by the cells, but mostly what had been lost by evaporation in the off-gas. The additions were used to maintain the concentration of methanol in the fermentation broth at between 10 and 30 mL/L, so as to guarantee efficient production while avoiding inhibition of cell growth.

The progression of the fermentation was followed by measurements of OD600 (optical density at 600 nm), glucose consumption, and ester production.

Glucose consumption throughout the fermentation was analyzed by High Pressure Liquid Chromatography (HPLC). The HPLC analysis was performed according to methods commonly used for certain sugars and organic acids in the art, using, for example, the following conditions: Agilent HPLC 1200 Series with Refractive Index detector; Column: Aminex HPX-87H, 300 mm×7.8 mm; column temperature: 35° C.; mobile phase: 0.01 M $H_2SO_4$ (aqueous); flow rate: 0.6 mL/min; injection volume: 20 μl.

The production of fatty acid methyl and ethyl esters was analyzed by gas chromatography with a flame ionization detector (GC-FID). The samples from fermentation broth were extracted with ethyl acetate in a ratio of 1:1 vol/vol. After strong vortexing, the samples were centrifuged and the organic phase was analyzed by gas chromatography (GC). The analysis conditions were as follows:

Instrument: Trace GC Ultra, Thermo Electron Corporation with Flame ionization detector (FID) detector;

Column: DB-1 (1% diphenyl siloxane; 99% dimethyl siloxane) CO1 UFM I/O.1/5 01 DET from Thermo Electron Corporation, phase pH 5, FT: 0.4 μm, length 5m, id: 0.1 mm;

Inlet conditions: 250° C. splitless, 3.8 minute 1/25 split method used depending upon sample concentration with split flow of 75 mL/min;

Carrier gas, flow rate: Helium, 3.0 mL/min;

Block temperature: 330° C.;

Oven temperature: 0.5 minute hold at 50° C.; 100° C./minute to 330° C.; 0.5 minute hold at 330° C.;

Detector temperature: 300° C.;

Injection volume: 2 μL;

Run time/flow rate: 6.3 min/3.0 mL/min (splitless method), 3.8 min/1.5 mL/min (split 1/25 method), 3.04 min/1.2 mL/min (split 1/50 method).

This protocol was applied in fermentation runs of two different strains: ID1 (MG1655 ΔfadE::$P_{TRC}$ tesA-fadD) and IDG5 (MG1655 ΔfadE ΔfhuA Δadh Δldh ΔpflB::$P_{TRC}$ tesA, $P_{T5L}$ fadD), neither of which contained the gene coding for an ester synthase. Cells were induced at 4 hours after inoculation by an IPTG addition, and methanol was fed to the fermentors to provide the alcohol for production of FAMEs. In separate experiments, the cultures were fed glucose at two different maximum feed rates: 6 and 10 g/L/h.

Figure 63:
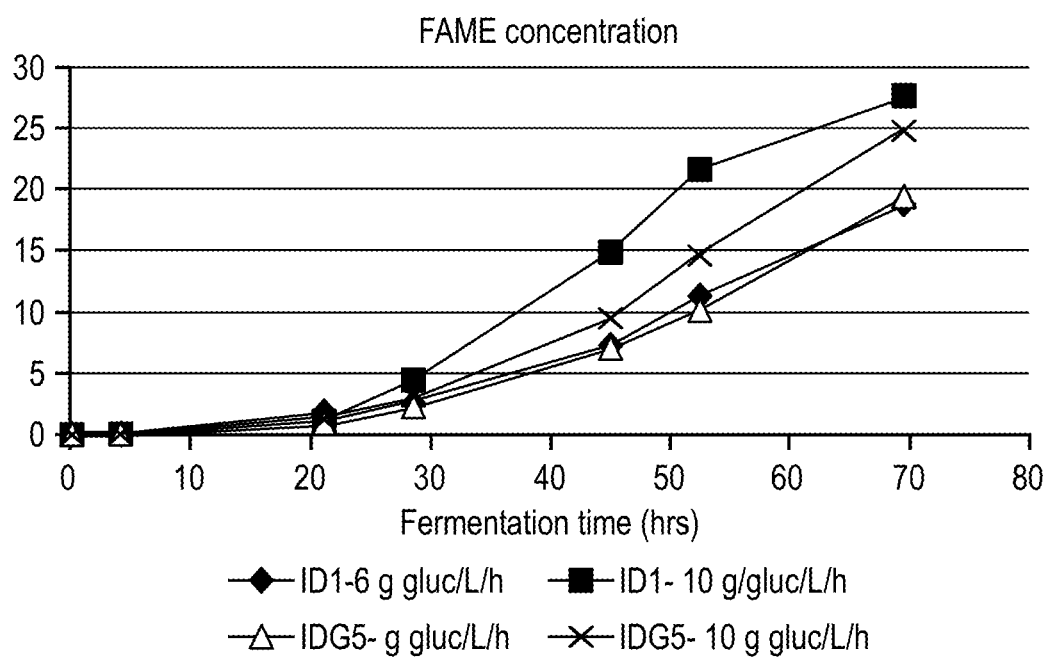
FIG. 63 (FIG. 63) is a graph of FAME production against time of a fermentation run with recombinant host cells that express thioesterase in the absence of exogenous ester synthase.
Figure 64:
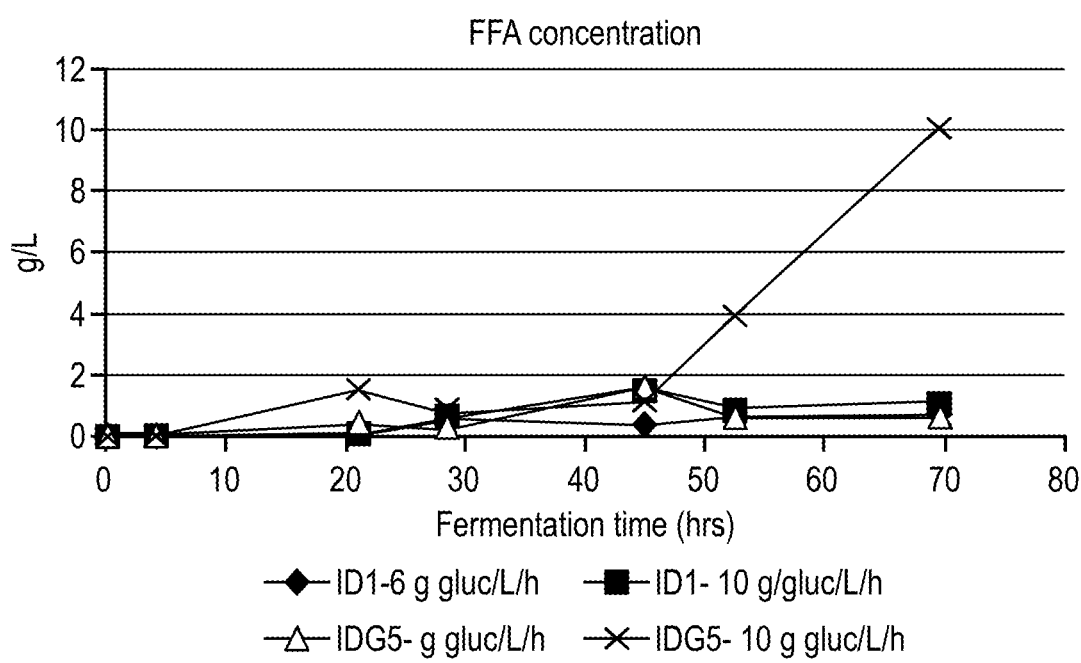
FIG. 64 (FIG. 64) is a graph of FFA production against time of a fermentation run with recombinant host cells that express thioesterase in the absence of exogenous ester synthase.

With both strains and at each glucose feed rate, the cultures indicated a preference for the production of FAME over free fatty acids, as shown in FIG. 63 and FIG. 64. In 70-hour fermentations, ID1 produced about 19 g/L of FAME and less than 1 g/L FFA when fed at 6 g/L/h, and produced 28 g/L FAME and about 1 g/L FFA when fed at 10 g/L/h. IDG5 produced 20 g/L FAME and less than 1 g/L FFA at the lower glucose feed, and produced 25 g/L FAME and about 10 g/L FFA at the higher glucose feed.

Example 38. Identification of Naturally-Occurring Thioesterases for Altered Properties Based on Protein Engineering Results

*E. coli* 'TesA engineering experiments conducted herein are useful in identifying many amino acid residues, the mutations of which lead to altered properties. 'TesA is an enzyme that belongs to the SGNH family, a broad category of enzymes. It is likely that other homologs of 'TesA can also be used in the production of biodiesel using the pathways described herein. This example identifies homologs of 'TesA with potentially altered properties as compared to 'TesA. The method is outlined below.

Homologs of 'TesA were identified using the strategy outlined below.

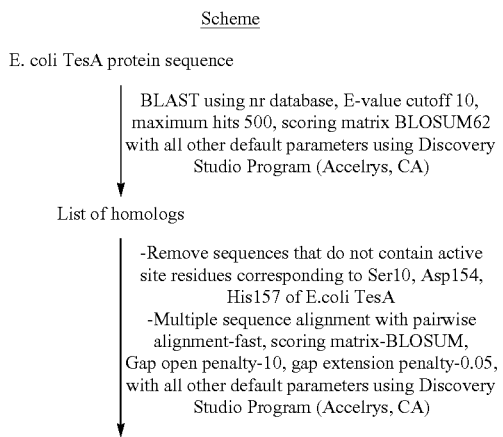

The homologs with substitutions at the positions corresponding to those identified in the 'TesA screen are shown in FIG. 55. The homolog ID and the sequence alignment near the positions of interest are also shown.

EQUIVALENTS

While specific examples of the subject inventions are explicitly disclosed herein, the above specification and examples herein are illustrative and not restrictive. Many variations of the inventions will become apparent to those skilled in the art upon review of this specification including the examples. The full scope of the inventions should be determined by reference to the examples, along with their full scope of equivalents, and the specification, along with such variations.

All publications, patents, patent applications, and other references cited in this application are herein incorporated by reference in their entirety as if each publication, patent, patent application or other reference were specifically and individually indicated to be incorporated by reference.

The invention claimed is:

1. A mutant thioesterase having an amino acid sequence at least 90% identical to SEQ ID NO: 73 and a substitution of an amino acid position selected from the group consisting of position 13, 19, 37, 39, 43, 44, 47, 76, 78, 87, 95, 104, 108, 132, 145, 158, 163, and 164, wherein the mutant thioesterase converts fatty acyl substrates to fatty esters and has increased substrate specificity for C10, C12, C14 substrates relative to SEQ ID NO: 73.

2. The mutant thioesterase of claim 1, wherein the substitution is selected from the group consisting of a substitution of methionine at amino acid position 78; a substitution of alanine at amino acid position 95; a substitution of tryptophan at amino acid position 108; a substitution of glutamic acid at amino acid position 132; a substitution of serine at amino acid position 145; a substitution of leucine at amino acid position 145; and a substitution of cysteine at amino acid position 145.

3. The mutant thioesterase of claim 1, wherein:
(a) the amino acid residue at position 13 is isoleucine, leucine, serine, threonine, tryptophan, or tyrosine; (b) the amino acid residue at position 37 is alanine, glycine, histidine, or serine; (c) the amino acid residue at position 39 is glutamic acid, glutamine, or arginine; (d) the amino acid residue at position 44 is phenylalanine or tyrosine; (e) the amino acid residue at position 47 is phenylalanine; (f) the amino acid residue at position 76 is alanine, phenylalanine, glycine, isoleucine, methionine, asparagine, threonine, or tryptophan; (g) the amino acid residue at position 87 is methionine, serine, or tryptophan; (h) the amino acid residue at position 95 is alanine, aspartic acid, glutamic acid, leucine, or methionine; (i) the amino acid residue at position 104 is alanine, cysteine, proline, glutamine, or tryptophan; (j) the amino acid residue at position 158 is alanine, glycine, glutamine, or serine; (k) the amino acid residue at position 163 is alanine, cysteine, glutamic acid, glycine, isoleucine, methionine, serine, threonine, or valine; or (l) the amino acid residue at position 164 is cysteine.

* * * * *